United States Patent
Lee et al.

(10) Patent No.: US 12,258,328 B2
(45) Date of Patent: *Mar. 25, 2025

(54) 6-MEMBERED HETEROARYL-CONTAINING AMINOPYRIDINE COMPOUNDS AS EGFR INHIBITORS

(71) Applicants: YUHAN CORPORATION, Seoul (KR); JANSSEN BIOTECH, INC., Horsham, PA (US)

(72) Inventors: Hyunjoo Lee, Suwon-si (KR); Su Bin Choi, Hwaseong-si (KR); Misong Kim, Suwon-si (KR); Young Ae Yoon, Seongnam-si (KR); Kwan Hoon Hyun, Incheon (KR); Jae Young Sim, Yongin-si (KR); Marian C. Bryan, Spring House, PA (US); Scott Kuduk, Spring House, PA (US); James Campbell Robertson, Spring House, PA (US)

(73) Assignees: YUHAN CORPORATION, Seoul (KR); JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/822,445

(22) Filed: Aug. 26, 2022

(65) Prior Publication Data

US 2023/0090406 A1 Mar. 23, 2023

Related U.S. Application Data

(60) Provisional application No. 63/237,653, filed on Aug. 27, 2021.

(51) Int. Cl.
| | | |
|---|---|---|
| C07D 401/14 | (2006.01) | |
| C07D 413/14 | (2006.01) | |
| A61K 31/506 | (2006.01) | |
| A61P 35/00 | (2006.01) | |
| A61P 37/00 | (2006.01) | |
| C07D 405/14 | (2006.01) | |

(52) U.S. Cl.
CPC ......... *C07D 401/14* (2013.01); *C07D 413/14* (2013.01)

(58) Field of Classification Search
CPC .. C07D 401/14; C07D 413/14; C07D 405/14; A61P 35/00; A61P 37/00
See application file for complete search history.

(56) References Cited

U.S. PATENT DOCUMENTS

| | | |
|---|---|---|
| 6,884,804 B2 | 4/2005 | Choon-Moon |
| 7,560,464 B2 | 7/2009 | Wang et al. |
| 7,642,354 B2 | 1/2010 | Wang et al. |
| 8,058,045 B2 | 11/2011 | Collins et al. |
| 8,367,658 B2 | 2/2013 | Collins et al. |
| 9,242,984 B2 | 1/2016 | Machacek et al. |
| 9,868,720 B2 | 1/2018 | Cohen et al. |
| 10,822,327 B2 | 11/2020 | Liu et al. |
| 2003/0144309 A1 | 7/2003 | Choon-Moon |
| 2004/0236084 A1 | 11/2004 | Biwersi et al. |
| 2005/0239800 A1 | 10/2005 | Wang et al. |
| 2005/0267089 A1 | 12/2005 | Wang et al. |
| 2008/0108600 A1 | 5/2008 | Wang et al. |
| 2010/0311730 A1 | 12/2010 | Collins et al. |
| 2012/0040967 A1 | 2/2012 | Collins et al. |
| 2015/0191461 A1 | 7/2015 | Machacek et al. |
| 2016/0046608 A1 | 2/2016 | Cohen et al. |
| 2019/0375727 A1 | 12/2019 | Liu et al. |
| 2020/0392156 A1 | 12/2020 | Kesicki |
| 2021/0317136 A1 | 10/2021 | Lindstrom et al. |
| 2022/0177459 A1 | 6/2022 | Du et al. |
| 2022/0298140 A1 | 9/2022 | Chen |
| 2022/0411407 A1 | 12/2022 | Wang et al. |

FOREIGN PATENT DOCUMENTS

| | | | |
|---|---|---|---|
| CN | 104761585 A | 7/2015 | |
| KR | 10-2020-0016567 A | 2/2020 | |
| WO | WO-2010038081 A2 * | 4/2010 | ........... C07D 239/48 |
| WO | 2019/222538 A1 | 11/2019 | |

OTHER PUBLICATIONS

Gao F, Xiao J, Huang G. Current scenario of tetrazole hybrids for antibacterial activity. Eur J Med Chem. Dec. 15, 2019;184:111744. doi: 10.1016/j.ejmech.2019.111744. Epub Sep. 27, 2019. PMID: 31605865. (Year: 2019).*
Cecil Textbook of Medicine, 20th Ed, vol. 1, pp. 1004-1010 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
Gleeson MP, Hersey A, Montanari D, Overington J. Probing the links between in vitro potency, ADMET and physicochemical parameters. Nat Rev Drug Discov. Mar. 2011;10(3):197-208. doi: 10.1038/nrd3367. PMID: 21358739; PMCID: PMC6317702. (Year: 2011).*
Hanan et al., "Discovery of Selective and Noncovalent Diaminopyrimidine-Based Inhibitors of Epidermal Growth Factor Receptor Containing the T790M Resistance Mutation", J. Med. Chem., 2014, vol. 57, pp. 10176-10191.

* cited by examiner

*Primary Examiner* — Bruck Kifle
*Assistant Examiner* — Kevin S Martin
(74) *Attorney, Agent, or Firm* — Vorys, Sater, Seymour and Pease LLP; Mih Suhn Koh

(57) ABSTRACT

Provided are 6-membered heteroaryl-containing aminopyridine compounds and pharmaceutically acceptable compositions thereof which exhibit inhibition activity against certain mutated forms of EGFR.

20 Claims, No Drawings

6-MEMBERED HETEROARYL-CONTAINING AMINOPYRIDINE COMPOUNDS AS EGFR INHIBITORS

FIELD OF THE INVENTION

The present invention relates to novel aminopyridine compounds and pharmaceutically acceptable compositions thereof which exhibit inhibition activity against certain mutated forms of EGFR.

BACKGROUND

A distinct subtype of lung cancer is epidermal growth factor receptor (EGFR) mutation positive non-small cell lung cancer (NSCLC). The human EGFR is a membrane-bound receptor tyrosine kinase of the ErbB family. The activation causes downstream effects via several signaling pathways including the RAS/RAF/MEK/ERK/MAPK and PI3K/PTEN/Akt/mTOR (Chen et al., 2020). The EGFR signaling pathway regulate a series of important events including proliferation, migration, differentiation, apoptosis, as well as those that regulate intercellular communication during development (Wee et al., 2017; Huang et al., 2015; Yewale et al., 2013).

Approximately 10% to 50% of NSCLC patients have EGFR activating mutations, such as in-frame deletions in exon 19 deletion (Del19) or a missense mutation in exon 21 (L858R). (Yang et al., 2018; Shigematsu et al., 2005; Shu et al., 2017; Zhang et al., 2010). These patients respond well to first and second-generation EGFR tyrosine kinase inhibitors (TKI), including gefitinib (IRESSA™), erlotinib (TARCEVA™), and afatinib (GIOTRIF™) allowing them as the initial therapy for in patients with advanced NSCLC harboring common EGFR mutations (Kashima et al., 2020); Mok et al., 2009; Zhou et al., 2011; Sequist et al., 2013). But ultimately acquired resistance to therapy with gefitinib or erlotinib arises predominantly by mutation of the gatekeeper residue T790M, which is detected in approximately half of clinically resistant patients, resulting in double mutants. L858R/T790M and Del19/T790M.

Several third-generation EGFR TKIs were being explored to overcome this resistance. Currently, osimertinib is the third-generation EGFR-TKI approved by major regulatory agencies for treatment of T790M-positive patients who have progressed on first- or second generation EGFR-TKIs (Leonetti et al., 2019; Soria et al., 2018).

Osimertinib is a powerful inhibitor that inhibits EGFR mutations and T790M resistant mutations, but it causes ineffective binding and C797S subsequent resistance in NSCLC patients (Arulananda et al., 2017). Unfortunately, it has been reported that acquired resistance mutations occur in lung cancer patients after the treatment with third-generation EGFR-TKIs. The C797S mutation is the frequently arise after the use of third generation EGFR TKIs in 10% to 30% of these patients. (Ramalingam et al., 2018; Thress et al., 2015; Oxnard et al., 2018; Starrett et al., 2020; Mehlman et al., 2019; Rangachari et al., 2019; Zhou et al., 2019). Osimertinib resistance resulting from EGFR triple mutations (Del19/T790M/C797S and L858R/T790M/C797S) has been reported, requiring the next generation EGFR-TKI to overcome the osimertinib resistant EGFR triple mutations (Kashima et al., 2020).

In front-line therapy with third generation TKI, C797S develops in the absence of T790M (Chen et al., 2020). Osimertinib was also approved in 2018 as first-line therapy for locally advanced or metastatic EGFR-mutated NSCLC, regardless of T790M mutation status (Leonetti et al., 2019). When osimertinib was administered as a front-line therapy, the frequency of the C797S mutation was 7%, making it the second most frequent mechanism, behind MET amplification, of drug resistance in this setting (Leonetti et al., 2019; Ramalingam et al., 2018).

When osimertinib was administered as a front-line therapy, the most common resistance mechanisms resulted to be the C797S mutation (7%) and MET amplification (15%). Other mechanisms included HER2 amplification, PIK3CA and RAS mutations (Ramalingam et al., 2018). Also, selectivity to wild-type (WT) EGFR is important for EGFR-TKIs, because WT EGFR inhibition causes adverse effects such as rashes and/or diarrhea, and these WT EGFR-derived toxicities cause dose-limiting effects (Kashima et al., 2020); Fakih et al., 2010; Takeda et al., 2015).

The next generation EGFR compounds would need to inhibit Del19/T790M/C797S, L858R/T790M/C797S, Del19/C797S and L858R/C797S and be highly selective versus WT EGFR to avoid adverse effects. Recently, mutant selective inhibitors, BI-4020 and BLU-945 were reported as potential therapeutic strategies to overcome the EGFR Del19/T790M/C797S mutations (Engelhardt et al., 2019; Schalm et al., 2020).

However, there have been no reports of these compounds inhibiting Del19/C797S and L858R/C797S. Therefore, novel EGFR-TKIs potently effective against EGFR triple/double mutations are urgently needed.

To address this unmet need, we are developing a next generation TKI targeting both C797S triple and double mutants. It is necessary to develop a novel selective (next generation) inhibitor for NSCLC patients with advanced or metastatic diseases carrying Del19/T790M/C797S, L858R/T790M/C797S, Del19/C797S and L858R/C797S mutation following second-line or upfront use of third-generation EGFR TKIs.

REFERENCES

Arulananda S, John T, Dobrovic A. et al. Combination Osimertinib and Gefitinib in C797S and T790M EGFR-Mutated Non-Small Cell Lung Cancer. Journal of Thoracic Oncology Vol. 12 No. 11: 1728-1732, 2017.

Chen J S, Riess J W. Advances in targeting acquired resistance mechanisms to epidermal growth factor receptor tyrosine kinase inhibitors. Justin A. Chen, Jonathan W. Riess. J Thorac Dis 2020; 12 (5): 2859-2876.

Engelhardt H, et al. Start Selective and Rigidify: The Discovery Path toward a Next Generation of EGFR Tyrosine Kinase Inhibitors. Cite This: J. Med. Chem. 2019, 62, 10272-10293.

Fakih M, Vincent M. Adverse events associated with anti-EGFR therapies for the treatment of metastatic colorectal cancer. Curr. Oncol. 2010; 17: S18-30.

Huang L, Fu L. Mechanisms of resistance to EGFR tyrosine kinase inhibitors. Acta Pharm Sin B 2015; 5: 390-401.

Kashima K, et al. CH7233163 Overcomes Osimertinib-Resistant EGFR-Del 19/T790M/C797S Mutation. Mol Cancer Ther: 19 (11) November 2020.

Leonetti A, et al. Resistance mechanisms to osimertinib in EGFR-mutated non-small cell lung cancer. British Journal of Cancer (2019) 121:725-737.

Mok T S, Wu Y L, Thongprasert S, Yang C H, Chu D T, Saijo N, et al. Gefitinib or carboplatin-paclitaxel in pulmonary adenocarcinoma. N Engl J Med 2009; 361: 947-57.

Mehlman C, Cadranel J, Rousseau-Bussac G, Lacave R, Pujals A, Girard N, et al. Resistance mechanisms to osimertinib in EGFR-mutated advanced non-smallcell lung cancer: A multicentric retrospective French study. Lung Cancer 2019; 137:149-56.

Oxnard G R, Hu Y, Mileham K F, Husain H, Costa D B, Tracy P, et al. Assessment of resistance mechanisms and clinical implications in patients with EGFR T790M-positive lung cancer and acquired resistance to osimertinib. JAMA Oncol. 2018; 4:1527-34.

Ramalingam S S, Yang J C, Lee C K, Kurata T, Kim D W, John T, et al. Osimertinib as first-line treatment of EGFR mutation-positive advanced non-small-cell lung cancer. J. Clin. Oncol. 2018; 36:841-9.

Rangachari D, To C, Shpilsky J E, VanderLaan P A, Kobayashi S S, Mushajiang M, et al. EGFR-mutated lung cancers resistant to osimertinib through EGFR C797S respond to first-generation reversible EGFR inhibitors but eventually acquire EGFR T790M/C797S in preclinical models and clinical samples. J. Thorac. Oncol. 2019; 14: 1995-2002.

Schalm S, et al. BLU-945, a highly potent and selective 4th-generation EGFR TKI for the treatment of EGFR+/T790M/C797S resistant NSCLC. 2020, ESMO.

Sequist L V, Yang J C, Yamamoto N, O'Byrne K, Hirsh V, Mok T, et al. Phase III study of afatinib or cisplatin plus pemetrexed in patients with metastatic lung adenocarcinoma with EGFR mutations. J. Clin. Oncol. 2013; 31:3327-34.

Shigematsu H, Lin L, Takahashi T, Nomura M, Suzuki M, Wistuba I I, et al. Clinical and biological features associated with epidermal growth factor receptor gene mutations in lung cancers. J Natl Cancer Inst 2005; 97:339-46.

Shu Y, Wu X, Tong X, Wang X, Chang Z, Mao Y, et al. Circulating tumor DNA mutation profiling by targeted next generation sequencing provides guidance for personalized treatments in multiple cancer types. Sci Rep 2017; 7:583.

Soria, J.-C., Ohe, Y., Vansteenkiste, J., Reungwetwattana, T., Chewaskulyong, B., Lee, K. H. et al. Osimertinib in untreated EGFR-mutated advanced non-small cell lung cancer. N. Engl. J. Med 378, 113-125 (2018).

Starrett J H, Guernet A A, Cuomo M E, Poels K E, van Alderwerelt van Rosenburgh I K, Nagelberg A, et al. Drug sensitivity and allele-specificity of first-line osimertinib resistance EGFR mutations. Cancer Res 2020; 80:2017-30.

Takeda M, Okamoto I, Nakagawa K. Pooled safety analysis of EGFR-TKI treatment for EGFR mutation-positive non-small cell lung cancer. Lung Cancer 2015; 88:74-9.

Thress K S, Paweletz C P, Felip E, Cho B C, Stetson D, Dougherty B, et al. Acquired EGFR C797S mutation mediates resistance to AZD9291 in non-small cell lung cancer harboring EGFR T790M. Nat Med 2015; 21:560-2.

Wee, P.; Wang, Z. Epidermal Growth Factor Receptor Cell Proliferation Signaling Pathways. Cancers 2017, 9, 52.

Yewale C, Baradia D, Vhora I, et al. Epidermal growth factor receptor targeting in cancer: a review of trends and strategies. Biomaterials 2013; 34:8690-707.

Yang Z, Yang N, et al. Investigating Novel Resistance Mechanisms to Third-Generation EGFR Tyrosine Clin Cancer Res: 2018

Zhang Z, Stiegler A L, Boggon T J, Kobayashi S, Halmos B. EGFR-mutated lung cancer: a paradigm of molecular oncology. Oncotarget 2010; 1:497-514.

Zhou C, Wu Y L, Chen G, Feng J, Liu X Q, Wang C, et al. Erlotinib versus chemotherapy as first-line treatment for patients with advanced EGFR mutation-positive non-small-cell lung cancer (OPTIMAL, CTONG-0802): a multicentre, open-label, randomised, phase 3 study. Lancet Oncol. 2011; 12:735-42.

Zhou Z, Zhao Y, Shen S, Gu L, Niu X, Xu Y, et al. Durable clinical response of lung adenocarcinoma harboring EGFR 19Del/T790M/in trans-C797S to combination therapy of first- and third-generation EGFR tyrosine kinase inhibitors. J. Thorac. Oncol. 2019; 14: e157-e9.

SUMMARY OF INVENTION

The present invention relates to novel aminopyridine compounds of Formula (I) shown below, or a pharmaceutically acceptable salt thereof:

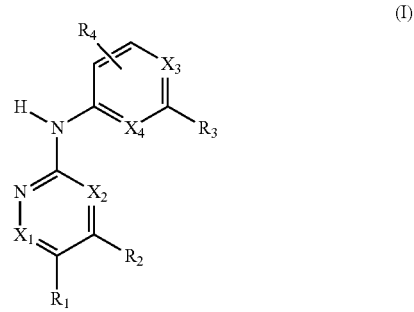

wherein $X_1$ and $X_2$ are, independently each other, —CH= or —N=, with the proviso that $X_1$ and $X_2$ cannot be —N= at the same time, $X_3$, and $X_4$ are, independently each other, —CH= or —N=, with the proviso that $X_3$ and $X_4$ cannot be —CH= at the same time, $R_1$ is -A-$(R_{1A})_m$, A is 6-10 membered heteroaryl, $R_{1A}$ is independently selected from the group consisting of

H;

OH;

halogen;

cyano;

$C_{1-6}$alkyl optionally substituted by one or more substituents selected from the group consisting of OH, halogen, $C_{1-3}$alkoxy, $C_{3-6}$cycloalkyl, —NH$C_{1-6}$alkyl, —N($C_{1-6}$alkyl)$_2$, and 4-7 membered heterocyclyl optionally or independently substituted by one or more substituents selected from the group consisting of OH, halogen, and $C_{1-6}$alkyl;

$C_{3-6}$cycloalkyl;

$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;

—NH$C_{1-6}$alkyl optionally substituted by one or more substituents selected from the group consisting of OH, halogen, —N($C_{1-6}$alkyl)$_2$ and 3-7 membered heterocyclyl optionally substituted by one or more substituents selected from the group consisting of OH, halogen, and $C_{1-6}$alkyl;

—NH$C_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more substituents selected from the group consisting of OH, halogen, and $C_{1-6}$alkyl;

—N($C_{1-6}$alkyl)$_2$ optionally substituted by one or more substituents selected from the group consisting of OH and halogen;

—NHC(O)$C_{1-6}$alkyl optionally substituted by one or more substituents selected from the group consisting of OH and halogen;

—NHC(O)$C_{3-6}$cycloalkyl optionally substituted by one or more substituents selected from the group consisting of OH and halogen;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, $C_{1-3}$alkoxy, $C_{1-6}$hydroxyalkyl, and $C_{1-6}$haloalkyl;

—S(O)$_2$$C_{1-6}$alkyl optionally substituted by one or more halogens;

—S(O)$_2$$C_{3-6}$cycloalkyl optionally substituted by one or more halogens;

—S(O)$_2$N($C_{1-6}$alkyl)$_2$ optionally substituted by one or more halogens;

—S(O)$_2$-3-7 membered heterocyclyl optionally substituted by one or more substituents selected from the group consisting of OH, halogen, and $C_{1-6}$alkyl;

—C(O)O$C_{1-6}$alkyl;

—C(O)$C_{1-6}$alkyl; and

—C(O)-3-7 membered heterocyclyl optionally substituted by one or more substituents selected from the group consisting of OH, halogen, and $C_{1-6}$alkyl, m is an integer of 0 to 2, $R_2$ is —X$C_{1-6}$alkyl optionally substituted by one or more substituents selected from the group consisting of OH, halogen, and —N($C_{1-6}$alkyl)$_2$; or —X(CH$_2$)$_n$—B—($R_{2A}$)$_o$, X is —NH—, —O—, bond or —C≡C—, n is an integer of 0 to 2, is an integer of 0 to 3, B is selected from the group consisting of $C_{3-8}$cycloalkyl, $C_{6-10}$ aryl; 4-11 membered heterocyclyl; and 5-6 membered heteroaryl, $R_{2A}$ is independently selected from the group consisting of

H;

OH;

halogen;

NH$_2$;

$C_{1-6}$alkyl optionally substituted by one or more substituents selected from the group consisting of OH, NH$_2$, halogen, $C_{3-6}$cycloalkyl, $C_{1-3}$alkoxy, —NHC$_{1-6}$alkyl, —NHC$_{1-6}$hydroxyalkyl, —NHC$_{1-6}$haloalkyl, —NHC$_{3-6}$cycloalkyl, —N($C_{1-6}$alkyl)$_2$, —N($C_{1-6}$haloalkyl)$_2$, —NHC(O)$C_{1-6}$alkyl, —C(O) NHC$_{1-6}$alkyl, —C(O)N($C_{1-6}$alkyl)$_2$ 3-7 membered heterocyclyl and 5-6 membered heteroaryl;

$C_{3-6}$cycloalkyl;

$C_{1-3}$alkoxy optionally substituted by one or more halogens;

—C(O) NHC$_{1-6}$alkyl optionally substituted by one or more substituents selected from the group consisting of OH and halogen;

—C(O)N($C_{1-6}$alkyl)$_2$ optionally substituted by one or more substituents selected from the group consisting of OH and halogen;

—NHC$_{1-6}$alkyl optionally substituted by one or more substituents selected from the group consisting of OH, halogen, —NHC$_{1-6}$alkyl, —N($C_{1-6}$alkyl)$_2$, 3-7 membered heterocyclyl optionally substituted by halogen or —N($C_{1-6}$alkyl)$_2$;

—N($C_{1-6}$alkyl)$_2$ where $C_{1-6}$alkyl is optionally substituted by one or more halogens;

—NH-4-7 membered heterocyclyl optionally substituted by $C_{1-6}$alkyl; and 4-7 membered heterocyclyl, $R_3$ is Y-Q-($R_{3A}$)$_p$, Y is —NH— or bond, Q is selected from the group consisting of acetylene; 4-7 membered heterocyclyl; $C_{6-10}$ aryl; and 5-10 membered heteroaryl, p is an integer of 0 to 2, $R_{3A}$ is independently selected from the group consisting of

H;

OH;

halogen;

$C_{1-3}$alkoxy;

$C_{1-6}$alkyl optionally substituted by one or more substituents selected from the group consisting of OH, halogen, $C_{3-6}$cycloalkyl, S(O)$_2$$C_{1-6}$alkyl, and $C_{1-3}$alkoxy;

$C_{2-6}$alkenyl;

$C_{3-6}$cycloalkyl;

4-7 membered heterocyclyl;

—C(O)$C_{1-6}$alkyl;

—C(O)N($C_{1-6}$alkyl)$_2$;

—S(O)$_2$$C_{1-6}$alkyl optionally substituted by one or more halogens;

—S(O)$_2$$C_{2-6}$alkenyl;

—S(O)$_2$$C_{3-6}$cycloalkyl optionally substituted by one or more halogens;

—S(O)$_2$N($C_{1-6}$alkyl)$_2$; and

—S(O)$_2$-4-7 membered heterocyclyl optionally substituted by one or more substituents selected from the group consisting of OH and halogen, and $R_4$ is selected from the group consisting of H, halogen and $C_{1-6}$alkyl.

The present invention also relates to methods of treating protein kinase-mediated disease, particularly mutant EGFR-mediated disease in a subject in need thereof comprising administering to said subject a therapeutically effective amount of said compounds of Formula (I) or a pharmaceutically acceptable salt thereof.

The present invention also relates to pharmaceutically acceptable compositions comprising said compounds of Formula (I) or a pharmaceutically acceptable salt thereof, which exhibit inhibition activity against at least one mutant EGFR selectively as compared to wild type EGFR.

DETAILED DESCRIPTION OF THE INVENTION

Hereinafter, the present invention will be described in more detail.

Unless otherwise defined, all technical terms used herein have the same meaning as commonly understood by one of ordinary skill in the art to which this invention belongs. Also, although the invention has been described in conjunction with specific methods and samples, their analogs or equivalents should be within the scope of the present invention. Furthermore, the numerical values set forth herein are considered to include the meaning of "about" unless explicitly stated. All publications and other references mentioned herein are hereby incorporated by reference in their entirety.

The definition of residues used herein is described in detail. Unless otherwise indicated, each residue has the following definition and is used in the sense as commonly understood by one of ordinary skill in the art.

As used herein, the term "halo" "halogen", "halide(s)" includes fluoro, chloro, bromo and iodo.

As used herein, the "alkyl" refers to an aliphatic hydrocarbon radical, and includes both linear and branched hydrocarbon radicals. For example, $C_{1-6}$ alkyl is an aliphatic hydrocarbon having 1 to 6 carbon atoms and includes methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl. Unless otherwise defined, the alkyl refers to $C_{1-6}$ alkyl, preferably $C_{1-4}$ alkyl, more preferably $C_{1-3}$ alkyl.

As used herein, the "alkenyl" refers to an aliphatic hydrocarbon radical comprising at least one carbon-carbon double bond, and includes both linear and branched hydrocarbon radicals. The unlimited example of the "alkenyl" is vinyl, allyl, but-1-enyl or but-2-enyl.

As used herein, the "alkynyl" refers to an aliphatic hydrocarbon radical comprising at least one carbon-carbon triple bond, and includes both linear and branched hydrocarbon radicals. The unlimited example of the "alkynyl" is ethynyl, propargyl, but-1-ynyl or but-2-ynyl.

As used herein, the "haloalkyl" refers to an alkyl group substituted with one or more halogen atom, and the alkyl group is defined as above. The "halo" refers to F, Cl, Br, or I, and the term is compatibly used with the term "halogen". Unless otherwise defined, the haloalkyl refers tofluoromethyl, difluoromethyl, chloromethyl, trifluoromethyl or 2,2,2-trifluoroethyl.

As used herein, the term "alkoxy" refers to —O-alkyl or alkyl-O-group, and the alkyl group is defined as shown above. For example, it includes methoxy, ethoxy, n-propoxy, n-butoxy and t-butoxy.

As used herein, the term "hydroxy" or "hydroxyl" alone or in combination with other terms means-OH.

As used herein, the term "hydroxyalkyl" refers to any hydroxyl derivative of alkyl radical. The term "hydroxyalkyl" includes any alkyl radical having one or more hydrogen atoms replaced by a hydroxy group.

As used herein, "amino" refers to —NH$_2$.

As used herein, the term "cycloalkyl" refers to a cyclic alkyl which may be substituted or unsubstituted, and for example, the $C_{3-20}$ cycloalkyl represents a monovalent saturated hydrocarbon ring system having 3 to 20 carbon atoms. Examples of the cycloalkyl include, but are not limited to, cyclopropyl, cyclobutyl, cyclopentyl, cyclohexyl, cycloheptyl, cyclooctyl and the like. Preferably, unless otherwise defined, the cycloalkyl may be $C_{3-8}$ cycloalkyl, or $C_{3-6}$ cycloalkyl.

As used herein, the term "aryl" refers to a monovalent aromatic hydrocarbon having, for example, 6 to 20 carbon atoms ($C_{6-20}$) that is derived by the removal of one hydrogen atom from a single carbon atom of a parent aromatic ring system. The aryl may include a bicyclic radical containing an aromatic ring fused to a saturated or partially unsaturated ring. Exemplary aryl groups may include radicals derived from benzene (phenyl), substituted phenyl, biphenyl, naphthyl, toluyl, naphthalenyl, anthracenyl, indenyl, indanyl, and the like. Unless otherwise defined, the aryl refers to $C_{6-12}$ aryl, preferably $C_{6-10}$ aryl.

As used herein, the "heterocycle" refers to an aromatic, saturated or partially unsaturated mono-, bi- or poly-ring system containing the specified number of ring atoms, and include one or more heteroatoms selected from N, O, and S as a ring member, wherein the heterocyclic ring is connected to the base molecule via a ring atom, which may be C or N. Bicyclic systems may be connected via a 1,1-fusion (spiro), a 1,2-fusion (fused) or a 1, >2-fusion (bridgehead).

As used herein, the "heteroaryl" refers to a monovalent or divalent substituent derived from a monoheterocyclic or polyheterocyclic aromatic hydrocarbon having 1 to 10 carbon ring members containing one or more, preferably one to three, heteroatoms selected among N, O, and S. Examples of the heteroaryl include, but are not limited to, thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl. 1,2,4-oxadiazoly, 1,1,3,4-oxadiazolyl, 1,2,4-thiadiazolyl, 1,3,4-thiadiazolyl, triazolyl, tetrazolyl, triazinyl, indolyl, and the like. Examples of the bicyclic heteroaryl include indolyl, benzothiophenyl, benzofuranyl, benzimidazolyl, benzoxazolyl, benzisoxazolyl, benzthiazolyl, benzthiadiazolyl, quinolinyl, isoquinolinyl, furopyridinyl and similar groups thereof, but are not limited thereto. Unless otherwise defined, the heteroaryl is 4-12 membered heteroaryl 1, preferably 4-10 membered heteroaryl, more preferably 4-7 heteroaryl.

As used herein, the "heterocycloalkyl" refers to monocyclic, bicyclic, tricyclic or higher cyclic alkyl having 3 to 10 carbon ring members containing one or more, for example, one to four, heteroatoms selected among N, O, and S. In addition, the heterocycle according to the present invention may also be a fused or bridged heterocycloalkyl. Examples of non-aromatic rings include azetidinyl, oxetanyl, tetrahydrothienyl, tetrahydrofuranyl, pyrrolinyl, pyrrolidinyl, imidazolinyl, imidazolidinyl, oxazolinyl, oxazolidinyl, oxapiperazinyl, oxapiperidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyranyl, dihydropyranyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, teterahydropyrazolopyridinyl, morpholinyl, indolinyl, thiomorpholinyl, azepanyl, diazepanyl, azaadamantanyl, diazamantanyl, and the like, but are not limited thereto. Attachment of a heterocycloalkyl substituent can occur via a carbon atom or a heteroatom. A heterocycloalkyl group may be optionally substituted with one or more suitable groups via one or more aforementioned groups. Unless otherwise defined, heterocycloalkyl refers to 4-12 membered heterocycloalkyl, preferably 4-10 membered heterocycloalkyl, more preferably 4-7 heterocycloalkyl.

The present invention provides novel compounds, a pharmaceutically acceptable salt, diastereomers, enantiomers, racemates, tautomers, prodrugs, hydrates, and solvates thereof that are useful for inhibiting epidermal growth factor receptor (EGFR) and for treating diseases and disorders that are mediated by the protein kinase, for example, cell proliferative diseases and disorders such as cancer, immune diseases such as arthritis, rheumatoid arthritis or autoimmune diseases, infections, cardiovascular diseases, and neurodegenerative diseases and disorders.

The present invention also provides pharmaceutical compositions comprising at least one of the compounds of Formula (I) together with a pharmaceutically acceptable carrier, diluent or excipient therefor.

The present invention provides compositions and methods for modulating the activity of the epidermal growth factor receptor (EGFR) mutants. In one aspect, the present invention provides compounds which act as inhibitors of EGFR mutants.

In one embodiment, provided herein is a compound of Formula (I) shown below, a pharmaceutically acceptable salt, diastereomers, enantiomers, racemates, tautomers, prodrugs, hydrates, or solvates thereof:

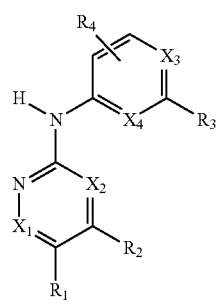

(I)

wherein $X_1$ and $X_2$ are, independently each other, —CH= or —N=, with the proviso that $X_1$ and $X_2$ cannot be —N= at the same time, $X_3$, and $X_4$ are, independently each other, —CH= or —N=, with the proviso that $X_3$ and $X_4$ cannot be —CH= at the same time, $R_1$ is -A-$(R_{1A})_m$, A is 6-10 membered heteroaryl, $R_{1A}$ is independently selected from the group consisting of

H;

OH;

halogen;

cyano;

$C_{1-6}$alkyl optionally substituted by one or more substituents selected from the group consisting of OH, halogen, $C_{1-3}$alkoxy, $C_{3-6}$cycloalkyl, —NHC$_{1-6}$alkyl, —N(C$_{1-6}$alkyl)$_2$, and 4-7 membered heterocyclyl optionally or independently substituted by one or more substituents selected from the group consisting of OH, halogen, and $C_{1-6}$alkyl;

$C_{3-6}$cycloalkyl;

$C_{1-3}$alkoxy optionally substituted by one or more substituents selected from the group consisting of OH, halogen, —N(C$_{1-6}$alkyl)$_2$, and 3-7 membered heterocyclyl optionally or independently substituted by one or more substituents selected from the group consisting of halogen and $C_{1-6}$alkyl;

—NHC1-6alkyl optionally substituted by one or more substituents selected from the group consisting of OH, halogen, —N(C$_{1-6}$alkyl)$_2$ and 3-7 membered heterocyclyl optionally substituted by one or more substituents selected from the group consisting of OH, halogen, and $C_{1-6}$alkyl;

—NHC$_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more substituents selected from the group consisting of OH, halogen, and $C_{1-6}$alkyl;

—N(C$_{1-6}$alkyl)$_2$ optionally substituted by one or more substituents selected from the group consisting of OH and halogen;

—NHC(O)C$_{1-6}$alkyl optionally substituted by one or more substituents selected from the group consisting of OH and halogen;

—NHC(O)C$_{3-6}$cycloalkyl optionally substituted by one or more substituents selected from the group consisting of OH and halogen;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, $C_{1-3}$alkoxy, $C_{1-6}$hydroxyalkyl, and $C_{1-6}$haloalkyl;

—S(O)$_2$C$_{1-6}$alkyl optionally substituted by one or more halogens;

—S(O)$_2$C$_{3-6}$cycloalkyl optionally substituted by one or more halogens;

—S(O)$_2$N(C$_{1-6}$alkyl)$_2$ optionally substituted by one or more halogens;

—S(O)$_2$-3-7 membered heterocyclyl optionally substituted by one or more substituents selected from the group consisting of OH, halogen, and $C_{1-6}$alkyl;

—C(O)OC$_{1-6}$alkyl;

—C(O)C$_{1-6}$alkyl; and

—C(O)-3-7 membered heterocyclyl optionally substituted by one or more substituents selected from the group consisting of OH, halogen, and $C_{1-6}$alkyl, m is an integer of 0 to 2, $R_2$ is —XC$_{1-6}$alkyl optionally substituted by one or more substituents selected from the group consisting of OH, halogen, and —N(C$_{1-6}$alkyl)$_2$; or —X(CH$_2$)$_n$—B—$(R_{2A})_o$, X is —NH—, —O—, bond or —C≡C—, n is an integer of 0 to 2, is an integer of 0 to 3, B is selected from the group consisting of $C_{3-8}$cycloalkyl, $C_{6-10}$aryl; 4-11 membered heterocyclyl; and 5-6 membered heteroaryl, $R_{2A}$ is independently selected from the group consisting of

H;

OH;

halogen;

NH$_2$;

$C_{1-6}$alkyl optionally substituted by one or more substituents selected from the group consisting of OH, NH$_2$, halogen, $C_{3-6}$cycloalkyl, $C_{1-3}$alkoxy, —NHC$_{1-6}$alkyl, —NHC$_{1-6}$hydroxyalkyl, —NHC$_{1-6}$haloalkyl, —NHC$_{3-6}$cycloalkyl, —N(C$_{1-6}$alkyl)$_2$, —N(C$_{1-6}$haloalkyl)$_2$, —NHC(O)C$_{1-6}$alkyl, —C(O) NHC$_{1-6}$alkyl, —C(O)N(C$_{1-6}$alkyl)$_2$ 3-7 membered heterocyclyl and 5-6 membered heteroaryl;

$C_{3-6}$cycloalkyl;

$C_{1-3}$alkoxy optionally substituted by one or more halogens;

—C(O) NHC$_{1-6}$alkyl optionally substituted by one or more substituents selected from the group consisting of OH and halogen;

—C(O)N($C_{1-6}$alkyl)$_2$ optionally substituted by one or more substituents selected from the group consisting of OH and halogen;

—NH$C_{1-6}$alkyl optionally substituted by one or more substituents selected from the group consisting of OH, halogen, —NH$C_{1-6}$alkyl, —N($C_{1-6}$alkyl)$_2$, 3-7 membered heterocyclyl optionally substituted by halogen or —N($C_{1-6}$alkyl)$_2$;

—N($C_{1-6}$alkyl)$_2$ where $C_{1-6}$alkyl is optionally substituted by one or more halogens;

—NH-4-7 membered heterocyclyl optionally substituted by $C_{1-6}$alkyl; and 4-7 membered heterocyclyl, $R_3$ is Y-Q-($R_{3A}$)$_p$, Y is —NH— or bond, Q is selected from the group consisting of acetylene; 4-7 membered heterocyclyl; $C_{6-10}$ aryl; and 5-10 membered heteroaryl, p is an integer of 0 to 2, $R_{3A}$ is independently selected from the group consisting of

H;

OH;

halogen;

$C_{1-3}$alkoxy;

$C_{1-6}$alkyl optionally substituted by one or more substituents selected from the group consisting of OH, halogen, $C_{3-6}$cycloalkyl, S(O)$_2$$C_{1-6}$alkyl, and $C_{1-3}$alkoxy;

$C_{2-6}$alkenyl;

$C_{3-6}$cycloalkyl;

4-7 membered heterocyclyl;

—C(O)$C_{1-6}$alkyl;

—C(O)N($C_{1-6}$alkyl)$_2$;

—S(O)$_2$$C_{1-6}$alkyl optionally substituted by one or more halogens;

—S(O)$_2$$C_{2-6}$alkenyl;

—S(O)$_2$$C_{3-6}$cycloalkyl optionally substituted by one or more halogens;

—S(O)$_2$N($C_{1-6}$alkyl)$_2$; and

—S(O)$_2$-4-7 membered heterocyclyl optionally substituted by one or more substituents selected from the group consisting of OH and halogen, and $R_4$ is selected from the group consisting of H, halogen and $C_{1-6}$alkyl.

In certain embodiment. $X_1$ and $X_2$ are —CH=.

In further certain embodiment, $X_3$ and $X_4$ are —N=.

In certain embodiment, A is pyridinyl, pyrimidinyl, pyridazinyl, or pyrazinyl.

In certain embodiment, $R_{1A}$ is H; OH; F; Cl; cyano; $C_{1-4}$alkyl optionally substituted by one to three substituents selected from the group consisting of OH, F, Cl, $C_{1-3}$alkoxy, $C_{3-6}$cycloalkyl, —NH$C_{1-4}$alkyl, —N($C_{1-4}$alkyl)$_2$, and 4-6 membered heterocyclyl optionally substituted by one to three substituents selected from the group consisting of OH, F, Cl and $C_{1-3}$alkyl; $C_{3-6}$cycloalkyl; $C_{1-2}$alkoxy optionally substituted by one to three F or Cl; —NH$C_{1-4}$alkyl optionally substituted by one to three substituents selected from the group consisting of OH F, Cl, —N($C_{1-6}$alkyl)$_2$ and 3-7 membered heterocyclyl optionally substituted by one to three substituents selected from the group consisting of OH, F, Cl and $C_{1-6}$alkyl; —NH$C_{3-6}$cycloalkyl optionally substituted by one to three substituents selected from the group consisting of OH, F, Cl, and $C_{1-6}$alkyl optionally substituted by OH; —NH 3-7 membered heterocyclyl optionally substituted by one to three substituents selected from the group consisting of $C_{1-6}$alkyls; —N($C_{1-6}$alkyl)$_2$ optionally substituted by one to three substituents selected from the group consisting of OH, F and Cl; —NHC(O)$C_{1-6}$alkyl optionally substituted by one to three substituents selected from the group consisting of OH, F and Cl; —NHC(O)$C_{3-6}$cycloalkyl optionally substituted by one to three substituents selected from the group consisting of OH, F and Cl; —O-4-6 membered heterocyclyl optionally or independently substituted by one or more substituents selected from the group consisting of $C_{1-6}$alkyl, $C_{1-6}$haloalkyl; 4-6 membered heterocyclyl optionally or independently substituted by one to three substituents selected from the group consisting of OH, F, Cl, $C_{1-6}$alkyl, $C_{1-3}$alkoxy, $C_{1-6}$hydroxyalkyl, and $C_{1-6}$haloalkyl; —S(O)$_2$$C_{1-6}$alkyl; —S(O)$_2$N($C_{1-6}$alkyl)$_2$; —S(O)$_2$-3-7 membered heterocyclyl optionally substituted by one to three substituents selected from the group consisting of $C_{1-6}$alkyls; —C(O)O$C_{1-6}$alkyl; —C(O)$C_{1-6}$alkyl; and —C(O)-3-7 membered heterocyclyl optionally substituted by one to three $C_{1-6}$alkyls.

In further certain embodiment, $R_{1A}$ is $C_{1-6}$alkyl optionally substituted by one or more substituents selected from the group consisting of OH, halogen, $C_{1-3}$alkoxy, $C_{3-6}$cycloalkyl, —NH$C_{1-6}$alkyl, —N($C_{1-6}$alkyl)$_2$, and 4-7 membered heterocyclyl optionally substituted by one or more substituents selected from the group consisting of OH, halogen and $C_{1-6}$alkyl.

In another further certain embodiment, $R_{1A}$ is independently selected from the group consisting of

H;

OH;

halogen;

cyano;

$C_{1-6}$alkyl optionally substituted by one or more substituents selected from the group consisting of OH, halogen, $C_{1-3}$alkoxy, —N($C_{1-6}$alkyl)$_2$, and 4-7 membered heterocyclyl optionally or independently substituted by one or more substituents selected from the group consisting of OH, halogen, and $C_{1-6}$alkyl;

$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;

—NHC 1-6alkyl optionally substituted by one or more substituents selected from the group consisting of OH, halogen, —N($C_{1-6}$alkyl)$_2$ and 3-7 membered heterocyclyl optionally substituted by one or more halogens;

—NH$C_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more $C_{1-6}$alkyls;

—N($C_{1-6}$alkyl)$_2$;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, and $C_{1-3}$alkoxy;

—S(O)$_2$$C_{1-6}$alkyl;

—S(O)$_2$N($C_{1-6}$alkyl)$_2$;

—S(O)$_2$-3-7 membered heterocyclyl optionally substituted by one or more $C_{1-6}$alkyls;

—C(O)$C_{1-6}$alkyl; and

—C(O)-3-7 membered heterocyclyl optionally substituted by one or more $C_{1-6}$alkyls.

In the above embodiments of $R_{1A}$, the 3-7 membered heterocyclyl or 4-7 membered heterocyclyl may be independently selected from the group consisting of azetidinyl, piperidinyl, piperazinyl, morpholinyl, tetrahydropyranyl, tetrahydrofuranyl, oxetanyl, 2-oxa-6-azaspiro[3.3]heptanyl, and pyrrolidinyl.

In certain embodiment, $R_2$ is —$XC_{1-6}$alkyl.

In further certain embodiment, $R_2$ is —$X(CH_2)_n$—B—$(R_{2A})_o$.

In certain embodiment, X is —NH— or bond.

In certain embodiment, B is $C_{3-6}$cycloalkyl; phenyl; 4-10 membered heterocycloalkyl having one to three heteroatoms selected from a group consisting of N, O and S; or 5-6 membered heteroaryl having one to three heteroatoms selected from a group consisting of N, O and S.

In further certain embodiment, B is $C_{3-6}$cycloalkyl.

In another further certain embodiment, B is 4-10 membered heterocycloalkyl or 5-6 membered heteroaryl having one to three heteroatoms selected from a group consisting of N and O.

In another further certain embodiment, B is $C_{3-8}$cycloalkyl, piperidinyl, or oxetanyl.

In certain embodiment, $R_{2A}$ is H; F; Cl; OH; $NH_2$; $C_{1-4}$alkyl optionally substituted by one or more substituents selected from the group consisting of OH, $NH_2$, F, Cl, $C_{3-6}$cycloalkyl, $C_{1-3}$alkoxy, —$NHC_{1-3}$alkyl, —$NHC_{1-3}$hydroxyalkyl, —$NHC_{1-3}$haloalkyl, —$NHC_{3-6}$cycloalkyl, —$N(C_{1-3}$alkyl$)_2$, —$N(C_{1-3}$haloalkyl$)_2$, —$NHC(O)C_{1-3}$alkyl, —C(O) $NHC_{1-3}$alkyl, —C(O)$N(C_{1-6}$alkyl$)_2$, 3-7 membered heterocyclyl and 5-6 membered heteroaryl having one to three heteroatoms selected from a group consisting of N, O and S; $C_{3-6}$cycloalkyl; $C_{1-3}$alkoxy optionally substituted by one to three F or Cl; —C(O) $NHC_{1-3}$alkyl optionally substituted by one to three substituents selected from the group consisting of OH, F and Cl; —C(O)$N(C_{1-3}$alkyl$)_2$ optionally substituted by one to three substituents selected from the group consisting of OH, F and Cl; —$NHC_{1-3}$alkyl optionally substituted by one to three substituents selected from the group consisting of OH, F, Cl, —$NHC_{1-3}$alkyl, —$N(C_{1-3}$alkyl$)_2$, 3-6 membered heterocyclyl one to three heteroatoms selected from a group consisting of N, O and S optionally substituted by F, Cl or —$N(C_{1-3}$alkyl$)_2$; —$N(C_{1-3}$alkyl$)_2$ where $C_{1-3}$alkyl is optionally substituted by one to three F or Cl; —NH-4-6 membered heterocyclyl one to three heteroatoms selected from a group consisting of N, O and S optionally substituted by $C_{1-3}$alkyl; or 4-7 membered heterocyclyl.

In further certain embodiment, $R_{2A}$ is OH; halogens; $C_{1-6}$alkyl optionally substituted by one or more substituents selected from the group consisting of OH, $NH_2$, halogen, $C_{3-6}$cycloalkyl, $C_{1-3}$alkoxy, —$NHC_{1-6}$alkyl, —$NHC_{1-6}$hydroxyalkyl, —$NHC_{1-6}$haloalkyl, —$NHC_{3-6}$cycloalkyl, —$N(C_{1-6}$alkyl$)_2$, —$N(C_{1-6}$haloalkyl$)_2$, —$NHC(O)C_{1-6}$alkyl, —C(O) $NHC_{1-6}$alkyl, —C(O)$N(C_{1-6}$alkyl$)_2$, 3-7 membered heterocyclyl and 5-6 membered heteroaryl having one to three heteroatoms selected from a group consisting of N, O and S; —C(O) $NHC_{1-3}$alkyl optionally substituted by one to three substituents selected from the group consisting of OH, F and Cl; —C(O)$N(C_{1-3}$alkyl$)_2$ optionally substituted by one to three substituents selected from the group consisting of OH, F and Cl; or —$NHC_{1-3}$alkyl optionally substituted by one to three substituents selected from the group consisting of OH, halogen, —$NHC_{1-3}$alkyl, —$N(C_{1-3}$alkyl$)_2$, 3-7 membered heterocyclyl one to three heteroatoms selected from a group consisting of N, O and S optionally substituted by halogen or —$N(C_{1-3}$alkyl$)_2$.

In another further certain embodiment, $R_{2A}$ is independently selected from the group consisting of

OH;

halogen;

$C_{1-6}$alkyl optionally substituted by one or more substituents selected from the group consisting of OH, halogen, and —$N(C_{1-6}$alkyl$)_2$;

—C(O)$N(C_{1-6}$alkyl$)_2$; and

—$NHC_{1-6}$alkyl optionally substituted by one or more halogens.

In certain embodiment, Y is bond.

In certain embodiment, Q is pyrazolyl, 3,4-dihydropyrano[2,3-b]pyridinyl, or piperidinyl.

In certain embodiment, $R_{3A}$ is independently selected from the group consisting of

H;

OH;

halogen;

$C_{1-3}$alkoxy;

$C_{1-6}$alkyl optionally substituted by one or more halogens;

—$S(O)_2C_{3-6}$cycloalkyl; and

—$S(O)_2N(C_{1-6}$alkyl$)_2$.

In certain embodiment, $R_4$ is H or halogen.

Representative compounds of Formula (I) are listed below:

(1) (1-(6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)-4-methylpiperidin-4-yl)methanol;

(2) $N^{6'}$-(2-(1-(Cyclopropylsulfonyl)-1H-pyrazol-4-yl)pyrimidin-4-yl)-$N^{4'}$-((1s,4s)-4-((2-fluoroethyl)amino)cyclohexyl)-5-((4-methylpiperazin-1-yl)methyl)-[2,3'-bipyridine]-4',6'-diamine;

(3) (1s,4s)-4-((6'-((2-(1-(Cyclopropylsulfonyl)-1H-pyrazol-4-yl)pyrimidin-4-yl)amino)-3-methoxy-[2,3'-bipyridin]-4'-yl)amino)-1-methylcyclohexan-1-ol;

(4) (1s,4s)-4-((6'-((2-(1-(Cyclopropylsulfonyl)-1H-pyrazol-4-yl)pyrimidin-4-yl)amino)-3-fluoro-[2,3'-bipyridin]-4'-yl)amino)-1-methylcyclohexan-1-ol;

(5) (1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)-1-methylcyclohexan-1-ol;

(6) (1s,4s)-4-((6'-((2-(1-(Cyclopropylsulfonyl)-1H-pyrazol-4-yl)pyrimidin-4-yl)amino)-5-fluoro-[2,3'-bipyridin]-4'-yl)amino)-1-methylcyclohexan-1-ol;

(7) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbonitrile;

(8) (1s,4s)-4-((6'-((2-(1-(Cyclopropylsulfonyl)-1H-pyrazol-4-yl)pyrimidin-4-yl)amino)-5-methyl-[2,3'-bipyridin]-4'-yl)amino)-1-methylcyclohexan-1-ol;

(9) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol;

(10) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)cyclohexyl)methanol;

(11) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-(hydroxymethyl)cyclohexan-1-ol;

(12) (1s,4s)-4-((6'-((2-(1-(Cyclopropylsulfonyl)-1H-pyrazol-4-yl)pyrimidin-4-yl)amino)-4-methyl-[2,3'-bipyridin]-4'-yl)amino)-1-methylcyclohexan-1-ol;

(13) (1s,4s)-4-((6'-((2-(1-(Cyclopropylsulfonyl)-1H-pyrazol-4-yl)pyrimidin-4-yl)amino)-3-fluoro-4-(hydroxymethyl)-[2,3'-bipyridin]-4'-yl)amino)-1-methylcyclohexan-1-ol;

(14) (1s,4s)-4-((6'-((2-(1-(cyclopropylsulfonyl)-1H-pyrazol-4-yl)pyrimidin-4-yl)amino)-6-(trifluoromethyl)-[2,3'-bipyridin]-4'-yl)amino)-1-methylcyclohexan-1-ol;

(15) (1s,4s)-4-((6'-((2-(1-(Cyclopropylsulfonyl)-1H-pyrazol-4-yl)pyrimidin-4-yl)amino)-6-methyl-[2,3'-bipyridin]-4'-yl)amino)-1-methylcyclohexan-1-ol;

(16) (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol;

(17) (1s,4s)-4-((6'-((2-(1-(Cyclopropylsulfonyl)-1H-pyrazol-4-yl)pyrimidin-4-yl)amino)-5-(trifluoromethyl)-[2,3'-bipyridin]-4'-yl)amino)-1-methylcyclohexan-1-ol;

(18) 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-6-yl)ethan-1-one;

(19) (1s,4s)-4-((6'-((2-(1-(Cyclopropylsulfonyl)-1H-pyrazol-4-yl)pyrimidin-4-yl)amino)-6-fluoro-4-methyl-[2,3'-bipyridin]-4'-yl)amino)-1-methylcyclohexan-1-ol;

(20) (1s,4s)-4-((6'-((2-(1-(Cyclopropylsulfonyl)-1H-pyrazol-4-yl)pyrimidin-4-yl)amino)-4-(trifluoromethyl)-[2,3'-bipyridin]-4'-yl)amino)-1-methylcyclohexan-1-ol;

(21) (6'-((2-(1-(Cyclopropylsulfonyl)-1H-pyrazol-4-yl)pyrimidin-4-yl)amino)-4'-(((1s,4s)-4-((2-fluoroethyl)amino)cyclohexyl)amino)-[2,3'-bipyridin]-5-yl)methanol;

(22) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methanol;

(23) (1s,4s)-4-((6'-((2-(1-(Cyclopropylsulfonyl)-1H-pyrazol-4-yl)pyrimidin-4-yl)amino)-6-(1-hydroxyethyl)-[2,3'-bipyridin]-4'-yl)amino)-1-methylcyclohexan-1-ol;

(24) 2-((1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol;

(25) 2-((1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol;

(26) 2-((1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)cyclohexyl)propan-2-ol;

(27) (1s,4s)-4-((6'-((2-(1-(Cyclopropylsulfonyl)-1H-pyrazol-4-yl)pyrimidin-4-yl)amino)-6-(hydroxymethyl)-[2,3'-bipyridin]-4'-yl)amino)-1-methylcyclohexan-1-ol;

(28) (1s,4s)-4-((6'-((2-(1-(Cyclopropylsulfonyl)-1H-pyrazol-4-yl)pyrimidin-4-yl)amino)-6-((4-methylpiperazin-1-yl)methyl)-[2,3'-bipyridin]-4'-yl)amino)-1-methylcyclohexan-1-ol;

(29) (1s,4s)-4-((6'-((2-(1-(Cyclopropylsulfonyl)-1H-pyrazol-4-yl)pyrimidin-4-yl)amino)-6-(morpholinomethyl)-[2,3'-bipyridin]-4'-yl)amino)-1-methylcyclohexan-1-ol;

(30) (1s,4s)-4-((6'-((2-(1-(Cyclopropylsulfonyl)-1H-pyrazol-4-yl)pyrimidin-4-yl)amino)-6-((dimethylamino)methyl)-[2,3'-bipyridin]-4'-yl)amino)-1-methylcyclohexan-1-ol;

(31) (1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)-1-methylcyclohexan-1-ol;

(32) (1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)-1-methylcyclohexan-1-ol;

(33) (1s,4s)-4-((6'-((2-(1-(Cyclopropylsulfonyl)-1H-pyrazol-4-yl)pyrimidin-4-yl)amino)-5-((4,4-difluoropiperidin-1-yl)methyl)-[2,3'-bipyridin]-4'-yl)amino)-1-methylcyclohexan-1-ol;

(34) (1s,4s)-4-((6'-((2-(1-(Cyclopropylsulfonyl)-1H-pyrazol-4-yl)pyrimidin-4-yl)amino)-5-((4-isopropylpiperazin-1-yl)methyl)-[2,3'-bipyridin]-4'-yl)amino)-1-methylcyclohexan-1-ol;

(35) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-methylcyclohexan-1-ol;

(36) $N^{6'}$-(2-(1-(Cyclopropylsulfonyl)-1H-pyrazol-4-yl)pyrimidin-4-yl)-$N^{4'}$-((1s,4s)-4-((2-fluoroethyl)amino)cyclohexyl)-[2,3'-bipyridine]-4',6-diamine;

(37) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-(hydroxy methyl)cyclohexan-1-ol;

(38) (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol;

(39) (1s,4s)-4-((2-((2-(1-(Cyclopropylsulfonyl)-1H-pyrazol-4-yl)pyrimidin-4-yl)amino)-5-(5-(dimethylamino)pyrimidin-2-yl)pyridin-4-yl)amino)-1-methylcyclohexan-1-ol;

(40) (1s,4s)-4-((6'-((2-(1-(Cyclopropylsulfonyl)-1H-pyrazol-4-yl)pyrimidin-4-yl)amino)-5-(dimethylamino)-[2,3'-bipyridin]-4'-yl)amino)-1-methylcyclohexan-1-ol;

(41) (1s,4s)-4-((2-((2-(1-(Cyclopropylsulfonyl)-1H-pyrazol-4-yl)pyrimidin-4-yl)amino)-5-(4-(dimethylamino)pyrimidin-2-yl)pyridin-4-yl)amino)-1-methylcyclohexan-1-ol;

(42) (1s,4s)-4-((2-((2-(1-(Cyclopropylsulfonyl)-1H-pyrazol-4-yl)pyrimidin-4-yl)amino)-5-(pyridazin-3-yl)pyridin-4-yl)amino)-1-methylcyclohexan-1-ol;

(43) (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol;

(44) (1s,4s)-4-((2-((2-(1-(Cyclopropylsulfonyl)-1H-pyrazol-4-yl)pyrimidin-4-yl)amino)-5-(5-morpholinopyrazin-2-yl)pyridin-4-yl)amino)-1-methylcyclohexan-1-ol;

(45) 2-((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)propan-2-ol;

(46) (1s,4s)-4-((2-((2-(1-(Cyclopropylsulfonyl)-1H-pyrazol-4-yl)pyrimidin-4-yl)amino)-5-(6-(4-methylpiperazin-1-yl)pyridazin-3-yl)pyridin-4-yl)amino)-1-methylcyclohexan-1-ol;

(47) (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol;

(48) (1s,4s)-4-((6'-((2-(1-(Cyclopropylsulfonyl)-1H-pyrazol-4-yl)pyrimidin-4-yl)amino)-4-morpholino-[2,3'-bipyridin]-4'-yl)amino)-1-methylcyclohexan-1-ol;

(49) 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl) piperidin-4-ol;

(50) (1s,4s)-4-((2-((2-(1-(Cyclopropylsulfonyl)-1H-pyrazol-4-yl)pyrimidin-4-yl)amino)-5-(5,6-dimethylpyridazin-3-yl)pyridin-4-yl)amino)-1-methylcyclohexan-1-ol;

(51) (1s,4s)-4-((2-((2-(1-(Cyclopropylsulfonyl)-1H-pyrazol-4-yl)pyrimidin-4-yl)amino)-5-(6-(trifluoromethyl)pyridazin-3-yl)pyridin-4-yl)amino)-1-methylcyclohexan-1-ol;

(52) (1s,4s)-4-((2-((2-(1-(Cyclopropylsulfonyl)-1H-pyrazol-4-yl)pyrimidin-4-yl)amino)-5-(6-methylpyridazin-3-yl)pyridin-4-yl)amino)-1-methylcyclohexan-1-ol;

(53) (1s,4s)-4-((2-((2-(1-(Cyclopropylsulfonyl)-1H-pyrazol-4-yl)pyrimidin-4-yl)amino)-5-(6-methoxypyridazin-3-yl)pyridin-4-yl)amino)-1-methylcyclohexan-1-ol;

(54) (1s,4s)-4-((6'-((2-(1-(Cyclopropylsulfonyl)-1H-pyrazol-4-yl)pyrimidin-4-yl)amino)-5-(piperidin-1-yl)-[2,3'-bipyridin]-4'-yl)amino)-1-methylcyclohexan-1-ol;

(55) (1s,4s)-4-((6'-((2-(1-(Cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol;

(56) (1s,4s)-4-((2-((2-(1-(Cyclopropylsulfonyl)-1H-pyrazol-4-yl)pyrimidin-4-yl)amino)-5-(5-methoxypyrazin-2-yl)pyridin-4-yl)amino)-1-methylcyclohexan-1-ol;

(57) ((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)methanol;

(58) (1s,4s)-4-((6'-((2-(1-(Cyclopropylsulfonyl)-1H-pyrazol-4-yl)pyrimidin-4-yl)amino)-4-(4-methylpiperazin-1-yl)-[2,3'-bipyridin]-4'-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(5-methylpyrazin-2-yl)pyridin-4-yl)amino)-1-methylcyclohexan-1-ol;

(60) (1s,4s)-4-((2-((2-(1-(Cyclopropylsulfonyl)-1H-pyrazol-4-yl)pyrimidin-4-yl)amino)-5-(5-(hydroxymethyl)pyrazin-2-yl)pyridin-4-yl)amino)-1-methylcyclohexan-1-ol;

(61) (1s,4s)-4-((6'-((2-(1-(Cyclopropylsulfonyl)-1H-pyrazol-4-yl)pyrimidin-4-yl)amino)-4-(morpholinomethyl)-[2,3'-bipyridin]-4'-yl)amino)-1-methylcyclohexan-1-ol;

(62) (1s,4s)-4-((2-((2-(1-(Cyclopropylsulfonyl)-1H-pyrazol-4-yl)pyrimidin-4-yl)amino)-5-(5-((4-methylpiperazin-1-yl)methyl) pyrazin-2-yl)pyridin-4-yl)amino)-1-methylcyclohexan-1-ol;

(63) (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-ol;

(64) (1s,4s)-4-((6'-((2-(1-(Cyclopropylsulfonyl)-1H-pyrazol-4-yl)pyrimidin-4-yl)amino)-4-((dimethylamino)methyl)-[2,3'-bipyridin]-4'-yl)amino)-1-methylcyclohexan-1-ol;

(65) (1s,4s)-4-((2-((2-(1-(Cyclopropylsulfonyl)-1H-pyrazol-4-yl)pyrimidin-4-yl)amino)-5-(5-((dimethylamino)methyl) pyrazin-2-yl)pyridin-4-yl)amino)-1-methylcyclohexan-1-ol;

(66) (1s,4s)-4-((2-((2-(1-(Cyclopropylsulfonyl)-1H-pyrazol-4-yl)pyrimidin-4-yl)amino)-5-(6-(3,3-difluoroazetidin-1-yl)pyridazin-3-yl)pyridin-4-yl)amino)-1-methylcyclohexan-1-ol;

(67) (1s,4s)-4-((5-(6-(2-Oxa-6-azaspiro[3.3]heptan-6-yl)pyridazin-3-yl)-2-((2-(1-(cyclopropylsulfonyl)-1H-pyrazol-4-yl)pyrimidin-4-yl)amino)pyridin-4-yl)amino)-1-methylcyclohexan-1-ol;

(68) (1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)-1-methylcyclohexan-1-ol;

(69) ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol;

(70) ((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)methanol;

(71) 2-((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)propan-2-ol;

(72) 2-((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)propan-2-ol;

(73) $N^2$-(2-(1-(Cyclopropylsulfonyl)-1H-pyrazol-4-yl)pyrimidin-4-yl)-5-(6-(4,4-difluoropiperidin-1-yl)pyridazin-3-yl)-$N^4$-((1s,4s)-4-((dimethylamino)methyl)cyclohexyl)pyridine-2,4-diamine;

(74) $N^2$-(2-(1-(Cyclopropylsulfonyl)-1H-pyrazol-4-yl)pyrimidin-4-yl)-5-(5-(4,4-difluoropiperidin-1-yl) pyrazin-2-yl)-$N^4$-((1s,4s)-4-((dimethylamino)methyl)cyclohexyl)pyridine-2,4-diamine;

(75) (1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)-1-methylcyclohexan-1-ol;

(76) (1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)-1-methylcyclohexan-1-ol;

(77) ((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)methanol;

(78) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)propan-2-ol;

(79) $N^{6'}$-(2-(1-(Cyclopropylsulfonyl)-1H-pyrazol-4-yl)pyrimidin-4-yl)-4-(difluoromethyl)-$N^{4'}$-((1s,4s)-4-((dimethylamino)methyl)cyclohexyl)-[2,3'-bipyridine]-4',6'-diamine;

(80) (1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)-1-methylcyclohexan-1-ol;

(81) ((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)methanol;

(82) 2-((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)propan-2-ol;

(83) (1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)-1-methylcyclohexan-1-ol;

(84) 2-((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)propan-2-ol;

(85) ((1s,4s)-4-((6'-((2-(1-(cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)methanol;

(86) (1s,4s)-4-((2-((2-(1-(Cyclopropylsulfonyl)-1H-pyrazol-4-yl)pyrimidin-4-yl)amino)-5-(6-(2-hydroxypropan-2-yl)pyridazin-3-yl)pyridin-4-yl)amino)-1-methylcyclohexan-1-ol;

(87) 2-(6-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyridazin-3-yl)propan-2-ol;

(88) 2-(6-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyridazin-3-yl)propan-2-ol;

(89) 2-(6-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)pyridazin-3-yl)propan-2-ol;

(90) (1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)-1-methylcyclohexan-1-ol;

(91) ((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)methanol;

(92) 2-((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)propan-2-ol;

(93) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(3-methoxyazetidin-1-yl)-[2,3'-bipyridine]-4',6'-diamine;

(94) 2-((1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol;

(95) 2-((1r,4r)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol;

(96) 2-((1r,4r)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol;

(97) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol;

(98) 1-((6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)methyl)piperidin-4-ol;

(99) 1-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methyl) piperidin-4-ol;

(100) ((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)methanol;

(101) $N^{6'}$-(2-(1-(Cyclopropylsulfonyl)-1H-pyrazol-4-yl)pyrimidin-4-yl)-4-(4,4-difluoropiperidin-1-yl)-$N^{4'}$-((1s,4s)-4-((dimethylamino)methyl)cyclohexyl)-[2,3'-bipyridine]-4',6'-diamine;

(102) (1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)-1-methylcyclohexan-1-ol;

(103) 2-((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)propan-2-ol;

(104) (1s,4s)-4-((6'-((2-(1-(Cyclopropylsulfonyl)-1H-pyrazol-4-yl)pyrimidin-4-yl)amino)-5-fluoro-4-(2-hydroxypropan-2-yl)-[2,3'-bipyridin]-4'-yl)amino)-1-methylcyclohexan-1-ol;

(105) 2-(6'-((2-(1-(Cyclopropylsulfonyl)-1H-pyrazol-4-yl)pyrimidin-4-yl)amino)-5-fluoro-4'-(((1s,4s)-4-(hydroxymethyl)cyclohexyl)amino)-[2,3'-bipyridin]-4-yl)propan-2-ol;

(106) 2-(6'-((2-(1-(Cyclopropylsulfonyl)-1H-pyrazol-4-yl)pyrimidin-4-yl)amino)-5-fluoro-4'-(((1s,4s)-4-(2-hydroxypropan-2-yl)cyclohexyl)amino)-[2,3'-bipyridin]-4-yl)propan-2-ol;

(107) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-5-fluoro-[2,3'-bipyridin]-4-yl)

(108) (1s,4s)-4-((6'-((2-(1-(Cyclopropylsulfonyl)-1H-pyrazol-4-yl)pyrimidin-4-yl)amino)-4-(2-hydroxypropan-2-yl)-[2,3'-bipyridin]-4'-yl)amino)-1-methylcyclohexan-1-ol;

(109) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-4-yl)propan-2-ol;

(110) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-4-yl)propan-2-ol;

(111) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-4-yl)propan-2-ol;

(112) (1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)-1-methylcyclohexan-1-ol;

(113) ((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)methanol;

(114) 2-((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)propan-2-ol;

(115) (1s,4s)-4-((2-((2-(1-(Cyclopropylsulfonyl)-1H-pyrazol-4-yl)pyrimidin-4-yl)amino)-5-(5-(2-(dimethylamino)ethoxy) pyrazin-2-yl)pyridin-4-yl)amino)-1-methylcyclohexan-1-ol;

(116) ((1s,4s)-4-((2-((2-(1-(Cyclopropylsulfonyl)-1H-pyrazol-4-yl)pyrimidin-4-yl)amino)-5-(5-(2-(dimethylamino)ethoxy) pyrazin-2-yl)pyridin-4-yl)amino)cyclohexyl)methanol;

(117) 2-((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)propan-2-ol;

(118) (1s,4s)-4-((2-((2-(1-(Cyclopropylsulfonyl)-1H-pyrazol-4-yl)pyrimidin-4-yl)amino)-5-(5-(2-hydroxypropan-2-yl) pyrazin-2-yl)pyridin-4-yl)amino)-1-methylcyclohexan-1-ol;

(119) 2-(5-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl) pyrazin-2-yl)propan-2-ol;

(120) 2-(5-(6-((2-(1-(Cyclopropylsulfonyl)-1H-pyrazol-4-yl)pyrimidin-4-yl)amino)-4-(121) 2-(5-(6-((2-(1-(Cyclopropylsulfonyl)-1H-pyrazol-4-yl)pyrimidin-4-yl)amino)-4-(isopropylamino)pyridin-3-yl) pyrazin-2-yl)propan-2-ol;

(122) $N^2$-(2-(1-(Cyclopropylsulfonyl)-1H-pyrazol-4-yl)pyrimidin-4-yl)-5-(5-(2-(dimethylamino) ethoxy) pyrazin-2-yl)-$N^4$-isopropylpyridine-2,4-diamine;

(123) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-morpholino-[2,3'-bipyridine]-4',6'-diamine;

(124) N⁶'-(2-(1-(Cyclopropylsulfonyl)-1H-pyrazol-4-yl)pyrimidin-4-yl)-N⁴'-isopropyl-5-morpholino-[2,3'-bipyridine]-4',6'-diamine;

(125) N⁶'-(2-(1-(Cyclopropylsulfonyl)-1H-pyrazol-4-yl)pyrimidin-4-yl)-N⁴'-isopropyl-5-(morpholinomethyl)-[2,3'-bipyridine]-4',6'-diamine;

(126) N⁶'-(2-(1-(Cyclopropylsulfonyl)-1H-pyrazol-4-yl)pyrimidin-4-yl)-N⁴'-((1s,4s)-4-fluorocyclohexyl)-5-(morpholinomethyl)-[2,3'-bipyridine]-4',6'-diamine;

(127) N²-(2-(1-(Cyclopropylsulfonyl)-1H-pyrazol-4-yl)pyrimidin-4-yl)-5-(5-(difluoromethoxy) pyrazin-2-yl)-N⁴-isopropylpyridine-2,4-diamine;

(128) (1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)-1-methylcyclohexan-1-ol;

(129) ((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)methanol;

(130) 2-((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)propan-2-ol;

(131) N²-(2-(1-(Cyclopropylsulfonyl)-1H-pyrazol-4-yl)pyrimidin-4-yl)-5-(5-(difluoromethoxy) pyrazin-2-yl)-N⁴-((1s,4s)-4-((dimethylamino)methyl)cyclohexyl)pyridine-2,4-diamine;

(132) N⁶'-(2-(1-(Cyclopropylsulfonyl)-1H-pyrazol-4-yl)pyrimidin-4-yl)-N⁴'-((1s,4s)-4-fluorocyclohexyl)-5-((1-methylpiperidin-4-yl)oxy)-[2,3'-bipyridine]-4',6'-diamine;

(133) N⁶'-(2-(1-(2,2-Difluoroethyl)-1H-pyrazol-4-yl)pyrimidin-4-yl)-N⁴'-((1s,4s)-4-fluorocyclohexyl)-5-((1-methylpiperidin-4-yl)oxy)-[2,3'-bipyridine]-4',6'-diamine;

(134) (1s,4s)-4-((2-((2-(1-(Cyclopropylsulfonyl)-1H-pyrazol-4-yl)pyrimidin-4-yl)amino)-5-(5-(trifluoromethyl) pyrazin-2-yl)pyridin-4-yl)amino)-1-methylcyclohexan-1-ol;

(135) N⁶'-(2-(1-(2,2-Difluoroethyl)-1H-pyrazol-4-yl)pyrimidin-4-yl)-N⁴'-((1s,4s)-4-fluorocyclohexyl)-5-((4-methylpiperazin-1-yl)methyl)-[2,3'-bipyridine]-4',6'-diamine;

(136) N⁶'-(2-(1-(2,2-difluoroethyl)-1H-pyrazol-4-yl)pyrimidin-4-yl)-N⁴'-((1s,4s)-4-fluorocyclohexyl)-5-(morpholinomethyl)-[2,3'-bipyridine]-4',6'-diamine;

(137) N⁶'-(2-(1-(2,2-Difluoroethyl)-1H-pyrazol-4-yl)pyrimidin-4-yl)-N⁴'-((1s,4s)-4-fluorocyclohexyl)-5-morpholino-[2,3'-bipyridine]-4',6'-diamine;

(138) N⁴'-(3,3-Difluorocyclopentyl)-N⁶'-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine;

(139) N⁴'-(3,3-Difluorocyclobutyl)-N⁶'-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine;

(140) N⁶'-(2-(1-(Cyclopropylsulfonyl)-1H-pyrazol-4-yl)pyrimidin-4-yl)-N⁴'-(3,3-difluorocyclobutyl)-5-((1-methylpiperidin-4-yl)oxy)-[2,3'-bipyridine]-4',6'-diamine;

(141) N⁶'-(2-(1-(2,2-Difluoroethyl)-1H-pyrazol-4-yl)pyrimidin-4-yl)-N⁴'-(3-fluorocyclohexyl)-5-((1-methylpiperidin-4-yl)oxy)-[2,3'-bipyridine]-4',6'-diamine;

(142) (1s,4s)-4-((6'-((2-(3,4-Dihydro-2H-pyrano[2,3-b]pyridin-6-yl)pyrimidin-4-yl)amino)-5-((1-methylpiperidin-4-yl)oxy)-[2,3'-bipyridin]-4'-yl)amino)-1-methylcyclohexan-1-ol;

(143) N⁶'-(2-(1-(Cyclopropylsulfonyl)-1H-pyrazol-4-yl)pyrimidin-4-yl)-N⁴'-(3,3-difluorocyclopentyl)-5-((1-methylpiperidin-4-yl)oxy)-[2,3'-bipyridine]-4',6'-diamine;

(144) N²-(2-(1-(Cyclopropylsulfonyl)-1H-pyrazol-4-yl)pyrimidin-4-yl)-N⁴-((1s,4s)-4-fluorocyclohexyl)-5-(5-((1-methylpiperidin-4-yl)oxy) pyrazin-2-yl)pyridine-2,4-diamine;

(145) (1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)-1-methylcyclohexan-1-ol;

(146) ((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)methanol;

(147) 2-((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)propan-2-ol;

(148) (1s,4s)-4-((2-((2-(1-(Cyclopropylsulfonyl)-1H-pyrazol-4-yl)pyrimidin-4-yl)amino)-5-(5-((tetrahydro-2H-pyran-4-yl)oxy) pyrazin-2-yl)pyridin-4-yl)amino)-1-methylcyclohexan-1-ol;

(149) (1s,4s)-4-((2-((2-(1-(Cyclopropylsulfonyl)-1H-pyrazol-4-yl)pyrimidin-4-yl)amino)-5-(5-((tetrahydrofuran-3-yl)oxy) pyrazin-2-yl)pyridin-4-yl)amino)-1-methylcyclohexan-1-ol;

(150) (1s,4s)-4-((2-((2-(1-(Cyclopropylsulfonyl)-1H-pyrazol-4-yl)pyrimidin-4-yl)amino)-5-(5-(oxetan-3-yloxy) pyrazin-2-yl)pyridin-4-yl)amino)-1-methylcyclohexan-1-ol;

(151) N²-(2-(1-(Cyclopropylsulfonyl)-1H-pyrazol-4-yl)pyrimidin-4-yl)-N⁴-((1s,4s)-4-fluorocyclohexyl)-5-(5-((tetrahydro-2H-pyran-4-yl)oxy) pyrazin-2-yl)pyridine-2,4-diamine;

(152) N²-(2-(1-(Cyclopropylsulfonyl)-1H-pyrazol-4-yl)pyrimidin-4-yl)-N⁴-((1s,4s)-4-fluorocyclohexyl)-5-(5-((tetrahydrofuran-3-yl)oxy) pyrazin-2-yl)pyridine-2,4-diamine;

(153) (1s,4s)-4-((2-((2-(1-(Cyclopropylsulfonyl)-1H-pyrazol-4-yl)pyrimidin-4-yl)amino)-5-(5-((1-(2-fluoroethyl)piperidin-4-yl)oxy) pyrazin-2-yl)pyridin-4-yl)amino)-1-methylcyclohexan-1-ol;

(154) (1s,4s)-4-((2-((2-(1-(Cyclopropylsulfonyl)-1H-pyrazol-4-yl)pyrimidin-4-yl)amino)-5-(5-((4-fluoro-1-methylpiperidin-4-yl) methoxy) pyrazin-2-yl)pyridin-4-yl)amino)-1-methylcyclohexan-1-ol;

(155) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-ol;

(156) (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol;

(157) N⁶'-(2-(1-(Cyclopropylsulfonyl)-1H-pyrazol-4-yl)pyrimidin-4-yl)-N⁴'-((1s,4s)-4-((2-fluoroethyl)amino)cyclohexyl)-5-(methylsulfonyl)-[2,3'-bipyridine]-4',6'-diamine;

(158) ((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)methanol;

(159) N⁶'-(2-(1-(Cyclopropylsulfonyl)-1H-pyrazol-4-yl)pyrimidin-4-yl)-N⁴'-((1s,4s)-4-((dimethylamino)methyl)cyclohexyl)-5-(methylsulfonyl)-[2,3'-bipyridine]-4',6'-diamine;

(160) 2-((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)propan-2-ol;

(161) (3-(((6'-((2-(1-(Cyclopropylsulfonyl)-1H-pyrazol-4-yl)pyrimidin-4-yl)amino)-6-fluoro-[2,3'-bipyridin]-4'-yl)amino)methyl) oxetan-3-yl)methanol;

(162) (4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-fluorocyclohexyl)methanol;

(163) 2-((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)propan-2-ol;

(164) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-N,N-dimethyl-[2,3'-bipyridine]-5-sulfonamide;

(165) 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-N,N-dimethyl-[2,3'-bipyridine]-5-sulfonamide;

(166) 6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-N,N-dimethyl-[2,3'-bipyridine]-5-sulfonamide;

(167) (1s,4s)-4-((6'-((2-(1-(Cyclopropylsulfonyl)-1H-pyrazol-4-yl)pyrimidin-4-yl)amino)-4-(dimethylamino)-[2,3'-bipyridin]-4'-yl)amino)-1-methylcyclohexan-1-ol;

(168) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol;

(169) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)propan-2-ol;

(170) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)propan-2-ol;

(171) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)propan-2-ol;

(172) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-N,N-dimethylcyclohexane-1-carboxamide;

(173) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol;

(174) 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)propan-2-ol;

(175) 2-(6'-((2-(1-(Cyclopropylsulfonyl)-1H-pyrazol-4-yl)pyrimidin-4-yl)amino)-4'-((4,4-difluorocyclohexyl)amino)-[2,3'-bipyridin]-5-yl)propan-2-ol;

(176) 2-(6'-((2-(1-(Cyclopropylsulfonyl)-1H-pyrazol-4-yl)pyrimidin-4-yl)amino)-4'-((1-(2-fluoroethyl) piperidin-4-yl)amino)-[2,3'-bipyridin]-5-yl)propan-2-ol;

(177) 2-(6'-((2-(1-(Cyclopropylsulfonyl)-1H-pyrazol-4-yl)pyrimidin-4-yl)amino)-4'-((1-(2-fluoroethyl) piperidin-3-yl)amino)-[2,3'-bipyridin]-5-yl)propan-2-ol;

(178) 2-(6'-((2-(1-(Cyclopropylsulfonyl)-1H-pyrazol-4-yl)pyrimidin-4-yl)amino)-4'-((1-(2,2-difluoroethyl) piperidin-4-yl)amino)-[2,3'-bipyridin]-5-yl)propan-2-ol;

(179) (1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)-1-methylcyclohexan-1-ol;

(180) 2-((1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)cyclohexyl)propan-2-ol;

(181) (1s,4s)-4-((6'-((2-(1-(Cyclopropylsulfonyl)-1H-pyrazol-4-yl)pyrimidin-4-yl)amino)-6-fluoro-5-(trifluoromethyl)-[2,3'-bipyridin]-4'-yl)amino)-1-methylcyclohexan-1-ol;

(182) (1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)-1-methylcyclohexan-1-ol;

(183) ((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)methanol;

(184) 2-((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)propan-2-ol;

(185) (1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)-1-methylcyclohexan-1-ol;

(186) 2-((1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)cyclohexyl)propan-2-ol;

(187) 2-((1s,4s)-4-((6'-((2-(1-(Cyclopropylsulfonyl)-1H-pyrazol-4-yl)pyrimidin-4-yl)amino)-5-((4-methylpiperidin-1-yl) sulfonyl)-[2,3'-bipyridin]-4'-yl)amino)cyclohexyl)propan-2-ol;

(188) (1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)-1-methylcyclohexan-1-ol;

(189) ((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)methanol;

(190) 2-((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)propan-2-ol;

(191) (1s,4s)-4-((4-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrimidin-2-yl)amino)-1-methylcyclohexan-1-ol;

(192) ((1s,4s)-4-((4-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyrimidin-2-yl)amino)cyclohexyl)methanol;

(193) 2-((1s,4s)-4-((4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyrimidin-2-yl)amino)cyclohexyl)propan-2-ol;

(194) (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol;

(195) ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol;

(196) 2-((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)propan-2-ol;

(197) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(trifluoromethoxy)-[2,3'-bipyridine]-4',6'-diamine;

(198) (1s,4s)-4-((6'-((2-(1-(Cyclopropylsulfonyl)-1H-pyrazol-4-yl)pyrimidin-4-yl)amino)-4-(methylsulfonyl)-[2,3'-bipyridin]-4'-yl)amino)-1-methylcyclohexan-1-ol;

(199) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(4-methylpiperazin-1-yl)methanone;

(200) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(morpholino)methanone;

(201) (6'-((2-(1-(Cyclopropylsulfonyl)-1H-pyrazol-4-yl)pyrimidin-4-yl)amino)-4'-(((1s,4s)-4-(2-hydroxy propan-2-yl)cyclohexyl)amino)-[2,3'-bipyridin]-5-yl)(morpholino)methanone;

(202) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(4-methylpiperazin-1-yl)methanone;

(203) (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(4-methylpiperazin-1-yl)methanone;

(204) (6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)(4-methylpiperazin-1-yl)methanone;

(205) (1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)-1-methylcyclohexan-1-ol;

(206) 2-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)oxy)ethan-1-ol;

(207) 2-((1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)cyclohexyl)propan-2-ol;

(208) (1s,4s)-4-((6'-((2-(1-(Cyclopropylsulfonyl)-1H-pyrazol-4-yl)pyrimidin-4-yl)amino)-5-(2-(dimethylamino)ethoxy)-[2,3'-bipyridin]-4'-yl)amino)-1-methylcyclohexan-1-ol;

(209) ((1s,4s)-4-((6'-((2-(1-(Cyclopropylsulfonyl)-1H-pyrazol-4-yl)pyrimidin-4-yl)amino)-5-(2-(dimethylamino)ethoxy)-[2,3'-bipyridin]-4'-yl)amino)cyclohexyl)methanol;

(210) 2-((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)propan-2-ol;

(211) (1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)-1-methylcyclohexan-1-ol;

(212) ((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)methanol;

(213) 2-((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)propan-2-ol;

(214) ((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)methanol;

(215) 2-((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)propan-2-ol;

(216) N$^{6'}$-(2-(1-(Cyclopropylsulfonyl)-1H-pyrazol-4-yl)pyrimidin-4-yl)-N$^{4'}$-(3,3-difluorocyclobutyl)-N$^{4'}$-((1s,4s)-4-((dimethylamino)methyl)cyclohexyl)-[2,3'-bipyridine]-4,4',6'-triamine;

(217) 2-((1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)cyclohexyl)propan-2-ol;

(218) (1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)-1-methylcyclohexan-1-ol;

(219) ((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol;

(220) 2-((1s,4s)-4-((6'-((2-(1-(Cyclopropylsulfonyl)-1H-pyrazol-4-yl)pyrimidin-4-(221) N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2,2,2-trifluoroethyl)-[2,3'-bipyridine]-4',6'-diamine;

(222) ((1S,3S)-3-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol;

(223) 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)ethan-1-ol;

(224) (1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)-1-methylcyclohexan-1-ol;

(225) 2-((1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)cyclohexyl)propan-2-ol;

(226) (1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)-1-methylcyclohexan-1-ol;

(227) 1-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2,2-trifluoroethan-1-ol;

(228) 1-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-2,2,2-trifluoroethan-1-ol;

(229) 2-((1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)cyclohexyl)propan-2-ol;

(230) (1s,4s)-4-((6'-((2-(1-(Cyclopropylsulfonyl)-1H-pyrazol-4-yl)pyrimidin-4-yl)amino)-5-(1,1,1-trifluoro-2-hydroxypropan-2-yl)-[2,3'-bipyridin]-4'-yl)amino)-1-methylcyclohexan-1-ol;

(231) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-1,1,1-trifluoropropan-2-ol;

(232) 2-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-1,1,1-trifluoropropan-2-ol;

(((1s,4s)-4-(2-hydroxypropan-2-yl)cyclohexyl)amino)-[2,3'-bipyridin]-5-yl)-1,1,1-trifluoropropan-2-ol;

(234) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-1,1,1-trifluoropropan-2-ol;

(235) ((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)methanol;

(236) 2-((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)propan-2-ol;

(237) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2-fluoropropan-2-yl)-[2,3'-bipyridine]-4',6'-diamine;

(238) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-(2-fluoropropan-2-yl)-[2,3'-bipyridine]-4',6'-diamine;

(239) $N^{6'}$-(2-(1-(Cyclopropylsulfonyl)-1H-pyrazol-4-yl)pyrimidin-4-yl)-$N^{4'}$-(4-fluorocyclohexyl)-5-(2-fluoropropan-2-yl)-[2,3'-bipyridine]-4',6'-diamine;

(240) $N^{6'}$-(2-(1-(Cyclopropylsulfonyl)-1H-pyrazol-4-yl)pyrimidin-4-yl)-$N^{4'}$-(4,4-difluorocyclohexyl)-5-(2-fluoropropan-2-yl)-[2,3'-bipyridine]-4',6'-diamine;

(241) ((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)methanol;

(242) 2-((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)propan-2-ol;

(243) $N^{6'}$-(2-(1-(Cyclopropylsulfonyl)-1H-pyrazol-4-yl)pyrimidin-4-yl)-5-(1,1-difluoroethyl)-$N^{4'}$-((1s,4s)-4-((dimethylamino)methyl)cyclohexyl)-[2,3'-bipyridine]-4',6'-diamine;

(244) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2-difluoroethan-1-ol;

(245) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-2,2-difluoroethan-1-ol;

(246) ((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)methanol;

(247) 2-((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)propan-2-ol;

(248) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-6-(2,2,2-trifluoroethyl)-[2,3'-bipyridine]-4',6'-diamine;

(249) $N^{6'}$-(2-(1-(Cyclopropylsulfonyl)-1H-pyrazol-4-yl)pyrimidin-4-yl)-$N^{4'}$-isopropyl-5-((1-methylpiperidin-4-yl)oxy)-[2,3'-bipyridine]-4',6'-diamine;

(250) (1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(251) ((1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(252) 2-((1r,4r)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol;

(253) ((1S,3S)-3-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(254) $N^{6'}$-(2-(1-(Cyclopropylsulfonyl)-1H-pyrazol-4-yl)pyrimidin-4-yl)-$N^{4'}$-(4-fluorocyclohexyl)-5-((1-methylpiperidin-4-yl)oxy)-[2,3'-bipyridine]-4',6'-diamine;

(255) $N^{6'}$-(2-(1-(Cyclopropylsulfonyl)-1H-pyrazol-4-yl)pyrimidin-4-yl)-$N^{4'}$-(4,4-difluorocyclohexyl)-5-((1-methylpiperidin-4-yl)oxy)-[2,3'-bipyridine]-4',6'-diamine;

(256) $N^{6'}$-(2-(1-(Cyclopropylsulfonyl)-1H-pyrazol-4-yl)pyrimidin-4-yl)-$N^{4'}$-(1-(2-fluoroethyl) piperidin-4-yl)-5-((1-methylpiperidin-4-yl)oxy)-[2,3'-bipyridine]-4',6'-diamine;

(257) $N^{6'}$-(2-(1-(Cyclopropylsulfonyl)-1H-pyrazol-4-yl)pyrimidin-4-yl)-$N^{4'}$-(1-(2-fluoroethyl) piperidin-3-yl)-5-((1-methylpiperidin-4-yl)oxy)-[2,3'-bipyridine]-4',6'-diamine;

(258) $N^{6'}$-(2-(1-(Cyclopropylsulfonyl)-1H-pyrazol-4-yl)pyrimidin-4-yl)-$N^{4'}$-(1-(2,2-difluoroethyl) piperidin-4-yl)-5-((1-methylpiperidin-4-yl)oxy)-[2,3'-bipyridine]-4',6'-diamine;

(259) (4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-fluorocyclohexyl)methanol;

(260) (1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)-1-methylcyclohexan-1-ol;

(261) ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)cyclohexyl)methanol;

(262) $N^{6'}$-(2-(1-(Cyclopropylsulfonyl)-1H-pyrazol-4-yl)pyrimidin-4-yl)-$N^{4'}$-((1s,4s)-4-((dimethylaminio)methyl)cyclohexyl)-5-(2,2,2-trifluoro-1-methyloxyethyl)-[2,3'-bipyridine]-4',6'-diamine;

(263) (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol;

(264) 5-(2-(Azetidin-1-yl) ethoxy)-$N^{6'}$-(2-(1-(cyclopropylsulfonyl)-1H-pyrazol-4-yl)pyrimidin-4-yl)-$N^{4'}$-((1s,4s)-4-fluorocyclohexyl)-[2,3'-bipyridine]-4',6'-diamine;

(265) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)-1,1,1-trifluoropropan-2-ol;

(266) 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)-1,1,1-trifluoropropan-2-ol;

(267) $N^2$-(2-(1-(Cyclopropylsulfonyl)-1H-pyrazol-4-yl)pyrimidin-4-yl)-5-(6-(4,4-difluoropiperidin-1-yl)pyridazin-3-yl)-$N^4$-(4-fluorocyclohexyl)pyridine-2,4-diamine;

(268) $N^2$-(2-(1-(Cyclopropylsulfonyl)-1H-pyrazol-4-yl)pyrimidin-4-yl)-$N^4$-(4,4-difluorocyclohexyl)-5-(6-(4,4-difluoropiperidin-1-yl)pyridazin-3-yl)pyridine-2,4-diamine;

(269) (1s,4s)-4-((2-((2-(1-(Cyclopropylsulfonyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol;

(270) N²-(2-(1-(Cyclopropylsulfonyl)-1H-pyrazol-4-yl)pyrimidin-4-yl)-N⁴-((1s,4s)-4-fluorocyclohexyl)-5-(6-((1-methylpiperidin-4-yl)oxy)pyridazin-3-yl)pyridine-2,4-diamine;

(271) (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol;

(272) ((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)methanol;

(273) N⁶'-(2-(1-(Cyclopropylsulfonyl)-1H-pyrazol-4-yl)pyrimidin-4-yl)-6-fluoro-N⁴'-((1s,4s)-4-((2-fluoroethyl)amino)cyclohexyl)-[2,3'-bipyridine]-4',6'-diamine;

(274) N⁶'-(2-(1-(Cyclopropylsulfonyl)-1H-pyrazol-4-yl)pyrimidin-4-yl)-N⁴'-((1s,4s)-4-((dimethylamino)methyl)cyclohexyl)-6-fluoro-[2,3'-bipyridine]-4',6'-diamine;

(275) N⁶'-(2-(1-(Cyclopropylsulfonyl)-1H-pyrazol-4-yl)pyrimidin-4-yl)-N⁴'-((1s,4s)-4-((2,2-difluoroethyl)amino)cyclohexyl)-6-fluoro-[2,3'-bipyridine]-4',6'-diamine;

(276) (1s,4s)-4-((6'-((2-(1-(Cyclopropylsulfonyl)-1H-pyrazol-4-yl)pyrimidin-4-yl)amino)-4-((2-(dimethylamino)ethyl)amino)-[2,3'-bipyridin]-4'-yl)amino)-1-methylcyclohexan-1-ol;

(277) (1s,4s)-4-((6'-((2-(1-(Cyclopropylsulfonyl)-1H-pyrazol-4-yl)pyrimidin-4-yl)amino)-4-((3,3,3-trifluoropropyl)amino)-[2,3'-bipyridin]-4'-yl)amino)-1-methylcyclohexan-1-ol;

(278) (1s,4s)-4-((6'-((2-(1-(Cyclopropylsulfonyl)-1H-pyrazol-4-yl)pyrimidin-4-yl)amino)-4-((1-methylpiperidin-4-yl)amino)-[2,3'-bipyridin]-4'-yl)amino)-1-methylcyclohexan-1-ol;

(279) (1s,4s)-4-((6'-((2-(1-(Cyclopropylsulfonyl)-1H-pyrazol-4-yl)pyrimidin-4-yl)amino)-4 ((2-morpholinoethyl)amino)-[2,3'-bipyridin]-4'-yl)amino)-1-methylcyclohexan-1-ol;

(280) (1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)-1-methylcyclohexan-1-ol;

(281) (1s,4s)-4-((6'-((2-(1-(Cyclopropylsulfonyl)-1H-pyrazol-4-yl)pyrimidin-4-yl)amino)-4-((2-(3-fluoroazetidin-1-yl)ethyl)amino)-[2,3'-bipyridin]-4'-yl)amino)-1-methylcyclohexan-1-ol;

(282) (1s,4s)-4-((6'-((2-(1-(Cyclopropylsulfonyl)-1H-pyrazol-4-yl)pyrimidin-4-yl)amino)-4-((3-hydroxypropyl)amino)-[2,3'-bipyridin]-4'-yl)amino)-1-methylcyclohexan-1-ol;

(283) (1s,4s)-4-((6'-((2-(1-(Cyclopropylsulfonyl)-1H-pyrazol-4-yl)pyrimidin-4-yl)amino)-4-((3-hydroxycyclobutyl)amino)-[2,3'-bipyridin]-4'-yl)amino)-1-methylcyclohexan-1-ol;

(284) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(morpholino)methanone;

(285) (1s,4s)-4-((6'-((2-(1-(Cyclopropylsulfonyl)-1H-pyrazol-4-yl)pyrimidin-4-yl)amino)-6-((2-hydroxyethyl)amino)-[2,3'-bipyridin]-4'-yl)amino)-1-methylcyclohexan-1-ol;

(286) (1s,4s)-4-((6'-((2-(1-(Cyclopropylsulfonyl)-1H-pyrazol-4-yl)pyrimidin-4-yl)amino)-6-((1-methylpiperidin-4-yl)oxy)-[2,3'-bipyridin]-4'-yl)amino)-1-methylcyclohexan-1-ol;

(287) (1s,4s)-4-((6'-((2-(1-(Cyclopropylsulfonyl)-1H-pyrazol-4-yl)pyrimidin-4-yl)amino)-4-(2-(dimethylamino)ethoxy)-[2,3'-bipyridin]-4'-yl)amino)-1-methylcyclohexan-1-ol;

(288) 1-((6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-4'-yl)methyl) azetidin-3-ol;

(289) (1s,4s)-4-((6'-((2-(1-(Cyclopropylsulfonyl)-1H-pyrazol-4-yl)pyrimidin-4-yl)amino)-5-((1-methylazetidin-3-yl)oxy)-[2,3'-bipyridin]-4'-yl)amino)-1-methylcyclohexan-1-ol;

(290) (1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)-1-methylcyclohexan-1-ol;

(291) (1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)-1-methylcyclohexan-1-ol;

(292) (1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)-1-methylcyclohexan-1-ol;

(293) (1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)-1-methylcyclohexan-1-ol;

(294) 1-(6'-((2-(1-(Cyclopropylsulfonyl)-1H-pyrazol-4-yl)pyrimidin-4-yl)amino)-4'-(isopropylamino)-[2,3'-bipyridin]-5-yl)-2,2,2-trifluoroethan-1-ol;

(295) 2-(6'-((2-(1-(Cyclopropylsulfonyl)-1H-pyrazol-4-yl)pyrimidin-4-yl)amino)-4'-(isopropylamino)-[2,3'-bipyridin]-5-yl)-1,1,1-trifluoropropan-2-ol;

(296) 4-(4-((4'-(((1s,4s)-4-Hydroxy-4-methylcyclohexyl)amino)-5-(2,2,2-trifluoroethyl)-[2,3'-bipyridin]-6'-yl)amino)pyrimidin-2-yl)-N,N-dimethyl-1H-pyrazole-1-sulfonamide;

(297) 4-(4-((4'-(((1s,4s)-4-Hydroxy-4-methylcyclohexyl)amino)-5-(2,2,2-trifluoro-1-hydroxyethyl)-[2,3'-bipyridin]-6'-yl)amino)pyrimidin-2-yl)-N,N-dimethyl-1H-pyrazole-1-sulfonamide;

(298) 4-(4-((4'-(((1s,4s)-4-Hydroxy-4-methylcyclohexyl)amino)-5-(1,1,1-trifluoro-2-hydroxypropan-2-yl)-[2,3'-bipyridin]-6'-yl)amino)pyrimidin-2-yl)-N,N-dimethyl-1H-pyrazole-1-sulfonamide;

(299) (1s,4s)-4-((6'-((2-(1-(Cyclopropylsulfonyl)-1H-pyrazol-4-yl)-5-fluoropyrimidin-4-yl)amino)-5-(2,2,2-trifluoroethyl)-[2,3'-bipyridin]-4'-yl)amino)-1-methylcyclohexan-1-ol;

(300) (1s,4s)-4-((6'-((2-(1-(Cyclopropylsulfonyl)-1H-pyrazol-4-yl)-5-fluoropyrimidin-4-yl)amino)-5-((1-methylpiperidin-4-yl)oxy)-[2,3'-bipyridin]-4'-yl)amino)-1-methylcyclohexan-1-ol;

(301) 4-(4-((4'-(((1s,4s)-4-Hydroxy-4-methylcyclohexyl)amino)-5-((1-methylpiperidin-4-yl)oxy)-[2,3'-bipyridin]-6'-yl)amino)pyrimidin-2-yl)-N,N-dimethyl-1H-pyrazole-1-sulfonamide;

(302) (1s,4s)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(303) (1s,4s)-1-Methyl-4-((6'-((2-(3-methyl-1-(2,2,2-trifluoroethyl)-1H-pyrazol-4-yl)pyrimidin-4-yl)amino)-5-((1-methylpiperidin-4-yl)oxy)-[2,3'-bipyridin]-4'-yl)amino)cyclohexan-1-ol;

(304) (1s,4s)-1-Methyl-4-((5-((1-methylpiperidin-4-yl)oxy)-6'-((2-(1-(2,2,2-trifluoroethyl)-1H-pyrazol-4-yl)pyrimidin-4-yl)amino)-[2,3'-bipyridin]-4'-yl)amino)cyclohexan-1-ol;

(305) 2-((1r,4r)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol;

(306) ((1S,3S)-3-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(307) N⁴'-((1s,4s)-4-fluorocyclohexyl)-5-((1-methylpiperidin-4-yl)oxy)-N⁶'-(2-(1-(2,2,2-trifluoroethyl)-1H-pyrazol-4-yl)pyrimidin-4-yl)-[2,3'-bipyridine]-4',6'-diamine;

(308) N⁶'-(2-(1-(2,2-Difluoroethyl)-1H-pyrazol-4-yl)pyrimidin-4-yl)-N⁴'-(4-fluorocyclohexyl)-5-((1-methylpiperidin-4-yl)oxy)-[2,3'-bipyridine]-4',6'-diamine;

(309) N⁶'-(2-(1-(Cyclopropylsulfonyl)-1H-pyrazol-4-yl)-5-fluoropyrimidin-4-yl)-N⁴'-(4-fluorocyclohexyl)-5-((1-methylpiperidin-4-yl)oxy)-[2,3'-bipyridine]-4',6'-diamine;

(310) (1s,4s)-4-((6-Fluoro-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(311) (1s,4s)-4-((6'-((2-(1-(Cyclopropylsulfonyl)-1H-pyrazol-4-yl)-5-fluoropyrimidin-4-yl)amino)-6-fluoro-[2,3'-bipyridin]-4'-yl)amino)-1-methylcyclohexan-1-ol;

(312) (1s,4s)-4-((5-(3,3-Difluoroazetidin-1-yl)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(313) (1s,4s)-4-((6'-((2-(1-(Cyclopropylsulfonyl)-1H-pyrazol-4-yl)-5-fluoropyrimidin-4-yl)amino)-5-(3,3-difluoroazetidin-1-yl)-[2,3'-bipyridin]-4'-yl)amino)-1-methylcyclohexan-1-ol;

(314) 2-(6'-((2-(1-(Cyclopropylsulfonyl)-1H-pyrazol-4-yl)-5-fluoropyrimidin-4-yl)amino)-4'-(((1s,4s)-4-fluorocyclohexyl)amino)-[2,3'-bipyridin]-5-yl)propan-2-ol;

(315) (1s,4s)-4-((2-((2-(1-(2,2-Difluoroethyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol;

(316) (1s,4s)-4-((5-(2-(Azetidin-1-yl) ethoxy)-6'-((2-(1-(2,2-difluoroethyl)-1H-pyrazol-4-yl)pyrimidin-4-yl)amino)-[2,3'-bipyridin]-4'-yl)amino)-1-methylcyclohexan-1-ol;

(317) (1s,4s)-4-((5-(2-(Azetidin-1-yl) ethoxy)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(318) (1s,4s)-4-((5-(2-(Azetidin-1-yl) ethoxy)-6'-((2-(1-(2,2-difluoroethyl)-3,5-dimethyl-1H-pyrazol-4-yl)pyrimidin-4-yl)amino)-[2,3'-bipyridin]-4'-yl)amino)-1-methylcyclohexan-1-ol;

(319) (1s,4s)-4-((5-(2-(Azetidin-1-yl) ethoxy)-6'-((2-(1-(2,2,3,3,3-tetrafluoropropyl)-1H-pyrazol-4-yl)pyrimidin-4-yl)amino)-[2,3'-bipyridin]-4'-yl)amino)-1-methylcyclohexan-1-ol;

(320) 3,3-Difluoro-1-(5-fluoro-4-((4'-(((1s,4s)-4-hydroxy-4-methylcyclohexyl)amino)-5-((1-methylpiperidin-4-yl)oxy)-[2,3'-bipyridin]-6'-yl)amino)pyrimidin-2-yl) piperidin-4-ol;

(321) (1s,4s)-4-((6'-((5-Fluoro-2-((3R,4S)-3-fluoro-4-methoxypiperidin-1-yl)pyrimidin-4-yl)amino)-5-((1-methylpiperidin-4-yl)oxy)-[2,3'-bipyridin]-4'-yl)amino)-1-methylcyclohexan-1-ol;

(322) (1s,4s)-4-((6'-((2-(1-(Cyclopropylsulfonyl)-1H-pyrazol-4-yl)pyrimidin-4-yl)amino)-5-((1-(2-fluoroethyl) piperidin-4-yl)oxy)-[2,3'-bipyridin]-4'-yl)amino)-1-methylcyclohexan-1-ol;

(323) N⁶'-(2-(1-(Cyclopropylsulfonyl)-1H-pyrazol-4-yl)pyrimidin-4-yl)-N⁴'-((1s,4s)-4-fluorocyclohexyl)-5-((1-(2-fluoroethyl) piperidin-4-yl)oxy)-[2,3'-bipyridine]-4',6'-diamine;

(324) N⁶'-(2-(1-(2,2-Difluoroethyl)-1H-pyrazol-4-yl)pyrimidin-4-yl)-N⁴'-((1s,4s)-4-fluorocyclohexyl)-5-((1-(2-fluoroethyl) piperidin-4-yl)oxy)-[2,3'-bipyridine]-4',6'-diamine;

(325) (1s,4s)-4-((2-((2-(1-(Cyclopropylsulfonyl)-1H-pyrazol-4-yl)pyrimidin-4-yl)amino)-5-(6-((1-(2-fluoroethyl) piperidin-4-yl)oxy)pyridazin-3-yl)pyridin-4-yl)amino)-1-methylcyclohexan-1-ol;

(326) (1s,4s)-4-((2-((2-(1-(Cyclopropylsulfonyl)-1H-pyrazol-4-yl)pyrimidin-4-yl)amino)-5-(3-methoxypyrazin-2-yl)pyridin-4-yl)amino)-1-methylcyclohexan-1-ol;

(327) (1s,4s)-4-((2-((2-(1-(Cyclopropylsulfonyl)-1H-pyrazol-4-yl)pyrimidin-4-yl)amino)-5-(3-fluoropyrazin-2-yl)pyridin-4-yl)amino)-1-methylcyclohexan-1-ol;

(328) (1s,4s)-4-((6'-((2-(1-(Cyclopropylsulfonyl)-1H-pyrazol-4-yl)pyrimidin-4-yl)amino)-5-fluoro-3-methoxy-[2,3'-bipyridin]-4'-yl)amino)-1-methylcyclohexan-1-ol;

(329) (1s,4s)-4-((6'-((2-(1-(Cyclopropylsulfonyl)-1H-pyrazol-4-yl)pyrimidin-4-yl)amino)-6-fluoro-3-methoxy-[2,3'-bipyridin]-4'-yl)amino)-1-methylcyclohexan-1-ol;

(330) (1s,4s)-4-((6'-((2-(1-(Cyclopropylsulfonyl)-1H-pyrazol-4-yl)pyrimidin-4-yl)amino)-3-(difluoromethoxy)-[2,3'-bipyridin]-4'-yl)amino)-1-methylcyclohexan-1-ol;

(331) (1s,4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol;

(332) (1s,4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol;

(333) (1s,4s)-4-((6'-((2-(1-(Cyclopropylsulfonyl)-1H-pyrazol-4-yl)pyrimidin-4-yl)amino)-3-(2,2,2-trifluoroethoxy)-[2,3'-bipyridin]-4'-yl)amino)-1-methylcyclohexan-1-ol;

(334) (1s,4s)-4-((6'-((2-(1-(Cyclopropylsulfonyl)-1H-pyrazol-4-yl)pyrimidin-4-yl)amino)-3-(2,2-difluoroethoxy)-[2,3'-bipyridin]-4'-yl)amino)-1-methylcyclohexan-1-ol;

(335) (1s,4s)-4-((6'-((2-(1-(Cyclopropylsulfonyl)-1H-pyrazol-4-yl)pyrimidin-4-yl)amino)-4-fluoro-3-methoxy-[2,3'-bipyridin]-4'-yl)amino)-1-methylcyclohexan-1-ol;

(336) (1s,4s)-4-((6'-((2-(1-(2,2-Difluoroethyl)-1H-pyrazol-4-yl)pyrimidin-4-yl)amino)-4-fluoro-3-methoxy-[2,3'-bipyridin]-4'-yl)amino)-1-methylcyclohexan-1-ol; and (337) (1s,4s)-4-((6'-((2-(1-(2,2-Difluoroethyl)-1H-pyrazol-4-yl)pyrimidin-4-yl)amino)-3-methoxy-5-((1-(2,2,2-trifluoroethyl) piperidin-4-yl)oxy)-[2,3'-bipyridin]-4'-yl)amino)-1-methylcyclohexan-1-ol.

Further representative compounds of Formula (I) are listed below:

(2) N⁶'-(2-(1-(Cyclopropylsulfonyl)-1H-pyrazol-4-yl)pyrimidin-4-yl)-N⁴'-((1s,4s)-4-((2-fluoroethyl)amino)cyclohexyl)-5-((4-methylpiperazin-1-yl)methyl)-[2,3'-bipyridine]-4',6'-diamine;

(4) (1s,4s)-4-((6'-((2-(1-(Cyclopropylsulfonyl)-1H-pyrazol-4-yl)pyrimidin-4-yl)amino)-3-fluoro-[2,3'-bipyridin]-4'-yl)amino)-1-methylcyclohexan-1-ol;

(5) (1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)-1-methylcyclohexan-1-ol;

(6) (1s,4s)-4-((6'-((2-(1-(Cyclopropylsulfonyl)-1H-pyrazol-4-yl)pyrimidin-4-yl)amino)-5-fluoro-[2,3'-bipyridin]-4'-yl)amino)-1-methylcyclohexan-1-ol;

(7) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbonitrile;

(8) (1s,4s)-4-((6'-((2-(1-(Cyclopropylsulfonyl)-1H-pyrazol-4-yl)pyrimidin-4-yl)amino)-5-methyl-[2,3'-bipyridin]-4'-yl)amino)-1-methylcyclohexan-1-ol;

(9) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol;

(10) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)cyclohexyl)methanol;

(12) (1s,4s)-4-((6'-((2-(1-(Cyclopropylsulfonyl)-1H-pyrazol-4-yl)pyrimidin-4-yl)amino)-4-methyl-[2,3'-bipyridin]-4'-yl)amino)-1-methylcyclohexan-1-ol;

(15) (1s,4s)-4-((6'-((2-(1-(Cyclopropylsulfonyl)-1H-pyrazol-4-yl)pyrimidin-4-yl)amino)-6-methyl-[2,3'-bipyridin]-4'-yl)amino)-1-methylcyclohexan-1-ol;

(16) (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol;

(17) (1s,4s)-4-((6'-((2-(1-(Cyclopropylsulfonyl)-1H-pyrazol-4-yl)pyrimidin-4-yl)amino)-5-(trifluoromethyl)-[2,3'-bipyridin]-4'-yl)amino)-1-methylcyclohexan-1-ol;

(19) (1s,4s)-4-((6'-((2-(1-(Cyclopropylsulfonyl)-1H-pyrazol-4-yl)pyrimidin-4-yl)amino)-6-fluoro-4-methyl-[2,3'-bipyridin]-4'-yl)amino)-1-methylcyclohexan-1-ol;

(21) (6'-((2-(1-(Cyclopropylsulfonyl)-1H-pyrazol-4-yl)pyrimidin-4-yl)amino)-4'-(((1s,4s)-4-((2-fluoroethyl)amino)cyclohexyl)amino)-[2,3'-bipyridin]-5-yl)methanol;

(22) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methanol;

(23) (1s,4s)-4-((6'-((2-(1-(Cyclopropylsulfonyl)-1H-pyrazol-4-yl)pyrimidin-4-yl)amino)-6-(1-hydroxyethyl)-[2,3'-bipyridin]-4'-yl)amino)-1-methylcyclohexan-1-ol;

(24) 2-((1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol;

(25) 2-((1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol;

(26) 2-((1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)cyclohexyl)propan-2-ol;

(27) (1s,4s)-4-((6'-((2-(1-(Cyclopropylsulfonyl)-1H-pyrazol-4-yl)pyrimidin-4-yl)amino)-6-(hydroxymethyl)-[2,3'-bipyridin]-4'-yl)amino)-1-methylcyclohexan-1-ol;

(28) (1s,4s)-4-((6'-((2-(1-(Cyclopropylsulfonyl)-1H-pyrazol-4-yl)pyrimidin-4-yl)amino)-6-((4-methylpiperazin-1-yl)methyl)-[2,3'-bipyridin]-4'-yl)amino)-1-methylcyclohexan-1-ol;

(29) (1s,4s)-4-((6'-((2-(1-(Cyclopropylsulfonyl)-1H-pyrazol-4-yl)pyrimidin-4-yl)amino)-6-(morpholinomethyl)-[2,3'-bipyridin]-4'-yl)amino)-1-methylcyclohexan-1-ol;

(30) (1s,4s)-4-((6'-((2-(1-(Cyclopropylsulfonyl)-1H-pyrazol-4-yl)pyrimidin-4-yl)amino)-6-((dimethylamino)methyl)-[2,3'-bipyridin]-4'-yl)amino)-1-methylcyclohexan-1-ol;

(31) (1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)-1-methylcyclohexan-1-ol;

(32) (1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)-1-methylcyclohexan-1-ol;

(33) (1s,4s)-4-((6'-((2-(1-(Cyclopropylsulfonyl)-1H-pyrazol-4-yl)pyrimidin-4-yl)amino)-5-((4,4-difluoropiperidin-1-yl)methyl)-[2,3'-bipyridin]-4'-yl)amino)-1-methylcyclohexan-1-ol;

(34) (1s,4s)-4-((6'-((2-(1-(Cyclopropylsulfonyl)-1H-pyrazol-4-yl)pyrimidin-4-yl)amino)-5-((4-isopropylpiperazin-1-yl)methyl)-[2,3'-bipyridin]-4'-yl)amino)-1-methylcyclohexan-1-ol;

(35) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-methylcyclohexan-1-ol;

(36) $N^{6'}$-(2-(1-(Cyclopropylsulfonyl)-1H-pyrazol-4-yl)pyrimidin-4-yl)-$N^{4'}$-((1s,4s)-4-((2-fluoroethyl)amino)cyclohexyl)-[2,3'-bipyridine]-4',6'-diamine;

(37) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-(hydroxymethyl)cyclohexan-1-ol;

(38) (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol;

(39) (1s,4s)-4-((2-((2-(1-(Cyclopropylsulfonyl)-1H-pyrazol-4-yl)pyrimidin-4-yl)amino)-5-(5-(dimethylamino)pyrimidin-2-yl)pyridin-4-yl)amino)-1-methylcyclohexan-1-ol;

(40) (1s,4s)-4-((6'-((2-(1-(Cyclopropylsulfonyl)-1H-pyrazol-4-yl)pyrimidin-4-yl)amino)-5-(dimethylamino)-[2,3'-bipyridin]-4'-yl)amino)-1-methylcyclohexan-1-ol;

(42) (1s,4s)-4-((2-((2-(1-(Cyclopropylsulfonyl)-1H-pyrazol-4-yl)pyrimidin-4-yl)amino)-5-(pyridazin-3-yl)pyridin-4-yl)amino)-1-methylcyclohexan-1-ol;

(43) (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol;

(44) (1s,4s)-4-((2-((2-(1-(Cyclopropylsulfonyl)-1H-pyrazol-4-yl)pyrimidin-4-yl)amino)-5-(5-morpholinopyrazin-2-yl)pyridin-4-yl)amino)-1-methylcyclohexan-1-ol;

(45) 2-((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)propan-2-ol;

(46) (1s,4s)-4-((2-((2-(1-(Cyclopropylsulfonyl)-1H-pyrazol-4-yl)pyrimidin-4-yl)amino)-5-(6-(4-methylpiperazin-1-yl)pyridazin-3-yl)pyridin-4-yl)amino)-1-methylcyclohexan-1-ol;

(47) (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol;

(49) 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl) piperidin-4-ol;

(50) (1s,4s)-4-((2-((2-(1-(Cyclopropylsulfonyl)-1H-pyrazol-4-yl)pyrimidin-4-yl)amino)-5-(5,6-dimethylpyridazin-3-yl)pyridin-4-yl)amino)-1-methylcyclohexan-1-ol;

(51) (1s,4s)-4-((2-((2-(1-(Cyclopropylsulfonyl)-1H-pyrazol-4-yl)pyrimidin-4-yl)amino)-5-(6-(trifluoromethyl)pyridazin-3-yl)pyridin-4-yl)amino)-1-methylcyclohexan-1-ol;

(52) (1s,4s)-4-((2-((2-(1-(Cyclopropylsulfonyl)-1H-pyrazol-4-yl)pyrimidin-4-yl)amino)-5-(6-methylpyridazin-3-yl)pyridin-4-yl)amino)-1-methylcyclohexan-1-ol;

(53) (1s,4s)-4-((2-((2-(1-(Cyclopropylsulfonyl)-1H-pyrazol-4-yl)pyrimidin-4-yl)amino)-5-(6-methoxypyridazin-3-yl)pyridin-4-yl)amino)-1-methylcyclohexan-1-ol;

(54) (1s,4s)-4-((6'-((2-(1-(Cyclopropylsulfonyl)-1H-pyrazol-4-yl)pyrimidin-4-yl)amino)-5-(piperidin-1-yl)-[2,3'-bipyridin]-4'-yl)amino)-1-methylcyclohexan-1-ol;

(55) (1s,4s)-4-((6'-((2-(1-(Cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol;

(56) (1s,4s)-4-((2-((2-(1-(Cyclopropylsulfonyl)-1H-pyrazol-4-yl)pyrimidin-4-yl)amino)-5-(5-methoxypyrazin-2-yl)pyridin-4-yl)amino)-1-methylcyclohexan-1-ol;

(57) ((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)methanol;

(59) (1s,4s)-4-((2-((2-(1-(Cyclopropylsulfonyl)-1H-pyrazol-4-yl)pyrimidin-4-yl)amino)-5-(5-methylpyrazin-2-yl)pyridin-4-yl)amino)-1-methylcyclohexan-1-ol;

(60) (1s,4s)-4-((2-((2-(1-(Cyclopropylsulfonyl)-1H-pyrazol-4-yl)pyrimidin-4-yl)amino)-5-(5-(hydroxy methyl)pyrazin-2-yl)pyridin-4-yl)amino)-1-methylcyclohexan-1-ol;

(61) (1s,4s)-4-((6'-((2-(1-(Cyclopropylsulfonyl)-1H-pyrazol-4-yl)pyrimidin-4-yl)amino)-4-(morpholinomethyl)-[2,3'-bipyridin]-4'-yl)amino)-1-methylcyclohexan-1-ol;

(62) (1s,4s)-4-((2-((2-(1-(Cyclopropylsulfonyl)-1H-pyrazol-4-yl)pyrimidin-4-yl)amino)-5-((4-methylpiperazin-1-yl)methyl) pyrazin-2-yl)pyridin-4-yl)amino)-1-methylcyclohexan-1-ol;

(63) (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-ol;

(64) (1s,4s)-4-((6'-((2-(1-(Cyclopropylsulfonyl)-1H-pyrazol-4-yl)pyrimidin-4-yl)amino)-4-((dimethylamino)methyl)-[2,3'-bipyridin]-4'-yl)amino)-1-methylcyclohexan-1-ol;

(65) (1s,4s)-4-((2-((2-(1-(Cyclopropylsulfonyl)-1H-pyrazol-4-yl)pyrimidin-4-yl)amino)-5-(5-((dimethylamino)methyl) pyrazin-2-yl)pyridin-4-yl)amino)-1-methylcyclohexan-1-ol;

(66) (1s,4s)-4-((2-((2-(1-(Cyclopropylsulfonyl)-1H-pyrazol-4-yl)pyrimidin-4-yl)amino)-5-(6-(3,3-difluoroazetidin-1-yl)pyridazin-3-yl)pyridin-4-yl)amino)-1-methylcyclohexan-1-ol;

(68) (1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)-1-methylcyclohexan-1-ol;

(69) ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol;

(70) ((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)methanol;

(76) (1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)-1-methylcyclohexan-1-ol;

(77) ((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)methanol;

(78) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)propan-2-ol;

(79) $N^{6'}$-(2-(1-(Cyclopropylsulfonyl)-1H-pyrazol-4-yl)pyrimidin-4-yl)-4-(difluoromethyl)-$N^{4'}$-((1s,4s)-4-((dimethylamino)methyl)cyclohexyl)-[2,3'-bipyridine]-4',6'-diamine;

(80) (1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)-1-methylcyclohexan-1-ol;

(81) ((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)methanol;

(83) (1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)-1-methylcyclohexan-1-ol;

(84) 2-((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)propan-2-ol;

(85) ((1s,4s)-4-((6'-((2-(1-(cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)methanol;

(86) (1s,4s)-4-((2-((2-(1-(Cyclopropylsulfonyl)-1H-pyrazol-4-yl)pyrimidin-4-yl)amino)-5-(6-(2-hydroxypropan-2-yl)pyridazin-3-yl)pyridin-4-yl)amino)-1-methylcyclohexan-1-ol;

(87) 2-(6-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyridazin-3-yl)propan-2-ol;

(88) 2-(6-(6-((2-(1-(Cyclopropylsulfonyl)-1H-pyrazol-4-yl)pyrimidin-4-yl)amino)-4-(((1s,4s)-4-(2-hydroxy propan-2-yl)cyclohexyl)amino)pyridin-3-yl)pyridazin-3-yl)propan-2-ol;

(89) 2-(6-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)pyridazin-3-yl)propan-2-ol;

(90) (1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)-1-methylcyclohexan-1-ol;

(91) ((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)methanol;

(92) 2-((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)propan-2-ol;

(93) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(3-methoxyazetidin-1-yl)-[2,3'-bipyridine]-4',6'-diamine;

(94) 2-((1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol;

(97) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol;

(98) 1-((6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)methyl)piperidin-4-ol;

(99) 1-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methyl) piperidin-4-ol;

(102) (1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)-1-methylcyclohexan-1-ol;

(104) (1s,4s)-4-((6'-((2-(1-(Cyclopropylsulfonyl)-1H-pyrazol-4-yl)pyrimidin-4-yl)amino)-5-fluoro-4-(2-hydroxypropan-2-yl)-[2,3'-bipyridin]-4'-yl)amino)-1-methylcyclohexan-1-ol;

(105) 2-(6'-((2-(1-(Cyclopropylsulfonyl)-1H-pyrazol-4-yl)pyrimidin-4-yl)amino)-5-fluoro-4'-(((1s,4s)-4-(hydroxymethyl)cyclohexyl)amino)-[2,3'-bipyridin]-4-yl)propan-2-ol;

(107) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-5-fluoro-[2,3'-bipyridin]-4-

(108) (1s,4s)-4-((6'-((2-(1-(Cyclopropylsulfonyl)-1H-pyrazol-4-yl)pyrimidin-4-yl)amino)-4-(2-hydroxypropan-2-yl)-[2,3'-bipyridin]-4'-yl)amino)-1-methylcyclohexan-1-ol;

(109) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-4-yl)propan-2-ol;

(110) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-4-yl)propan-2-ol;

(111) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-4-yl)propan-2-ol;

(112) (1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)-1-methylcyclohexan-1-ol;

(113) ((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)methanol;

(114) 2-((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)propan-2-ol;

(115) (1s,4s)-4-((2-((2-(1-(Cyclopropylsulfonyl)-1H-pyrazol-4-yl)pyrimidin-4-yl)amino)-5-(5-(2-(dimethylamino)ethoxy) pyrazin-2-yl)pyridin-4-yl)amino)-1-methylcyclohexan-1-ol;

(116) ((1s,4s)-4-((2-((2-(1-(Cyclopropylsulfonyl)-1H-pyrazol-4-yl)pyrimidin-4-yl)amino)-5-(5-(2-(dimethylamino)ethoxy) pyrazin-2-yl)pyridin-4-yl)amino)cyclohexyl)methanol;

(117) 2-((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)propan-2-ol;

(118) (1s,4s)-4-((2-((2-(1-(Cyclopropylsulfonyl)-1H-pyrazol-4-yl)pyrimidin-4-yl)amino)-5-(5-(2-hydroxypropan-2-yl) pyrazin-2-yl)pyridin-4-yl)amino)-1-methylcyclohexan-1-ol;

(119) 2-(5-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl) pyrazin-2-yl)propan-2-ol;

(120) 2-(5-(6-((2-(1-(Cyclopropylsulfonyl)-1H-pyrazol-4-yl)pyrimidin-4-yl)amino)-4-( (123) N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-morpholino-[2,3'-bipyridine]-4',6'-diamine;

(125) N$^{6'}$-(2-(1-(Cyclopropylsulfonyl)-1H-pyrazol-4-yl)pyrimidin-4-yl)-N$^{4'}$-isopropyl-5-(morpholinomethyl)-[2,3'-bipyridine]-4',6'-diamine;

(126) N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-(morpholinomethyl)-[2,3'-bipyridine]-4',6'-diamine;

(129) ((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)methanol;

(132) N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-((1-methylpiperidin-4-yl)oxy)-[2,3'-bipyridine]-4',6'-diamine;

(141) N$^{6'}$-(2-(1-(2,2-Difluoroethyl)-1H-pyrazol-4-yl)pyrimidin-4-yl)-N$^{4'}$-(3-fluorocyclohexyl)-5-((1-methylpiperidin-4-yl)oxy)-[2,3'-bipyridine]-4',6'-diamine;

(145) (1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)-1-methylcyclohexan-1-ol;

(146) ((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)methanol;

(147) 2-((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)propan-2-ol;

(148) (1s,4s)-4-((2-((2-(1-(Cyclopropylsulfonyl)-1H-pyrazol-4-yl)pyrimidin-4-yl)amino)-5-(5-((tetrahydro-2H-pyran-4-yl)oxy) pyrazin-2-yl)pyridin-4-yl)amino)-1-methylcyclohexan-1-ol;

(149) (1s,4s)-4-((2-((2-(1-(Cyclopropylsulfonyl)-1H-pyrazol-4-yl)pyrimidin-4-yl)amino)-5-(5-((tetrahydrofuran-3-yl)oxy) pyrazin-2-yl)pyridin-4-yl)amino)-1-methylcyclohexan-1-ol;

(150) (1s,4s)-4-((2-((2-(1-(Cyclopropylsulfonyl)-1H-pyrazol-4-yl)pyrimidin-4-yl)amino)-5-(5-(oxetan-3-yloxy) pyrazin-2-yl)pyridin-4-yl)amino)-1-methylcyclohexan-1-ol;

(153) (1s,4s)-4-((2-((2-(1-(Cyclopropylsulfonyl)-1H-pyrazol-4-yl)pyrimidin-4-yl)amino)-5-(5-((1-(2-fluoroethyl)piperidin-4-yl)oxy) pyrazin-2-yl)pyridin-4-yl)amino)-1-methylcyclohexan-1-ol;

(154) (1s,4s)-4-((2-((2-(1-(Cyclopropylsulfonyl)-1H-pyrazol-4-yl)pyrimidin-4-yl)amino)-5-(5-((4-fluoro-1-methylpiperidin-4-yl) methoxy) pyrazin-2-yl)pyridin-4-yl)amino)-1-methylcyclohexan-1-ol;

(155) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-ol;

(156) (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol;

(158) ((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)methanol;

(159) N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(methylsulfonyl)-[2,3'-bipyridine]-4',6'-diamine;

(160) 2-((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)propan-2-ol;

(163) 2-((1s,4s)-4-((6'-((2-(2-(1-(Cyclopropylsulfonyl)-1H-pyrazol-4-yl)pyrimidin-4-yl)amino)-6-fluoro-[2,3'-bipyridin]-4'-yl)amino)cyclohexyl)propan-2-ol;

(164) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-N,N-dimethyl-[2,3'-bipyridine]-5-sulfonamide;

(165) 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-N,N-dimethyl-[2,3'-bipyridine]-5-sulfonamide;

(166) 6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-N,N-dimethyl-[2,3'-bipyridine]-5-sulfonamide;

(168) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol;

(169) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)propan-2-ol;

(170) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)propan-2-ol;

(171) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)propan-2-ol;

(172) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-N,N-dimethylcyclohexane-1-carboxamide;

(173) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol;

(174) 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)propan-2-ol;

(175) 2-(6'-((2-(1-(Cyclopropylsulfonyl)-1H-pyrazol-4-yl)pyrimidin-4-yl)amino)-4'-((4,4-difluorocyclohexyl)amino)-[2,3'-bipyridin]-5-yl)propan-2-ol;

(176) 2-(6'-((2-(1-(Cyclopropylsulfonyl)-1H-pyrazol-4-yl)pyrimidin-4-yl)amino)-4'-((1-(2-fluoroethyl) piperidin-4-yl)amino)-[2,3'-bipyridin]-5-yl)propan-2-ol;

(177) 2-(6'-((2-(1-(Cyclopropylsulfonyl)-1H-pyrazol-4-yl)pyrimidin-4-yl)amino)-4'-((1-(2-fluoroethyl) piperidin-3-yl)amino)-[2,3'-bipyridin]-5-yl)propan-2-ol;

(178) 2-(6'-((2-(1-(Cyclopropylsulfonyl)-1H-pyrazol-4-yl)pyrimidin-4-yl)amino)-4'-((1-(2,2-difluoroethyl) piperidin-4-yl)amino)-[2,3'-bipyridin]-5-yl)propan-2-ol;

(179) (1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)-1-methylcyclohexan-1-ol;

(182) (1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)-1-methylcyclohexan-1-ol;

(183) ((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)methanol;

(184) 2-((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)propan-2-ol;

(185) (1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)-1-methylcyclohexan-1-ol;

(188) (1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)-1-methylcyclohexan-1-ol;

(189) ((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl) methanol;

(190) 2-((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)propan-2-ol;

(191) (1s,4s)-4-((4-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrimidin-2-yl)amino)-1-methylcyclohexan-1-ol;

(192) ((1s,4s)-4-((4-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyrimidin-2-yl)amino)cyclohexyl)methanol;

(194) (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol;

(195) ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol;

(196) 2-((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)propan-2-ol;

(197) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(trifluoromethoxy)-[2,3'-bipyridine]-4',6'-diamine;

(198) (1s,4s)-4-((6'-((2-(1-(Cyclopropylsulfonyl)-1H-pyrazol-4-yl)pyrimidin-4-yl)amino)-4-(methylsulfonyl)-[2,3'-bipyridin]-4'-yl)amino)-1-methylcyclohexan-1-ol;

(199) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(4-methylpiperazin-1-yl)methanone;

(200) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(morpholino) methanone;

(201) (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(morpholino) methanone;

(202) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(4-methylpiperazin-1-yl)methanone;

(203) (6'-((2-(1-(Cyclopropylsulfonyl)-1H-pyrazol-4-yl)pyrimidin-4-yl)amino)-4'-(((1s,4s)-4-(2-hydroxy propan-2-yl)cyclohexyl)amino)-[2,3'-bipyridin]-5-yl)(4-methylpiperazin-1-yl)methanone;

(204) (6'-((2-(1-(Cyclopropylsulfonyl)-1H-pyrazol-4-yl)pyrimidin-4-yl)amino)-4'-(((1s,4s)-4-((dimethylamino) methyl)cyclohexyl)amino)-[2,3'-bipyridin]-5-yl)(4-methylpiperazin-1-yl)methanone;

(205) (1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)-1-methylcyclohexan-1-ol;

(206) 2-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)oxy)ethan-1-ol;

(207) 2-((1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)cyclohexyl)propan-2-ol;

(208) (1s,4s)-4-((6'-((2-(1-(Cyclopropylsulfonyl)-1H-pyrazol-4-yl)pyrimidin-4-yl)amino)-5-(2-(dimethylamino)ethoxy)-[2,3'-bipyridin]-4'-yl)amino)-1-methylcyclohexan-1-ol;

(209) ((1s,4s)-4-((6'-((2-(1-(Cyclopropylsulfonyl)-1H-pyrazol-4-yl)pyrimidin-4-yl)amino)-5-(2-(dimethylamino)ethoxy)-[2,3'-bipyridin]-4'-yl)amino)cyclohexyl)methanol;

(210) 2-((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)propan-2-ol;

(211) (1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)-1-methylcyclohexan-1-ol;

(212) ((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)methanol;

(214) ((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)methanol;

(215) 2-((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)propan-2-ol;

(216) $N^{6'}$-(2-(1-(Cyclopropylsulfonyl)-1H-pyrazol-4-yl)pyrimidin-4-yl)-$N^{4'}$-(3,3-difluorocyclobutyl)-$N^{4'}$-((1s,4s)-4-((dimethylamino)methyl)cyclohexyl)-[2,3'-bipyridine]-4,4',6'-triamine;

(217) 2-((1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)cyclohexyl)propan-2-ol;

(218) (1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)-1-methylcyclohexan-1-ol;

(219) ((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol;

(220) 2-((1s,4s)-4-((6'-((2-(1-(Cyclopropylsulfonyl)-1H-pyrazol-4-yl)pyrimidin-4-(221) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2,2,2-trifluoroethyl)-[2,3'-bipyridine]-4',6'-diamine;

(222) ((1S,3S)-3-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)methanol;

(223) 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)ethan-1-ol;

(224) (1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)-1-methylcyclohexan-1-ol;

(225) 2-((1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)cyclohexyl)propan-2-ol;

(226) (1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)-1-methylcyclohexan-1-ol;

(227) 1-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2,2-trifluoroethan-1-ol;

(228) 1-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-2,2,2-trifluoroethan-1-ol;

(229) 2-((1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)cyclohexyl)propan-2-ol;

(230) (1s,4s)-4-((6'-((2-(1-(Cyclopropylsulfonyl)-1H-pyrazol-4-yl)pyrimidin-4-yl)amino)-5-(1,1,1-trifluoro-2-hydroxypropan-2-yl)-[2,3'-bipyridin]-4'-yl)amino)-1-methylcyclohexan-1-ol;

(231) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-1,1,1-trifluoropropan-2-ol;

(232) 2-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-1,1,1-trifluoropropan-2-ol;

(((1s,4s)-4-(2-hydroxypropan-2-yl)cyclohexyl)amino)-[2,3'-bipyridin]-5-yl)-1,1,1-trifluoropropan-2-ol;

(234) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-1,1,1-trifluoropropan-2-ol;

(235) ((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)methanol;

(236) 2-((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)propan-2-ol;

(237) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2-fluoropropan-2-yl)-[2,3'-bipyridine]-4',6'-diamine;

(241) ((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)methanol;

(242) 2-((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)propan-2-ol;

(243) $N^{6'}$-(2-(1-(Cyclopropylsulfonyl)-1H-pyrazol-4-yl)pyrimidin-4-yl)-5-(1,1-difluoroethyl)-$N^{4'}$-((1s,4s)-4-((dimethylamino)methyl)cyclohexyl)-[2,3'-bipyridine]-4',6'-diamine;

(244) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2-difluoroethan-1-ol;

(250) (1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(251) ((1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(252) 2-((1r,4r)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol;

(253) ((1S,3S)-3-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(254) $N^{6'}$-(2-(1-(Cyclopropylsulfonyl)-1H-pyrazol-4-yl)pyrimidin-4-yl)-$N^{4'}$-(4-fluorocyclohexyl)-5-((1-methylpiperidin-4-yl)oxy)-[2,3'-bipyridine]-4',6'-diamine;

(260) (1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)-1-methylcyclohexan-1-ol;

(261) ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)cyclohexyl)methanol;

(262) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2,2,2-trifluoro-1-methoxyethyl)-[2,3'-bipyridine]-4',6'-diamine;

(263) (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol;

(269) (1s,4s)-4-((2-((2-(1-(Cyclopropylsulfonyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol;

(271) (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol;

(272) ((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)methanol;

(274) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-6-fluoro-[2,3'-bipyridine]-4',6'-diamine;

(275) $N^{6'}$-(2-(1-(Cyclopropylsulfonyl)-1H-pyrazol-4-yl)pyrimidin-4-yl)-$N^{4'}$-((1s,4s)-4-((2,2-difluoroethyl)amino)cyclohexyl)-6-fluoro-[2,3'-bipyridine]-4',6'-diamine;

(277) (1s,4s)-4-((6'-((2-(1-(Cyclopropylsulfonyl)-1H-pyrazol-4-yl)pyrimidin-4-yl)amino)-4-((3,3,3-trifluoropropyl)amino)-[2,3'-bipyridin]-4'-yl)amino)-1-methylcyclohexan-1-ol;

(280) (1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)-1-methylcyclohexan-1-ol;

(281) (1s,4s)-4-((6'-((2-(1-(Cyclopropylsulfonyl)-1H-pyrazol-4-yl)pyrimidin-4-yl)amino)-4-((2-(3-fluoroazetidin-1-yl)ethyl)amino)-[2,3'-bipyridin]-4'-yl)amino)-1-methylcyclohexan-1-ol;

(284) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(morpholino)methanone;

(285) (1s,4s)-4-((6'-((2-(1-(Cyclopropylsulfonyl)-1H-pyrazol-4-yl)pyrimidin-4-yl)amino)-6-((2-hydroxyethyl)amino)-[2,3'-bipyridin]-4'-yl)amino)-1-methylcyclohexan-1-ol;

(287) (1s,4s)-4-((6'-((2-(1-(Cyclopropylsulfonyl)-1H-pyrazol-4-yl)pyrimidin-4-yl)amino)-4-(2-(dimethylamino)ethoxy)-[2,3'-bipyridin]-4'-yl)amino)-1-methylcyclohexan-1-ol;

(289) (1s,4s)-4-((6'-((2-(1-(Cyclopropylsulfonyl)-1H-pyrazol-4-yl)pyrimidin-4-yl)amino)-5-((1-methylazetidin-3-yl)oxy)-[2,3'-bipyridin]-4'-yl)amino)-1-methylcyclohexan-1-ol;

(290) (1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)-1-methylcyclohexan-1-ol;

(291) (1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)-1-methylcyclohexan-1-ol;

(292) (1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)-1-methylcyclohexan-1-ol;

(296) 4-(4-((4'-(((1s,4s)-4-Hydroxy-4-methylcyclohexyl)amino)-5-(2,2,2-trifluoroethyl)-[2,3'-bipyridin]-6'-yl)amino)pyrimidin-2-yl)-N,N-dimethyl-1H-pyrazole-1-sulfonamide;

(297) 4-(4-((4'-(((1s,4s)-4-Hydroxy-4-methylcyclohexyl)amino)-5-(2,2,2-trifluoro-1-hydroxyethyl)-[2,3'-bipyridin]-6'-yl)amino)pyrimidin-2-yl)-N,N-dimethyl-1H-pyrazole-1-sulfonamide;

(298) 4-(4-((4'-(((1s,4s)-4-Hydroxy-4-methylcyclohexyl)amino)-5-(1,1,1-trifluoro-2-hydroxypropan-2-yl)-[2,3'-bipyridin]-6'-yl)amino)pyrimidin-2-yl)-N,N-dimethyl-1H-pyrazole-1-sulfonamide;

(301) 4-(4-((4'-(((1s,4s)-4-Hydroxy-4-methylcyclohexyl)amino)-5-((1-methylpiperidin-4-yl)oxy)-[2,3'-bipyridin]-6'-yl)amino)pyrimidin-2-yl)-N,N-dimethyl-1H-pyrazole-1-sulfonamide;

(302) (1s,4s)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(303) (1s,4s)-1-Methyl-4-((6'-((2-(3-methyl-1-(2,2,2-trifluoroethyl)-1H-pyrazol-4-yl)pyrimidin-4-yl)amino)-5-((1-methylpiperidin-4-yl)oxy)-[2,3'-bipyridin]-4'-yl)amino)cyclohexan-1-ol;

(304) (1s,4s)-1-Methyl-4-((5-((1-methylpiperidin-4-yl)oxy)-6'-((2-(1-(2,2,2-trifluoroethyl)-1H-pyrazol-4-yl)pyrimidin-4-yl)amino)-[2,3'-bipyridin]-4'-yl)amino)cyclohexan-1-ol;

(308) $N^{6'}$-(2-(1-(2,2-Difluoroethyl-1H-pyrazol-4-yl)pyrimidin-4-yl)-$N^{4'}$-(4-fluorocyclohexyl)-5-((1-methylpiperidin-4-yl)oxy)-[2,3'-bipyridine]-4',6'-diamine;

(310) (1s,4s)-4-((6-Fluoro-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(316) (1s,4s)-4-((5-(2-(Azetidin-1-yl) ethoxy)-6'-((2-(1-(2,2-difluoroethyl)-1H-pyrazol-4-yl)pyrimidin-4-yl)amino)-[2,3'-bipyridin]-4'-yl)amino)-1-methylcyclohexan-1-ol;

(322) (1s,4s)-4-((6'-((2-(1-(Cyclopropylsulfonyl)-1H-pyrazol-4-yl)pyrimidin-4-yl)amino)-5-((1-(2-fluoroethyl) piperidin-4-yl)oxy)-[2,3'-bipyridin]-4'-yl)amino)-1-methylcyclohexan-1-ol;

(323) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine;

(326) (1s,4s)-4-((2-((2-(1-(Cyclopropylsulfonyl)-1H-pyrazol-4-yl)pyrimidin-4-yl)amino)-5-(3-methoxypyrazin-2-yl)pyridin-4-yl)amino)-1-methylcyclohexan-1-ol;

(327) (1s,4s)-4-((2-((2-(1-(Cyclopropylsulfonyl)-1H-pyrazol-4-yl)pyrimidin-4-yl)amino)-5-(3-fluoropyrazin-2-yl)pyridin-4-yl)amino)-1-methylcyclohexan-1-ol;

(328) (1s,4s)-4-((6'-((2-(1-(Cyclopropylsulfonyl)-1H-pyrazol-4-yl)pyrimidin-4-yl)amino)-5-fluoro-3-methoxy-[2,3'-bipyridin]-4'-yl)amino)-1-methylcyclohexan-1-ol;

(329) (1s,4s)-4-((6'-((2-(1-(Cyclopropylsulfonyl)-1H-pyrazol-4-yl)pyrimidin-4-yl)amino)-6-fluoro-3-methoxy-[2,3'-bipyridin]-4'-yl)amino)-1-methylcyclohexan-1-ol;

(330) (1s,4s)-4-((6'-((2-(1-(Cyclopropylsulfonyl)-1H-pyrazol-4-yl)pyrimidin-4-yl)amino)-3-(difluoromethoxy)-[2,3'-bipyridin]-4'-yl)amino)-1-methylcyclohexan-1-ol;

(331) (1s,4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol;

(332) (1s,4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol; and (337) (1s,4s)-4-((6'-((2-(1-(2,2-Difluoroethyl)-1H-pyrazol-4-yl)pyrimidin-4-yl)amino)-3-methoxy-5-((1-(2,2,2-trifluoroethyl) piperidin-4-yl)oxy)-[2,3'-bipyridin]-4'-yl)amino)-1-methylcyclohexan-1-ol.

Further preferable representative compounds of Formula (I) are listed below;

(9) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol;

(38) (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol;

(43) (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol;

(47) (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol;

(63) (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-ol;

(129) ((1s,4s)-4-((2-((2-(1-(Cyclopropylsulfonyl)-1H-pyrazol-4-yl)pyrimidin-4-yl)amino)-5-(5-(difluoromethoxy)pyrazin-2-yl)pyridin-4-yl)amino)cyclohexyl)methanol;

(150) (1s,4s)-4-((2-((2-(1-(Cyclopropylsulfonyl)-1H-pyrazol-4-yl)pyrimidin-4-yl)amino)-5-(5-(oxetan-3-yloxy)pyrazin-2-yl)pyridin-4-yl)amino)-1-methylcyclohexan-1-ol;

(156) (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol;

(168) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol;

(169) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)propan-2-ol;

(173) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol;

(194) (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol;

(195) ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol;

(263) (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol;

(271) (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol;

(274) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-6-fluoro-[2,3'-bipyridine]-4',6'-diamine;

(331) (1s,4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol; and (332) (1s,4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol.

Single stereochemical isomers, enantiomers, diastereomers, and pharmaceutically acceptable salts of the above exemplified compounds are also within the scope of the present invention. Pharmaceutically acceptable salts may be, for example, derived from suitable inorganic and organic acids and bases.

Acid addition salts can be prepared by reacting the purified compound in its free-based form, if possible, with a suitable organic or inorganic acid and isolating the salt thus formed. Examples of pharmaceutically acceptable acid addition salts include, without limitations, salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid.

Base addition salts can be prepared by reacting the purified compound in its acid form with a suitable organic or inorganic base and isolating the salt thus formed. Such salts include, without limitations, alkali metal (e.g., sodium, lithium, and potassium), alkaline earth metal (e.g., magnesium and calcium), ammonium and $N^+$ ($C_{1-4}$alkyl)$_4$ salts.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, and valerate salts.

The compounds of the present invention may be synthesized by methods known in the art or by methods illustrated in Examples 1-337 below.

Pharmaceutical Compositions, Methods and Use

In one embodiment, the present invention relates to a method for treating protein kinase-mediated disease in a subject in need thereof, comprising administering to said subject a therapeutically effective amount of a compound of Formula (I) or a pharmaceutically acceptable salt, diastereomers, enantiomers, racemates, tautomers, prodrugs, hydrates, or solvates thereof In specific embodiment, the protein kinase-mediated disease is a cancer or immune disease.

As used herein, the term "cancer" refers to an abnormal growth of cells which tend to proliferate in an uncontrolled way and, in some cases, to metastasize. The types of cancer include, but is not limited to, solid tumors, such as those of the bladder cancer, colorectal cancer, brain cancer, breast cancer, ovarian cancer, endometrium cancer, uterine cancer, heart cancer, kidney cancer, lung cancer, liver cancer, stomach cancer, lymphoma, pancreatic cancer, head and neck cancer, or other endocrine organ (thyroid cancer), prostate cancer, skin (melanoma) or hematological tumors (such as the leukemias). In another embodiment, the cancer is non-small cell lung cancer (NSCLC).

In one embodiment, the method disclosed herein relates to treatment of cancer, wherein the cancer results from at least one mutation of EGFR.

In one embodiment, the method of treatment of cancer is particularly useful for patient who is resistant to a kinase inhibitor other that a compound of the invention, or a pharmaceutically acceptable salt, solvate, ester, or prodrug thereof. In another embodiment, the kinase inhibitor is a mutated EGFR inhibitor.

The invention also relates to a method for inhibiting at least one mutant of EGFR selectively as compared to wild type EGFR, in biological sample or in a patient, comprising contacting the biological sample with or administering to the patient a compound to the patient a therapeutically effective amount of a compound of the invention, or a pharmaceutically acceptable salt thereof.

In one embodiment, the at least one mutant is at least one single mutant selected from Table 1 shown below.

In one embodiment, the at least one mutant is at least one double mutant selected from Table 1 shown below.

In one embodiment, the at least one mutant is at least one triple mutant selected from Table 1 shown below.

TABLE 1

| Number (#) | Mutation type |
|---|---|
| 1 | EGFR Del19 (Del E746-A750) |
| 2 | EGFR L858R |
| 3 | EGFR Del19/T790M |
| 4 | EGFR Del19/C797S |
| 5 | EGFR Del19/C797X (X = G, N) |
| 6 | EGFR Del19/L792X (X = F, H, P, R, V, Y) |
| 7 | EGFR Del19/L718X (X = Q, V) |
| 8 | EGFR L858R/T790M |
| 9 | EGFR L858R/C797S |
| 10 | EGFR L858R/C797X (X = G, N) |
| 11 | EGFR L858R/L792X (X = F, H, P, R, V, Y) |
| 12 | EGFR L858R/L718X (X = Q, V) |
| 13 | EGFR Del19/T790M/C797S |
| 14 | EGFR Del19/T790M/C797X (X = G, N) |
| 15 | EGFR Del19/T790M/L792X (X = F, H, P, R, V, Y) |
| 16 | EGFR Del19/T790M/L718X (X = Q, V) |
| 17 | EGFR L858R/T790M/C797S |
| 18 | EGFR L858R/T790M/C797X (X = G, N) |
| 19 | EGFR L858R/T790M/L792X (X = F, H, P, R, V, Y) |
| 20 | EGFR L858R/T790M/L718X (X = Q, V) |

The invention further relates to therapeutic methods and uses comprising administering the compounds of the invention, or a pharmaceutically acceptable salt, diastereomers, enantiomers, racemates, tautomers, prodrugs, hydrates, or solvates thereof alone or in combination with other therapeutic or palliative agents.

A further embodiment of the invention relates to a compound of the invention for use as a medicament, and in particular for use in the treatment of diseases where the inhibition of mutated EGFR protein (e.g., those described in Table 1) activity may induce benefit, such as cancer. A still further embodiment of the present invention relates to the use of the compounds of the invention, or a pharmaceutically acceptable salt, diastereomers, enantiomers, racemates, tautomers, prodrugs, hydrates, or solvates thereof, for the manufacture of a drug having an EGFR inhibitory activity for the treatment of EGFR mediated diseases and/or conditions, in particular the diseases and/or conditions listed above.

The term "therapeutically effective amount" refers to that amount of a compound being administered which will relieve to some extent one or more of the symptoms of the disorder being treated. Regarding the treatment of cancer, a therapeutically effective amount refers to that amount which has the effect of reducing the size of the tumor, inhibiting (i.e., slowing or stopping) tumor metastases, inhibiting (i.e. slowing or stopping) tumor growth or tumor invasiveness, and/or relieving to some extent one or more signs or symptoms related to the cancer.

A therapeutically effective amount can be readily determined by the attending diagnostician, as one skilled in the art, by the use of conventional techniques and by observing results obtained under analogous circumstances. In determining the therapeutically effective amount, the dose, a number of factors are considered by the attending diagnostician, including, but not limited to: the species of mammal; its size, age, and general health; the specific disease involved; the degree of involvement or the severity of the disease; the response of the individual patient; the particular compound administered; the mode of administration; the bioavailability characteristic of the preparation administered; the dose regimen selected; the use of concomitant medication; and other relevant circumstances.

The term "treating", as used herein, unless otherwise indicated, means reversing, alleviating, inhibiting the progress of, or preventing the disorder or condition to which such term applies, or one or more symptoms of such disorder or condition. The term "treatment" also refers to the act of treating as "treating" is defined immediately above. The term "treating" also includes adjuvant treatment of a mammal.

As used herein, the term "subject" or "patient" encompasses mammals and nonmammals. Examples of mammals include, but are not limited to, humans, chimpanzees, apes monkeys, cattle, horses, sheep, goats, swine; rabbits, dogs, cats, rats, mice, guineapigs, and the like. Examples of non-mammals include, but are not limited to, birds, fish and the like.

As used herein, the term "biological sample" encompasses cells, tissues, and body fluids obtained (isolated) from mammals, such as humans (e.g., patients having cancers) or nonmammals exemplified hereinabove, and cultures thereof.

Administration of the compounds of the invention may be effected by any method that enables delivery of the compounds to the site of action. These methods include oral routes, intraduodenal routes, parenteral injection (including intravenous, subcutaneous, intramuscular, intravascular or infusion), topical, and rectal administration.

Also provided herein, in other aspects, is a pharmaceutical composition comprising a compound of t Formula (I), a pharmaceutically acceptable salt, diastereomers, enantiomers, racemates, tautomers, prodrugs, hydrates, or solvates thereof as an active ingredient, and pharmaceutically acceptable excipients. In one embodiment, the pharmaceutical composition is for treating a protein kinase-mediated disease. In another embodiment, the pharmaceutical composition is for selectively inhibiting at least one mutant of EGFR as compared to wild type EGFR.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid.

Examples of carriers, excipients and diluents that can be included in the composition, may include lactose, dextrose, sucrose, sorbitol, mannitol, xylitol, erythritol, maltitol, starch, arabic gum, alginate, gelatin, calcium phosphate, calcium silicate, cellulose, methylcellulose, microcrystalline cellulose, polyvinyl pyrrolidone, water, methyl hydroxy benzoate, propyl hydroxy benzoate, talc, magnesium stearate, and mineral oil, but are not limited thereto. When formulated into a preparation, a diluting agent or an excipient, such as commonly-used fillers, stabilizing agents, binding agents, disintegrating agents, and surfactants can be used. Solid preparations for oral administration include tablets, pills, powders, granules, capsules, and the like, and these solid preparations may be prepared by mixing the compound of the present invention with at least one excipient, for example, starch, microcrystalline cellulose, sucrose, lactose, low-substituted hydroxypropyl cellulose, hypromellose or the like. In addition to the simple excipient, a lubricant such as magnesium stearate and talc are also used. Liquid preparations for oral administration include a suspension, a liquid for internal use, an emulsion, a syrup, etc. In addition to a commonly used simple diluent such as water and liquid paraffin, various excipients such as a humectant, a sweetener, an aromatic, a preservative, etc. may also be contained. Formulations for parenteral administration include a sterilized aqueous solution, a non-aqueous solution, a suspension, an emulsion, a lyophilized formulation and a suppository. The non-aqueous solution or suspension may contain propylene glycol, polyethylene glycol, a vegetable oil such as olive oil, an injectable ester such as ethyl oleate, etc. As a base of the suppository, witepsol, macrogol, tween 61, cocoa butter, laurin butter, glycerogelatin, etc. may be used. In order to formulate the formulation for parenteral administration, the compound of Formula I or a pharmaceutically acceptable salt thereof may be mixed in water together with sterilized and/or contain adjuvants such as preservatives, stabilizers, auxiliary agents such as wettable powder or emulsifying accelerators, salt for controlling osmotic pressure and/or buffers and the like, and other therapeutically useful substances, to prepare a solution or suspension, which is then manufactured in the form of an ampoule or vial unit administration.

General Reaction Scheme and Summary of the Synthesis Route

The present invention includes, within its scope, a process for preparing a compound of formula (I) or a pharmaceutically acceptable salt, diastereomers, enantiomers, racemates, tautomers, prodrugs, hydrates, or solvates thereof, in accordance with the following Scheme 1:

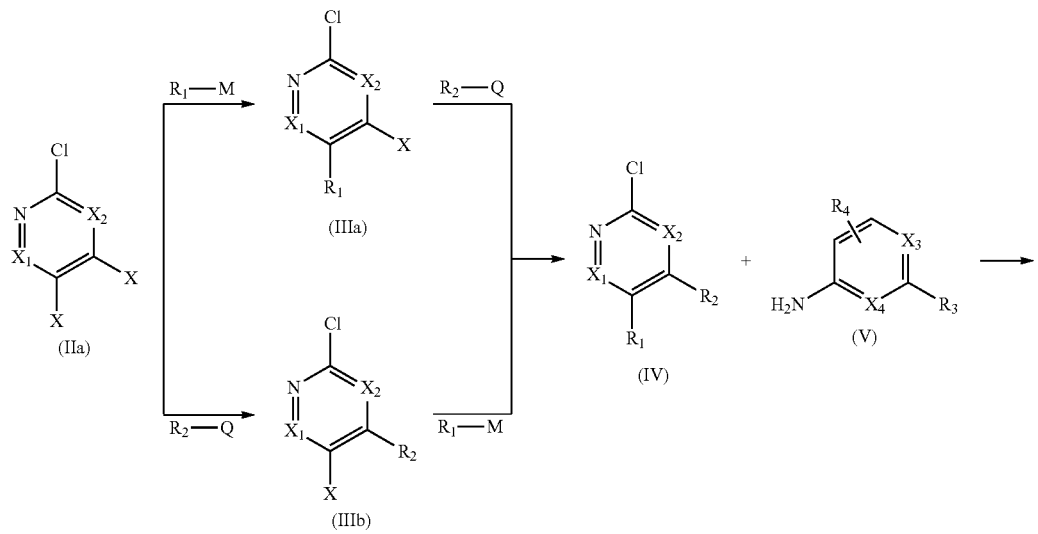

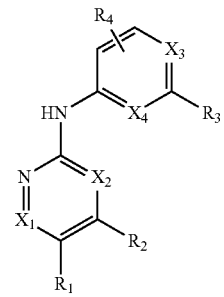

(I)

wherein, $R_1$, $R_2$, $R_3$, $R_4$, $X_1$, $X_2$, $X_3$, and $X_4$ are the same as defined in the above; X is halogen; M is $B(OH)_2$ or BPin; and Q is hydrogen, $B(OH)_2$ or BPin.

Specifically, the compound of formula (I) or its pharmaceutically acceptable salt may be prepared using a process which comprises: reacting a compound of formula (IIa) with $R_1$-M to obtain a compound of formula (IIIa), reacting the compound of formula (IIIa) with $R_2$-Q to obtain a compound of formula (IV) and reacting the compound of formula (IV) with a compound of formula (V) to obtain the compound of formula (I).

In the processes of Scheme 1, the compounds of formula (IIa), $R_1$-M, $R_2$-Q and (V) are commercially available. The reaction of the compound of formula (IIa) and $R_1$-M may be performed in the presence of a base, such as sodium carbonate, potassium carbonate, etc. and a ligand-coupled palladium catalyst such as $Pd(dppf)Cl_2$, $Pd(PPh_3)_4$, etc. Further, the reaction may be carried out in an anhydrous organic solvent, e.g., DME, THF, 1,4-dioxane, etc. under heating. e.g. at a temperature of 40-120° C.

The reaction of the compound of formula (IIIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that Q is $B(OH)_2$ or BPin, the reaction may be carried out in an anhydrous organic solvent, e.g., DME, THF, 1,4-dioxane, etc. under heating, e.g. at a temperature of 40-120° C.

The compound of formula (IV) is coupled with a compound of formula (V) to obtain a compound of formula (I) by Buchwald-Hartwig reaction. The reaction of the compound of formula (IV) and (V) may be performed in the presence of a base such as sodium carbonate potassium carbonate, cesium carbonate, etc. Further, the reaction may be performed in the presence of a palladium catalyst such as $Pd(OAc)_2$, $Pd_2(dba)_3$, $Pd(PPh_3)_4$, $Pd(dppf)Cl_2$, BrettPhos Pd G1 methyl t-butyl ether adduct, etc. and a ligand such as BINAP, SPhos, XPhos, Xantphos, BrettPhos, etc. Further, the reaction may be carried out in an anhydrous organic solvent, e.g., 1,4-dioxane or toluene, etc. under heating, e.g. at a temperature of 80-120° C.

Alternately, the compound of formula (IV) may be prepared by reacting a compound of formula (IIa) with $R_2$-Q to obtain a compound of formula (IIIb) and reacting the compound of formula (IIIb) with $R_1$-M.

The reaction of the compound of formula (IIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that Q is $B(OH)_2$ or BPin, the reaction may be carried out in an anhydrous organic solvent, e.g., DME, THF. 1,4-dioxane, etc. under heating, e.g. at a temperature of 40-120° C.

The reaction of the compound of formula (IIIb) and $R_1$-M may be performed in the presence of a base, such as sodium carbonate, potassium carbonate, etc. and a ligand-coupled palladium catalyst such as $Pd(dppf)Cl_2$, $Pd(PPh_3)_4$, etc. Further, the reaction may be carried out in an anhydrous organic solvent, e.g., DME, THF, 1,4-dioxane, etc. under heating, e.g. at a temperature of 40-120° C.

In accordance with another aspect of the present invention, the compound of formula (I) or its pharmaceutically acceptable salt may be prepared in accordance with the following Scheme 2:

Scheme 2.

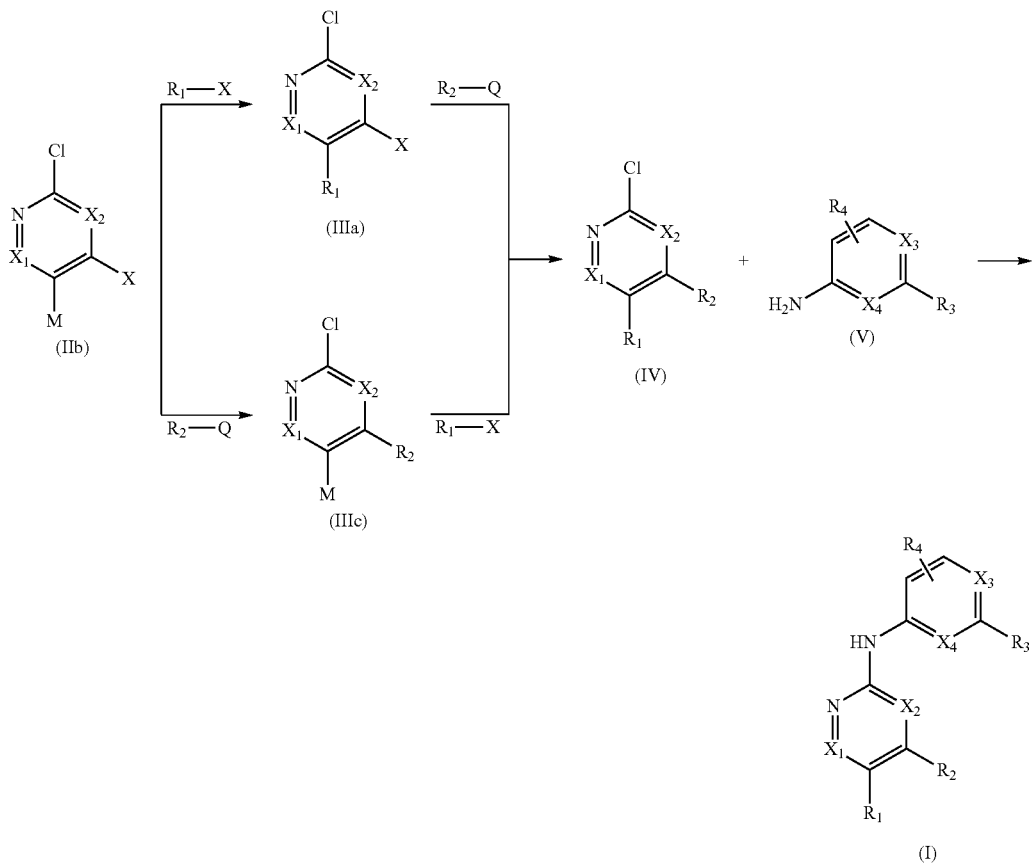

wherein, $R_1$, $R_2$, $R_3$, $R_4$, $X_1$, $X_2$, $X_3$, and $X_4$ are the same as defined in the above; X is halogen; M is $B(OH)_2$ or BPin; and Q is hydrogen, $B(OH)_2$ or BPin.

Specifically, the compound of formula (I) or its pharmaceutically acceptable salt may be prepared using a process which comprises: reacting a compound of formula (IIb) with $R_1$—X to obtain a compound of formula (IIIa), reacting the compound of formula (IIIa) with $R_2$-Q to obtain a compound of formula (IV) and reacting the compound of formula (IV) with a compound of formula (V) to obtain the compound of formula (I).

In the processes of Scheme 2, the compounds of formula (IIb), $R_1$—X, $R_2$-Q and (V) are commercially available. The reaction of the compound of formula (IIb) and $R_1$—X may be performed in the presence of a base, such as sodium carbonate, potassium carbonate, etc. and a ligand-coupled palladium catalyst such as $Pd(dppf)Cl_2$, $Pd(PPh_3)_4$, etc. Further, the reaction may be carried out in an anhydrous organic solvent, e.g., DME, THF, 1,4-dioxane, etc. under heating, e.g. at a temperature of 40-120° C.

The reaction of the compound of formula (IIIa) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as $Pd(dppf)Cl_2$, $Pd(PPh_3)_4$, etc. Further, in case that Q is $B(OH)_2$ or BPin, the reaction may be carried out in an anhydrous organic solvent, e.g., DME, THF. 1,4-dioxane, etc. under heating, e.g. at a temperature of 40-120° C.

The compound of formula (IV) is coupled with a compound of formula (V) to obtain a compound of formula (I) by Buchwald-Hartwig reaction. The reaction of the compound of formula (IV) and (V) may be performed in the presence of a base such as sodium carbonate potassium carbonate, cesium carbonate, etc. Further, the reaction may be performed in the presence of a palladium catalyst such as $Pd(OAc)_2$, $Pd_2(dba)_3$, $Pd(PPh_3)_4$, $Pd(dppf)Cl_2$, BrettPhos Pd G1 methyl t-butyl ether adduct, etc. and a ligand such as BINAP, SPhos, XPhos, Xantphos, BrettPhos, etc. Further, the reaction may be carried out in an anhydrous organic solvent, e.g., 1,4-dioxane or toluene, etc. under heating, e.g. at a temperature of 80-120° C.

Alternately, the compound of formula (IV) may be prepared by reacting a compound of formula (IIb) with $R_2$-Q to obtain a compound of formula (IIIc) and reacting the compound of formula (IIIc) with $R_1$—X.

The reaction of the compound of formula (IIb) and $R_2$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. and at room temperature or under heating, e.g., at a temperature of 40-140° C. In case that Q is $B(OH)_2$ or BPin, the reaction may be carried out in the presence of a base such as sodium carbonate, potassium carbonate, etc. and a ligand-coupled palladium catalyst such as Pd(dppf)Cl$_2$, Pd(PPh$_3$)$_4$, etc. Further, in case that Q is B(OH)$_2$ or BPin, the reaction may be carried out in an anhydrous organic solvent, e.g., DME, THF, 1,4-dioxane, etc. under heating, e.g. at a temperature of 40-120° C.

The reaction of the compound of formula (IIIc) and R$_1$—X may be performed in the presence of a base, such as sodium carbonate, potassium carbonate, etc. and a ligand-coupled palladium catalyst such as Pd(dppf)Cl$_2$, Pd(PPh$_3$)$_4$, etc. Further, the reaction may be carried out in an anhydrous organic solvent, e.g., DME, THF, 1,4-dioxane, etc. under heating, e.g. at a temperature of 40-120° C.

In accordance with another aspect of the present invention, the compound of formula (V) may be obtained by reacting a compound of formula (VI) with a compound of formula R$_3$-Q in accordance with the following Scheme 3:

Scheme 3.

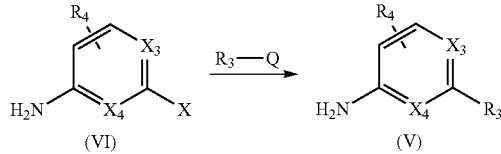

wherein, R$_3$, R$_4$. X$_3$, and X$_4$ are the same as defined in the above; X is halogen; and Q is hydrogen, B(OH)$_2$ or BPin.

The reaction of the compound of formula (VI) and R$_3$-Q may be performed in the presence of a base, such as sodium hydride, potassium carbonate, cesium carbonate, potassium hydroxide, TEA, DIPEA, etc. Further, the reaction may be carried out in an organic solvent, such as anhydrous THF, DMF, DMA, etc. at room temperature or under heating, e.g., at a temperature of 40-140° C. In case that Q is B(OH)$_2$ or BPin, the reaction may be carried out in the presence of a base such as sodium carbonate, potassium carbonate, etc. and a ligand-coupled palladium catalyst such as PdCl$_2$(PPh$_3$)$_2$, Pd(dppf)Cl$_2$, Pd(PPh$_3$)$_4$, etc. Further, in case that Q is B(OH)$_2$ or BPin, the reaction may be carried out in an anhydrous organic solvent, e.g., THF, 1,4-dioxane, acetonitrile, etc. under heating, e.g. at a temperature of 40-120° C.

EXAMPLES

The present invention is Further exemplified by the following examples that illustrate the preparation of compounds of Formula (I) according to the invention. The examples are for illustrative purpose only and are not intended, nor should they be construed as limiting the invention in any manner. Those skilled in the aroom temperature will appreciate that variations and modifications can be made without changing the scope of the invention.

The analyses of the compounds prepared in the following examples were carried out as follows: Nuclear magnetic resonance (NMR) spectrum analysis was carried out using Bruker 400 MHz spectrometer and Agilent 600 MHz spectrometer and chemical shifts thereof were analyzed in ppm. Further, the indicated molecular weights were measured by using liquid chromatography/mass selective detector (MSD) of Agilent 1260 Infinity series equipped with an electrostatic spray interface (by using Single Quadrupole, it indicates a value of m/z in ESI+ (ESI-MS (cation), which is represented by the (M+H)$^+$ peak). Column chromatography was carried out on silica gel (Merck, 70-230 mesh). (W. C. Still, J. Org. Chem., 43, 2923, 1978). Further, the staroom temperature-ing materials in each Example are known compounds, which were synthesized according to literatures or obtained from the market such as Sigma-Aldrich. Further, the abbreviations used in the following examples are as follows:

TABLE 2

| List of abbreviations | |
|---|---|
| DCM | Methylene chloride |
| DIPEA | N,N-Diisopropylethylamine |
| DMA | N,N-Dimethylacetamide |
| DMF | N,N-Dimethylformamide |
| DMSO | Dimethyl sulfoxide |
| EA | Ethyl acetate |
| HATU | Hexafluorophosphate azabenzotriazole tetramethyl uronium |
| K$_2$CO$_3$ | Potassium carbonate |
| MeCN | Acetonitrile |
| MeOH | Methanol |
| MgSO$_4$ | Magnesium sulfate |
| n-Hex | n-Hexane |
| sat. NaHCO$_3$ soln. | saturated sodium bicarbonate solution |
| TFA | Trifluoroacetic acid |
| XPhos | [2-Dicyclohexylphosphino-2',4',6'-triisopropylbiphenyl] |

Reference Example 1. (1s,4s)-4-((6'-Chloro-5-((1-methylpiperidin-4-yl)oxy)-[2,3'-bipyridin]-4'-yl)amino)-1-methylcyclohexan-1-ol Step 1. 6'-Chloro-4'-fluoro-5-((1-methylpiperidin-4-yl)oxy)-2,3'-bipyridine To a solution of 2-bromo-5-((1-methyl-4-piperidyl)oxy)pyridine (500 mg, 1.84 mmol) in 1,4-dioxane (4.53 mL) were added 2-chloro-4-fluoro-5-(4,4,5,5-tetramethyl-1,3,2-dioxaborolan-2-yl)pyridine (617 mg, 2.4 mmol), [1,1'-bis(diphenylphosphino)ferrocene]dichloropalladium (II), complex with dichloromethane (151 mg, 0.180 mmol) and 3M K$_2$CO$_3$ soln. (1.84 mL, 5.53 mmol). The reaction mixture was stirred at 90° C. for 2 hours. The reaction mixture was cooled to room temperature, and quenched with water, then extracted with DCM. The organic layer was dried over MgSO$_4$, filtered, and concentrated. The crude residue was purified by silica gel column chromatography (EA/n-Hex=0-30%) to give 6'-chloro-4'-fluoro-5-((1-methylpiperidin-4-yl)oxy)-2,3'-bipyridine (531 mg) as a pale brown solid. MS (ESI) m/z=322.1 (M+H)$^+$ Step 2. (1s,4s)-4-((6'-Chloro-5-((1-methylpiperidin-4-yl)oxy)-[2,3'-bipyridin]-4'-yl)amino)-1-methylcyclohexan-1-ol To a solution of 6'-chloro-4'-fluoro-5-((1-methylpiperidin-4-yl)oxy)-2,3'-bipyridine (96 mg, 0.298 mmol) in DMA (2 mL) were added DIPEA (0.21 mL, 1.19 mmol) and cis-4-amino-1-methylcyclohexanol (58 mg, 0.450 mmol). The reaction mixture was stirred at 90° C. for 4 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-30%) to give (1s,4s)-4-((6'-chloro-5-((1-methylpiperidin-4-yl)oxy)-[2,3'-bipyridin]-4'-yl)amino)-1-methylcyclohexan-1-ol (92 mg) as a pale brown solid. MS (ESI) m/z=431.2 (M+H)$^+$

Reference Example 2. 6'-Chloro-N-(4-fluorocyclohexyl)-5-((1-methylpiperidin-4-yl)oxy)-[2,3'-bipyridin]-4'-amine The title compound as a brown solid (92 mg) was prepared in the same fashion as Step 2 of Reference Example 1, except that 4-fluorocyclohexan-1-amine hydrochloride (72 mg, 0.466 mmol) was used instead of cis-4-amino-1-methylcyclohexanol. MS (ESI) m/z=419.2 (M+H)$^+$

Reference Example 3. (1s,4s)-4-((2-Chloro-5-(4,4,5,5-tetramethyl-1,3,2-dioxaborolan-2-yl)pyridin-4-yl)amino)-1-methylcyclohexan-1-ol To a solution of 2-chloro-4-fluoropyridine-5-boronic acid pinacol ester (1000 mg, 3.88 mmol) in DMA (10 mL) were added cis-4-amino-1-methylcyclohexanol (753 mg, 5.83 mmol) and DIPEA (1.73 mL, 9.71 mmol). The reaction mixture was heated to 90° C. for 4 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-50%) to give (1s,4s)-4-((2-chloro-5-(4,4,5,5-tetramethyl-1,3,2-dioxaborolan-2-yl)pyridin-4-yl)amino)-1-methylcyclohexan-1-ol (1313 mg, 3.581 mmol) as a pale yellow solid. $^1$H-NMR (CDCl$_3$, 400 MHz) δ 8.26 (s, 1H), 6.39 (d, 1H), 6.37 (s, 1H), 3.27-3.20 (m, 1H), 1.90-1.86 (m, 2H), 1.76-1.73 (m, 2H), 1.69-1.49 (m, 4H), 1.33 (s, 12H), 1.30 (s, 3H); MS (ESI) m/z=285.1 (M+H)$^+$

Reference Example 4. 6'-Chloro-4'-fluoro-[2,3'-bipyridin]-5-ol

To a solution of 2-bromo-5-hydroxypyridine (84 mg, 0.485 mmol) in 1,4-dioxane (3 mL) were added 2-chloro-4-fluoro-5-(4,4,5,5,-tetramethyl-1,3,2-dioxaborolan-2-yl)pyridine (150 mg, 0.583 mmol), [1,1'-bis(diphenylphosphino)ferrocene]dichloropalladium (II), complex with dichloromethane (48 mg, 0.058 mmol) and 3M K$_2$CO$_3$ soln. (0.49 mL, 1.456 mmol). The reaction mixture was stirred at 90° C. for 2 hours. The reaction mixture was cooled to room temperature, and quenched with water, then extracted with DCM. The organic layer was dried over MgSO$_4$, filtered, and concentrated. The crude residue was purified by silica gel column chromatography (EA/n-Hex=0-40%) to give 6'-chloro-4'-fluoro-[2,3'-bipyridin]-5-ol (112 mg) as a pale yellow solid. MS (ESI) m/z=225.0 (M+H)$^+$

Reference Example 5. 2-Chloro-4-fluoro-5-(5-methylsulfonyl-2-pyridyl)pyridine To a solution of 2-bromo-5-(methylsulfonyl)pyridine (300 mg, 1.27 mmol) in 1,4-dioxane (4.53 mL) were added 2-chloro-4-fluoro-5-(4,4,5,5,-tetramethyl-1,3,2-dioxaborolan-2-yl)pyridine (425 mg, 1.65 mmol), [1,1'-bis(diphenylphosphino)ferrocene]dichloropalladium (II), complex with dichloromethane (104 mg. 0.130 mmol) and 3M K$_2$CO$_3$ soln. (1.27 mL, 3.81 mmol). The reaction mixture was stirred at 90° C. for 2 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-30%) to give 2-chloro-4-fluoro-5-(5-methylsulfonyl-2-pyridyl)pyridine (332 mg) as a pale yellow solid. $^1$H-NMR (CDCl$_3$, 400 MHz) δ 9.27 (s, 1H), 9.15 (d, 1H), 8.34 (d, 1H), 7.99 (d, 1H), 7.27 (d, 1H), 3.18 (s, 3H); MS (ESI) m/z=287.0 (M+H)$^+$

Reference Example 6. 6'-Chloro-4',6-difluoro-2,3'-bipyridine

To a solution of 2-chloro-4-fluoro-5-iodopyridine (1000 mg. 3.88 mmol) in 1,4-dioxane (19.4 mL) were added 6-fluoropyridine-2-boronic acid (657 mg, 4.66 mmol), [1,1'-bis(diphenylphosphino)ferrocene]dichloropalladium (II), complex with dichloromethane (317 mg, 0.390 mmol) and 3M K$_2$CO$_3$ soln. (3.88 mL, 11.65 mmol). The reaction mixture was stirred at 90° C. for 3 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-50%) to give 6'-chloro-4',6-difluoro-2,3'-bipyridine (790 mg) as a white solid. $^1$H-NMR (CDCl$_3$, 400 MHz) δ 9.07 (d, 1H), 7.92 (q, 1H), 7.69 (d, 1H), 7.22 (d, 1H), 7.00 (dd, 1H)

Reference Example 7. 2-(6'-Chloro-4'-fluoro-[2,3'-bipyridin]-5-yl)propan-2-ol The title compound as a white solid (545 mg) was prepared in the same fashion as Reference Example 4, except that 2-(6-bromo-3-pyridyl)propan-2-ol (700 mg. 3.24 mmol) was used instead of 2-bromo-5-hydroxypyridine. $^1$H-NMR CDCl$_3$, 400 MHz) δ 8.99 (d, 1H), 8.85 (d, 1H), 7.93 (dd, 1H), 7.70 (dd, 1H), 7.19 (d, 1H), 2.24 (s, 1H), 1.65 (s, 6H); MS (ESI) m/z=267.0 (M+H)$^+$

Reference Example 8. 6'-Chloro-4'-fluoro-5-(2,2,2-trifluoroethyl)-2,3'-bipyridine The title compound as a white solid (488 mg) was prepared in the same fashion as Reference Example 4, except that 2-bromo-5-(2,2,2-trifluoroethyl)pyridine (500 mg, 2.08 mmol) was used instead of 2-bromo-5-hydroxypyridine. $^1$H-NMR (CDCl$_3$, 400 MHz) δ 9.06 (d, 1H), 8.68 (s, 1H), 7.78 (s, 2H), 7.22 (d, 1H), 3.47 (q, 2H); MS (ESI) m/z=(M+H)$^+$

Reference Example 9. 6'-Chloro-5-(3,3-difluoroazetidin-1-yl)-4'-fluoro-2,3'-bipyridine The title compound as an off-white solid (185 mg) was prepared in the same fashion as Reference Example 4, except that 2-bromo-5-(3,3-difluoroazetidin-1-yl)pyridine (500 mg, 2.01 mmol) was used instead of 2-bromo-5-hydroxypyridine. $^1$H-NMR (CDCl$_3$, 400 MHz) δ 8.99 (d, 1H), 8.04 (d, 1H), 7.65 (d, 1H), 7.17 (d, 1H), 6.88 (dd, 1H), 4.37 (q, 4H)

Reference Example 10. 1-(6'-Chloro-4'-fluoro-[2,3'-bipyridin]-5-yl)-2,2,2-trifluoroethan-1-ol The title compound as an off-white solid (185 mg) was prepared in the same fashion as Reference Example 4, except that 1-(6-bromo-3-pyridyl)-2,2,2-trifluoro-ethanol (514 mg, 2.01 mmol) was used instead of 2-bromo-5-hydroxypyridine. MS (ESI) m/z=307.0 (M+H)$^+$

Reference Example 11. 2-(6'-Chloro-4'-fluoro-[2,3'-bipyridin]-5-yl)-1,1,1-trifluoropropan-2-ol The title compound as an off-white solid (185 mg) was prepared in the same fashion as Reference Example 4, except that 2-(6-bromo-3-pyridyl)-1,1,1-trifluoro-propan-2-ol (542 mg, 2.01 mmol) was used instead of 2-bromo-5-hydroxypyridine. MS (ESI) m/z=321.0 (M+H)⁺

Reference Example 12. 6'-Chloro-4'-fluoro-5-(2-fluoropropan-2-yl)-2,3'-bipyridine The title compound as an off-white solid (402 mg) was prepared in the same fashion as Reference Example 4, except that 2-bromo-5-(1-fluoro-1-methyl-ethyl)pyridine (436 mg, 2 mmol) was used instead of 2-bromo-5-hydroxypyridine. MS (ESI) m/z 269.0=(M+H)⁺

Reference Example 13. 5-(2-(azetidin-1-yl)ethoxy)-6'-chloro-4'-fluoro-2,3'-bipyridine The title compound as a pale brown solid (113 mg) was prepared in the same fashion as Reference Example 4, except that 5-[2-(azetidin-1-yl) ethoxy]-2-bromo-pyridine (100 mg, 0.390 mmol) was used instead of 2-bromo-5-hydroxypyridine. MS (ESI) m/z=308.0 (M+H)⁺

Reference Example 14. (1s,4s)-4-((2-Chloro-5-iodopyridin-4-yl)amino)-1-methylcyclohexan-1-ol The title compound as a white solid (2.12 g) was prepared in the same fashion as Step 2 of Reference Example 1, except that 2-chloro-4-fluoro-5-iodopyridine (2.0 g. 7.769 mmol) was used instead of 6'-chloro-4'-fluoro-5-((1-methylpiperidin-4-yl)oxy)-2,3'-bipyridine. MS (ESI) m/z=367.0 (M+H)⁺

Reference Example 15. 6'-Chloro-N-(3,3-difluorocyclobutyl)-4'-fluoro-[2,3'-bipyridin]-4-amine Step 1.
2-Bromo-N-(3,3-difluorocyclobutyl)pyridin-4-amine The reaction mixture of 2-bromo-4-fluoropyridine (500 mg, 2.841 mmol), 3,3-difluorocyclobutan-1-amine hydrochloride (489 mg, 3.409 mmol) and DIPEA (1.24 mL, 7.103 mmol) in DMA (5 mL) was stirred at 90° C. for 4 hours. The reaction mixture was cooled to room temperature, diluted in DCM, washed by water, dried over MgSO₄, and then concentrated. The crude product was purified by column chromatography (EA/n-Hex=0-50%) to yield 2-bromo-N-(3,3-difluorocyclobutyl)pyridin-4-amine (567 mg) as a pale yellow solid. ¹H-NMR (CDCl₃, 400 MHz) δ 7.95 (d, 1H), 6.57 (s, 1H), 6.38 (d, 1H), 4.86 (s, 1H), 3.88 (s, 1H), 3.15-3.05 (m, 2H), 2.55-2.44 (m, 2H)

Step 2. 6'-Chloro-N-(3,3-difluorocyclobutyl)-4'-fluoro-[2,3'-bipyridin]-4-amine

The title compound as a white solid (631 mg) was prepared in the same fashion as Step 1 of Reference Example 1, except that 2-bromo-N-(3,3-difluorocyclobutyl)pyridin-4-amine (567 mg, 2.16 mmol) prepared in Step 1 were used instead of 2-bromo-5-((1-methyl-4-piperidyl)oxy)pyridine. ¹H-NMR (CDCl₃, 400 MHz) δ 8.97 (d, 1H), 8.36 (d, 1H), 7.18 (d, 1H), 6.83 (s, 1H), 6.44 (s, 1H), 4.64 (s, 1H), 3.96 (s, 1H), 3.17-3.07 (m, 2H), 2.58-2.46 (m, 2H)

Reference Example 16. 2-(1-(Cyclopropylsulfonyl)-1H-pyrazol-4-yl)-5-fluoropyrimidin-4-amine To a solution of 4-amino-2-chloro-5-fluoropyrimidine (1500 mg, 10.17 mmol) in 1,4-dioxane (50.85 mL) were added 1-(cyclopropanesulfonyl)-4-(tetramethyl-1,3,2-dioxaborolan-2-yl)-1H-pyrazole (3638 mg, 12.2 mmol), [1,1'-bis(diphenylphosphino)ferrocene]dichloropalladium (II), complex with dichloromethane (830 mg, 1.02 mmol) and 3M K₂CO₃ soln. (10.17 mL, 30.5 mmol). The reaction mixture was stirred at 90° C. for 3 hours. The reaction mixture was cooled to room temperature, quenched with water, and then extracted with DCM. The organic layer was dried over MgSO₄, filtered, and concentrated. The crude residue was purified by silica gel column chromatography (EA/n-Hex=0-60%) to give 2-(1-(cyclopropylsulfonyl)-1H-pyrazol-4-yl)-5-fluoropyrimidin-4-amine (1494 mg) as a yellowish solid. ¹H-NMR (DMSO-d₆, 400 MHz) δ 8.47 (s, 1H), 8.29 (s, 1H), 8.19 (d, 1H), 7.38 (s, 2H), 3.26-3.19 (m, 1H), 1.33-1.20 (m, 4H); MS (ESI) m/z=284.0 (M+H)⁺

Reference Example 17. 2-(1-(2,2-difluoroethyl)-1H-pyrazol-4-yl)pyrimidin-4-amine To a solution of 2-bromo-4-pyrimidinamine (500 mg, 2.874 mmol) in 1,4-dioxane (9 mL) were added 1-(2,2-difluoroethyl)-4-(4,4,5,5-tetramethyl-1,3,2-dioxaborolan-2-yl)pyrazole (964 mg, 3.736 mmol), [1,1'-bis(diphenylphosphino)ferrocene]dichloropalladium (II), complex with dichloromethane (235 mg, 0.290 mmol) and 3M K₂CO₃ soln. (2.87 mL, 8.62 mmol). The reaction mixture was stirred at 90° C. for 3 hours. The reaction mixture was cooled to room temperature, quenched with water, and then extracted with DCM. The organic layer was dried over MgSO₄, filtered, and concentrated. The crude residue was purified by silica gel column chromatography (EA/n-Hex=0-50%) to give 2-(1-(2,2-difluoroethyl)-1H-pyrazol-4-yl)pyrimidin-4-amine (325 mg) as a yellowish solid. ¹H-NMR (CDCl₃, 400 MHz) δ 8.23 (d, 1H), 8.18 (s, 1H), 8.12 (s, 1H), 6.27 (d, 1H), 6.13 (tt, 1H), 4.87 (s, 2H), 4.50 (td, 2H); MS (ESI) m/z=226.0 (M+H)⁺

Reference Example 18. 2-(1-(2,2,2-Trifluoroethyl)-1H-pyrazol-4-yl)pyrimidin-4-amine The title compound as a white solid (303 mg) was prepared in the same fashion as Reference Example 17, except that 4-(4,4,5,5-tetramethyl-1,3,2-dioxaborolan-2-yl)-1-(2,2,2-trifluoroethyl)-1H-pyrazole (619 mg, 2.241 mmol) was used instead of 1-(2,2-difluoroethyl)-4-(4,4,5,5-tetramethyl-1,3,2-dioxaborolan-2-yl)pyrazole. ¹H-NMR (MeOD, 400 MHz) δ 8.30 (s, 1H), 8.13 (s, 1H), 8.04 (d, 1H), 6.36 (d, 1H), 5.01 (q, 2H); MS (ESI) m/z=244.0 (M+H)⁺

Reference Example 19. 2-(3-Methyl-1-(2,2,2-trifluoroethyl)-1H-pyrazol-4-yl)pyrimidin-4-amine The title compound as a white solid (325 mg) was prepared in the same fashion as Reference Example 17, except that 3-methyl-4-(4,4,5,5-tetramethyl-1,3,2-dioxaborolan-2-yl)-1-(2,2,2-trifluoroethyl)pyrazole (650 mg. 2.241 mmol) was used instead of 1-(2,2-difluoroethyl)-4-(4,4,5,5-tetramethyl-1,3,2-dioxaborolan-2-yl)pyrazole. MS (ESI) m/z=284.0 (M+H)⁺

Reference Example 20. 4-(4-Aminopyrimidin-2-yl)-N,N-dimethyl-1H-pyrazole-1-sulfonamide The title compound as a white solid (344 mg) was prepared in the same fashion as Reference Example 17, except that 4-amino-2-chloropyrimidine (250 mg, 1.93 mmol) and N,N-dimethyl-4-(4,4,5,5-tetramethyl-1,3,2-dioxaborolan-2-yl)pyrazole-1-sulfonamide (697 mg., 2.316 mmol) were used instead of 2-bromo-4-pyrimidinamine and 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.59 (s, 1H), 8.33 (s, 1H), 8.25 (sd, 1H), 6.31 (d, 1H), 4.95 (s, 2H), 2.98 (s, 6H)

Reference Example 21. 2-(1-(2,2-Difluoroethyl)-3, 5-dimethyl-1H-pyrazol-4-yl)pyrimidin-4-amine The title compound as a white solid (123 mg) was prepared in the same fashion as Reference Example 17, except that 1-(2,2-difluoroethyl)-3,5-dimethyl-4-(4,4,5,5-tetramethyl-1,3,2-dioxaborolan-2-yl)-1H-pyrazole (641 mg, 2.24 mmol) was used instead of 1-(2,2-difluoroethyl)-4-(4, 4,5,5-tetramethyl-1,3,2-dioxaborolan-2-yl)pyrazole
$^1$H-NMR (CDCl$_3$, 400 MHz) δ 8.29 (d, 1H), 6.26 (d, 1H), 6.12 (tt, 1H), 4.78 (s, 2H), 4.39 (td, 2H), 2.62 (s, 3H), 2.52 (s, 3H)

Reference Example 22. 2-(1-(2,2,3,3-Tetrafluoropropyl)-1H-pyrazol-4-yl)pyrimidin-4-amine The title compound as a white solid (293 mg) was prepared in the same fashion as Reference Example 17, except that 1-(2,2,3,3-tetrafluoropropyl)-4-(4,4,5,5-tetramethyl-1,3,2-dioxaborolan-2-yl)-1H-pyrazole (691 mg. 2.24 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 8.24 (d, 1H), 8.20 (s, 1H), 8.16 (s, 1H), 6.28 (d, 1H), 5.88 (tt, 1H), 4.85 (s, 2H), 4.70 (t, 2H)

Reference Example 23. 1-(4-Amino-5-fluoropyrimidin-2-yl)-3,3-difluoropiperidin-4-ol To a solution of 2-chloro-5-fluoropyrimidin-4-amine (150 mg, 1.017 mmol) in DMA (2 mL) were added DIPEA (0.53 mL, 3.05 mmol) and 3,3-difluoropiperidin-4-ol hydrochloride (229 mg, 1.322 mmol). The reaction mixture was stirred at 90° C. overnight. The reaction mixture was cooled to room temperature, and quenched with water, then extracted with DCM. The organic layer was dried over MgSO$_4$, filtered, and concentrated. The crude residue was purified by silica gel column chromatography (EA/MeOH=0-20%) to give 1-(4-amino-5-fluoropyrimidin-2-yl)-3,3-difluoropiperidin-4-ol (122 mg) as a pale yellow oil. MS (ESI) m/z=249.1 (M+H)$^+$ Reference Example 24. 5-Fluoro-2-((3R,4S)-3-fluoro-4-methoxypiperidin-1-yl)pyrimidin-4-amine The title compound as a pale yellow oil (202 mg) was prepared in the same fashion as Reference Example 23, except that (3R,4S)-3-fluoro-4-methoxypiperidine hydrochloride (224 mg. 1.322 mmol) was used instead of 3,3-difluoropiperidin-4-ol hydrochloride. MS (ESI) m/z=245.1 (M+H)$^+$ Reference Example 25. 4-(6'-Chloro-4'-fluoro-[2,3'-bipyridin]-5-yl) morpholine The reaction mixture of 2-chloro-4-fluoro-5-(4,4,5,5-tetramethyl-1,3,2-dioxaborolan-2-yl)pyridine (159 mg, 0.620 mmol), 4-(6-bromo-3-pyridyl) morpholine (150 mg, 0.617 mmol), [1,1'-bis(diphenylphosphino)ferrocene]dichloropalladium (II), complex with dichloromethane (50 mg, 0.062 mmol), and 3M K$_2$CO$_3$ soln. (0.62 mL, 1.851 mmol) in 1,4-dioxane (2 mL) was stirred at 70° C. for 3 hours. The reaction mixture was cooled to room temperature and extracted with DCM. The organic layer was dried over MgSO$_4$, filtered, and concentrated. The crude residue was purified by silica gel column chromatography (EA/n-Hex=10-60%) to give 4-(6'-chloro-4'-fluoro-[2,3'-bipyridin]-5-yl) morpholine (93 mg) as a pale yellow solid. $^1$H-NMR (CDCl$_3$, 400 MHz) δ 9.01 (d, 1H), 8.42 (d, 1H), 7.65 (dd, 1H), 7.23 (dd, 1H) 7.17 (d, 1H), 3.91 (t, 4H), 3.29 (t, 4H)

Reference Example 26. ((1s,4s)-4-((2-Chloro-5-iodopyridin-4-yl)amino)cyclohexyl)methanol The title compound as pale yellow liquid (606 mg) was prepared in the same fashion as Step 2 of Reference Example 1, except that 2-chloro-4-fluoro-5-iodopyridine (500 mg, 1.942 mmol) and ((1s,4s)-4-aminocyclohexyl) methanol (376 mg, 2.91 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=367.0 (M+H)$^+$ Reference Example 27. (1s,4s)-N$^1$-(2-Chloro-5-iodopyridin-4-yl)-N$^4$-(2-fluoroethyl)cyclohexane-1, 4-diamine The title compound as pale yellow liquid (635 mg) was prepared in the same fashion as Step 2 of Reference Example 1, except that 2-chloro-4-fluoro-5-iodopyridine (500 mg, 1.942 mmol) and (1s,4s)-N$^1$-(2-fluoroethyl)cyclohexane-1,4-diamine (160 mg. 2.91 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=398.0 (M+H)$^+$ Reference Example 28. 2-Chloro-N-((1s,4s)-4-((dimethylamino)methyl)cyclohexyl)-5-iodopyridin-4-amine The title compound as pale yellow liquid (661 mg) was prepared in the same fashion as Step 2 of Reference Example 1, except that 2-chloro-4-fluoro-5-iodopyridine (500 mg, 1.942 mmol) and (1s,4s)-4-((dimethylamino) methyl)cyclohexan-1-amine dihydrochloride (668 mg. 2.91 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=394.0 (M+H)$^+$ Example 1. (1-(6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)-4-methylpiperidin-4-yl)methanol Step 1. 6'-Chloro-4'-fluoro-5-((4-methylpiperazin-1-yl)methyl)-2,3'-bipyridine To a solution of 2-chloro-4-fluoropyridine-5-boronic acid pinacol ester (100 mg, 0.390 mmol) in 1,4-dioxane (2 mL) were added 1-((6-bromopyridin-3-yl)methyl)-4-methylpiperazine (115 mg, 0.430 mmol), (1,1'-bis(diphenylphosphino) ferrocene)-dichloropalladium (II), complex with dichloromethane (3 mg, 0.040 mmol) and 3 M K$_2$CO$_3$ soln. (0.4 mL, 1.170 mmol). The reaction mixture was stirred at 90° C. for 3 hours. The reaction mixture was cooled to room temperature, and diluted with water and DCM, then extracted with DCM. The organic layer was dried over MgSO$_4$, filtered, and concentrated. The crude residue was purified by silica gel column chromatography (MeOH/DCM=0-10%) to give 6'-chloro-4'-fluoro-5-((4-methylpiperazin-1-yl)methyl)-2,3'-bipyridine (93 mg) as a pale yellow solid. $^1$H-NMR (CDCl$_3$, 400 MHz) δ 9.01 (d, 1H), 8.65 (s, 1H), 7.76 (d, 1H), 7.67 (d, 1H), 7.18 (d, 1H), 3.56 (s, 2H), 2.45 (brs, 8H), 2.28 (s, 3H); MS (ESI) m/z=321.1 (M+H)$^+$ Step 2. (1-(6'-Chloro-5-((4-methylpiperazin-1-yl)methyl)-[2,3'-bipyridin]-4'-yl)-4-methylpiperidin-4-yl)methanol The reaction mixture of 6'-chloro-4'-fluoro-5-((4-methylpiperazin-1-yl)methyl)-2,3'-bipyridine (45 mg, 0.130 mmol) prepared in Step 1, (4-methylpiperidin-4-yl)methanol (25 mg, 0.195 mmol) and DIPEA (0.04 mL, 0.27 mmol) in DMA (5 mL) was stirred at 90° C. overnight. The reaction mixture was cooled, diluted in EA, washed by water, dried over MgSO$_4$, and then concentrated. The crude product was purified by column chromatography (MeOH/DCM=10%) to yield (1-(6'-chloro-5-((4-methylpiperazin-1-yl)methyl)-[2,3'-bipyridin]-4'-yl)-4-methylpiperidin-4-yl)methanol (36 mg) as a solid. $^1$H-NMR (CDCl$_3$, 400 MHz) δ 8.60 (d, 1H), 8.23 (s, 1H), 7.71 (dd, 1H), 7.62 (d, 1H), 6.84 (s, 1H), 3.57 (s, 2H), 3.33 (s, 2H), 2.97-2.03 (m, 2H), 2.89-2.83 (m, 2H), 2.49 (brs, 8H), 2.29 (s, 3H), 1.50-1.43 (m, 2H), 0.93 (s, 3H)

Step 3. (1-(6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)-4-methylpiperidin-4-yl)methanol The suspension of 2-(1-(cyclopropylsulfonyl)-1H-pyrazol-4-yl)pyrimidin-4-amine (10 mg, 0.038 mmol), tris(dibenzylideneacetone) dipalladium (0) (7 mg, 0.01 mmol), Xphos (7 mg, 0.02 mmol, cesium carbonate (31 mg, 0.09 mmol) and (1-(6'-chloro-5-((4-methylpiperazin-1-yl)methyl)-[2,3'-bipyridin]-4'-yl)-4-methylpiperidin-4-yl)methanol (21 mg, 0.050 mmol) prepared in Step 2 in 1,4-dioxane (5 mL) was stirred at 110° C. overnight. The mixture was diluted in DCM, filtered through Celite, and then concentrated. The crude product was purified by column chromatography (EA/n-Hex=35-50%) to yield (1-(6'-((2-(1-(cyclopropylsulfonyl)-1H-pyrazol-4-yl)pyrimidin-4-yl)amino)-5-((4-methylpiperazin-1-yl)methyl)-[2,3'-bipyridin]-4'-yl)-4-methylpiperidin-4-yl)methanol (8.5 mg) as an off-white solid. $^1$H-NMR (CDCl$_3$, 400 MHz) δ 8.64 (s, 1H), 8.45 (d, 1H), 8.38-8.34 (m, 3H), 8.01 (s, 1H), 7.74 (dd, 1H), 7.63 (d, 1H), 6.99 (d, 1H), 3.68 (s, 2H), 3.41 (s, 2H), 3.27-3.24 (m, 2H), 3.15-3.03 (m, 6H), 2.88-2.79 (m, 5H), 2.69 (s, 3H), 1.62-1.52 (m, 4H), 1.38-1.34 (m, 2H), 1.28-1.24 (m, 2H), 1.00 (s, 3H); MS (ESI) m/z=659.3 (M+H)$^+$ Example 2. N$^{6'}$-(2-(1-(Cyclopropylsulfonyl)-1H-pyrazol-4-yl)pyrimidin-4-yl)-N$^{4'}$-((1s,4s)-4-((2-fluoroethyl)amino)cyclohexyl)-5-((4-methylpiperazin-1-yl)methyl)-[2,3'-bipyridine]-4',6-diamine Step 1. (1s,4s)—N$^1$-(6'-Chloro-5-((4-methylpiperazin-1-yl)methyl)-[2,3'-bipyridin]-4'-yl)-N$^4$-(2-fluoroethyl)cyclohexane-1,4-diamine The title compound as a solid (48 mg) was prepared in the same fashion as Step 2 in Example 1 except that (1s,4s)—N$^1$-(2-fluoroethyl)cyclohexane-1,4-diamine (31 mg, 0.195 mmol) was used instead of (4-methylpiperidin-4-yl)methanol. $^1$H-NMR (CDCl$_3$, 400 MHz) δ 9.77 (d, 1H), 8.50 (d, 1H), 8.40 (s, 1H), 7.77 (dd, 1H), 7.69 (d, 1H), 6.55 (s, 1H), 4.61 (dd, 1H), 4.49 (dd, 1H), 3.65-3.62 (m, 1H), 3.54 (s, 2H), 2.96 (dd, 1H), 2.89 (dd, 1H), 2.68-2.63 (m, 1H), 2.46 (brs, 8H), 2.29 (s, 3H), 1.93-1.88 (m, 2H), 1.81-1.73 (m, 4H), 1.56-1.42 (m, 2H)

Step 2. N$^{6'}$-(2-(1-(Cyclopropylsulfonyl)-1H-pyrazol-4-yl)pyrimidin-4-yl)-N$^{4'}$-((1s,4s)-4-((2-fluoroethyl)amino)cyclohexyl)-5-((4-methylpiperazin-1-yl)methyl)-[2,3'-bipyridine]-4',6-diamine The title compound (4.6 mg) was prepared in the same fashion as Step 3 in Example 1, except that (1s,4s)—N$^1$-(6'-chloro-5-((4-methylpiperazin-1-yl)methyl)-[2,3'-bipyridin]-4'-yl)-N$^4$-(2-fluoroethyl)cyclohexane-1,4-diamine (23 mg, 0.050 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.61 (d, 1H), 8.45 (d, 1H), 8.37-8.34 (m, 3H), 8.13 (s, 1H), 7.82-7.72 (m, 3H), 7.06 (d, 1H), 4.78 (brs, 1H), 4.66 (brs, 1H), 4.08 (brs, 1H), 3.71 (s, 2H) 3.26-3.02 (m, 6H), 2.88-2.77 (m, 5H), 2.66 (s, 3H), 2.20-1.94 (m, 6H), 1.74-1.68 (m, 2H), 1.57-1.55 (m, 2H), 1.28-1.25 (m, 2H); MS (ESI) m/z=659.3 (M+H)$^+$ Example 3. (1s,4s)-4-((6'-((2-(1-(Cyclopropylsulfonyl)-1H-pyrazol-4-yl)pyrimidin-4-yl)amino)-3-methoxy-[2,3'-bipyridin]-4'-yl)amino)-1-methylcyclohexan-1-ol Step 1.
2-Chloro-4-fluoro-5-(3-methoxy-2-pyridyl)pyridine The title compound as an off-white solid (142 mg) was prepared in the same fashion as Step 1 in Example 1, except that 2-bromo-3-methoxypyridine (183 mg, 0.97 mmol) was used instead of 1-((6-bromopyridin-3-yl)methyl)-4-methylpiperazine. $^1$H-NMR (CDCl$_3$, 400 MHz) δ 8.51 (d, 1H), 8.29 (s, 1H), 7.31 (m, 2H), 7.13 (d, 1H), 3.82 (s, 3H)

Step 2. (1s,4s)-4-((6'-Chloro-3-methoxy-[2,3'-bipyridin]-4'-yl)amino)-1-methylcyclohexan-1-ol The title compound as a white solid (135 mg) was prepared in the same fashion as Step 2 in Example 1, except that 2-chloro-4-fluoro-5-(3-methoxy-2-pyridyl)pyridine (142 mg, 0.59 mmol) prepared in Step 1 and cis-4-amino-1-methylcyclohexanol (115 mg, 0.89 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.32 (s, 1H), 8.17 (d, 1H), 7.27 (d, 1H), 7.19 (m, 2H), 6.52 (s, 1H), 3.77 (s, 3H), 3.23 (m, 1H), 1.99 (m, 2H), 1.80 (m, 2H), 1.69-1.46 (m, 4H), 1.21 (s, 3H); MS (ESI) m/z=348.0 (M+H)$^+$ Step 3. (1s,4s)-4-((6'-((2-(1-(Cyclopropylsulfonyl)-1H-pyrazol-4-yl)pyrimidin-4-yl)amino)-3-methoxy-[2,3'-bipyridin]-4'-yl)amino)-1-methylcyclohexan-1-ol The title compound as an off-white solid (3.4 mg) was prepared in the same fashion as Step 3 in Example 1, except that (1s,4s)-4-((6'-chloro-3-methoxy-[2,3'-bipyridin]-4'-yl)amino)-1-methylcyclohexan-1-ol (98 mg, 0.28 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400

MHz) δ 8.94 (s, 1H), 8.60 (m, 3H), 8.30 (m, 1H), 7.70 (d, 1H), 7.52 (m, 1H), 6.94 (m, 1H), 6.64 (s, 1H), 3.99 (s, 3H), 3.56 (m, 1H), 3.05 (m, 1H), 1.79 (m, 2H), 1.77 (m, 4H), 1.59 (m, 2H), 1.46 (m, 2H), 1.26 (m, 5H); MS (ESI) m/z=577.2 (M+H)$^+$

Example 4. (1s,4s)-4-((6'-((2-(1-(Cyclopropylsulfonyl)-1H-pyrazol-4-yl)pyrimidin-4-yl)amino)-3-fluoro-[2,3'-bipyridin]-4'-yl)amino)-1-methylcyclohexan-1-ol Step 1. 2-Chloro-4-fluoro-5-(3-fluoro-2-pyridyl)pyridine The title compound as an off-white solid (160 mg) was prepared in the same fashion as Step 1 in Example 1, except that 2-bromo-3-fluoropyridine (171 mg, 0.97 mmol) was used instead of 1-((6-bromopyridin-3-yl)methyl)-4-methylpiperazine. $^1$H-NMR (CDCl$_3$, 400 MHz) δ 8.66 (d, 1H), 8.56 (m, 1H), 7.55 (t, 1H), 7.43 (m, 1H), 7.21 (d, 1H); MS (ESI) m/z=226.8 (M+H)$^+$ Step 2. (1s,4s)-4-((6'-Chloro-3-fluoro-[2,3'-bipyridin]-4'-yl)amino)-1-methylcyclohexan-1-ol The title compound as a white solid (122 mg) was prepared in the same fashion as Step 2 in Example 1, except that 2-chloro-4-fluoro-5-(3-fluoro-2-pyridyl)pyridine (160 mg, 0.70 mmol) prepared in Step 1 and cis-4-amino-1-methylcyclohexanol (136 mg, 1.06 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.37 (d, 1H), 8.32 (d, 1H), 8.03 (m, 1H), 7.47 (m, 1H), 7.23 (m, 1H), 6.55 (s, 1H), 3.25 (m, 1H), 1.82 (m, 2H), 1.68-1.66 (m, 4H), 1.48 (m, 2H), 1.23 (s, 3H); MS (ESI) m/z=336.0 (M+H)$^+$ Step 3. (1s,4s)-4-((6'-((2-(1-(Cyclopropylsulfonyl)-1H-pyrazol-4-yl)pyrimidin-4-yl)amino)-3-fluoro-[2,3'-bipyridin]-4'-yl)amino)-1-methylcyclohexan-1-ol The title compound as an off-white solid (3.3 mg) was prepared in the same fashion as Step 3 in Example 1, except that (1s,4s)-4-((6'-chloro-3-fluoro-[2,3'-bipyridin]-4'-yl)amino)-1-methylcyclohexan-1-ol (76 mg. 0.23 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.84 (s, 1H), 8.52 (s, 2H), 8.47 (m, 1H), 8.42 (m, 1H), 7.80 (m, 1H), 7.48 (m, 1H), 7.20 (m, 1H), 7.03 (m, 1H), 3.56 (m, 1H), 3.04 (m, 1H), 1.92 (m, 2H), 1.76 (m, 4H), 1.58 (m, 2H), 1.50 (m, 2H), 1.25 (m, 5H); MS (ESI) m/z=565.1 (M+H)$^+$ Example 5. (1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)-1-methylcyclohexan-1-ol Step 1. (6'-Chloro-4'-fluoro-[2,3'-bipyridin]-5-yl)methanol The title compound as an off-white solid (1600 mg) was prepared in the same fashion as Step 1 in Example 1, except that 6-bromo-3-pyridinemethanol (2920 mg, 15.6 mmol) was used instead of 1-((6-bromopyridin-3-yl)methyl)-4-methylpiperazine. $^1$H-NMR (CDCl$_3$, 400 MHz) δ 9.01 (d, 1H), 8.72 (d, 1H), 7.84 (d, 1H), 7.74 (d, 1H), 7.21 (d, 1H), 4.82 (d, 2H), 2.18 (t, 1H); MS (ESI) m/z=238.8 (M+H)$^+$ Step 2. (1s,4s)-4-((6'-Chloro-5-(hydroxymethyl)-[2,3'-bipyridin]-4'-yl)amino)-1-methylcyclohexan-1-ol The title compound as a white solid (510 mg) was prepared in the same fashion as Step 2 in Example 1, except that (6'-chloro-4'-fluoro-[2,3'-bipyridin]-5-yl)methanol (388 mg, 1.625 mmol) prepared in Step 1 and cis-4-amino-1-methylcyclohexan-1-ol (210 mg, 1.625 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.36 (d, 1H), 8.58 (s, 1H), 8.40 (s, 1H), 7.82 (d, 1H), 7.73 (d, 1H), 6.58 (s, 1H), 4.79 (d, 2H), 3.35 (m, 1H), 1.94 (m, 2H), 1.78-1.67 (m, 4H), 1.62-1.55 (m, 2H), 1.31 (s, 3H); MS (ESI) m/z=348.0 (M+H)$^+$ Step 3. (1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)-1-methylcyclohexan-1-ol The title compound as an off-white solid (110 mg) was prepared in the same fashion as Step 3 in Example 1, except that (1s,4s)-4-((6'-chloro-5-(hydroxymethyl)-[2,3'-bipyridin]-4'-yl)amino)-1-methylcyclohexan-1-ol (110 mg. 0.415 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.02 (s, 1H), 9.49 (d, 1H), 8.65 (s, 1H), 8.53 (d, 1H), 8.47 (s, 1H), 8.43 (d, 1H), 7.95 (d, 1H), 7.81 (d, 1H), 7.53 (s, 1H), 7.31 (s, 1H), 5.36 (t, 1H), 4.56 (d, 2H) 3.45 (m, 1H), 3.30-3.22 (m, 1H), 1.84 (m, 2H), 1.68-1.56 (m, 4H), 1.45-1.39 (m, 2H), 1.31 (m, 2H), 1.24 (m, 2H), 1.14 (s, 3H); MS (ESI) m/z=577.2 (M+H)$^+$ Example 6. (1s,4s)-4-((6'-((2-(1-(Cyclopropylsulfonyl)-1H-pyrazol-4-yl)pyrimidin-4-yl)amino)-5-fluoro-[2,3'-bipyridin]-4'-yl)amino)-1-methylcyclohexan-1-ol Step 1. 6'-Chloro-4',5-difluoro-2,3'-bipyridine The title compound as an off-white solid (71 mg) was prepared in the same fashion as Step 1 in Example 1, except that 2-bromo-5-fluoropyridine (137 mg, 0.78 mmol) was used instead of 1-((6-bromopyridin-3-yl)methyl)-4-methylpiperazine. $^1$H-NMR (CDCl$_3$, 400 MHz) δ 9.01 (d, 1H), 8.61 (d, 1H), 7.80-7.76 (m, 1H), 7.55-7.50 (m, 1H), 7.21 (d, 1H); MS (ESI) m/z=227.0 (M+H)$^+$ Step 2. (1s,4s)-4-((6'-Chloro-5-fluoro-[2,3'-bipyridin]-4'-yl)amino)-1-methylcyclohexan-1-ol The title compound as a white solid (58 mg) was prepared in the same fashion as Step 2 in Example 1, except that 6'-chloro-4',5-difluoro-2,3'-bipyridine (53 mg, 0.231 mmol) prepared in Step 1 and cis-4-amino-1-methylcyclohexan-1-ol (30 mg, 0.231 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.90 (d, 1H), 8.45 (d, 1H), 8.34 (s, 1H), 7.73 (dd, 1H), 7.54 (m, 1H), 6.58 (s, 1H), 3.39-3.31 (m, 1H), 1.96-1.92 (m, 2H), 1.78-1.66 (m, 4H), 1.61-1.55 (m, 2H), 1.31 (s, 3H)

Step 3. (1s,4s)-4-((6'-((2-(1-(Cyclopropylsulfonyl)-1H-pyrazol-4-yl)pyrimidin-4-yl)amino)-5-fluoro-[2,3'-bipyridin]-4'-yl)amino)-1-methylcyclohexan-1-ol The title compound as an off-white solid (12.9 mg) was prepared in the same fashion as Step 3 in Example 1, except that (1s,4s)-4-((6'-chloro-5-fluoro-[2,3'-bipyridin]-4'-yl)amino)-1-methylcyclohexan-1-ol (51 mg, 0.151 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanolS. $^1$H-NMR (CDCl$_3$, 400 MHz) δ 8.99 (d, 1H), 8.67 (s, 1H), 8.48 (s, 1H), 8.42-8.45 (m, 2H), 8.36 (brs, 1H), 7.71-7.75 (m, 1H), 7.60 (s, 1H), 7.50-7.55 (m, 1H), 7.33 (d, 1H), 7.00 (s, 1H), 3.51 (m, 1H), 2.85-2.80 (m, 1H), 2.06-1.99 (m, 2H), 1.77-1.51 (m, 8H), 1.32 (s, 3H), 1.23-1.18 (m, 2H); MS (ESI) m/z=565.2 (M+H)$^+$ Example 7. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbonitrile Step 1. 6'-Chloro-4'-fluoro-[2,3'-bipyridine]-5-carbonitrile The title compound as an off-white solid (132 mg) was prepared in the same fashion as Step 1 in Example 1, except that 2-bromo-5-cyanopyridine (284 mg, 1.56 mmol) was used instead of 1-((6-bromopyridin-3-yl)methyl)-4-methylpiperazine. $^1$H-NMR (CDCl$_3$, 400 MHz) δ 9.01 (d, 1H), 8.97 (d, 1H), 8.09 (dd, 1H), 7.93 (d, 1H), 7.26 (d, 1H); MS (ESI) m/z=234.0 (M+H)$^+$ Step 2. 6'-Chloro-4'-(((1s, 4s)-4-hydroxy-4-methylcyclohexyl)amino)-[2,3'-bipyridine]-5-carbonitrile The title compound as a white solid (87 mg) was prepared in the same fashion as Step 2 in Example 1, except that 6'-chloro-4'-fluoro-[2,3'-bipyridine]-5-carbonitrile (72 mg, 0.308 mmol) prepared in Step 1 and cis-4-amino-1-methylcyclohexan-1-ol (40 mg, 0.308 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.26 (d, 1H), 8.85 (d, 1H), 8.48 (s, 1H), 8.15 (dd, 1H), 8.02 (dd, 1H), 7.87 (d, 1H), 6.62 (s, 1H), 3.40-3.34 (m, 1H), 1.97-1.93 (m, 2H), 1.80-1.69 (m, 4H), 1.62-1.54 (m, 2H), 1.32 (s, 3H); MS (ESI) m/z=343.1 (M+H)$^+$ Step 3. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbonitrile The title compound as an off-white solid (3.4 mg) was prepared in the same fashion as Step 3 in Example 1, except that 6'-chloro-4'-(((1s,4s)-4-hydroxy-4-methylcyclohexyl)amino)-[2,3'-bipyridine]-5-carbonitrile (52 mg, 0.151 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.82 (d, 1H), 8.62 (s, 1H), 8.42 (s, 1H), 8.39-8.36 (m, 2H), 8.16 (s, 1H), 7.97 (d, 1H), 7.87 (d, 1H), 7.54 (s, 1H), 7.07 (d, 1H), 3.55 (m, 1H), 2.82-2.78 (m, 1H), 1.91- 1.83 (m, 2H), 1.80-1.65 (m, 4H), 1.55-1.45 (m, 4H), 1.24 (s, 3H), 1.23-1.18 (m, 2H); MS (ESI) m/z=572.1 (M+H)$^+$ Example 8. (1s,4s)-4-((6'-((2-(1-(Cyclopropylsulfonyl)-1H-pyrazol-4-yl)pyrimidin-4-yl)amino)-5-methyl-[2,3'-bipyridin]-4'-yl)amino)-1-methylcyclohexan-1-ol Step 1. 6'-Chloro-4'-fluoro-5-methyl-2,3'-bipyridine The title compound as an off-white solid (92 mg) was prepared in the same fashion as Step 1 in Example 1, except that 2-bromo-5-methylpyridine (267 mg, 1.55 mmol) was used instead of 1-((6-bromopyridin-3-yl)methyl)-4-methylpiperazine. $^1$H-NMR (CDCl$_3$, 400 MHz) δ 9.01 (d, 1H), 8.57 (s, 1H), 7.65-7.59 (m, 2H), 7.18 (d, 1H), 2.40 (s, 3H); MS (ESI) m/z=223.1 (M+H)$^+$ Step 2. (1s,4s)-4-((6'-Chloro-5-methyl-[2,3'-bipyridin]-4'-yl)amino)-1-methylcyclohexan-1-ol The title compound as a white solid (73 mg) was prepared in the same fashion as Step 2 in Example 1, except that 6'-chloro-4'-fluoro-5-methyl-2,3'-bipyridine (52 mg, 0.231 mmol) prepared in Step 1 and cis-4-amino-1-methylcyclohexan-1-ol (30 mg, 0.231 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.33 (d, 1H), 8.41 (s, 1H), 8.36 (s, 1H), 7.61 (t, 2H), 6.56 (s, 1H), 3.39-3.31 (m, 1H), 2.38 (s, 3H), 1.98-1.93 (m, 2H), 1.78-1.67 (m, 4H), 1.61-1.54 (m, 2H), 1.31 (s, 3H); MS (ESI) m/z=332.1 (M+H)$^+$ Step 3. (1s,4s)-4-((6'-((2-(1-(Cyclopropylsulfonyl)-1H-pyrazol-4-yl)pyrimidin-4-yl)amino)-5-methyl-[2,3'-bipyridin]-4'-yl)amino)-1-methylcyclohexan-1-ol The title compound as an off-white solid (15.9 mg) was prepared in the same fashion as Step 3 in Example 1, except that (1s,4s)-4-((6'-chloro-5-methyl-[2,3'-bipyridin]-4'-yl)amino)-1-methylcyclohexan-1-ol (50 mg, 0.151 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanolS. $^1$H-NMR (DMSO-d$_6$, 400 MHz) δ 10.00 (s, 1H), 9.43 (d, 1H), 8.72 (s, 1H), 8.65-8.44 (m, 4H), 7.87 (d, 1H), 7.70 (dd, 1H), 7.55 (brs, 1H), 7.28 (brs, 1H), 3.45 (m, 1H), 3.27-3.22 (m, 1H), 2.33 (s, 3H), 1.84 (m, 2H), 1.67-1.56 (m, 4H), 1.45-1.39 (m, 2H), 1.33 (m, 2H), 1.26 (m, 2H), 1.14 (s, 3H); MS (ESI) m/z=561.2 (M+H)$^+$ Example 9. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol Step 1. (1s,4s)-4-((6'-Chloro-5-((4-methylpiperazin-1-yl)methyl)-[2,3'-bipyridin]-4'-yl)amino)-1-methylcyclohexan-1-ol The title compound as a white solid (84 mg) was prepared in the same fashion as Step 2 in Example 1, except that cis-4-amino-1-methylcyclohexan-1-ol (58 mg, 0.446 mmol) was used instead of (4-methylpiperidin-4-yl)methanol. $^1$H-NMR (CDCl$_3$, 400 MHz) δ 9.44 (d, 1H), 8.49 (d, 1H), 8.38 (s, 1H), 7.76 (dd, 1H), 7.67 (d, 1H), 6.56 (s, 1H), 3.54 (s, 2H), 3.35-3.24 (m, 1H), 2.50 (m, 8H), 2.29 (s, 3H), 1.93

(m, 2H), 1.77-1.67 (m, 4H), 1.60-1.52 (m, 2H), 1.30 (s, 3H); MS (ESI) m/z=430.2 (M+H)+

Step 2. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol The title compound as an off-white solid (5 mg) was prepared in the same fashion as Step 3 in Example 1, except that (1s,4s)-4-((6'-chloro-5-((4-methylpiperazin-1-yl)methyl)-[2,3'-bipyridin]-4'-yl)amino)-1-methylcyclohexan-1-ol (32 mg, 0.075 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.57 (s, 1H), 8.53 (s, 1H), 8.49 (s, 1H), 8.45 (d, 1H), 8.21 (s, 1H), 7.92 (s, 1H), 7.81 (d, 2H), 7.68 (d, 1H), 7.10 (d, 1H), 3.68 (m, 1H), 3.60 (s, 2H), 2.82 (m, 1H), 2.63 (m, 8H), 2.44 (s, 3H), 2.02 (m, 2H), 1.81 (m, 4H), 1.62 (m, 2H), 1.54 (m, 2H), 1.33 (s, 3H), 1.23 (m, 2H); MS (ESI) m/z=659.2 (M+H)+

Example 10. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)cyclohexyl)methanol Step 1. (1s,4s)-4-((6'-chloro-5-((4-methylpiperazin-1-yl)methyl)-[2,3'-bipyridin]-4'-yl)amino)cyclohexyl)methanol The title compound as a white solid (94 mg) was prepared in the same fashion as Step 2 in Example 1, except that ((1s,4s)-4-aminocyclohexyl)methanol (58 mg, 0.446 mmol) was used instead of (4-methylpiperidin-4-yl)methanol. $^1$H-NMR (CDCl$_3$, 400 MHz) δ 9.50 (d, 1H), 8.49 (d, 1H), 8.37 (s, 1H), 7.76 (dd, 1H), 7.67 (d, 1H), 6.56 (s, 1H), 3.54 (s, 2H), 3.49 (s, 2H), 3.35 (m, 1H), 3.26 (brs, 1H), 2.50 (m, 8H), 2.29 (s, 3H), 2.19 (brs, 1H), 1.98 (m, 2H), 1.85-1.69 (m, 4H), 1.50-1.42 (m, 2H); MS (ESI) m/z=430.2 (M+H)+

Step 2. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)cyclohexyl)methanol The title compound as an off-white solid (7 mg) was prepared in the same fashion as Step 3 in Example 1, except that (1s,4s)-4-((6'-chloro-5-((4-methylpiperazin-1-yl)methyl)-[2,3'-bipyridin]-4'-yl)amino)cyclohexyl)methanol (32 mg, 0.075 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.64 (s, 1H), 8.59 (s, 1H), 8.53 (s, 1H), 8.45 (s, 1H), 8.44 (s, 1H), 8.23 (s, 1H), 8.03 (brs, 1H), 7.84 (dd, 1H), 7.72 (d, 1H), 7.07 (d, 1H), 4.10 (m, 1H), 3.64 (s, 2H), 3.56 (d, 2H), 2.83 (m, 1H), 2.68 (m, 8H), 2.50 (s, 3H), 1.95 (m, 2H), 1.79 (m, 4H), 1.55 (m, 2H), 1.39 (m, 2H), 1.24 (m, 2H); MS (ESI) m/z=659.3 (M+H)+

Example 11. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-(hydroxymethyl)cyclohexan-1-ol Step 1. (1s,4s)-4-((6'-Chloro-5-((4-methylpiperazin-1-yl)methyl)-[2,3'-bipyridin]-4'-yl)amino)-1-(hydroxymethyl)cyclohexan-1-ol The title compound as a white solid (94 mg) was prepared in the same fashion as Step 2 in Example 1, except that (1s,4s)-4-amino-1-(hydroxymethyl)cyclohexan-1-ol (64 mg. 0.446 mmol) was used instead of (4-methylpiperidin-4-yl)methanol. $^1$H-NMR (CDCl$_3$, 400 MHz) δ 9.89 (d, 1H), 8.49 (d, 1H), 8.43 (s, 1H), 7.79-7.73 (m, 2H), 6.58 (s, 1H), 3.80 (m, 1H), 3.79-3.52 (m, 4H), 2.50 (m, 8H), 2.30 (s, 3H), 1.95-1.91 (m, 2H), 1.73-1.62 (m, 4H), 1.40-1.34 (m, 2H); MS (ESI) m/z=446.1 (M+H)+

Step 2. (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-(hydroxymethyl)cyclohexan-1-ol The title compound as an off-white solid (3 mg) was prepared in the same fashion as Step 3 in Example 1, except that (1s,4s)-4-((6'-chloro-5-((4-methylpiperazin-1-yl)methyl)-[2,3'-bipyridin]-4'-yl)amino)-1-(hydroxymethyl)cyclohexan-1-ol (34 mg, 0.075 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.70 (s, 1H), 8.54 (s, 1H), 8.49 (s, 1H), 8.42-8.30 (m, 3H), 7.84-7.76 (m, 1H), 7.15 (m, 1H), 3.55 (s, 2H), 3.50 (m, 1H), 2.78 (m, 8H), 2.30 (s, 3H), 1.98 (m, 2H), 1.79-1.71 (m, 4H), 1.62-1.49 (m, 4H), 1.30 (s, 3H), 1.23-1.17 (m, 2H); MS (ESI) m/z=675.3 (M+H)+

Example 12. (1s,4s)-4-((6'-((2-(1-(Cyclopropylsulfonyl)-1H-pyrazol-4-yl)pyrimidin-4-yl)amino)-4-methyl-[2,3'-bipyridin]-4'-yl)amino)-1-methylcyclohexan-1-ol Step 1. 6'-Chloro-4'-fluoro-4-methyl-2,3'-bipyridine The title compound as an off-white solid (114 mg) was prepared in the same fashion as Step 1 in Example 1, except that 2-bromo-4-methylpyridine (145 mg, 0.776 mmol) was used instead of 1-((6-bromopyridin-3-yl)methyl)-4-methylpiperazine. $^1$H-NMR (CDCl$_3$, 400 MHz) δ 9.01 (d, 1H), 8.61 (d, 1H), 7.56 (s, 1H), 7.22-7.16 (m, 1H), 2.45 (s, 3H); MS (ESI) m/z=223.0 (M+H)+

Step 2. (1s,4s)-4-((6'-Chloro-4-methyl-[2,3'-bipyridin]-4'-yl)amino)-1-methylcyclohexan-1-ol The title compound as a white solid (88 mg) was prepared in the same fashion as Step 2 in Example 1, except that 6'-chloro-4'-fluoro-4-methyl-2,3'-bipyridine (103 mg, 0.464 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 8.32 (s, 1H), 7.71 (t, 1H), 7.60 (d, 1H), 7.14 (d, 1H), 3.41-3.36 (m, 1H), 2.54 (s, 3H), 1.89-1.85 (m, 2H), 1.74-1.65 (m, 4H), 1.59-1.52 (m, 2H), 1.24 (s, 3H); MS (ESI) m/z=332.1 (M+H)+

Step 3. (1s, 4s)-4-((6'-((2-(1-(Cyclopropylsulfonyl)-1H-pyrazol-4-yl)pyrimidin-4-yl)amino)-4-methyl-[2,3'-bipyridin]-4'-yl)amino)-1-methylcyclohexan-1-ol The title compound as an off-white solid (19.6 mg) was prepared in the same fashion as Step 3 in Example 1, except that (1s,4s)-4-((6'-chloro-4-methyl-[2,3'-bipyridin]-4'-yl)amino)-1-methylcyclohexan-1-ol (56 mg. 0.17 mmol) prepared in Step 2 was used instead of (1-(6'-chloro-5-((4-methylpiperazin-1-yl)methyl)-[2,3'-bipyridin]-4'-yl)-4- methylpiperidin-4-yl)methanol. $^1$H-NMR (CDCl$_3$, 400 MHz) δ 9.77 (d, 1H), 8.67 (s, 1H), 8.48 (s, 1H), 8.44 (s, 1H), 8.40 (d, 1H), 7.67 (t, 1H), 7.54 (d, 1H), 7.28 (m, 1H), 7.06 (d, 1H), 7.01 (s, 1H), 3.53 (m, 1H), 2.84-2.81 (m, 1H), 2.60 (s, 3H), 2.04-2.01 (m, 2H), 1.78-1.51 (m, 8H), 1.31 (s, 3H), 1.22-1.19 (m, 2H); MS (ESI) m/z=561.2 (M+H)$^+$ Example 13. (1s,4s)-4-((6'-((2-(1-(Cyclopropylsulfonyl)-1H-pyrazol-4-yl)pyrimidin-4-yl)amino)-3-fluoro-4-(hydroxymethyl)-[2,3'-bipyridin]-4'-yl)amino)-1-methylcyclohexan-1-ol Step 1. (6'-Chloro-3,4'-difluoro-[2,3'-bipyridin]-4-yl)methanol The title compound as an off-white solid (148 mg) was prepared in the same fashion as Step 1 in Example 1, except that (2-bromo-3-fluoropyridin-4-yl)methanol (320 mg, 3.100 mmol) was used instead of 1-((6-bromopyridin-3-yl)methyl)-4-methylpiperazine. $^1$H-NMR (CDCl$_3$, 400 MHz) δ 8.65 (d, 1H), 8.58 (d, 1H), 7.63 (t, 1H), 7.24 (d, 1H), 4.93 (d, 2H), 2.12 (t, 1H); MS (ESI) m/z=257.0 (M+H)$^+$ Step 2. (1s,4s)-4-((6'-chloro-3-fluoro-4-(hydroxymethyl)-[2,3'-bipyridin]-4'-yl)amino)-1-methylcyclohexan-1-ol The title compound as a white solid (104 mg) was prepared in the same fashion as Step 2 in Example 1, except that (6'-chloro-3,4'-difluoro-[2,3'-bipyridin]-4-yl)methanol (119 mg, 0.464 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 8.47 (d, 1H), 8.15 (d, 1H), 7.58 (t, 1H), 6.76 (s, 1H), 4.80 (s, 2H), 3.44-3.40 (m, 1H), 1.83-1.80 (m, 2H), 1.71-1.52 (m, 6H), 1.23 (s, 3H); MS (ESI) m/z=366.1 (M+H)$^+$ Step 3. (1s,4s)-4-((6'-((2-(1-(cyclopropylsulfonyl)-1H-pyrazol-4-yl)pyrimidin-4-yl)amino)-3-fluoro-4-(hydroxymethyl)-[2,3'-bipyridin]-4'-yl)amino)-1-methylcyclohexan-1-ol The title compound as an off-white solid (21.1 mg) was prepared in the same fashion as Step 3 in Example 1, except that (1s,4s)-4-((6'-chloro-3-fluoro-4-(hydroxymethyl)-[2,3'-bipyridin]-4'-yl)amino)-1-methylcyclohexan-1-ol (56 mg. 0.17 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.75 (s, 1H), 8.49 (s, 1H), 8.47 (d, 1H), 8.38 (d, 1H), 8.24 (d, 1H), 7.55 (t, 1H), 7.41 (d, 1H), 7.32 (s, 1H), 4.75 (s, 2H), 4.62 (s, 1H), 3.54 (m, 1H), 3.05-3.00 (m, 1H), 1.94-1.90 (m, 2H), 1.72-1.64 (m, 4H), 1.59-1.53 (m, 2H), 1.47-1.43 (m, 2H), 1.29-1.25 (m, 2H), 1.24 (s, 3H); MS (ESI) m/z=595.2 (M+H)$^+$ Example 14. (1s,4s)-4-((6'-((2-(1-(cyclopropylsulfonyl)-1H-pyrazol-4-yl)pyrimidin-4-yl)amino)-6-(trifluoromethyl)-[2,3'-bipyridin]-4'-yl)amino)-1-methylcyclohexan-1-ol Step 1. 6'-chloro-4'-fluoro-6-(trifluoromethyl)-2,3'-bipyridine The title compound as an off-white solid (176 mg) was prepared in the same fashion as Step 1 in Example 1, except that 2-bromo-6-(trifluoromethyl)pyridine (183 mg, 0.776 mmol) was used instead of 1-((6-bromopyridin-3-yl)methyl)-4-methylpiperazine. $^1$H-NMR (CDCl$_3$, 400 MHz) δ 9.12 (d, 1H), 8.04-7.96 (m, 2H), 7.73 (d, 1H), 7.24 (d, 1H); MS (ESI) m/z=276.9 (M+H)$^+$ Step 2. (1s,4s)-4-((6'-chloro-6-(trifluoromethyl)-[2,3'-bipyridin]-4'-yl)amino)-1-methylcyclohexan-1-ol The title compound as a white solid (93 mg) was prepared in the same fashion as Step 2 in Example 1, except that 6'-chloro-4'-fluoro-6-(trifluoromethyl)-2,3'-bipyridine (128 mg, 0.464 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 9.46 (s, 1H), 8.50 (s, 1H), 8.13 (m, 2H), 7.73 (s, 1H), 3.42 (m, 1H), 1.87 (m, 2H), 1.73 (m, 4H), 1.59 (m, 2H), 1.24 (s, 3H); MS (ESI) m/z=386.1 (M+H)$^+$ Step 3. (1s,4s)-4-((6'-((2-(1-(Cyclopropylsulfonyl)-1H-pyrazol-4-yl)pyrimidin-4-yl)amino)-6-(trifluoromethyl)-[2,3'-bipyridin]-4'-yl)amino)-1-methylcyclohexan-1-ol The title compound as an off-white solid (7.5 mg) was prepared in the same fashion as Step 3 in Example 1, except that (1s,4s)-4-((6'-chloro-6-(trifluoromethyl)-[2,3'-bipyridin]-4'-yl)amino)-1-methylcyclohexan-1-ol (65 mg. 0.17 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.30 (d, 1H), 8.67 (s, 1H), 8.52 (s, 1H), 8.48 (s, 1H), 8.43 (d, 1H), 7.94 (d, 1H), 7.80 (brs, 1H), 7.56 (t, 1H), 7.32 (d, 1H), 7.03 (brs, 1H), 3.49 (m, 1H), 2.85-2.80 (m, 1H), 2.05-2.00 (m, 2H), 1.80-1.73 (m, 4H), 1.63-1.51 (m, 4H), 1.29 (s, 3H), 1.23-1.19 (m, 2H); MS (ESI) m/z=615.1 (M+H)$^+$ Example 15. (1s,4s)-4-((6'-((2-(1-(Cyclopropylsulfonyl)-1H-pyrazol-4-yl)pyrimidin-4-yl)amino)-6-methyl-[2,3'-bipyridin]-4'-yl)amino)-1-methylcyclohexan-1-ol Step 1. 6'-Chloro-4'-fluoro-6-methyl-2,3'-bipyridine The title compound as an off-white solid (134 mg) was prepared in the same fashion as Step 1 in Example 1, except that 2-bromo-6-methylpyridine (183 mg, 0.776 mmol) was used instead of 1-((6-bromopyridin-3-yl)methyl)-4-methylpiperazine. $^1$H-NMR (CDCl$_3$, 400 MHz) δ 9.01 (d, 1H), 7.69 (t, 1H), 7.54 (d, 1H), 7.22-7.18 (m, 2H), 2.65 (s, 3H); MS (ESI) m/z=223.0 (M+H)$^+$ Step 2. (1s,4s)-4-((6'-Chloro-6-methyl-[2,3'-bipyridin]-4'-yl)amino)-1-methylcyclohexan-1-ol The title compound as a white solid (134 mg) was prepared in the same fashion as Step 2 in Example 1, except that 6'-chloro-4'-fluoro-6-methyl-2,3'-bipyridine (103 mg. 0.464 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 8.43 (d, 1H), 8.30 (s, 1H), 7.66 (s, 1H), 7.16 (d, 1H), 6.68 (s, 1H), 3.44-3.39 (m, 1H), 2.42 (s, 3H), 1.87-1.83 (m, 2H), 1.67-1.63 (m, 4H), 1.60-1.52 (m, 2H), 1.24 (s, 3H); MS (ESI) m/z=332.1 (M+H)+

Step 3. (1s,4s)-4-((6'-((2-(1-(Cyclopropylsulfonyl)-1H-pyrazol-4-yl)pyrimidin-4-yl)amino)-6-methyl-[2,3'-bipyridin]-4'-yl)amino)-1-methylcyclohexan-1-ol The title compound as an off-white solid (15 mg) was prepared in the same fashion as Step 3 in Example 1, except that (1s,4s)-4-((6'-chloro-6-methyl-[2,3'-bipyridin]-4'-yl)amino)-1-methylcyclohexan-1-ol (56 mg. 0.17 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.42 (d, 1H), 8.66 (s, 1H), 8.48 (s, 1H), 8.44-8.40 (m, 3H), 7.52 (s, 1H), 7.29 (m, 1H), 7.03 (m, 2H), 3.50 (m, 1H), 2.85-2.79 (m, 1H), 2.43 (s, 3H), 2.04-1.97 (m, 2H), 1.81-1.51 (m, 8H), 1.31 (s, 3H), 1.22-1.18 (m, 2H); MS (ESI) m/z=561.2 (M+H)+

Example 16. (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol Step 1. (6'-Chloro-4'-fluoro-[2,3'-bipyridin]-4-yl)methanol The title compound as an off-white solid (147 mg) was prepared in the same fashion as Step 1 in Example 1, except that (2-bromopyridin-4-yl)methanol (219 mg, 1.16 mmol) was used instead of 1-((6-bromopyridin-3-yl)methyl)-4-methylpiperazine. $^1$H-NMR (CDCl$_3$, 400 MHz) δ 9.02 (d, 1H), 8.72 (d, 1H), 7.75 (s, 1H), 7.35 (d, 1H), 7.22 (d, 1H), 4.84 (d, 2H), 2.09 (t, 1H); MS (ESI) m/z=239.0 (M+H)+

Step 2. (1s,4s)-4-((6'-Chloro-4-(hydroxymethyl)-[2,3'-bipyridin]-4'-yl)amino)-1-methylcyclohexan-1-ol The title compound as a white solid (88 mg) was prepared in the same fashion as Step 2 in Example 1, except that (6'-chloro-4'-fluoro-[2,3'-bipyridin]-4-yl)methanol (111 mg, 0.464 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 8.53 (d, 1H), 8.33 (s, 1H), 7.80 (s, 1H), 7.30 (d, 1H), 6.69 (s, 1H), 4.71 (S, 2H), 3.45-3.39 (m, 1H), 1.87-1.83 (m, 2H), 1.74-1.64 (m, 4H), 1.59-1.52 (m, 2H), 1.24 (s, 3H); MS (ESI) m/z=348.1 (M+H)+

Step 3. (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol The title compound as an off-white solid (15 mg) was prepared in the same fashion as Step 3 in Example 1, except that (1s,4s)-4-((6'-chloro-4-(hydroxymethyl)-[2,3'-bipyridin]-4'-yl)amino)-1-methylcyclohexan-1-ol (62 mg, 0.17 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.74 (s, 1H), 8.54 (d, 1H), 8.48 (s, 1H), 8.42 (s, 1H), 8.36 (d, 1H), 7.82 (s, 1H), 7.37 (d, 1H), 7.27 (d, 2H), 4.62 (s, 2H), 3.57 (m, 1H), 3.07-3.01 (m, 1H), 1.98-1.94 (m, 2H), 1.79-1.71 (m, 4H), 1.61-1.55 (m, 2H), 1.47-1.43 (m, 2H), 1.26 (m, 2H), 1.24 (s, 3H); MS (ESI) m/z=577.2 (M+H)+

Example 17. (1s,4s)-4-((6'-((2-(1-(Cyclopropylsulfonyl)-1H-pyrazol-4-yl)pyrimidin-4-yl)amino)-5-(trifluoromethyl)-[2,3'-bipyridin]-4'-yl)amino)-1-methylcyclohexan-1-ol Step 1. 6'-Chloro-4'-fluoro-5-(trifluoromethyl)-2,3'-bipyridine The title compound as an off-white solid (131 mg) was prepared in the same fashion as Step 1 in Example 1, except that 2-bromo-5-(trifluoromethyl)pyridine (210 mg, 0.932 mmol) was used instead of 1-((6-bromopyridin-3-yl)methyl)-4-methylpiperazine. $^1$H-NMR (CDCl$_3$, 400 MHz) δ 9.12 (d, 1H), 9.02 (s, 1H), 8.06 (d, 1H), 7.92 (d, 1H), 7.27 (m, 1H)

Step 2. (1s,4s)-4-((6'-Chloro-5-(trifluoromethyl)-[2,3'-bipyridin]-4'-yl)amino)-1-methylcyclohexan-1-ol The title compound as a white solid (80 mg) was prepared in the same fashion as Step 2 in Example 1, except that 6'-chloro-4'-fluoro-5-(trifluoromethyl)-2,3'-bipyridine (107 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.33 (d, 1H), 8.83 (s, 1H), 8.44 (s, 1H), 7.99 (dd, 1H), 7.85 (d, 1H), 6.60 (s, 1H), 3.37-3.32 (m, 1H), 1.95-1.91 (m, 2H), 1.78-1.69 (m, 4H), 1.60-1.53 (m, 2H), 1.30 (s, 3H)

Step 3. (1s,4s)-4-((6'-((2-(1-(Cyclopropylsulfonyl)-1H-pyrazol-4-yl)pyrimidin-4-yl)amino)-5-(trifluoromethyl)-[2,3'-bipyridin]-4'-yl)amino)-1-methylcyclohexan-1-ol The title compound as an off-white solid (37 mg) was prepared in the same fashion as Step 3 in Example 1, except that (1s,4s)-4-((6'-chloro-5-(trifluoromethyl)-[2,3'-bipyridin]-4'-yl)amino)-1-methylcyclohexan-1-ol (44 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.47 (d, 1H), 8.84 (s, 1H), 8.67 (s, 1H), 8.50 (d, 2H), 8.44 (d, 1H), 7.98 (dd 1H), 7.86 (d, 1H), 7.78 (brs, 1H), 7.29 (m, 1H), 7.09 (s, 1H), 3.53 (m, 1H), 2.84-2.81 (m, 1H), 2.03-1.99 (m, 2H), 1.83-1.52 (m, 8H), 1.32 (s, 3H), 1.25-1.21 (m, 2H); MS (ESI) m/z=615.2 (M+H)+

Example 18. 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-6-yl)ethan-1-one Step 1. 1-(6'-Chloro-4'-fluoro-[2,3'-bipyridin]-6-yl)ethan-1-one The title compound as an off-white solid (115 mg) was prepared in the same fashion as Step 1 in Example 1, except that 2-acetyl-6-bromopyridine (186 mg, 0.932 mmol) was used instead of 1-((6-bromopyridin-3-yl)methyl)-4-methylpiperazine. $^1$H-NMR (CDCl$_3$, 400 MHz) δ 9.17 (d, 1H), 8.10-7.96 (m, 3H), 7.24 (d, 1H), 2.79 (s, 3H)

Step 2. 1-(6'-Chloro-4'-(((1s,4s)-4-hydroxy-4-methylcyclohexyl)amino)-[2,3'-bipyridin]-6-yl)ethan-1-one The title compound as a white solid (85 mg) was prepared in the same fashion as Step 2 in Example 1, except that 1-(6'-chloro-4'-fluoro-[2,3'-bipyridin]-6-yl)ethan-1-one (97 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.83 (d, 1H), 8.37 (s, 1H), 8.02-7.86 (m, 3H), 6.61 (s, 1H), 3.39-3.35 (m, 1H), 2.72 (s, 3H), 1.97-1.93 (m, 2H), 1.79-1.66 (m, 4H), 1.60-1.53 (m, 2H), 1.29 (s, 3H)

Step 3. 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-6-yl)ethan-1-one The title compound as an off-white solid (31 mg) was prepared in the same fashion as Step 3 in Example 1, except that 1-(6'-chloro-4'-(((1s,4s)-4-hydroxy-4-methylcyclohexyl)amino)-[2,3'-bipyridin]-6-yl)ethan-1-one (35 mg, 0.098 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.89 (d, 1H), 8.67 (s, 1H), 8.49 (s, 1H), 8.42 (t, 1H), 8.18 (s, 1H), 7.97-7.88 (m, 3H), 7.31 (d, 1H), 7.12 (s, 1H), 3.53 (m, 1H), 2.84-2.80 (m, 1H), 2.04 (m, 2H), 1.76 (m, 4H), 1.63-1.50 (m, 4H), 1.30 (S, 3H), 1.26 (m, 2H); MS (ESI) m/z=589.2 (M+H)$^+$

Example 19. (1s,4s)-4-((6'-((2-(1-(Cyclopropylsulfonyl)-1H-pyrazol-4-yl)pyrimidin-4-yl)amino)-6-fluoro-4-methyl-[2,3'-bipyridin]-4'-yl)amino)-1-methylcyclohexan-1-ol

Step 1. 6'-Chloro-4',6-difluoro-4-methyl-2,3'-bipyridine

The title compound as an off-white solid (102 mg) was prepared in the same fashion as Step 1 in Example 1, except that 2-bromo-6-fluoro-4-methylpyridine (616 mg, 3.26 mmol) was used instead of 1-((6-bromopyridin-3-yl)methyl)-4-methylpiperazine. $^1$H-NMR (CDCl$_3$, 400 MHz) δ 9.04 (d, 1H), 7.50 (s, 1H), 7.22 (d, 1H), 6.81 (s, 1H), 2.49 (s, 3H); MS (ESI) m/z=241.0 (M+H)$^+$

Step 2. (1s,4s)-4-((6'-Chloro-6-fluoro-4-methyl-[2,3'-bipyridin]-4'-yl)amino)-1-methylcyclohexan-1-ol The title compound as a white solid (39 mg) was prepared in the same fashion as Step 2 in Example 1, except that 6'-chloro-4',6-difluoro-4-methyl-2,3'-bipyridine (93 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.73 (d, 1H), 8.37 (s, 1H), 7.38 (s, 1H), 6.69 (s, 1H), 6.56 (s, 1H), 3.38-3.31 (m, 1H), 2.46 (s, 3H), 1.93 (m, 2H), 1.78-1.68 (m, 4H), 1.61-1.53 (m, 2H), 1.27 (s, 3H)

Step 3. (1s,4s)-4-((6'-((2-(1-(Cyclopropylsulfonyl)-1H-pyrazol-4-yl)pyrimidin-4-yl)amino)-6-fluoro-4-methyl-[2,3'-bipyridin]-4'-yl)amino)-1-methylcyclohexan-1-ol The title compound as an off-white solid (8.8 mg) was prepared in the same fashion as Step 3 in Example 1, except that (1s,4s)-4-((6'-chloro-6-fluoro-4-methyl-[2,3'-bipyridin]-4'-yl)amino)-1-methylcyclohexan-1-ol (34 mg, 0.098 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.88 (d, 1H), 8.66 (s, 1H), 8.48 (s, 1H), 8.42 (d, 1H), 8.39 (s, 1H), 7.39 (s, 1H), 7.13 (s, 1H), 6.66 (s, 1H), 3.54 (m, 1H), 2.86-2.80 (m, 1H), 2.47 (s, 3H), 2.05-1.98 (m, 2H), 1.84-1.74 (m, 4H), 1.65-1.53 (m, 4H), 1.28 (m, 3H), 1.25 (m, 2H); MS (ESI) m/z=579.2 (M+H)$^+$

Example 20. (1s,4s)-4-((6'-((2-(1-(Cyclopropylsulfonyl)-1H-pyrazol-4-yl)pyrimidin-4-yl)amino)-4-(trifluoromethyl)-[2,3'-bipyridin]-4'-yl)amino)-1-methylcyclohexan-1-ol

Step 1. 6'-Chloro-4'-fluoro-4-(trifluoromethyl)-2,3'-bipyridine

The title compound as an off-white solid (144 mg) was prepared in the same fashion as Step 1 in Example 1, except that 2-bromo-4-(trifluoromethyl)pyridine (210 mg, 0.932 mmol) was used instead of 1-((6-bromopyridin-3-yl)methyl)-4-methylpiperazine. $^1$H-NMR (CDCl$_3$, 400 MHz) δ 9.11 (d, 1H), 8.95 (d, 1H), 7.99 (s, 1H), 7.58 (d, 1H), 7.26 (d, 1H), 4.84 (d, 2H), 2.09 (t, 1H)

Step 2. (1s,4s)-4-((6'-Chloro-4-(trifluoromethyl)-[2,3'-bipyridin]-4'-yl)amino)-1-methylcyclohexan-1-ol The title compound as a white solid (80 mg) was prepared in the same fashion as Step 2 in Example 1, except that 6'-chloro-4'-fluoro-4-(trifluoromethyl)-2,3'-bipyridine (108 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.20 (d, 1H), 8.74 (s, 1H), 8.41 (s, 1H), 7.90 (s, 1H), 7.43 (d, 1H), 6.59 (s, 1H), 3.37-3.33 (m, 1H), 1.94-1.90 (m, 2H), 1.79-1.68 (m, 4H), 1.60-1.52 (m, 2H), 1.30 (s, 3H)

Step 3. (1s,4s)-4-((6'-((2-(1-(Cyclopropylsulfonyl)-1H-pyrazol-4-yl)pyrimidin-4-yl)amino)-4-(trifluoromethyl)-[2,3'-bipyridin]-4'-yl)amino)-1-methylcyclohexan-1-ol The title compound as an off-white solid (28.7 mg) was prepared in the same fashion as Step 3 in Example 1, except that (1s,4s)-4-((6'-chloro-4-(trifluoromethyl)-[2,3'-bipyridin]-4'-yl)amino)-1-methylcyclohexan-1-ol (38 mg, 0.098 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.48 (s, 1H), 8.77 (d, 1H), 8.69 (s, 1H), 8.51 (s, 1H), 8.45 (m, 2H), 7.97 (s, 1H), 7.43 (d, 1H), 7.29 (s, 1H), 4.94 (brs, 1H), 3.59 (m, 1H), 2.85 (m, 1H), 1.98 (m, 2H), 1.89-1.76 (m, 4H), 1.66-1.56 (m, 4H), 1.28 (s, 3H), 1.24 (m, 2H); MS (ESI) m/z=615.1 (M+H)$^+$ Example 21. (6'-((2-(1-(Cyclopropylsulfonyl)-1H-pyrazol-4-yl)pyrimidin-4-yl)amino)-4'-(((1s,4s)-4-((2-fluoroethyl)amino)cyclohexyl)amino)-[2,3'-bipyridin]-5-yl)methanol Step 1. (6'-Chloro-4'-(((1s,4s)-4-((2-fluoroethyl)amino)cyclohexyl)amino)-[2,3'-bipyridin]-5-yl)methanol The title compound as a white solid (100 mg) was prepared in the same fashion as Step 2 in Example 1, except that (6'-chloro-4'-fluoro-[2,3'-bipyridin]-5-yl)methanol (82 mg, 0.344 mmol) prepared in Step 1 of Example 5 and (1s,4s)—N[1]-2-fluoroethyl)cyclohexane-1,4-diamine (55 mg, 0.344 mmol) were used instead of 6'-chloro-4'-fluoro-5-((4-methylpiperazin-1-yl)methyl)-2,3'-bipyridine and (4-methylpiperidin-4-yl)methanol. MS (ESI) m/z=379.1 (M+H)+

Step 2. (6'-((2-(1-(Cyclopropylsulfonyl)-1H-pyrazol-4-yl)pyrimidin-4-yl)amino)-4'-(((1s,4s)-4-((2-fluoroethyl)amino)cyclohexyl)amino)-[2,3'-bipyridin]-5-yl)methanol The title compound as an off-white solid (16 mg) was prepared in the same fashion as Step 3 in Example 1, except that (6'-chloro-4'-(((1s,4s)-4-((2-fluoroethyl)amino)cyclohexyl)amino)-[2,3'-bipyridin]-5-yl)methanol (100 mg, 0.264 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.86 (d, 1H), 8.66 (s, 1H), 8.60 (s, 1H), 8.46 (s, 1H), 8.42 (s, 1H), 8.40 (d, 1H), 7.79 (dd, 1H), 7.73 (d, 1H), 7.25 (m, 1H), 7.12 (d, 1H), 4.77 (s, 2H), 4.63 (t, 1H), 4.51 (t, 1H), 3.87 (m 1H), 2.99 (t, 1H), 2.92 (t, 1H), 2.83 (m, 1H), 2.66 (m, 1H), 2.04 (m, 2H), 1.84-1.46 (m, 8H), 1.27-1.21 (m, 2H); MS (ESI) m/z=608.2 (M+H)+

Example 22. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methanol Step 1. (6'-Chloro-4'-(((1s,4s)-4-(hydroxymethyl)cyclohexyl)amino)-[2,3'-bipyridin]-5-yl)methanol The title compound as a white solid (104 mg) was prepared in the same fashion as Step 2 in Example 1, except that (6'-chloro-4'-fluoro-[2,3'-bipyridin]-5-yl)methanol (82 mg, 0.344 mmol) prepared in Step 1 of Example 5 and ((1s,4s)-4-aminocyclohexyl)methanol (43 mg, 0.464 mmol) were used instead of 6'-chloro-4'-fluoro-5-((4-methylpiperazin-1-yl)methyl)-2,3'-bipyridine and (4-methylpiperidin-4-yl)methanol. MS (ESI) m/z=348.1 (M+H)+

Step 2. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methanol The title compound as an off-white solid (37 mg) was prepared in the same fashion as Step 3 in Example 1, except that (6'-chloro-4'-(((1s,4s)-4-(hydroxymethyl)cyclohexyl)amino)-[2,3'-bipyridin]-5-yl)methanol (92 mg, 0.264 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 9.99 (d, 1H), 8.66 (s, 1H), 8.57 (s, 1H), 8.46 (s, 1H), 8.41 (s, 1H), 8.39 (d, 1H), 7.80-7.73 (m, 2H), 7.30 (s, 1H), 7.09 (d, 1H), 4.77 (s, 2H), 3.98 (m, 1H), 3.54 (d, 2H), 2.86-2.82 (m, 1H), 2.04 (m, 2H), 1.82-1.70 (m, 5H), 1.54 (m, 2H), 1.43-1.34 (m, 3H), 1.26 (m, 2H); MS (ESI) m/z=577.2 (M+H)+

Example 23. (1s,4s)-4-((6'-((2-(1-(Cyclopropylsulfonyl)-1H-pyrazol-4-yl)pyrimidin-4-yl)amino)-6-(1-hydroxyethyl)-[2,3'-bipyridin]-4'-yl)amino)-1-methylcyclohexan-1-ol The solution of 1-(6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-6-yl)ethan-1-one (20 mg, 0.034 mmol) prepared in Example 18 in MeOH (0.5 mL) was added sodium borohydride (6 mg, 0.17 mmol) at room temperature. This mixture was stirred at room temperature for 30 mins. The mixture was diluted with DCM. The organic layer was washed by water, dried over MgSO$_4$, and then concentrated. The crude product was purified by column chromatography (MeOH/DCM=0-10%) to yield (1s,4s)-4-((6'-((2-(1-(cyclopropylsulfonyl)-1H-pyrazol-4-yl)pyrimidin-4-yl)amino)-6-(1-hydroxyethyl)-[2,3'-bipyridin]-4'-yl)amino)-1-methylcyclohexan-1-ol (20.2 mg) as an off-white solid. $^1$H-NMR (CDCl$_3$, 400 MHz) δ 8.78 (d, 1H), 8.66 (d, 1H), 8.47 (s, 1H), 8.39 (d, 1H), 8.32 (s, 1H), 7.79 (t, 1H), 7.55 (d, 1H), 7.25 (s, 1H), 7.22 (d, 1H), 7.13 (s, 1H), 4.98 (m, 1H), 3.56 (m, 1H), 3.49 (s, 3H), 2.85-2.81 (m, 1H), 1.97 (m, 2H), 1.89 (m, 4H), 1.76-1.50 (m, 7H), 1.29 (s, 3H), 1.26-1.19 (m, 2H); MS (ESI) m/z=591.2 (M+H)+

Example 24. 2-((1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol Step 1. 2-((1s,4s)-4-((6'-Chloro-5-(hydroxymethyl)-[2,3'-bipyridin]-4'-yl)amino)cyclohexyl)propan-2-ol The title compound as a white solid (133 mg) was prepared in the same fashion as Step 2 in Example 1, except that (6'-chloro-4'-fluoro-[2,3'-bipyridin]-5-yl)methanol (150 mg, 0.629 mmol) prepared in Step 1 of Example 5 and 2-((1s,4s)-4-aminocyclohexyl)propan-2-ol (99 mg, 0.629 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (MeOD, 400 MHz) δ 8.69 (s, 1H), 8.41 (s, 1H), 7.93-7.86 (m, 2H), 6.70 (s, 1H), 4.69 (s, 2H), 3.87 (m, 1H), 1.95 (m, 2H), 1.79-1.62 (m, 4H), 1.43-1.38 (m, 3H), 1.17 (s, 6H); MS (ESI) m/z=348.0 (M+H)+

Step 2. 2-((1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol The title compound as an off-white solid (5 mg) was prepared in the same fashion as Step 3 in Example 1, except that 2-((1s,4s)-4-((6'-chloro-5-(hydroxymethyl)-[2,3'-bipyridin]-4'-yl)amino)cyclohexyl)propan-2-ol (78 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.65 (s, 1H), 8.54 (s, 1H), 8.39 (s, 2H), 8.28 (d, 1H), 7.81 (s, 2H), 7.38 (d, 1H), 7.17 (d, 1H), 4.65 (s, 2H), 3.94 (m, 1H), 3.07-3.01 (m, 1H), 2.05 (m, 2H), 1.75 (m, 4H), 1.47-1.37 (m, 4H), 1.30-1.26 (m, 3H), 1.17 (s, 6H); MS (ESI) m/z=605.2 (M+H)$^+$ Example 25. 2-((1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol Step 1. 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde To a solution of the 2-((1s,4s)-4-((6'-((2-(1-(cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol (100 mg. 0.166 mmol) prepared in Example 24 in DCM (2.4 mL) was added Dess-Maroom temperature in periodinane (140 mg. 0.33 mmol). The reaction mixture was stirred at room temperature for an hour, diluted with DCM, washed with 10% aqueous Na$_2$S$_2$O$_3$, and then extracted with DCM. The organic layer was dried over MgSO$_4$, filtered, and concentrated. The crude residue was purified by silica gel column chromatography (MeOH/DCM=0-10%) to give 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde (70 mg) as an off-white solid. MS (ESI) m/z=603.2 (M+H)$^+$ Step 2. 2-((1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol The a solution 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde (26 mg. 0.044 mmol) prepared in Step 1 in DCM (1 mL) was added morpholine (8 mg, 0.088 mmol). This mixture was stirred for 20 minutes and cooled to 0° C. To this mixture was added sodium triacetoxy borohydride (46 mg. 0.218 mmol) at 0° C., and then the reaction mixture was stirred at room temperature for 4 hours. The reaction mixture was added to sat. NaHCO$_3$ and diluted with water and DCM, and then extracted with DCM. The organic layer was dried over MgSO$_4$, filtered, and concentrated. The crude residue was purified by silica gel column chromatography (MeOH/DCM=0-10%) to give 2-((1s,4s)-4-((6'-((2-(1-(cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol (7.5 mg) as an off-white solid. $^1$H-NMR (CDCl$_3$, 400 MHz) δ 8.63 (s, 1H), 8.54-8.45 (m, 4H), 8.30 (s, 1H), 8.18 (m, 1H), 7.87 (d, 1H), 7.78 (d, 1H), 7.07 (s, 1H), 4.13 (m, 1H), 3.74 (brs, 4H), 3.59 (s, 2H), 2.85 (m, 1H), 2.52 (brs, 4H), 2.14 (m, 2H), 1.89 (m, 4H), 1.56-1.41 (m, 5H), 1.25 (m, 8H) MS (ESI) m/z=674.3 (M+H)$^+$ Example 26. 2-((1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)cyclohexyl)propan-2-ol The title compound as an off-white solid (9.6 mg) was prepared in the same fashion as Step 2 in Example 25, except that dimethylamine (4 mg, 0.088 mmol) was used instead of morpholine. $^1$H-NMR (CDCl$_3$, 400 MHz) δ 10.10 (d, 1H), 8.66 (s, 1H), 8.46 (s, 3H), 8.39 (d, 1H), 7.76 (s, 2H), 7.36 (s, 1H), 7.07 (d, 1H), 4.00 (m, 1H), 3.47 (s, 2H), 2.84 (m, 1H), 2.28 (s, 6H), 2.12 (m, 2H), 1.79 (m, 4H), 1.54-1.44 (m, 5H), 1.24 (m, 8H); MS (ESI) m/z=632.3 (M+H)$^+$ Example 27. (1s,4s)-4-((6'-((2-(1-(Cyclopropylsulfonyl)-1H-pyrazol-4-yl)pyrimidin-4-yl)amino)-6-(hydroxy methyl)-[2,3'-bipyridin]-4'-yl)amino)-1-methylcyclohexan-1-ol Step 1. (6'-Chloro-4'-fluoro-[2,3'-bipyridin]-6-yl)methanol The title compound as an off-white solid (220 mg) was prepared in the same fashion as Step 1 in Example 1, except that (6-bromo-2-pyridyl)methanol (261 mg, 1.39 mmol) was used instead of 1-((6-bromopyridin-3-yl)methyl)-4-methylpiperazine. MS (ESI) m/z=239.0 (M+H)$^+$ Step 2. (1s,4s)-4-((6'-Chloro-6-(hydroxymethyl)-[2,3'-bipyridin]-4'-yl)amino)-1-methylcyclohexan-1-ol The title compound as a white solid (226 mg) was prepared in the same fashion as Step 2 in Example 1, except that (6'-chloro-4'-fluoro-[2,3'-bipyridin]-6-yl)methanol (184 mg, 0.774 mmol) prepared in Step 1 and cis-4-amino-1-methylcyclohexan-1-ol (100 mg, 0.774 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.96 (d, 1H), 8.36 (s, 1H), 7.83 (t, 1H), 7.60 (d, 1H), 6.59 (s, 1H), 4.85 (s, 2H), 3.43 (m, 1H), 1.89 (m, 2H), 1.74 (m, 4H), 1.58 (m, 2H), 1.31 (s, 3H); MS (ESI) m/z=348.1 (M+H)$^+$ Step 3. (1s,4s)-4-((6'-((2-(1-(Cyclopropylsulfonyl)-1H-pyrazol-4-yl)pyrimidin-4-yl)amino)-6-(hydroxy methyl)-[2,3'-bipyridin]-4'-yl)amino)-1-methylcyclohexan-1-ol The title compound as an off-white solid (15 mg) was prepared in the same fashion as Step 3 in Example 1, except that (1s,4s)-4-((6'-chloro-6-(hydroxymethyl)-[2,3'-bipyridin]-4'-yl)amino)-1-methylcyclohexan-1-ol (100 mg, 0.287 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.34 (d, 1H), 8.62 (s, 1H), 8.44 (s, 1H), 8.30 (d, 1H), 7.70 (t, 1H), 7.51 (d, 1H), 7.26 (d, 1H), 7.19 (d, 1H), 7.06 (brs, 1H), 4.78 (s, 2H), 3.60 (m, 1H), 2.82 (m, 1H), 1.89 (m, 2H), 1.74 (m, 4H), 1.56 (m, 2H), 1.49 (m, 2H), 1.26 (s, 3H), 1.19 (m, 2H); MS (ESI) m/z=577.2 (M+H)$^+$ Example 28. (1s,4s)-4-((6'-((2-(1-(Cyclopropylsulfonyl)-1H-pyrazol-4-yl)pyrimidin-4-yl)amino)-6-((4-methylpiperazin-1-yl)methyl)-[2,3'-bipyridin]-4'-yl)amino)-1-methylcyclohexan-1-ol Step 1. 6'-Chloro-4'-fluoro-6-((4-methylpiperazin-1-yl)methyl)-2,3'-bipyridine The title compound as an off-white solid (219 mg) was prepared in the same fashion as Step 1 in Example 1, except that 1-((6-bromo-2-pyridyl)methyl)-4-methyl-piperazine (374 mg, 1.39 mmol) was used instead of 1-((6-bromopyridin-3-yl)methyl)-4-methylpiperazine. MS (ESI) m/z=321.0 (M+H)$^+$

Step 2. (1s,4s)-4-((6'-Chloro-6-((4-methylpiperazin-1-yl)methyl)-[2,3'-bipyridin]-4'-yl)amino)-1-methylcyclohexan-1-ol The title compound as a white solid (151 mg) was prepared in the same fashion as Step 2 in Example 1, except that 6'-chloro-4'-fluoro-6-((4-methylpiperazin-1-yl)methyl)-2,3'-bipyridine (124 mg. 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.70 (d, 1H), 8.40 (s, 1H), 7.75 (t, 1H), 7.61 (d, 1H), 7.35 (d, 1H), 6.56 (s, 1H), 3.66 (s, 2H), 3.34 (m, 1H), 2.53 (m, 8H), 2.29 (m, 3H), 1.94 (m, 2H), 1.75 (m, 4H), 1.56 (m, 2H), 1.29 (s, 3H)

Step 3. (1s,4s)-4-((6'-((2-(1-(Cyclopropylsulfonyl)-1H-pyrazol-4-yl)pyrimidin-4-yl)amino)-6-((4-methylpiperazin-1-yl)methyl)-[2,3'-bipyridin]-4'-yl)amino)-1-methylcyclohexan-1-ol The title compound as an off-white solid (12.9 mg) was prepared in the same fashion as Step 3 in Example 1, except that (1s,4s)-4-((6'-chloro-6-((4-methylpiperazin-1-yl)methyl)-[2,3'-bipyridin]-4'-yl)amino)-1-methylcyclohexan-1-ol (49 mg. 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.76 (d, 1H), 8.66 (s, 1H), 8.44 (m, 3H), 7.75 (s, 1H), 7.62 (s, 1H), 7.30 (m, 2H), 7.07 (s, 1H), 3.68 (s, 2H), 3.49 (m, 1H), 2.82 (m, 1H), 2.55 (m, 8H), 2.30 (s, 3H), 2.01 (m, 2H), 1.76 (m, 4H), 1.53 (m, 4H), 1.29 (s, 3H), 1.22 (m, 2H); MS (ESI) m/z=659.3 (M+H)$^+$

Example 29. (1s,4s)-4-((6'-((2-(1-(Cyclopropylsulfonyl)-1H-pyrazol-4-yl)pyrimidin-4-yl)amino)-6-(morpholinomethyl)-[2,3'-bipyridin]-4'-yl)amino)-1-methylcyclohexan-1-ol

Step 1. 4-((6'-Chloro-4'-fluoro-[2,3'-bipyridin]-6-yl)methyl) morpholine

The title compound as an off-white solid (127 mg) was prepared in the same fashion as Step 1 in Example 1, except that 4-((6-bromo-2-pyridyl)methyl) morpholine (119 mg, 0.462 mmol) was used instead of 1-((6-bromopyridin-3-yl)methyl)-4-methylpiperazine. MS (ESI) m/z=308.0 (M+H)$^+$

Step 2. (1s,4s)-4-((6'-Chloro-6-(morpholinomethyl)-[2,3'-bipyridin]-4'-yl)amino)-1-methylcyclohexan-1-ol The title compound as a white solid (127 mg) was prepared in the same fashion as Step 2 in Example 1, except that 4-((6'-chloro-4'-fluoro-[2,3'-bipyridin]-6-yl)methyl) morpholine (119 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.66 (d, 1H), 8.37 (s, 1H), 7.73 (t, 1H), 7.58 (d, 1H), 7.33 (d, 1H), 6.54 (s, 1H), 3.71 (brs, 4H), 3.63 (s, 2H), 3.32 (m, 1H), 2.50 (brs, 4H), 1.92 (m, 2H), 1.74 (m, 4H), 1.54 (m, 2H), 1.27 (s, 3H); MS (ESI) m/z=417.2 (M+H)$^+$

Step 3. (1s,4s)-4-((6'-((2-(1-(Cyclopropylsulfonyl)-1H-pyrazol-4-yl)pyrimidin-4-yl)amino)-6-(morpholinomethyl)-[2,3'-bipyridin]-4'-yl)amino)-1-methylcyclohexan-1-ol The title compound as an off-white solid (3 mg) was prepared in the same fashion as Step 3 in Example 1, except that (1s,4s)-4-((6'-chloro-6-(morpholinomethyl)-[2,3'-bipyridin]-4'-yl)amino)-1-methylcyclohexan-1-ol (47 mg. 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.70 (d, 1H), 8.66 (s, 1H), 8.43 (m, 3H), 7.78 (s, 1H), 7.63 (s, 1H), 7.37 (m, 2H), 7.00 (s, 1H), 3.76 (brs, 4H), 3.68 (s, 2H), 3.37 (m, 1H), 2.82 (m, 1H), 2.55 (brs, 4H), 1.97 (m, 2H), 1.74 (m, 8H), 1.31 (s, 3H), 1.25 (m, 2H); MS (ESI) m/z=646.2 (M+H)$^+$

Example 30. (1s,4s)-4-((6'-((2-(1-(Cyclopropylsulfonyl)-1H-pyrazol-4-yl)pyrimidin-4-yl)amino)-6-((dimethylamino)methyl)-[2,3'-bipyridin]-4'-yl)amino)-1-methylcyclohexan-1-ol

Step 1. 1-(6'-Chloro-4'-fluoro-[2,3'-bipyridin]-6-yl)-N,N-dimethylmethanamine The title compound as an off-white solid (103 mg) was prepared in the same fashion as Step 1 in Example 1, except that 1-(6-bromo-2-pyridyl)-N,N-dimethyl-methanamine (99 mg, 0.462 mmol) was used instead of 1-((6-bromopyridin-3-yl)methyl)-4-methylpiperazine. MS (ESI) m/z=266.0 (M+H)$^+$

Step 2. (1s,4s)-4-((6'-Chloro-6-((dimethylamino)methyl)-[2,3'-bipyridin]-4'-yl)amino)-1-methylcyclohexan-1-ol The title compound as a white solid (112 mg) was prepared in the same fashion as Step 2 in Example 1, except that 1-(6'-chloro-4'-fluoro-[2,3'-bipyridin]-6-yl)-N,N-dimethylmethanamine (103 mg, 0.387 mmol) prepared in Step 1 and cis-4-amino-1-methylcyclohexan-1-ol (50 mg, 0.387 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.39 (d, 1H), 8.48 (d, 1H), 8.38 (s, 1H), 7.65 (s, 1H), 7.21 (d, 1H), 6.55 (s, 1H), 3.47 (s, 2H), 3.32 (m, 1H), 2.26 (s, 6H), 1.92 (m, 2H), 1.72 (m, 4H), 1.54 (m, 2H), 1.29 (s, 3H); MS (ESI) m/z=375.1 (M+H)$^+$

Step 3. (1s,4s)-4-((6'-((2-(1-(Cyclopropylsulfonyl)-1H-pyrazol-4-yl)pyrimidin-4-yl)amino)-6-((dimethylamino)methyl)-[2,3'-bipyridin]-4'-yl)amino)-1-methylcyclohexan-1-ol The title compound as an off-white solid (48.2 mg) was prepared in the same fashion as Step 3 in Example 1, except that (1s,4s)-4-((6'-chloro-6-((dimethylamino)methyl)-[2,3'-bipyridin]-4'-yl)amino)-1-methylcyclohexan-1-ol (42 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.52 (d, 1H), 8.66 (s, 1H), 8.43 (m, 4H), 7.69 (s, 1H), 7.17 (m, 3H), 3.48 (m, 3H), 2.82 (m, 1H), 2.28 (s, 6H), 1.97 (m, 2H), 1.74 (m, 4H), 1.53 (m, 4H), 1.30 (s, 3H), 1.21 (m, 2H); MS (ESI) m/z=604.3 (M+H)$^+$ Example 31. (1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)-1-methylcyclohexan-1-ol Step 1. 6'-Chloro-5-(1,3-dioxolan-2-yl)-4'-fluoro-2,3'-bipyridine The title compound as an off-white solid (1250 mg) was prepared in the same fashion as Step 1 in Example 1, except that 2-bromo-5-(1,3-dioxolan-2-yl)pyridine (2680 mg, 11.65 mmol) was used instead of 1-((6-bromopyridin-3-yl)methyl)-4-methylpiperazine. MS (ESI) m/z=280.9 (M+H)$^+$ Step 2. (1s,4s)-4-((6'-Chloro-5-(1,3-dioxolan-2-yl)-[2,3'-bipyridin]-4'-yl)amino)-1-methylcyclohexan-1-ol The title compound as a white solid (1367 mg) was prepared in the same fashion as Step 2 in Example 1, except that 6'-chloro-5-(1,3-dioxolan-2-yl)-4'-fluoro-2,3'-bipyridine (1076 mg. 3.83 mmol) prepared in Step 1 and cis-4-amino-1-methylcyclohexan-1-ol (495 mg, 3.83 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 600 MHz) δ 9.38 (d, 1H), 8.66 (s, 1H), 7.88 (dd, 1H), 7.73 (d, 1H), 6.56 (s, 1H), 5.89 (s, 1H), 4.17-4.07 (m, 4H), 3.35 (m, 1H), 1.93 (m, 2H), 1.72 (m, 4H), 1.57 (m, 2H), 1.30 (s, 3H)

Step 3. (1s,4s)-4-((6'-((2-(1-(Cyclopropylsulfonyl)-1H-pyrazol-4-yl)pyrimidin-4-yl)amino)-5-(1,3-dioxolan-2-yl)-[2,3'-bipyridin]-4'-yl)amino)-1-methylcyclohexan-1-ol The title compound as an off-white solid (600 mg) was prepared in the same fashion as Step 3 in Example 1, except that (1s,4s)-4-((6'-chloro-5-(1,3-dioxolan-2-yl)-[2,3'-bipyridin]-4'-yl)amino)-1-methylcyclohexan-1-ol (1175 mg. 3.02 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.48 (d, 1H), 8.67 (d, 2H), 8.48 (s, 1H), 8.45 (s, 1H), 8.41 (d, 1H), 7.87 (m, 2H), 7.54 (d, 1H), 7.02 (brs, 1H), 5.89 (s, 1H), 4.19-4.07 (m, 4H), 3.53 (m, 1H), 2.82 (m, 1H), 1.99 (m, 2H), 1.76 (m, 4H), 1.62 (m, 2H), 1.53 (m, 2H), 1.30 (s, 3H), 1.22 (m, 2H); MS (ESI) m/z=619.2 (M+H)$^+$ Step 4. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde To a solution of (1s,4s)-4-((6'-((2-(1-(cyclopropylsulfonyl)-1H-pyrazol-4-yl)pyrimidin-4-yl)amino)-5-(1,3-dioxolan-2-yl)-[2,3'-bipyridin]-4'-yl)amino)-1-methylcyclohexan-1-ol (520) mg. 0.84 mmol) prepared in Step 3 in 1,4-dioxane (8 mL) was added 4N hydrochloric acid solution (2 mL). This mixture was stirred at room temperature for 10 hours. The reaction mixture was basified with sat. NaHCO$_3$ soln., diluted with DCM and water, and then extracted with DCM. The organic layer was dried over MgSO$_4$, filtered, and concentrated. The crude residue was purified by silica gel column chromatography (MeOH/DCM=0-10%) to give 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde (450 mg) as a white solid. $^1$H-NMR (DMSO-d$_6$, 400 MHz) δ 10.13 (s, 1H), 10.07 (s, 1H), 9.67 (d, 1H), 9.10 (s, 1H), 8.67 (m, 2H), 8.45 (m, 1H), 8.23 (s, 2H), 7.50 (s, 1H), 7.40 (s, 1H), 3.45 (m, 1H), 3.25 (m, 1H), 1.85 (m, 2H), 1.70 (m, 2H), 1.59 (m, 2H), 1.44 (m, 2H), 1.33 (m, 2H), 1.23 (m, 2H), 1.14 (s, 3H); MS (ESI) m/z=575.2 (M+H)$^+$ Step 5. (1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)-1-methylcyclohexan-1-ol The title compound as an off-white solid (10 mg) was prepared in the same fashion as Step 2 in Example 25, except that 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde (25 mg. 0.044 mmol) and dimethylamine (8 mg. 0.174 mmol) were used instead of 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde and morpholine. $^1$H-NMR (CDCl$_3$, 400 MHz) δ 10.73 (d, 1H), 8.65 (s, 1H), 8.59 (s, 1H), 8.54 (s, 1H), 8.48 (s, 1H), 8.45 (d, 1H), 8.22 (s, 1H), 8.00 (s, 1H), 7.85 (d, 1H), 7.10 (d, 1H), 7.07 (d, 1H), 3.66 (m, 1H), 3.57 (s, 2H), 2.84 (m, 1H), 2.34 (s, 6H), 2.02 (m, 2H), 1.86 (m, 2H), 1.74 (m, 2H), 1.65 (m, 2H), 1.54 (m, 2H), 1.32 (s, 3H), 1.24 (m, 2H); MS (ESI) m/z=604.2 (M+H)$^+$ Example 32. (1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)-1-methylcyclohexan-1-ol The title compound as an off-white solid (11.2 mg) was prepared in the same fashion as Step 2 in Example 25, except that 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde (30 mg, 0.052 mmol) in Step 4 of Example 31 was used instead of 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde. $^1$H-NMR (CDCl$_3$, 400 MHz) δ 10.97 (d, 1H), 8.67 (s, 1H), 8.56 (s, 1H), 8.49 (d, 2H), 8.41 (s, 1H), 8.26 (m, 3H), 8.07 (s, 1H), 7.88 (d, 1H), 7.07 (d, 1H), 3.77 (m, 4H), 3.70 (m, 1H), 3.65 (s, 2H), 2.83 (m, 1H), 2.58 (m, 4H), 2.03 (m, 2H), 1.88 (m, 2H), 1.75 (m, 2H), 1.65 (m, 2H), 1.55 (m, 2H), 1.33 (s, 3H), 1.24 (m, 2H); MS (ESI) m/z=646.2 (M+H)$^+$ Example 33. (1s,4s)-4-((6'-((2-(1-(Cyclopropylsulfonyl)-1H-pyrazol-4-yl)pyrimidin-4-yl)amino)-5-((4,4-difluoropiperidin-1-yl)methyl)-[2,3'-bipyridin]-4'-yl)amino)-1-methylcyclohexan-1-ol The title compound as an off-white solid (11.1 mg) was prepared in the same fashion as Step 2 in Example 25, except that 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde (30 mg, 0.052 mmol) in Step 4 of Example 31 and 4,4-difluoropiperidine (19 mg, 0.156 mmol) were used instead of 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde and morpholine. $^1$H-NMR (CDCl$_3$, 400 MHz) δ 10.99 (d, 1H), 8.66 (s, 1H), 8.54 (s, 1H), 8.47 (m, 4H), 8.32 (s, 1H), 8.07 (s, 1H), 7.85

(d, 1H), 7.75 (d, 1H), 7.07 (d, 1H), 3.69 (m, 1H), 3.63 (s, 2H), 2.84 (m, 1H), 2.62 (brs, 4H), 2.10-2.02 (m, 6H), 1.87 (m, 2H), 1.75 (m, 2H), 1.62 (m, 2H), 1.55 (m, 2H), 1.33 (s, 3H), 1.23 (m, 2H); MS (ESI) m/z=680.2 (M+H)$^+$ Example 34. (1s,4s)-4-((6'-((2-(1-(Cyclopropylsulfonyl)-1H-pyrazol-4-yl)pyrimidin-4-yl)amino)-5-((4-isopropylpiperazin-1-yl)methyl)-[2,3'-bipyridin]-4'-yl)amino)-1-methylcyclohexan-1-ol The title compound as an off-white solid (10.5 mg) was prepared in the same fashion as Step 2 in Example 25, except that 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbaldehyde (25 mg, 0.044 mmol) in Step 4 of Example 31 and 1-isopropylpiperazine (17 mg, 0.131 mmol) were used instead of 6'-((2-(1-(cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridine]-5-carbaldehyde and morpholine. $^1$H-NMR (MeOD, 400 MHz) δ 8.79 (s, 1H), 8.59 (s, 1H), 8.50 (d, 2H), 8.43 (d, 1H), 8.38 (s, 2H), 7.90 (s, 2H), 7.23 (d, 1H), 7.14 (s, 1H), 3.72 (s, 2H), 3.60 (m, 1H), 3.47 (m, 1H), 3.28 (m, 8H), 3.03 (m, 1H), 1.97 (m, 2H), 1.78 (m, 4H), 1.59 (m, 2H), 1.46 (m, 2H), 1.37 (s, 6H), 1.25 (m, 5H); MS (ESI) m/z=687.3 (M+H)$^+$ Example 35. (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-methylcyclohexan-1-ol Step 1. 6'-Chloro-4'-fluoro-2,3'-bipyridine The title compound as a white solid (364 mg) was prepared in the same fashion as Step 1 in Example 1 except that 2-bromopyridine (307 mg, 1.942 mmol) was used instead of 1-((6-bromopyridin-3-yl)methyl)-4-methylpiperazine. $^1$H-NMR (CDCl$_3$, 400 MHz) δ 9.03 (d, 1H), 8.77 (d, 1H), 7.83-7.79 (m, 1H) 7.76-7.74 (m, 1H), 7.36-7.33 (m, 1H), 7.21 (d, 1H); MS (ESI) m/z=208.9 (M+H)$^+$ Step 2. (1s,4s)-4-((6'-Chloro-[2,3'-bipyridin]-4'-yl)amino)-1-methylcyclohexan-1-ol The title compound as a white solid (220 mg) was prepared in the same fashion as Step 2 in Example 1 except that 6'-chloro-4'-fluoro-2,3'-bipyridine (150 mg, 0.719 mmol) prepared in Step 1 and cis-4-amino-1-methylcyclohexan-1-ol (111 mg. 0.863 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.38 (s, 1H), 8.58-8.57 (m, 1H), 8.40 (s, 1H), 7.82-7.77 (m, 1H), 7.73-7.71 (m, 1H), 7.26-7.23 (m, 1H), 6.58 (s, 1H), 3.39-3.33 (m, 1H), 1.96-1.94 (m, 2H), 1.78-1.63 (m, 4H), 1.58-1.55 (m, 2H), 1.31 (s, 3H), 1.20 (s, 1H); MS (ESI) m/z=319.1 (M+H)$^+$ Step 3. (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-methylcyclohexan-1-ol The title compound (50 mg) as a white solid was prepared in the same fashion as Step 3 in Example 1, except that (1s,4s)-4-((6'-chloro-[2,3'-bipyridin]-4'-yl)amino)-1-methylcyclohexan-1-ol (173 mg. 0.543 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.61 (s, 1H), 8.47-8.45 (m, 4H), 8.26 (s, 1H), 8.11 (s, 1H), 7.84 (t, 1H), 7.75 (d, 1H), 7.27 (t, 1H), 7.06 (d, 1H), 4.71 (t, 1H), 4.59 (t, 1H), 4.04 (s, 1H), 3.13 (t, 1H), 3.06 (t, 1H), 2.88-2.83 (m, 2H), 2.15-2.11 (m, 2H), 2.00-1.90 (m, 4H), 1.63-1.54 (m, 2H), 1.27-1.25 (m, 3H); MS (ESI) m/z=547.1 (M+H)$^+$ Example 36. N$^{6'}$-(2-(1-(Cyclopropylsulfonyl)-1H-pyrazol-4-yl)pyrimidin-4-yl)-N$^{4'}$-((1s,4s)-4-((2-fluoroethyl)amino)cyclohexyl)-[2,3'-bipyridine]-4',6'-diamine Step 1. (1s,4s)—N$^1$-(6'-Chloro-[2,3'-bipyridin]-4'-yl)-N$^4$-(2-fluoroethyl)cyclohexane-1,4-diamine The title compound as a white solid (195 mg) was prepared in the same fashion as Step 2 in Example 1 except that 6'-chloro-4'-fluoro-2,3'-bipyridine (150 mg, 0.719 mmol) prepared in Step 1 of Example 35 and (1s,4s)—N$^1$-(2-fluoroethyl)cyclohexane-1,4-diamine (138 mg, 0.863 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.69 (s, 1H), 8.78 (d, 1H), 8.42 (s, 1H), 7.81-7.78 (m, 1H), 7.74 (d, 1H), 7.25-7.23 (m, 1H), 6.58 (s, 1H), 4.62 (t, 1H), 4.50 (t, 1H), 3.66 (s, 1H), 2.97 (t, 1H), 2.90 (t, 1H), 2.78-2.58 (m, 1H), 1.93-1.90 (m, 2H), 1.82-1.70 (m, 4H), 1.55-1.49 (m, 3H); MS (ESI) m/z=349.1 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-((2-fluoroethyl)amino)cyclohexyl)-[2,3'-bipyridine]-4',6'-diamine The title compound (5 mg) as a white solid was prepared in the same fashion as Step 3 in Example 1, except that (1s,4s)—N$^1$-(6'-chloro-[2,3'-bipyridin]-4'-yl)-N$^4$-(2-fluoroethyl)cyclohexane-1,4-diamine (189 mg, 0.543 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.47 (s, 1H), 8.67 (s, 1H), 8.58 (d, 1H), 8.49 (s, 1H), 8.44-8.42 (m, 2H), 7.80-7.72 (m, 2H), 7.53 (s, 1H), 7.36 (d, 1H), 7.20 (t, 1H), 6.97 (s, 1H), 3.50 (br, 1H), 2.85-2.81 (m, 1H), 2.03-1.99 (m, 2H), 1.82-1.74 (m, 4H), 1.59-1.58 (m, 1H), 1.55-1.53 (m, 3H), 1.32 (s, 3H), 1.23-1.21 (m, 3H); MS (ESI) m/z=578.2 (M+H)$^+$ Example 37. (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-(hydroxymethyl)cyclohexan-1-ol Step 1. (1s,4s)-4-((6'-Chloro-[2,3'-bipyridin]-4'-yl)amino)-1-(hydroxymethyl)cyclohexan-1-ol The title compound as a white solid (220 mg) was prepared in the same fashion as Step 2 in Example 1 except that 6'-chloro-4'-fluoro-2,3'-bipyridine (150 mg, 0.719 mmol) prepared in Step 1 of Example 35 and (1s,4s)-4-amino-1-(hydroxymethyl)cyclohexan-1-ol (125 mg, 0.863 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.32 (d, 1H), 8.47 (d, 1H), 8.28-8.26 (m, 1H), 7.72-7.60 (m, 2H), 7.16-7.13 (d, 1H), 6.49-6.47 (m, 1H), 4.16-4.14 (m, 1H), 3.41 (s, 1H), 3.26 (s, 2H), 1.86 (s, 2H), 1.75-1.67 (m, 4H), 1.40-1.37 (m, 2H); MS (ESI) m/z=334.0 (M+H)+

Step 2. (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-(hydroxymethyl)cyclohexan-1-ol The title compound (53 mg) as a white solid was prepared in the same fashion as Step 3 in Example 1, except that (1s,4s)-4-((6'-chloro-[2,3'-bipyridin]-4'-yl)amino)-1-(hydroxymethyl)cyclohexan-1-ol (194 mg. 0.58 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.53 (d, 1H), 8.66 (s, 1H), 8.64-8.54 (m, 1H) 8.49 (s, 1H), 8.43-8.37 (m, 2H), 7.80-7.61 (m, 2H), 7.53 (s, 1H), 7.21-7.18 (m, 3H), 2.87-2.83 (m, 1H), 2.08-2.05 (m, 2H), 1.81-1.62 (m, 5H), 1.56-1.50 (m, 4H), 1.26-1.23 (m, 3H)+ MS (ESI) m/z=563.0 (M+H)+

Example 38. (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol Step 1. (1s,4s)-4-((6'-Chloro-5-morpholino-[2,3'-bipyridin]-4'-yl)amino)-1-methylcyclohexan-1-ol The title compound as a white solid (111 mg) was prepared in the same fashion as Step 2 in Example 1 except that 4-(6'-chloro-4'-fluoro-[2,3'-bipyridin]-5-yl) morpholine (93 mg, 0.316 mmol) prepared in Reference Example 25 and cis-4-amino-1-methylcyclohexan-1-ol (49 mg, 0.379 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.21 (d, 1H), 8.29 (s, 1H), 8.22 (d, 1H), 7.60 (d, 1H), 7.29 (d, 1H), 6.53 (s, 1H) 3.89 (t, 4H), 3.33-3.32 (m, 1H), 3.23 (t, 4H), 1.94-1.91 (m, 3H), 1.77-1.66 (m, 4H), 1.56-1.53 (m, 2H), 1.45 (s, 1H), 1.25 (s, 3H); MS (ESI) m/z=403.0 (M+H)+

Step 2. (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol The title compound (3.6 mg) as a pale yellow solid was prepared in the same fashion as Step 3 in Example 1, except that (1s,4s)-4-((6'-chloro-5-morpholino-[2,3'-bipyridin]-4'-yl)amino)-1-methylcyclohexan-1-ol (105 mg, 0.261 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.33 (s, 1H), 8.66 (s, 1H), 8.45 (d, 1H), 8.40 (s, 1H), 8.28 (d, 1H), 8.24 (s, 1H), 7.84 (br, 1H), 7.63 (d, 1H), 7.31 (d, 2H), 7.01 (s, 1H), 3.91 (t, 4H), 3.50 (s, 1H), 3.25 (t, 4H), 2.85-2.80 (m, 1H), 1.99-1.81 (m, 3H), 1.76-1.52 (m, 6H), 1.31 (s, 3H), 1.28-1.19 (m, 3H); MS (ESI) m/z=632.3 (M+H)+

Example 39. (1s,4s)-4-((2-((2-(1-(Cyclopropylsulfonyl)-1H-pyrazol-4-yl)pyrimidin-4-yl)amino)-5-(dimethylamino)pyrimidin-2-yl)pyridin-4-yl)amino)-1-methylcyclohexan-1-ol Step 1. 2-(6-Chloro-4-fluoropyridin-3-yl)-N,N-dimethylpyrimidin-5-amine The title compound as a white solid (59 mg) was prepared in the same fashion as Step 1 in Example 1 except that 2-bromo-N,N-dimethylpyrimidin-5-amine (88 mg, 0.436 mmol) was used instead of 1-((6-bromopyridin-3-yl)methyl)-4-methylpiperazine. $^1$H-NMR (CDCl$_3$, 400 MHz) δ 9.07 (d, 1H), 8.33 (s, 2H), 7.19 (d, 1H), 3.09 (s, 6H); MS (ESI) m/z=252.9 (M+H)+

Step 2. (1s,4s)-4-((2-Chloro-5-(5-(dimethylamino)pyrimidin-2-yl)pyridin-4-yl)amino)-1-methylcyclohexan-1-ol The title compound as a white solid (80 mg) was prepared in the same fashion as Step 2 in Example 1 except that 2-(6-chloro-4-fluoropyridin-3-yl)-N,N-dimethylpyrimidin-5-amine (59 mg. 0.233 mmol) prepared in Step 1 and cis-4-amino-1-methylcyclohexan-1-ol (56 mg, 0.436 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.51 (d, 1H), 9.13 (s, 1H), 8.25 (s, 2H), 6.55 (s, 1H), 3.39-3.36 (m, 1H), 3.02 (s, 6H), 1.99-1.94 (m, 2H), 1.79-1.70 (m, 4H), 1.29 (s, 3H), 1.26-1.19 (m, 3H); MS (ESI) m/z=362.1 (M+H)+

Step 3. (1s,4s)-4-((2-((2-(1-(Cyclopropylsulfonyl)-1H-pyrazol-4-yl)pyrimidin-4-yl)amino)-5-(5-(dimethylamino)pyrimidin-2-yl)pyridin-4-yl)amino)-1-methylcyclohexan-1-ol The title compound (10 mg) as a pale yellow solid was prepared in the same fashion as Step 3 in Example 1, except that (1s,4s)-4-((2-chloro-5-(5-(dimethylamino)pyrimidin-2-yl)pyridin-4-yl)amino)-1-methylcyclohexan-1-ol (85 mg. 0.235 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.61 (s, 1H), 9.13 (s, 1H), 8.67 (s, 1H), 8.49 (s, 1H), 8.40 (d, 1H), 8.26 (s, 2H), 7.13 (s, 1H), 7.08 (s, 1H) 7.06-6.99 (m, 1H), 3.57-3.50 (m, 1H), 3.50 (s, 5H), 2.86-2.80 (m, 1H), 2.08-2.02 (m, 2H), 1.85-1.76 (m, 4H), 1.54-1.53 (m, 4H), 1.33 (s, 3H), 1.29-2.27 (m, 6H); MS (ESI) m/z=591.2 (M+H)+

Example 40. (1s,4s)-4-((6'-((2-(1-(Cyclopropylsulfonyl)-1H-pyrazol-4-yl)pyrimidin-4-yl)amino)-5-(dimethylamino)-[2,3'-bipyridin]-4'-yl)amino)-1-methylcyclohexan-1-ol Step 1. 6'-Chloro-4'-fluoro-N,N-dimethyl-[2,3'-bipyridin]-5-amine The title compound as a white solid (46 mg) was prepared in the same fashion as Step 1 in Example 1 except that 6-bromo-N,N-dimethylpyridin-3-amine (88 mg, 0.436 mmol) was used instead of 1-((6-bromopyridin-3-yl)methyl)-4-methylpiperazine. $^1$H-NMR (CDCl$_3$, 400 MHz) δ 9.00 (d, 1H), 8.26 (d, 1H), 7.61 (t, 1H), 7.15 (d, 1H), 7.03 (dd, 1H), 3.07 (s, 6H); MS (ESI) m/z=251.9 (M+H)+

Step 2. (1s,4s)-4-((6'-Chloro-5-(dimethylamino)-[2,3'-bipyridin]-4'-yl)amino)-1-methylcyclohexan-1-ol The title compound as a white solid (65 mg) was prepared in the same fashion as Step 2 in Example 1 except that 6'-chloro-4'-fluoro-N,N-dimethyl-[2,3'-bipyridin]-5-amine (46 mg, 0.183 mmol) prepared in Step 1 and cis-4-amino-1-methylcyclohexan-1-ol (56 mg, 0.436 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.24 (d, 1H), 8.27 (s, 1H), 8.07 (d, 1H), 7.50 (d, 1H), 7.10 (dd, 1H), 6.52 (s, 1H), 3.35-3.32 (m, 1H), 2.95 (s, 6H), 1.96-1.93 (m, 2H), 1.78-1.70 (m, 4H), 1.65-1.55 (m, 3H), 1.26-1.22 (m, 2H); MS (ESI) m/z=361.0 (M+H)$^+$ Step 3. (1s,4s)-4-((6'-((2-(1-(Cyclopropylsulfonyl)-1H-pyrazol-4-yl)pyrimidin-4-yl)amino)-5-(dimethylamino)-[2,3'-bipyridin]-4'-yl)amino)-1-methylcyclohexan-1-ol The title compound (4.4 mg) as a solid was prepared in the same fashion as Step 3 in Example 1, except that (1s,4s)-4-((6'-chloro-5-(dimethylamino)-[2,3'-bipyridin]-4'-yl)amino)-1-methylcyclohexan-1-ol (70 mg, 0.194 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (MeOD, 400 MHz) δ 8.85 (s, 1H), 8.54 (s, 1H), 8.48-8.46 (m, 3H), 8.37 (s, 1H), 7.73 (d, 1H), 7.27 (dd, 1H), 7.10 (d, 1H), 6.88 (s, 1H), 4.50 (s, 1H), 3.57 (s, 1H), 3.06 (s, 6H), 1.98-1.94 (m, 3H), 1.83-1.78 (m, 5H), 1.63-1.56 (m, 3H), 1.49-1.44 (m, 3H), 1.39-1.33 (m, 2H); MS (ESI) m/z=590.2 (M+H)$^+$ Example 41. (1s,4s)-4-((2-((2-(1-(Cyclopropylsulfonyl)-1H-pyrazol-4-yl)pyrimidin-4-yl)amino)-5-(4-(dimethylamino)pyrimidin-2-yl)pyridin-4-yl)amino)-1-methylcyclohexan-1-ol Step 1. 2-(6-Chloro-4-fluoropyridin-3-yl)-N,N-dimethylpyrimidin-4-amine The title compound as a white solid (152 mg) was prepared in the same fashion as Step 1 in Example 1 except that 2-bromo-N,N-dimethyl-pyrimidin-4-amine (157 mg, 0.777 mmol) was used instead of 1-((6-bromopyridin-3-yl)methyl)-4-methylpiperazine. ¹H-NMR (CDCl₃, 400 MHz) δ 9.11 (d, 1H), 8.32 (d, 1H), 7.95 (d, 1H), 7.19 (d, 1H), 6.42 (d, 1H), 6.34 (d, 1H), 3.18 (s, 6H); MS (ESI) m/z=252.9 (M+H)$^+$ Step 2. (1s,4s)-4-((2-Chloro-5-(4-(dimethylamino)pyrimidin-2-yl)pyridin-4-yl)amino)-1-methylcyclohexan-1-ol The title compound as a white solid (108 mg) was prepared in the same fashion as Step 2 in Example 1 except that 2-(6-chloro-4-fluoropyridin-3-yl)-N,N-dimethylpyrimidin-4-amine (150 mg, 0.594 mmol) prepared in Step 1 and cis-4-amino-1-methylcyclohexan-1-ol (115 mg, 0.89 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.88 (d, 1H), 9.22 (s, 1H), 8.18 (d, 1H), 6.54 (s, 1H), 6.33 (d, 1H), 3.37-3.32 (m, 1H), 3.17 (s, 6H), 2.06-1.94 (m, 2H), 1.78-1.60 (m, 5H), 1.31 (s, 3H), 1.16 (s, 1H); MS (ESI) m/z=362.1 (M+H)$^+$ Step 3. (1s,4s)-4-((2-((2-(1-(Cyclopropylsulfonyl)-1H-pyrazol-4-yl)pyrimidin-4-yl)amino)-5-(4-(dimethylamino)pyrimidin-2-yl)pyridin-4-yl)amino)-1-methylcyclohexan-1-ol The title compound (13 mg) as a pale yellow solid was prepared in the same fashion as Step 3 in Example 1 except that (1s,4s)-4-((2-chloro-5-(4-(dimethylamino)pyrimidin-2-yl)pyridin-4-yl)amino)-1-methylcyclohexan-1-ol (105 mg, 0.29 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 9.67 (d, 1H), 9.09 (s, 1H), 8.66 (s, 1H), 8.47 (s, 1H), 8.42 (d, 1H), 8.22 (d, 1H), 7.49 (s, 1H), 7.28 (s, 1H), 6.54 (d, 1H), 3.23-3.12 (m, 2H), 3.02 (s, 6H), 1.85-1.82 (m, 2H), 1.64-1.56 (m, 4H), 1.44-1.38 (m, 2H), 1.33-1.31 (m, 2H) 1.31-1.25 (m, 3H), 1.24 (s, 3H); MS (ESI) m/z=591.3 (M+H)$^+$ Example 42. (1s,4s)-4-((2-((2-(1-(Cyclopropylsulfonyl)-1H-pyrazol-4-yl)pyrimidin-4-yl)amino)-5-(pyridazin-3-yl)pyridin-4-yl)amino)-1-methylcyclohexan-1-ol Step 1. 3-(6-Chloro-4-fluoro-3-pyridyl)pyridazine The title compound as a white solid (34 mg) was prepared in the same fashion as Step 1 in Example 1 except that 3-bromopyridazine (123 mg, 0.777 mmol) was used instead of 1-((6-bromopyridin-3-yl)methyl)-4-methylpiperazine. ¹H-NMR (CDCl₃, 400 MHz) δ 9.27 (d, 1H), 9.24 (dd, 1H), 7.94 (d, 1H), 7.63 (dd, 1H), 7.30 (s, 1H); MS (ESI) m/z=209.9 (M+H)$^+$ Step 2. (1s,4s)-4-((2-Chloro-5-(pyridazin-3-yl)pyridin-4-yl)amino)-1-methylcyclohexan-1-ol The title compound as a white solid (38 mg) was prepared in the same fashion as Step 2 in Example 1 except that 3-(6-chloro-4-fluoro-3-pyridyl)pyridazine (35 mg, 0.167 mmol) prepared in Step 1 and cis-4-amino-1-methylcyclohexan-1-ol (32 mg, 0.25 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.53 (s, 1H), 9.11 (t, 1H), 7.94 (d, 1H), 7.60 (dd, 1H), 6.66 (s, 1H), 3.42-3.40 (m, 1H), 1.98-1.94 (m, 2H), 1.80-1.76 (m, 4h), 1.59-1.55 (m, 2H), 1.31 (s, 3H), 1.26 (s, 1H); MS (ESI) m/z=319.0 (M+H)$^+$ Step 3. (1s,4s)-4-((2-((2-(1-(Cyclopropylsulfonyl)-1H-pyrazol-4-yl)pyrimidin-4-yl)amino)-5-(pyridazin-3-yl)pyridin-4-yl)amino)-1-methylcyclohexan-1-ol The title compound (10 mg) as a pale yellow solid was prepared in the same fashion as Step 3 in Example 1 except that (1s,4s)-4-((2-chloro-5-(pyridazin-3-yl)pyridin-4-yl)amino)-1-methylcyclohexan-1-ol (59 mg, 0.185 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.62 (d, 1H), 9.07 (t, 1H), 8.68 (s, 1H), 8.49 (s, 1H), 8.45 (d, 1H), 7.94 (d, 1H), 7.58-7.50 (m, 2H), 7.35 (d, 1H), 7.08 (s, 1H), 3.58-3.57 (m, 1H), 2.86-2.82 (m, 1H), 2.06-2.00 (m, 2H), 1.88-1.62 (m, 5H), 1.58-1.52 (m, 4H), 1.26-1.20 (m, 4H), 1.15-1.13 (m, 1H); MS (ESI) m/z=548.2 (M+H)$^+$ Example 43. (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol Step 1. 4-(6-(6-Chloro-4-fluoropyridin-3-yl)pyridazin-3-yl) morpholine The title compound as a beige solid (67 mg) was prepared in the same fashion as Step 1 in Example 1 except that 4-(6-bromo-3-pyridazinyl) morpholine (142 mg, 0.583 mmol) was used instead of 1-((6-bromopyridin-3-yl)methyl)-4-methylpiperazine. $^1$H-NMR (CDCl$_3$, 400 MHz) δ 9.17 (d, 1H), 7.70 (dd, 1H), 7.21 (d, 1H), 6.84 (d, 1H), 3.89 (t, 4H), 3.73 (t, 4H)

Step 2. (1s,4s)-4-((2-Chloro-5-(6-morpholino-pyridazin-3-yl)pyridin-4-yl)amino)-1-methylcyclohexan-1-ol The title compound as a white solid (74 mg) was prepared in the same fashion as Step 2 in Example 1 except that 4-(6-(6-chloro-4-fluoropyridin-3-yl)pyridazin-3-yl) morpholine (58 mg, 0.197 mmol) prepared in Step 1 and cis-4-amino-1-methylcyclohexan-1-ol (38 mg, 0.295 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.27 (d, 1H), 8.27 (s, 1H), 7.69 (d, 1H), 7.04 (d, 1H), 6.61 (s, 1H), 4.13 (t, 4H), 3.89 (t, 4H), 3.38-3.36 (m, 1H), 1.96-1.94 (m, 2H), 1.82-1.73 (m, 4H), 1.61-1.60 (m, 1H), 1.54 (s, 1H), 1.20 (s, 3H); MS (ESI) m/z=404.0 (M+H)$^+$ Step 3. (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol The title compound (14.9 mg) as a solid was prepared in the same fashion as Step 3 in Example 1, except that (1s,4s)-4-((2-chloro-5-(6-morpholinopyridazin-3-yl)pyridin-4-yl)amino)-1-methylcyclohexan-1-ol (70 mg, 0.173 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.30 (d, 1H), 8.67 (s, 1H), 8.48 (s, 1H), 8.43 (d, 1H), 8.29 (s, 1H), 7.72 (d, 1H), 7.50 (s, 1H), 7.38 (d, 1H), 7.05 (d, 1H), 6.69 (s, 1H), 3.89 (t, 4H), 3.67 (t, 4H), 3.53-3.51 (m, 1H), 2.85-2.81 (m, 1H), 2.06-1.99 (m, 2H), 1.85-1.74 (m, 5H), 1.56-1.52 (m, 3H), 1.31 (s, H) 1.29-1.19 (m, 3H); MS (ESI) m/z=633.3 (M+H)$^+$ Example 44. (1s,4s)-4-((2-((2-(1-(Cyclopropylsulfonyl)-1H-pyrazol-4-yl)pyrimidin-4-yl)amino)-5-(5-morpholinopyrazin-2-yl)pyridin-4-yl)amino)-1-methylcyclohexan-1-ol Step 1. 4-(5-(6-Chloro-4-fluoropyridin-3-yl)pyrazin-2-yl) morpholine The reaction mixture of 2-chloro-4-fluoro-5-iodopyridine (133 mg, 0.515 mmol), 4-(5-(4,4,5,5-tetramethyl-1,3,2-dioxaborolan-2-yl) pyrazin-2-yl) morpholine (150 mg, 0.515 mmol), [1,1'-bis(diphenylphosphino)ferrocene]dichloropalladium (II), complex with dichloromethane (42 mg, 0.05 mmol), and 3 M K$_2$CO$_3$ soln. (0.77 mL, 2.32 mmol) in 1,4-dioxane (4 mL) was stirred at 70° C. for 3 hours. The reaction mixture was cooled to room temperature and extracted with DCM. The organic layer was dried over MgSO$_4$, filtered, and concentrated. The crude residue was purified by silica gel column chromatography (EA/n-Hex=10-60%) to give 4-(5-(6-chloro-4-fluoropyridin-3-yl) pyrazin-2-yl) morpholine (130 mg) as a pale yellow solid. $^1$H-NMR (CDCl$_3$, 400 MHz) δ 8.98 (d, 1H), 8.56 (s, 1H), 8.24 (s, 1H), 7.19 (d, 1H), 3.87 (t, 4H), 3.67 (t, 4H); MS (ESI) m/z=294.9 (M+H)$^+$ Step 2. (1s,4s)-4-((2-Chloro-5-(5-morpholinopyrazin-2-yl)pyridin-4-yl)amino)-1-methylcyclohexan-1-ol The title compound as a white solid (103 mg) was prepared in the same fashion as Step 2 in Example 1 except that 4-(5-(6-chloro-4-fluoropyridin-3-yl) pyrazin-2-yl) morpholine (130 mg, 0.441 mmol) prepared in Step 1 and cis-4-amino-1-methylcyclohexan-1-ol (85 mg, 0.662 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.50 (s, 1H), 8.29 (s, 1H), 8.06 (s, 1H), 6.55 (s, 1H), 3.87 (t, 4H), 3.61 (t, 4H), 3.35-3.33 (t, 1H), 1.95-1.91 (m, 2H), 1.77-1.70 (m, 3H), 1.67-1.54 (m, 3H), 1.31 (s, 3H); MS (ESI) m/z=404.0 (M+H)$^+$ Step 3. (1s,4s)-4-((2-((2-(1-(Cyclopropylsulfonyl)-1H-pyrazol-4-yl)pyrimidin-4-yl)amino)-5-(5-morpholinopyrazin-2-yl)pyridin-4-yl)amino)-1-methylcyclohexan-1-ol The title compound (11 mg) as a pale yellow solid was prepared in the same fashion as Step 3 in Example 1, except that (1s,4s)-4-((2-chloro-5-(5-morpholinopyrazin-2-yl)pyridin-4-yl)amino)-1-methylcyclohexan-1-ol (89 mg, 0.22 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.53 (s, 1H), 8.48 (s, 1H), 8.42 (d, 1H), 8.39 (d, 1H), 8.31 (s, 1H), 8.07 (s, 1H), 7.53 (s, 1H), 7.35 (d, 1H), 6.97 (s, 1H), 3.88 (t, 4H), 3.65 (t, 4H), 3.50 (s, 1H), 2.84-2.81 (m, 1H), 2.00-1.98 (m, 2H), 1.75-1.70 (m, 5H), 1.56-1.51 (m, 3H), 1.32 (s, 3H), 1.29-1.27 (m, 3H); MS (ESI) m/z=633.2 (M+H)$^+$ Example 45. 2-((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)propan-2-ol Step 1. 2-((1s,4s)-4-((6'-Chloro-5-morpholino-[2,3'-bipyridin]-4'-yl)amino)cyclohexyl)propan-2-ol The title compound as a pale yellow solid (94 mg) was prepared in the same fashion as Step 2 in Example 1 except that 4-(6'-chloro-4'-fluoro-[2,3'-bipyridin]-5-yl) morpholine (85 mg. 0.289 mmol) prepared in Reference Example 25 and 2-((1s,4s)-4-aminocyclohexyl)propan-2-ol (59 mg, 0.376 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.79 (d, 1H), 8.36 (s, 1H), 8.20 (d, 1H), 7.67 (d, 1H), 7.32 (dd, 1H), 6.56 (s, 1H), 3.91 (t, 1H), 3.84-3.82 (m, 1H), 3.23 (t, 4H), 2.03-2.00 (m, 2H), 1.78-1.65 (m, 2H), 1.43-1.33 (m, 4H), 1.26 (s, 2H), 1.22 (s, 6H); MS (ESI) m/z=403.0 (M+H)$^+$ Step 2. 2-((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)propan-2-ol The title compound (6.6 mg) as a pale yellow solid was prepared in the same fashion as Step 3 in Example 1, except that 2-((1s,4s)-4-((6'-chloro-5-morpholino-[2,3'-bipyridin]-4'-yl)amino)cyclohexyl)propan-2-ol (85 mg, 0.197 mmol)

prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.90 (d, 1H), 8.66 (s, 1H), 8.46 (s, 1H), 8.39 (d, 1H), 8.36 (s, 1H), 7.69 (d, 1H), 7.34-7.29 (m, 1H), 7.10 (d, 1H), 3.98 (s, 1H), 3.91 (t, 4H), 3.23 (t, 4H), 2.87-2.83 (m, 1H), 2.12-2.10 (m, 2H), 1.80-1.75 (m, 4H), 1.56-1.53 (m, 5H), 1.23 (s, 7H), 1.14 (d, 2H); MS (ESI) m/z=660.3 (M+H)$^+$ Example 46. (1s,4s)-4-((2-((2-(1-(Cyclopropylsulfonyl)-1H-pyrazol-4-yl)pyrimidin-4-yl)amino)-5-(6-(4-methylpiperazin-1-yl)pyridazin-3-yl)pyridin-4-yl)amino)-1-methylcyclohexan-1-ol Step 1. 3-(6-Chloro-4-fluoropyridin-3-yl)-6-(4-methylpiperazin-1-yl)pyridazine The title compound as a pale yellow solid (102 mg) was prepared in the same fashion as Step 1 in Example 1 except that 3-bromo-6-(4-methylpiperazin-1-yl)pyridazine (149 mg, 0.583 mmol) was used instead of 1-((6-bromopyridin-3-yl)methyl)-4-methylpiperazine. 1H-NMR (CDCl$_3$, 400 MHz) δ 8.99 (d, 1H), 8.43 (d, 1H), 7.63 (t, 1H), 7.16 (d, 1H), 4.23 (t, 1H), 3.34 (t, 4H), 2.61 (t, 4H), 2.38 (s, 3H); MS (ESI) m/z=307.9 (M+H)$^+$ Step 2. (1s,4s)-4-((2-Chloro-5-(6-(4-methylpiperazin-1-yl)pyridazin-3-yl)pyridin-4-yl)amino)-1-methylcyclohexan-1-ol The title compound as a beige solid (47 mg) was prepared in the same fashion as Step 2 in Example 1 except that 3-(6-chloro-4-fluoropyridin-3-yl)-6-(4-methylpiperazin-1-yl)pyridazine (93 mg, 0.303 mmol) prepared in Step 1 and cis-4-amino-1-methylcyclohexan-1-ol (59 mg, 0.455 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.29 (d, 1H), 8.25 (s, 1H), 7.66 (d, 1H), 7.05 (d, 1H), 6.60 (s, 1H), 3.73 (t, 4H), 3.58 (t, 4H), 3.38-3.36 (m, 1H), 2.38 (s, 3H), 1.96-1.94 (m, 2H), 1.81-1.73 (m, 5H), 1.57-1.54 (m, 2H), 1.26 (s, 3H); MS (ESI) m/z=417.1 (M+H)$^+$ Step 3. (1s,4s)-4-((2-((2-(1-(Cyclopropylsulfonyl)-1H-pyrazol-4-yl)pyrimidin-4-yl)amino)-5-(6-(4-methylpiperazin-1-yl)pyridazin-3-yl)pyridin-4-yl)amino)-1-methylcyclohexan-1-ol The title compound (6.1 mg) as a pale yellow solid was prepared in the same fashion as Step 3 in Example 1, except that (1s,4s)-4-((2-chloro-5-(6-(4-methylpiperazin-1-yl)pyridazin-3-yl)pyridin-4-yl)amino)-1-methylcyclohexan-1-ol (45 mg, 0.108 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.30 (d, 1H), 8.66 (s, 1H), 8.48 (s, 1H), 8.41 (d, 1H) 8.28 (s, 1H), 7.68 (d, 1H), 7.34 (d, 1H), 7.06 (d, 1H), 7.00 (s, 1H), 3.71 (t, 4H), 3.50 (s, 1H), 2.85-2.81 (m, 1H), 2.58 (t, 4H), 2.38 (s, 3H), 2.01-1.97 (m, 2H), 1.85-1.82 (m, 3H), 1.75-1.51 (m, 6H), 1.30 (s, 3H), 1.24-1.19 (m, 2H); MS (ESI) m/z=646.2 (M+H)$^+$ Example 47. (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol Step 1. 6'-Chloro-5-(4,4-difluoropiperidin-1-yl)-4'-fluoro-2,3'-bipyridine The title compound as a white solid (97 mg) was prepared in the same fashion as Step 1 in Example 1 except that 2-bromo-5-(4,4-difluoropiperidin-1-yl)pyridine (161 mg, 0.583 mmol) was used instead of 1-((6-bromopyridin-3-yl)methyl)-4-methylpiperazine. $^1$H-NMR (CDCl$_3$, 400 MHz) δ 9.01 (d, 1H), 8.45 (d, 1H), 7.65 (d, 1H), 7.17 (d, 1H), 3.50 (t, 4H), 2.20-2.01 (m, 5H); MS (ESI) m/z=327.9 (M+H)$^+$ Step 2. (1s,4s)-4-((6'-Chloro-5-(4,4-difluoropiperidin-1-yl)-[2,3'-bipyridin]-4'-yl)amino)-1-methylcyclohexan-1-ol The title compound as a white solid (102 mg) was prepared in the same fashion as Step 2 in Example 1 except that 6'-chloro-5-(4,4-difluoropiperidin-1-yl)-4'-fluoro-2,3'-bipyridine (92 mg, 0.28 mmol) prepared in Step 1 and cis-4-amino-1-methylcyclohexan-1-ol (54 mg, 0.42 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.20 (d, 1H), 8.31 (s, 1H), 8.27 (d, 1H), 7.62 (d, 1H), 7.34 (dd, 1H), 6.55 (s, 1H), 3.45 (t, 4H), 3.38-3.31 (m, 1H), 2.19-2.10 (m, 4H), 1.98-1.93 (m, 2H), 1.78-1.66 (m, 5H), 1.31 (s, 3H), 1.29-1.25 (m, 2H), 1.17-1.15 (m, 1H); MS (ESI) m/z=437.0 (M+H)$^+$ Step 3. (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol The title compound (21 mg) as a solid was prepared in the same fashion as Step 3 in Example 1, except that (1s,4s)-4-((6'-chloro-5-(4,4-difluoropiperidin-1-yl)-[2,3'-bipyridin]-4'-yl)amino)-1-methylcyclohexan-1-ol (97 mg, 0.223 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.27 (d, 1H), 8.66 (s, 1H), 8.48 (s, 1H), 8.41 (d, 1H), 8.33 (s, 1H), 8.28 (s, 1H), 8.27 (s, 1H), 7.63 (d, 1H), 7.37-7.32 (m, 2H), 7.00 (s, 1H), 3.50 (s, 1H), 3.45 (t, 4H), 2.85-2.81 (m, 1H), 2.20-2.11 (m, 4H), 2.02-2.00 (m, 2H), 1.81-1.74 (m, 4H), 1.64-1.54 (m, 4H), 1.32 (s, 3H), 1.26-1.19 (m. 3H); MS (ESI) m/z=666.3 (M+H)$^+$ Example 48. (1s,4s)-4-((6'-((2-(1-(Cyclopropylsulfonyl)-1H-pyrazol-4-yl)pyrimidin-4-yl)amino)-4-morpholino-[2,3'-bipyridin]-4'-yl)amino)-1-methylcyclohexan-1-ol Step 1. 4-(6'-Chloro-4'-fluoro-[2,3'-bipyridin]-4-yl)morpholine The title compound as a white solid (77 mg) was prepared in the same fashion as Step 1 in Example 1 except that 4-(2-bromopyridin-4-yl) morpholine (142 mg, 0.583 mmol) was used instead of 1-((6-bromopyridin-3-yl)methyl)-4-methylpiperazine. $^1$H-NMR (CDCl$_3$, 400 MHz) δ 8.95 (d, 1H), 8.43 (d, 1H), 7.19 (d, 1H), 7.09 (s, 1H), 6.71 (dd, 1H), 3.88 (t, 4H), 3.36 (t, 4H); MS (ESI) m/z=294.0 (M+H)$^+$ Step 2. (1s,4s)-4-((6'-Chloro-4-morpholino-[2,3'-bipyridin]-4'-yl)amino)-1-methylcyclohexan-1-ol The title compound as a white solid (98 mg) was prepared in the same fashion as Step 2 in Example 1 except that 4-(6'-chloro-4'-fluoro-[2,3'-bipyridin]-4-yl) morpholine (74 mg, 0.252 mmol) prepared in Step 1 and cis-4-amino-1-methylcyclohexan-1-ol (49 mg, 0.378 mmol) were used instead of 6'-chloro-4'-fluoro-5-((4-methylpiperazin-1-yl) methyl)-2,3'-bipyridine and (4-methylpiperidin-4-yl)methanol. ¹H-NMR (CDCl₃, 400 MHz) δ 9.02 (d, 1H), 8.28 (d, 1H), 8.25 (s, 1H), 6.96 (d, 1H), 6.65 (dd, 1H), 6.53 (s, 1H), 3.87 (t, 4H), 3.36 (t, 4H), 3.31 (s, 1H), 1.94-1.90 (m, 2H), 1.76-1.67 (m, 4H), 1.56-1.53 (m, 2H), 1.30 (s, 3H); MS (ESI) m/z=403.1 (M+H)⁺

Step 3. (1s,4s)-4-((6'-((2-(1-(Cyclopropylsulfonyl)-1H-pyrazol-4-yl)pyrimidin-4-yl)amino)-4-morpholino-[2,3'-bipyridin]-4'-yl)amino)-1-methylcyclohexan-1-ol The title compound (34 mg) as a white solid was prepared in the same fashion as Step 3 in Example 1, except that (1s,4s)-4-((6'-chloro-4-morpholino-[2,3'-bipyridin]-4'-yl) amino)-1-methylcyclohexan-1-ol (95 mg, 0.236 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.14 (s, 1H), 8.66 (s, 1H), 8.48 (s, 1H), 8.42 (d, 1H), 8.29 (d, 1H), 7.53 (s, 1H), 7.36 (d, 1H), 7.23 (s, 1H), 7.00 (t, 1H), 6.93 (s, 1H), 6.64 (dd, 1H), 3.88 (t, 4H), 3.46 (s, 1H), 3.37 (t, 4H), 2.85-2.81 (m, 1H), 1.99-1.97 (m, 2H), 1.79-1.73 (m, 5H), 1.56-1.52 (m, 3H), 1.31 (m, 3H), 1.30-1.27 (m, 3H); MS (ESI) m/z=632.3 (M+H)⁺

Example 49. 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl) piperidin-4-ol Step 1. 1-(6'-Chloro-4'-fluoro-[2,3'-bipyridin]-5-yl) piperidin-4-ol The title compound as a white solid (143 mg) was prepared in the same fashion as Step 1 in Example 1 except that 1-(6-bromo-3-pyridyl) piperidin-4-ol (150 mg, 0.583 mmol) was used instead of 1-((6-bromopyridin-3-yl) methyl)-4-methylpiperazine. ¹H-NMR (CDCl₃, 400 MHz) δ 9.00 (d, 1H), 8.44 (s, 1H), 7.62 (d, 1H), 7.29 (d, 1H), 7.25 (d, 1H), 7.16 (d, 1H), 3.97-3.92 (m, 2H), 3.71-3.67 (m, 2H), 3.66-3.52 (m, 1H), 3.14-3.13 (m, 2H), 3.11-3.08 (m, 1H), 2.08-2.03 (m, 3H), 1.74-1.62 (m, 3H); MS (ESI) m/z=307.9 (M+H)⁺

Step 2. 1-(6'-Chloro-4'-(((1s,4s)-4-hydroxy-4-methylcyclohexyl)amino)-[2,3'-bipyridin]-5-yl) piperidin-4-ol The title compound as a white solid (95 mg) was prepared in the same fashion as Step 2 in Example 1 except that 1-(6'-chloro-4'-fluoro-[2,3'-bipyridin]-5-yl) piperidin-4-ol (86 mg, 0.28 mmol) prepared in Step 1 and cis-4-amino-1-methylcyclohexan-1-ol (54 mg, 0.839 mmol) were used instead of 6'-chloro-4'-fluoro-5-((4-methylpiperazin-1-yl) methyl)-2,3'-bipyridine and (4-methylpiperidin-4-yl)methanol. ¹H-NMR (CDCl₃, 400 MHz) δ 9.24 (d, 1H), 8.30 (s, 1H), 8.25 (d, 1H), 7.58 (d, 1H), 7.32 (dd, 1H), 6.53 (s, 1H), 3.96-3.93 (m, 1H), 3.67-3.62 (m, 2H), 3.35-3.33 (m, 1H), 3.10-3.03 (m, 2H), 2.07-2.03 (m, 2H), 1.95-1.93 (m, 2H), 1.78-1.69 (m, 6H), 1.29 (s, 3H), 1.27-1.26 (m, 1H), 1.18 (s, 1H); MS (ESI) m/z=417.1 (M+H)⁺

Step 3. 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl) piperidin-4-ol The title compound (7 mg) as a solid was prepared in the same fashion as Step 3 in Example 1, except that 1-(6'-chloro-4'-(((1s,4s)-4-hydroxy-4-methylcyclohexyl)amino)-[2,3'-bipyridin]-5-yl) piperidin-4-ol (93 mg, 0.223 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.36 (s, 1H), 8.66 (s, 1H), 8.48 (s, 1H), 8.41 (d, 1H), 8.31 (s, 1H), 8.26 (d, 1H), 7.59 (d, 1H), 7.35-7.32 (m, 2H), 7.01 (s, 1H), 3.94-3.93 (m, 1H), 3.67-3.63 (m, 2H), 3.62 (s, 1H), 3.09-3.03 (m, 2H), 2.83-2.82 (m, 1H), 2.08-2.01 (m, 5H), 1.99-1.71 (m, 6H), 1.56-1.51 (m, 3H), 1.26 (s, 3H), 1.22-1.21 (m, 3H); MS (ESI) m/z=646.3 (M+H)⁺

Example 50. (1s,4s)-4-((2-((2-(1-(Cyclopropylsulfonyl)-1H-pyrazol-4-yl)pyrimidin-4-yl)amino)-5-(5,6-dimethylpyridazin-3-yl)pyridin-4-yl)amino)-1-methylcyclohexan-1-ol Step 1. 6-(6-Chloro-4-fluoropyridin-3-yl)-3,4-dimethylpyridazine The title compound as a pale yellow solid (95 mg) was prepared in the same fashion as Step 1 in Example 1 except that 6-bromo-3,4-dimethyl-pyridazine (145 mg, 0.777 mmol) was used instead of 1-((6-bromopyridin-3-yl) methyl)-4-methylpiperazine. ¹H-NMR (CDCl₃, 400 MHz) δ 9.17 (d, 1H), 7.62 (s, 1H), 7.25 (d, 1H), 2.75 (s, 3H), 2.40 (s, 3H); MS (ESI) m/z=237.9 (M+H)⁺

Step 2. (1s,4s)-4-((2-Chloro-5-(5,6-dimethylpyridazin-3-yl)pyridin-4-yl)amino)-1-methylcyclohexan-1-ol The title compound as a white solid (81 mg) was prepared in the same fashion as Step 2 in Example 1 except that 6-(6-chloro-4-fluoropyridin-3-yl)-3,4-dimethylpyridazine (90 mg, 0.379 mmol) prepared in Step 1 and cis-4-amino-1-methylcyclohexan-1-ol (73 mg, 0.568 mmol) were used instead of 6'-chloro-4'-fluoro-5-((4-methylpiperazin-1-yl) methyl)-2,3'-bipyridine and (4-methylpiperidin-4-yl)methanol. ¹H-NMR (CDCl₃, 400 MHz) δ 9.54 (d, 1H), 8.37 (s, 1H), 7.63 (s, 1H), 6.63 (s, 1H), 3.40-3.36 (m, 1H), 2.70 (s, 3H), 2.40 (s, 3H), 1.95-1.92 (m, 2H), 1.82-1.72 (m, 4H), 1.54-1.53 (m, 2H), 1.26 (s, 3H); MS (ESI) m/z=347.0 (M+H)⁺

Step 3. 1 (1s,4s)-4-((2-((2-(1-(Cyclopropylsulfonyl)-1H-pyrazol-4-yl)pyrimidin-4-yl)amino)-5-(5,6-dimethylpyridazin-3-yl)pyridin-4-yl)amino)-1-methylcyclohexan-1-ol The title compound (22.5 mg) as a solid was prepared in the same fashion as Step 3 in Example 1, except that (1s,4s)-4-((2-chloro-5-(5,6-dimethylpyridazin-3-yl)pyridin-4-yl)amino)-1-methylcyclohexan-1-ol (80 mg, 0.231 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.59 (d, 1H), 8.67 (s, 1H), 8.48 (s, 1H), 8.43 (d, 1H), 8.40 (s, 1H), 7.64 (s, 1H), 7.59 (s, 1H), 7.33 (d, 1H), 7.05 (s, 1H), 3.57-3.55 (m, 1H), 2.85-2.80 (m, 1H), 2.70 (s 3H), 2.40 (s, 3H), 2.02-1.98 (m, 2H), 1.86-1.68 (m, 5H), 1.60-1.49 (m, 5H), 1.30 (s, 3H), 1.27-1.20 (m, 1H); MS (ESI) m/z=576.2 (M+H)⁺

Example 51. (1s,4s)-4-((2-((2-(1-(Cyclopropylsulfonyl)-1H-pyrazol-4-yl)pyrimidin-4-yl)amino)-5-(6-(trifluoromethyl)pyridazin-3-yl)pyridin-4-yl)amino)-1-methylcyclohexan-1-ol

Step 1. 3-(6-Chloro-4-fluoropyridin-3-yl)-6-(trifluoromethyl)pyridazine

The title compound as a pale yellow solid (177 mg) was prepared in the same fashion as Step 1 in Example 1 except that 3-bromo-6-(trifluoromethyl)pyridazine (176 mg, 0.777 mmol) was used instead of 1-((6-bromopyridin-3-yl)methyl)-4-methylpiperazine. $^1$H-NMR (CDCl$_3$, 400 MHz) δ 9.31 (d, 1H), 8.14 (d, 1H), 7.96 (d, 1H), 7.33 (d, 1H); MS (ESI) m/z=278.0 (M+H)$^+$

Step 2. (1s,4s)-4-((2-Chloro-5-(6-(trifluoromethyl)pyridazin-3-yl)pyridin-4-yl)amino)-1-methylcyclohexan-1-ol The title compound as a white solid (135 mg) was prepared in the same fashion as Step 2 in Example 1 except that 3-(6-chloro-4-fluoropyridin-3-yl)-6-(trifluoromethyl)pyridazine (105 mg, 0.379 mmol) prepared in Step 1 and cis-4-amino-1-methylcyclohexan-1-ol (73 mg, 0.568 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.46 (d, 1H), 8.47 (s, 1H), 8.14 (d, 1H), 7.91 (d, 1H), 6.70 (s, 1H), 3.45-3.41 (m, 1H), 1.97-1.94 (m, 2H), 1.85-1.76 (m, 4H), 1.55 (s, 2H), 1.31 (s, 3H), 1.26-1.20 (m, 1H); MS (ESI) m/z=387.0 (M+H)$^+$

Step 3. (1s,4s)-4-((2-((2-(1-(Cyclopropylsulfonyl)-1H-pyrazol-4-yl)pyrimidin-4-yl)amino)-5-(6-(trifluoromethyl)pyridazin-3-yl)pyridin-4-yl)amino)-1-methylcyclohexan-1-ol The title compound (19 mg) as a solid was prepared in the same fashion as Step 3 in Example 1, except that (1s,4s)-4-((2-chloro-5-(6-(trifluoromethyl)pyridazin-3-yl)pyridin-4-yl)amino)-1-methylcyclohexan-1-ol (89 mg, 0.231 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.55 (d, 1H), 8.68 (s, 1H), 8.49 (s, 2H), 8.47 (d, 1H), 8.12 (d, 1H), 7.86 (d, 1H), 7.52 (d, 1H), 7.33 (d, 1H), 7.14 (s, 1H), 3.60-3.58 (m, 1H), 2.86-2.81 (m, 1H), 2.06-2.01 (m, 2H), 1.89-1.75 (m, 5H), 1.56-1.50 (m, 3H), 1.32 (s, 3H), 1.26-1.20 (m, 3H); MS (ESI) m/z=616.2 (M+H)$^+$

Example 52. (1s,4s)-4-((2-((2-(1-(Cyclopropylsulfonyl)-1H-pyrazol-4-yl)pyrimidin-4-yl)amino)-5-(6-methylpyridazin-3-yl)pyridin-4-yl)amino)-1-methylcyclohexan-1-ol

Step 1. 3-(6-Chloro-4-fluoropyridin-3-yl)-6-methylpyridazine

The title compound as a white solid (76 mg) was prepared in the same fashion as Step 1 in Example 1 except that 3-bromo-6-methyl-pyridazine (134.38 mg, 0.777 mmol) was used instead of 1-((6-bromopyridin-3-yl)methyl)-4-methylpiperazine. $^1$H-NMR (CDCl$_3$, 400 MHz) δ 9.20 (d, 1H), 7.81 (dd, 1H), 7.46 (d, 1H), 7.25 (s, 1H), 2.81 (s, 3H); MS (ESI) m/z=223.9 (M+H)$^+$

Step 2. (1s,4s)-4-((2-Chloro-5-(6-methylpyridazin-3-yl)pyridin-4-yl)amino)-1-methylcyclohexan-1-ol The title compound as a white solid (103 mg) was prepared in the same fashion as Step 2 in Example 1 except that 3-(6-chloro-4-fluoropyridin-3-yl)-6-methylpyridazine (75 mg, 0.335 mmol) prepared in Step 1 and cis-4-amino-1-methylcyclohexan-1-ol (65 mg. 0.503 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.56 (d, 1H), 8.38 (s, 1H), 7.84 (d, 1H), 7.45 (d, 1H), 6.64 (s, 1H), 3.42-3.39 (m, 1H), 2.95 (s, 3H), 1.97-1.93 (m, 2H), 1.83-1.71 (m, 4H), 1.61-1.58 (m, 2H), 1.30 (s, 3H); MS (ESI) m/z=333.0 (M+H)$^+$

Step 3. (1s,4s)-4-((2-((2-(1-(Cyclopropylsulfonyl)-1H-pyrazol-4-yl)pyrimidin-4-yl)amino)-5-(6-methylpyridazin-3-yl)pyridin-4-yl)amino)-1-methylcyclohexan-1-ol The title compound (24.6 mg) as a beige solid was prepared in the same fashion as Step 3 in Example 1, except that (1s,4s)-4-((2-chloro-5-(6-methylpyridazin-3-yl)pyridin-4-yl)amino)-1-methylcyclohexan-1-ol (100 mg. 0.3 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.62 (d, 1H), 8.67 (s, 1H), 8.48 (s, 1H), 8.43 (d, 1H), 8.41 (s, 2H), 7.85 (d, 1H), 7.68 (s, 1H), 7.42 (d, 1H), 7.36 (d, 1H), 7.06 (s, 1H), 3.56-3.55 (m, 1H), 2.86-2.80 (m, 1H), 2.75 (s, 3H), 2.03-1.99 (m, 2H), 1.87-1.78 (m, 3H), 1.64-1.53 (m, 5H), 1.30 (s, 3H); MS (ESI) m/z=562.2 (M+H)$^+$

Example 53. (1s,4s)-4-((2-((2-(1-(Cyclopropylsulfonyl)-1H-pyrazol-4-yl)pyrimidin-4-yl)amino)-5-(6-methoxypyridazin-3-yl)pyridin-4-yl)amino)-1-methylcyclohexan-1-ol

Step 1. 3-(6-Chloro-4-fluoropyridin-3-yl)-6-methoxypyridazine

The title compound as a white solid (84 mg) was prepared in the same fashion as Step 1 in Example 1 except that 3-bromo-6-methoxy-pyridazine (147 mg, 0.777 mmol) was used instead of 1-((6-bromopyridin-3-yl)methyl)-4-methylpiperazine. $^1$H-NMR (CDCl$_3$, 400 MHz) δ 9.14 (d, 1H), 7.81 (dd, 1H), 7.25 (d, 1H), 7.11 (d, 1H), 4.22 (s, 3H); MS (ESI) m/z=239.9 (M+H)$^+$

Step 2. (1s,4s)-4-((2-Chloro-5-(6-methoxypyridazin-3-yl)pyridin-4-yl)amino)-1-methylcyclohexan-1-ol The title compound as a white solid (105 mg) was prepared in the same fashion as Step 2 in Example 1 except that 3-(6-chloro-4-fluoropyridin-3-yl)-6-methoxypyridazine (80 mg, 0.335 mmol) prepared in Step 1 and cis-4-amino-1-methylcyclohexan-1-ol (65 mg, 0.503 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.27 (d, 1H), 8.32 (s, 1H), 7.82 (d, 1H), 7.10 (d, 1H), 6.63 (s, 1H), 4.18 (s, 3H), 3.40-3.37 (m, 1H), 1.99-1.94 (m, 2H), 1.80-1.77 (m, 5H), 1.58-1.55 (m, 2H), 1.31 (s, 3H); MS (ESI) m/z=333.0 (M+H)$^+$

Step 3. (1s,4s)-4-((2-((2-(1-(Cyclopropylsulfonyl)-1H-pyrazol-4-yl)pyrimidin-4-yl)amino)-5-(6-methoxypyridazin-3-yl)pyridin-4-yl)amino)-1-methylcyclohexan-1-ol The title compound (71 mg) as off white solid was prepared in the same fashion as Step 3 in Example 1, except that (1s,4s)-4-((2-chloro-5-(6-methoxypyridazin-3-yl)pyridin-4-yl)amino)-1-methylcyclohexan-1-ol (105 mg, 0.3 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.30 (d, 1H), 8.67 (s, 1H), 8.49 (s, 1H), 8.44 (d, 1H), 8.34 (s, 1H), 7.84 (d, 1H), 7.47 (s, 1H), 7.38 (d, 1H), 7.30 (s, 1H), 7.09 (d, 1H), 7.01 (s, 1H), 4.18 (s, 3H), 3.60-3.54 (m, 1H), 2.86-2.80 (m, 1H), 2.05-1.95 (m, 2H), 1.87-1.75 (m, 4H), 1.56-1.40 (m, 3H), 1.32 (s, 3H), 1.26-1.10 (m, 4H); MS (ESI) m/z=578.2 (M+H)$^+$

Example 54. (1s,4s)-4-((6'-((2-(1-(Cyclopropylsulfonyl)-1H-pyrazol-4-yl)pyrimidin-4-yl)amino)-5-(piperidin-1-yl)-[2,3'-bipyridin]-4'-yl)amino)-1-methylcyclohexan-1-ol

Step 1. 6'-Chloro-4'-fluoro-5-(piperidin-1-yl)-2,3'-bipyridine

The title compound as a white solid (130 mg) was prepared in the same fashion as Step 1 in Example 1 except that 2-bromo-5-(1-piperidyl)pyridine (187 mg, 0.777 mmol) was used instead of 1-((6-bromopyridin-3-yl)methyl)-4-methylpiperazine. $^1$H-NMR (CDCl$_3$, 400 MHz) δ 9.00 (d, 1H), 8.42 (d, 1H), 7.61 (dd, 1H), 7.23 (d, 1H), 7.16 (d, 1H), 3.31 (t, 4H), 1.77-1.71 (m, 4H), 1.67-1.65 (m, 2H); MS (ESI) m/z=291.9 (M+H)$^+$

Step 2. (1s,4s)-4-((6'-Chloro-5-(piperidin-1-yl)-[2,3'-bipyridin]-4'-yl)amino)-1-methylcyclohexan-1-ol The title compound as a white solid (130 mg) was prepared in the same fashion as Step 2 in Example 1 except that 6'-chloro-4'-fluoro-5-(piperidin-1-yl)-2,3'-bipyridine (98 mg, 0.335 mmol) prepared in Step 1 and cis-4-amino-1-methylcyclohexan-1-ol (65 mg, 0.503 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.27 (d, 1H), 8.30 (s, 1H), 8.23 (d, 1H), 7.57 (d, 1H), 7.30 (dd, 1H), 6.53 (s, 1H) 3.35-3.33 (m, 1H), 3.26 (t, 4H), 1.95-1.93 (m, 2H), 1.78-1.69 (m, 8H), 1.66-1.62 (m, 3H), 1.31 (s, 3H), 1.17 (s, 1H); MS (ESI) m/z=401.1 (M+H)$^+$

Step 3. (1s,4s)-4-((6'-((2-(1-(Cyclopropylsulfonyl)-1H-pyrazol-4-yl)pyrimidin-4-yl)amino)-5-(piperidin-1-yl)-[2,3'-bipyridin]-4'-yl)amino)-1-methylcyclohexan-1-ol The title compound (10.5 mg) as beige solid was prepared in the same fashion as Step 3 in Example 1, except that (1s,4s)-4-((6'-chloro-5-(piperidin-1-yl)-[2,3'-bipyridin]-4'-yl)amino)-1-methylcyclohexan-1-ol (120 mg, 0.3 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.32 (d, 1H), 8.66 (s, 1H), 8.48 (s, 1H), 8.43 (s, 1H), 8.39 (d, 1H), 8.24 (d, 1H), 7.58 (d, 1H), 7.33-7.30 (m, 2H), 6.95 (s, 3H), 3.50-3.49 (m, 2H), 3.26 (t, 4H), 2.85-2.81 (m, 1H), 2.01-1.99 (m, 2H), 1.74-1.64 (m, 8H), 1.60-1.52 (m, 3H), 1.31 (s, 3H), 1.26-1.19 (m. 3H); MS (ESI) m/z=630.3 (M+H)$^+$

Example 55. (1s,4s)-4-((6'-((2-(1-(Cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol

Step 1. (6'-Chloro-4'-fluoro-[2,3'-bipyridin]-4-yl)methanol

The title compound as a white solid (480 mg) was prepared in the same fashion as Step 1 in Example 1 except that 2-bromo-4-(hydroxymethyl)pyridine (500 mg, 2.659 mmol) was used instead of 1-((6-bromopyridin-3-yl)methyl)-4-methylpiperazine. $^1$H-NMR (CDCl$_3$, 400 MHz) δ 9.00 (d, 1H), 8.71 (d, 1H), 7.74 (s, 1H), 7.35 (d, 1H), 7.21 (d, 1H), 4.83 (d, 2H), 2.31 (t, 1H); MS (ESI) m/z=238.9 (M+H)$^+$

Step 2. (1s,4s)-4-((6'-Chloro-4-(hydroxymethyl)-[2,3'-bipyridin]-4'-yl)amino)-1-methylcyclohexan-1-ol The title compound as a white solid (449 mg) was prepared in the same fashion as Step 2 in Example 1 except that (6'-chloro-4'-fluoro-[2,3'-bipyridin]-4-yl)methanol (475 mg, 1.99 mmol) prepared in Step 1 and cis-4-amino-1-methylcyclohexan-1-ol (386 mg, 2.986 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.37 (d, 1H), 8.54 (d, 1H), 8.41 (s, 1H), 7.72 (s, 1H), 7.01 (s, 1H), 6.57 (s, 1H), 3.36-3.34 (m, 1H), 1.96-1.93 (m, 2H), 1.78-1.68 (m, 4H), 1.31-1.26 (m, 6H); MS (ESI) m/z=348.0 (M+H)$^+$

Step 3. (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol The title compound (273 mg) as white solid was prepared in the same fashion as Step 3 in Example 1, except that (1s,4s)-4-((6'-chloro-4-(hydroxymethyl)-[2,3'-bipyridin]-4'-yl)amino)-1-methylcyclohexan-1-ol (445 mg, 1.279 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.49 (d, 1H), 8.67 (s, 1H), 8.54 (d, 1H), 8.48 (s, 1H), 8.44-8.42 (m, 2H), 7.74 (s, 1H), 7.30 (s, 1H), 7.20 (d, 1H), 7.03 (d, 1H), 4.83 (s, 2H), 3.53 (s, 1H), 3.50 (s, 2H), 2.85-2.82 (m, 2H), 2.02-1.74 (m, 5H), 1.61-1.42 (m, 3H), 1.32-1.23 (m, 8H); MS (ESI) m/z=577.2 (M+H)$^+$

Step 4. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-4-carbaldehyde The reaction mixture of (1s,4s)-4-((6'-((2-(1-(cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol (235 mg. 0.410 mmol) and Dess-Martin Periodinane (346 mg, 0.820 mmol) in DCM (4 mL) was stirred for 20 minutes. Then the reaction mixture was quenched with sat. NaHCO$_3$ soln, and the organic layer was concentrated. The crude reaction mixture was purified by column chromatography (MeOH/DCM=0-20%) to give 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-4-carbaldehyde (247 mg) as a yellow solid. 1H-NMR (CDCl$_3$, 400 MHz) δ 10.15 (s, 1H), 9.55 (d, 1H), 8.81 (d, 1H), 8.67 (s, 1H), 8.53 (s, 1H), 8.47 (d, 1H), 8.16 (s, 1H), 7.61 (d, 1H), 7.23 (s, 2H), 3.57-3.50 (m, 1H), 2.85-2.80 (m, 1H), 2.06-2.01 (m, 2H), 1.84-1.74 (m, 7H), 1.66-1.62 (m, 3H), 1.59-1.48 (m, 2H), 1.33 (s, 3H), 1.29-1.20 (m, 1H); MS (ESI) m/z=575.1 (M+H)$^+$

Step 5. (1s,4s)-4-((6'-((2-(1-(Cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol The reaction mixture of 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-4-carbaldehyde (30 mg, 0.050 mmol), sodium triacetoxy borohydride (55 mg, 0.260 mmol), and 1-methylpiperazine (0.02 mL, 0.160 mmol) was stirred for 4 hours. And the reaction mixture was quenched with sat. NaHCO$_3$ soln. Then the organic layers was dried over MgSO$_4$, filtered, and concentrated. The crude residue was purified by column chromatography (MeOH/DCM=0-20%) to give (1s,4s)-4-((6'-((2-(1-(cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol (7.9 mg) as an off-white solid. $^1$H-NMR (CDCl$_3$, 400 MHz) δ 9.47 (d, 1H), 8.67 (s, 1H), 8.50-8.48 (m, 2H), 8.44 (s, 1H), 8.42 (d, 1H), 7.72 (s, 1H), 7.33 (d, 1H), 7.18 (d, 1H), 7.00 (s, 1H), 3.57 (s, 2H), 3.51-3.50 (m, 1H), 2.86-2.80 (m, 1H), 2.53 (br, 6H), 2.31 (s, 3H), 2.02-1.98 (m, 2H), 1.81-1.74 (m, 6H), 1.63-1.51 (m, 5H), 1.31 (s, 3H), 1.29-1.19 (m, 2H); MS (ESI) m/z=659.3 (M+H)$^+$

Example 56. (1s,4s)-4-((2-((2-(1-(Cyclopropylsulfonyl)-1H-pyrazol-4-yl)pyrimidin-4-yl)amino)-5-(5-methoxypyrazin-2-yl)pyridin-4-yl)amino)-1-methylcyclohexan-1-ol

Step 1. 2-(6-Chloro-4-fluoropyridin-3-yl)-5-methoxypyrazine

The title compound as a white solid (127 mg) was prepared in the same fashion as Step 1 in Example 1 except that 2-bromo-5-methoxy-pyrazine (147 mg, 0.777 mmol) was used instead of 1-((6-bromopyridin-3-yl)methyl)-4-methylpiperazine. $^1$H-NMR (CDCl$_3$, 400 MHz) δ 9.01 (d, 1H), 8.58 (s, 1H), 8.36 (s, 1H), 7.23 (d, 1H), 4.05 (s, 3H); MS (ESI) m/z=239.9 (M+H)$^+$

Step 2. (1s,4s)-4-((2-Chloro-5-(5-methoxypyrazin-2-yl)pyridin-4-yl)amino)-1-methylcyclohexan-1-ol The title compound as a white solid (141 mg) was prepared in the same fashion as Step 2 in Example 1 except that 2-(6-chloro-4-fluoropyridin-3-yl)-5-methoxypyrazine (125 mg, 0.522 mmol) prepared in Step 1 and cis-4-amino-1-methylcyclohexan-1-ol (81 mg, 0.626 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.49 (d, 1H), 8.30 (s, 1H), 8.20 (d, 1H), 8.15 (d, 1H), 6.57 (s, 1H), 4.02 (s, 3H), 3.35-3.31 (m, 1H), 1.95-1.91 (m, 2H), 1.77-1.67 (m, 4H), 1.63-1.54 (m, 2H), 1.31 (s, 3H), 1.29-1.26 (m, 1H); MS (ESI) m/z=349.0 (M+H)$^+$

Step 3. (1s,4s)-4-((2-((2-(1-(Cyclopropylsulfonyl)-1H-pyrazol-4-yl)pyrimidin-4-yl)amino)-5-(5-methoxypyrazin-2-yl)pyridin-4-yl)amino)-1-methylcyclohexan-1-ol The title compound (12 mg) as a white solid was prepared in the same fashion as Step 3 in Example 1, except that (1s,4s)-4-((2-chloro-5-(5-methoxypyrazin-2-yl)pyridin-4-yl)amino)-1-methylcyclohexan-1-ol (92 mg, 0.264 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.01 (s, 1H), 8.72 (s, 1H), 8.66 (s, 1H), 8.46 (s, 1H), 8.43-8.39 (m, 2H), 8.35 (s, 1H), 8.10 (d, 1H), 7.55 (s, 1H), 7.25 (s, 1H), 3.94 (s, 3H), 1.97-1.78 (m, 2H), 1.60-1.42 (m, 4H), 1.40-1.36 (m, 2H), 1.33-1.26 (m, 2H), 1.25-1.24 (m, 3H), 1.11 (s, 3H); MS (ESI) m/z=578.2 (M+H)$^+$

Example 57. ((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)methanol

Step 1. ((1s,4s)-4-((6'-Chloro-5-morpholino-[2,3'-bipyridin]-4'-yl)amino)cyclohexyl)methanol The title compound as a white solid (113 mg) was prepared in the same fashion as Step 2 in Example 1 except that 4-(6'-chloro-4'-fluoro-[2,3'-bipyridin]-5-yl) morpholine (100 mg, 0.34 mmol) prepared in Reference Example 25 and cis-(4-aminocyclohexyl)methanol hydrochloride (73 mg, 0.443 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.69 (d, 1H), 8.33 (s, 1H), 8.21 (d, 1H), 7.64 (d, 1H), 7.29 (dd, 1H), 6.52 (s, 1H), 3.89 (t, 1H), 3.74-3.72 (m, 1H), 3.24 (t, 1H), 2.37 (br, 1H), 2.14 (d, 2H), 1.89-1.86 (m, 2H), 1.71-1.58 (m, 5H), 1.31-1.28 (m, 2H); MS (ESI) m/z=403.1 (M+H)$^+$

Step 2. ((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)methanol The title compound (4.8 mg) as a solid was prepared in the same fashion as Step 3 in Example 1, except that ((1s,4s)-4-((6'-chloro-5-morpholino-[2,3'-bipyridin]-4'-yl)amino)cyclohexyl)methanol (105 mg, 0.261 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.62 (d, 1H), 8.46-8.44 (m, 2H), 8.21 (s, 1H), 8.12 (d, 1H), 7.63 (d, 1H), 7.32 (dd, 1H), 7.06 (d, 1H), 4.11 (s, 1H), 3.90 (t, 4H), 3.58 (d, 2H), 3.27 (t, 4H), 2.87-2.83 (m, 1H), 2.11-2.05 (m, 2H), 1.95-1.81 (m, 2H), 1.78-1.72 (m, 2H), 1.57-1.54 (m, 1H), 1.53-1.40 (m, 2H), 1.26-1.22 (m, 3H); MS (ESI) m/z=632.3 (M+H)$^+$

Example 58. (1s,4s)-4-((6'-((2-(1-(Cyclopropylsulfonyl)-1H-pyrazol-4-yl)pyrimidin-4-yl)amino)-4-(4-methylpiperazin-1-yl)-[2,3'-bipyridin]-4'-yl)amino)-1-methylcyclohexan-1-ol

Step 1. 6'-Chloro-4'-fluoro-4-(4-methylpiperazin-1-yl)-2,3'-bipyridine

The title compound as a solid (156 mg) was prepared in the same fashion as Step 1 in Example 1 except that 1-(2-bromo-4-pyridyl)-4-methyl-piperazine (199 mg, 0.777 mmol) was used instead of 1-((6-bromopyridin-3-yl)methyl)-4-methylpiperazine. $^1$H-NMR (CDCl$_3$, 400 MHz) δ 8.91 (d, 1H), 8.37 (d, 1H), 7.17 (d, 1H), 7.06 (s, 1H), 6.69 (dd, 1H), 3.40 (t, 1H), 2.55 (t, 4H), 2.35 (s, 3H); MS (ESI) m/z=307.0 (M+H)$^+$

Step 2. (1s,4s)-4-((6'-Chloro-4-(4-methylpiperazin-1-yl)-[2,3'-bipyridin]-4'-yl)amino)-1-methylcyclohexan-1-ol The title compound as a white solid (110 mg) was prepared in the same fashion as Step 2 in Example 1 except that 6'-chloro-4'-fluoro-4-(4-methylpiperazin-1-yl)-2,3'-bipyridine (160 mg. 0.522 mmol) prepared in Step 1 and cis-4-amino-1-methylcyclohexan-1-ol (81 mg, 0.626 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.00 (d, 1H), 8.24-8.23 (m, 2H), 6.94 (d, 1H), 6.64 (dd, 1H), 6.52 (s, 1H), 3.41 (t, 4H), 3.33-3.26 (m, 1H), 2.56 (t, 4H), 2.36 (s, 3H), 2.05-1.89 (m, 3H), 1.78-1.63 (m, 5H), 1.58-1.52 (m, 2H), 1.29 (s, 3H); MS (ESI) m/z=416.0 (M+H)$^+$

Step 3. (1s,4s)-4-((6'-((2-(1-(Cyclopropylsulfonyl)-1H-pyrazol-4-yl)pyrimidin-4-yl)amino)-4-(4-methylpiperazin-1-yl)-[2,3'-bipyridin]-4'-yl)amino)-1-methylcyclohexan-1-ol The title compound (21 mg) as a off white solid was prepared in the same fashion as Step 3 in Example 1, except that (1s,4s)-4-((6'-chloro-4-(4-methylpiperazin-1-yl)-[2,3'-bipyridin]-4'-yl)amino)-1-methylcyclohexan-1-ol (110 mg, 0.264 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.11 (d, 1H), 8.66 (s, 1H), 8.47 (s, 1H), 8.39 (d, 1H), 8.30 (s, 1H), 8.26 (d, 1H), 7.34 (d, 1H), 6.99 (d, 1H), 6.95 (s, 1H), 6.63 (dd, 1H), 3.49-3.41 (m, 5H), 2.82-2.81 (m, 1H), 2.56 (t, 4H), 2.37 (s, 3H), 1.99-1.95 (m, 3H), 1.84 (br, 4H), 1.78-1.71 (m, 2H), 1.61-1.50 (m, 3H), 1.30 (s, 3H), 1.27-1.19 (m, 2H); MS (ESI) m/z=645.3 (M+H)$^+$

Example 59. (1s,4s)-4-((2-((2-(1-(Cyclopropylsulfonyl)-1H-pyrazol-4-yl)pyrimidin-4-yl)amino)-5-(5-methylpyrazin-2-yl)pyridin-4-yl)amino)-1-methylcyclohexan-1-ol

Step 1. 2-(6-Chloro-4-fluoropyridin-3-yl)-5-methylpyrazine

The title compound as a solid (100 mg) was prepared in the same fashion as Step 1 in Example 1 except that 2-bromo-5-methyl-pyrazine (134 mg, 0.777 mmol) was used instead of 1-((6-bromopyridin-3-yl)methyl)-4-methylpiperazine. $^1$H-NMR (CDCl$_3$, 400 MHz) δ 9.04 (d, 1H), 8.93 (s, 1H), 8.60 (s, 1H), 7.25 (d, 1H), 2.66 (s, 3H); MS (ESI) m/z=224.0 (M+H)$^+$

Step 2. (1s,4s)-4-((2-Chloro-5-(5-methylpyrazin-2-yl)pyridin-4-yl)amino)-1-methylcyclohexan-1-ol The title compound as a white solid (117 mg) was prepared in the same fashion as Step 2 in Example 1 except that 2-(6-chloro-4-fluoropyridin-3-yl)-5-methylpyrazine (107 mg, 0.522 mmol) prepared in Step 1 and cis-4-amino-1-methylcyclohexan-1-ol (81 mg, 0.626 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.88 (s, 1H), 8.72 (d, 1H), 8.41 (s, 1H), 8.37 (s, 1H), 6.57 (s, 1H), 3.36-3.32 (m, 1H), 2.59 (s, 3H), 1.96-1.90 (m, 2H), 1.88-1.76 (m, 4H), 1.74-1.68 (m, 2H), 1.28 (s, 3H); MS (ESI) m/z=333.1 (M+H)$^+$

Step 3. (1s,4s)-4-((2-((2-(1-(Cyclopropylsulfonyl)-1H-pyrazol-4-yl)pyrimidin-4-yl)amino)-5-(5-methylpyrazin-2-yl)pyridin-4-yl)amino)-1-methylcyclohexan-1-ol The title compound (39.7 mg) as a white solid was prepared in the same fashion as Step 3 in Example 1, except that (1s,4s)-4-((2-chloro-5-(5-methylpyrazin-2-yl)pyridin-4-yl)amino)-1-methylcyclohexan-1-ol (88 mg, 0.264 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.09 (s, 1H), 8.74 (s, 1H), 8.66 (s, 1H), 8.58 (s, 1H), 8.52 (s, 1H), 8.46 (s, 1H), 8.42 (d, 1H), 7.51 (s, 1H), 7.32 (s, 1H), 3.22-3.15 (m, 1H), 1.80 (s, 2H), 1.63-1.54 (m, 4H), 1.43-1.38 (m, 2H), 1.32-1.31 (m, 2H), 1.24-1.21 (m, 4H), 1.12 (s, 3H); MS (ESI) m/z=562.2 (M+H)$^+$

Example 60. (1s,4s)-4-((2-((2-(1-(Cyclopropylsulfonyl)-1H-pyrazol-4-yl)pyrimidin-4-yl)amino)-5-(5-(hydroxy methyl) pyrazin-2-yl)pyridin-4-yl)amino)-1-methylcyclohexan-1-ol

Step 1. (5-(6-Chloro-4-fluoropyridin-3-yl) pyrazin-2-yl)methanol

The title compound as a solid (480 mg) was prepared in the same fashion as Step 1 in Example 1 except that (5-bromopyrazin-2-yl)methanol (503 mg, 2.659 mmol) was used instead of 1-((6-bromopyridin-3-yl)methyl)-4-methylpiperazine. $^1$H-NMR (CDCl$_3$, 400 MHz) δ 9.07 (d, 1H), 9.00 (s, 1H), 8.78 (s, 1H), 4.93 (d, 2H), 3.26 (t, 1H); MS (ESI) m/z=239.9 (M+H)$^+$

Step 2. (1s,4s)-4-((2-Chloro-5-(5-(hydroxymethyl) pyrazin-2-yl)pyridin-4-yl)amino)-1-methylcyclohexan-1-ol The title compound as a white solid (464 mg) was prepared in the same fashion as Step 2 in Example 1 except that (5-(6-chloro-4-fluoropyridin-3-yl) pyrazin-2-yl)methanol (475 mg, 1.982 mmol) prepared in Step 1 and cis-4-amino-1-methylcyclohexan-1-ol (384 mg, 2.973 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.99 (s, 1H), 8.80 (d, 1H), 8.59 (s, 1H), 8.49 (s, 1H), 6.62 (s, 1H), 4.89 (s 2H), 3.50-3.36 (m, 1H), 2.09-1.92 (m, 2H), 1.78-1.61 (m, 4H), 1.57-1.43 (m, 4H), 1.26 (s, 3H); MS (ESI) m/z=349.0 (M+H)$^+$

Step 3. (1s,4s)-4-((2-((2-(1-(Cyclopropylsulfonyl)-1H-pyrazol-4-yl)pyrimidin-4-yl)amino)-5-(5-(hydroxymethyl) pyrazin-2-yl)pyridin-4-yl)amino)-1-methylcyclohexan-1-ol The title compound (85 mg) as a white solid was prepared in the same fashion as Step 3 in Example 1, except that (1s,4s)-4-((2-chloro-5-(5-(hydroxymethyl) pyrazin-2-yl)pyridin-4-yl)amino)-1-methylcyclohexan-1-ol (316 mg, 0.906 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.05 (s, 1H), 9.15 (d, 1H), 8.85 (s, 1H), 8.66-8.63 (m, 2H), 8.46 (s, 1H), 8.42 (d, 1H), 7.50 (s, 1H), 7.34 (s, 1H), 5.70-5.67 (s, 1H), 4.64 (d, 2H), 4.29 (s, 1H), 3.22-3.18 (m, 1H), 1.80 (s, 2H), 1.65-1.55 (m, 5H), 1.44-1.38 (m, 2H), 1.33-1.28 (m, 2H), 1.26-1.24 (m, 3H), 1.23 (s, 3H); MS (ESI) m/z=578.2 (M+H)$^+$

Example 61. (1s,4s)-4-((6'-((2-(1-(Cyclopropylsulfonyl)-1H-pyrazol-4-yl)pyrimidin-4-yl)amino)-4-(morpholinomethyl)-[2,3'-bipyridin]-4'-yl)amino)-1-methylcyclohexan-1-ol The title compound (7.2 mg) as a solid was prepared in the same fashion as Step 5 in Example 55, except that morpholine (0.01 mL, 0.157 mmol) was used instead of 1-methylpiperazine. $^1$H-NMR (CDCl$_3$, 600 MHz) δ 9.63 (s, 1H), 8.65 (s, 1H), 8.49 (d, 1H), 8.47 (s, 1H), 8.41-8.39 (m, 2H), 7.71 (s, 1H), 7.20 (s, 1H), 7.18 (d, 1H), 3.74 (t, 4H), 3.55 (s, 2H), 3.52 (s, 1H), 2.82-2.80 (m, 1H), 2.49 (s, 4H), 2.04-1.98 (m, 5H), 1.78-1.72 (m, 5H), 1.61-1.59 (m, 2H), 1.59-1.51 (m, 2H), 1.30 (s, 3H), 1.25-1.20 (m, 5H); MS (ESI) m/z=646.3 (M+H)$^+$

Example 62. (1s,4s)-4-((2-((2-(1-(Cyclopropylsulfonyl)-1H-pyrazol-4-yl)pyrimidin-4-yl)amino)-5-((4-methylpiperazin-1-yl)methyl) pyrazin-2-yl)pyridin-4-yl)amino)-1-methylcyclohexan-1-ol

Step 1. 5-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrazine-2-carbaldehyde The title compound (50 mg) as a yellow solid was prepared in the same fashion as Step 4 in Example 55, except that (1s,4s)-4-((2-((2-(1-(cyclopropylsulfonyl)-1H-pyrazol-4-yl)pyrimidin-4-yl)amino)-5-(5-(hydroxymethyl) pyrazin-2-yl)pyridin-4-yl)amino)-1-methylcyclohexan-1-ol (50 mg, 0.087 mmol) prepared in Example 60 was used instead of (1s,4s)-4-((6'-((2-(1-(cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol. $^1$H-NMR (DMSO-d$_6$, 400 MHz) δ 10.19 (s, 1H), 10.03 (s, 1H), 9.50 (d, 1H), 9.29 (d, 1H), 9.06 (d, 1H), 8.89 (s, 1H), 8.67 (s, 1H), 8.47-8.45 (m, 2H) 7.47 (s, 1H), 7.43 (s, 1H), 1.84-1.82 (m, 2H), 1.71-1.69 (m, 2H), 1.66-1.56 (m, 2H), 1.44-1.42 (m, 2H), 1.39-1.31 (m, 2H), 1.28-1.25 (m, 4H), 1.12 (s, 3H); MS (ESI) m/z=576.2 (M+H)$^+$

Step 2. (1s,4s)-4-((2-((2-(1-(Cyclopropylsulfonyl)-1H-pyrazol-4-yl)pyrimidin-4-yl)amino)-5-(5-((4-methylpiperazin-1-yl)methyl) pyrazin-2-yl)pyridin-4-yl)amino)-1-methylcyclohexan-1-ol The title compound (5.8 mg) as a solid was prepared in the same fashion as Step 5 in Example 55, except that 5-(6-((2-(1-(cyclopropylsulfonyl)-1H-pyrazol-4-yl)pyrimidin-4-yl)amino)-4-(((1s,4s)-4-hydroxy-4-methylcyclohexyl)amino) pyridin-3-yl)pyrazine-2-carbaldehyde (15 mg, 0.026 mmol) prepared in Step 1 was used instead of 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-4-carbaldehyde. $^1$H-NMR (CDCl$_3$, 600 MHz) δ 9.01 (d, 2H), 8.66 (s, 1H), 8.53 (d, 1H), 8.47 (s, 1H), 8.43 (s, 1H), 8.42 (s, 1H), 7.71 (s, 1H), 7.30 (s, 1H), 7.07 (s, 1H), 3.73 (s, 2H), 3.48 (s, 1H), 2.83-2.82 (m, 1H), 2.80-2.61 (m, 6H), 2.30 (s, 4H), 2.00-1.97 (m, 3H), 1.77-1.72 (m, 3H), 1.62-1.57 (m, 3H), 1.53-1.51 (m, 3H), 1.31 (s, 4H), 1.30-1.19 (m, 6H); MS (ESI) m/z=660.3 (M+H)$^+$

Example 63. (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-ol

Step 1. 6'-Chloro-5-(difluoromethyl)-4'-fluoro-2,3'-bipyridine

The title compound as a solid (130 mg) was prepared in the same fashion as Step 1 in Example 1 except that 2-bromo-5-(difluoromethyl)pyridine (162 mg, 0.777 mmol) was used instead of 1-((6-bromopyridin-3-yl)methyl)-4-methylpiperazine. $^1$H-NMR (CDCl$_3$, 400 MHz) δ 9.10 (d, 1H), 8.89 (s, 1H), 7.97 (d, 1H), 7.87 (d, 1H), 7.24 (d, 1H), 6.79 (t, 1H); MS (ESI) m/z=258.9 (M+H)$^+$

Step 2. (1s,4s)-4-((6'-Chloro-5-(difluoromethyl)-[2,3'-bipyridin]-4'-yl)amino)-1-methylcyclohexan-1-ol The title compound as a white solid (125 mg) was prepared in the same fashion as Step 2 in Example 1 except that 6'-chloro-5-(difluoromethyl)-4'-fluoro-2,3'-bipyridine (85 mg, 0.329 mmol) prepared in Step 1 and cis-4-amino-1-methylcyclohexan-1-ol (64 mg, 0.494 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.33 (d, 1H), 8.72 (d, 1H), 8.44 (s, 1H), 7.94 (dd, 1H), 7.83 (d, 1H), 6.76 (t, 1H), 6.60 (s, 1H), 3.38-3.35 (m, 1H), 1.96-1.93 (m, 2H), 1.78-1.63 (m, 4H), 1.58-1.54 (m, 1H), 1.26 (s, 3H), 1.20 (s, 1H); MS (ESI) m/z=368.0 (M+H)$^+$

Step 3. (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-old The title compound (25 mg) as a solid was prepared in the same fashion as Step 3 in Example 1, except that (1s,4s)-4-((6'-chloro-5-(difluoromethyl)-[2,3'-bipyridin]-4'-yl)amino)-1-methylcyclohexan-1-ol (120 mg, 0.326 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 600 MHz) δ 9.47 (d, 1H), 8.70 (s, 1H), 8.66 (s, 1H), 8.47 (s, 2H), 8.43 (d, 1H), 7.91 (d, 1H), 7.83 (d, 1H), 7.30 (s, 1H), 7.26

(s, 1H), 7.05 (s, 1H), 6.75 (t, 1H), 3.53 (s, 1H), 2.83-2.81 (m, 1H), 2.04-1.99 (m, 3H), 1.80-1.76 (m, 6H), 1.74-1.51 (m, 3H), 1.31 (s, 4H); MS (ESI) m/z=597.3 (M+H)$^+$

Example 64. (1s,4s)-4-((6'-((2-(1-(Cyclopropylsulfonyl)-1H-pyrazol-4-yl)pyrimidin-4-yl)amino)-4-((dimethylamino)methyl)-[2,3'-bipyridin]-4'-yl)amino)-1-methylcyclohexan-1-ol The title compound (1 mg) as a solid was prepared in the same fashion as Step 5 in Example 55, except that dimethylamine (0.01 mL, 0.157 mmol) was used instead of 1-methylpiperazine. $^1$H-NMR (CDCl$_3$, 400 MHz) δ 9.66 (d, 1H), 8.66 (s, 1H), 8.51 (d, 1H), 8.49 (s, 1H), 8.42-8.41 (m, 2H), 7.70 (s, 1H), 7.01 (s, 2H), 3.55 (s, 1H), 3.50 (s, 2H), 2.85-2.80 (m, 1H), 2.30 (s, 4H), 2.04-1.99 (m, 3H), 1.80-1.77 (m, 2H), 1.64-1.61 (m, 4H), 1.54-1.51 (m, 3H), 1.34 (s, 3H), 1.23-1.20 (m, 2H); MS (ESI) m/z=604.3 (M+H)$^+$ Example 65. (1s,4s)-4-((2-((2-(1-(Cyclopropylsulfonyl)-1H-pyrazol-4-yl)pyrimidin-4-yl)amino)-5-(5-((dimethylamino)methyl) pyrazin-2-yl)pyridin-4-yl)amino)-1-methylcyclohexan-1-ol The title compound (1.9 mg) as a solid was prepared in the same fashion as Step 5 in Example 55, except that 5-(6-((2-(1-(cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrazine-2-carbaldehyde (15 mg, 0.026 mmol) prepared in Step 1 of Example 62 and dimethylamine (4 mg, 0.078 mmol) were used instead of 6'-((2-(1-(cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-4-carbaldehyde and 1-methylpiperazine. $^1$H-NMR (MeOD, 400 MHz) δ 9.12 (s, 1H), 8.74 (s, 1H), 8.63 (s, 1H), 8.59 (s, 1H), 8.49 (s, 1H), 8.38 (d, 1H), 7.43 (d, 1H), 7.34 (s, 1H), 3.72 (s, 2H), 3.61 (s, 1H), 3.03 (s, 1H), 2.36 (s, 5H), 2.04-1.90 (m, 4H), 1.81-1.72 (m, 4H), 1.61-1.55 (m, 4H), 1.44 (s, 2H), 1.29-1.26 (m, 4H); MS (ESI) m/z=605.2 (M+H)$^+$ Example 66. (1s,4s)-4-((2-((2-(1-(Cyclopropylsulfonyl)-1H-pyrazol-4-yl)pyrimidin-4-yl)amino)-5-(6-(3,3-difluoroazetidin-1-yl)pyridazin-3-yl)pyridin-4-yl)amino)-1-methylcyclohexan-1-ol Step 1.
3-Bromo-6-(3,3-difluoroazetidin-1-yl)pyridazine The reaction mixture of 3-bromo-6-fluoro-pyridazine (100 mg, 0.570 mmol), 3,3-difluoroazetidine hydrochloride (110 mg, 0.848 mmol), and DIPEA (0.49 mL, 2.825 mmol) in DMA (3 mL) was stirred at 100° C. for 4 hours. The reaction mixture was cooled, diluted in EA, washed by water, dried over MgSO$_4$, and then concentrated. The crude residue was purified by column chromatography (MeOH/DCM=0-10%) to yield 3-bromo-6-(3,3-difluoroazetidin-1-yl)pyridazine (123 mg). $^1$H-NMR (CDCl$_3$, 400 MHz) δ 7.41 (d, 1H), 6.56 (d, 1H), 4.49 (t, 4H); MS (ESI) m/z=231.9 (M+H)$^+$ Step 2. 3-(6-Chloro-4-fluoropyridin-3-yl)-6-(3,3-difluoroazetidin-1-yl)pyridazine The title compound as a solid (53 mg) was prepared in the same fashion as Step 1 in Example 1 except that 3-bromo-6-(3,3-difluoroazetidin-1-yl)pyridazine (87 mg, 0.349 mmol) prepared in Step 1 was used instead of 1-((6-bromopyridin-3-yl)methyl)-4-methylpiperazine. $^1$H-NMR (CDCl$_3$, 400 MHz) δ 9.14 (d, 1H), 7.73 (d, 1H), 7.22 (d, 1H), 6.75 (d, 1H), 4.58 (t, 4H); MS (ESI) m/z=301.0 (M+H)$^+$ Step 3. (1s,4s)-4-((2-Chloro-5-(6-(3,3-difluoroazetidin-1-yl)pyridazin-3-yl)pyridin-4-yl)amino)-1-methylcyclohexan-1-ol The title compound as a white solid (68 mg) was prepared in the same fashion as Step 2 in Example 1 except that 3-(6-chloro-4-fluoropyridin-3-yl)-6-(3,3-difluoroazetidin-1-yl)pyridazine (54 mg, 0.179 mmol) prepared in Step 2 and cis-4-amino-1-methylcyclohexan-1-ol (35 mg, 0.269 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.16 (d, 1H), 8.26 (s, 1H), 7.74 (d, 1H), 6.79 (d, 1H), 6.61 (s, 1H), 4.59-4.52 (m, 4H), 3.38-3.35 (m, 1H), 1.95-1.81 (m, 1H), 1.77-1.60 (m, 4H), 1.59-1.53 (m, 3H), 1.29 (s, 3H); MS (ESI) m/z=410.0 (M+H)$^+$ Step 4. (1s,4s)-4-((2-((2-(1-(Cyclopropylsulfonyl)-1H-pyrazol-4-yl)pyrimidin-4-yl)amino)-5-(6-(3,3-difluoroazetidin-1-yl)pyridazin-3-yl)pyridin-4-yl)amino)-1-methylcyclohexan-1-ol The title compound (8 mg) as a white solid was prepared in the same fashion as Step 3 in Example 1, except that (1s,4s)-4-((2-chloro-5-(6-(3,3-difluoroazetidin-1-yl)pyridazin-3-yl)pyridin-4-yl)amino)-1-methylcyclohexan-1-ol (50 mg, 0.122 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.22 (d, 1H), 8.67 (s, 1H), 8.48 (s, 1H), 8.43 (d, 1H), 8.28 (s, 1H), 7.76 (d, 1H), 7.61 (s, 1H), 7.36 (d, 1H), 7.01 (d, 1H), 6.81 (d, 1H), 4.59-4.53 (m, 4H), 3.52-3.50 (m, 1H), 2.85-2.81 (m, 1H), 2.05-1.99 (m, 3H), 1.86-1.74 (m, 5H), 1.55-1.52 (m, 3H), 1.31 (s, 3H), 1.30-1.29 (m, 3H); MS (ESI) m/z=639.2 (M+H)$^+$ Example 67. (1s,4s)-4-((5-(6-(2-Oxa-6-azaspiro[3.3]heptan-6-yl)pyridazin-3-yl)-2-((2-(1-(cyclopropylsulfonyl)-1H-pyrazol-4-yl)pyrimidin-4-yl)amino) pyridin-4-yl)amino)-1-methylcyclohexan-1-ol Step 1. 6-(6-Bromopyridazin-3-yl)-2-oxa-6-azaspiro[3.3]heptane The title compound (40 mg) as a solid was prepared in the same fashion as Step 1 in Example 66, except that 2-oxa-6-azaspiro[3.3]heptane (84 mg, 0848 mmol) was used instead of 3,3-difluoroazetidine. $^1$H-NMR (CDCl$_3$, 400 MHz) δ 7.31 (d, 1H), 6.44 (d, 1H), 4.87 (s, 4H), 4.29 (s, 4H); MS (ESI) m/z=257.9 (M+H)$^+$ Step 2. 6-(6-(6-Chloro-4-fluoropyridin-3-yl) pyridazin-3-yl)-2-oxa-6-azaspiro[3.3]heptane The title compound as a solid (59 mg) was prepared in the same fashion as Step 1 in Example 1 except that 6-(6-bromopyridazin-3-yl)-2-oxa-6-azaspiro[3.3]heptane (89 mg, 0.348 mmol) prepared in Step 1 was used instead of 1-((6-bromopyridin-3-yl)methyl)-4-methylpiperazine. $^1$H-NMR (CDCl$_3$, 400 MHz) δ 9.13 (d, 1H), 7.65 (d, 1H), 7.20 (d, 1H), 6.62 (d, 1H), 4.90 (s, 4H), 4.39 (s, 4H), 4.37 (s, 4H); MS (ESI) m/z=307.0 (M+H)⁺

Step 3. (1s,4s)-4-((5-(6-(2-Oxa-6-azaspiro[3.3]heptan-6-yl)pyridazin-3-yl)-2-chloropyridin-4-yl)amino)-1-methylcyclohexan-1-ol The title compound as a white solid (67 mg) was prepared in the same fashion as Step 2 in Example 1 except that 6-(6-(6-chloro-4-fluoropyridin-3-yl)pyridazin-3-yl)-2-oxa-6-azaspiro[3.3]heptane (55 mg, 0.179 mmol) prepared in Step 2 and cis-4-amino-1-methylcyclohexan-1-ol (35 mg, 0.269 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl₃, 400 MHz) δ 8.98 (d, 1H), 8.24 (s, 1H), 7.66 (d, 1H), 6.69 (d, 1H), 6.60 (s, 1H), 4.90 (s, 4H), 3.38-3.35 (m, 1H), 1.94-1.92 (m, 2H), 1.77-1.71 (m, 4H), 1.57-1.44 (m, 2H), 1.29 (s, 3H); MS (ESI) m/z=416.1 (M+H)⁺

Step 4. (1s,4s)-4-((5-(6-(2-Oxa-6-azaspiro[3.3]heptan-6-yl)pyridazin-3-yl)-2-((2-(1-(cyclopropylsulfonyl)-1H-pyrazol-4-yl)pyrimidin-4-yl)amino)pyridin-4-yl)amino)-1-methylcyclohexan-1-ol The title compound (3 mg) as a white solid was prepared in the same fashion as Step 3 in Example 1, except that (1s,4s)-4-((5-(6-(2-oxa-6-azaspiro[3.3]heptan-6-yl)pyridazin-3-yl)-2-chloropyridin-4-yl)amino)-1-methylcyclohexan-1-ol (51 mg, 0.122 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.26 (d, 1H), 8.66 (s, 1H), 8.48 (s, 1H), 8.42 (d, 1H), 8.25 (s, 1H), 7.80 (br, 1H), 7.67 (d, 1H), 7.33 (d, 1H), 7.03 (s, 1H), 6.70 (d, 1H), 4.90 (s, 4H), 4.37 (s, 4H), 3.52 (s, 1H), 2.85-2.83 (s, 1H), 2.05-1.97 (m, 2H), 1.84-1.77 (m, 2H), 1.63-1.53 (m, 3H), 1.30 (s, 3H), 1.26-1.25 (m, 3H); MS (ESI) m/z=645.3 (M+H)⁺

Example 68. (1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)-1-methylcyclohexan-1-ol Step 1. 3-(6-Chloro-4-fluoropyridin-3-yl)-6-(4,4-difluoropiperidin-1-yl)pyridazine The title compound as a white solid (327 mg) was prepared in the same fashion as Step 1 in Example 1 except that 3-bromo-6-(4,4-difluoropiperidin-1-yl)pyridazine (652 mg, 2.343 mmol) was used instead of 1-((6-bromopyridin-3-yl)methyl)-4-methylpiperazine. ¹H-NMR (CDCl₃, 400 MHz) δ 9.16 (d, 1H), 7.70 (dd, 1H), 7.22 (d, 1H), 7.06 (d, 1H), 3.93 (t, 4H), 2.17-2.07 (m, 4H); MS (ESI) m/z=329.0 (M+H)⁺

Step 2. (1s,4s)-4-((2-Chloro-5-(6-(4,4-difluoropiperidin-1-yl)pyridazin-3-yl)pyridin-4-yl)amino)-1-methylcyclohexan-1-ol The title compound as a white solid (90 mg) was prepared in the same fashion as Step 2 in Example 1 except that 3-(6-chloro-4-fluoropyridin-3-yl)-6-(4,4-difluoropiperidin-1-yl)pyridazine (75 mg, 0.228 mmol) prepared in Step 1 and cis-4-amino-1-methylcyclohexan-1-ol (44 mg, 0.342 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.24 (d, 1H), 8.26 (s, 1H), 7.19 (d, 1H), 7.10 (d, 1H), 6.61 (s, 1H), 3.88 (t, 4H), 3.38-3.37 (m, 1H), 2.16-2.06 (m, 4H), 1.96-1.94 (m, 2H), 1.82-1.60 (m, 4H), 1.55-1.54 (m, 2H), 1.30 (s, 3H); MS (ESI) m/z=438.0 (M+H)⁺

Step 3. (1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)-1-methylcyclohexan-1-ol The title compound (17.7 mg) as a white solid was prepared in the same fashion as Step 3 in Example 1, except that (1s,4s)-4-((2-chloro-5-(6-(4,4-difluoropiperidin-1-yl)pyridazin-3-yl)pyridin-4-yl)amino)-1-methylcyclohexan-1-ol (85 mg, 0.194 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.27 (d, 1H), 8.67 (s, 1H), 8.49 (s, 1H), 8.43 (d, 1H), 8.29 (s, 1H), 7.72 (d, 1H), 7.50 (s, 1H), 7.37 (d, 1H), 7.06 (d, 1H), 6.99 (s, 1H), 3.88 (t, 4H), 3.53 (s, 1H), 2.84-2.80 (m, 1H), 2.16-2.07 (m, 4H), 2.03-2.00 (m, 2H), 1.86-1.75 (m, 4H), 1.31 (s, 3H), 1.27 (s, 3H); MS (ESI) m/z=667.3 (M+H)⁺

Example 69. ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol Step 1. ((1s,4s)-4-((2-Chloro-5-(6-(4,4-difluoropiperidin-1-yl)pyridazin-3-yl)pyridin-4-yl)amino)cyclohexyl)methanol The title compound as a white solid (100 mg) was prepared in the same fashion as Step 2 in Example 1 except that 3-(6-chloro-4-fluoropyridin-3-yl)-6-(4,4-difluoropiperidin-1-yl)pyridazine (75 mg, 0.228 mmol) prepared in Step 1 of Example 68 and cis-(4-aminocyclohexyl)methanol hydrochloride (54 mg, 0.342 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.82 (d, 1H), 8.30 (d, 1H), 7.74 (d, 1H), 7.12 (d, 1H), 6.62 (s, 1H), 3.87 (t, 4H), 3.82 (s, 1H), 3.58 (d, 1H), 2.17-2.07 (m, 4H), 1.92-1.89 (m, 2H), 1.74-1.68 (m, 5H), 1.53-1.46 (m, 2H); MS (ESI) m/z=438.1 (M+H)⁺

Step 2. ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol The title compound (16.3 mg) as a white solid was prepared in the same fashion as Step 3 in Example 1, except that ((1s,4s)-4-((2-chloro-5-(6-(4,4-difluoropiperidin-1-yl)pyridazin-3-yl)pyridin-4-yl)amino)cyclohexyl)methanol (85 mg. 0.194 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.89 (d, 1H), 8.67 (s, 1H), 8.47 (s, 1H), 8.42 (d, 1H), 8.32 (s, 1H), 7.76 (d, 1H), 7.53 (s, 1H), 7.17 (d, 1H), 7.12 (d, 1H), 4.00 (s, 1H), 3.87 (t, 4H), 3.58 (d, 1H), 2.88-2.84 (m, 1H), 2.16-2.02 (m, 6H), 1.85-1.78 (m, 5H), 1.55-1.52 (m, 4H), 1.48-1.27 (m, 3H); MS (ESI) m/z=667.3 (M+H)⁺

Example 70. ((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)methanol Step 1. 2-(6-Chloro-4-fluoropyridin-3-yl)-5-(4,4-difluoropiperidin-1-yl)pyrazine The title compound as a white solid (423 mg) was prepared in the same fashion as Step 1 in Example 1 except that 2-bromo-5-(4,4-difluoropiperidin-1-yl)pyrazine (652 mg. 2.343 mmol) was used instead of 1-((6-bromopyridin-3-yl)methyl)-4-methylpiperazine. $^1$H-NMR (CDCl$_3$, 400 MHz) δ 8.98 (d, 1H), 8.56 (t, 1H), 8.32 (d, 1H), 7.19 (d, 1H), 3.87 (t, 4H), 2.13-2.06 (m, 4H); MS (ESI) m/z=329.0 (M+H)$^+$ Step 2. ((1s,4s)-4-((2-Chloro-5-(5-(4,4-difluoropiperidin-1-yl) pyrazin-2-yl)pyridin-4-yl)amino)cyclohexyl)methanol The title compound as a white solid (98 mg) was prepared in the same fashion as Step 2 in Example 1 except that 2-(6-chloro-4-fluoropyridin-3-yl)-5-(4,4-difluoropiperidin-1-yl)pyrazine (84 mg, 0.259 mmol) prepared in Step 1 and cis-(4-aminocyclohexyl)methanol hydrochloride (64 mg, 0.388 mmol) were used instead of 6'-chloro-4'-fluoro-5-((4-methylpiperazin-1-yl)methyl)-2,3'-bipyridine. $^1$H-NMR (CDCl$_3$, 400 MHz) δ 8.82 (d, 1H), 8.55 (s, 1H), 8.33 (s, 1H), 8.12 (s, 1H), 6.56 (s, 1H), 3.83 (t, 4H), 3.78-3.77 (m, 1H), 3.54 (d, 2H), 2.14-2.06 (m, 4H), 1.92-1.89 (m, 2H), 1.72-1.68 (m, 3H), 1.65 (s, 2H), 1.50 (s, 1H), 1.37-1.28 (m, 2H); MS (ESI) m/z=438.0 (M+H)$^+$ Step 3. ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol The title compound (10.5 mg) as a white solid was prepared in the same fashion as Step 3 in Example 1, ((1s,4s)-4-((2-chloro-5-(5-(4,4-difluoropiperidin-1-yl)pyrazin-2-yl)pyridin-4-yl)amino)cyclohexyl)methanol (84 mg, 0.191 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.92 (d 1H), 8.66 (s, 1H), 8.58 (s, 1H), 8.47 (s, 1H), 8.41 (s, 1H), 8.34 (s, 1H), 8.13 (s, 1H), 7.71 (s, 1H), 7.15 (d, 1H), 3.96 (s, 1H), 3.83 (t, 4H), 3.55 (d, 2H), 2.84 (s, 1H), 2.14-2.01 (m, 6H), 1.83-1.71 (m, 5H), 1.55-1.49 (m, 3H), 1.39-1.26 (m, 4H), 1.24-2.20 (m, 5H); MS (ESI) m/z=667.2 (M+H)$^+$ Example 71. 2-((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)propan-2-ol Step 1. 2-((1s,4s)-4-((2-Chloro-5-(6-(4,4-difluoropiperidin-1-yl)pyridazin-3-yl)pyridin-4-yl)amino)cyclohexyl)propan-2-ol The title compound as a white solid (86 mg) was prepared in the same fashion as Step 2 in Example 1 except that 3-(6-chloro-4-fluoropyridin-3-yl)-6-(4,4-difluoropiperidin-1-yl)pyridazine (75 mg, 0.228 mmol) prepared in Step 1 of Example 68 and 2-((1s,4s)-4-aminocyclohexyl)propan-2-ol (54 mg, 0.342 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 10.45 (d, 1H), 8.33 (s, 1H), 7.76 (d, 1H), 7.11 (d, 1H), 6.63 (s, 1H), 3.90 (s, 1H), 3.87-3.85 (m, 4H), 2.12-2.06 (m, 4H), 2.02-1.98 (m, 2H), 1.75 (m, 2H), 1.49-1.44 (m, 3H), 1.22 (m, 6H); MS (ESI) m/z=466.1 (M+H)$^+$ Step 2. 2-((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)propan-2-ol The title compound (7.5 mg) as a white solid was prepared in the same fashion as Step 3 in Example 1, except that 2-((1s,4s)-4-((2-chloro-5-(6-(4,4-difluoropiperidin-1-yl)pyridazin-3-yl)pyridin-4-yl)amino)cyclohexyl)propan-2-ol (79 mg. 0.169 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.47 (s, 1H), 8.41 (d, 1H), 8.34 (s, 1H), 7.78 (d, 1H), 7.55 (s, 1H), 7.34 (s, 1H), 7.12 (d, 2H), 4.08-4.06 (m, 1H), 3.85 (t, 2H), 2.86-2.82 (m, 1H), 2.23-2.06 (m, 6H), 1.79-1.73 (m, 4H), 1.56-1.39 (m, 4H), 1.13 (s, 7H); MS (ESI) m/z=695.3 (M+H)$^+$ Example 72. 2-((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)propan-2-ol Step 1. 2-((1s,4s)-4-((2-Chloro-5-(5-(4,4-difluoropiperidin-1-yl) pyrazin-2-yl)pyridin-4-yl)amino)cyclohexyl)propan-2-ol The title compound as a white solid (98 mg) was prepared in the same fashion as Step 2 in Example 1 except that 2-(6-chloro-4-fluoropyridin-3-yl)-5-(4,4-difluoropiperidin-1-yl)pyrazine (85 mg, 0.259 mmol) prepared in Step 1 of Example 70 and 2-((1s,4s)-4-aminocyclohexyl)propan-2-ol (61 mg, 0.388 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.87 (d, 1H), 8.56 (s, 1H), 8.34 (s, 1H), 8.09 (s, 1H), 6.57 (s, 1H), 3.81 (t, 5H), 2.13-1.99 (m, 6H), 1.78-1.75 (m, 2H), 1.41-1.25 (m, 4H), 1.22 (s, 6H); MS (ESI) m/z=466.0 (M+H)$^+$ Step 2. 2-((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)propan-2-ol The title compound (13 mg) as a white solid was prepared in the same fashion as Step 3 in Example 1, except that 2-((1s,4s)-4-((2-chloro-5-(5-(4,4-difluoropiperidin-1-yl)pyrazin-2-yl)pyridin-4-yl)amino)cyclohexyl)propan-2-ol (79 mg, 0.169 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.92 (d, 1H), 8.66 (s, 1H), 8.59 (s, 1H), 8.47 (s, 1H), 8.41 (d, 1H), 8.35 (s, 1H), 8.11 (s, 1H), 7.53 (s, 1H), 7.13 (d, 1H), 3.98 (s, 1H), 3.81 (t, 4H), 2.85-2.83 (m, 1H), 2.12-2.06 (m, 6H), 1.80-1.72 (m, 4H), 1.55-1.54 (m, 3H), 1.46-1.33 (m, 4H), 1.23 (s, 6H); MS (ESI) m/z=695.2 (M+H)$^+$

Example 73. N²-(2-(1-(Cyclopropylsulfonyl)-1H-pyrazol-4-yl)pyrimidin-4-yl)-5-(6-(4,4-difluoropiperidin-1-yl)pyridazin-3-yl)-N⁴-((1s,4s)-4-((dimethylamino)methyl)cyclohexyl)pyridine-2,4-diamine

Step 1. 2-Chloro-5-(6-(4,4-difluoropiperidin-1-yl)pyridazin-3-yl)-N-((1s,4s)-4-((dimethylamino)methyl)cyclohexyl)pyridin-4-amine The title compound as a white solid (85 mg) was prepared in the same fashion as Step 2 in Example 1 except that 3-(6-chloro-4-fluoropyridin-3-yl)-6-(4,4-difluoropiperidin-1-yl)pyridazine (75 mg, 0.228 mmol) prepared in Step 1 of Example 68 and (1s,4s)-4-((dimethylamino)methyl)cyclohexan-1-amine dihydrochloride (78 mg, 0.342 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.65 (d, 1H), 8.29 (d, 1H), 7.27 (d, 1H), 7.11 (d, 1H), 6.61 (s, 1H), 3.88 (t, 4H), 3.73 (s, 1H), 2.24 (s, 6H), 2.20-2.07 (m, 6H), 1.86-1.83 (m, 2H), 1.74-1.63 (m, 5H), 1.43-1.34 (m, 2H); MS (ESI) m/z=465.1 (M+H)⁺

Step 2. N²-(2-(1-(Cyclopropylsulfonyl)-1H-pyrazol-4-yl)pyrimidin-4-yl)-5-(6-(4,4-difluoropiperidin-1-yl)pyridazin-3-yl)-N⁴-((1s,4s)-4-((dimethylamino)methyl)cyclohexyl)pyridine-2,4-diamine The title compound (5 mg) as a white solid was prepared in the same fashion as Step 3 in Example 1, except that 2-chloro-5-(6-(4,4-difluoropiperidin-1-yl)pyridazin-3-yl)-N-((1s,4s)-4-((dimethylamino)methyl)cyclohexyl)pyridin-4-amine (79 mg, 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.74 (d, 1H), 8.67 (s, 1H), 8.47 (s, 1H), 8.42 (d, 1H), 8.31 (s, 1H), 7.75 (d, 1H), 7.60 (s, 1H), 7.30-7.18 (m, 2H), 7.12 (d, 1H), 3.92 (s, 1H), 3.87 (t, 4H), 2.85-2.83 (m, 1H), 2.23 (s, 6H), 2.18-2.09 (m, 6H), 1.99-1.96 (m, 2H), 1.83-1.77 (m, 2H), 1.61-1.55 (m, 2H), 1.42-1.39 (m, 3H); MS (ESI) m/z=694.3 (M+H)⁺

Example 74. N²-(2-(1-(Cyclopropylsulfonyl)-1H-pyrazol-4-yl)pyrimidin-4-yl)-5-(5-(4,4-difluoropiperidin-1-yl) pyrazin-2-yl)-N⁴-((1s,4s)-4-((dimethylamino)methyl)cyclohexyl)pyridine-2,4-diamine

Step 1. 2-Chloro-5-(5-(4,4-difluoropiperidin-1-yl) pyrazin-2-yl)-N-((1s,4s)-4-((dimethylamino)methyl)cyclohexyl)pyridin-4-amine The title compound as a pale yellow solid (83 mg) was prepared in the same fashion as Step 2 in Example 1 except that 2-(6-chloro-4-fluoropyridin-3-yl)-5-(4,4-difluoropiperidin-1-yl)pyrazine (85 mg, 0.259 mmol) prepared in Step 1 of Example 70 and (1s,4s)-4-((dimethylamino)methyl)cyclohexan-1-amine dihydrochloride (89 mg, 0.388 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 8.79 (d, 1H), 8.56 (s, 1H), 8.34 (s, 1H), 8.15 (s, 1H), 6.55 (s, 1H), 3.84 (t, 4H), 3.34 (s, 1H), 2.53 (s, 6H), 2.18-2.05 (m, 6H), 1.89-1.86 (m, 2H), 1.73-1.62 (m, 3H), 1.29-1.23 (m, 2H); MS (ESI) m/z=465.1 (M+H)⁺

Step 2. N²-(2-(1-(Cyclopropylsulfonyl)-1H-pyrazol-4-yl)pyrimidin-4-yl)-5-(5-(4,4-difluoropiperidin-1-yl) pyrazin-2-yl)-N⁴-((1s,4s)-4-((dimethylamino)methyl)cyclohexyl)pyridine-2,4-diamine The title compound (16 mg) as a solid was prepared in the same fashion as Step 3 in Example 1, except that 2-chloro-5-(5-(4,4-difluoropiperidin-1-yl) pyrazin-2-yl)-N-((1s,4s)-4-((dimethylamino)methyl)cyclohexyl)pyridin-4-amine (79 mg, 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 8.88 (d, 1H), 8.66 (s, 1H), 8.63 (s, 1H), 8.58 (s, 1H), 8.41 (d, 1H), 8.35 (s, 1H), 8.14 (s, 1H), 7.69 (s, 1H), 7.19 (s, 2H), 3.92 (s, 2H), 3.83 (t, 4H), 2.85-2.83 (m, 1H), 2.16 (s, 6H), 2.14-2.06 (m, 6H), 2.02-1.98 (m, 2H), 1.81-1.66 (m, 4H), 1.54-1.53 (m, 3H), 1.29-1.26 (m, 4H); MS (ESI) m/z=694.3 (M+H)⁺

Example 75. (1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)-1-methylcyclohexan-1-ol

Step 1. (1s,4s)-4-((2-Chloro-5-(5-(4,4-difluoropiperidin-1-yl) pyrazin-2-yl)pyridin-4-yl)amino)-1-methylcyclohexan-1-ol The title compound as a pale yellow solid (112 mg) was prepared in the same fashion as Step 2 in Example 1 except that 2-(6-chloro-4-fluoropyridin-3-yl)-5-(4,4-difluoropiperidin-1-yl)pyrazine (85 mg, 0.259 mmol) prepared in Step 1 of Example 70 and cis-4-amino-1-methylcyclohexan-1-ol (50 mg, 0.388 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl₃, 400 MHz) δ 8.50 (s, 1H), 8.33 (d, 1H), 8.29 (s, 1H), 8.13 (s, 1H), 6.55 (s, 1H), 3.82 (t, 4H), 3.35-3.33 (m, 1H), 2.13-2.04 (m, 4H), 1.94-1.91 (m, 2H), 1.77-1.54 (m, 5H), 1.31 (s, 3H); MS (ESI) m/z=438.0 (M+H)⁺

Step 2. (1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)-1-methylcyclohexan-1-ol The title compound (12 mg) as a white solid was prepared in the same fashion as Step 3 in Example 1, except that (1s,4s)-4-((2-chloro-5-(5-(4,4-difluoropiperidin-1-yl) pyrazin-2-yl)pyridin-4-yl)amino)-1-methylcyclohexan-1-ol (84 mg, 0.191 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.70 (d, 1H), 8.68 (s, 1H), 8.63 (s, 1H), 8.54 (s, 1H), 8.45-8.43 (m, 2H), 8.14 (s, 1H), 8.10 (s, 1H), 7.92 (s, 1H), 7.08 (d, 1H), 4.06 (s, 1H), 3.83 (t, 4H), 2.86-2.84 (m, 1H), 2.13-2.06 (m, 6H), 1.85 (s, 4H), 1.54 (s, 2H), 1.49-1.34 (m, 3H); MS (ESI) m/z=667.3 (M+H)⁺

Example 76. (1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)-1-methylcyclohexan-1-ol

Step 1. 6'-Chloro-4-(difluoromethyl)-4'-fluoro-2,3'-bipyridine

The title compound as a white solid (376 mg) was prepared in the same fashion as Step 1 in Example 1 except that 2-bromo-4-(difluoromethyl)pyridine (500 mg, 2.404 mmol) was used instead of 1-((6-bromopyridin-3-yl)methyl)-4-methylpiperazine. $^1$H-NMR (CDCl$_3$, 400 MHz) δ 9.09 (d, 1H), 8.89 (d, 1H), 7.88 (s, 1H), 7.48 (d, 1H), 7.25 (d, 1H), 6.72 (t, 1H); MS (ESI) m/z=259.0 (M+H)$^+$ Step 2. (1s,4s)-4-((6'-Chloro-4-(difluoromethyl)-[2,3'-bipyridin]-4'-yl)amino)-1-methylcyclohexan-1-ol The title compound as a white solid (108 mg) was prepared in the same fashion as Step 2 in Example 1 except that 6'-chloro-4-(difluoromethyl)-4'-fluoro-2,3'-bipyridine (80 mg, 0.309 mmol) prepared in Step 1 and cis-4-amino-1-methylcyclohexan-1-ol (60 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.26 (d, 1H), 8.70 (d, 1H), 8.43 (s, 1H), 7.81 (s, 1H), 7.37 (d, 1H), 6.70 (t, 1H), 6.60 (s, 1H), 3.35 (s, 1H), 1.96-1.93 (d, 2H), 1.78-1.65 (m, 4H), 1.61-1.54 (m, 2H), 1.31 (s, 3H); MS (ESI) m/z=368.0 (M+H)$^+$ Step 3. (1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)-1-methylcyclohexan-1-ol The title compound (35 mg) as a white solid was prepared in the same fashion as Step 3 in Example 1, except that (1s,4s)-4-((6'-chloro-4-(difluoromethyl)-[2,3'-bipyridin]-4'-yl)amino)-1-methylcyclohexan-1-ol (80 mg, 0.217 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.39 (d, 1H), 8.70 (d, 1H), 8.67 (s, 1H), 8.48 (d, 2H), 8.44 (d, 1H), 7.84 (s, 1H), 7.55 (s, 1H), 7.32 (d, 2H), 7.05 (s, 1H), 6.70 (t, 1H), 3.53 (s, 1H), 2.84-2.82 (m, 1H), 2.02-2.00 (m, 2H), 1.80-1.74 (m, 4H), 1.54-1.53 (m, 3H), 1.32 (s, 3H), 1.26-1.19 (m, 3H); MS (ESI) m/z=597.2 (M+H)$^+$ Example 77. ((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)methanol Step 1. ((1s,4s)-4-((6'-Chloro-4-(difluoromethyl)-[2,3'-bipyridin]-4'-yl)amino)cyclohexyl)methanol The title compound as a white solid (109 mg) was prepared in the same fashion as Step 2 in Example 1 except that 6'-chloro-4-(difluoromethyl)-4'-fluoro-2,3'-bipyridine (80 mg, 0.309 mmol) prepared in Step 1 of Example 76 and cis-(4-aminocyclohexyl)methanol hydrochloride (79 mg, 0.464 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.76 (d, 1H), 8.70 (d, 1H), 8.44 (s, 1H), 7.84 (s, 1H), 7.36 (d, 1H), 6.70 (t, 1H), 6.60 (s, 1H), 3.80 (s, 1H), 3.53 (d, 2H), 1.91-1.89 (m, 2H), 1.73-1.65 (m, 4H), 1.38-1.29 (m, 2H); MS (ESI) m/z=(M+H)$^+$ Step 2. ((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)methanol The title compound (12 mg) as a white solid was prepared in the same fashion as Step 3 in Example 1, except that ((1s,4s)-4-((6'-chloro-4-(difluoromethyl)-[2,3'-bipyridin]-4'-yl)amino)cyclohexyl)methanol (80 mg, 0.217 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.89 (d, 1H), 8.70 (d, 1H), 8.67 (s, 1H), 8.49 (d, 1H), 8.42 (d, 1H), 7.88 (s, 1H), 7.63 (s, 1H), 7.32 (d, 1H), 7.11 (d, 1H), 6.71 (t, 1H), 4.01 (s, 1H), 3.54 (d, 2H), 2.85-2.84 (m, 1H), 2.06-2.04 (d, 2H), 1.85-1.73 (m, 3H), 1.55-1.42 (m, 2H), 1.39-1.26 (m, 2H), 1.24-1.22 (m, 4H); MS (ESI) m/z=597.2 (M+H)$^+$ Example 78. 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)propan-2-ol Step 1. 2-((1s,4s)-4-((6'-Chloro-4-(difluoromethyl)-[2,3'-bipyridin]-4'-yl)amino)cyclohexyl)propan-2-ol The title compound as a white solid (117 mg) was prepared in the same fashion as Step 2 in Example 1 except that 6'-chloro-4-(difluoromethyl)-4'-fluoro-2,3'-bipyridine (80 mg, 0.309 mmol) prepared in Step 1 of Example 76 and 2-((1s,4s)-4-aminocyclohexyl)propan-2-ol (73 mg, 0.464 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.81 (d, 1H), 8.70 (d, 1H), 8.46 (s, 1H), 7.86 (s, 1H), 7.36 (d, 1H), 6.71 (t, 1H), 6.61 (s, 1H), 3.84 (s, 1H), 2.05-1.98 (m, 2H), 1.80-1.77 (m, 3H), 1.66-1.60 (m, 2H), 1.43-1.34 (m, 6H); MS (ESI) m/z=396.0 (M+H)$^+$ Step 2. 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)propan-2-ol The title compound (13 mg) as a white solid was prepared in the same fashion as Step 3 in Example 1, except that 2-((1s,4s)-4-((6'-chloro-4-(difluoromethyl)-[2,3'-bipyridin]-4'-yl)amino)cyclohexyl)propan-2-ol (86 mg, 0.217 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.91 (d, 1H), 8.69 (d, 1H), 8.67 (s, 1H), 8.51 (s, 1H), 8.47 (s, 1H), 8.42 (d, 1H), 7.89 (s, 1H), 7.61 (s, 1H), 7.37 (s, 1H), 7.31 (d, 1H), 7.09 (d, 1H), 6.71 (t, 1H), 4.02 (s, 1H), 2.86-2.84 (d, 1H), 2.13-2.06 (m, 2H), 1.81-1.75 (m, 4H), 1.57-1.54 (m, 2H), 1.46-1.41 (m, 3H), 1.26 (s, 8H); MS (ESI) m/z=625.2 (M+H)$^+$ Example 79. N$^{6'}$-(2-(1-(Cyclopropylsulfonyl)-1H-pyrazol-4-yl)pyrimidin-4-yl)-4-(difluoromethyl)-N$^{4'}$-((1s,4s)-4-((dimethylamino)methyl)cyclohexyl)-[2,3'-bipyridine]-4',6'-diamine Step 1. 6'-Chloro-4-(difluoromethyl)-N—((1s,4s)-4-((dimethylamino)methyl)cyclohexyl)-[2,3'-bipyridin]-4'-amine The title compound as a white solid (103 mg) was prepared in the same fashion as Step 2 in Example 1 except that 6'-chloro-4-(difluoromethyl)-4'-fluoro-2,3'-bipyridine (80 mg, 0.309 mmol) prepared in Step 1 of Example 76 and (1s,4s)-4-((dimethylamino)methyl)cyclohexan-1-amine dihydrochloride (106 mg, 0.464 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.70 (d, 1H), 8.71 (d, 1H), 8.46 (s, 1H), 7.86 (s, 1H), 7.38 (d, 1H), 6.71 (t, 1H), 6.60 (s, 1H), 3.78 (s, 1H), 2.24 (s, 6H), 2.15-2.01 (m, 2H), 1.94-1.87 (m, 2H), 1.75-1.65 (m, 5H), 1.31-1.22 (m, 2H); MS (ESI) m/z=395.1 (M+H)$^+$ Step 2. N$^{6'}$-(2-(1-(Cyclopropylsulfonyl)-1H-pyrazol-4-yl)pyrimidin-4-yl)-4-(difluoromethyl)-N$^{4'}$-((1s,4s)-4-((dimethylamino)methyl)cyclohexyl)-[2,3'-bipyridine]-4',6'-diamine The title compound (35 mg) as a solid was prepared in the same fashion as Step 3 in Example 1, except that 6'-chloro-4-(difluoromethyl)-N-((1s,4s)-4-((dimethylamino)methyl)cyclohexyl)-[2,3'-bipyridin]-4'-amine (86 mg, 0.217 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.84 (d, 1H), 8.70 (d, 1H), 8.67 (s, 1H), 8.51 (s, 1H), 8.47 (s, 1H), 8.42 (d, 1H), 7.88 (s, 1H), 7.60 (s, 1H), 7.32 (d, 1H), 7.13 (d, 1H), 6.71 (t, 1H), 3.98 (s, 1H), 2.86-2.84 (m, 1H), 2.25 (s, 6H), 2.17-2.15 (m, 2H), 2.03-2.00 (m, 2H), 1.83-1.68 (m, 4H), 1.55-1.54 (m, 2H), 1.32-1.24 (m, 4H); MS (ESI) m/z=624.2 (M+H)$^+$ Example 80. (1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)-1-methylcyclohexan-1-ol Step 1. 6'-Chloro-4'-fluoro-5-(pyrrolidin-1-yl)-2,3'-bipyridine The title compound as a white solid (339 mg) was prepared in the same fashion as Step 1 in Example 1 except that 2-bromo-5-(pyrrolidin-1-yl)pyridine (546 mg, 2.404 mmol) was used instead of 1-((6-bromopyridin-3-yl)methyl)-4-methylpiperazine. $^1$H-NMR (CDCl$_3$, 400 MHz) δ 9.00 (d, 1H), 8.11 (s, 1H), 7.60 (d, 1H), 7.14 (d, 1H), 6.87 (d, 1H), 3.38 (s, 4H), 2.08 (s, 4H); MS (ESI) m/z=278.0 (M+H)$^+$ Step 2. (1s,4s)-4-((6'-Chloro-5-(pyrrolidin-1-yl)-[2,3'-bipyridin]-4'-yl)amino)-1-methylcyclohexan-1-ol The title compound as a white solid (107 mg) was prepared in the same fashion as Step 2 in Example 1 except that 6'-chloro-4'-fluoro-5-(pyrrolidin-1-yl)-2,3'-bipyridine (80 mg, 0.288 mmol) prepared in Step 1 and cis-4-amino-1-methylcyclohexan-1-ol (56 mg, 0.432 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.21 (d, 1H), 8.26 (s, 1H), 7.93 (s, 1H), 7.54 (d, 1H), 6.94 (d, 1H), 6.52 (s, 1H), 3.35 (s, 4H), 2.07 (s, 4H), 1.96-1.93 (m, 2H), 1.78-1.67 (m, 5H), 1.27 (s, 3H), 1.27-1.18 (m, 2H); MS (ESI) m/z=387.2 (M+H)$^+$ Step 3. (1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)-1-methylcyclohexan-1-ol The title compound (20 mg) as a pale yellow solid was prepared in the same fashion as Step 3 in Example 1, except that ((1s,4s)-4-((6'-chloro-5-(pyrrolidin-1-yl)-[2,3'-bipyridin]-4'-yl)amino)-1-methylcyclohexan-1-ol (85 mg, 0.22 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.31 (s, 1H), 8.66 (s, 1H), 8.48 (s, 1H), 8.40 (d, 1H), 8.27 (s, 1H), 7.94 (s, 2H), 7.55 (d, 1H), 7.34 (s, 1H), 6.97-6.95 (m, 2H), 3.50 (s, 1H), 3.36 (s, 4H), 2.83-2.82 (m, 1H), 2.08 (s, 4H), 2.03-2.00 (m, 2H), 1.82-1.74 (m, 4H), 1.54-1.48 (m, 2H), 1.32 (s, 4H), 1.27 (s, 2H), 1.24 (s, 2H), 1.22-1.20 (m, 2H); MS (ESI) m/z=616.3 (M+H)$^+$ Example 81. ((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)methanol Step 1. ((1s,4s)-4-((6'-Chloro-5-(pyrrolidin-1-yl)-[2,3'-bipyridin]-4'-yl)amino)cyclohexyl)methanol The title compound as a white solid (100 mg) was prepared in the same fashion as Step 2 in Example 1 except that 6'-chloro-4'-fluoro-5-(pyrrolidin-1-yl)-2,3'-bipyridine (80 mg, 0.288 mmol) prepared in Step 1 of Example 80 and cis-(4-aminocyclohexyl)methanol hydrochloride (68 mg. 0.432 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.73 (d, 1H), 8.30 (s, 1H), 7.91 (s, 1H), 7.58 (d, 1H), 6.95 (d, 1H), 6.53 (s, 1H), 3.78 (s, 1H), 3.54 (d, 1H), 3.36 (t, 4H), 2.07 (s, 4H), 1.94-1.91 (m, 2H), 1.61 (s, 5H), 1.42-1.27 (m, 2H); MS (ESI) m/z=387.1 (M+H)$^+$ Step 2. ((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)methanol The title compound (14.5 mg) as a pale yellow solid was prepared in the same fashion as Step 3 in Example 1, except that ((1s,4s)-4-((6'-chloro-5-(pyrrolidin-1-yl)-[2,3'-bipyridin]-4'-yl)amino)cyclohexyl)methanol (85 mg, 0.220 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.81 (d, 1H), 8.66 (s, 1H), 8.47 (s, 1H), 8.38 (d, 1H), 8.30 (s, 1H), 7.92 (s, 1H), 7.60 (d, 1H), 7.17 (d, 2H), 6.97 (d, 1H), 3.96 (s, 1H), 3.55 (d, 1H), 3.37 (s, 4H), 2.84 (s, 1H), 2.08 (s, 4H), 2.03 (s, 1H), 1.82-1.71 (m, 4H), 1.56-1.48 (m, 4H), 1.44-1.29 (m, 3H), 1.27-1.25 (m, 3H); MS (ESI) m/z=616.3 (M+H)$^+$ Example 82. 2-((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)propan-2-ol Step 1. 2-((1s,4s)-4-((6'-Chloro-5-(pyrrolidin-1-yl)-[2,3'-bipyridin]-4'-yl)amino)cyclohexyl)propan-2-ol The title compound as a white solid (92 mg) was prepared in the same fashion as Step 2 in Example 1 except that 6'-chloro-4'-fluoro-5-(pyrrolidin-1-yl)-2,3'-bipyridine (80 mg, 0.288 mmol) prepared in Step 1 of Example 80 and 2-((1s,4s)-4-aminocyclohexyl)propan-2-ol (68 mg. 0.432 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.83 (d, 1H), 8.30 (s, 1H), 7.89 (s, 1H), 7.59 (d, 1H), 6.68 (d, 1H), 6.53 (s, 1H), 3.82-3.81 (m, H), 3.35 (s, 4H), 2.06 (s, 4H), 2.03-1.99 (m, 2H), 1.74 (s, 3H), 1.63-1.57 (m, 2H), 1.40-1.67 (m, 1H), 1.22 (s, 6H); MS (ESI) m/z=415.2 (M+H)⁺

Step 2. 2-((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)propan-2-ol The title compound (23 mg) as a white solid was prepared in the same fashion as Step 3 in Example 1, except that 2-((1s,4s)-4-((6'-chloro-5-(pyrrolidin-1-yl)-[2,3'-bipyridin]-4'-yl)amino)cyclohexyl)propan-2-ol (70 mg, 0.169 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.93 (d, 1H), 8.66 (s, 1H), 8.46 (s, 1H), 8.38 (d, 1H), 8.30 (s, 1H), 7.91 (d, 1H), 7.60 (d, 1H), 7.13 (d, 1H), 6.98 (dd, 1H), 3.98 (s, 1H), 3.35 (t, 4H), 2.85-2.83 (m, 1H), 2.13 (s, 1H), 2.09-2.05 (m, 4H), 1.75-1.71 (m, 4H), 1.56-1.54 (m, 3H), 1.52-1.43 (m, 3H), 1.32-1.26 (m, 2H), 1.25-1.23 (m, 8H); MS (ESI) m/z=644.3 (M+H)⁺

Example 83. (1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)-1-methylcyclohexan-1-ol Step 1. 6'-Chloro-4'-fluoro-5-(4-methylpiperazin-1-yl)-2,3'-bipyridine The title compound as a solid (392 mg) was prepared in the same fashion as Step 1 in Example 1 except that 1-(6-bromopyridin-3-yl)-4-methylpiperazine (500 mg, 1.952 mmol) was used instead of 1-((6-bromopyridin-3-yl)methyl)-4-methylpiperazine. ¹H-NMR (CDCl₃, 400 MHz) δ 9.00 (d, 1H), 8.43 (s, 1H), 7.63 (d, 1H), 7.24 (d, 1H), 7.16 (d, 1H), 3.34 (t, 4H), 2.61 (t, 4H), 2.38 (s, 3H); MS (ESI) m/z=307.0 (M+H)⁺

Step 2. (1s,4s)-4-((6'-Chloro-5-(4-methylpiperazin-1-yl)-[2,3'-bipyridin]-4'-yl)amino)-1-methylcyclohexan-1-ol The title compound as a pale brown solid (80 mg) was prepared in the same fashion as Step 2 in Example 1 except that 6'-chloro-4'-fluoro-5-(4-methylpiperazin-1-yl)-2,3'-bipyridine (80 mg, 0.261 mmol) prepared in Step 1 and cis-4-amino-1-methylcyclohexan-1-ol (51 mg, 0.391 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.23 (d, 1H), 8.30 (s, 1H), 8.23 (d, 1H), 7.59 (d, 1H), 7.31 (dd, 1H), 6.53 (s, 1H), 3.35-3.33 (m, 1H), 3.30 (t, 4H), 2.61 (t, 4H), 2.38 (s, 3H), 1.95-1.92 (m, 2H), 1.77-1.72 (m, 4H), 1.69-1.57 (m, 2H), 1.40 (s, 3H); MS (ESI) m/z=416.1 (M+H)⁺

Step 3. (1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)-1-methylcyclohexan-1-ol The title compound (14 mg) as a pale yellow solid was prepared in the same fashion as Step 3 in Example 1, except that (1s,4s)-4-((6'-chloro-5-(4-methylpiperazin-1-yl)-[2,3'-bipyridin]-4'-yl)amino)-1-methylcyclohexan-1-ol (64 mg, 0.153 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.28 (d, 1H), 8.66 (s, 1H), 8.48 (s, 1H), 8.41 (d, 1H), 8.33 (s, 1H), 8.25 (d, 1H), 7.61 (d, 1H), 7.47 (s, 1H), 7.35-7.30 (m, 2H), 6.93 (s, 1H), 3.50-3.48 (m, 1H), 3.30 (t, 4H), 2.85-2.81 (m, 1H), 2.62 (t, 4H), 2.39 (s, 3H), 2.02-1.98 (m, 2H), 1.81-1.74 (m, 4H), 1.54-1.51 (m, 3H), 1.32 (s, 3H), 1.28-1.24 (m, 4H); MS (ESI) m/z=645.3 (M+H)⁺

Example 84. 2-((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)propan-2-ol Step 1. 2-((1s,4s)-4-((6'-Chloro-5-(4-methylpiperazin-1-yl)-[2,3'-bipyridin]-4'-yl)amino)cyclohexyl)propan-2-ol The title compound as a pale brown solid (80 mg) was prepared in the same fashion as Step 2 in Example 1 except that 6'-chloro-4'-fluoro-5-(4-methylpiperazin-1-yl)-2,3'-bipyridine (80 mg, 0.261 mmol) prepared in Step 1 of Example 83 and 2-((1s,4s)-4-aminocyclohexyl)propan-2-ol (62 mg. 0.391 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.80 (d, 1H), 8.34 (s, 1H), 8.21 (d, 1H), 7.64 (d, 1H), 7.32 (dd, 1H), 6.55 (s, 1H), 3.83-3.81 (m, 1H), 3.28 (t, 4H), 2.61 (t, 4H), 2.05 (s, 3H), 2.05-1.99 (m, 2H), 1.77-1.74 (m, 2H), 1.64-1.58 (m, 3H), 1.40-1.32 (m, 3H), 1.21 (s, 6H); MS (ESI) m/z=444.1 (M+H)⁺

Step 2. 2-((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)propan-2-ol The title compound (21 mg) as a pale yellow solid was prepared in the same fashion as Step 3 in Example 1, except that 2-((1s,4s)-4-((6'-chloro-5-(4-methylpiperazin-1-yl)-[2,3'-bipyridin]-4'-yl)amino)cyclohexyl)propan-2-ol (68 mg, 0.153 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.90 (d, 1H), 8.66 (s, 1H), 8.46 (s, 1H), 8.39 (d, 1H), 8.35 (s, 1H), 8.22 (d, 1H), 7.81 (s, 1H), 7.65 (d, 1H), 7.33 (dd, 1H), 7.12 (d, 1H), 3.99 (s, 1H), 3.28 (t, 4H), 2.85-2.82 (m, 1H), 2.61 (t, 4H), 2.38 (s, 3H), 2.14-2.09 (m, 2H), 1.79-1.75 (m, 6H), 1.55 (d, 1H), 1.54-1.52 (m, 3H), 1.29-1.22 (m, 2H), 1.21 (s, 7H); MS (ESI) m/z=673.3 (M+H)⁺

Example 85. ((1s,4s)-4-((6'-((2-(1-(cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)methanol Step 1. ((1s,4s)-4-((6'-Chloro-5-(4-methylpiperazin-1-yl)-[2,3'-bipyridin]-4'-yl)amino)cyclohexyl)methanol The title compound as a pale brown solid (64 mg) was prepared in the same fashion as Step 2 in Example 1 except that 6'-chloro-4'-fluoro-5-(4-methylpiperazin-1-yl)-2,3'-bipyridine (80 mg, 0.261 mmol) prepared in Step 1 of Example 83 and cis-(4-aminocyclohexyl)methanol hydrochloride (62 mg, 0.391 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.74 (d, 1H), 8.33 (s, 1H), 8.22 (d, 1H), 7.63 (d, 1H), 7.31 (dd, 1H), 6.54 (s, 1H), 3.80-3.76 (m, 1H), 3.54 (d, 2H), 3.31 (t, 4H), 2.62 (t, 4H), 2.38 (s, 3H), 1.94-1.90 (m, 2H), 1.73-1.61 (m, 4H), 1.41-1.32 (m, 2H); MS (ESI) m/z=416.1 (M+H)$^+$ Step 2. ((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)methanol The title compound (10 mg) as a white solid was prepared in the same fashion as Step 3 in Example 1, except that ((1s,4s)-4-((6'-chloro-5-(4-methylpiperazin-1-yl)-[2,3'-bipyridin]-4'-yl)amino)cyclohexyl)methanol (55 mg. 0.132 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.81 (d, 1H), 8.66 (S, 1H), 8.47 (s, 1H), 8.39 (d, 1H), 8.36 (s, 1H), 8.23 (d, 1H), 7.66 (d, 1H), 7.35 (s, 1H), 7.32 (d, 1H), 7.19 (s, 1H), 7.16 (d, 1H), 3.97 (s, 1H), 3.55 (d, 2H), 3.30 (t, 4H), 2.85-2.82 (m, 1H), 2.62 (t, 4H), 2.39 (s, 3H), 2.06-2.03 (m, 2H), 1.82-1.53 (m, 4H), 1.44-1.38 (m, 3H), 1.26-1.21 (m, 5H); MS (ESI) m/z=645.1 (M+H)$^+$ Example 86. (1s,4s)-4-((2-((2-(1-(Cyclopropylsulfonyl)-1H-pyrazol-4-yl)pyrimidin-4-yl)amino)-5-(6-(2-hydroxypropan-2-yl)pyridazin-3-yl)pyridin-4-yl)amino)-1-methylcyclohexan-1-ol Step 1. 2-(6-(6-Chloro-4-fluoropyridin-3-yl)pyridazin-3-yl)propan-2-ol The title compound as a white solid (450 mg) was prepared in the same fashion as Step 1 in Example 1 except that 2-(6-bromopyridazin-3-yl)propan-2-ol (500 mg. 2.304 mmol) was used instead of 1-((6-bromopyridin-3-yl)methyl)-4-methylpiperazine. $^1$H-NMR (CDCl$_3$, 400 MHz) δ 9.21 (d, 1H), 7.92 (d, 1H), 7.82 (d, 1H), 7.29 (s, 1H), 1.72 (s, 6H); MS (ESI) m/z=267.9 (M+H)$^+$ Step 2. (1s,4s)-4-((2-Chloro-5-(6-(2-hydroxypropan-2-yl)pyridazin-3-yl)pyridin-4-yl)amino)-1-methylcyclohexan-1-ol The title compound as a white solid (65 mg) was prepared in the same fashion as Step 2 in Example 1 except that 2-(6-(6-chloro-4-fluoropyridin-3-yl)pyridazin-3-yl)propan-2-ol (100 mg. 0.374 mmol) prepared in Step 1 and cis-4-amino-1-methylcyclohexan-1-ol (72 mg, 0.56 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.40 (d, 1H), 8.39 (s, 1H), 7.92 (d, 1H), 7.77 (d, 1H), 6.65 (s, 1H), 4.07 (s, 1H), 3.42-3.38 (m, 1H), 2.08-1.94 (m, 2H), 1.84-1.71 (m, 5H), 1.62 (s, 6H), 1.62-1.55 (m, 2H), 1.30 (s, 3H); MS (ESI) m/z=377.0 (M+H)$^+$ Step 3. (1s,4s)-4-((2-((2-(1-(Cyclopropylsulfonyl)-1H-pyrazol-4-yl)pyrimidin-4-yl)amino)-5-(6-(2-hydroxypropan-2-yl)pyridazin-3-yl)pyridin-4-yl)amino)-1-methylcyclohexan-1-ol The title compound (16 mg) as a solid was prepared in the same fashion as Step 3 in Example 1, except that (1s,4s)-4-((2-chloro-5-(6-(2-hydroxypropan-2-yl)pyridazin-3-yl)pyridin-4-yl)amino)-1-methylcyclohexan-1-ol (52 mg, 0.138 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.47 (d, 1H), 8.68 (s, 1H), 8.49 (s, 1H), 8.45 (d, 1H), 8.43 (s, 1H), 7.93 (d, 1H), 7.72 (d, 1H), 7.53 (s, 1H), 7.36 (d, 1H), 7.06 (s, 1H), 3.57-3.55 (m, 1H), 2.87-2.80 (m, 1H), 2.03-2.01 (m, 1H), 1.86-1.80 (m, 4H), 1.69 (s, 6H), 1.57-1.52 (m, 3H), 1.29 (s, 3H), 1.27-1.23 (m, 3H); MS (ESI) m/z=606.2 (M+H)$^+$ Example 87. 2-(6-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyridazin-3-yl)propan-2-ol Step 1. 2-(6-(6-Chloro-4-(((1s,4s)-4-(hydroxymethyl)cyclohexyl)amino)pyridin-3-yl)pyridazin-3-yl)propan-2-ol The title compound as a white solid (68 mg) was prepared in the same fashion as Step 2 in Example 1 except that 2-(6-(6-chloro-4-fluoropyridin-3-yl)pyridazin-3-yl)propan-2-ol (100 mg, 0.374 mmol) prepared in Step 1 of Example 86 and cis-(4-aminocyclohexyl)methanol hydrochloride (93 mg, 0.56 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.93 (d, 1H), 8.44 (s, 1H), 7.97 (d, 1H), 7.75 (d, 1H), 6.67 (s, 1H), 4.21 (s, 1H), 3.86-3.83 (m, 1H), 3.56 (d, 2H), 1.95-1.91 (m, 2H), 1.77-1.70 (m, 4H), 1.69 (s, 6H), 1.49-1.46 (m, 2H); MS (ESI) m/z=377.0 (M+H)$^+$ Step 2. 2-(6-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyridazin-3-yl)propan-2-ol The title compound (28.7 mg) as a solid was prepared in the same fashion as Step 3 in Example 1, except that 2-(6-(6-chloro-4-(((1s,4s)-4-(hydroxy methyl)cyclohexyl)amino)pyridin-3-yl)pyridazin-3-yl)propan-2-ol (52 mg, 0.138 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.05 (d, 1H), 8.67 (s, 1H), 8.46 (d, 2H), 8.44 (d, 1H), 7.98 (d, 1H), 7.71 (d, 1H), 7.64 (s, 1H), 7.36 (s, 1H), 7.15 (d, 1H), 4.04-4.03 (m, 1H), 3.57 (d, 1H), 2.87-2.83 (m, 1H), 2.07-2.04 (m, 2H), 1.87-1.81 (m, 2H), 1.76-1.73 (m, 2H), 1.70 (s, 6H), 1.61-1.41 (m, 6H), 1.26-1.22 (m, 3H); MS (ESI) m/z=606.2 (M+H)$^+$ Example 88. 2-(6-(6-((2-(1-(Cyclopropylsulfonyl)-1H-pyrazol-4-yl)pyrimidin-4-yl)amino)-4-(((1s,4s)-4-(2-hydroxy propan-2-yl)cyclohexyl)amino)pyridin-3-yl)pyridazin-3-yl)propan-2-ol Step 1. 2-(6-(6-Chloro-4-(((1s,4s)-4-(2-hydroxy propan-2-yl)cyclohexyl)amino)pyridin-3-yl)pyridazin-3-yl)propan-2-ol The title compound as a white solid (86 mg) was prepared in the same fashion as Step 2 in Example 1 except that 2-(6-(6-chloro-4-fluoropyridin-3-yl)pyridazin-3-yl)propan-2-ol (100 mg. 0.374 mmol) prepared in Step 1 of Example 86 and 2-((1s,4s)-4-aminocyclohexyl)propan-2-ol (88 mg, 0.56 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 10.19 (d, 1H), 8.47 (s, 1H), 7.98 (d, 1H), 7.75 (d, 1H), 6.69 (s, 1H), 3.95-3.91 (m, 1H), 2.04-2.01 (m, 2H), 1.79-1.76 (m, 2H), 1.66 (s, 7H), 1.62 (s, 3H), 1.45-1.43 (m, 2H), 1.37-1.25 (m, 2H), 1.21 (s, 6H); MS (ESI) m/z=405.0 (M+H)$^+$ Step 2. 2-(6-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyridazin-3-yl)propan-2-ol The title compound (35 mg) as a white solid was prepared in the same fashion as Step 3 in Example 1, except that 2-(6-(6-chloro-4-(((1s,4s)-4-(2-hydroxypropan-2-yl)cyclohexyl)amino)pyridin-3-yl)pyridazin-3-yl)propan-2-ol (76 mg. 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.23 (d, 1H), 8.67 (s, 1H), 8.47 (s, 1H), 8.43 (d, 1H), 8.00 (d, 1H), 7.71 (d, 1H), 7.60 (s, 1H), 7.42 (s, 1H), 7.10 (d, 1H), 4.25 (br, 1H), 4.12-4.08 (m, 1H), 2.88-2.82 (br, 1H), 2.14-2.11 (m, 2H), 1.78 (s, 4H), 1.62 (s, 6H), 1.57-1.48 (m, 5H), 1.26-1.24 (m, 2H), 1.22 (s, 6H); MS (ESI) m/z=634.3 (M+H)$^+$ Example 89. 2-(6-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)pyridazin-3-yl)propan-2-ol Step 1. 2-(6-(6-Chloro-4-(((1s,4s)-4-((dimethylamino)methyl)cyclohexyl)amino)pyridin-3-yl)pyridazin-3-yl)propan-2-ol The title compound as a white solid (55 mg) was prepared in the same fashion as Step 2 in Example 1 except that 2-(6-(6-chloro-4-fluoropyridin-3-yl)pyridazin-3-yl)propan-2-ol (100 mg, 0.374 mmol) prepared in Step 1 of Example 86 and (1s,4s)-4-((dimethylamino)methyl)cyclohexan-1-amine dihydrochloride (128 mg, 0.56 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.84 (d, 1H), 8.43 (s, 1H), 7.96 (d, 1H), 7.74 (d, 1H), 6.66 (s, 1H), 3.78 (s, 1H), 2.24 (s, 6H), 2.21-2.20 (m, 2H), 1.88-1.85 (m, 2H), 1.75-1.70 (m, 4H), 1.68 (s, 6H), 1.42-1.37 (m, 2H); MS (ESI) m/z=404.0 (M+H)$^+$ Step 2. 2-(6-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)pyridazin-3-yl)propan-2-ol The title compound (15.5 mg) as a pale yellow solid was prepared in the same fashion as Step 3 in Example 1, except that 2-(6-(6-chloro-4-(((1s,4s)-4-((dimethylamino)methyl)cyclohexyl)amino)pyridin-3-yl)pyridazin-3-yl)propan-2-ol (41 mg, 0.101 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.94 (d, 1H), 8.67 (s, 1H), 8.46 (d, 2H), 8.41 (d, 1H), 7.96 (d, 1H), 7.90 (s, 1H), 7.69 (d, 1H), 7.31 (s, 1H), 7.16 (d, 1H), 3.97 (s, 1H), 2.86-2.82 (m, 1H), 2.21 (s, 6H), 2.17-2.15 (m, 2H), 2.05-1.97 (m, 2H), 1.84-1.56 (m, 5H), 1.54 (s, 6H), 1.53-1.52 (m, 2H), 1.40-1.28 (m, 2H), 1.26-1.21 (m, 3H), 1.13 (d, 1H); MS (ESI) m/z=633.3 (M+H)$^+$ Example 90. (1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)-1-methylcyclohexan-1-ol Step 1. 6'-Chloro-4'-fluoro-5-(3-methoxyazetidin-1-yl)-2,3'-bipyridine The title compound as a solid (455 mg) was prepared in the same fashion as Step 1 in Example 1 except that 2-bromo-5-(3-methoxyazetidin-1-yl)pyridine (550 mg, 2.626 mmol) was used instead of 1-((6-bromopyridin-3-yl)methyl)-4-methylpiperazine. $^1$H-NMR (CDCl$_3$, 400 MHz) δ 8.97 (d, 1H), 7.98 (d, 1H), 7.59 (dd, 1H), 7.15 (d, 1H), 6.80 (dd, 1H), 4.43-4.39 (m, 1H), 4.23 (t, 2H), 3.86 (t, 2H), 3.37 (s, 3H); MS (ESI) m/z=294.1 (M+H)$^+$ Step 2. (1s,4s)-4-((6'-Chloro-5-(3-methoxyazetidin-1-yl)-[2,3'-bipyridin]-4'-yl)amino)-1-methylcyclohexan-1-ol The title compound as a white solid (90 mg) was prepared in the same fashion as Step 2 in Example 1 except that 6'-chloro-4'-fluoro-5-(3-methoxyazetidin-1-yl)-2,3'-bipyridine (109 mg. 0.371 mmol) prepared in Step 1 and cis-4-amino-1-methylcyclohexan-1-ol (72 mg, 0.557 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.12 (d, 1H), 8.26 (s, 1H), 7.82 (d, 2H), 7.53 (d, 1H), 6.87 (dd, 1H), 6.52 (s, 1H), 4.42-4.39 (m, 1H), 4.20 (t, 2H), 3.83 (t, 4H), 3.37 (s, 3H), 3.35-3.31 (m, 1H), 1.95-1.92 (m, 2H), 1.77-1.66 (m, 4H), 1.61-1.57 (m, 2H), 1.30 (s, 3H); MS (ESI) m/z=403.1 (M+H)$^+$ Step 3. (1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)-1-methylcyclohexan-1-ol The title compound (19.3 mg) as a solid was prepared in the same fashion as Step 3 in Example 1, except that (1s,4s)-4-((6'-chloro-5-(3-methoxyazetidin-1-yl)-[2,3'-bipyridin]-4'-yl)amino)-1-methylcyclohexan-1-ol (115 mg, 0.285 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.23 (d, 1H), 8.66 (s, 1H), 8.48 (s, 1H), 8.40 (d, 1H), 8.27 (s, 1H), 7.85 (s, 1H), 7.55 (d, 1H), 7.34 (d, 1H), 6.90 (s, 1H), 6.88 (d, 1H), 4.41-4.40 (m, 1H), 4.21 (t, 2H), 3.83 (t, 2H), 3.48 (s, 1H), 3.37 (s, 3H), 2.84-2.82 (m, 1H), 2.05-1.98 (m, 2H), 1.77-1.61 (m, 5H), 1.54-1.51 (m, 3H), 1.31 (s, 3H), 1.29-1.20 (m, 4H); MS (ESI) m/z=632.3 (M+H)$^+$ Example 91. ((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)methanol Step 1. ((1s,4s)-4-((6'-Chloro-5-(3-methoxyazetidin-1-yl)-[2,3'-bipyridin]-4'-yl)amino)cyclohexyl)methanol The title compound as a white solid (82 mg) was prepared in the same fashion as Step 2 in Example 1 except that 6'-chloro-4'-fluoro-5-(3-methoxyazetidin-1-yl)-2,3'-bipyridine (109 mg, 0.371 mmol) prepared in Step 1 of Example 90 and cis-(4-aminocyclohexyl)methanol hydrochloride (92 mg, 0.557 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.61 (d, 1H), 8.29 (s, 1H), 7.80 (d, 1H), 7.58 (d, 1H), 6.87 (dd, 1H), 6.53 (s, 1H), 4.43-4.38 (m, 1H), 4.21 (t, 2H), 3.83 (t, 2H), 3.81-3.76 (m, 1H), 3.54 (d, 2H), 3.37 (s, 3H), 1.94-1.90 (m, 2H), 1.72-1.64 (m, 3H), 1.43-1.30 (m, 2H); MS (ESI) m/z=403.0 (M+H)$^+$

Step 2. ((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)methanol The title compound (15 mg) as a solid was prepared in the same fashion as Step 3 in Example 1, except that ((1s,4s)-4-((6'-chloro-5-(3-methoxyazetidin-1-yl)-[2,3'-bipyridin]-4'-yl)amino)cyclohexyl)methanol (70 mg. 0.174 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.72 (d, 1H), 8.66 (s, 1H), 8.46 (s, 1H), 8.39 (d, 1H), 8.30 (s, 1H), 7.82 (d, 1H), 7.60 (d, 1H), 7.20 (s, 1H), 7.15 (d, 1H), 6.89 (d, 1H), 4.42-4.40 (m, 1H), 4.22 (t, 2H), 3.96 (s, 1H), 3.84 (t, 2H), 3.54 (d, 2H), 3.37 (s, 3H), 2.84-2.82 (m, 1H), 2.05-2.03 (m, 1H), 1.82-1.71 (m, 4H), 1.54-1.51 (m, 3H), 1.41-1.32 (m, 3H), 1.29-1.21 (m, 4H); MS (ESI) m/z=632.3 (M+H)$^+$

Example 92. 2-((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)propan-2-ol

Step 1. 2-((1s,4s)-4-((6'-Chloro-5-(3-methoxyazetidin-1-yl)-[2,3'-bipyridin]-4'-yl)amino)cyclohexyl)propan-2-ol The title compound as a white solid (126 mg) was prepared in the same fashion as Step 2 in Example 1 except that 6'-chloro-4'-fluoro-5-(3-methoxyazetidin-1-yl)-2,3'-bipyridine (109 mg. 0.371 mmol) prepared in Step 1 of Example 90 and 2-((1s,4s)-4-aminocyclohexyl)propan-2-ol (88 mg, 0.557 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.69 (d, 1H), 8.30 (s, 1H), 7.78 (d, 1H), 7.59 (d, 1H), 6.88 (dd, 1H), 6.54 (s, 1H), 4.43-4.38 (m, 1H), 4.19 (t, 2H), 3.82-3.79 (m, 3H), 3.37 (s, 3H), 2.02-1.99 (m, 2H), 1.76-1.73 (m, 2H), 1.60-1.57 (m, 2H), 1.42-1.30 (m, 4H), 1.21 (s, 6H); MS (ESI) m/z=431.0 (M+H)$^+$

Step 2. 2-((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)propan-2-ol The title compound (20 mg) as a solid was prepared in the same fashion as Step 3 in Example 1, except that 2-((1s,4s)-4-((6'-chloro-5-(3-methoxyazetidin-1-yl)-[2,3'-bipyridin]-4'-yl)amino)cyclohexyl)propan-2-ol (75 mg. 0.174 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.75 (d, 1H), 8.66 (s, 1H), 8.46 (s, 1H), 8.38 (d, 1H), 8.31 (s, 1H), 7.81 (s, 1H), 7.60 (d, 1H), 7.24 (s, 1H), 7.12 (d, 1H), 6.90 (dd, 1H), 4.41-4.40 (m, 1H), 4.20 (t, 2H), 3.96 (s, 1H), 3.82 (t, 2H), 3.37 (s, 3H), 2.85-2.83 (m, 1H), 2.12-2.05 (m, 2H), 1.78-1.63 (m, 4H), 1.55-1.52 (m, 3H), 1.44-1.40 (m, 3H), 1.28-1.23 (m, 2H), 1.20 (s, 6H); MS (ESI) m/z=660.3 (M+H)$^+$

Example 93. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(3-methoxyazetidin-1-yl)-[2,3'-bipyridine]-4',6'-diamine

Step 1. 6'-Chloro-N-((1s,4s)-4-((dimethylamino)methyl)cyclohexyl)-5-(3-methoxyazetidin-1-yl)-[2,3'-bipyridin]-4'-amine The title compound as a white solid (88 mg) was prepared in the same fashion as Step 2 in Example 1 except that 6'-chloro-4'-fluoro-5-(3-methoxyazetidin-1-yl)-2,3'-bipyridine (109 mg, 0.371 mmol) prepared in Step 1 of Example 90 and (1s,4s)-4-((dimethylamino)methyl)cyclohexan-1-amine dihydrochloride (128 mg, 0.557 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.60 (d, 1H), 8.30 (s, 1H), 7.82 (d, 1H), 7.58 (d, 1H), 6.88 (dd, 1H), 6.52 (s, 1H), 4.43-4.39 (m, 1H), 4.21 (t, 2H), 3.82 (t, 2H), 3.74-3.72 (m, 1H), 3.37 (s, 3H), 2.24 (s, 6H), 2.17-2.05 (m, 2H), 1.90-1.86 (m, 2H), 1.75-1.62 (m, 4H), 1.29-1.24 (m, 2H); MS (ESI) m/z=430.1 (M+H)$^+$

Step 2. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(3-methoxyazetidin-1-yl)-[2,3'-bipyridine]-4',6'-diamine The title compound (7 mg) as a solid was prepared in the same fashion as Step 3 in Example 1, except that 6'-chloro-N-((1s,4s)-4-((dimethylamino)methyl)cyclohexyl)-5-(3-methoxyazetidin-1-yl)-[2,3'-bipyridin]-4'-amine (75 mg. 0.174 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.73 (d, 1H), 8.66 (s, 1H), 8.46 (s 1H), 8.38 (d, 1H), 8.31 (s, 1H), 7.83 (d, 1H), 7.59 (d, 1H), 7.17-7.15 (m, 2H), 6.90 (d, 1H), 4.43-4.40 (m, 1H), 4.21 (t, 2H), 3.92 (s, 1H), 3.83 (t, 2H), 3.37 (s, 3H), 2.85-2.81 (m, 1H), 2.24 (s, 6H), 2.15 (d, 1H), 2.02-1.99 (m, 2H), 1.66-1.64 (m, 2H), 1.55-1.51 (m, 2H), 1.34-1.19 (m, 6H); MS (ESI) m/z=659.3 (M+H)$^+$

Example 94. 2-((1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol

Step 1. 2-((1s,4s)-4-((6'-Chloro-5-(difluoromethyl)-[2,3'-bipyridin]-4'-yl)amino)cyclohexyl)ethan-1-ol The title compound as a white solid (128 mg) was prepared in the same fashion as Step 2 in Example 1 except that 6'-chloro-5-(difluoromethyl)-4'-fluoro-2,3'-bipyridine (100 mg, 0.387 mmol) prepared in Step 1 of Example 63 and 2-((1s,4s)-4-aminocyclohexyl)ethan-1-ol (72 mg. 0.503 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.77 (d, 1H), 8.71 (s, 1H), 8.48 (s, 1H), 7.95 (d, 1H), 7.88 (d, 1H), 6.77 (t, 1H), 6.61 (s, 1H), 3.79-3.72 (m, 3H), 1.90-1.86 (m, 2H), 1.72-1.65 (m, 3H), 1.61-1.55 (m, 3H), 1.35-1.31 (m, 3H); MS (ESI) m/z=382.0 (M+H)⁺

Step 2. 2-((1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol The title compound (47.9 mg) as a white solid was prepared in the same fashion as Step 3 in Example 1, except that 2-((1s,4s)-4-((6'-chloro-5-(difluoromethyl)-[2,3'-bipyridin]-4'-yl)amino)cyclohexyl)ethan-1-ol (111 mg, 0.291 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.91 (d, 1H), 8.70 (s, 1H), 8.66 (s, 1H), 8.52 (s, 1H), 8.47 (s, 1H), 8.42 (d, 1H), 7.94-7.88 (m, 2H), 7.53 (s, 1H), 7.12 (d, 1H), 6.77 (t, 1H), 3.97-3.96 (m, 2H), 2.88-2.81 (m, 1H), 2.02-1.99 (m, 2H), 1.84-1.71 (m, 4H), 1.55-1.52 (m, 2H), 1.48-1.32 (m, 3H), 1.29-1.20 (m, 5H); MS (ESI) m/z=611.2 (M+H);

Example 95. 2-((1r,4r)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol Step 1. 2-((1r,4r)-4-((6'-Chloro-5-(difluoromethyl)-[2,3'-bipyridin]-4'-yl)amino)cyclohexyl)ethan-1-ol The title compound as a white solid (118 mg) was prepared in the same fashion as Step 2 in Example 1 except that 6'-chloro-5-(difluoromethyl)-4'-fluoro-2,3'-bipyridine (100 mg, 0.987 mmol) prepared in Step 1 of Example 63 and 2-((1r,4r)-4-aminocyclohexyl)ethan-1-ol hydrochloride (90 mg. 0.503 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl₃, 400 MHz) δ 9.21 (d, 1H), 8.71 (s, 1H), 8.43 (s, 1H), 7.93 (d, 1H), 7.83 (d, 1H), 6.76 (t, 1H), 6.60 (s, 1H), 3.73 (t, 2H), 3.36-3.28 (m, 1H), 2.17 (d, 2H), 1.90 (d, 2H), 1.56-1.51 (m, 3H), 1.36-1.26 (m, 3H), 1.25-1.11 (m, 2H); MS (ESI) m/z=382.0 (M+H)⁺

Step 2. 2-((1r,4r)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol The title compound (61.7 mg) as a white solid was prepared in the same fashion as Step 3 in Example 1, except that 2-((1r,4r)-4-((6'-chloro-5-(difluoromethyl)-[2,3'-bipyridin]-4'-yl)amino)cyclohexyl)ethan-1-ol (111 mg, 0.291 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.29 (d, 1H), 8.70 (s, 1H), 8.67 (s, 1H), 8.48 (d, 2H), 8.44 (d, 1H), 7.91 (d, 1H), 7.83 (d, 1H), 7.49 (s, 1H), 7.37 (d, 1H), 6.96 (s, 1H), 6.76 (t, 1H), 3.73 (t, 1H), 3.46-3.42 (m, 1H), 2.87-2.83 (m, 1H), 2.23 (d, 2H), 1.88 (d, 2H), 1.56-1.52 (m, 3H), 1.37-1.29 (m, 3H), 1.26 (s, 3H), 1.24-1.18 (m, 3H); MS (ESI) m/z=611.2 (M+H)⁺

Example 96. 2-((1r,4r)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol Step 1. 2-((1r,4r)-4-((6'-Chloro-4-(difluoromethyl)-[2,3'-bipyridin]-4'-yl)amino)cyclohexyl)ethan-1-ol The title compound as a white solid (121 mg) was prepared in the same fashion as Step 2 in Example 1 except that 6'-chloro-4-(difluoromethyl)-4'-fluoro-2,3'-bipyridine (100 mg, 0.387 mmol) prepared in Step 1 of Example 76 and 2-((1r,4r)-4-aminocyclohexyl)ethan-1-ol hydrochloride (90 mg, 0.503 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl₃, 400 MHz) δ 9.14 (d, 1H), 8.70 (d, 1H), 8.42 (d, 1H), 7.81 (s, 1H), 7.37 (d, 1H), 6.70 (t, 1H), 6.60 (s, 1H), 3.73 (t, 2H), 3.35-3.28 (m, 1H), 2.17 (d, 2H), 1.90 (d, 2H), 1.58-1.49 (m, 3H), 1.36-1.33 (m, 4H), 1.32-1.19 (m, 2H); MS (ESI) m/z=382.0 (M+H)⁺

Step 2. 2-((1r,4r)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol The title compound (19 mg) as a solid was prepared in the same fashion as Step 3 in Example 1, except that 2-((1r,4r)-4-((6'-chloro-4-(difluoromethyl)-[2,3'-bipyridin]-4'-yl)amino)cyclohexyl)ethan-1-ol (110 mg, 0.288 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.23 (d, 1H), 8.69 (d, 1H), 8.67 (s, 1H), 8.49 (s, 1H), 8.45 (d, 1H), 8.43 (s, 1H), 7.83 (s, 1H), 7.53 (s, 1H), 7.37 (d, 1H), 7.31 (d, 1H), 7.01 (s, 1H), 6.70 (t, 1H), 3.72 (t, 2H), 3.45-3.42 (m, 1H), 2.87-2.83 (m, 1H), 2.23 (d, 2H), 1.88 (d, 2H), 1.56-1.42 (m, 3H), 1.39-1.26 (m, 3H), 1.24-1.13 (m, 4H); MS (ESI) m/z=611.2 (M+H)⁺

Example 97. 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol Step 1. 2-((1s,4s)-4-((6'-Chloro-4-(difluoromethyl)-[2,3'-bipyridin]-4'-yl)amino)cyclohexyl)ethan-1-ol The title compound as a white solid (125 mg) was prepared in the same fashion as Step 2 in Example 1 except that 6'-chloro-4-(difluoromethyl)-4'-fluoro-2,3'-bipyridine (100 mg, 0.387 mmol) prepared in Step 1 of Example 76 and 2-((1s,4s)-4-aminocyclohexyl)ethan-1-ol (72 mg, 0.503 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.70 (d, 1H), 8.71 (d, 1H), 8.46 (s, 1H), 7.86 (d, 1H), 7.38 (d, 1H), 6.71 (t, 1H), 6.60 (s, 1H), 3.78-3.77 (m, 1H), 3.73 (t, 1H), 1.89-1.86 (m, 2H), 1.72-1.65 (m, 4H), 1.57-1.54 (m, 2H), 1.34-1.25 (m, 4H); MS (ESI) m/z=381.9 (M+H)⁺

Step 2. 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol The title compound (5.5 mg) as a solid was prepared in the same fashion as Step 3 in Example 1, except that 2-((1s, 4s)-4-((6'-chloro-4-(difluoromethyl)-[2,3'-bipyridin]-4'-yl) amino)cyclohexyl)ethan-1-ol (110 mg, 0.288 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.86 (d, 1H), 8.70 (d, 1H), 8.66 (s, 1H), 8.49 (s, 1H), 8.47 (s, 1H), 8.42 (d, 1H), 7.88 (s, 1H), 7.53 (s, 1H), 7.34-7.31 (m, 2H), 7.13 (d, 1H), 6.71 (t, 1H), 4.16-4.14 (m, 1H), 4.12-3.98 (m, 1H), 3.74 (t, 2H), 2.87-2.83 (m, 1H), 2.02-1.98 (m, 2H), 1.84-1.69 (m, 4H), 1.45-1.29 (m, 4H), 1.28-1.22 (m, 6H); MS (ESI) m/z=611.3 (M+H)$^+$

Example 98. 1-((6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)methyl) piperidin-4-ol

Step 1. 1-((6'-Chloro-4'-fluoro-[2,3'-bipyridin]-5-yl)methyl) piperidin-4-ol The title compound as a solid (506 mg) was prepared in the same fashion as Step 1 in Example 1 except that 1-[(6-bromo-3-pyridyl)methyl]piperidin-4-ol (580 mg, 2.139 mmol) was used instead of 1-((6-bromopyridin-3-yl)methyl)-4-methylpiperazine. $^1$H-NMR (CDCl$_3$, 400 MHz) δ 9.03 (d, 1H), 8.67 (s, 1H), 7.79 (dd, 1H), 7.71 (d, 1H), 7.20 (d, 1H), 3.77-3.73 (m, 1H), 3.57 (s, 2H), 2.79-2.76 (m, 2H), 2.23 (t, 2H), 1.93-1.89 (m, 2H), 1.66-1.62 (m, 1H), 1.27 (br, 1H); MS (ESI) m/z=322.0 (M+H)$^+$

Step 2. 1-((6'-Chloro-4'-(((1s,4s)-4-(2-hydroxypropan-2-yl)cyclohexyl)amino)-[2,3'-bipyridin]-5-yl) methyl) piperidin-4-ol The title compound as a beige solid (78 mg) was prepared in the same fashion as Step 2 in Example 1 except that 1-((6'-chloro-4'-fluoro-[2,3'-bipyridin]-5-yl)methyl) piperidin-4-ol (120 mg, 0.373 mmol) prepared in Step 1 and 2-((1s,4s)-4-aminocyclohexyl)propan-2-ol (88 mg, 0.559 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 10.00 (d, 1H), 8.48 (s, 1H), 8.44 (s, 1H), 7.80-7.73 (m, 2H), 6.58 (s, 1H), 3.85 (s, 1H), 3.81 (s, 1H), 3.54 (s, 2H), 2.77-2.74 (m, 2H), 2.19 (t, 2H), 2.02 (d, 2H), 1.92-1.89 (m, 2H), 1.78-1.75 (m, 2H), 1.65-1.62 (m, 4H), 1.40-1.33 (m, 3H), 1.21 (s, 6H); MS (ESI) m/z=459.1 (M+H)$^+$

Step 3. 1-((6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)methyl) piperidin-4-ol The title compound (27.1 mg) as a pale yellow solid was prepared in the same fashion as Step 3 in Example 1, except that 1-((6'-chloro-4'-(((1s,4s)-4-(2-hydroxypropan-2-yl)cyclohexyl)amino)-[2,3'-bipyridin]-5-yl)methyl) piperidin-4-ol (72 mg, 0.157 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.09 (d, 1H), 8.66 (s, 1H), 8.47-8.46 (m, 3H), 8.41 (d, 1H), 7.76 (s, 2H), 7.61 (s, 1H), 7.31 (s, 1H), 7.11 (d, 1H), 4.14-4.12 (m, 1H), 4.01 (s, 1H), 3.75-3.74 (m, 1H), 3.54 (s, 2H), 2.85-2.83 (m, 1H), 2.78-2.75 (m, 2H), 2.21 (t, 2H), 2.12 (d, 2H), 1.92-1.90 (m, 2H), 1.80-1.74 (m, 4H), 1.61-1.52 (m, 4H), 1.25 (s, 3H), 1.32 (s, 6H); MS (ESI) m/z=688.3 (M+H)$^+$

Example 99. 1-((6'-((2-(1-(Cyclopropylsulfonyl)-1H-pyrazol-4-yl)pyrimidin-4-yl)amino)-4'-(((1s,4s)-4-(hydroxy methyl)cyclohexyl)amino)-[2,3'-bipyridin]-5-yl)methyl) piperidin-4-ol

Step 1. 1-((6'-Chloro-4'-(((1s,4s)-4-(hydroxymethyl) cyclohexyl)amino)-[2,3'-bipyridin]-5-yl)methyl) piperidin-4-ol The title compound as a beige solid (55 mg) was prepared in the same fashion as Step 2 in Example 1 except that 1-((6'-chloro-4'-fluoro-[2,3'-bipyridin]-5-yl)methyl) piperidin-4-ol (120 mg. 0.373 mmol) prepared in Step 1 of Example 98 and cis-(4-aminocyclohexyl)methanol hydrochloride (93 mg, 0.559 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.95 (d, 1H), 8.50 (s, 1H), 8.44 (s, 1H), 7.80-7.73 (m, 2H), 6.58 (s, 1H), 3.82-3.76 (m, 2H), 3.55-3.54 (m, 4H), 2.79-2.76 (m, 2H), 2.23-2.21 (m, 2H), 1.94-1.91 (m, 4H), 1.74-1.61 (m, 4H), 1.38-1.35 (m, 3H), 1.26 (s, 1H); MS (ESI) m/z=431.0 (M+H)$^+$

Step 2. 1-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methyl) piperidin-4-ol The title compound (3 mg) as a pale yellow solid was prepared in the same fashion as Step 3 in Example 1, except that 1-((6'-chloro-4'-(((1s,4s)-4-(hydroxy methyl)cyclohexyl)amino)-[2,3'-bipyridin]-5-yl)methyl) piperidin-4-ol (50 mg, 0.116 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.08 (d, 1H), 8.66 (s, 1H), 8.49-8.46 (m, 3H), 8.41 (d, 1H), 7.75-7.73 (m, 3H), 7.13 (d, 1H), 4.14-4.12 (m, 1H), 3.99 (s, 1H), 3.76 (s, 1H), 3.55 (s, 4H), 2.86-2.82 (m, 1H), 2.81-2.77 (m, 2H), 2.23-2.20 (m, 2H), 2.05-1.93 (m, 2H), 1.93-1.91 (m, 2H), 1.83-1.62 (m, 5H), 1.53-1.41 (m, 3H), 1.38-1.32 (m, 3H), 1.29-1.20 (m, 5H); MS (ESI) m/z=660.3 (M+H)$^+$

Example 100. ((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl) amino)cyclohexyl)methanol

Step 1. 6'-Chloro-4-(4,4-difluoropiperidin-1-yl)-4'-fluoro-2,3'-bipyridine

The title compound as a pale yellow solid (396 mg) was prepared in the same fashion as Step 1 in Example 1 except that 2-bromo-4-(4,4-difluoropiperidin-1-yl)pyridine (592 mg, 2.136 mmol) was used instead of 1-((6-bromopyridin-3-yl)methyl)-4-methylpiperazine. 1H-NMR (CDCl$_3$, 400 MHz) δ 8.96 (d, 1H), 8.43 (d, 1H), 7.19 (d, 1H), 7.11 (s, 1H), 6.74 (dd, 1H), 3.59 (t, 4H), 2.14-2.06 (m, 4H); MS (ESI) m/z=328.0 (M+H)$^+$

Step 2. ((1s,4s)-4-((6'-Chloro-4-(4,4-difluoropiperidin-1-yl)-[2,3'-bipyridin]-4'-yl)amino)cyclohexyl) methanol The title compound as a solid (85 mg) was prepared in the same fashion as Step 2 in Example 1 except that 6'-chloro- 4-(4,4-difluoropiperidin-1-yl)-4'-fluoro-2,3'-bipyridine (90 mg. 0.275 mmol) prepared in Step 1 and cis-(4-aminocyclohexyl)methanol hydrochloride (68 mg, 0.412 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.00 (d, 1H), 8.27 (d, 1H), 8.25 (s, 1H), 6.98 (s, 1H), 6.68 (d, 1H), 6.54 (s, 1H), 3.59 (t, 4H), 3.33-3.31 (m, 1H), 2.14-2.04 (m, 4H), 1.92 (d, 1H), 1.77-1.65 (m, 4H), 1.60 (s, 1H), 1.54 (s, 1H), 1.30 (s, 3H); MS (ESI) m/z=437.0 (M+H)⁺

Step 3. ((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)methanol The title compound (16.5 mg) as a solid was prepared in the same fashion as Step 3 in Example 1, except that ((1s,4s)-4-((6'-chloro-4-(4,4-difluoropiperidin-1-yl)-[2,3'-bipyridin]-4'-yl)amino)cyclohexyl)methanol (77 mg, 0.176 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.69 (d, 1H), 8.65 (s, 1H), 8.46 (s, 1H), 8.39 (d, 1H), 8.34 (s, 1H), 8.29 (d, 1H), 7.60 (br, 1H), 7.21 (s, 1H), 7.15 (d, 1H), 7.06 (s, 1H), 6.66 (d 1H), 4.14-4.10 (m, 1H), 3.94 (s, 1H), 3.60 (t, 4H), 3.53 (d, 2H), 2.85-2.82 (m, 1H), 2.14-2.08 (m, 3H), 2.05-2.00 (m, 2H), 1.80-1.69 (m, 5H), 1.55-1.51 (m, 2H), 1.41-1.32 (m, 2H), 1.28-1.19 (m, 4H); MS (ESI) m/z=666.2 (M+H)⁺

Example 101. $N^{6'}$-(2-(1-(Cyclopropylsulfonyl)-1H-pyrazol-4-yl)pyrimidin-4-yl)-4-(4,4-difluoropiperidin-1-yl)-$N^{4'}$-((1s,4s)-4-((dimethylamino)methyl)cyclohexyl)-[2,3'-bipyridine]-4',6'-diamine Step 1. 6'-Chloro-4-(4,4-difluoropiperidin-1-yl)-N-((1s,4s)-4-((dimethylamino)methyl)cyclohexyl)-[2,3'-bipyridin]-4'-amine The title compound as a solid (89 mg) was prepared in the same fashion as Step 2 in Example 1 except that 6'-chloro-4-(4,4-difluoropiperidin-1-yl)-4'-fluoro-2,3'-bipyridine (90 mg, 0.275 mmol) prepared in Step 1 of Example 100 and (1s,4s)-4-((dimethylamino)methyl)cyclohexan-1-amine dihydrochloride (94 mg, 0.412 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.55 (d, 1H), 8.29-8.28 (m, 2H), 7.03 (s, 1H), 6.68 (d, 1H), 6.54 (s, 1H), 3.72 (s, 1H), 3.60 (t, 4H), 2.24 (s, 6H), 2.17-2.05 (m, 6H), 1.87-1.84 (m, 2H), 1.71-1.68 (m, 2H), 1.65-1.62 (m, 2H), 1.32-1.27 (m, 3H); MS (ESI) m/z=464.1 (M+H)⁺

Step 2. $N^{6'}$-(2-(1-(Cyclopropylsulfonyl)-1H-pyrazol-4-yl)pyrimidin-4-yl)-4-(4,4-difluoropiperidin-1-yl)-$N^{4'}$-((1s,4s)-4-((dimethylamino)methyl)cyclohexyl)-[2,3'-bipyridine]-4',6'-diamine The title compound (26.5 mg) as a solid was prepared in the same fashion as Step 3 in Example 1, except that 6'-chloro-4-(4,4-difluoropiperidin-1-yl)-N-((1s,4s)-4-((dimethylamino)methyl)cyclohexyl)-[2,3'-bipyridin]-4'-amine (82 mg, 0.176 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 9.97 (s, 1H), 9.88 (d, 1H), 8.62 (d, 1H), 8.53 (s, 1H), 8.44 (s, 1H), 8.41 (d, 1H), 8.20 (d, 1H), 7.48 (s, 1H), 7.34 (s, 2H), 6.88 (d, 1H), 4.05-4.00 (m, 1H), 3.84 (s, 1H), 3.64 (s, 3H), 3.31 (s, 1H), 2.07 (s, 6H), 2.05-1.98 (m, 4H), 1.89 (s, 2H), 1.84-1.81 (m, 2H), 1.71-1.62 (m, 3H), 1.46-1.45 (m, 2H), 1.34-1.23 (m, 4H), 1.18-1.15 (m, 3H); MS (ESI) m/z=693.3 (M+H)⁺

Example 102. (1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)-1-methylcyclohexan-1-ol Step 1. (1s,4s)-4-((6'-Chloro-4-(4,4-difluoropiperidin-1-yl)-[2,3'-bipyridin]-4'-yl)amino)-1-methylcyclohexan-1-ol The title compound as a solid (95 mg) was prepared in the same fashion as Step 2 in Example 1 except that 6'-chloro-4-(4,4-difluoropiperidin-1-yl)-4'-fluoro-2,3'-bipyridine (90 mg. 0.275 mmol) prepared in Step 1 of Example 100 and cis-4-amino-1-methylcyclohexan-1-ol (53 mg, 0.412 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.00 (d, 1H), 8.28 (d, 1H), 8.25 (s, 1H), 6.99 (s, 1H), 6.67 (d, 1H), 6.54 (s, 1H), 3.59 (t, 4H), 3.33-3.31 (d, 1H), 2.14-2.04 (m, 4H), 1.94-1.91 (m, 1H), 1.77-1.65 (m, 4H), 1.60-1.57 (m, 1H), 1.54 (s, 1H), 1.27 (s, 3H); MS (ESI) m/z=437.1 (M+H)⁺

Step 2. (1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)-1-methylcyclohexan-1-ol The title compound (21.3 mg) as a solid was prepared in the same fashion as Step 3 in Example 1, except that (1s,4s)-4-((6'-chloro-4-(4,4-difluoropiperidin-1-yl)-[2,3'-bipyridin]-4'-yl)amino)-1-methylcyclohexan-1-ol (90 mg, 0.206 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 9.94 (s, 1H), 9.38 (d, 1H), 8.64 (s, 1H), 8.47 (d, 2H), 8.43 (d, 1H), 8.22 (d, 1H), 7.60 (s, 1H), 7.30 (s, 1H), 7.20 (s, 1H), 6.87 (d, 1H), 4.14 (s, 1H), 4.05-4.00 (m, 1H), 3.63 (s, 4H), 3.37 (s, 1H), 3.24-3.23 (m, 1H), 2.05-2.01 (m, 3H), 1.82-2.80 (m, 2H), 1.64-1.55 (m, 4H), 1.47-1.44 (m, 2H), 1.41 (s, 2H), 1.38-1.34 (m, 3H), 1.13 (s, 3H); MS (ESI) m/z=666.3 (M+H)⁺

Example 103. 2-((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)propan-2-ol Step 1. 2-((1s,4s)-4-((6'-Chloro-4-(4,4-difluoropiperidin-1-yl)-[2,3'-bipyridin]-4'-yl)amino)cyclohexyl)propan-2-ol The title compound as a solid (111 mg) was prepared in the same fashion as Step 2 in Example 1 except that 6'-chloro-4-(4,4-difluoropiperidin-1-yl)-4'-fluoro-2,3'-bipyridine (90 mg. 0.275 mmol) prepared in Step 1 of Example 100 and 2-((1s,4s)-4-aminocyclohexyl)propan-2-ol (65 mg, 0.412 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.65 (d, 1H), 8.30 (s, 1H), 8.27 (d, 1H), 7.04 (s, 1H), 6.67 (d, 1H), 6.56 (s, 1H), 3.81 (s, 1H), 3.60 (t, 4H), 2.14-2.06 (m, 4H), 2.01-1.98 (m, 2H), 1.76-1.73 (m, 2H), 1.63-1.60 (m, 2H), 1.41-1.34 (m, 3H), 1.22 (s, 6H); MS (ESI) m/z=465.1 (M+H)$^+$ Step 2. 2-((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)propan-2-ol The title compound (37.9 mg) as a solid was prepared in the same fashion as Step 3 in Example 1, except that 2-((1s,4s)-4-((6'-chloro-4-(4,4-difluoropiperidin-1-yl)-[2,3'-bipyridin]-4'-yl)amino)cyclohexyl)propan-2-ol (96 mg. 0.206 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.72 (d, 1H), 8.66 (s, 1H), 8.46 (s, 1H), 8.40 (d, 1H), 8.33 (s, 1H), 8.28 (d, 1H), 7.53 (s, 1H), 7.21 (s, 1H), 7.16 (d, 1H), 7.07 (s, 1H), 6.65 (d, 1H), 3.96 (s, 1H), 3.61 (t, 4H), 2.85-2.83 (m, 1H), 2.13-2.07 (m, 6H), 1.76-1.71 (m, 4H), 1.62 (s, 3H), 1.56-1.54 (m, 3H), 1.43-1.41 (m, 3H), 1.20 (s, 6H); MS (ESI) m/z=694.3 (M+H)$^+$ Example 104. (1s,4s)-4-((6'-((2-(1-(Cyclopropylsulfonyl)-1H-pyrazol-4-yl)pyrimidin-4-yl)amino)-5-fluoro-4-(2-hydroxypropan-2-yl)-[2,3'-bipyridin]-4'-yl)amino)-1-methylcyclohexan-1-ol Step 1. 2-(6'-Chloro-4',5-difluoro-[2,3'-bipyridin]-4-yl)propan-2-ol The title compound as a solid (365 mg) was prepared in the same fashion as Step 1 in Example 1 except that 2-(2-bromo-5-fluoropyridin-4-yl)propan-2-ol (500 mg, 2.136 mmol) was used instead of 1-((6-bromopyridin-3-yl)methyl)-4-methylpiperazine. $^1$H-NMR (CDCl$_3$, 400 MHz) δ 8.97 (d, 1H), 8.50 (d, 1H), 8.03 (d, 1H), 7.21 (d, 1H), 1.99 (s, 1H), 1.70 (s, 6H); MS (ESI) m/z=294.9 (M+H)$^+$ Step 2. (1s,4s)-4-((6'-Chloro-5-fluoro-4-(2-hydroxypropan-2-yl)-[2,3'-bipyridin]-4'-yl)amino)-1-methylcyclohexan-1-ol The title compound as a white solid (99 mg) was prepared in the same fashion as Step 2 in Example 1 except that 2-(6'-chloro-4',5-difluoro-[2,3'-bipyridin]-4-yl)propan-2-ol (89 mg, 0.313 mmol) prepared in Step 1 and cis-4-amino-1-methylcyclohexan-1-ol (61 mg, 0.469 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.87 (d, 1H), 8.39 (s, 1H), 8.34 (d, 1H), 8.01 (d, 1H), 6.57 (s, 1H), 3.35-3.33 (m, 1H), 2.35 (s, 1H), 1.95-1.92 (m, 2H), 1.77-1.72 (m, 3H), 1.70 (s, 6H), 1.58 (s, 1H), 1.54 (s, 1H), 1.26 (s, 3H); MS (ESI) m/z=394.1 (M+H)$^+$ Step 3. (1s,4s)-4-((6'-((2-(1-(Cyclopropylsulfonyl)-1H-pyrazol-4-yl)pyrimidin-4-yl)amino)-5-fluoro-4-(2-hydroxypropan-2-yl)-[2,3'-bipyridin]-4'-yl)amino)-1-methylcyclohexan-1-ol The title compound (50.5 mg) as a solid was prepared in the same fashion as Step 3 in Example 1, except that (1s,4s)-4-((6'-chloro-5-fluoro-4-(2-hydroxypropan-2-yl)-[2,3'-bipyridin]-4'-yl)amino)-1-methylcyclohexan-1-ol (89 mg. 0.225 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.05 (s, 1H), 8.87 (s, 1H), 8.65 (s, 1H), 8.51 (s, 1H), 8.47 (s, 1H), 8.42 (d, 1H), 8.40 (s, 1H), 8.01 (d, 1H), 7.50 (s, 1H), 7.35 (s, 1H) 5.61 (s, 1H), 4.14 (s, 1H), 3.44 (s, 1H), 3.24 (t, 1H), 1.84-1.81 (m, 2H), 1.64-1.58 (m, 3H), 1.53 (s, 6H), 1.44-1.39 (m, 2H), 1.34 (s, 2H), 1.25-1.23 (d, 2H), 1.13 (s, 3H); MS (ESI) m/z=623.3 (M+H)$^+$ Example 105. 2-(6'-((2-(1-(Cyclopropylsulfonyl)-1H-pyrazol-4-yl)pyrimidin-4-yl)amino)-5-fluoro-4'-(((1s,4s)-4-(hydroxymethyl)cyclohexyl)amino)-[2,3'-bipyridin]-4-yl)propan-2-ol Step 1. 2-(6'-Chloro-5-fluoro-4'-(((1s,4s)-4-(hydroxymethyl)cyclohexyl)amino)-[2,3'-bipyridin]-4-yl)propan-2-ol The title compound as a white solid (106 mg) was prepared in the same fashion as Step 2 in Example 1 except that 2-(6'-chloro-4',5-difluoro-[2,3'-bipyridin]-4-yl)propan-2-ol (89 mg, 0.313 mmol) prepared in Step 1 of Example 104 and cis-(4-aminocyclohexyl)methanol hydrochloride (78 mg, 0.469 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.35 (d, 1H), 8.43 (s, 1H), 8.35 (s, 1H), 8.06 (d, 1H), 6.58 (s, 1H), 3.80-3.78 (m, 1H), 3.55 (d, 1H), 3.50 (s, 1H), 2.28 (s, 1H), 1.92-1.89 (m, 1H), 1.70-1.65 (m, 10H), 1.39-1.26 (m, 3H); MS (ESI) m/z=394.1 (M+H)$^+$ Step 2. 2-(6'-((2-(1-(Cyclopropylsulfonyl)-1H-pyrazol-4-yl)pyrimidin-4-yl)amino)-5-fluoro-4'-(((1s,4s)-4-(hydroxymethyl)cyclohexyl)amino)-[2,3'-bipyridin]-4-yl)propan-2-ol The title compound (20 mg) as a solid was prepared in the same fashion as Step 3 in Example 1, except that 2-(6'-chloro-5-fluoro-4'-(((1s,4s)-4-(hydroxymethyl)cyclohexyl)amino)-[2,3'-bipyridin]-4-yl)propan-2-ol (89 mg, 0.225 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.10 (s, 1H), 9.41 (d, 1H), 8.63 (s, 1H), 8.48 (s, 1H), 8.45 (s, 2H), 8.41 (d, 1H), 8.07 (d, 1H), 7.54 (s, 1H), 7.36 (s, 1H), 5.63 (s, 1H), 4.41 (t, 1H), 4.04-3.99 (m, 1H), 3.91 (s, 1H), 3.27-3.26 (m, 3H), 1.98 (s, 2H), 1.87-1.85 (m, 2H), 1.73-7.67 (m, 2H), 1.62-1.59 (m, 6H), 1.54 (s, 6H), 1.48 (s, 1H), 1.34 (s, 2H), 1.33-1.19 (m, 5H); MS (ESI) m/z=623.3 (M+H)$^+$ Example 106. 2-(6'-((2-(1-(Cyclopropylsulfonyl)-1H-pyrazol-4-yl)pyrimidin-4-yl)amino)-5-fluoro-4'-(((1s,4s)-4-(2-hydroxypropan-2-yl)cyclohexyl)amino)-[2,3'-bipyridin]-4-yl)propan-2-ol Step 1. 2-(6'-Chloro-5-fluoro-4'-(((1s,4s)-4-(2-hydroxypropan-2-yl)cyclohexyl)amino)-[2,3'-bipyridin]-4-yl)propan-2-ol The title compound as a white solid (115 mg) was prepared in the same fashion as Step 2 in Example 1 except that 2-(6'-chloro-4',5-difluoro-[2,3'-bipyridin]-4-yl)propan-2-ol (89 mg, 0.313 mmol) prepared in Step 1 of Example 104 and 2-((1s,4s)-4-aminocyclohexyl)propan-2-ol (74 mg, 0.469 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.40 (d, 1H), 8.43 (s, 1H), 8.32 (s, 1H), 8.08 (d, 1H), 6.58 (s, 1H), 3.83-3.82 (m, 1H), 3.50 (s, 1H), 2.51 (s, 1H), 2.01-1.98 (m, 2H), 1.78-1.76 (m, 2H), 1.71 (s, 6H), 1.64-1.58 (m, 1H), 1.42-1.33 (m, 3H), 1.23 (s, 6H); MS (ESI) m/z=422.1 (M+H)$^+$ Step 2. 2-(6'-((2-(1-(Cyclopropylsulfonyl)-1H-pyrazol-4-yl)pyrimidin-4-yl)amino)-5-fluoro-4'-(((1s,4s)-4-(2-hydroxypropan-2-yl)cyclohexyl)amino)-[2,3'-bipyridin]-4-yl)propan-2-ol The title compound (51.6 mg) as a solid was prepared in the same fashion as Step 3 in Example 1, except that 2-(6'-chloro-5-fluoro-4'-(((1s,4s)-4-(2-hydroxypropan-2-yl)cyclohexyl)amino)-[2,3'-bipyridin]-4-yl)propan-2-ol (95 mg. 0.225 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.11 (s, 1H), 9.49 (d, 1H), 8.62 (s, 1H), 8.46-8.40 (d, 4H) 8.08 (d, 1H), 7.60 (s, 1H), 7.31 (s, 1H), 5.63 (s, 1H), 4.06 (s, 1H), 4.05-4.01 (m, 1H), 3.96 (s, 1H), 3.28-3.27 (m, 1H), 1.98-1.94 (m, 3H), 1.69-1.63 (m, 4H), 1.54 (s, 6H), 1.34-1.33 (m, 2H), 1.30-1.22 (m, 6H), 1.18-1.15 (m, 1H), 1.04 (s, 6H); MS (ESI) m/z=651.3 (M+H)$^+$ Example 107. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-5-fluoro-[2,3'-bipyridin]-4-yl)propan-2-ol Step 1. 2-(6'-Chloro-4'-(((1s,4s)-4-((dimethylamino)methyl)cyclohexyl)amino)-5-fluoro-[2,3'-bipyridin]-4-yl)propan-2-ol The title compound as a white solid (66 mg) was prepared in the same fashion as Step 2 in Example 1 except that 2-(6'-chloro-4',5-difluoro-[2,3'-bipyridin]-4-yl)propan-2-ol (89 mg, 0.313 mmol) prepared in Step 1 of Example 104 and (1s,4s)-4-((dimethylamino)methyl)cyclohexan-1-amine dihydrochloride (107 mg, 0.469 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.35 (d, 1H), 8.43 (s, 1H), 8.34 (d, 1H), 8.06 (d, 1H), 6.57 (s, 1H), 3.75-3.74 (m, 1H), 2.23 (s, 6H), 2.16-2.15 (m, 2H), 1.87-1.84 (m, 3H), 1.74-1.64 (m, 10H), 1.30-1.24 (m, 2H); MS (ESI) m/z=421.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-5-fluoro-[2,3'-bipyridin]-4-yl)propan-2-ol The title compound (28 mg) as a solid was prepared in the same fashion as Step 3 in Example 1, except that 2-(6'-chloro-4'-(((1s,4s)-4-((dimethylamino)methyl)cyclohexyl)amino)-5-fluoro-[2,3'-bipyridin]-4-yl)propan-2-ol (77 mg, 0.183 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d6, 400 MHz) δ 10.09 (s, 1H), 9.29 (d, 1H), 8.63 (s, 1H), 8.49 (s, 2H), 8.44 (s, 1H), 8.41 (d, 1H), 8.06 (d, 1H), 7.49 (s, 1H), 7.40 (s, 1H), 3.88 (s, 1H), 3.27-3.26 (m, 1H), 2.07 (s, 6H), 2.07-2.05 (m, 2H), 1.85-1.82 (m, 2H), 1.73-1.63 (m, 4H), 1.54 (s, 6H), 1.34-1.33 (m, 2H), 1.26-1.17 (m, 5H); MS (ESI) m/z=650.2 (M+H)$^+$ Example 108. (1s,4s)-4-((6'-((2-(1-(Cyclopropylsulfonyl)-1H-pyrazol-4-yl)pyrimidin-4-yl)amino)-4-(2-hydroxypropan-2-yl)-[2,3'-bipyridin]-4'-yl)amino)-1-methylcyclohexan-1-ol Step 1. 2-(6'-Chloro-4'-fluoro-[2,3'-bipyridin]-4-yl)propan-2-ol The title compound as a solid (471 mg) was prepared in the same fashion as Step 1 in Example 1 except that 2-(2-bromopyridin-4-yl)propan-2-ol (462 mg. 2.136 mmol) was used instead of 1-((6-bromopyridin-3-yl)methyl)-4-methylpiperazine. $^1$H-NMR (CDCl$_3$, 400 MHz) δ 8.97 (d, 1H), 8.69 (d, 1H), 7.84 (s, 1H), 7.42 (d, 1H), 7.20 (d, 1H), 1.24 (s, 6H); MS (ESI) m/z=266.9 (M+H)$^+$ Step 2. (1s,4s)-4-((6'-Chloro-4-(2-hydroxypropan-2-yl)-[2,3'-bipyridin]-4'-yl)amino)-1-methylcyclohexan-1-ol The title compound as a solid (113 mg) was prepared in the same fashion as Step 2 in Example 1 except that 2-(6'-chloro-4'-fluoro-[2,3'-bipyridin]-4-yl)propan-2-ol (100 mg. 0.375 mmol) prepared in Step 1 and cis-4-amino-1-methylcyclohexan-1-ol (73 mg, 0.562 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.26 (d, 1H), 8.53 (d, 1H), 8.41 (s, 1H), 7.33 (d, 1H), 6.57 (s, 1H), 3.36-3.34 (m, 1H), 1.96-1.90 (m, 3H), 1.78-1.67 (m, 4H), 1.62 (s, 6H), 1.31 (s, 3H), 1.29-1.25 (m, 2H); MS (ESI) m/z=375.1 (M+H)$^+$ Step 3. (1s,4s)-4-((6'-((2-(1-(Cyclopropylsulfonyl)-1H-pyrazol-4-yl)pyrimidin-4-yl)amino)-4-(2-hydroxy propan-2-yl)-[2,3'-bipyridin]-4'-yl)amino)-1-methylcyclohexan-1-ol The title compound (72 mg) as a solid was prepared in the same fashion as Step 3 in Example 1, except that (1s,4s)-4-((6'-chloro-4-(2-hydroxypropan-2-yl)-[2,3'-bipyridin]-4'-yl)amino)-1-methylcyclohexan-1-ol (99 mg, 0.262 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.02 (s, 1H), 9.39 (d, 1H), 8.65 (s, 1H), 8.53-8.51 (m, 2H), 8.47 (s, 1H), 8.62 (d, 1H), 7.94 (s, 1H), 7.54 (s, 1H), 7.38 (d, 1H), 7.32 (s, 1H), 5.30 (s, 1H), 4.16 (s, 1H), 3.43 (s, 1H), 3.25-3.23 (m, 1H), 1.85-1.82 (m, 2H), 1.65-1.56 (m, 4H), 1.47 (s, 6H), 1.42 (s, 2H), 1.34-1.33 (m, 2H), 1.25-1.24 (m, 2H), 1.13 (s, 3H); MS (ESI) m/z=605.2 (M+H)$^+$ Example 109. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-4-yl)propan-2-ol Step 1. 2-(6'-Chloro-4'-(((1s,4s)-4-(2-hydroxypropan-2-yl)cyclohexyl)amino)-[2,3'-bipyridin]-4-yl)propan-2-ol The title compound as a white solid (106 mg) was prepared in the same fashion as Step 2 in Example 1 except that 2-(6'-chloro-4'-fluoro-[2,3'-bipyridin]-4-yl)propan-2-ol (100 mg, 0.375 mmol) prepared in Step 1 of Example 108 and 2-((1s,4s)-4-aminocyclohexyl)propan-2-ol (88 mg, 0.562 mmol) were used instead of 6'-chloro-4'-fluoro-5-((4- methylpiperazin-1-yl)methyl)-2,3'-bipyridine and (4-methylpiperidin-4-yl)methanol. $^1$H-NMR (CDCl$_3$, 400 MHz) δ 9.85 (d, 1H), 8.52 (d, 1H), 8.46 (s, 1H), 7.89 (s, 1H), 7.32 (d, 1H), 6.59 (s, 1H), 3.83 (d, 1H), 2.05-1.99 (m, 3H), 1.78-1.75 (m, 2H), 1.65 (s, 6H), 1.41-1.36 (m, 3H), 1.26-1.25 (m, 1H), 1.22 (s, 6H); MS (ESI) m/z=404.2 (M+H)$^+$ Step 2. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-4-yl)propan-2-ol The title compound (37.1 mg) as a solid was prepared in the same fashion as Step 3 in Example 1, except that 2-(6'-chloro-4'-(((1s,4s)-4-(2-hydroxypropan-2-yl)cyclohexyl)amino)-[2,3'-bipyridin]-4-yl)propan-2-ol (106 mg, 0.262 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.07 (s, 1H), 10.02 (d, 1H), 8.62 (s, 1H), 8.57 (s, 1H), 8.48 (d, 1H), 8.45 (s, 1H), 8.41 (d, 1H), 8.00 (s, 1H), 7.56 (s, 1H), 7.39 (d, 1H), 7. 35 (s, 1H), 5.31 (s, 1H), 4.07 (s, 1H), 3.95 (d, 1H), 3.31-3.28 (m, 2H), 1.97-1.94 (m, 2H), 1.70-1.66 (m, 4H), 1.48 (s, 5H), 1.34-1.26 (m, 7H), 1.05 (s, 6H); MS (ESI) m/z=633.3 (M+H)$^+$ Example 110. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-4-yl)propan-2-ol Step 1. 2-(6'-Chloro-4'-(((1s,4s)-4-((dimethylamino)methyl)cyclohexyl)amino)-[2,3'-bipyridin]-4-yl)propan-2-ol The title compound as a white solid (101 mg) was prepared in the same fashion as Step 2 in Example 1 except that 2-(6'-chloro-4'-fluoro-[2,3'-bipyridin]-4-yl)propan-2-ol (100 mg, 0.375 mmol) prepared in Step 1 of Example 108 and (1s,4s)-4-((dimethylamino)methyl)cyclohexan-1-amine dihydrochloride (129 mg, 0.562 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.77 (d, 1H), 8.53 (d, 1H), 8.45 (s, 1H), 7.87 (s, 1H), 7.33 (d, 1H), 6.57 (s, 1H), 3.76 (s, 1H), 2.24 (s, 6H), 2.16 (d, 2H), 1.89-1.86 (m, 2H), 1.73-1.67 (m, 3H), 1.63 (s, 7H), 1.33-1.24 (m, 3H); MS (ESI) m/z=403.2 (M+H)$^+$ Step 2. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-4-yl)propan-2-ol The title compound (22.7 mg) as a solid was prepared in the same fashion as Step 3 in Example 1, except that 2-(6'-chloro-4'-(((1s,4s)-4-((dimethylamino)methyl)cyclohexyl)amino)-[2,3'-bipyridin]-4-yl)propan-2-ol (106 mg, 0.262 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.06 (s, 1H), 9.87 (d, 1H), 8.63 (s, 1H), 8.56 (s, 1H), 8.50 (d, 1H), 8.47 (s, 1H), 8.41 (d, 1H), 7.99 (s, 1H), 7.45-7.44 (m, 1H), 7.41-7.39 (m, 1H), 5.32 (s, 1H), 3.89 (s, 1H), 3.27-3.24 (m, 1H), 2.11 (s, 6H), 2.05 (d, 2H), 1.87-1.84 (m, 2H), 1.74-1.64 (m, 4H), 1.56 (m, 1H), 1.48 (s, 6H), 1.34-1.33 (m, 2H), 1.26-1.23 (m, 5H); MS (ESI) m/z=632.3 (M+H)

Example 111. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-4-yl)propan-2-ol Step 1. 2-(6'-Chloro-4'-(((1s,4s)-4-(hydroxymethyl)cyclohexyl)amino)-[2,3'-bipyridin]-4-yl)propan-2-ol The title compound as a white solid (61 mg) was prepared in the same fashion as Step 2 in Example 1 except that 2-(6'-chloro-4'-fluoro-[2,3'-bipyridin]-4-yl)propan-2-ol (100 mg, 0.375 mmol) prepared in Step 1 of Example 108 and cis-(4-aminocyclohexyl)methanol hydrochloride (93 mg, 0.562 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.26 (d, 1H), 8.53 (d, 1H) 8.41 (s, 1H), 7.82 (s, 1H), 7.33 (d, 1H), 6.57 (s, 1H), 3.36-3.34 (m, 1H), 1.96-1.90 (m, 3H), 1.78-1.67 (m, 4H), 1.62 (s, 6H), 1.31 (s, 3H), 1.29-1.25 (m, 2H); MS (ESI) m/z=375.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-4-yl)propan-2-ol The title compound (36. 1 mg) as a solid was prepared in the same fashion as Step 3 in Example 1, except that 2-(6'-chloro-4'-(((1s,4s)-4-(hydroxymethyl)cyclohexyl)amino)-[2,3'-bipyridin]-4-yl)propan-2-ol (61 mg, 0.162 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.06 (s, 1H), 9.95 (d, 1H), 8.62 (s, 1H), 8.56 (s, 1H), 8.50 (d, 1H), 8.45 (s, 1H), 8.41 (d, 1H), 7.99 (s, 1H), 7.50 (s, 1H), 7.39 (d, 2H), 5.31 (s, 1H), 4.42 (t, 1H), 3.91 (s, 1H), 3.27-3.24 (m, 2H), 1.89-1.83 (m, 2H), 1.73-1.61 (m, 4H), 1.48 (s, 7H), 1.34-1.33 (m, 2H), 1.27-1.21 (m, 4H); MS (ESI) m/z=605.3 (M+H)$^+$ Example 112. (1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)-1-methylcyclohexan-1-ol Step 1. 6'-Chloro-4-((4,4-difluoropiperidin-1-yl)methyl)-4'-fluoro-2,3'-bipyridine The title compound as a solid (498 mg) was prepared in the same fashion as Step 1 in Example 1 except that 2-bromo-4-[(4,4-difluoro-1-piperidyl)methyl]pyridine (622 mg, 2.136 mmol) was used instead of 1-((6-bromopyridin-3-yl)methyl)-4-methylpiperazine. $^1$H-NMR (CDCl$_3$, 400 MHz) δ 9.02 (d, 1H), 8.68 (d, 1H), 7.73 (s, 1H), 7.32 (d, 1H), 7.21 (d, 1H), 3.64 (s, 2H), 2.60 (t, 4H), 2.08-1.99 (m, 4H); MS (ESI) m/z=342.0 (M+H)$^+$ Step 2. (1s,4s)-4-((6'-Chloro-4-((4,4-difluoropiperidin-1-yl)methyl)-[2,3'-bipyridin]-4'-yl)amino)-1-methylcyclohexan-1-ol The title compound as a solid (150 mg) was prepared in the same fashion as Step 2 in Example 1 except that 6'-chloro-4-((4,4-difluoropiperidin-1-yl)methyl)-4'-fluoro-2,3'-bipyridine (120 mg. 0.351 mmol) prepared in Step 1 and cis-4-amino-1-methylcyclohexan-1-ol (68 mg, 0.527 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.36 (d, 1H), 8.51 (d, 1H), 8.39 (s, 1H), 7.69 (s, 1H), 7.23 (d, 1H), 6.57 (s, 1H), 3.62 (s, 2H), 3.34 (s, 1H), 2.60-2.59 (m, 4H), 2.08-1.93 (m, 8H), 1.78-1.61 (m, 4H), 1.31 (s, 3H); MS (ESI) m/z=451.1 (M+H)$^+$ Step 3. (1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)-1-methylcyclohexan-1-ol The title compound (39 mg) as a solid was prepared in the same fashion as Step 3 in Example 1, except that (1s,4s)-4-((6'-chloro-4-((4,4-difluoropiperidin-1-yl)methyl)-[2,3'-bipyridin]-4'-yl)amino)-1-methylcyclohexan-1-ol (12 mg. 0.284 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.46 (d, 1H), 8.67 (s, 1H), 8.51 (d, 1H), 8.48 (s, 1H), 8.44-8.42 (m, 2H), 7.72 (s, 1H), 7.45 (s, 1H), 7.36 (d, 1H), 7.19 (d, 1H), 6.96 (s, 1H), 3.62 (s, 2H), 3.51-3.50 (m, 1H), 2.86-2.80 (m, 1H), 2.61 (s, 4H), 2.09-2.00 (m, 6H), 1.82-1.74 (m, 4H), 1.64-1.63 (m, 1H), 1.54-1.53 (m, 2H), 1.32 (s, 3H), 1.26-1.19 (m, 2H); MS (ESI) m/z=680.3 (M+H)

Example 113. ((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)methanol Step 1. ((1s,4s)-4-((6'-Chloro-4-((4,4-difluoropiperidin-1-yl)methyl)-[2,3'-bipyridin]-4'-yl)amino)cyclohexyl)methanol The title compound as a solid (136 mg) was prepared in the same fashion as Step 2 in Example 1 except that 6'-chloro-4-((4,4-difluoropiperidin-1-yl)methyl)-4'-fluoro-2,3'-bipyridine (120 mg, 0.351 mmol) prepared in Step 1 of Example 112 and cis-(4-aminocyclohexyl)methanol hydrochloride (87 mg, 0.527 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.21 (d, 1H), 8.52 (d, 1H), 8.44 (s, 1H), 7.74 (s, 1H), 7.24 (d, 1H), 6.59 (s, 1H), 3.81 (s, 1H), 3.63 (s, 2H), 3.54 (d, 2H), 2.61 (s, 4H), 2.08-2.00 (m, 5H), 1.94-1.91 (m, 2H), 1.70-1.65 (m, 5H), 1.41-1.29 (m, 5H); MS (ESI) m/z=451.2 (M+H)$^+$ Step 2. ((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)methanol The title compound (59 mg) as a solid was prepared in the same fashion as Step 3 in Example 1, except that ((1s,4s)-4-((6'-chloro-4-((4,4-difluoropiperidin-1-yl)methyl)-[2,3'-bipyridin]-4'-yl)amino)cyclohexyl)methanol (128 mg, 0.284 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.02 (d, 1H), 8.66 (s, 1H), 8.51 (d, 1H), 8.47 (s, 1H), 8.41 (d, 1H), 7.76 (s, 1H), 7.70 (s, 1H), 7.19 (d, 1H), 7.15 (d, 1H), 3.99 (s, 1H), 3.63 (s, 2H), 3.54 (d, 2H), 2.85-2.83 (m, 2H), 2.61 (s, 4H), 2.09-2.03 (m, 4H), 2.01-1.99 (m, 2H), 1.83-1.76 (m, 4H), 1.65-1.53 (m, 2H), 1.43-1.41 (m, 2H), 1.37-1.27 (m, 2H); MS (ESI) m/z=680.3 (M+H)$^+$ Example 114. 2-((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)propan-2-ol Step 1. 2-((1s,4s)-4-((6'-Chloro-4-((4,4-difluoropiperidin-1-yl)methyl)-[2,3'-bipyridin]-4'-yl)amino)cyclohexyl)propan-2-ol The title compound as a solid (136 mg) was prepared in the same fashion as Step 2 in Example 1 except that 6'-chloro-4-((4,4-difluoropiperidin-1-yl)methyl)-4'-fluoro-2,3'-bipyridine (120 mg. 0.351 mmol) prepared in Step 1 of Example 112 and 2-((1s,4s)-4-aminocyclohexyl)propan-2-ol (83 mg, 0.527 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.95 (d, 1H), 8.51 (d, 1H), 8.44 (s, 1H), 7.74 (s, 1H), 7.23 (d, 2H), 6.59 (s, 1H), 3.85-3.84 (m, 1H), 3.63 (s, 2H), 2.60 (s, 4H), 2.07-2.00 (m, 4H), 1.78-1.76 (m, 2H), 1.66-1.63 (m, 2H), 1.41-1.33 (m, 5H), 1.29 (s, 6H); MS (ESI) m/z=479.2 (M+H)$^+$ Step 2. 2-((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)propan-2-ol The title compound (59 mg) as a solid was prepared in the same fashion as Step 3 in Example 1, except that 2-((1s,4s)-4-((6'-chloro-4-((4,4-difluoropiperidin-1-yl)methyl)-[2,3'-bipyridin]-4'-yl)amino)cyclohexyl)propan-2-ol (136 mg. 0.284 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.05 (d, 1H), 8.66 (s, 1H), 8.51 (d, 1H), 8.47 (s, 2H), 8.41 (d, 1H), 7.76 (s, 1H), 7.62 (s, 1H), 7.30 (s, 1H), 7.18 (d, 1H), 7.13 (d, 1H), 4.00 (s, 1H), 3.63 (s, 2H), 2.86-2.83 (m, 1H), 2.61 (s, 4H), 2.12-2.00 (m, 4H), 1.79-1.73 (m, 4H) 1.57-1.54 (m, 2H), 1.45 (s, 3H), 1.23 (s, 6H); MS (ESI) m/z=708.3 (M+H)$^+$ Example 115. (1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)-1-methylcyclohexan-1-ol Step 1. 2-((5-(6-Chloro-4-fluoropyridin-3-yl) pyrazin-2-yl)oxy)-N,N-dimethylethan-1-amine The title compound as a white solid (227 mg) was prepared in the same fashion as Step 1 in Example 1 except that 2-((5-bromopyrazin-2-yl)oxy)-N,N-dimethylethan-1-amine (478 mg, 1.942 mmol) was used instead of 1-((6-bromopyridin-3-yl)methyl)-4-methylpiperazine. $^1$H-NMR (CDCl$_3$, 400 MHz) δ 9.00 (d, 1H), 8.55 (s, 1H), 8.39 (s, 1H), 7.22 (d, 1H), 4.51 (t, 2H), 2.77 (t, 2H), 2.36 (s, 6H); MS (ESI) m/z=297.0 (M+H)$^+$ Step 2. (1s,4s)-4-((2-Chloro-5-(5-(2-(dimethylamino) ethoxy) pyrazin-2-yl)pyridin-4-yl)amino)-1-methylcyclohexan-1-ol The title compound as a solid (53 mg) was prepared in the same fashion as Step 2 in Example 1 except that 2-((5-(6-chloro-4-fluoropyridin-3-yl) pyrazin-2-yl)oxy)-N,N-dimethylethan-1-amine (55 mg. 0.185 mmol) prepared in Step 1 and cis-4-amino-1-methylcyclohexan-1-ol (36 mg, 0.278 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.47 (s, 1H), 8.30 (s, 1H), 8.23 (s, 1H), 8.13 (d, 1H), 6.57 (s, 1H), 4.49 (t, 2H), 3.32 (s, 1H), 2.77 (t, 2H), 2.36 (s, 6H), 1.94-1.91 (m, 2H), 1.77-1.70 (m, 4H), 1.64-1.57 (m, 3H), 1.30 (s, 3H); MS (ESI) m/z=406.1 (M+H)$^+$ Step 3. (1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)-1-methylcyclohexan-1-ol The title compound (15.7 mg) as a solid was prepared in the same fashion as Step 3 in Example 1, except that (1s,4s)-4-((2-chloro-5-(5-(2-(dimethylamino) ethoxy) pyrazin-2-yl)pyridin-4-yl)amino)-1-methylcyclohexan-1-ol (40 mg, 0.099 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.48 (s, 2H), 8.43 (d, 1H), 8.31 (s, 2H), 8.24 (s, 1H), 8.18 (d, 1H), 7.48 (s, 1H), 7.37 (d, 1H), 6.96 (s, 1H), 4.49 (t, 1H), 3.48 (s, 1H), 2.83 (s, 1H), 2.77 (t, 2H), 2.37 (s, 6H), 2.00-1.97 (m, 2H), 1.75-1.69 (m, 4H), 1.56-1.53 (m, 2H), 1.31 (s, 3H), 1.26-1.21 (m, 2H); MS (ESI) m/z=635.3 (M+H)$^+$ Example 116. ((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)methanol Step 1. ((1s,4s)-4-((2-Chloro-5-(5-(2-(dimethylamino) ethoxy) pyrazin-2-yl)pyridin-4-yl)amino) cyclohexyl)methanol The title compound as a solid (44 mg) was prepared in the same fashion as Step 2 in Example 1 except that 2-((5-(6-chloro-4-fluoropyridin-3-yl) pyrazin-2-yl)oxy)-N,N-dimethylethan-1-amine (55 mg. 0.185 mmol) prepared in Step 1 of Example 115 and cis-(4-aminocyclohexyl)methanol hydrochloride (46 mg, 0.278 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.70 (d, 1H), 8.53 (s, 1H), 8.34 (s, 1H), 8.22 (s, 1H), 6.59 (s, 1H), 4.50 (t, 2H), 3.82 (s, 1H), 2.77 (t, 2H), 2.37 (s, 6H), 2.01-2.00 (m, 2H), 1.78-1.74 (m, 3H), 1.69-1.65 (m, 2H), 1.41-1.29 (m, 4H), 1.26 (s, 6H); MS (ESI) m/z=406.1 (M+H)$^+$ Step 2. ((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)methanol The title compound (13.6 mg) as a solid was prepared in the same fashion as Step 3 in Example 1, except that ((1s,4s)-4-((2-chloro-5-(5-(2-(dimethylamino) ethoxy) pyrazin-2-yl)pyridin-4-yl)amino)cyclohexyl)methanol (40 mg, 0.099 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.68 (d, 1H), 8.65 (s, 1H), 8.52 (s, 1H), 8.46 (s, 1H), 8.40 (d, 1H), 8.35 (s, 1H), 8.24 (s, 1H), 7.68 (s, 1H), 7.23 (s, 1H), 7.16 (d, 1H), 4.49 (t, 2H), 3.95 (s, 1H), 3.52 (d, 2H), 2.85-2.82 (m, 1H), 2.77 (t, 2H), 2.36 (s, 6H), 2.02-1.99 (m, 6H), 1.81-1.69 (m, 5H), 1.54-1.53 (m, 2H), 1.34-1.25 (m, 5H); MS (ESI) m/z=635.3 (M+H)$^+$ Example 117. 2-((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)propan-2-ol Step 1. 2-((1s,4s)-4-((2-Chloro-5-(5-(2-(dimethylamino) ethoxy) pyrazin-2-yl)pyridin-4-yl)amino) cyclohexyl)propan-2-ol The title compound as a solid (40 mg) was prepared in the same fashion as Step 2 in Example 1 except that 2-((5-(6-chloro-4-fluoropyridin-3-yl) pyrazin-2-yl)oxy)-N,N-dimethylethan-1-amine (55 mg, 0.185 mmol) prepared in Step 1 of Example 115 and 2-((1s,4s)-4-aminocyclohexyl)propan-2-ol (44 mg. 0.278 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.62 (d, 1H), 8.52 (s, 1H), 8.34 (s, 1H), 8.24 (s, 1H), 6.58 (s, 1H), 4.50 (t, 2H), 3.78 (s, 1H), 3.52 (d, 2H), 2.77 (t, 2H), 2.32 (s, 6H), 1.90-1.87 (m, 2H), 1.68 (s, 3H), 1.33-1.26 (m, 3H); MS (ESI) m/z=434.1 (M+H)$^+$ Step 2. 2-((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)propan-2-ol The title compound (15 mg) as a solid was prepared in the same fashion as Step 3 in Example 1, except that 2-((1s,4s)-4-((2-chloro-5-(5-(2-(dimethylamino) ethoxy) pyrazin-2-yl)pyridin-4-yl)amino)cyclohexyl)propan-2-ol (43 mg, 0.099 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.72 (d, 1H), 8.67 (s, 1H), 8.54 (s, 1H), 8.46 (s, 1H), 8.41 (d, 1H), 8.35 (s, 1H), 8.23 (s, 1H), 7.49 (s, 1H), 7.14 (d, 1H), 4.48 (t, 2H), 3.96 (s, 1H), 2.85-2.83 (m, 1H), 2.76 (t, 2H), 2.36 (s, 6H), 2.09-2.06 (m, 2H), 1.79-1.65 (m, 4H), 1.54-1.53 (m, 2H), 1.46-1.35 (m, 3H), 1.22 (s, 7H); MS (ESI) m/z=663.3 (M+H)$^+$ Example 118. (1s,4s)-4-((2-((2-(1-(Cyclopropylsulfonyl)-1H-pyrazol-4-yl)pyrimidin-4-yl)amino)-5-(5-(2-hydroxypropan-2-yl) pyrazin-2-yl)pyridin-4-yl)amino)-1-methylcyclohexan-1-ol Step 1. 2-(5-(6-Chloro-4-fluoropyridin-3-yl) pyrazin-2-yl)propan-2-ol The title compound as a solid (348 mg) was prepared in the same fashion as Step 1 in Example 1 except that 2-(5-bromopyrazin-2-yl)propan-2-ol (422 mg, 1.942 mmol) was used instead of 1-((6-bromopyridin-3-yl)methyl)-4-methylpiperazine. $^1$H-NMR (CDCl$_3$, 400 MHz) δ 9.07 (d, 1H), 8.94 (d, 2H), 7.26 (d, 1H), 3.72 (d, 1H), 1.67 (s, 6H); MS (ESI) m/z=268.0 (M+H)$^+$ Step 2. (1s,4s)-4-((2-Chloro-5-(5-(2-hydroxypropan-2-yl) pyrazin-2-yl)pyridin-4-yl)amino)-1-methylcyclohexan-1-ol The title compound as a white solid (97 mg) was prepared in the same fashion as Step 2 in Example 1 except that 2-(5-(6-chloro-4-fluoropyridin-3-yl) pyrazin-2-yl)propan-2-ol (82 mg. 0.306 mmol) prepared in Step 1 and cis-4-amino-1-methylcyclohexan-1-ol (59 mg, 0.459 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.96 (s, 1H), 8.85 (d, 1H), 8.73 (s, 1H), 8.50 (s, 1H), 6.62 (s, 1H), 3.37 (s, 1H), 1.96-1.93 (m, 2H), 1.79-1.68 (m, 3H), 1.66 (s, 6H), 1.32 (s, 3H), 1.28-1.26 (m, 3H); MS (ESI) m/z=377.1 (M+H)$^+$ Step 3. (1s,4s)-4-((2-((2-(1-(Cyclopropylsulfonyl)-1H-pyrazol-4-yl)pyrimidin-4-yl)amino)-5-(5-(2-hydroxypropan-2-yl) pyrazin-2-yl)pyridin-4-yl) amino)-1-methylcyclohexan-1-ol The title compound (53.2 mg) as a white solid was prepared in the same fashion as Step 3 in Example 1, except that (1s,4s)-4-((2-chloro-5-(5-(2-hydroxypropan-2-yl) pyrazin-2-yl)pyridin-4-yl)amino)-1-methylcyclohexan-1-ol (93 mg, 0.247 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.98-8.96 (m, 2H), 8.70 (s, 1H), 8.67 (s, 1H), 8.54 (s, 1H), 8.49 (s, 1H), 8.45 (d, 1H), 7.45 (s, 1H), 7.34 (d, 1H), 7.05 (s, 1H), 3.73 (S, 1H), 3.68 (s, 1H), 2.83-2.82 (m, 1H), 2.02-2.00 (m, 2H), 1.82-1.74 (m, 4H), 1.66 (s, 6H), 1.58-1.55 (m, 2H), 1.33 (s, 3H), 1.25-1.23 (m, 2H); MS (ESI) m/z=606.2 (M+H)$^+$ Example 119. 2-(5-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl) pyrazin-2-yl)propan-2-ol Step 1. 2-(5-(6-Chloro-4-(((1s,4s)-4-(hydroxymethyl)cyclohexyl)amino)pyridin-3-yl) pyrazin-2-yl) propan-2-ol The title compound as a white solid (95 mg) was prepared in the same fashion as Step 2 in Example 1 except that 2-(5-(6-chloro-4-fluoropyridin-3-yl) pyrazin-2-yl)propan-2-ol (82 mg, 0.306 mmol) prepared in Step 1 of Example 118 and cis-(4-aminocyclohexyl)methanol hydrochloride (76 mg, 0.459 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 9.32 (d, 1H), 9.01 (s, 1H), 8.72 (s, 1H), 8.55 (s, 1H), 6.63 (s, 1H), 3.81 (s, 1H), 3.56 (s, 2H), 1.93-1.91 (m, 2H), 1.74-1.72 (m, 3H), 1.66 (s, 6H), 1.39-1.25 (m, 6H); MS (ESI) m/z=377.1 (M+H)$^+$ Step 2. 2-(5-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl) pyrazin-2-yl)propan-2-ol The title compound (41.3 mg) as a solid was prepared in the same fashion as Step 3 in Example 1, except that 2-(5-(6-chloro-4-(((1s,4s)-4-(hydroxy methyl)cyclohexyl) amino)pyridin-3-yl) pyrazin-2-yl)propan-2-ol (93 mg, 0.247 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.43 (d, 1H), 9.02 (s, 1H), 8.70 (s, 1H), 8.66 (s, 1H), 8.57 (s, 1H), 8.47 (s, 1H), 8.43 (d, 1H), 7.54 (s, 1H), 7.32 (s, 1H), 7.13 (d, 1H), 4.00 (s, 1H), 3.63 (s, 1H), 3.56 (d, 1H), 2.86-2.84 (m, 1H), 2.06-2.03 (m, 2H), 1.85-1.74 (m, 4H), 1.67 (s, 6H), 1.55-1.54 (m, 2H), 1.41-1.35 (m, 2H), 1.26-1.22 (m, 2H); MS (ESI) m/z=606.2 (M+H)$^+$ Example 120. 2-(5-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl) pyrazin-2-yl)propan-2-ol Step 1. 2-(5-(6-Chloro-4-(((1s,4s)-4-(2-hydroxypropan-2-yl)cyclohexyl)amino)pyridin-3-yl) pyrazin-2-yl)propan-2-ol The title compound as a white solid (102 mg) was prepared in the same fashion as Step 2 in Example 1 except that 2-(5-(6-chloro-4-fluoropyridin-3-yl) pyrazin-2-yl)propan-2-ol (82 mg. 0.306 mmol) prepared in Step 1 of Example 118 and 2-((1s,4s)-4-aminocyclohexyl)propan-2-ol (72 mg, 0.459 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.37 (d, 1H), 9.01 (s, 1H), 8.70 (s, 1H), 8.55 (s, 1H), 6.64 (s, 1H), 3.86 (s, 1H), 2.03-2.00 (m, 2H), 1.81-1.77 (m, 2H), 1.68 (s, 7H) 1.43-1.27 (m, 5H), 1.22 (s, 7H); MS (ESI) m/z=405.2 (M+H)$^+$ Step 2. 2-(5-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl) pyrazin-2-yl)propan-2-ol The title compound (56.9 mg) as a solid was prepared in the same fashion as Step 3 in Example 1, except that 2-(5-(6-chloro-4-(((1s,4s)-4-(2-hydroxypropan-2-yl)cyclohexyl)amino)pyridin-3-yl) pyrazin-2-yl)propan-2-ol (100 mg. 0.247 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.45 (d, 1H), 9.02 (s, 1H), 8.67 (d, 2H), 8.57 (s, 1H), 8.47 (s, 1H), 8.43 (d, 1H), 7.55 (s, 1H), 7.37 (s, 1H), 7.10 (d, 1H), 4.02 (s, 1H), 3.62 (s, 1H), 2.88-2.81 (m, 1H), 2.13-2.09 (m, 2H), 1.81-1.75 (m, 4H), 1.66 (s, 6H), 1.59-1.54 (m, 2H), 1.48-1.37 (m, 3H), 1.23 (s, 6H); MS (ESI) m/z=634.3 (M+H)$^+$ Example 121. 2-(5-(6-((2-(1-(Cyclopropylsulfonyl)-1H-pyrazol-4-yl)pyrimidin-4-yl)amino)-4-(isopropylamino)pyridin-3-yl) pyrazin-2-yl)propan-2-ol Step 1. 2-(5-(6-Chloro-4-(isopropylamino)pyridin-3-yl) pyrazin-2-yl)propan-2-ol The title compound as a white solid (68 mg) was prepared in the same fashion as Step 2 in Example 1 except that 2-(5-(6-chloro-4-fluoropyridin-3-yl) pyrazin-2-yl)propan-2-ol (76 mg, 0.284 mmol) prepared in Step 1 of Example 118 and isopropylamine hydrochloride (41 mg. 0.426 mmol) were used instead of 6'-chloro-4'-fluoro-5-((4-methylpiperazin-1-yl)methyl)-2,3'-bipyridine and (4-methylpiperidin-4- yl)methanol. $^1$H-NMR (CDCl$_3$, 400 MHz) δ 8.96 (d, 1H), 8.74 (d, 1H), 8.71 (d, 1H), 8.50 (s, 1H), 6.63 (s, 1H), 1.66 (s, 6H), 1.33 (s, 3H), 1.31 (s, 3H); MS (ESI) m/z=306.9 (M+H)$^+$ Step 2. 2-(5-(6-((2-(1-(Cyclopropylsulfonyl)-1H-pyrazol-4-yl)pyrimidin-4-yl)amino)-4-(isopropylamino)pyridin-3-yl) pyrazin-2-yl)propan-2-ol The title compound as a white solid (30 mg) was prepared in the same fashion as Step 3 in Example 1, except that 2-(5-(6-chloro-4-(isopropylamino)pyridin-3-yl) pyrazin-2-yl)propan-2-ol (35 mg, 0.116 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.97 (d, 1H), 8.82 (d, 1H), 8.72 (d, 1H), 8.68 (s, 1H), 8.52 (s, 1H), 8.48 (s, 1H), 8.44 (d, 1H), 7.39 (s, 1H), 7.18 (d, 1H), 3.92-3.87 (m, 1H), 3.69 (s, 1H), 2.87-2.83 (m, 1H), 1.67 (s, 6H), 1.41 (s, 3H), 1.40 (s, 3H), 1.26-1.21 (m, 2H); MS (ESI) m/z=536.2 (M+H)$^+$ Example 122. N$^2$-(2-(1-(Cyclopropylsulfonyl)-1H-pyrazol-4-yl)pyrimidin-4-yl)-5-(5-(2-(dimethylamino) ethoxy) pyrazin-2-yl)-N$^4$-isopropylpyridine-2,4-diamine Step 1. 2-Chloro-5-(5-(2-(dimethylamino) ethoxy) pyrazin-2-yl)-N-isopropylpyridin-4-amine The title compound as a white solid (43 mg) was prepared in the same fashion as Step 2 in Example 1 except that 2-((5-(6-chloro-4-fluoropyridin-3-yl) pyrazin-2-yl)oxy)-N,N-dimethylethan-1-amine (84 mg, 0.284 mmol) prepared in Step 1 of Example 115 and isopropylamine hydrochloride (41 mg, 0.426 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.46 (d, 1H), 8.29 (s, 1H), 8.24 (d, 1H), 7.96 (d, 1H), 7.01 (s, 1H), 4.49 (t, 2H), 3.72-3.65 (m, 1H), 2.77 (t, 2H), 2.36 (s, 6H), 1.29 (s, 3H), 1.28 (s, 3H); MS (ESI) m/z=336.0 (M+H)$^+$ Step 2. N$^2$-(2-(1-(Cyclopropylsulfonyl)-1H-pyrazol-4-yl)pyrimidin-4-yl)-5-(5-(2-(dimethylamino) ethoxy) pyrazin-2-yl)-N$^4$-isopropylpyridine-2,4-diamine The title compound as a pale yellow solid (13 mg) was prepared in the same fashion as Step 3 in Example 1, except that 2-chloro-5-(5-(2-(dimethylamino) ethoxy) pyrazin-2-yl)-N-isopropylpyridin-4-amine (39 mg, 0.118 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.47 (d, 2H), 8.43 (d, 1H), 8.30 (s, 1H), 8.25 (d, 1H), 8.00 (d, 1H), 7.40 (s, 1H), 7.22 (d, 1H), 7.17 (s, 1H), 4.49 (t, 2H), 3.87-3.82 (m, 1H), 2.87-2.81 (m, 1H), 2.77 (t, 2H), 2.37 (s, 6H), 1.38 (s, 3H), 1.36 (s, 3H), 1.27-1.23 (m, 4H); MS (ESI) m/z=565.3 (M+H)$^+$ Example 123. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-morpholino-[2,3'-bipyridine]-4',6'-diamine Step 1. 6'-Chloro-N-((1s,4s)-4-fluorocyclohexyl)-5-morpholino-[2,3'-bipyridin]-4'-amine The title compound as a solid (76 mg) was prepared in the same fashion as Step 2 in Example 1, except that 4-(6'-chloro-4'-fluoro-[2,3'-bipyridin]-5-yl) morpholine (83 mg, 0.283 mmol) prepared in Reference Example 25 and (1s,4s)-4-fluorocyclohexan-1-amine hydrochloride (65 mg, 0.424 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.40 (d, 1H), 8.34 (s, 1H), 8.24 (d, 1H), 7.64 (d, 1H), 7.31 (dd, 1H), 6.55 (s, 1H), 4.87-4.74 (m, 1H), 3.91 (t, 4H), 3.48-3.47 (m, 1H), 3.26 (t, 4H), 2.06-2.03 (m, 2H), 1.93-1.89 (m, 2H), 1.83-1.71 (m, 4H); MS (ESI) m/z=391.0 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-morpholino-[2,3'-bipyridine]-4',6'-diamine The title compound as a white solid (10 mg) was prepared in the same fashion as Step 3 in Example 1, except that 6'-chloro-N-((1s,4s)-4-fluorocyclohexyl)-5-morpholino-[2,3'-bipyridin]-4'-amine (76 mg. 0.194 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.48 (d, 1H), 8.66 (s, 1H), 8.46 (s, 1H), 8.42 (d, 1H), 8.37 (s, 1H), 8.25 (d, 1H), 7.66 (d, 1H), 7.34-7.31 (m, 2H), 7.01 (s, 1H), 4.85-4.73 (m, 1H), 3.92 (t, 4H), 3.65 (s, 1H), 3.26 (t, 4H), 2.86-2.81 (m, 1H), 1.02-1.81 (m, 8H), 1.79-1.76 (m, 2H), 1.25-1.19 (m, 2H); MS (ESI) m/z=620.3 (M+H)$^+$ Example 124. N$^{6'}$-(2-(1-(Cyclopropylsulfonyl)-1H-pyrazol-4-yl)pyrimidin-4-yl)-N$^{4'}$-isopropyl-5-morpholino-[2,3'-bipyridine]-4',6'-diamine Step 1. 6'-Chloro-N-isopropyl-5-morpholino-[2,3'-bipyridin]-4'-amine The title compound as a white solid (59 mg) was prepared in the same fashion as Step 2 in Example 1, except that 4-(6'-chloro-4'-fluoro-[2,3'-bipyridin]-5-yl) morpholine (80 mg, 0.271 mmol) prepared in Reference Example 25 and isopropylamine hydrochloride (39 mg, 0.406 mmol) was used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.02 (d, 1H), 8.30 (s, 1H), 8.25 (d, 1H), 7.61 (d, 1H), 7.31 (dd, 1H), 6.55 (s, 1H), 3.91 (t, 4H), 3.70-3.69 (m, 1H), 3.25 (t, 4H), 1.31 (s, 3H), 1.29 (s, 3H); MS (ESI) m/z=333.1 (M+H)$^+$ Step 2. N$^{6'}$-(2-(1-(Cyclopropylsulfonyl)-1H-pyrazol-4-yl)pyrimidin-4-yl)-N$^{4'}$-isopropyl-5-morpholino-[2,3'-bipyridine]-4',6'-diamine The title compound as a white solid (5 mg) was prepared in the same fashion as Step 3 in Example 1, except that 6'-chloro-N-isopropyl-5-morpholino-[2,3'-bipyridin]-4'-amine (73 mg, 0.218 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.06 (d, 1H), 8.67 (s, 1H), 8.47 (s, 1H), 8.40 (d, 1H), 8.33 (s, 1H), 8.26 (d, 1H), 7.63 (d, 1H), 7.49 (s, 1H), 7.32 (dd, 1H), 7.20 (d, 1H), 7.15 (s, 1H), 3.92 (t, 4H), 3.87-3.82 (m, 1H), 3.25 (t, 4H), 2.86-2.82 (m, 1H), 1.56-1.52 (m, 2H), 1.40 (s, 3H), 1.38 (s, 3H), 1.26-1.21 (m, 2H); MS (ESI) m/z=562.2 (M+H)$^+$

Example 125. N⁶'-(2-(1-(Cyclopropylsulfonyl)-1H-pyrazol-4-yl)pyrimidin-4-yl)-N⁴'-isopropyl-5-(morpholinomethyl)-[2,3'-bipyridine]-4',6'-diamine

Step 1. 4-((6-Bromopyridin-3-yl)methyl) morpholine

To the solution of morpholine (0.26 mL, 2.957 mmol) in DCM (5 mL) was added 6-bromo-3-pyridinecarboxaldehyde (500 mg, 2.688 mmol) and sodium triacetoxy borohydride (1709 mg, 8.06 mmol). The reaction mixture was stirred at 45° C. for 3 hours. The reaction mixture was cooled, added to sat. NaHCO₃ soln., extracted with DCM, washed by water, dried over MgSO₄, and then concentrated. The crude product was purified by column chromatography (MeOH/DCM=0-100%) to yield 4-((6-bromopyridin-3-yl)methyl) morpholine (493 mg) as a beige solid. ¹H-NMR (CDCl₃, 400 MHz) δ 8.31 (d, 1H), 7.57 (dd, 1H), 7.45 (d, 1H), 3.71 (t, 4H), 3.47 (s, 2H), 2.44 (t, 4H); MS (ESI) m/z=257.0 (M+H)⁺

Step 2. 4-((6'-Chloro-4'-fluoro-[2,3'-bipyridin]-5-yl)methyl) morpholine

The title compound as a solid (355 mg) was prepared in the same fashion as Step 1 in Example 1 except that 4-((6-bromopyridin-3-yl)methyl) morpholine (466 mg, 1.814 mmol) prepared in Step 1 was used instead of 1-((6-bromopyridin-3-yl)methyl)-4-methylpiperazine. ¹H-NMR (CDCl₃, 400 MHz) δ 9.04 (d, 1H), 8.69 (s, 1H), 7.80 (dd, 1H), 7.72 (dd, 1H), 7.21 (d, 1H), 3.74 (t, 4H), 3.58 (s, 2H), 2.50 (t, 4H); MS (ESI) m/z=307.9 (M+H)⁺

Step 3. 6'-Chloro-N-isopropyl-5-(morpholinomethyl)-[2,3'-bipyridin]-4'-amine The title compound as a solid (58 mg) was prepared in the same fashion as Step 2 in Example 1, except that 4-((6'-chloro-4'-fluoro-[2,3'-bipyridin]-5-yl)methyl) morpholine (83 mg, 0.271 mmol) prepared in Step 2 and isopropylamine hydrochloride (39 mg, 0.406 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.28 (d, 1H), 8.53 (s, 1H), 8.40 (s, 1H), 7.78 (dd, 1H), 7.70 (d, 1H), 6.58 (s, 1H), 3.74 (t, 4H), 3.55 (s, 2H), 2.49 (t, 4H), 1.32 (s, 3H), 1.30 (s, 3H); MS (ESI) m/z=347.0 (M+H)⁺

Step 4. N⁶'-(2-(1-(Cyclopropylsulfonyl)-1H-pyrazol-4-yl)pyrimidin-4-yl)-N⁴'-isopropyl-5-(morpholinomethyl)-[2,3'-bipyridine]-4',6'-diamine The title compound as a solid (5.5 mg) was prepared in the same fashion as Step 3 in Example 1, except that 6'-chloro-N-isopropyl-5-(morpholinomethyl)-[2,3'-bipyridin]-4'-amine (55 mg, 0.159 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl₃, 400 MHz) δ 9.38 (d, 1H), 8.67 (s, 1H), 8.52 (s, 1H), 8.48 (s, 1H), 8.42 (d, 2H), 7.77 (d, 1H), 7.71 (d, 1H), 7.56 (s, 1H), 7.22-7.18 (m, 2H), 4.00-3.85 (m, 1H), 3.74 (t, 4H), 3.55 (s, 2H), 2.86-2.81 (m, 1H), 2.50 (s, 4H), 2.25-2.21 (m, 1H), 2.06 (s, 1H), 1.56-1.52 (m, 2H), 1.41 (s, 3H), 1.39 (s, 3H), 1.41-1.39 (m, 2H), 1.27-1.22 (m, 2H); MS (ESI) m/z=576.2 (M+H)⁺

Example 126. N⁶'-(2-(1-(Cyclopropylsulfonyl)-1H-pyrazol-4-yl)pyrimidin-4-yl)-N⁴'-((1s,4s)-4-fluorocyclohexyl)-5-(morpholinomethyl)-[2,3'-bipyridine]-4',6'-diamine

Step 1. 6'-Chloro-N-((1s,4s)-4-fluorocyclohexyl)-5-(morpholinomethyl)-[2,3'-bipyridin]-4'-amine The title compound as a solid (85 mg) was prepared in the same fashion as Step 2 in Example 1, except that 4-((6'-chloro-4'-fluoro-[2,3'-bipyridin]-5-yl)methyl) morpholine (83 mg, 0.27 mmol) prepared in Step 2 of Example 125 and (1s,4s)-4-fluorocyclohexan-1-amine hydrochloride (39 mg, 0.406 mmol) was used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.62 (d, 1H), 8.52 (s, 1H), 8.43 (s, 1H), 7.79 (d, 1H), 7.72 (d, 1H), 6.58 (s, 1H), 4.81 (d, 1H), 3.74 (t, 4H), 3.55 (s, 2H), 2.49 (t, 4H), 2.09-2.05 (m, 3H), 1.92-1.89 (m, 2H), 1.81-1.75 (m, 2H), 1.71-1.63 (m, 4H), 1.32-1.26 (m, 1H); MS (ESI) m/z=405.0 (M+H)⁺

Step 2. N⁶'-(2-(1-(Cyclopropylsulfonyl)-1H-pyrazol-4-yl)pyrimidin-4-yl)-N⁴'-((1s,4s)-4-fluorocyclohexyl)-5-(morpholinomethyl)-[2,3'-bipyridine]-4',6'-diamine The title compound as a solid (3 mg) was prepared in the same fashion as Step 3 in Example 1, except that 6'-chloro-N-((1s,4s)-4-fluorocyclohexyl)-5-(morpholinomethyl)-[2,3'-bipyridin]-4'-amine (52 mg. 0.129 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.75 (d, 1H), 8.66 (s, 1H), 8.52 (s, 1H), 8.47 (s, 2H), 8.43 (d, 1H), 7.79 (d, 1H), 7.74 (d, 1H), 7.32-7.30 (m, 2H), 7.04-7.01 (m, 1H), 4.86-4.85 (m, 1H), 3.75 (t, 4H), 3.67 (s, 1H), 3.55 (s, 2H), 2.88-2.80 (m, 1H), 2.50 (s, 4H), 2.05-1.79 (m, 8H), 1.27-1.21 (m, 2H); MS (ESI) m/z=634.3 (M+H)⁺

Example 127. N²-(2-(1-(Cyclopropylsulfonyl)-1H-pyrazol-4-yl)pyrimidin-4-yl)-5-(5-(difluoromethoxy)pyrazin-2-yl)-N⁴-isopropylpyridine-2,4-diamine

Step 1. 2-(6-Chloro-4-fluoropyridin-3-yl)-5-(difluoromethoxy)pyrazine

The title compound as a white solid (470 mg) was prepared in the same fashion as Step 1 in Example 1 except that 2-bromo-5-(difluoromethoxy)pyrazine (500 mg, 2.222 mmol) was used instead of 1-((6-bromopyridin-3-yl)methyl)-4-methylpiperazine. ¹H-NMR (CDCl₃, 400 MHz) δ 9.05 (d, 1H), 8.64 (s, 1H), 8.52 (s, 1H), 7.47 (t, 1H), 7.25 (s, 1H); MS (ESI) m/z=276.0 (M+H)⁺

Step 2. 2-Chloro-5-(5-(difluoromethoxy) pyrazin-2-yl)-N-isopropylpyridin-4-amine The title compound as a white solid (100 mg) was prepared in the same fashion as Step 2 in Example 1 except that 2-(6-chloro-4-fluoropyridin-3-yl)-5-(difluoromethoxy)pyrazine (90 mg, 0.327 mmol) prepared in Step 1 and isopropylamine hydrochloride (47 mg, 0.49 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 8.58 (s, 1H), 8.37

(s, 2H), 8.10-8.08 (m, 1H), 7.45 (t, 1H), 6.62 (s, 1H), 3.75-3.70 (m, 1H), 1.31 (s, 3H), 1.29 (s, 3H); MS (ESI) m/z=314.9 (M+H)+

Step 3. $N^2$-(2-(1-(Cyclopropylsulfonyl)-1H-pyrazol-4-yl)pyrimidin-4-yl)-5-(5-(difluoromethoxy) pyrazin-2-yl)-$N^4$-isopropylpyridine-2,4-diamine The title compound (5 mg) as a solid was prepared in the same fashion as Step 3 in Example 1, except that 2-chloro-5-(5-(difluoromethoxy) pyrazin-2-yl)-N-isopropylpyridin-4-amine (85 mg, 0.27 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl$_3$, 400 MHz) δ 8.67 (s, 1H), 8.60 (s, 1H), 8.47 (s, 1H), 8.44 (d, 1H), 8.39 (s, 1H), 8.36 (s, 1H), 8.18 (d, 1H), 7.44 (t, 1H), 7.38 (s, 1H), 7.26 (s, 1H), 7.19 (d, 1H), 3.90-3.85 (m, 1H), 2.86-2.82 (m, 1H), 1.55-1.52 (m, 2H), 1.40 (s, 3H), 1.38 (s, 3H), 1.30-1.20 (m, 3H); MS (ESI) m/z=544.2 (M+H)+

Example 128. (1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)-1-methylcyclohexan-1-ol Step 1. (1s,4s)-4-((2-Chloro-5-(5-(difluoromethoxy) pyrazin-2-yl)pyridin-4-yl)amino)-1-methylcyclohexan-1-ol The title compound as a white solid (111 mg) was prepared in the same fashion as Step 2 in Example 1 except that 2-(6-chloro-4-fluoropyridin-3-yl)-5-(difluoromethoxy)pyrazine (90 mg, 0.327 mmol) prepared in Step 1 of Example 127 and cis-4-amino-1-methylcyclohexan-1-ol (63 mg, 0.49 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.59 (s, 1H), 8.38 (s, 1H), 8.36 (s, 1H), 8.24 (d, 1H), 7.44 (t, 1H), 6.62 (s, 1H), 4.16-4.11 (m, 1H), 3.37-3.34 (m, 1H), 1.94-1.92 (m, 2H), 1.78-1.69 (m, 4H), 1.61-1.57 (m, 1H), 1.31 (s, 3H), 1.28-1.25 (m, 1H); MS (ESI) m/z=385.0 (M+H)+

Step 2. (1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)-1-methylcyclohexan-1-ol The title compound (30 mg) as a solid was prepared in the same fashion as Step 3 in Example 1, except that (1s,4s)-4-((2-chloro-5-(5-(difluoromethoxy) pyrazin-2-yl)pyridin-4-yl)amino)-1-methylcyclohexan-1-ol (104 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl$_3$, 400 MHz) δ 8.67 (s, 1H), 8.60 (s, 1H), 8.48 (s, 1H), 8.45 (d, 1H), 8.40 (s, 1H), 8.35-8.32 (m, 2H), 7.44 (t, 1H), 7.37-7.35 (m, 2H), 7.00 (s, 1H), 3.50 (s, 1H), 2.85-2.81 (m, 1H), 2.01-2.00 (m, 2H), 1.76-1.74 (m, 4H), 1.63-1.52 (m, 2H), 1.32 (s, 3H), 1.27-1.22 (m, 3H), 1.13 (s, 1H); MS (ESI) m/z=614.1 (M+H)+

Example 129. ((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)methanol Step 1. ((1s,4s)-4-((2-Chloro-5-(5-(difluoromethoxy) pyrazin-2-yl)pyridin-4-yl)amino)cyclohexyl)methanol The title compound as a white solid (104 mg) was prepared in the same fashion as Step 2 in Example 1 except that 2-(6-chloro-4-fluoropyridin-3-yl)-5-(difluoromethoxy)pyrazine (90 mg, 0.327 mmol) prepared in Step 1 of Example 127 and cis-(4-aminocyclohexyl)methanol hydrochloride (81 mg, 0.49 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.70 (d, 1H), 8.64 (s, 1H), 8.42 (s, 1H), 8.36 (d, 1H), 7.45 (t, 1H), 6.63 (s, 1H), 3.81-3.79 (m, 1H), 3.55 (t, 2H), 1.92-1.88 (m, 2H), 1.75-1.66 (m, 5H), 1.33-1.30 (m, 2H); MS (ESI) m/z=385.1 (M+H)+

Step 2. ((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)methanol The title compound (23 mg) as a solid was prepared in the same fashion as Step 3 in Example 1, except that (1s,4s)-4-((2-chloro-5-(5-(difluoromethoxy) pyrazin-2-yl)pyridin-4-yl)amino)cyclohexyl)methanol (104 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.81 (d, 1H), 8.66 (d, 2H), 8.47 (s, 1H), 8.44 (t, 2H), 8.35 (s, 1H), 7.44 (t, 1H), 7.28 (s, 1H), 7.15 (d, 1H), 3.98-3.97 (m, 1H), 3.55 (m, 2H), 2.87-2.83 (m, 1H), 2.06-2.00 (m, 2H), 1.85-1.66 (m, 6H), 1.38-1.29 (m, 6H); MS (ESI) m/z=614.2 (M+H)+

Example 130. 2-((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)propan-2-ol Step 1. 2-((1s,4s)-4-((2-Chloro-5-(5-(difluoromethoxy) pyrazin-2-yl)pyridin-4-yl)amino)cyclohexyl)propan-2-ol The title compound as a white solid (114 mg) was prepared in the same fashion as Step 2 in Example 1 except that 2-(6-chloro-4-fluoropyridin-3-yl)-5-(difluoromethoxy)pyrazine (90 mg, mmol) prepared in Step 1 of Example 127 and 2-((1s,4s)-4-aminocyclohexyl)propan-2-ol hydrochloride (95 mg, 0.49 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.78 (d, 1H), 8.65 (s, 1H), 8.42 (s, 1H), 8.33 (s, 1H), 7.45 (t, 1H), 6.63 (s, 1H), 3.85-3.84 (m, 1H), 2.01-1.97 (m, 2H), 1.80-1.78 (m, 2H), 1.64 (t, 2H), 1.42-1.27 (m, 3H), 1.23 (s, 6H); MS (ESI) m/z=413.0 (M+H)+

Step 2. 2-((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)propan-2-ol The title compound (9 mg) as a solid was prepared in the same fashion as Step 3 in Example 1, except that 2-((1s, 4s)-4-((2-chloro-5-(5-(difluoromethoxy) pyrazin-2-yl)pyridin-4-yl)amino)cyclohexyl)propan-2-ol (112 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.87 (d, 1H), 8.66 (s, 2H), 8.47 (s, 1H), 8.44 (t, 2H), 8.33 (s, 1H), 7.44 (t, 1H), 7.40 (s, 1H), 7.34 (s, 1H), 7.12 (d, 1H), 4.01 (s, 1H), 2.87-2.83 (m, 1H), 2.10-2.06 (m, 2H), 1.81-1.74 (m, 4H), 1.56-1.30 (m, 4H), 1.24 (s, 6H); MS (ESI) m/z=642.2 (M+H)$^+$ Example 131. N$^2$-(2-(1-(Cyclopropylsulfonyl)-1H-pyrazol-4-yl)pyrimidin-4-yl)-5-(5-(difluoromethoxy) pyrazin-2-yl)-N$^4$-((1s,4s)-4-((dimethylamino) methyl)cyclohexyl)pyridine-2,4-diamine Step 1. 2-Chloro-5-(5-(difluoromethoxy) pyrazin-2-yl)-N-((1s,4s)-4-((dimethylamino)methyl)cyclohexyl)pyridin-4-amine The title compound as a white solid (76 mg) was prepared in the same fashion as Step 2 in Example 1 except that 2-(6-chloro-4-fluoropyridin-3-yl)-5-(difluoromethoxy)pyrazine (90 mg, 0.327 mmol) prepared in Step 1 of Example 127 and (1s,4s)-4-((dimethylamino)methyl)cyclohexan-1-amine dihydrochloride (112 mg, 0.49 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.66-8.63 (m, 2H), 8.41 (s, 1H), 8.35 (s, 1H), 7.45 (t, 1H), 6.62 (s, 1H), 3.77-3.75 (m, 1H), 2.23 (s, 6H), 2.14-2.12 (m, 1H), 1.86-1.83 (m, 2H), 1.75-1.66 (m, 5H), 1.26-1.20 (m, 3H); MS (ESI) m/z=412.0 (M+H)$^+$ Step 2. N$^2$-(2-(1-(Cyclopropylsulfonyl)-1H-pyrazol-4-yl)pyrimidin-4-yl)-5-(5-(difluoromethoxy) pyrazin-2-yl)-N$^4$-((1s,4s)-4-((dimethylamino) methyl)cyclohexyl)pyridine-2,4-diamine The title compound (25 mg) as a solid was prepared in the same fashion as Step 3 in Example 1, except that 2-chloro-5-(5-(difluoromethoxy) pyrazin-2-yl)-N-((1s,4s)-4-((dimethylamino)methyl)cyclohexyl)pyridin-4-amine (111 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.78 (d, 1H), 8.66 (s, 1H), 8.65 (s, 1H), 8.47 (s, 1H), 8.44-8.43 (m, 2H), 8.34 (d, 1H), 7.45 (t, 1H), 7.44 (s, 1H), 7.25 (s, 1H), 7.18 (d, 1H), 3.95-3.94 (m, 1H), 2.86-2.82 (m, 1H), 2.23 (s, 6H), 2.14-2.12 (m, 2H), 1.99-1.96 (m, 2H), 1.83-1.73 (m, 4H), 1.55-1.53 (m, 2H), 1.29-1.20 (m, 6H); MS (ESI) m/z=641.3 (M+H)$^+$ Example 132. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-((1-methylpiperidin-4-yl)oxy)-[2,3'-bipyridine]-4',6'-diamine Step 1. 6'-Chloro-N-((1s,4s)-4-fluorocyclohexyl)-5-((1-methylpiperidin-4-yl)oxy)-[2,3'-bipyridin]-4'-amine The title compound as a solid (114 mg) was prepared in the same fashion as Step 2 in Example 1, except that 6'-chloro-4'-fluoro-5-((1-methylpiperidin-4-yl)oxy)-2,3'-bipyridine (100 mg, 0.311 mmol) prepared in Step 1 of Reference Example 1 and (1s,4s)-4-fluorocyclohexan-1-amine hydrochloride (57 mg, 0.373 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.24 (d, 1H), 8.33 (s, 1H), 8.27 (d, 1H), 7.65 (d, 1H), 7.34 (dd, 1H), 6.56 (s, 1H), 4.87-4.75 (m, 1H), 4.42-4.41 (m, 1H), 3.48 (s, 1H), 2.72 (s, 2H), 2.33 (s, 6H), 2.06-2.05 (m, 5H), 1.91-1.89 (m, 4H), 1.80-1.70 (m, 3H); MS (ESI) m/z=419.0 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-((1-methylpiperidin-4-yl)oxy)-[2,3'-bipyridine]-4',6'-diamine The title compound (6.4 mg) as a white solid was prepared in the same fashion as Step 3 in Example 1, except that 6'-chloro-N-((1s,4s)-4-fluorocyclohexyl)-5-((1-methylpiperidin-4-yl)oxy)-[2,3'-bipyridin]-4'-amine (52 mg. 0.124 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.55 (d, 1H), 8.63 (s, 1H), 8.50-8.45 (m, 2H), 8.30 (d, 1H), 8.18 (s, 1H), 8.06 (s, 1H), 7.71 (d, 1H), 7.41 (d, 1H), 7.05 (d, 1H), 4.85-4.69 (m, 1H), 3.81 (s, 1H), 3.11-3.04 (m, 4H), 2.84 (s, 1H), 2.66 (s, 3H), 2.35-2.32 (m, 2H), 2.15-2.12 (m, 3H), 2.05-2.19 (m, 5H), 1.55-1.54 (m, 2H), 1.25-1.23 (m, 2H); MS (ESI) m/z=648.2 (M+H)$^+$ Example 133. N$^{6'}$-(2-(1-(2,2-Difluoroethyl)-1H-pyrazol-4-yl)pyrimidin-4-yl)-N$^{4'}$-((1s,4s)-4-fluorocyclohexyl)-5-((1-methylpiperidin-4-yl)oxy)-[2,3'-bipyridine]-4',6'-diamine The title compound (2.8 mg) as a white solid was prepared in the same fashion as Step 3 in Example 1, except that 6'-chloro-N-((1s,4s)-4-fluorocyclohexyl)-5-((1-methylpiperidin-4-yl)oxy)-[2,3'-bipyridin]-4'-amine (52 mg. 0.124 mmol) prepared in Step 1 of Example 132 and 2-(1-(2,2-difluoroethyl)-1H-pyrazol-4-yl)pyrimidin-4-amine (34 mg, 0.149 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.27 (d, 1H), 8.39 (d, 1H), 8.36 (s, 1H), 8.27 (s, 1H), 8.24 (s, 1H), 8.18 (d, 1H), 7.67 (d, 1H), 7.34 (d, 1H), 6.97 (s, 1H), 6.15 (tt, 1H), 4.86-4.74 (m, 1H), 4.52 (td, 2H), 4.44-4.41 (m, 1H), 3.64 (s, 1H), 2.73 (s, 2H), 2.34 (s, 5H), 1.94-1.90 (m, 4H), 1.87-1.75 (m, 8H); MS (ESI) m/z=608.2 (M+H)$^+$ Example 134. (1s,4s)-4-((2-((2-(1-(Cyclopropylsulfonyl)-1H-pyrazol-4-yl)pyrimidin-4-yl)amino)-5-(5-(trifluoromethyl) pyrazin-2-yl)pyridin-4-yl) amino)-1-methylcyclohexan-1-ol Step 1. 2-(6-Chloro-4-fluoropyridin-3-yl)-5-(trifluoromethyl)pyrazine The title compound as a brown solid (97 mg) was prepared in the same fashion as Step 1 in Example 1 except that 2-bromo-5-(trifluoromethyl)pyrazine (190 mg, 0.837 mmol) was used instead of 1-((6-bromopyridin-3-yl)methyl)-4-methylpiperazine. $^1$H-NMR (CDCl$_3$, 400 MHz) δ 9.18 (s, 1H), 9.14 (d, 1H), 9.09 (s, 1H), 7.32 (d, 1H)

Step 2. (1s,4s)-4-((2-Chloro-5-(5-(trifluoromethyl) pyrazin-2-yl)pyridin-4-yl)amino)-1-methylcyclohexan-1-ol The title compound as a solid (60 mg) was prepared in the same fashion as Step 2 in Example 1, except that 2-(6-chloro-4-fluoropyridin-3-yl)-5-(trifluoromethyl)pyrazine (47 mg, 0.169 mmol) prepared in Step 1 and cis-4-amino-1-methylcyclohexan-1-ol (33 mg, 0.254 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.18 (s, 1H), 8.95 (d, 1H), 8.88 (s, 1H), 8.62 (s, 1H), 6.67 (s, 1H), 3.41-3.39 (m, 1H), 1.96-1.93 (m, 2H), 1.80-1.70 (m, 4H), 1.62-1.57 (m, 1H), 1.32 (s, 3H), 1.27-1.25 (m, 1H); MS (ESI) m/z=387.1 (M+H)$^+$

Step 3. (1s,4s)-4-((2-((2-(1-(Cyclopropylsulfonyl)-1H-pyrazol-4-yl)pyrimidin-4-yl)amino)-5-(5-(trifluoromethyl) pyrazin-2-yl)pyridin-4-yl)amino)-1-methylcyclohexan-1-ol The title compound (5 mg) as a pale yellow solid was prepared in the same fashion as Step 3 in Example 1, except that (1s,4s)-4-((2-chloro-5-(5-(trifluoromethyl) pyrazin-2-yl)pyridin-4-yl)amino)-1-methylcyclohexan-1-ol (30 mg, 0.087 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.19 (s, 1H), 9.50 (s, 1H), 9.14 (s, 1H), 9.02 (d, 1H), 8.86 (s, 1H), 8.67 (s, 1H), 8.48-8.46 (d, 2H) 7.53 (s, 1H), 7.43 (s, 1H), 2.00-1.98 (m, 1H), 1.82 (s, 2H), 1.71-1.57 (m, 5H), 1.45-1.31 (m, 5H), 1.25 (s, 3H); MS (ESI) m/z=616.2 (M+H)$^+$

Example 135. N$^{6'}$-(2-(1-(2,2-Difluoroethyl)-1H-pyrazol-4-yl)pyrimidin-4-yl)-N$^{4'}$-((1s,4s)-4-fluorocyclohexyl)-5-((4-methylpiperazin-1-yl)methyl)-[2,3'-bipyridine]-4',6'-diamine

Step 1. 6'-Chloro-N-((1s,4s)-4-fluorocyclohexyl)-5-((4-methylpiperazin-1-yl)methyl)-[2,3'-bipyridin]-4'-amine The title compound as a solid (151 mg) was prepared in the same fashion as Step 2 in Example 1, except that 6'-chloro-4'-fluoro-5-((4-methylpiperazin-1-yl)methyl)-2,3'-bipyridine (173 mg, 0.539 mmol) prepared in Step 1 of Example 1 and (1s,4s)-4-fluorocyclohexan-1-amine hydrochloride (99 mg, 0.647 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 9.63 (d, 1H), 8.51 (s, 1H), 8.43 (s, 1H), 7.78 (d, 1H), 7.71 (d, 1H), 6.58 (s, 1H), 4.87-4.75 (m, 1H), 3.56 (s, 2H), 3.74 (S, 1H), 2.51 (s, 7H), 2.31-2.05 (m, 2H), 1.91-1.89 (m, 2H), 1.81-1.71 (m, 6H); MS (ESI) m/z=418.2 (M+H)$^+$

Step 2. N$^{6'}$-(2-(1-(2,2-Difluoroethyl)-1H-pyrazol-4-yl)pyrimidin-4-yl)-N$^{4'}$-((1s,4s)-4-fluorocyclohexyl)-5-((4-methylpiperazin-1-yl)methyl)-[2,3'-bipyridine]-4',6'-diamine The title compound (9 mg) as a white solid was prepared in the same fashion as Step 3 in Example 1, except that 6'-chloro-N-((1s,4s)-4-fluorocyclohexyl)-5-((4-methylpiperazin-1-yl)methyl)-[2,3'-bipyridin]-4'-amine (46 mg, 0.11 mmol) prepared in Step 1 and 2-(1-(2,2-difluoroethyl)-1H-pyrazol-4-yl)pyrimidin-4-amine (30 mg. 0.132 mmol) prepared Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.71 (d, 1H), 8.51 (s, 1H), 8.46 (s, 1H), 8.39 (d, 1H), 8.24 (s, 1H), 8.17 (s, 1H), 7.78-7.71 (m, 2H), 7.39 (s, 1H), 7.25 (s, 1H), 7.03 (s, 1H), 6.15 (tt, 1H), 4.86-4.74 (m, 1H), 4.52 (td, 2H), 3.67-3.65 (m, 1H), 3.56 (s, 2H), 2.53 (s, 7H), 2.31 (s, 3H), 2.05-1.94 (m, 2H), 1.92-1.83 (m, 5H), 1.78-1.72 (m, 1H), 1.27 (s, 1H); MS (ESI) m/z=608.3 (M+H)$^+$

Example 136. N$^{6'}$-(2-(1-(2,2-difluoroethyl)-1H-pyrazol-4-yl)pyrimidin-4-yl)-N$^{4'}$-((1s,4s)-4-fluorocyclohexyl)-5-(morpholinomethyl)-[2,3'-bipyridine]-4',6'-diamine The title compound (8 mg) as a white solid was prepared in the same fashion as Step 3 in Example 1, except that 6'-chloro-N-((1s,4s)-4-fluorocyclohexyl)-5-(morpholinomethyl)-[2,3'-bipyridin]-4'-amine (45 mg, 0.11 mmol) prepared in Step 1 of Example 126 and 2-(1-(2,2-difluoroethyl)-1H-pyrazol-4-yl)pyrimidin-4-amine (30 mg. 0.132 mmol) prepared Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.69 (d, 1H), 8.51 (s, 1H), 8.46 (s, 1H), 8.40 (d, 1H), 8.24 (s, 1H), 8.17 (s, 1H), 7.79-7.72 (m, 2H), 7.35 (s, 1H), 7.24 (s, 1H), 7.03-7.01 (m, 1H), 6.15 (tt, 1H), 4.86-4.74 (m, 1H), 4.53 (td, 2H), 3.74 (s, 4H), 3.67 (s, 1H), 3.55 (s, 2H), 2.50 (s, 4H), 2.07-2.06 (m, 2H), 1.98-1.86 (m, 5H), 1.79-1.75 (m, 2H); MS (ESI) m/z=594.3 (M+H)$^+$

Example 137. N$^{6'}$-(2-(1-(2,2-Difluoroethyl)-1H-pyrazol-4-yl)pyrimidin-4-yl)-N$^{4'}$-((1s,4s)-4-fluorocyclohexyl)-5-morpholino-[2,3'-bipyridine]-4',6'-diamine The title compound (9 mg) as a white solid was prepared in the same fashion as Step 3 in Example 1, except that 6'-chloro-N-((1s,4s)-4-fluorocyclohexyl)-5-morpholino-[2,3'-bipyridin]-4'-amine (43 mg. 0.11 mmol) prepared in Step 1 of Example 123 and 2-(1-(2,2-difluoroethyl)-1H-pyrazol-4-yl)pyrimidin-4-amine (30 mg, 0.132 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.42 (d, 1H), 8.39-8.37 (m, 2H), 8.24 (s, 2H), 8.17 (s, 1H), 7.65 (d, 1H), 7.34-7.32 (m, 3H), 6.97 (s, 1H), 6.15 (tt, 1H), 4.85-4.74 (m, 1H), 4.52 (td, 2H), 3.92 (t, 4H), 3.65 (s, 1H), 3.26 (t, 4H), 2.06-2.03 (m, 2H), 1.97-1.84 (m, 5H), 1.76-1.57 (m, 1H); MS (ESI) m/z=580.3 (M+H)$^+$

Example 138. N$^{4'}$-(3,3-Difluorocyclopentyl)-N$^{6'}$-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine

Step 1. 6'-Chloro-N-(3,3-difluorocyclopentyl)-5-((1-methylpiperidin-4-yl)oxy)-[2,3'-bipyridin]-4'-amine The title compound as a solid (70 mg) was prepared in the same fashion as Step 2 in Example 1, except that 6'-chloro- 4'-fluoro-5-((1-methylpiperidin-4-yl)oxy)-2,3'-bipyridine (79 mg, 0.246 mmol) prepared in Step 1 of Reference Example 1 and 3,3-difluorocyclopentanamine hydrochloride (50 mg, 0.319 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.47 (d, 1H), 8.36 (s, 1H), 8.26 (d, 1H), 7.67 (d, 1H), 7.34 (dd, 1H), 6.52 (s, 1H), 4.41 (s, 1H), 4.07-4.06 (m, 1H), 2.72-2.63 (m, 3H), 2.36-1.30 (m, 8H), 2.07-2.05 (m, 3H), 1.93-1.89 (m, 4H); MS (ESI) m/z=423.0 (M+H)⁺

Step 2. N⁴'-(3,3-Difluorocyclopentyl)-N⁶'-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine The title compound as a white solid (12.2 mg) was prepared in the same fashion as Step 3 in Example 1, except that 6'-chloro-N-(3,3-difluorocyclopentyl)-5-((1-methylpiperidin-4-yl)oxy)-[2,3'-bipyridin]-4'-amine (66 mg, 0.155 mmol) prepared in Step 1 and 2-(1-(2,2-difluoroethyl)-1H-pyrazol-4-yl)pyrimidin-4-amine (42 mg. 0.186 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. ¹H-NMR (CDCl₃, 400 MHz) δ 8.53 (s, 1H), 8.40 (d, 1H), 8.38 (s, 1H), 8.25-8.17 (m, 3H), 7.94 (s, 1H), 7.66 (d, 1H), 7.38 (d, 1H), 7.37 (dd, 1H), 7.27 (s, 1H), 7.97 (d, 1H), 6.15 (tt, 1H), 4.63 (s, 1H), 4.55 (td, 2H), 4.33-4.31 (m, 1H), 2.97 (s, 3H), 2.73-2.63 (m, 1H), 2.59 (s, 3H), 2.44-2.23 (m, 5H), 2.10-2.02 (m, 1H), 1.98-1.97 (m, 1H); MS (ESI) m/z=612.2 (M+H);

Example 139. N⁴'-(3,3-Difluorocyclobutyl)-N⁶'-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine Step 1. 6'-Chloro-N-(3,3-difluorocyclobutyl)-5-((1-methylpiperidin-4-yl)oxy)-[2,3'-bipyridin]-4'-amine The title compound as a solid (71 mg) was prepared in the same fashion as Step 2 in Example 1, except that 6'-chloro-4'-fluoro-5-((1-methylpiperidin-4-yl)oxy)-2,3'-bipyridine (79 mg. 0.246 mmol) prepared in Step 1 of Reference Example 1 and 3,3-difluorocyclobutanamine hydrochloride (46 mg. 0.319 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.43 (s, 1H), 8.38 (s, 1H), 8.28 (s, 1H), 7.68 (d, 1H), 7.36 (d, 1H), 6.39 (s, 1H), 4.43-4.42 (m, 1H), 3.91 (s, 1H), 3.20-3.12 (m, 2H), 2.63-2.54 (m, 4H), 2.33 (s, 4H), 2.09-2.05 (m, 3H), 1.91-1.89 (m, 2H); MS (ESI) m/z=409.0 (M+H)⁺ Step 2. N⁴'-(3,3-Difluorocyclobutyl)-N⁶'-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine The title compound as a white solid (15.5 mg) was prepared in the same fashion as Step 3 in Example 1, except that 6'-chloro-N-(3,3-difluorocyclobutyl)-5-((1-methylpiperidin-4-yl)oxy)-[2,3'-bipyridin]-4'-amine (63 mg, 0.155 mmol) prepared in Step 1 and 2-(1-(2,2-difluoroethyl)-1H-pyrazol-4-yl)pyrimidin-4-amine (42 mg. 0.186 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. ¹H-NMR (CDCl₃, 400 MHz) δ 8.51 (s, 2H), 8.39 (d, 1H), 8.27 (d, 1H), 8.20-8.18 (m, 3H), 7.79 (s, 1H), 7.67 (d, 1H), 7.37 (dd, 1H), 6.95 (d, 1H), 6.16 (tt, 1H), 4.64 (s, 1H), 4.56 (td, 2H), 4.16 (s, 1H), 3.48-3.16 (m, 2H), 3.02-3.01 (m, 3H), 2.64-2.57 (m, 5H), 2.35-2.30 (m, 2H), 2.12-2.08 (m, 2H); MS (ESI) m/z=598.2 (M+H)⁺

Example 140. N⁶'-(2-(1-(Cyclopropylsulfonyl)-1H-pyrazol-4-yl)pyrimidin-4-yl)-N⁴'-(3,3-difluorocyclobutyl)-5-((1-methylpiperidin-4-yl)oxy)-[2,3'-bipyridine]-4',6'-diamine The title compound (7 mg) as a white solid was prepared in the same fashion as Step 3 in Example 1, except that 6'-chloro-N-(3,3-difluorocyclobutyl)-5-((1-methylpiperidin-4-yl)oxy)-[2,3'-bipyridin]-4'-amine (58 mg. 0.142 mmol) prepared in Step 1 of Example 139 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 10.04 (d, 1H), 8.67 (s, 1H), 8.58 (s, 1H), 8.44 (d, 2H), 8.28-8.25 (m, 2H), 7.66 (d, 1H), 7.38-7.36 (m, 2H), 7.18 (d, 1H), 4.53 (s, 1H), 4.12-4.11 (m, 1H), 3.23-3.19 (m, 2H), 2.85-2.83 (m, 3H), 2.66-2.58 (m, 4H), 2.46 (s, 3H), 2.21-2.16 (m, 2H), 2.01 (s, 2H), 1.56-1.55 (m, 2H), 1.26-1.23 (m, 3H); MS (ESI) m/z=638.2 (M+H)⁺

Example 141. N⁶'-(2-(1-(2,2-Difluoroethyl)-1H-pyrazol-4-yl)pyrimidin-4-yl)-N⁴'-(3-fluorocyclohexyl)-5-((1-methylpiperidin-4-yl)oxy)-[2,3'-bipyridine]-4',6'-diamine Step 1. 6'-Chloro-N-(3-fluorocyclohexyl)-5-((1-methylpiperidin-4-yl)oxy)-[2,3'-bipyridin]-4'-amine The title compound as a solid (66 mg) was prepared in the same fashion as Step 2 in Example 1, except that 6'-chloro-4'-fluoro-5-((1-methylpiperidin-4-yl)oxy)-2,3'-bipyridine (79 mg, 0.246 mmol) prepared in Step 1 of Reference Example 1 and 3-fluorocyclohexanamine hydrochloride (49 mg, 0.319 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 9.09 (d, 1H), 8.32 (s, 1H), 8.25 (d, 1H), 7.65 (d, 1H), 7.34 (dd, 1H), 6.61 (s, 1H), 5.04-4.92 (m, 1H), 4.41-4.40 (m, 1H), 3.81-3.79 (m, 1H), 2.72 (m, 2H), 2.09 (s, 7H), 2.33-2.05 (m, 3H), 1.93-1.86 (m, 3H), 1.73-1.68 (m, 3H), 1.47-1.36 (m, 1H); MS (ESI) m/z=419.0 (M+H)⁺

Step 2. N⁶'-(2-(1-(2,2-Difluoroethyl)-1H-pyrazol-4-yl)pyrimidin-4-yl)-N⁴'-(3-fluorocyclohexyl)-5-((1-methylpiperidin-4-yl)oxy)-[2,3'-bipyridine]-4',6'-diamine The title compound as a white solid (6.4 mg) was prepared in the same fashion as Step 3 in Example 1, except that 6'-chloro-N-(3-fluorocyclohexyl)-5-((1-methylpiperidin-4-yl)oxy)-[2,3'-bipyridin]-4'-amine (65 mg, 0.155 mmol) prepared in Step 1 and 2-(1-(2,2-difluoroethyl)-1H-pyrazol-4-yl)pyrimidin-4-amine (42 mg, 0.186 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. ¹H-NMR (CDCl₃, 400 MHz) δ 10.63-10.17 (m, 1H), 8.59 (s, 1H), 8.42-8.40 (m, 1H), 8.26 (s, 2H), 8.18 (s, 1H), 8.11-8.09 (m, 1H), 8.01-7.92 (m, 1H), 7.66-7.61 (m, 1H), 7.39-7.37 (m, 1H), 7.01-6.99 (m, 1H), 6.15 (t, 1H), 5.15-4.94 (m, 1H), 4.58-4.52 (m, 3H), 4.08-3.98 (m, 1H), 2.90-2.78 (m, 4H), 2.45 (s, 3H), 2.22 (s, 1H), 2.22 (s, 3H), 2.05-2.04 (m, 3H), 1.91-1.80 (m, 2H), 1.74-1.45 (m, 4H); MS (ESI) m/z=608.3 (M+H)$^+$ Example 142. (1s,4s)-4-((6'-((2-(3,4-Dihydro-2H-pyrano[2,3-b]pyridin-6-yl)pyrimidin-4-yl)amino)-5-((1-methylpiperidin-4-yl)oxy)-[2,3'-bipyridin]-4'-yl)amino)-1-methylcyclohexan-1-ol Step 1. 2-(3,4-Dihydro-2H-pyrano[2,3-b]pyridin-6-yl)pyrimidin-4-amine The title compound (93 mg) as a solid was prepared in the same fashion as Reference Example 17, except that 6-(4,4,5,5-tetramethyl-1,3,2-dioxaborolan-2-yl)-3,4-dihydro-2H-pyrano[2,3-b]pyridine (225 mg, 0.862 mmol) was used instead of 1-(2,2-difluoroethyl)-4-(4,4,5,5-tetramethyl-1,3,2-dioxaborolan-2-yl)pyrazole. $^1$H-NMR (CDCl$_3$, 400 MHz) δ 9.04 (s, 1H), 8.34 (s, 1H), 8.30 (d, 1H), 6.33 (d, 1H), 4.92 (s, 2H), 4.41 (t, 2H), 2.89 (t, 2H), 2.09-2.03 (m, 3H); MS (ESI) m/z=229.1 (M+H)$^+$ Step 2. (1s,4s)-4-((6'-((2-(3,4-Dihydro-2H-pyrano[2,3-b]pyridin-6-yl)pyrimidin-4-yl)amino)-5-((1-methylpiperidin-4-yl)oxy)-[2,3'-bipyridin]-4'-yl)amino)-1-methylcyclohexan-1-ol The title compound as a white solid (9 mg) was prepared in the same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (65 mg, 0.151 mmol) prepared in Reference Example 1 and 2-(3,4-dihydro-2H-pyrano[2,3-b]pyridin-6-yl)pyrimidin-4-amine (40 mg, 0.173 mmol) prepared in Step 1 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.95 (s, 1H), 8.38 (d, 2H), 8.29 (s, 2H), 7.75 (d, 1H), 7.48 (d, 1H), 7.34-7.31 (m, 2H), 4.54 (s, 1H), 4.43 (m, 2H), 3.48 (s, 1H), 2.94 (t, 2H), 2.75 (s, 2H), 2.41 (s, 2H), 2.33 (s, 3H), 2.09-2.06 (m, 4H), 1.93-1.85 (m, 4H), 1.73-1.64 (m, 4H), 1.49-1.46 (s, 2H), 1.20 (s, 3H); MS (ESI) m/z=623.3 (M+H)$^+$ Example 143. N$^{6'}$-(2-(1-(Cyclopropylsulfonyl)-1H-pyrazol-4-yl)pyrimidin-4-yl)-N$^{4'}$-(3,3-difluorocyclopentyl)-5-((1-methylpiperidin-4-yl)oxy)-[2,3'-bipyridine]-4',6'-diamine The title compound (12 mg) as a white solid was prepared in the same fashion as Step 3 in Example 1, except that 6'-chloro-N-(3,3-difluorocyclopentyl)-5-((1-methylpiperidin-4-yl)oxy)-[2,3'-bipyridin]-4'-amine (65 mg, 0.154 mmol) prepared in Step 1 of Example 138 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.63 (s, 1H), 8.50 (s, 2H), 8.46-8.43 (m, 2H), 8.26 (s, 1H), 8.20 (s, 1H), 8.01 (s, 1H), 7.70 (d, 1H), 7.39 (d, 1H), 7.03 (d, 1H), 4.68 (s, 1H), 4.35 (s, 1H), 3.49-3.01 (m, 4H), 2.85-2.69 (m, 2H), 2.66 (s, 3H), 2.49-2.44 (m, 1H), 2.38-2.28 (m, 5H), 2.14-2.04 (m, 3H), 1.56-1.55 (m, 2H), 1.25 (d, 2H); MS (ESI) m/z=652.3 (M+H)$^+$ Example 144. N$^2$-(2-(1-(Cyclopropylsulfonyl)-1H-pyrazol-4-yl)pyrimidin-4-yl)-N$^4$-((1s,4s)-4-fluorocyclohexyl)-5-(5-((1-methylpiperidin-4-yl)oxy)pyrazin-2-yl)pyridine-2,4-diamine Step 1.
2-Bromo-5-((1-methylpiperidin-4-yl)oxy)pyrazine To a solution of 4-hydroxy-1-methylpiperidine (213 mg, 1.85 mmol) in THF (2 mL) was added sodium hydride (61 mg. 2.522 mmol) at room temperature. The reaction mixture was stirred for 5 minutes and 2,5-dibromopyrazine (400 mg, 1.682 mmol) was added to the mixture. The reaction mixture was stirred at 50° C. for 4 hours and quenched by water. The aqueous phase was extracted with DCM. The combined organic phase was dried over MgSO$_4$, filtered, and concentrated. The crude product was purified by column chromatography (MeOH/EA=0-15%) to yield 2-bromo-5-((1-methylpiperidin-4-yl)oxy)pyrazine (450 mg) as an off-white solid. $^1$H-NMR (CDCl$_3$, 400 MHz) δ 8.16 (s, 1H), 7.99 (s, 1H), 5.00 (s, 1H), 2.71 (s, 2H), 2.32 (s, 5H), 2.05-2.04 (m, 2H), 1.90-1.82 (m, 2H), 1.67-1.66 (m, 1H); MS (ESI) m/z=273.8 (M+H)$^+$ Step 2. 2-(6-Chloro-4-fluoropyridin-3-yl)-5-((1-methylpiperidin-4-yl)oxy)pyrazine The title compound as a solid (400 mg) was prepared in the same fashion as Step 1 in Example 1 except that 2-bromo-5-((1-methylpiperidin-4-yl)oxy)pyrazine (414 mg, 1.521 mmol) prepared in Step 1 was used instead of 1-((6-bromopyridin-3-yl)methyl)-4-methylpiperazine. $^1$H-NMR (CDCl$_3$, 400 MHz) δ 9.00 (d, 1H), 8.53 (s, 1H), 8.31 (s, 1H), 7.21 (d, 1H), 2.75 (s, 2H), 2.34 (s, 6H), 2.09-2.05 (m, 2H), 1.94-1.73 (m, 2H); MS (ESI) m/z=323.0 (M+H)$^+$ Step 3. 2-Chloro-N-((1s,4s)-4-fluorocyclohexyl)-5-(5-((1-methylpiperidin-4-yl)oxy) pyrazin-2-yl)pyridin-4-amine The title compound as a white solid (78 mg) was prepared in the same fashion as Step 2 in Example 1, except that 2-(6-chloro-4-fluoropyridin-3-yl)-5-((1-methylpiperidin-4-yl)oxy)pyrazine (95 mg, 0.294 mmol) prepared in Step 2 and (1s,4s)-4-fluorocyclohexan-1-amine hydrochloride (68 mg, 0.441 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.47 (s, 1H), 8.32 (s, 1H), 8.29 (d, 1H), 8.17 (s, 1H), 6.58 (s, 1H), 5.31 (s, 1H), 4.87-4.75 (m, 1H), 3.46 (s, 1H), 2.76 (s, 2H), 2.34 (s, 1H), 2.09-2.06 (m, 5H), 1.92-1.89 (m, 7H), 1.82-1.68 (m, 5H); MS (ESI) m/z=420.1 (M+H)$^+$ Step 4. N$^2$-(2-(1-(Cyclopropylsulfonyl)-1H-pyrazol-4-yl)pyrimidin-4-yl)-N$^4$-((1s,4s)-4-fluorocyclohexyl)-5-(5-((1-methylpiperidin-4-yl)oxy) pyrazin-2-yl)pyridine-2,4-diamine The title compound (6 mg) as a white solid was prepared in the same fashion as Step 3 in Example 1, except that 2-chloro-N-((1s,4s)-4-fluorocyclohexyl)-5-(5-((1-methylpiperidin-4-yl)oxy) pyrazin-2-yl)pyridin-4-amine (78 mg. 0.185 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.65 (s, 1H), 8.49 (s, 1H), 8.46 (s, 1H), 8.43 (d, 1H), 8.38 (d, 1H), 8.33 (s, 1H), 8.18 (s, 1H), 7.46 (s, 1H), 7.32 (d, 1H), 7.04 (s, 1H), 5.10 (s, 1H), 4.84-4.72 (m, 1H), 3.62 (s, 1H), 2.85-2.81 (m, 1H), 2.77-2.76 (m, 2H), 2.34 (s, 5H), 2.00-1.97 (m, 3H), 1.95-1.63 (m, 8H), 1.78 (s, 2H), 1.63-1.53 (m, 3H), 1.27-1.22 (m, 2H); MS (ESI) m/z=649.3 (M+H)$^+$

Example 145. (1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)-1-methylcyclohexan-1-ol

Step 1. (1s,4s)-4-((2-Chloro-5-(5-((1-methylpiperidin-4-yl)oxy) pyrazin-2-yl)pyridin-4-yl)amino)-1-methylcyclohexan-1-ol The title compound as a white solid (80 mg) was prepared in the same fashion as Step 2 in Example 1, except that 2-(6-chloro-4-fluoropyridin-3-yl)-5-((1-methylpiperidin-4-yl)oxy)pyrazine (95 mg, 0.294 mmol) prepared in Step 2 of Example 144 and cis-4-amino-1-methylcyclohexan-1-ol (57 mg, 0.441 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.45 (s, 1H), 8.29 (s, 1H), 8.15 (s, 2H), 6.57 (s, 1H), 3.34-3.32 (m, 1H), 2.75 (s, 2H), 2.34 (s, 6H), 2.09-2.05 (m, 2H), 1.92-1.88 (m, 4H), 1.77-1.56 (m, 9H) 1.31 (s, 3H); MS (ESI) m/z=432.1 (M+H)$^+$

Step 2. (1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)-1-methylcyclohexan-1-ol The title compound (8 mg) as a white solid was prepared in the same fashion as Step 3 in Example 1, except that (1s,4s)-4-((2-chloro-5-(5-((1-methylpiperidin-4-yl)oxy) pyrazin-2-yl)pyridin-4-yl)amino)-1-methylcyclohexan-1-ol (80 mg, 0.185 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.47 (d, 2H), 8.43 (d, 1H), 8.31 (s, 1H), 8.19-8.16 (m, 2H), 7.41-7.37 (m, 2H), 6.94 (s, 1H), 5.09 (s, 1H), 3.50 (s, 1H), 2.84-1.82 (m, 1H), 2.75 (s, 2H), 2.34 (s, 5H), 2.90 (s, 2H), 2.00-1.89 (m, 4H), 1.75-1.70 (m, 5H), 1.62-1.54 (m, 4H), 1.32 (s, 3H), 1.23-1.21 (m, 2H); MS (ESI) m/z=661.2 (M+H)$^+$

Example 146. ((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)methanol

Step 1. ((1s,4s)-4-((2-Chloro-5-(5-((1-methylpiperidin-4-yl)oxy) pyrazin-2-yl)pyridin-4-yl)amino)cyclohexyl)methanol The title compound as a white solid (77 mg) was prepared in the same fashion as Step 2 in Example 1, except that 2-(6-chloro-4-fluoropyridin-3-yl)-5-((1-methylpiperidin-4-yl)oxy)pyrazine (95 mg, 0.294 mmol) prepared in Step 2 of Example 144 and cis-(4-aminocyclohexyl)methanol hydrochloride (73 mg, 0.441 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.68 (d, 1H), 8.51 (s, 1H), 8.34 (s, 1H), 8.17 (s, 1H), 6.58 (s, 1H), 5.11-5.09 (m, 1H), 3.78 (d, 1H), 3.53 (d, 2H), 2.74 (m, 2H), 2.34 (s, 5H), 2.08-2.06 (m, 2H), 2.92-1.88 (m, 4H), 1.72-1.61 (m, 5H), 1.35-1.27 (m, 2H); MS (ESI) m/z=432.1 (M+H)$^+$

Step 2. ((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)methanol The title compound (6 mg) as a white solid was prepared in the same fashion as Step 3 in Example 1, except that ((1s,4s)-4-((2-chloro-5-(5-((1-methylpiperidin-4-yl)oxy) pyrazin-2-yl)pyridin-4-yl)amino)cyclohexyl)methanol (80 mg, 0.185 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.74 (d, 1H), 8.66 (s, 1H), 8.52 (s, 1H), 8.47 (s, 1H), 8.42 (d, 1H), 8.36 (s, 1H), 8.17 (s, 1H), 7.42 (s, 1H), 7.20-7.17 (m, 2H), 5.11 (s, 1H), 3.95 (s, 1H), 3.54-3.50 (m, 2H), 2.85-2.83 (m, 1H), 2.75 (s, 2H), 2.34 (s, 5H), 2.03-2.00 (m, 2H), 1.91-1.89 (m, 2H), 1.82-1.67 (m, 6H), 1.55 (s, 2H), 1.37-1.27 (m, 5H); MS (ESI) m/z=661.2 (M+H)$^+$

Example 147. 2-((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)propan-2-ol

Step 1. 2-((1s,4s)-4-((2-Chloro-5-(5-((1-methylpiperidin-4-yl)oxy) pyrazin-2-yl)pyridin-4-yl)amino) cyclohexyl)propan-2-ol The title compound as a white solid (76 mg) was prepared in the same fashion as Step 2 in Example 1, except that 2-(6-chloro-4-fluoropyridin-3-yl)-5-((1-methylpiperidin-4-yl)oxy)pyrazine (95 mg, 0.294 mmol) prepared in Step 2 of Example 144 and 2-((1s,4s)-4-aminocyclohexyl)propan-2-ol hydrochloride (86 mg, 0.441 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.72 (d, 1H), 7.51 (s, 1H), 8.34 (s, 1H), 8.14 (s, 1H), 6.59 (s, 1H), 5.11-5.10 (m, 1H), 3.83-3.81 (m, 1H), 2.74 (s, 2H), 2.34 (s, 6H), 2.09-2.05 (m, 2H), 1.97-1.91 (m, 2H), 1.89-1.87 (m, 2H), 1.78-1.75 (m, 3H), 1.65-1.58 (m, 2H), 1.41-1.30 (m, 3H), 1.23 (s, 7H); MS (ESI) m/z=460.1 (M+H)$^+$

Step 2. 2-((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino)cyclohexyl)propan-2-ol The title compound (7 mg) as a white solid was prepared in the same fashion as Step 3 in Example 1, except that 2-((1s,4s)-4-((2-chloro-5-(5-((1-methylpiperidin-4-yl)oxy) pyrazin-2-yl)pyridin-4-yl)amino)cyclohexyl)propan-2-ol (85 mg. 0.185 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.74 (d, 1H), 8.73 (s, 1H), 8.52 (s, 1H), 8.46 (s, 1H), 8.42 (d, 1H), 8.35 (s, 1H), 8.15 (s, 1H), 7.40 (s, 1H), 7.25 (s, 1H), 7.15 (d, 1H), 5.10 (s, 1H), 3.99 (s, 1H), 2.85-2.84 (m, 1H), 2.75 (s, 2H), 2.34 (s, 5H), 2.10-2.08 (m, 4H), 1.92-1.88 (m, 2H), 1.79-1.72 (m, 4H), 1.55 (s, 3H), 1.46-1.36 (m, 3H), 1.24 (s, 9H); MS (ESI) m/z=689.3 (M+H)$^+$

Example 148. (1s,4s)-4-((2-((2-(1-(Cyclopropylsulfonyl)-1H-pyrazol-4-yl)pyrimidin-4-yl)amino)-5-(5-((tetrahydro-2H-pyran-4-yl)oxy) pyrazin-2-yl) pyridin-4-yl)amino)-1-methylcyclohexan-1-ol

Step 1. 2-Bromo-5-((tetrahydro-2H-pyran-4-yl)oxy) pyrazine

The title compound (160 mg) as a white solid was prepared in the same fashion as Step 1 of Example 144, except that tetrahydro-2H-pyran-4-ol (86 mg, 0.841 mmol) was used instead of 4-hydroxy-1-methylpiperidine. $^1$H-NMR (CDCl$_3$, 400 MHz) δ 8.16 (s, 1H), 8.01 (s, 1H), 5.19-5.15 (m, 1H), 4.02-3.96 (m, 2H), 3.64-3.58 (m, 2H), 2.08-2.04 (m, 2H), 1.85-1.78 (m, 2H)

Step 2. 2-(6-Chloro-4-fluoropyridin-3-yl)-5-((tetrahydro-2H-pyran-4-yl)oxy)pyrazine The title compound as a solid (109 mg) was prepared in the same fashion as Step 1 in Example 1 except that 2-bromo-5-((tetrahydro-2H-pyran-4-yl)oxy)pyrazine (156 mg, 0.602 mmol) prepared in Step 1 was used instead of 1-((6-bromopyridin-3-yl)methyl)-4-methylpiperazine. $^1$H-NMR (CDCl$_3$, 400 MHz) δ 9.00 (d, 1H), 8.54 (s, 1H), 8.33 (s, 1H), 7.22 (d, 1H), 5.31-5.28 (m, 1H) 4.04-4.01 (m, 2H), 3.67-3.62 (m, 2H), 2.13-1.91 (m, 2H), 1.91-1.82 (m, 2H); MS (ESI) m/z=310.0 (M+H)$^+$

Step 3. (1s,4s)-4-((2-Chloro-5-(5-((tetrahydro-2H-pyran-4-yl)oxy) pyrazin-2-yl)pyridin-4-yl)amino)-1-methylcyclohexan-1-ol The title compound as a white solid (55 mg) was prepared in the same fashion as Step 2 in Example 1, except that 2-(6-chloro-4-fluoropyridin-3-yl)-5-((tetrahydro-2H-pyran-4-yl)oxy)pyrazine (50 mg, 0.161 mmol) prepared in Step 2 and cis-4-amino-1-methylcyclohexan-1-ol (31 mg, 0.242 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.45 (s, 1H), 8.30 (s, 1H), 8.17-8.13 (m, 2H), 6.58 (s, 1H), 5.29-5.25 (m, 1H), 4.04-4.01 (m, 2H), 3.66-3.61 (m, 2H), 3.34-3.33 (m, 1H), 2.12 (s, 1H), 1.91-1.84 (m, 4H), 1.78-1.65 (m, 5H), 1.60 (s, 1H), 1.31 (s, 3H), 1.13 (s, 1H); MS (ESI) m/z=419.2 (M+H)$^+$

Step 4. (1s,4s)-4-((2-((2-(1-(Cyclopropylsulfonyl)-1H-pyrazol-4-yl)pyrimidin-4-yl)amino)-5-(5-((tetrahydro-2H-pyran-4-yl)oxy) pyrazin-2-yl)pyridin-4-yl)amino)-1-methylcyclohexan-1-ol The title compound (16 mg) as a white solid was prepared in the same fashion as Step 3 in Example 1, except that (1s,4s)-4-((2-chloro-5-(5-((tetrahydro-2H-pyran-4-yl)oxy)pyrazin-2-yl)pyridin-4-yl)amino)-1-methylcyclohexan-1-ol (55 mg. 0.131 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.47 (d, 2H), 8.44 (d, 1H), 8.32 (s, 1H), 8.18 (s, 2H), 7.38 (d, 2H), 6.95 (s, 1H), 5.28-5.25 (m, 1H), 4.05-4.02 (m, 2H), 3.67-3.62 (m, 2H), 3.49-3.48 (m, 1H), 2.84-2.82 (m, 2H), 2.13-2.10 (m, 2H), 2.01-1.98 (m, 2H), 1.91-1.85 (m, 4H), 1.75-1.59 (m, 2H), 1.32 (s, 3H), 1.26-1.25 (m, 2H), 1.23 (s, 1H); MS (ESI) m/z=648.3 (M+H)$^+$

Example 149. (1s,4s)-4-((2-((2-(1-(Cyclopropylsulfonyl)-1H-pyrazol-4-yl)pyrimidin-4-yl)amino)-5-(5-((tetrahydrofuran-3-yl)oxy) pyrazin-2-yl)pyridin-4-yl)amino)-1-methylcyclohexan-1-ol

Step 1. 2-Bromo-5-((tetrahydrofuran-3-yl)oxy)pyrazine

The title compound (137 mg) as a white solid was prepared in the same fashion as Step 1 of Example 144, except that tetrahydrofuran-3-ol (74 mg, 0.841 mmol) was used instead of 4-hydroxy-1-methylpiperidine. $^1$H-NMR (CDCl$_3$, 400 MHz) δ 8.18 (s, 1H), 8.03 (s, 1H), 5.49 (d, 1H), 4.05-4.00 (m, 2H), 3.98-3.92 (m, 2H), 2.30-2.26 (m, 1H), 2.16-2.14 (m, 1H)

Step 2. 2-(6-Chloro-4-fluoropyridin-3-yl)-5-((tetrahydrofuran-3-yl)oxy)pyrazine The title compound as a solid (125 mg) was prepared in the same fashion as Step 1 in Example 1 except that 2-bromo-5-((tetrahydrofuran-3-yl)oxy)pyrazine (148 mg, 0.602 mmol) prepared in Step 1 was used instead of 1-((6-bromopyridin-3-yl)methyl)-4-methylpiperazine. $^1$H-NMR (CDCl$_3$, 400 MHz) δ 9.01 (d, 1H), 8.55 (s, 1H), 8.35 (s, 1H), 7.22 (d, 1H), 5.61 (s, 1H), 4.14-3.92 (m, 5H), 2.36-2.29 (m, 1H), 2.23-2.17 (m, 1H); MS (ESI) m/z=295.8 (M+H)$^+$

Step 3. (1s,4s)-4-((2-Chloro-5-(5-((tetrahydrofuran-3-yl)oxy) pyrazin-2-yl)pyridin-4-yl)amino)-1-methylcyclohexan-1-ol The title compound as a white solid (54 mg) was prepared in the same fashion as Step 2 in Example 1, except that 2-(6-chloro-4-fluoropyridin-3-yl)-5-((tetrahydrofuran-3-yl)oxy)pyrazine (48 mg, 0.161 mmol) prepared in Step 2 and cis-4-amino-1-methylcyclohexan-1-ol (31 mg, 0.242 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.47 (s, 1H), 8.30 (s, 1H), 8.19 (s, 1H), 8.15 (d, 1H), 6.58 (s, 1H), 5.59 (s, 1H), 4.09-3.93 (m, 4H), 3.33-3.32 (m, 1H), 2.35-2.30 (m, 1H), 2.21 (s, 1H), 1.94-1.91 (m, 2H), 1.77-1.68 (m, 4H), 1.60 (s, 1H), 1.54 (s, 1H), 1.31 (s, 3H), 1.13 (s, 1H); MS (ESI) m/z=405.1 (M+H)$^+$

Step 4. (1s,4s)-4-((2-((2-(1-(Cyclopropylsulfonyl)-1H-pyrazol-4-yl)pyrimidin-4-yl)amino)-5-(5-((tetrahydrofuran-3-yl)oxy) pyrazin-2-yl)pyridin-4-yl) amino)-1-methylcyclohexan-1-ol The title compound (8 mg) as a white solid was prepared in the same fashion as Step 3 in Example 1, except that (1s,4s)-4-((2-chloro-5-(5-((tetrahydrofuran-3-yl)oxy) pyrazin-2-yl)pyridin-4-yl)amino)-1-methylcyclohexan-1-ol (53 mg, 0.131 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.48 (s, 2H), 8.43 (d, 1H), 8.32 (s, 1H), 8.20-8.18 (m, 2H), 7.41-7.36 (m, 2H), 6.96 (s, 1H), 5.59 (s, 1H), 4.10-3.92 (m, 4H), 3.50 (s, 1H), 2.85-2.82 (m, 1H), 2.35-2.30 (m, 1H), 2.22-2.18 (m, 1H), 2.02-1.98 (m, 2H), 1.75-1.70 (m, 4H), 1.62 (s, 1H), 1.55-1.54 (m, 2H), 1.32 (s, 3H), 1.26-1.19 (m, 2H), 1.16 (s, 1H); MS (ESI) m/z=634.3 (M+H)$^+$

Example 150. (1s,4s)-4-((2-((2-(1-(Cyclopropylsulfonyl)-1H-pyrazol-4-yl)pyrimidin-4-yl)amino)-5-(5-(oxetan-3-yloxy) pyrazin-2-yl)pyridin-4-yl)amino)-1-methylcyclohexan-1-ol

Step 1. 2-Bromo-5-(oxetan-3-yloxy)pyrazine

The title compound (157 mg) as a white solid was prepared in the same fashion as Step 1 of Example 144, except that oxetan-3-ol (74 mg, 0.841 mmol) was used instead of 4-hydroxy-1-methylpiperidine. $^1$H-NMR (CDCl$_3$, 400 MHz) δ 8.12 (d, 1H), 5.61-5.55 (m, 1H), 4.99 (t, 2H), 4.74 (t, 2H)

Step 2. 2-(6-Chloro-4-fluoropyridin-3-yl)-5-(oxetan-3-yloxy)pyrazine

The title compound as a solid (81 mg) was prepared in the same fashion as Step 1 in Example 1 except that 2-bromo-5-(oxetan-3-yloxy)pyrazine (139 mg, 0.602 mmol) prepared in Step 1 was used instead of 1-((6-bromopyridin-3-yl)methyl)-4-methylpiperazine. $^1$H-NMR (CDCl$_3$, 400 MHz) δ 9.02 (d, 1H), 8.51 (s, 1H), 8.43 (s, 1H), 7.23 (d, 1H), 5.70-5.67 (m, 1H), 5.04 (t, 2H), 4.80 (t, 2H); MS (ESI) m/z=281.9 (M+H)$^+$

Step 3. (1s,4s)-4-((2-Chloro-5-(5-(oxetan-3-yloxy) pyrazin-2-yl)pyridin-4-yl)amino)-1-methylcyclohexan-1-ol The title compound as a white solid (60 mg) was prepared in the same fashion as Step 2 in Example 1, except that 2-(6-chloro-4-fluoropyridin-3-yl)-5-(oxetan-3-yloxy)pyrazine (45 mg, 0.161 mmol) prepared in Step 2 and cis-4-amino-1-methylcyclohexan-1-ol (31 mg, 0.242 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.43 (s, 1H), 8.29 (s, 1H) 8.26 (s, 1H), 8.15 (d, 1H), 6.58 (s, 1H), 5.67-5.64 (m, 1H), 5.03 (t, 2H), 4.78 (t, 2H), 3.32 (s, 1H), 1.93-1.91 (m, 2H), 1.77-1.71 (m, 3H), 1.65-1.54 (m, 2H), 1.31 (s, 3H), 1.24 (s, 1H); MS (ESI) m/z=391.1 (M+H)$^+$

Step 4. (1s,4s)-4-((2-((2-(1-(Cyclopropylsulfonyl)-1H-pyrazol-4-yl)pyrimidin-4-yl)amino)-5-(5-(oxetan-3-yloxy) pyrazin-2-yl)pyridin-4-yl)amino)-1-methylcyclohexan-1-ol The title compound (16 mg) as a white solid was prepared in the same fashion as Step 3 in Example 1, except that (1s,4s)-4-((2-chloro-5-(5-(oxetan-3-yloxy) pyrazin-2-yl)pyridin-4-yl)amino)-1-methylcyclohexan-1-ol (51 mg, 0.131 mmol) prepared in Step 3 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.66 (s, 1H), 8.48 (s, 1H), 8.44 (s, 2H), 8.31 (s, 1H), 8.27 (s, 1H), 8.21 (d, 1H), 7.36 (d, 2H), 6.98 (s, 1H), 5.67 (s, 1H), 5.04 (t, 2H), 4.80 (t, 2H), 3.50 (s, 1H), 2.84-2.81 (m, 1H), 2.01-1.98 (m, 2H), 1.76-1.73 (m, 4H), 1.63 (s, 2H), 1.32 (s, 3H), 1.27-1.15 (m, 3H); MS (ESI) m/z=620.2 (M+H)$^+$

Example 151. N$^2$-(2-(1-(Cyclopropylsulfonyl)-1H-pyrazol-4-yl)pyrimidin-4-yl)-N$^4$-((1s,4s)-4-fluorocyclohexyl)-5-(5-((tetrahydro-2H-pyran-4-yl)oxy) pyrazin-2-yl)pyridine-2,4-diamine

Step 1. 2-Chloro-N-((1s,4s)-4-fluorocyclohexyl)-5-(5-((tetrahydro-2H-pyran-4-yl)oxy) pyrazin-2-yl)pyridin-4-amine The title compound as a solid (79 mg) was prepared in the same fashion as Step 2 in Example 1, except that 2-(6-chloro-4-fluoropyridin-3-yl)-5-((tetrahydro-2H-pyran-4-yl)oxy)pyrazine (47 mg, 0.152 mmol) prepared in Step 2 of Example 148 and (1s,4s)-4-fluorocyclohexan-1-amine hydrochloride (35 mg, 0.228 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.47 (s, 1H), 8.32 (s, 1H), 8.28 (d, 1H), 8.18 (s, 1H), 6.58 (s, 1H), 5.31-5.27 (m, 1H), 4.88-4.76 (m, 1H), 4.04-4.01 (m, 2H), 3.67-3.61 (m, 2H), 3.46 (s, 1H), 2.12-1.92 (m, 4H), 1.90-1.65 (m, 8H); MS (ESI) m/z=407.1 (M+H)$^+$

Step 2. N$^2$-(2-(1-(Cyclopropylsulfonyl)-1H-pyrazol-4-yl)pyrimidin-4-yl)-N$^4$-((1s,4s)-4-fluorocyclohexyl)-5-(5-((tetrahydro-2H-pyran-4-yl)oxy) pyrazin-2-yl)pyridine-2,4-diamine The title compound (18 mg) as a white solid was prepared in the same fashion as Step 3 in Example 1, except that 2-chloro-N-((1s,4s)-4-fluorocyclohexyl)-5-(5-((tetrahydro-2H-pyran-4-yl)oxy) pyrazin-2-yl)pyridin-4-amine (41.89 mg, 0.103 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.65 (s, 1H), 8.49 (s, 1H), 8.46 (s, 1H), 8.44 (d, 1H), 8.38 (d, 1H), 8.33 (s, 1H), 8.19 (s, 1H), 7.51 (s, 1H), 7.31 (d, 1H), 7.06 (s, 1H), 5.29-5.27 (m, 1H), 4.85-4.73 (m, 1H), 4.05-4.01 (m, 2H), 3.68-3.63 (m, 3H), 2.84-2.82 (m, 1H), 2.13-2.10 (m, 2H), 2.01-1.75 (m, 10H), 1.56-1.54 (m, 2H), 1.27-1.22 (m, 2H); MS (ESI) m/z=636.2 (M+H)$^+$

Example 152. N$^2$-(2-(1-(Cyclopropylsulfonyl)-1H-pyrazol-4-yl)pyrimidin-4-yl)-N$^4$-((1s,4s)-4-fluorocyclohexyl)-5-(5-((tetrahydrofuran-3-yl)oxy) pyrazin-2-yl)pyridine-2,4-diamine

Step 1. 2-Chloro-N-((1s,4s)-4-fluorocyclohexyl)-5-(5-((tetrahydrofuran-3-yl)oxy) pyrazin-2-yl)pyridin-4-amine The title compound as a solid (79 mg) was prepared in the same fashion as Step 2 in Example 1, except that 2-(6-chloro-4-fluoropyridin-3-yl)-5-((tetrahydrofuran-3-yl)oxy)pyrazine (45 mg, 0.152 mmol) prepared in Step 2 of Example 149 and (1s,4s)-4-fluorocyclohexan-1-amine hydrochloride (35 mg, 0.228 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.49 (s, 1H), 8.33 (s, 1H), 8.28 (d, 1H), 8.20 (s, 1H), 6.59 (S, 1H), 5.61-5.60 (m, 1H), 4.88-4.75 (m, 1H), 4.10-3.94 (m, 5H), 3.46 (s, 1H), 2.34-2.30 (m, 1H), 2.21-2.18 (m, 1H), 2.06-2.04 (m, 2H), 1.93-1.90 (m, 1H), 1.78-1.68 (m, 4H); MS (ESI) m/z=393.1 (M+H)$^+$

Step 2. N²-(2-(1-(Cyclopropylsulfonyl)-1H-pyrazol-4-yl)pyrimidin-4-yl)-N⁴-((1s,4s)-4-fluorocyclohexyl)-5-(5-((tetrahydrofuran-3-yl)oxy) pyrazin-2-yl)pyridine-2,4-diamine The title compound (17 mg) as a white solid was prepared in the same fashion as Step 3 in Example 1, 2-chloro-N-((1s,4s)-4-fluorocyclohexyl)-5-(5-((tetrahydrofuran-3-yl)oxy) pyrazin-2-yl)pyridin-4-amine (40 mg. 0.103 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 8.65 (s, 1H), 8.50 (s, 1H), 8.46 (s, 1H), 8.44 (d, 1H), 8.37-8.35 (m, 2H), 8.21 (s, 1H), 7.40 (s, 1H), 7.32 (d, 1H), 7.04 (s, 1H), 6.00 (s, 1H), 4.85-4.73 (m, 1H), 4.11-3.95 (m, 5H), 3.63-3.61 (m, 1H), 2.84-2.82 (m, 1H), 2.34-2.31 (m, 1H), 2.22-2.19 (m, 1H), 2.05-1.96 (m, 4H), 1.84-1.74 (m, 4H), 1.54-1.52 (m, 2H), 1.25-1.20 (m, 2H); MS (ESI) m/z=622.2 (M+H)⁺

Example 153. (1s,4s)-4-((2-((2-(1-(Cyclopropylsulfonyl)-1H-pyrazol-4-yl)pyrimidin-4-yl)amino)-5-(5-((1-(2-fluoroethyl) piperidin-4-yl)oxy) pyrazin-2-yl)pyridin-4-yl)amino)-1-methylcyclohexan-1-ol

Step 1. tert-Butyl 4-((5-bromopyrazin-2-yl)oxy)piperidine-1-carboxylate

The title compound (548 mg) as an off-white solid was prepared in the same fashion as Step 1 in Example 144, except that 1-(tert-butoxy carbonyl)-4-hydroxypiperidine (372 mg, 1.85 mmol) was used instead of 4-hydroxy-1-methylpiperidine. ¹H-NMR (CDCl₃, 400 MHz) δ 8.16 (s, 1H), 8.00 (s, 1H), 5.15 (s, 1H), 3.79-3.76 (m, 2H), 3.33-3.26 (m, 2H), 1.97 (s, 2H), 1.76-1.73 (m, 2H), 1.48 (s, 9H)

Step 2. tert-Butyl 4-((5-(6-chloro-4-fluoropyridin-3-yl) pyrazin-2-yl)oxy)piperidine-1-carboxylate The title compound as a solid (431 mg) was prepared in the same fashion as Step 1 in Example 1 except that tert-butyl 4-((5-bromopyrazin-2-yl)oxy)piperidine-1-carboxylate (545 mg, 1.521 mmol) prepared in Step 1 was used instead of 1-((6-bromopyridin-3-yl)methyl)-4-methylpiperazine. ¹H-NMR (CDCl₃, 400 MHz) δ 9.01 (d, 1H), 8.54 (s, 1H), 8.32 (s, 1H), 7.22 (d, 1H), 5.28-5.27 (m, 1H), 3.83-3.80 (m, 2H), 3.35-3.29 (m, 2H), 2.02 (s, 2H), 1.83-1.76 (m, 2H), 1.49 (s, 9H)

Step 3. 2-(6-Chloro-4-fluoropyridin-3-yl)-5-(piperidin-4-yloxy)pyrazine

TFA (794 uL, 10.37 mmol) was added to the solution of tert-butyl 4-((5-(6-chloro-4-fluoropyridin-3-yl) pyrazin-2-yl)oxy)piperidine-1-carboxylate (424 mg, 1.037 mmol) prepared in Step 2 in DCM (4 mL). The reaction mixture was stirred for 1.5 hours at room temperature. The reaction mixture was dissolved in DCM and evaporated. The crude product was purified by column chromatography (MeOH/EA=0-45%) to yield 2-(6-chloro-4-fluoropyridin-3-yl)-5-(piperidin-4-yloxy)pyrazine (402 mg) as a white solid. ¹H-NMR (MeOD, 400 MHz) δ 8.95 (d, 1H), 8.62 (s, 1H), 8.42 (s, 1H), 7.53 (d, 1H), 5.47-5.46 (m, 1H), 3.49-3.43 (m, 2H), 3.32-3.26 (m, 2H), 2.31-2.26 (m, 2H), 2.17-2.12 (m, 2H); MS (ESI) m/z=308.9 (M+H)⁺

Step 4. 2-(6-Chloro-4-fluoropyridin-3-yl)-5-((1-(2-fluoroethyl) piperidin-4-yl)oxy)pyrazine The reaction mixture of 2-(6-chloro-4-fluoropyridin-3-yl)-5-(piperidin-4-yloxy)pyrazine (130 mg, 0.421 mmol) prepared in Step 3, 1-fluoro-2-iodoethane (81 mg, 0.463 mmol), and cesium carbonate (343 mg, 1.053 mmol) in DMF (2 mL) was stirred at 60° C. for 19 hours. The reaction mixture was dissolved in EA, washed by water, dried over MgSO₄, and then concentrated. The crude product was purified by column chromatography (EA/n-Hex=40-100%) to yield 2-(6-chloro-4-fluoropyridin-3-yl)-5-((1-(2-fluoroethyl) piperidin-4-yl)oxy)pyrazine (20 mg) as a yellow solid. ¹H-NMR (CDCl₃, 400 MHz) δ 8.86 (d, 1H), 8.61 (s, 1H), 8.45 (s, 1H), 7.81 (d, 1H), 5.08-5.05 (m, 1H), 4.59 (t 1H), 4.47 (t, 1H), 2.80 (s, 2H), 2.77-2.72 (m, 1H), 2.67-2.61 (m, 1H), 2.33 (t, 2H), 2.00 (s, 2H), 1.74-1.72 (m, 2H), 1.23 (s, 1H); MS (ESI) m/z=355.0 (M+H)⁺

Step 5. (1s,4s)-4-((2-Chloro-5-(5-((1-(2-fluoroethyl) piperidin-4-yl)oxy) pyrazin-2-yl)pyridin-4-yl) amino)-1-methylcyclohexan-1-ol The title compound as a white solid (20 mg) was prepared in the same fashion as Step 2 in Example 1, except that 2-(6-chloro-4-fluoropyridin-3-yl)-5-((1-(2-fluoroethyl) piperidin-4-yl)oxy)pyrazine (19 mg, 0.054 mmol) prepared in Step 4 and cis-4-amino-1-methylcyclohexan-1-ol (10 mg, 0.08 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl₃, 400 MHz) δ 8.44 (s, 1H), 8.28 (S, 1H), 8.15-8.12 (d, 2H), 6.56 (s, 1H), 5.12-5.10 (m, 1H), 4.67 (t, 1H), 4.55 (t, 1H), 3.33 (s, 1H), 2.94 (s, 2H), 2.87 (t, 1H), 2.80 (t, 1H), 2.74 (t, 2H), 2.08-2.05 (m, 2H), 1.98-1.90 (m, 4H), 1.82-1.70 (m, 9H), 1.30 (s, 3H); MS (ESI) m/z=464.1 (M+H)⁺

Step 6. (1s,4s)-4-((2-((2-(1-(Cyclopropylsulfonyl)-1H-pyrazol-4-yl)pyrimidin-4-yl)amino)-5-(5-((1-(2-fluoroethyl) piperidin-4-yl)oxy) pyrazin-2-yl)pyridin-4-yl)amino)-1-methylcyclohexan-1-ol The title compound (3 mg) as a white solid was prepared in the same fashion as Step 3 in Example 1, except that (1s,4s)-4-((2-chloro-5-(5-((1-(2-fluoroethyl) piperidin-4-yl)oxy) pyrazin-2-yl)pyridin-4-yl)amino)-1-methylcyclohexan-1-ol (19 mg, 0.049 mmol) prepared in Step 5 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 8.66 (s, 1H), 8.47 (d, 2H), 8.44 (d, 1H), 8.31 (s, 1H), 8.19 (d, 1H), 8.17 (s, 1H), 7.43 (s, 1H), 7.38 (d, 1H), 6.96 (s, 1H), 5.12 (s, 1H), 4.67 (t, 1H), 4.55 (t, 1H), 3.50 (s, 2H), 2.89-2.79 (m, 3H), 2.73 (t, 1H), 2.48 (t, 2H), 2.10 (s, 2H), 2.00-1.89 (m, 4H), 1.75-1.70 (m, 4H), 1.62 (s, 1H), 1.55-1.53 (m, 3H), 1.32 (s, 3H), 1.23-1.19 (m, 2H); MS (ESI) m/z=693.3 (M+H)⁺

Example 154. (1s,4s)-4-((2-((2-(1-(Cyclopropylsulfonyl)-1H-pyrazol-4-yl)pyrimidin-4-yl)amino)-5-(5-((4-fluoro-1-methylpiperidin-4-yl) methoxy) pyrazin-2-yl)pyridin-4-yl)amino)-1-methylcyclohexan-1-ol

Step 1. 2-Bromo-5-((4-fluoro-1-methylpiperidin-4-yl) methoxy)pyrazine

The title compound as a solid (154 mg) was prepared in the same fashion as Step 1 in Example 144 except that 4-fluoro-1-methyl-4-piperidinemethanol (93 mg, 0.631 mmol) was used instead of 4-hydroxy-1-methylpiperidine. $^1$H-NMR (CDCl$_3$, 400 MHz) δ 8.18 (s, 1H), 8.09 (s, 1H), 4.35 (d, 2H), 2.73-2.70 (m, 2H), 2.38-2.33 (m, 5H), 2.05-1.99 (m, 2H), 1.92-1.76 (m, 2H)

Step 2. 2-(6-Chloro-4-fluoropyridin-3-yl)-5-((4-fluoro-1-methylpiperidin-4-yl) methoxy)pyrazine The title compound as a solid (122 mg) was prepared in the same fashion as Step 1 in Example 1 except that 2-bromo-5-((4-fluoro-1-methylpiperidin-4-yl) methoxy)pyrazine (150 mg. 0.493 mmol) prepared in Step 1 was used instead of 1-((6-bromopyridin-3-yl)methyl)-4-methylpiperazine. $^1$H-NMR (CDCl$_3$, 400 MHz) δ 9.00 (d, 1H), 8.55 (s, 1H), 8.41 (s, 1H), 7.22 (d, 1H), 4.45 (d, 2H), 2.75-2.72 (m, 3H), 2.40-2.38 (m, 2H), 1.09-2.03 (m, 3H), 1.92-1.83 (m, 3H)

Step 3. (1s,4s)-4-((2-Chloro-5-(5-((4-fluoro-1-methylpiperidin-4-yl) methoxy) pyrazin-2-yl)pyridin-4-yl)amino)-1-methylcyclohexan-1-ol The title compound as a white solid (60 mg) was prepared in the same fashion as Step 2 in Example 1, except that 2-(6-chloro-4-fluoropyridin-3-yl)-5-((4-fluoro-1-methylpiperidin-4-yl) methoxy)pyrazine (60 mg, 0.169 mmol) prepared in Step 2 and cis-4-amino-1-methylcyclohexan-1-ol (33 mg, 0.254 mmol) were used instead of 6'-chloro-4'-fluoro-5-((4-methylpiperazin-1-yl)methyl)-2,3'-bipyridine and (4-methylpiperidin-4-yl)methanol. 1H-NMR (CDCl$_3$, 400 MHz) δ 8.47 (s, 1H), 8.30 (s, 1H), 8.25 (s, 1H), 8.12 (d, 1H), 6.58 (s, 1H), 4.45 (s, 1H), 4.41 (s, 1H), 3.32 (s, 1H), 2.74-2.71 (m, 2H), 2.39-2.35 (m, 5H), 2.08-2.02 (m, 3H), 1.94-1.86 (m, 3H), 1.82-1.60 (m, 5H), 1.31-1.25 (m, 4H), 1.11 (s, 1H); MS (ESI) m/z=464.2 (M+H)$^+$ Step 4. (1s,4s)-4-((2-((2-(1-(Cyclopropylsulfonyl)-1H-pyrazol-4-yl)pyrimidin-4-yl)amino)-5-(5-((4-fluoro-1-methylpiperidin-4-yl) methoxy) pyrazin-2-yl)pyridin-4-yl)amino)-1-methylcyclohexan-1-ol The title compound (5 mg) as a white solid was prepared in the same fashion as Step 3 in Example 1, except that (1s,4s)-4-((2-chloro-5-(5-((4-fluoro-1-methylpiperidin-4-yl) methoxy) pyrazin-2-yl)pyridin-4-yl)amino)-1-methylcyclohexan-1-ol (40 mg, 0.086 mmol) prepared in Step 3 was used instead of (1-(6'-chloro-5-((4-methylpiperazin-1-yl) methyl)-[2,3'-bipyridin]-4'-yl)-4-methylpiperidin-4-yl) methanol. $^1$H-NMR (CDCl$_3$, 400 MHz) δ 8.66 (s, 1H), 8.48 (s, 2H), 8.44 (d, 1H), 8.32 (s, 1H), 8.26 (s, 1H), 8.16 (d, 1H), 7.39 (s, 1H), 6.94 (s, 1H), 4.43 (d, 2H), 3.53 (s, 1H), 3.50 (s, 1H), 2.84-2.82 (m, 1H), 2.74-2.71 (m, 2H), 2.40-2.35 (m, 5H), 2.09-1.83 (m, 7H), 1.75-1.72 (m, 3H), 1.69 (s, 1H), 1.58-1.54 (m, 2H), 1.32 (s, 3H), 1.26-1.21 (m, 2H); MS (ESI) m/z=693.3 (M+H)$^+$ Example 155. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-ol Step 1. 6'-Chloro-4'-(((1s,4s)-4-hydroxy-4-methylcyclohexyl)amino)-[2,3'-bipyridin]-5-ol The title compound as a solid (60 mg) was prepared in the same fashion as Step 2 in Reference Example 1, except that 6'-chloro-4'-fluoro-[2,3'-bipyridin]-5-ol (55 mg, 0.245 mmol) prepared in Reference Example 4 was used instead of 6'-chloro-4'-fluoro-5-((1-methylpiperidin-4-yl)oxy)-2,3'-bipyridine. MS (ESI) m/z=334.1 (M+H)$^+$ Step 2. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-ol The title compound as a pale yellow solid (2.2 mg) was prepared in the same fashion as Step 3 in Example 1, except that 6'-chloro-4'-(((1s,4s)-4-hydroxy-4-methylcyclohexyl) amino)-[2,3'-bipyridin]-5-ol (42 mg. 0.124 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.09 (s, 1H), 9.95 (s, 1H), 9.11 (s, 1H), 8.64 (s, 1H), 8.46 (s, 1H), 8.41 (d, 1H), 8.36 (s, 1H), 8.15 (d, 1H), 7.79 (d, 1H), 7.29 (dd, 1H), 4.19 (s, 1H), 3.28-3.21 (m, 1H), 1.84-1.81 (m, 2H), 1.63-1.56 (m, 4H), 1.45-1.39 (m, 2H), 1.34-1.32 (m, 2H), 1.25-1.23 (m, 2H), 1.13 (s, 3H)

Example 156. (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol Step 1. (1s,4s)-4-((6'-Chloro-5-(methylsulfonyl)-[2,3'-bipyridin]-4'-yl)amino)-1-methylcyclohexan-1-ol The title compound as a solid (96 mg) was prepared in the same fashion as Step 2 in Reference Example 1, except that 6'-chloro-4'-fluoro-5-(methylsulfonyl)-2,3'-bipyridine (70 mg. 0.244 mmol) prepared in Reference Example 5 was used instead of 6'-chloro-4'-fluoro-5-((1-methylpiperidin-4-yl)oxy)-2,3'-bipyridine. MS (ESI) m/z=396.1 (M+H)$^+$ Step 2. (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol The title compound as a pale yellow solid (25 mg) was prepared in the same fashion as Step 3 in Example 1, except that (1s,4s)-4-((6'-chloro-5-(methylsulfonyl)-[2,3'-bipyridin]-4'-yl)amino)-1-methylcyclohexan-1-ol (49 mg, 0.124 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.15 (s, 1H), 9.52 (s, 1H), 9.07 (s, 1H), 8.70 (s, 1H), 8.67 (s, 1H), 8.48 (s, 1H), 8.46 (d, 1H), 8.29 (s, 2H), 7.52 (s, 1H), 7.41 (s, 1H), 4.21 (s, 1H), 3.28-3.22 (m, 1H), 1.99-1.97 (m, 2H), 1.84-1.57 (m, 4H), 1.46-1.40 (m, 2H), 1.34-1.32 (m, 2H), 1.26-1.24 (m, 2H), 1.17 (s, 3H); MS (ESI) m/z=625.2 (M+H)$^+$ Example 157. N$^{6'}$-(2-(1-(Cyclopropylsulfonyl)-1H-pyrazol-4-yl)pyrimidin-4-yl)-N$^{4'}$-((1s,4s)-4-((2-fluoroethyl)amino)cyclohexyl)-5-(methylsulfonyl)-[2,3'-bipyridine]-4',6'-diamine Step 1. (1s,4s)—N$^1$-(6'-Chloro-5-(methylsulfonyl)-[2,3'-bipyridin]-4'-yl)-N$^4$-(2-fluoroethyl)cyclohexane-1,4-diamine The title compound as a solid (89 mg) was prepared in the same fashion as Step 2 in Reference Example 1, except that 6'-chloro-4'-fluoro-5-(methylsulfonyl)-2,3'-bipyridine (70 mg, 0.244 mmol) prepared in Reference Example 5 and (1s,4s)—N¹-(2-fluoroethyl)cyclohexane-1,4-diamine (59 mg, 0.366 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=427.1 (M+H)⁺

Step 2. N⁶'-(2-(1-(Cyclopropylsulfonyl)-1H-pyrazol-4-yl)pyrimidin-4-yl)-N⁴'-((1s,4s)-4-((2-fluoroethyl)amino)cyclohexyl)-5-(methylsulfonyl)-[2,3'-bipyridine]-4',6'-diamine The title compound as a pale yellow solid (27 mg) was prepared in the same fashion as Step 3 in Example 1, except that (1s,4s)—N¹-(6'-chloro-5-(methylsulfonyl)-[2,3'-bipyridin]-4'-yl)-N⁴-(2-fluoroethyl)cyclohexane-1,4-diamine (48 mg, 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.89 (d, 1H), 9.12 (d, 1H), 8.66 (s, 1H), 8.57 (s, 1H), 8.47 (s, 1H), 8.44 (d, 1H), 8.24 (dd, 1H), 7.95 (d, 1H), 7.65 (s, 1H), 7.34 (s, 1H), 7.10 (d, 1H), 4.64 (t, 1H), 4.52 (t, 1H), 3.91 (brs, 1H), 3.18 (s, 3H), 3.00 (t, 1H), 2.93 (t, 1H), 2.88-2.82 (m, 1H), 2.71-2.66 (m, 1H), 2.07-2.05 (m, 2H), 1.88-1.82 (m, 4H), 1.57-1.43 (m, 4H), 1.26-1.21 (m, 2H); MS (ESI) m/z=656.2 (M+H)⁺

Example 158. ((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)methanol Step 1. ((1s,4s)-4-((6'-Chloro-5-(methylsulfonyl)-[2,3'-bipyridin]-4'-yl)amino)cyclohexyl)methanol The title compound as a solid (88 mg) was prepared in the same fashion as Step 2 in Reference Example 1, except that 6'-chloro-4'-fluoro-5-(methylsulfonyl)-2,3'-bipyridine (70 mg, 0.244 mmol) prepared in Reference Example 5 and ((1s,4s)-4-aminocyclohexyl)methanol (47 mg, 0.366 mmol) were used instead of 6'-chloro-4'-fluoro-5-((1-methylpiperidin-4-yl)oxy)-2,3'-bipyridine and cis-4-amino-1-methylcyclohexanol. 1H-NMR (DMSO-d₆, 400 MHz) δ 9.94 (d, 1H), 9.08 (d, 1H), 8.69 (s, 1H), 8.41-8.34 (m, 2H), 6.82 (s, 1H), 4.50 (t, 1H), 3.94-3.91 (m, 1H), 3.29 (t, 2H), 1.76-1.72 (m, 2H), 1.63-1.57 (m, 4H), 1.49-1.46 (m, 1H), 1.28-1.25 (m, 2H)

Step 2. ((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)methanol The title compound as a pale yellow solid (48.6 mg) was prepared in the same fashion as Step 3 in Example 1, except that ((1s,4s)-4-((6'-chloro-5-(methylsulfonyl)-[2,3'-bipyridin]-4'-yl)amino)cyclohexyl)methanol (86 mg, 0.218 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 10.02 (d, 1H), 9.08 (d, 1H), 8.66 (s, 1H), 8.58 (s, 1H), 8.46 (s, 1H), 8.42 (d, 1H), 8.23 (dd, 1H), 7.96 (d, 1H), 7.93 (d, 1H), 7.41 (s, 1H), 7.06 (d, 1H), 4.02 (brs, 1H), 3.56 (d, 2H), 3.17 (s, 3H), 2.88-2.82 (m, 1H), 2.05-2.03 (m, 2H), 1.86-1.75 (m, 5H), 1.56-1.52 (m, 2H), 1.41-1.32 (m, 2H), 1.28-1.21 (m, 2H); MS (ESI) m/z=625.1 (M+H)⁺

Example 159. N⁶'-(2-(1-(Cyclopropylsulfonyl)-1H-pyrazol-4-yl)pyrimidin-4-yl)-N⁴'-((1s,4s)-4-((dimethylamino)methyl)cyclohexyl)-5-(methylsulfonyl)-[2,3'-bipyridine]-4',6'-diamine Step 1. 6'-chloro-N-((1s,4s)-4-((dimethylamino)methyl)cyclohexyl)-5-(methylsulfonyl)-[2,3'-bipyridin]-4'-amine The title compound as a solid (89 mg) was prepared in the same fashion as Step 2 in Reference Example 1, except that 6'-chloro-4'-fluoro-5-(methylsulfonyl)-2,3'-bipyridine (70 mg. 0.244 mmol) prepared in Reference Example 5 and (1s,4s)-4-((dimethylamino)methyl)cyclohexan-1-amine dihydrochloride (84 mg, 0.366 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=423.1 (M+H)⁺

Step 2. N⁶'-(2-(1-(Cyclopropylsulfonyl)-1H-pyrazol-4-yl)pyrimidin-4-yl)-N⁴'-((1s,4s)-4-((dimethylamino)methyl)cyclohexyl)-5-(methylsulfonyl)-[2,3'-bipyridine]-4',6'-diamine The title compound as a pale yellow solid (44.2 mg) was prepared in the same fashion as Step 3 in Example 1, except that 6'-chloro-N-((1s,4s)-4-((dimethylamino)methyl)cyclohexyl)-5-(methylsulfonyl)-[2,3'-bipyridin]-4'-amine (88 mg. 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 10.97 (d, 1H), 9.08 (s, 1H), 8.67 (s, 1H), 8.56 (s, 1H), 8.47 (s, 1H), 8.43 (d, 1H), 8.24 (d, 1H), 7.97 (d, 1H), 7.70 (s, 1H), 7.34 (s, 1H), 7.11 (d, 1H), 4.00 (brs, 1H), 3.17 (s, 3H), 2.88-2.82 (m, 1H), 2.24 (s, 6H), 2.16 (d, 2H), 2.03-2.00 (m, 2H), 1.85-1.73 (m, 5H), 1.57-1.52 (m, 2H), 1.28-1.21 (m, 4H); MS (ESI) m/z=652.2 (M+H)⁺

Example 160. 2-((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)propan-2-ol Step 1. 2-((1s,4s)-4-((6'-Chloro-5-(methylsulfonyl)-[2,3'-bipyridin]-4'-yl)amino)cyclohexyl)propan-2-ol The title compound as a solid (152 mg) was prepared in the same fashion as Step 2 in Reference Example 1, except that 6'-chloro-4'-fluoro-5-(methylsulfonyl)-2,3'-bipyridine (100 mg, 0.349 mmol) prepared in Reference Example 5 and 2-((1s,4s)-4-aminocyclohexyl)propan-2-ol (82 mg, 0.523 mmol) were used instead of 6'-chloro-4'-fluoro-5-((1-methylpiperidin-4-yl)oxy)-2,3'-bipyridine and cis-4-amino-1-methylcyclohexanol. 1H-NMR (CDCl₃, 400 MHz) δ 9.87 (d, 1H), 9.07 (d, 1H), 8.53 (d, 1H), 8.27 (dt, 1H), 7.98 (dd, 1H), 6.64 (d, 1H), 3.86-3.84 (m, 1H), 3.15 (s, 3H), 2.04-1.91 (m, 2H), 1.81-1.78 (m, 2H), 1.68-1.61 (m, 2H), 1.43-1.30 (m, 3H), 1.22 (s, 6H)

Step 2. 2-((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)propan-2-ol The title compound as a pale yellow solid (52 mg) was prepared in the same fashion as Step 3 in Example 1, except that 2-((1s,4s)-4-((6'-chloro-5-(methylsulfonyl)-[2,3'-bipyridin]-4'-yl)amino)cyclohexyl)propan-2-ol (141 mg, 0.332 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.00 (d, 1H), 9.07 (d, 1H), 8.66 (s, 1H), 8.58 (s, 1H), 8.47 (s, 1H), 8.44 (d, 1H), 8.24 (dd, 1H), 7.97 (d, 1H), 7.62 (s, 1H), 7.42 (s, 1H), 7.06 (d, 1H), 4.03 (brs, 1H), 3.16 (s, 3H), 2.88-2.82 (m, 1H), 2.13-2.10 (m, 2H), 1.84-1.76 (m, 4H), 1.57-1.53 (m, 2H), 1.48-1.40 (m, 2H), 1.29-1.22 (m, 8H); MS (ESI) m/z=6532 (M+H)$^+$ Example 161. (3-(((6'-((2-(1-(Cyclopropylsulfonyl)-1H-pyrazol-4-yl)pyrimidin-4-yl)amino)-6-fluoro-[2,3'-bipyridin]-4'-yl)amino)methyl) oxetan-3-yl)methanol Step 1. (3-(((6'-Chloro-6-fluoro-[2,3'-bipyridin]-4'-yl)amino)methyl) oxetan-3-yl)methanol The title compound as a solid (119 mg) was prepared in the same fashion as Step 2 in Reference Example 1, except that 6'-chloro-4',6-difluoro-2,3'-bipyridine (100 mg, 0.441 mmol) prepared in Reference Example 6 and (3-(aminomethyl) oxetan-3-yl)methanol (78 mg, 0.662 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (DMSO-d$_6$, 400 MHz) δ 8.68 (t, 1H), 8.47 (s, 1H), 8.11 (q, 1H), 7.89 (dd, 1H), 7.18 (dd, 1H), 6.87 (s, 1H), 5.14 (t, 1H), 4.35 (s, 4H), 3.70 (d, 2H), 3.52 (d, 2H)

Step 2. (3-(((6'-((2-(1-(Cyclopropylsulfonyl)-1H-pyrazol-4-yl)pyrimidin-4-yl)amino)-6-fluoro-[2,3'-bipyridin]-4'-yl)amino)methyl) oxetan-3-yl)methanol The title compound as a pale yellow solid (35.6 mg) was prepared in the same fashion as Step 3 in Example 1, except that (3-(((6'-chloro-6-fluoro-[2,3'-bipyridin]-4'-yl)amino)methyl) oxetan-3-yl)methanol (107 mg. 0.332 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.15 (s, 1H), 8.74 (t, 1H), 8.68 (s, 1H), 8.56 (s, 1H), 8.48 (s, 1H), 8.45 (d, 1H), 8.06 (q, 1H), 7.91 (dd, 1H), 7.51 (s, 1H), 7.44 (s, 1H), 7.08 (dd, 1H), 5.13 (t, 1H), 4.42 (brs, 4H), 3.75 (d, 2H), 3.59 (d, 2H), 3.30-3.23 (m, 1H), 1.36-1.32 (m, 2H), 1.27-1.22 (m, 2H); MS (ESI) m/z=553.2 (M+H)$^+$ Example 162. (4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-fluorocyclohexyl)methanol Step 1. (4-((6'-Chloro-6-fluoro-[2,3'-bipyridin]-4'-yl)amino)-1-fluorocyclohexyl)methanol The title compound as a solid (121 mg) was prepared in the same fashion as Step 2 in Reference Example 1, except that 6'-chloro-4',6-difluoro-2,3'-bipyridine (100 mg, 0.441 mmol) prepared in Reference Example 6 and (4-amino-1-fluorocyclohexyl)methanol (97 mg, 0.662 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (DMSO-d$_6$, 400 MHz) δ 8.48 (d, 1H), 8.46 (d 1H), 8.14-8.08 (m, 1H), 7.90 (d, 1H), 7.18 (d, 1H), 6.86 (s, 1H), 5.00 (t, 1H), 3.59 (brs, 1H), 3.43-3.41 (brs, 1H), 1.90-1.82 (m, 4H), 1.71-1.55 (m, 2H), 1.49-1.41 (m, 2H)

Step 2. (4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-fluorocyclohexyl)methanol The title compound as a pale yellow solid (53.7 mg) was prepared in the same fashion as Step 3 in Example 1, except that (4-((6'-chloro-6-fluoro-[2,3'-bipyridin]-4'-yl)amino)-1-fluorocyclohexyl)methanol (117 mg. 0.332 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.08 (s, 1H), 8.66 (s, 1H), 8.63 (d, 1H), 8.57 (s, 1H), 8.47 (s, 1H), 8.45 (d, 1H), 8.06 (q, 1H), 7.91 (dd, 1H), 7.64 (s, 1H), 7.24 (s, 1H), 7.09 (dd, 1H), 4.97 (t, 1H), 3.50-3.52 (m, 1H), 3.45 (d, 2H), 3.28-3.22 (m, 1H), 2.02-1.98 (m, 2H), 1.90-1.86 (m, 2H), 1.66-1.52 (m, 4H), 1.37-1.28 (m, 4H); MS (ESI) m/z=583.1 (M+H)$^+$ Example 163. 2-((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)propan-2-ol Step 1. 2-((1s,4s)-4-((6'-Chloro-6-fluoro-[2,3'-bipyridin]-4'-yl)amino)cyclohexyl)propan-2-ol The title compound as a solid (171 mg) was prepared in the same fashion as Step 2 in Reference Example 1, except that 6'-chloro-4',6-difluoro-2,3'-bipyridine (100 mg, 0.441 mmol) prepared in Reference Example 6 and 2-((1s,4s)-4-aminocyclohexyl)propan-2-ol (104 mg. 0.662 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=364.1 (M+H)$^+$ Step 2. 2-((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)propan-2-ol The title compound as a pale yellow solid (68.4 mg) was prepared in the same fashion as Step 3 in Example 1, except that 2-((1s,4s)-4-((6'-chloro-6-fluoro-[2,3'-bipyridin]-4'-yl)amino)cyclohexyl)propan-2-ol (121 mg, 0.332 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.34 (d, 1H), 8.66 (s, 1H), 8.50 (s, 1H), 8.47 (s, 1H), 8.41 (d, 1H), 7.87 (q, 1H), 7.72 (s, 1H), 7.65 (dd, 1H), 7.32 (s, 1H), 7.09 (d, 1H), 6.83 (dd, 1H), 4.00 (brs, 1H), 2.88-2.82 (m, 1H), 2.13-2.10 (m, 2H), 1.80-1.74 (m, 4H), 1.57-1.48 (m, 4H), 1.27-1.23 (m, 8H); MS (ESI) m/z=593.2 (M+H)$^+$ Example 164. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-N,N-dimethyl-[2,3'-bipyridine]-5-sulfonamide Step 1. 6'-Chloro-4'-fluoro-N,N-dimethyl-[2,3'-bipyridine]-5-sulfonamide The title compound as a solid (221 mg) was prepared in the same fashion as Reference Example 5, except that 6-bromo-N,N-dimethylpyridine-3-sulfonamide (300 mg, 1.132 mmol) was used instead of 2-bromo-5-(methylsulfonyl)pyridine. MS (ESI) m/z=316.0 (M+H)+

Step 2. 6'-Chloro-4'-(((1s,4s)-4-hydroxy-4-methylcyclohexyl)amino)-N,N-dimethyl-[2,3'-bipyridine]-5-sulfonamide The title compound as a solid (87 mg) was prepared in the same fashion as Step 2 in Reference Example 1, except that 6'-chloro-4'-fluoro-N,N-dimethyl-[2,3'-bipyridine]-5-sulfonamide (70 mg, 0.22 mmol) prepared in Step 1 was used instead of 6'-chloro-4'-fluoro-5-((1-methylpiperidin-4-yl)oxy)-2,3'-bipyridine. MS (ESI) m/z=425.1 (M+H)+

Step 3. 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-N,N-dimethyl-[2,3'-bipyridine]-5-sulfonamide The title compound as a pale yellow solid (11 mg) was prepared in the same fashion as Step 3 in Example 1, except that 6'-chloro-4'-(((1s,4s)-4-hydroxy-4-methylcyclohexyl)amino)-N,N-dimethyl-[2,3'-bipyridine]-5-sulfonamide (79 mg, 0.19 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.57 (d, 1H), 8.94 (s, 1H), 8.67 (s, 1H), 8.54 (s, 1H), 8.49 (s, 1H), 8.45 (d, 1H), 8.09 (d, 1H), 7.91 (d, 1H), 7.57 (s, 1H), 7.28 (s, 1H), 7.10 (s, 1H), 3.54 (brs, 1H), 2.82 (s, 7H), 2.03-2.00 (m, 2H), 1.84-1.75 (m, 4H), 1.64-1.54 (m, 4H), 1.33 (s, 3H), 1.26-1.22 (m, 2H)

Example 165. 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-N,N-dimethyl-[2,3'-bipyridine]-5-sulfonamide Step 1. 6'-Chloro-4'-(((1s,4s)-4-(2-hydroxypropan-2-yl)cyclohexyl)amino)-N,N-dimethyl-[2,3'-bipyridine]-5-sulfonamide The title compound as a solid (91 mg) was prepared in the same fashion as Step 2 in Reference Example 1, except that 6'-chloro-4'-fluoro-N,N-dimethyl-[2,3'-bipyridine]-5-sulfonamide (70 mg, 0.22 mmol) prepared in Step 1 of Example 164 and 2-((1s,4s)-4-aminocyclohexyl)propan-2-ol (52 mg, 0.33 mmol) were used instead of 6'-chloro-4'-fluoro-5-((1-methylpiperidin-4-yl)oxy)-2,3'-bipyridine and cis-4-amino-1-methylcyclohexanol. 1H-NMR (CDCl$_3$, 400 MHz) δ 9.92 (d, 1H), 8.93 (d, 1H), 8.54 (s, 1H), 8.13 (dd, 1H), 7.96 (d, 1H), 6.64 (s, 1H), 3.88-3.86 (m, 1H), 2.80 (s, 6H), 2.04-2.00 (m, 2H), 1.82-1.70 (m, 2H), 1.68-1.62 (m, 1H), 1.44-1.30 (m, 4H), 1.22 (s, 6H)

Step 2. 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-N,N-dimethyl-[2,3'-bipyridine]-5-sulfonamide The title compound as a pale yellow solid (41.3 mg) was prepared in the same fashion as Step 3 in Example 1, except that 6'-chloro-4'-(((1s,4s)-4-(2-hydroxypropan-2-yl)cyclohexyl)amino)-N,N-dimethyl-[2,3'-bipyridine]-5-sulfonamide (85 mg. 0.19 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.07 (s, 1H), 8.92 (s, 1H), 8.67 (d, 1H), 8.58 (d, 1H), 8.48 (d, 1H), 8.43 (d, 1H), 8.09 (d, 1H), 7.96 (d, 1H), 7.64 (s, 1H), 7.43 (s, 1H), 7.06 (s, 1H), 4.05 (s, 1H), 2.85-2.82 (m, 1H), 2.80 (s, 6H), 2.12-2.05 (m, 2H), 1.84-1.80 (m, 4H), 1.56-1.40 (m, 5H), 1.24-1.13 (m, 8H)

Example 166. 6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-N,N-dimethyl-[2,3'-bipyridine]-5-sulfonamide Step 1. 6'-Chloro-4'-(((1s,4s)-4-(hydroxymethyl)cyclohexyl)amino)-N,N-dimethyl-[2,3'-bipyridine]-5-sulfonamide The title compound as a solid (83 mg) was prepared in the same fashion as Step 2 in Reference Example 1, except that 6'-chloro-4'-fluoro-N,N-dimethyl-[2,3'-bipyridine]-5-sulfonamide (70 mg, 0.22 mmol) prepared in Step 1 of Example 164 and ((1s,4s)-4-aminocyclohexyl)methanol hydrochloride (155 mg, 0.33 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.84 (d, 1H), 8.95 (d, 1H), 8.53 (s, 1H), 8.13 (dd, 1H), 7.95 (d, 1H), 6.64 (s, 1H), 3.84-3.82 (m, 1H), 3.55 (d, 2H), 2.81 (s, 6H), 1.94-1.91 (m, 2H), 1.77-1.71 (m, 4H), 1.55 (brs, 1H), 1.40-1.30 (m, 2H)

Step 2. 6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-N,N-dimethyl-[2,3'-bipyridine]-5-sulfonamide The title compound as a pale yellow solid (18.9 mg) was prepared in the same fashion as Step 3 in Example 1, except that 6'-chloro-4'-(((1s,4s)-4-(hydroxymethyl)cyclohexyl)amino)-N,N-dimethyl-[2,3'-bipyridine]-5-sulfonamide (62 mg, 0.15 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.01 (d, 1H), 8.93 (d, 1H), 8.67 (s, 1H), 8.56 (s, 1H), 8.47 (s, 1H), 8.43 (d, 1H), 8.10 (dd, 1H), 7.94 (d, 1H), 7.72 (brs, 1H), 7.39 (s, 1H), 7.08 (d, 1H), 4.02 (brs, 1H), 3.55 (d, 2H), 2.88-2.82 (m, 1H), 2.82 (s, 6H), 2.07-2.04 (m, 2H), 1.86-1.75 (m, 5H), 1.57-1.53 (m, 2H), 1.41-1.33 (m, 2H), 1.29-1.21 (m, 2H); MS (ESI) m/z=654.2 (M+H)+

Example 167. (1s,4s)-4-((6'-((2-(1-(Cyclopropylsulfonyl)-1H-pyrazol-4-yl)pyrimidin-4-yl)amino)-4-(dimethylamino)-[2,3'-bipyridin]-4'-yl)amino)-1-methylcyclohexan-1-ol Step 1. 6'-Chloro-4'-fluoro-N,N-dimethyl-[2,3'-bipyridine]-4-amine The title compound as a white solid (74 mg) was prepared in the same fashion as Reference Example 5, except that 2-bromo-N,N-dimethyl-pyridin-4-amine (200 mg, 0.995 mmol) was used instead of 2-bromo-5-(methylsulfonyl)pyridine. MS (ESI) m/z=252.0 (M+H)+

Step 2. (1s,4s)-4-((6'-Chloro-4-(dimethylamino)-[2,3'-bipyridin]-4'-yl)amino)-1-methylcyclohexan-1-ol The title compound as a solid (92 mg) was prepared in the same fashion as Step 2 in Reference Example 1, except that 6'-chloro-4'-fluoro-N,N-dimethyl-[2,3'-bipyridine]-4-amine (70 mg, 0.278 mmol) prepared in Step 1 was used instead of 6'-chloro-4'-fluoro-5-((1-methylpiperidin-4-yl)oxy)-2,3'-bipyridine. MS (ESI) m/z=361.1 (M+H)+

Step 3. (1s,4s)-4-((6'-((2-(1-(Cyclopropylsulfonyl)-1H-pyrazol-4-yl)pyrimidin-4-yl)amino)-4-(dimethylamino)-[2,3'-bipyridin]-4'-yl)amino)-1-methylcyclohexan-1-ol The title compound as a pale yellow solid (25.2 mg) was prepared in the same fashion as Step 3 in Example 1, except that (1s,4s)-4-((6'-chloro-4-(dimethylamino)-[2,3'-bipyridin]-4'-yl)amino)-1-methylcyclohexan-1-ol (82 mg, 0.23 mmol) prepared in Step 2 was used instead of 6'-chloro-4'-fluoro-5-((1-methylpiperidin-4-yl)oxy)-2,3'-bipyridine. 1H-NMR (CDCl3, 400 MHz) δ 9.17 (s, 1H), 8.66 (s, 1H), 8.48 (s, 1H), 8.41 (d, 1H), 8.32 (s, 1H), 8.22 (d, 1H), 7.40 (d, 1H), 6.88 (s, 1H), 6.80 (d, 1H), 6.48 (dd, 1H), 3.45 (brs, 1H), 3.08 (s, 6H), 2.86-2.80 (m, 1H), 1.99-1.96 (m, 2H), 1.76-1.70 (m, 4H), 1.58-1.52 (m, 4H), 1.31 (s, 3H), 1.24-1.21 (m, 2H); MS (ESI) m/z=590.2 (M+H)+

Example 168. (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol Step 1. (1s,4s)-4-((6'-Chloro-5-(2-hydroxypropan-2-yl)-[2,3'-bipyridin]-4'-yl)amino)-1-methylcyclohexan-1-ol The title compound as a solid (120 mg) was prepared in the same fashion as Step 2 in Reference Example 1, except that 2-(6'-chloro-4'-fluoro-[2,3'-bipyridin]-5-yl)propan-2-ol (100 mg, 0.37 mmol) prepared in Reference Example 7 was used instead of 6'-chloro-4'-fluoro-5-((1-methylpiperidin-4-yl)oxy)-2,3'-bipyridine. MS (ESI) m/z=376.1 (M+H)+

Step 2. (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol The title compound as a pale yellow solid (40 mg) was prepared in the same fashion as Step 3 in Example 1, except that (1s,4s)-4-((6'-chloro-5-(2-hydroxypropan-2-yl)-[2,3'-bipyridin]-4'-yl)amino)-1-methylcyclohexan-1-ol (85 mg. 0.23 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl3, 400 MHz) δ 10.01 (s, 1H), 9.57 (s, 1H), 8.69 (s, 1H), 8.65 (s, 1H), 8.52 (s, 1H), 8.47 (s, 1H), 8.42 (d, 1H), 7.83 (d, 2H), 7.55 (brs, 1H), 7.29 (brs, 1H), 4.20 (s, 1H), 3.27-3.21 (m, 1H), 1.85-1.83 (m, 2H), 1.66-1.57 (m, 4H), 1.49 (s, 6H), 1.46-1.39 (m, 2H), 1.36-1.32 (m, 2H), 1.27-1.23 (m, 2H), 1.14 (s, 3H); MS (ESI) m/z=605.2 (M+H)+

Example 169. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)propan-2-ol Step 1. 2-(6'-Chloro-4'-(((1s,4s)-4-(2-hydroxypropan-2-yl)cyclohexyl)amino)-[2,3'-bipyridin]-5-yl)propan-2-ol The title compound as a solid (133 mg) was prepared in the same fashion as Step 2 in Reference Example 1, except that 2-(6'-chloro-4'-fluoro-[2,3'-bipyridin]-5-yl)propan-2-ol (100 mg, 0.37 mmol) prepared in Reference Example 7 and 2-((1s,4s)-4-aminocyclohexyl)propan-2-ol (88 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=404.2 (M+H)+

Step 2. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)propan-2-ol The title compound as a pale yellow solid (47.8 mg) was prepared in the same fashion as Step 3 in Example 1, except that 2-(6'-chloro-4'-(((1s,4s)-4-(2-hydroxypropan-2-yl)cyclohexyl)amino)-[2,3'-bipyridin]-5-yl)propan-2-ol (91 mg, 0.23 mmol) prepared in Step 1 was used instead of (1-(6'-chloro-5-((4-methylpiperazin-1-yl)methyl)-[2,3'-bipyridin]-4'-yl-4-methylpiperidin-4-yl)methanol. 1H-NMR (CDCl3, 400 MHz) δ 10.12 (d, 1H), 10.06 (s, 1H), 8.66 (d, 1H), 8.62 (s, 1H), 8.56 (s, 1H), 8.45 (s, 1H), 8.41 (d, 1H), 7.98-7.91 (m, 2H), 7.52 (brs, 1H), 7.37 (brs, 1H), 4.12 (s, 1H), 3.95 (brs, 1H), 3.31-3.25 (m, 1H), 1.98-1.95 (m, 2H), 1.81-1.63 (m, 4H), 1.47 (s, 6H), 1.35-1.26 (m, 7H), 1.07 (s, 6H); MS (ESI) m/z=633.3 (M+H)+

Example 170. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)propan-2-ol Step 1. 2-(6'-Chloro-4'-(((1s,4s)-4-(hydroxymethyl)cyclohexyl)amino)-[2,3'-bipyridin]-5-yl)propan-2-ol The title compound as a solid (140 mg) was prepared in the same fashion as Step 2 in Reference Example 1, except that 2-(6'-chloro-4'-fluoro-[2,3'-bipyridin]-5-yl)propan-2-ol (100 mg, 0.37 mmol) prepared in Reference Example 7 and ((1s,4s)-4-aminocyclohexyl)methanol hydrochloride (93 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=376.2 (M+H)+

Step 2. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)propan-2-ol The title compound as a pale yellow solid (28.7 mg) was prepared in the same fashion as Step 3 in Example 1, except that 2-(6'-chloro-4'-(((1s,4s)-4-(hydroxy methyl)cyclohexyl)amino)-[2,3'-bipyridin]-5-yl)propan-2-ol (132 mg. 0.35 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl3, 400 MHz) δ 10.11 (s, 1H), 8.71 (s, 1H), 8.66 (s, 1H), 8.46 (s, 1H), 8.45 (d, 1H), 8.38 (d, 1H), 7.87 (d, 1H), 7.72 (d, 1H), 7.32 (s, 1H), 7.09 (s, 1H), 3.98 (brs, 1H), 3.55 (d, 2H), 2.86-2.81 (m, 1H), 2.05-2.03 (m, 2H), 1.82-1.67 (m, 4H), 1.53-1.38 (m, 4H), 1.26-1.22 (m, 3H); MS (ESI) m/z=605.2 (M+H)+

Example 171. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)propan-2-ol Step 1. 2-(6'-Chloro-4'-(((1s,4s)-4-((dimethylamino)methyl)cyclohexyl)amino)-[2,3'-bipyridin]-5-yl)propan-2-ol The title compound as a solid (109 mg) was prepared in the same fashion as Step 2 in Reference Example 1, except that 2-(6'-chloro-4'-fluoro-[2,3'-bipyridin]-5-yl)propan-2-ol (100 mg, 0.37 mmol) prepared in Reference Example 7 and (1s,4s)-4-((dimethylamino)methyl)cyclohexan-1-amine dihydrochloride (129 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=403.2 (M+H)$^+$ Step 2. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)propan-2-ol The title compound as a pale yellow solid (21.7 mg) was prepared in the same fashion as Step 3 in Example 1, except that 2-(6'-chloro-4'-(((1s,4s)-4-((dimethylamino)methyl)cyclohexyl)amino)-[2,3'-bipyridin]-5-yl)propan-2-ol (106 mg, 0.26 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.06 (s, 1H), 8.69 (d, 2H), 8.45-8.37 (m, 3H), 7.88 (s, 1H), 7.72 (s, 1H), 7.30 (d, 2H), 7.08 (s, 1H), 3.95 (brs, 1H), 2.84 (brs, 1H), 2.23 (s, 6H), 2.17 (d, 2H), 2.01-1.98 (m, 2H), 1.74-1.53 (m, 7H), 1.30-1.23 (m, 4H); MS (ESI) m/z=632.3 (M+H)$^+$ Example 172. (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-N,N-dimethylcyclohexane-1-carboxamide Step 1. (1s,4s)-4-((6'-Chloro-5-(2-hydroxypropan-2-yl)-[2,3'-bipyridin]-4'-yl)amino)-N,N-dimethylcyclohexane-1-carboxamide The title compound as a solid (125 mg) was prepared in the same fashion as Step 2 in Reference Example 1, except that 2-(6'-chloro-4'-fluoro-[2,3'-bipyridin]-5-yl)propan-2-ol (100 mg, 0.37 mmol) prepared in Reference Example 7 and (1s,4s)-4-amino-N,N-dimethylcyclohexane-1-carboxamide (116 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=417.2 (M+H)$^+$ Step 2. (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-N,N-dimethylcyclohexane-1-carboxamide The title compound as a pale yellow solid (33.1 mg) was prepared in the same fashion as Step 3 in Example 1, except that (1s,4s)-4-((6'-chloro-5-(2-hydroxypropan-2-yl)-[2,3'-bipyridin]-4'-yl)amino)-N,N-dimethylcyclohexane-1-carboxamide (110 mg, 0.26 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.24 (d, 1H), 8.85 (d, 1H), 8.66 (s, 1H), 8.47 (s, 1H), 8.46 (d, 1H), 8.39 (d, 1H), 7.78 (dd, 1H), 7.71 (d, 1H), 7.38 (s, 1H), 7.04 (d, 1H), 4.00 (brs, 1H), 3.09 (s, 3H), 2.94 (s, 3H), 2.89-2.82 (m, 1H), 2.69-2.64 (m, 1H), 2.12-2.10 (m, 2H), 1.95-1.82 (m, 4H), 1.64 (s, 6H), 1.56-1.51 (m, 2H), 1.30-1.20 (m, 4H); MS (ESI) m/z=646.3 (M+H)$^+$ Example 173. 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol Step 1. 2-(6'-Chloro-4'-(((1s,4s)-4-fluorocyclohexyl)amino)-[2,3'-bipyridin]-5-yl)propan-2-ol The title compound as a solid (98 mg) was prepared in the same fashion as Step 2 in Reference Example 1, except that 2-(6'-chloro-4'-fluoro-[2,3'-bipyridin]-5-yl)propan-2-ol (74 mg, 0.28 mmol) prepared in Reference Example 7 and (1s,4s)-4-fluorocyclohexan-1-amine hydrochloride (64 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=364.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol The title compound as a pale yellow solid (9 mg) was prepared in the same fashion as Step 3 in Example 1, except that 2-(6'-chloro-4'-(((1s,4s)-4-fluorocyclohexyl)amino)-[2,3'-bipyridin]-5-yl)propan-2-ol (45 mg, 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.03 (s, 1H), 9.80 (br, 1H), 8.69 (s, 1H), 8.65 (s, 1H), 8.56 (s, 1H), 8.46 (s, 1H), 8.43 (d, 1H), 7.97-7.91 (m, 2H), 7.58 (br, 1H), 7.26 (br, 1H), 4.77 (d, 1H), 3.64-3.58 (m, 1H), 3.28-3.23 (m, 1H), 2.01-1.84 (m, 5H), 1.75-1.69 (m, 3H), 1.49 (s, 6H), 1.35-1.33 (m, 2H), 1.26-1.22 (m, 2H); MS (ESI) m/z=593.2 (M+H)$^+$ Example 174. 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)propan-2-ol Step 1. 2-(6'-Chloro-4'-((4-fluorocyclohexyl)amino)-[2,3'-bipyridin]-5-yl)propan-2-ol The title compound as a solid (98 mg) was prepared in the same fashion as Step 2 in Reference Example 1, except that 2-(6'-chloro-4'-fluoro-[2,3'-bipyridin]-5-yl)propan-2-ol (74 mg, 0.28 mmol) prepared in Reference Example 7 and 4-fluorocyclohexan-1-amine hydrochloride (64 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=364.2 (M+H)$^+$ Step 2. 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)propan-2-ol The title compound as a pale yellow solid (11.5 mg) was prepared in the same fashion as Step 3 in Example 1, except that 2-(6'-chloro-4'-((4-fluorocyclohexyl)amino)-[2,3'-bipyridin]-5-yl)propan-2-ol (45 mg, 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.02 (s, 1H), 9.75 (d, 1H), 8.68 (d, 1H), 8.65 (s, 1H), 8.55 (d, 1H), 8.46 (d, 1H), 8.44 (d, 1H), 7.97-7.90 (m, 2H), 7.59 (br, 1H), 7.25 (d, 1H), 4.82-4.68 (m, 1H), 3.64-3.60 (m, 1H), 3.29-3.23 (m, 1H), 2.11-2.02 (m, 1H), 1.97-1.84 (m, 4H), 1.76-1.65 (m, 2H), 1.54-1.52 (m, 7H), 1.49-1.36 (m, 4H); MS (ESI) m/z=593.2 (M+H)$^+$ Example 175. 2-(6'-((2-(1-(Cyclopropylsulfonyl)-1H-pyrazol-4-yl)pyrimidin-4-yl)amino)-4'-((4,4-difluorocyclohexyl)amino)-[2,3'-bipyridin]-5-yl)propan-2-ol Step 1. 2-(6'-Chloro-4'-((4,4-difluorocyclohexyl)amino)-[2,3'-bipyridin]-5-yl)propan-2-ol The title compound as a solid (100 mg) was prepared in the same fashion as Step 2 in Reference Example 1, except that 2-(6'-chloro-4'-fluoro-[2,3'-bipyridin]-5-yl)propan-2-ol (74 mg, 0.28 mmol) prepared in Reference Example 7 and 4,4-difluorocyclohexan-1-amine hydrochloride (72 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=382.2 (M+H)$^+$ Step 2. 2-(6'-((2-(1-(Cyclopropylsulfonyl)-1H-pyrazol-4-yl)pyrimidin-4-yl)amino)-4'-((4,4-difluorocyclohexyl)amino)-[2,3'-bipyridin]-5-yl)propan-2-ol The title compound as a pale yellow solid (6.5 mg) was prepared in the same fashion as Step 3 in Example 1, except that 2-(6'-chloro-4'-((4,4-difluorocyclohexyl)amino)-[2,3'-bipyridin]-5-yl)propan-2-ol (48 mg, 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.02 (s, 1H), 9.75 (d, 1H), 8.68 (d, 1H), 8.65 (s, 1H), 8.55 (d, 1H), 8.46 (d, 1H), 8.44 (d, 1H), 7.97-7.90 (m, 2H), 7.59 (br, 1H), 7.25 (d, 1H), 4.82-4.68 (m, 1H), 3.64-3.60 (m, 1H), 3.29-3.23 (m, 1H), 2.11-2.02 (m, 1H), 1.97-1.84 (m, 4H), 1.76-1.65 (m, 2H), 1.54-1.52 (m, 7H), 1.49-1.36 (m, 4H); MS (ESI) m/z=611.2 (M+H)$^+$ Example 176. 2-(6'-((2-(1-(Cyclopropylsulfonyl)-1H-pyrazol-4-yl)pyrimidin-4-yl)amino)-4'-((1-(2-fluoroethyl) piperidin-4-yl)amino)-[2,3'-bipyridin]-5-yl)propan-2-ol Step 1. 2-(6'-Chloro-4'-((1-(2-fluoroethyl) piperidin-4-yl)amino)-[2,3'-bipyridin]-5-yl)propan-2-ol The title compound as a solid (93 mg) was prepared in the same fashion as Step 2 in Reference Example 1, except that 2-(6'-chloro-4'-fluoro-[2,3'-bipyridin]-5-yl)propan-2-ol (70 mg, 0.26 mmol) prepared in Reference Example 7 and 1-(2-fluoroethyl) piperidin-4-amine hydrochloride (62 mg. 0.34 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.63 (d, 1H), 8.69 (d, 1H), 8.37 (s, 1H), 7.90 (dd, 1H), 7.69 (d, 1H), 6.57 (s, 1H), 4.65 (t, 1H), 4.53 (t, 1H), 3.49-3.46 (m, 1H), 2.90-2.88 (m, 2H), 2.78 (t, 1H), 2.71 (t, 1H), 2.39 (t, 2H), 2.08-2.06 (m, 2H), 1.74-1.69 (m, 2H), 1.65 (s, 6H)

Step 2. 2-(6'-((2-(1-(Cyclopropylsulfonyl)-1H-pyrazol-4-yl)pyrimidin-4-yl)amino)-4'-((1-(2-fluoroethyl) piperidin-4-yl)amino)-[2,3'-bipyridin]-5-yl)propan-2-ol The title compound as a pale yellow solid (23.4 mg) was prepared in the same fashion as Step 3 in Example 1, except that 2-(6'-chloro-4'-((1-(2-fluoroethyl) piperidin-4-yl) amino)-[2,3'-bipyridin]-5-yl)propan-2-ol (89 mg, 0.23 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.02 (s, 1H), 8.74 (s, 1H), 8.69 (s, 1H), 8.57 (s, 1H), 8.47 (s, 1H), 8.45 (d, 1H), 7.95 (s, 2H), 7.64 (brs, 1H), 7.20 (brs, 1H), 4.74-4.66 (m, 2H), 3.62 (brs, 1H), 3.27-3.23 (m, 1H), 2.81 (brs, 4H), 2.15 (brs, 2H), 1.70 (brs, 2H), 1.49 (s, 6H), 1.35-1.23 (m, 4H); MS (ESI) m/z=622.3 (M+H)$^+$ Example 177. 2-(6'-((2-(1-(Cyclopropylsulfonyl)-1H-pyrazol-4-yl)pyrimidin-4-yl)amino)-4'-((1-(2-fluoroethyl) piperidin-3-yl)amino)-[2,3'-bipyridin]-5-yl)propan-2-ol Step 1. 2-(6'-Chloro-4'-((1-(2-fluoroethyl) piperidin-3-yl)amino)-[2,3'-bipyridin]-5-yl)propan-2-ol The title compound as a solid (96 mg) was prepared in the same fashion as Step 2 in Reference Example 1, except that 2-(6'-chloro-4'-fluoro-[2,3'-bipyridin]-5-yl)propan-2-ol (70 mg. 0.26 mmol) prepared in Reference Example 7 and 1-(2-fluoroethyl) piperidin-3-amine dihydrochloride (75 mg, 0.34 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.64 (d, 1H), 8.72 (d, 1H), 8.31 (s, 1H), 7.89 (dd, 1H), 7.64 (d, 1H), 6.58 (s, 1H), 4.61 (t, 1H), 4.49 (t, 1H), 3.66-3.64 (m, 1H), 2.84-2.81 (m, 1H), 2.75-2.71 (m, 2H), 2.69-2.66 (m, 1H), 2.55-2.52 (m, 2H), 2.43-2.40 (m, 1H), 1.81-1.79 (m, 2H), 1.63 (s, 6H), 1.63-1.60 (m, 2H)

Step 2. 2-(6'-((2-(1-(Cyclopropylsulfonyl)-1H-pyrazol-4-yl)pyrimidin-4-yl)amino)-4'-((1-(2-fluoroethyl) piperidin-3-yl)amino)-[2,3'-bipyridin]-5-yl)propan-2-ol The title compound as a pale yellow solid (29.4 mg) was prepared in the same fashion as Step 3 in Example 1, except that 2-(6'-chloro-4'-((1-(2-fluoroethyl) piperidin-3-yl) amino)-[2,3'-bipyridin]-5-yl)propan-2-ol (89 mg, 0.23 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.13 (s, 1H), 9.87 (brs, 1H), 8.68 (d, 2H), 8.55 (s, 1H), 8.47 (s, 1H), 8.44 (d, 1H), 7.95-7.90 (m, 2H), 7.55 (brs, 1H), 7.20 (brs, 1H), 4.65-4.53 (m, 2H), 3.79 (brs, 1H), 3.28-3.23 (m, 1H), 2.94-2.58 (brs, 6H), 1.73-1.61 (m, 4H), 1.49 (s, 6H), 1.35-1.17 (m, 4H); MS (ESI) m/z=622.2 (M+H)$^+$ Example 178. 2-(6'-((2-(1-(Cyclopropylsulfonyl)-1H-pyrazol-4-yl)pyrimidin-4-yl)amino)-4'-((1-(2,2-difluoroethyl) piperidin-4-yl)amino)-[2,3'-bipyridin]-5-yl)propan-2-ol Step 1. 2-(6'-Chloro-4'-((1-(2,2-difluoroethyl) piperidin-4-yl)amino)-[2,3'-bipyridin]-5-yl)propan-2-ol The title compound as a solid (99 mg) was prepared in the same fashion as Step 2 in Reference Example 1, except that 2-(6'-chloro-4'-fluoro-[2,3'-bipyridin]-5-yl)propan-2-ol (70 mg, 0.26 mmol) prepared in Reference Example 7 and 1-(2,2-difluoroethyl) piperidin-4-amine (56 mg, 0.34 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.63 (d, 1H), 8.69 (d, 1H), 8.35 (s, 1H), 7.90 (dd, 1H), 7.67 (d, 1H), 6.55 (s, 1H), 5.88 (tt, 1H), 3.47-3.44 (m, 1H), 2.93-2.90 (m, 2H), 2.89-2.73 (m, 3H), 2.48 (t, 2H), 2.07-2.03 (m, 2H), 1.71-1.66 (m, 2H), 1.64 (s, 6H)

Step 2. 2-(6'-((2-(1-(Cyclopropylsulfonyl)-1H-pyrazol-4-yl)pyrimidin-4-yl)amino)-4'-((1-(2,2-difluoroethyl) piperidin-4-yl)amino)-[2,3'-bipyridin]-5-yl)propan-2-ol The title compound as a pale yellow solid (19.8 mg) was prepared in the same fashion as Step 3 in Example 1, except that 2-(6'-chloro-4'-((1-(2,2-difluoroethyl) piperidin-4-yl) amino)-[2,3'-bipyridin]-5-yl)propan-2-ol (93 mg, 0.23 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.03 (s, 1H), 9.88 (brs, 1H), 8.77 (s, 2H), 8.63 (s, 1H), 8.52 (s, 1H), 8.49 (d, 1H), 8.07-7.95 (m, 2H), 7.43 (brs, 1H), 7.09 (brs, 1H), 6.18 (tt, 1H), 3.61 (brs, 1H), 3.28-3.23 (m, 1H), 2.85 (brs, 4H), 2.04-1.93 (m, 2H), 1.65 (brs, 2H), 1.50 (s, 6H), 1.36-1.24 (m, 4H); MS (ESI) m/z=640.2 (M+H)$^+$ Example 179. (1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)-1-methylcyclohexan-1-ol Step 1. 6'-Chloro-4',6-difluoro-5-methyl-2,3'-bipyridine The title compound as a solid (302 mg) was prepared in the same fashion as Reference Example 5, except that 6-bromo-2-fluoro-3-methylpyridine (300 mg, 1.579 mmol) was used instead of 2-bromo-5-(methylsulfonyl)pyridine. $^1$H-NMR (CDCl$_3$, 400 MHz) δ 9.04 (d, 1H), 7.72 (t, 1H), 7.59 (d, 1H), 7.20 (d, 1H), 2.36 (s, 3H)

Step 2. (1s,4s)-4-((6'-Chloro-6-fluoro-5-methyl-[2,3'-bipyridin]-4'-yl)amino)-1-methylcyclohexan-1-ol The title compound as a solid (50 mg) was prepared in the same fashion as Step 2 in Reference Example 1, except that 6'-chloro-4',6-difluoro-5-methyl-2,3'-bipyridine (100 mg, 0.42 mmol) prepared in Step 1 was used instead of 6'-chloro-4'-fluoro-5-((1-methylpiperidin-4-yl)oxy)-2,3'-bipyridine. $^1$H-NMR (DMSO-d6), 400 MHz) δ 8.52 (d, 1H), 8.44 (s, 1H), 7.95 (t, 1H), 7.82 (dd, 1H), 6.75 (s, 1H), 4.17 (s, 1H), 3.43 (s, 1H), 2.28 (s, 3H), 1.73-1.71 (m, 2H), 1.61-1.55 (m, 4H), 1.49-1.41 (m, 2H), 1.12 (s, 3H); MS (ESI) m/z=350.1 (M+H)$^+$ Step 3. (1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)-1-methylcyclohexan-1-ol The title compound as a pale yellow solid (47.4 mg) was prepared in the same fashion as Step 3 in Example 1, except that (1s,4s)-4-((6'-chloro-6-fluoro-5-methyl-[2,3'-bipyridin]-4'-yl)amino)-1-methylcyclohexan-1-ol (102 mg, 0.29 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.05 (s, 1H), 8.65 (s, 1H), 8.60 (d, 1H), 8.51 (s, 1H), 8.47 (s, 1H), 8.43 (d, 1H), 7.91 (t, 1H), 7.80 (t, 1H), 7.53 (brs, 1H), 7.30 (brs, 1H), 4.20 (s, 1H), 3.27-3.21 (m, 1H), 2.27 (s, 3H), 1.85-1.83 (m, 2H), 1.67-1.57 (m, 4H), 1.44-1.39 (m, 2H), 1.36-1.32 (m, 2H), 1.27-1.22 (m, 2H), 1.13 (s, 3H); MS (ESI) m/z=579.2 (M+H)$^+$ Example 180. 2-((1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)cyclohexyl)propan-2-ol Step 1. 2-((1s,4s)-4-((6'-Chloro-6-fluoro-5-methyl-[2,3'-bipyridin]-4'-yl)amino)cyclohexyl)propan-2-ol The title compound as a solid (111 mg) was prepared in the same fashion as Step 2 in Reference Example 1, except that 6'-chloro-4',6-difluoro-5-methyl-2,3'-bipyridine (100 mg, 0.42 mmol) prepared in Step 1 of Example 179 and 2-((1s,4s)-4-aminocyclohexyl)propan-2-ol (98 mg, 0.62 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (DMSO-d$_6$, 400 MHz) δ 9.12 (d, 1H), 8.53 (s, 1H), 7.96 (t, 1H), 7.89 (dd, 1H), 6.72 (s, 1H), 4.10 (s, 1H), 3.90-3.88 (m, 1H), 2.27 (s, 3H), 1.82 (d, 2H), 1.68 (d, 2H), 1.53 (t, 2H), 1.28-1.15 (m, 3), 1.02 (s, 6H); MS (ESI) m/z=378.1 (M+H)$^+$ Step 2. 2-((1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)cyclohexyl)propan-2-ol The title compound as a pale yellow solid (53.8 mg) was prepared in the same fashion as Step 3 in Example 1, except that 2-((1s,4s)-4-((6'-chloro-6-fluoro-5-methyl-[2,3'-bipyridin]-4'-yl)amino)cyclohexyl)propan-2-ol (110 mg, 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.09 (s, 1H), 9.11 (d, 1H), 8.62 (d, 1H), 8.57 (d, 1H), 8.45 (d, 1H), 8.42 (t, 1H), 7.92-7.85 (m, 2H), 7.53 (brs, 1H), 7.36 (brs, 1H), 4.10 (s, 1H), 3.94 (brs, 1H), 3.31-3.25 (m, 1H), 2.26 (s, 3H), 1.99-1.96 (m, 2H), 1.72-1.64 (m, 4H), 1.35-1.26 (m, 7H), 1.03 (s, 6H); MS (ESI) m/z=607.2 (M+H)$^+$ Example 181. (1s,4s)-4-((6'-((2-(1-(Cyclopropylsulfonyl)-1H-pyrazol-4-yl)pyrimidin-4-yl)amino)-6-fluoro-5-(trifluoromethyl)-[2,3'-bipyridin]-4'-yl)amino)-1-methylcyclohexan-1-ol Step 1. 6'-Chloro-4',6-difluoro-5-(trifluoromethyl)-2,3'-bipyridine The title compound as a solid (319 mg) was prepared in the same fashion as Reference Example 5, except that 6-bromo-2-fluoro-3-(trifluoromethyl)pyridine (300 mg, 1.23 mmol) was used instead of 2-bromo-5-(methylsulfonyl) pyridine. MS (ESI) m/z=295.0 (M+H)$^+$

Step 2. (1s,4s)-4-((6'-Chloro-6-fluoro-5-(trifluoromethyl)-[2,3'-bipyridin]-4'-yl)amino)-1-methylcyclohexan-1-ol The title compound as a solid (121 mg) was prepared in the same fashion as Step 2 in Reference Example 1, except that 6'-chloro-4',6-difluoro-5-(trifluoromethyl)-2,3'-bipyridine (100 mg, 0.34 mmol) prepared in Step 1 was used instead of 6'-chloro-4'-fluoro-5-((1-methylpiperidin-4-yl)oxy)-2,3'-bipyridine. MS (ESI) m/z=404.0 (M+H)$^+$

Step 3. (1s,4s)-4-((6'-((2-(1-(Cyclopropylsulfonyl)-1H-pyrazol-4-yl)pyrimidin-4-yl)amino)-6-fluoro-5-(trifluoromethyl)-[2,3'-bipyridin]-4'-yl)amino)-1-methylcyclohexan-1-ol The title compound as a pale yellow solid (5.6 mg) was prepared in the same fashion as Step 3 in Example 1, except that (1s,4s)-4-((6'-chloro-6-fluoro-5-(trifluoromethyl)-[2,3'-bipyridin]-4'-yl)amino)-1-methylcyclohexan-1-ol (117 mg, 0.29 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.18 (s, 1H), 8.67 (s, 2H), 8.53 (d, 1H), 8.48 (s, 1H), 8.46 (d, 1H), 8.37 (t, 1H), 8.12 (d, 1H), 7.51 (brs, 1H), 7.39 (s, 1H), 4.21 (s, 1H), 3.27-3.21 (m, 1H), 1.87-1.83 (m, 2H), 1.70-1.57 (m, 4H), 1.45-1.36 (m, 2H), 1.32-1.22 (m, 4H), 1.13 (s, 3H); MS (ESI) m/z=633.2 (M+H)$^+$

Example 182. (1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)-1-methylcyclohexan-1-ol

Step 1. 4-((6'-Chloro-4'-fluoro-[2,3'-bipyridin]-5-yl) sulfonyl) morpholine

The title compound as a solid (195 mg) was prepared in the same fashion as Reference Example 5, except that 4-((6-bromopyridin-3-yl) sulfonyl) morpholine (300 mg, 0.977 mmol) was used instead of 2-bromo-5-(methylsulfonyl)pyridine. MS (ESI) m/z=358.0 (M+H)$^+$

Step 2. (1s,4s)-4-((6'-Chloro-5-(morpholinosulfonyl)-[2,3'-bipyridin]-4'-yl)amino)-1-methylcyclohexan-1-ol The title compound as a solid (80 mg) was prepared in the same fashion as Step 2 in Reference Example 1, except that 4-((6'-chloro-4'-fluoro-[2,3'-bipyridin]-5-yl) sulfonyl) morpholine (60 mg, 0.17 mmol) prepared in Step 1 was used instead of 6'-chloro-4'-fluoro-5-((1-methylpiperidin-4-yl)oxy)-2,3'-bipyridine. MS (ESI) m/z=467.1 (M+H)$^+$

Step 3. (1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)-1-methylcyclohexan-1-ol The title compound as a pale yellow solid (16.1 mg) was prepared in the same fashion as Step 3 in Example 1, except that (1s,4s)-4-((6'-chloro-5-(morpholinosulfonyl)-[2,3'-bipyridin]-4'-yl)amino)-1-methylcyclohexan-1-ol (68 mg, 0.15 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.57 (d, 1H), 8.91 (d, 1H), 8.67 (s, 1H), 8.55 (s, 1H), 8.49 (s, 1H), 8.45 (d, 1H), 8.06 (dd, 1H), 7.92 (d, 1H), 7.71 (brs, 1H), 7.12 (s, 1H), 3.80 (t, 4H), 3.55 (brs, 1H), 3.11 (t, 4H), 2.87-2.80 (m, 1H), 2.03-2.00 (m, 2H), 1.84-1.57 (m, 6H), 1.56-1.52 (m, 2H), 1.33 (s, 3H), 1.26-1.20 (m, 2H); MS (ESI) m/z=696.2 (M+H)$^+$

Example 183. ((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)methanol

Step 1. ((1s,4s)-4-((6'-Chloro-5-(morpholinosulfonyl)-[2,3'-bipyridin]-4'-yl)amino)cyclohexyl)methanol The title compound as a solid (87 mg) was prepared in the same fashion as Step 2 in Reference Example 1, except that 4-((6'-chloro-4'-fluoro-[2,3'-bipyridin]-5-yl) sulfonyl) morpholine (60 mg, 0.17 mmol) prepared in Step 1 of Example 182 and ((1s,4s)-4-aminocyclohexyl)methanol hydrochloride (42 mg, 0.25 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=399.0 (M+H)$^+$

Step 2. ((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)methanol The title compound as a pale yellow solid (15 mg) was prepared in the same fashion as Step 3 in Example 1, except that ((1s,4s)-4-((6'-chloro-5-(morpholinosulfonyl)-[2,3'-bipyridin]-4'-yl)amino)cyclohexyl)methanol (68 mg, 0.25 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.03 (d, 1H), 8.91 (d, 1H), 8.66 (s, 1H), 8.55 (s, 1H), 8.47 (s, 1H), 8.44 (d, 1H), 8.07 (dd, 1H), 7.95 (d, 1H), 7.44 (s, 1H), 7.08 (d, 1H), 4.03 (brs, 1H), 3.80 (t, 4H), 3.55 (d, 2H), 3.11 (t, 4H), 2.88-2.82 (m, 1H), 2.07-2.04 (m, 2H), 1.87-1.73 (m, 5H), 1.57-1.53 (m, 2H), 1.42-1.32 (m, 2H), 1.29-1.22 (m, 2H); MS (ESI) m/z=969.2 (M+H)$^+$

Example 184. 2-((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)propan-2-ol Step 1. 2-((1s,4s)-4-((6'-Chloro-5-(morpholinosulfonyl)-[2,3'-bipyridin]-4'-yl)amino)cyclohexyl)propan-2-ol The title compound as a solid (76 mg) was prepared in the same fashion as Step 2 in Reference Example 1, except that 4-((6'-chloro-4'-fluoro-[2,3'-bipyridin]-5-yl) sulfonyl) morpholine (60 mg, 0.17 mmol) prepared in Step 1 of Example 182 and 2-((1s,4s)-4-aminocyclohexyl)propan-2-ol (40 mg, 0.25 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=495.1 (M+H)$^+$

Step 2. 2-((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)propan-2-ol The title compound as a pale yellow solid (23.6 mg) was prepared in the same fashion as Step 3 in Example 1, except that 2-((1s,4s)-4-((6'-chloro-5-(morpholinosulfonyl)-[2,3'-bipyridin]-4'-yl)amino)cyclohexyl)propan-2-ol (72 mg, 0.15 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 10.04 (d, 1H), 8.89 (d, 1H), 8.66 (s, 1H), 8.57 (s, 1H), 8.46 (s, 1H), 8.42 (d, 1H), 8.06 (d, 1H), 7.95 (d, 1H), 7.47 (s, 1H), 7.03 (d, 1H), 4.04 (brs, 1H), 3.79 (t, 4H), 3.08 (t, 4H), 2.88-2.82 (m, 1H), 2.13-2.10 (m, 2H), 1.84-1.73 (m, 5H), 1.54-1.39 (m, 4H), 1.25-1.22 (m, 8H); MS (ESI) m/z=724.2 (M+H)$^+$ Example 185. (1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)-1-methylcyclohexan-1-ol Step 1. 2-(6-Chloro-4-fluoropyridin-3-yl)-5-fluoropyrazine The title compound as a solid (322 mg) was prepared in the same fashion as Reference Example 5, except that 2-bromo-5-fluoropyrazine (300 mg, 1.695 mmol) was used instead of 2-bromo-5-(methylsulfonyl)pyridine. MS (ESI) m/z=228.0 (M+H)$^+$ Step 2. (1s,4s)-4-((2-Chloro-5-(5-fluoropyrazin-2-yl)pyridin-4-yl)amino)-1-methylcyclohexan-1-ol The title compound as a solid (33 mg) was prepared in the same fashion as Step 2 in Reference Example 1, except that 2-(6-chloro-4-fluoropyridin-3-yl)-5-fluoropyrazine (100 mg, 0.44 mmol) prepared in Step 1 was used instead of 6'-chloro-4'-fluoro-5-((1-methylpiperidin-4-yl)oxy)-2,3'-bipyridine. MS (ESI) m/z=337.1 (M+H)$^+$ Step 3. (1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)-1-methylcyclohexan-1-ol The title compound as a pale yellow solid (5.3 mg) was prepared in the same fashion as Step 3 in Example 1, except that (1s,4s)-4-((2-chloro-5-(5-fluoropyrazin-2-yl)pyridin-4-yl)amino)-1-methylcyclohexan-1-ol (32 mg, 0.09 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.09 (s, 1H), 8.91 (s, 1H), 8.73 (d, 1H), 8.66 (s, 1H), 8.57 (s, 1H), 8.47 (s, 1H), 8.45 (d, 1H), 8.25 (d, 1H), 7.56 (brs, 1H), 7.34 (brs, 1H), 4.17 (s, 1H), 3.27-3.21 (m, 1H), 1.83-1.81 (m, 2H), 1.64-1.55 (m, 4H), 1.44-1.33 (m, 4H), 1.27-1.25 (m, 2H), 1.13 (s, 3H); MS (ESI) m/z=566.2 (M+H)$^+$ Example 186. 2-((1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)cyclohexyl)propan-2-ol Step 1. 2-((1s,4s)-4-((2-Chloro-5-(5-fluoropyrazin-2-yl)pyridin-4-yl)amino)cyclohexyl)propan-2-ol The title compound as a solid (51 mg) was prepared in the same fashion as Step 2 in Reference Example 1, except that 2-(6-chloro-4-fluoropyridin-3-yl)-5-fluoropyrazine (100 mg, 0.44 mmol) prepared in Step 1 of Example 185 and 2-((1s,4s)-4-aminocyclohexyl)propan-2-ol (104 mg, 0.66 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=365.1 (M+H)$^+$ Step 2. 2-((1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)cyclohexyl)propan-2-ol The title compound as a pale yellow solid (7.7 mg) was prepared in the same fashion as Step 3 in Example 1, except that 2-((1s,4s)-4-((2-chloro-5-(5-fluoropyrazin-2-yl)pyridin-4-yl)amino)cyclohexyl)propan-2-ol (37 mg, 0.10 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. MS (ESI) m/z=594.2 (M+H)$^+$ Example 187. 2-((1s,4s)-4-((6'-((2-(1-(Cyclopropylsulfonyl)-1H-pyrazol-4-yl)pyrimidin-4-yl)amino)-5-((4-methylpiperidin-1-yl) sulfonyl)-[2,3'-bipyridin]-4'-yl)amino)cyclohexyl)propan-2-ol Step 1. 6'-Chloro-4'-fluoro-5-((4-methylpiperidin-1-yl) sulfonyl)-2,3'-bipyridine The title compound as a solid (162 mg) was prepared in the same fashion as Reference Example 5, except that 2-bromo-5-((4-methylpiperidin-1-yl) sulfonyl)pyridine (300 mg, 0.94 mmol) was used instead of 2-bromo-5-(methylsulfonyl)pyridine. MS (ESI) m/z=370.0 (M+H)$^+$ Step 2. 2-((1s,4s)-4-((6'-Chloro-5-((4-methylpiperidin-1-yl) sulfonyl)-[2,3'-bipyridin]-4'-yl)amino)cyclohexyl)propan-2-ol The title compound as a solid (66 mg) was prepared in the same fashion as Step 2 in Reference Example 1, except that 6'-chloro-4'-fluoro-5-((4-methylpiperidin-1-yl) sulfonyl)-2,3'-bipyridine (50 mg, 0.14 mmol) prepared in Step 1 and 2-((1s,4s)-4-aminocyclohexyl)propan-2-ol (32 mg, 0.20 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=507.2 (M)$^+$ Step 3. 2-((1s,4s)-4-((6'-((2-(1-(Cyclopropylsulfonyl)-1H-pyrazol-4-yl)pyrimidin-4-yl)amino)-5-((4-methylpiperidin-1-yl) sulfonyl)-[2,3'-bipyridin]-4'-yl)amino)cyclohexyl)propan-2-ol The title compound as a pale yellow solid (4.1 mg) was prepared in the same fashion as Step 3 in Example 1, except that 2-((1s,4s)-4-((6'-chloro-5-((4-methylpiperidin-1-yl) sulfonyl)-[2,3'-bipyridin]-4'-yl)amino)cyclohexyl)propan-2-ol (63 mg, 0.12 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol.
$^1$H-NMR (CDCl$_3$, 400 MHz) δ 10.08 (d, 1H), 8.89 (d, 1H), 8.66 (s, 1H), 8.57 (s, 1H), 8.47 (s, 1H), 8.42 (d, 1H), 8.06 (dd, 1H), 7.93 (d, 1H), 7.74 (brs, 1H), 7.44 (s, 1H), 7.05 (d, 1H), 4.03 (brs, 1H), 3.81 (d, 2H), 2.88-2.82 (m, 1H), 2.35 (t, 2H), 2.13-2.09 (m, 2H), 1.83-1.70 (m, 5H), 1.57-1.53 (m, 2H), 1.48-1.25 (m, 9H), 1.22 (s, 6H), 0.94 (d, 3H); MS (ESI) m/z=736.2 (M+H)$^+$

Example 188. (1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)-1-methylcyclohexan-1-ol

Step 1. 6'-Chloro-4'-fluoro-5-((4-methylpiperazin-1-yl) sulfonyl)-2,3'-bipyridine The title compound as a solid (310 mg) was prepared in the same fashion as Reference Example 5, except that 1-((6-bromopyridin-3-yl) sulfonyl)-4-methylpiperazine (301 mg, 0.94 mmol) was used instead of 2-bromo-5-(methylsulfonyl)pyridine. MS (ESI) m/z=371.0 (M+H)$^+$

Step 2. (1s,4s)-4-((6'-Chloro-5-((4-methylpiperazin-1-yl) sulfonyl)-[2,3'-bipyridin]-4'-yl)amino)-1-methylcyclohexan-1-ol The title compound as a solid (101 mg) was prepared in the same fashion as Step 2 in Reference Example 1, except that 6'-chloro-4'-fluoro-5-((4-methylpiperazin-1-yl) sulfonyl)-2,3'-bipyridine (80 mg, 0.216 mmol) prepared in Step 1 was used instead of 6'-chloro-4'-fluoro-5-((1-methylpiperidin-4-yl)oxy)-2,3'-bipyridine. MS (ESI) m/z=480.1 (M+H)$^+$

Step 3. (1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)-1-methylcyclohexan-1-ol The title compound as a pale yellow solid (25.2 mg) was prepared in the same fashion as Step 3 in Example 1, except that (1s,4s)-4-((6'-chloro-5-((4-methylpiperazin-1-yl) sulfonyl)-[2,3'-bipyridin]-4'-yl)amino)-1-methylcyclohexan-1-ol (54 mg. 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.50 (d, 1H), 8.91 (s, 1H), 8.67 (s, 1H), 8.51 (s, 1H), 8.49 (s, 1H), 8.45 (d, 1H), 8.06 (d, 1H), 7.88 (d, 1H), 7.67 (brs, 1H), 7.30 (s, 1H), 7.09 (s, 1H), 3.54 (brs, 1H), 3.14 (brs, 4H), 2.85-2.83 (m, 1H), 2.54 (brs, 4H), 2.30 (s, 3H), 2.03-2.00 (m, 2H), 1.84-1.54 (m, 8H), 1.32 (s, 3H), 1.29-1.22 (m, 2H); MS (ESI) m/z=709.2 (M+H)$^+$

Example 189. ((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)methanol

Step 1. ((1s,4s)-4-((6'-Chloro-5-((4-methylpiperazin-1-yl) sulfonyl)-[2,3'-bipyridin]-4'-yl)amino)cyclohexyl)methanol The title compound as a solid (105 mg) was prepared in the same fashion as Step 2 in Reference Example 1, except that 6'-chloro-4'-fluoro-5-((4-methylpiperazin-1-yl) sulfonyl)-2,3'-bipyridine (80 mg. 0.216 mmol) prepared in Step 1 of Example 188 and ((1s,4s)-4-aminocyclohexyl)methanol hydrochloride (54 mg, 0.324 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=480.2 (M+H)$^+$

Step 2. ((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)methanol The title compound as a pale yellow solid (28.1 mg) was prepared in the same fashion as Step 3 in Example 1, except that ((1s,4s)-4-((6'-chloro-5-((4-methylpiperazin-1-yl) sulfonyl)-[2,3'-bipyridin]-4'-yl)amino)cyclohexyl)methanol (54 mg. 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.76 (d, 1H), 8.90 (s, 1H), 8.66 (d, 1H), 8.51 (s, 1H), 8.46 (d, 1H), 8.42 (dd, 1H), 8.07 (d, 1H), 7.90 (t, 2H), 7.39 (s, 1H), 7.08 (s, 1H), 4.02 (brs, 1H), 3.50 (d, 2H), 3.13 (brs, 4H), 2.86-2.83 (m, 1H), 2.54 (brs, 4H), 2.30 (s, 3H), 2.09-2.04 (m, 2H), 1.82-1.67 (m, 5H), 1.57-1.53 (m, 2H), 1.39-1.22 (m, 4H); MS (ESI) m/z=709.2 (M+H)$^+$

Example 190. 2-((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)propan-2-ol

Step 1. 2-((1s,4s)-4-((6'-Chloro-5-((4-methylpiperazin-1-yl) sulfonyl)-[2,3'-bipyridin]-4'-yl)amino)cyclohexyl)propan-2-ol The title compound as a solid (105 mg) was prepared in the same fashion as Step 2 in Reference Example 1, except that 6'-chloro-4'-fluoro-5-((4-methylpiperazin-1-yl) sulfonyl)-2,3'-bipyridine (80 mg, 0.216 mmol) prepared in Step 1 of Example 188 and 2-((1s,4s)-4-aminocyclohexyl)propan-2-ol (51 mg, 0.324 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=508.2 (M+H)$^+$

Step 2. 2-((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)propan-2-ol The title compound as a pale yellow solid (5.1 mg) was prepared in the same fashion as Step 3 in Example 1, except that 2-((1s,4s)-4-((6'-chloro-5-((4-methylpiperazin-1-yl) sulfonyl)-[2,3'-bipyridin]-4'-yl)amino)cyclohexyl)propan-2-ol (57 mg. 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.89 (d, 1H), 8.89 (d, 1H), 8.66 (s, 1H), 8.53 (s, 1H), 8.47 (s, 1H), 8.42 (d, 1H), 8.07 (dd, 1H), 7.91 (d, 1H), 7.44 (s, 1H), 7.05 (d, 1H), 4.03 (brs, 1H), 3.11 (brs, 4H), 2.88-2.82 (m, 1H), 2.52 (brs, 4H), 2.29 (s, 3H), 2.13-2.10 (m, 2H), 1.83-1.70 (m, 4H), 1.57-1.53 (m, 2H), 1.40-1.36 (m, 3H), 1.26-1.22 (m, 2H), 1.20 (s, 6H)

Example 191. (1s,4s)-4-((4-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrimidin-2-yl)amino)-1-methylcyclohexan-1-ol

Step 1. 4-(6-Chloro-4-fluoropyridin-3-yl)-2-fluoropyrimidine

The title compound as a solid (227 mg) was prepared in the same fashion as Reference Example 5, except that 4-bromo-2-fluoro-pyrimidine (300 mg, 1.695 mmol) was used instead of 2-bromo-5-(methylsulfonyl)pyridine. MS (ESI) m/z=227.9 (M)$^+$ Step 2. (1s,4s)-4-((4-(6-Chloro-4-(((1s,4s)-4-hydroxy-4-methylcyclohexyl)amino)pyridin-3-yl)pyrimidin-2-yl)amino)-1-methylcyclohexan-1-ol The title compound as a solid (87 mg) was prepared in the same fashion as Step 2 in Reference Example 1, except that 4-(6-chloro-4-fluoropyridin-3-yl)-2-fluoropyrimidine (70 mg, 0.308 mmol) prepared in Step 1 was used instead of 6'-chloro-4'-fluoro-5-((1-methylpiperidin-4-yl)oxy)-2,3'-bipyridine. MS (ESI) m/z=446.2 (M)$^+$ Step 3. (1s,4s)-4-((4-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrimidin-2-yl)amino)-1-methylcyclohexan-1-ol The title compound as a pale yellow solid (28.2 mg) was prepared in the same fashion as Step 3 in Example 1, except that (1s,4s)-4-((4-(6-chloro-4-(((1s,4s)-4-hydroxy-4-methylcyclohexyl)amino)pyridin-3-yl)pyrimidin-2-yl)amino)-1-methylcyclohexan-1-ol (84 mg, 0.188 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d6, 400 MHz) δ 10.07 (s, 1H), 9.13 (brs, 1H), 8.66 (s, 1H), 8.48 (d, 2H), 8.44 (d, 1H), 8.23 (d, 1H), 7.55 (brs, 1H), 7.26 (brs, 1H), 7.10 (brs, 1H), 7.01 (d, 1H), 4.14-4.03 (m, 2H), 3.27-3.20 (m, 1H), 1.84-1.82 (m, 2H), 1.70-1.55 (m, 10H), 1.44-1.40 (m, 4H), 1.36-1.32 (m, 2H), 1.27-1.21 (m, 2H), 1.13 (s, 6H); MS (ESI) m/z=675.3 (M+H)$^+$ Example 192. ((1s,4s)-4-((4-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyrimidin-2-yl)amino)cyclohexyl)methanol Step 1. ((1s,4s)-4-((4-(6-Chloro-4-(((1s,4s)-4-(hydroxymethyl)cyclohexyl)amino)pyridin-3-yl)pyrimidin-2-yl)amino)cyclohexyl)methanol The title compound as a solid (97 mg) was prepared in the same fashion as Step 2 in Reference Example 1, except that 4-(6-chloro-4-fluoropyridin-3-yl)-2-fluoropyrimidine (70 mg. 0.308 mmol) prepared in Step 1 of Example 191 and ((1s,4s)-4-aminocyclohexyl)methanol hydrochloride (109 mg, 0.659 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=446.2 (M)$^+$ Step 2. ((1s,4s)-4-((4-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyrimidin-2-yl)amino)cyclohexyl)methanol The title compound as a pale yellow solid (48.1 mg) was prepared in the same fashion as Step 3 in Example 1, except that ((1s,4s)-4-((4-(6-chloro-4-(((1s,4s)-4-(hydroxymethyl)cyclohexyl)amino)pyridin-3-yl)pyrimidin-2-yl)amino)cyclohexyl)methanol (84 mg, 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (DMSO-d$_6$, 400 MHz) δ 10.10 (s, 1H), 8.63 (s, 1H), 8.48-8.42 (m, 3H), 8.28 (d, 1H), 7.43 (brs, 2H), 7.05 (d, 1H), 4.56 (brs, 1H), 4.39 (t, 1H), 3.94 (brs, 1H), 3.82 (brs, 1H), 3.27-3.24 (m, 1H), 1.88 (brs, 2H), 1.71-1.68 (m, 4H), 1.57-1.43 (m, 12H), 1.40-1.33 (m, 2H), 1.30-1.26 (m, 2H); MS (ESI) m/z=675.3 (M+H)$^+$ Example 193. 2-((1s,4s)-4-((4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyrimidin-2-yl)amino)cyclohexyl)propan-2-ol Step 1. 2-((1s,4s)-4-((4-(6-Chloro-4-(((1s,4s)-4-(2-hydroxypropan-2-yl)cyclohexyl)amino)pyridin-3-yl)pyrimidin-2-yl)amino)cyclohexyl)propan-2-ol The title compound as a solid (90 mg) was prepared in the same fashion as Step 2 in Reference Example 1, except that 4-(6-chloro-4-fluoropyridin-3-yl)-2-fluoropyrimidine (70 mg. 0.308 mmol) prepared in Step 1 of Example 191 and 2-((1s,4s)-4-aminocyclohexyl)propan-2-ol (104 mg. 0.659 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=503.2 (M+H)$^+$ Step 2. 2-((1s,4s)-4-((4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyrimidin-2-yl)amino)cyclohexyl)propan-2-ol The title compound as a pale yellow solid (30.3 mg) was prepared in the same fashion as Step 3 in Example 1, except that 2-((1s,4s)-4-((4-(6-chloro-4-(((1s,4s)-4-(2-hydroxypropan-2-yl)cyclohexyl)amino)pyridin-3-yl)pyrimidin-2-yl)amino)cyclohexyl)propan-2-ol (95 mg, 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.13 (s, 1H), 8.62 (s, 1H), 8.51 (s, 1H), 8.45 (s, 1H), 8.43 (d, 1H), 8.29 (d, 1H), 7.52 (brs, 1H), 7.36 (brs, 1H), 7.08 (d, 1H), 4.11 (brs, 2H), 4.02 (s, 1H), 3.92 (brs, 1H), 3.28-3.25 (m, 1H), 2.11-2.08 (m, 2H), 1.96-1.93 (m, 2H), 1.64-1.57 (m, 6H), 1.52-1.45 (m, 2H), 1.36-1.30 (m, 4H), 1.29-1.25 (m, 6H), 1.03 (s, 6H), 1.00 (s, 6H); MS (ESI) m/z=731.3 (M+H)$^+$ Example 194. (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol Step 1. 6'-Chloro-4'-fluoro-5-(trifluoromethoxy)-2,3'-bipyridine The title compound as a solid (386 mg) was prepared in the same fashion as Reference Example 5, except that 2-bromo-5-(trifluoromethoxy)pyridine (410 mg, 1.695 mmol) was used instead of 2-bromo-5-(methylsulfonyl)pyridine. MS (ESI) m/z=293.0 (M+H)$^+$ Step 2. (1s,4s)-4-((6'-Chloro-5-(trifluoromethoxy)-[2,3'-bipyridin]-4'-yl)amino)-1-methylcyclohexan-1-ol The title compound as a solid (150 mg) was prepared in the same fashion as Step 2 in Reference Example 1, except that 6'-chloro-4'-fluoro-5-(trifluoromethoxy)-2,3'-bipyridine (100 mg. 0.342 mmol) prepared in Step 1 was used instead of 6'-chloro-4'-fluoro-5-((1-methylpiperidin-4-yl)oxy)-2,3'-bipyridine. MS (ESI) m/z=402.1 (M+H)$^+$ Step 3. (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol The title compound as a pale yellow solid (53 mg) was prepared in the same fashion as Step 3 in Example 1, except that (1s,4s)-4-((6'-chloro-5-(trifluoromethoxy)-[2,3'-bipyridin]-4'-yl)amino)-1-methylcyclohexan-1-ol (125 mg, 0.311 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.07 (s, 1H), 9.10 (d, 1H), 8.72 (d, 1H), 8.66 (s, 1H), 8.55 (s, 1H), 8.47 (s, 1H), 8.44 (d, 1H), 8.13 (d, 1H), 7.96 (t, 1H), 7.55 (brs, 1H), 7.32 (brs, 1H), 4.19 (s, 1H), 3.30-3.21 (m, 1H), 1.85-1.82 (m, 2H), 1.66-1.56 (m, 4H), 1.45-1.42 (m, 2H), 1.34-1.25 (m, 4H), 1.13 (s, 3H); MS (ESI) m/z=631.2 (M+H)$^+$ Example 195. ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol Step 1. ((1s,4s)-4-((6'-Chloro-5-(trifluoromethoxy)-[2,3'-bipyridin]-4'-yl)amino)cyclohexyl)methanol The title compound as a solid (144 mg) was prepared in the same fashion as Step 2 in Reference Example 1, except that 6'-chloro-4'-fluoro-5-(trifluoromethoxy)-2,3'-bipyridine (100 mg, 0.342 mmol) prepared in Step 1 of Example 194 and ((1s,4s)-4-aminocyclohexyl)methanol hydrochloride (85 mg, 0.513 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=402.1 (M+H)$^+$ Step 2. ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol The title compound as a pale yellow solid (56.1 mg) was prepared in the same fashion as Step 3 in Example 1, except that ((1s,4s)-4-((6'-chloro-5-(trifluoromethoxy)-[2,3'-bipyridin]-4'-yl)amino)cyclohexyl)methanol (125 mg, 0.311 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.11 (s, 1H), 9.61 (d, 1H), 8.68 (d, 1H), 8.63 (s, 1H), 8.60 (s, 1H), 8.45 (s, 1H), 8.43 (d, 1H), 8.19 (d, 1H), 7.98 (dd, 1H), 7.51 (brs, 1H), 7.40 (brs, 1H), 4.46 (t, 1H), 3.92 (brs, 1H), 3.30-3.25 (m, 3H), 1.88-1.86 (m, 2H), 1.74-1.67 (m, 2H), 1.63-1.59 (m, 2H), 1.48-1.45 (m, 1H), 1.36-1.23 (m, 4H); MS (ESI) m/z=631.2 (M+H)$^+$ Example 196. 2-((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)propan-2-ol Step 1. 2-((1s,4s)-4-((6'-Chloro-5-(trifluoromethoxy)-[2,3'-bipyridin]-4'-yl)amino)cyclohexyl)propan-2-ol The title compound as a solid (152 mg) was prepared in the same fashion as Step 2 in Reference Example 1, except that 6'-chloro-4'-fluoro-5-(trifluoromethoxy)-2,3'-bipyridine (100 mg, 0.342 mmol) prepared in Step 1 of Example 194 and 2-((1s,4s)-4-aminocyclohexyl)propan-2-ol (81 mg, 0.513 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=430.1 (M+H)$^+$ Step 2. 2-((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)propan-2-ol The title compound as a pale yellow solid (47 mg) was prepared in the same fashion as Step 3 in Example 1, except that 2-((1s,4s)-4-((6'-chloro-5-(trifluoromethoxy)-[2,3'-bipyridin]-4'-yl)amino)cyclohexyl)propan-2-ol (134 mg, 0.311 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.12 (s, 1H), 9.69 (d, 1H), 8.64 (d, 1H), 8.62 (s, 1H), 8.61 (s, 1H), 8.45 (s, 1H), 8.42 (d, 1H), 8.20 (d, 1H), 7.98 (dd, 1H), 7.58 (brs, 1H), 7.35 (brs, 1H), 4.10 (s, 1H), 3.98 (brs, 1H), 3.31-3.25 (m, 1H), 1.98-1.95 (m, 2H), 1.69-1.63 (m, 4H), 1.37-1.22 (m, 7H), 1.02 (s, 6H); MS (ESI) m/z=659.2 (M+H)$^+$ Example 197. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(trifluoromethoxy)-[2,3'-bipyridine]-4',6'-diamine Step 1. 6'-Chloro-N-((1s,4s)-4-((dimethylamino)methyl)cyclohexyl)-5-(trifluoromethoxy)-[2,3'-bipyridin]-4'-amine The title compound as a solid (176 mg) was prepared in the same fashion as Step 2 in Reference Example 1, except that 6'-chloro-4'-fluoro-5-(trifluoromethoxy)-2,3'-bipyridine (150 mg, 0.513 mmol) prepared in Step 1 of Example 194 and (1s,4s)-4-((dimethylamino)methyl)cyclohexan-1-amine dihydrochloride (176 mg, 0.769 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=429.1 (M+H)$^+$ Step 2. 2 N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(trifluoromethoxy)-[2,3'-bipyridine]-4',6'-diamine The title compound as a pale yellow solid (57.8 mg) was prepared in the same fashion as Step 3 in Example 1, except that 6'-chloro-N-((1s,4s)-4-((dimethylamino)methyl)cyclohexyl)-5-(trifluoromethoxy)-[2,3'-bipyridin]-4'-amine (170 mg. 0.396 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.61 (d, 1H), 8.66 (s, 1H), 8.51 (s, 1H), 8.46 (d, 2H), 8.41 (d, 1H), 7.84 (brs, 1H), 7.83 (d, 1H), 7.66 (d, 1H), 7.30 (s, 1H), 7.11 (d, 1H), 3.96 (brs, 1H), 2.85-2.83 (m, 1H), 2.24 (s, 6H), 2.15 (d, 2H), 2.05-1.99 (m, 2H), 1.85-1.70 (m, 4H), 1.65 (brs, 1H), 1.56-1.52 (m, 2H), 1.31-1.21 (m, 4H); MS (ESI) m/z=658.2 (M+H)$^+$

Example 198. (1s,4s)-4-((6'-((2-(1-(Cyclopropylsulfonyl)-1H-pyrazol-4-yl)pyrimidin-4-yl)amino)-4-(methylsulfonyl)-[2,3'-bipyridin]-4'-yl)amino)-1-methylcyclohexan-1-ol Step 1. 6'-Chloro-4'-fluoro-4-(methylsulfonyl)-2,3'-bipyridine The title compound as a solid (297 mg) was prepared in the same fashion as Reference Example 5, except that 2-bromo-4-(methylsulfonyl)pyridine (295 mg, 1.251 mmol) was used instead of 2-bromo-5-(methylsulfonyl)pyridine. MS (ESI) m/z=287.0 (M+H)$^+$ Step 2. (1s,4s)-4-((6'-Chloro-4-(methylsulfonyl)-[2,3'-bipyridin]-4'-yl)amino)-1-methylcyclohexan-1-ol The title compound as a solid (136 mg) was prepared in the same fashion as Step 2 in Reference Example 1, except that 6'-chloro-4'-fluoro-4-(methylsulfonyl)-2,3'-bipyridine (100 mg, 0.349 mmol) prepared in Step 1 was used instead of 6'-chloro-4'-fluoro-5-((1-methylpiperidin-4-yl)oxy)-2,3'-bipyridine. MS (ESI) m/z=396.1 (M+H)$^+$ Step 3. (1s,4s)-4-((6'-((2-(1-(Cyclopropylsulfonyl)-1H-pyrazol-4-yl)pyrimidin-4-yl)amino)-4-(methylsulfonyl)-[2,3'-bipyridin]-4'-yl)amino)-1-methylcyclohexan-1-ol The title compound as a pale yellow solid (53 mg) was prepared in the same fashion as Step 3 in Example 1, except that (1s,4s)-4-((6'-chloro-4-(methylsulfonyl)-[2,3'-bipyridin]-4'-yl)amino)-1-methylcyclohexan-1-ol (115 mg, 0.29 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.15 (s, 1H), 9.27 (s, 1H), 8.93 (s, 1H), 8.68 (d, 2H), 8.47-8.42 (m, 3H), 7.75 (s, 1H), 7.46 (d, 2H), 4.21 (brs, 1H), 3.28-3.25 (m, 1H), 1.86-1.84 (m, 2H), 1.66-1.58 (m, 4H), 1.44-1.25 (m, 6H), 1.14 (s, 3H); MS (ESI) m/z=625.2 (M+H)$^+$

Example 199. (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(4-methylpiperazin-1-yl)methanone Step 1. (6'-Chloro-4'-fluoro-[2,3'-bipyridin]-5-yl)(4-methylpiperazin-1-yl)methanone The title compound as a solid (255 mg) was prepared in the same fashion as Reference Example 5, except that (6-bromo-3-pyridyl)-(4-methylpiperazin-1-yl)methanone (355 mg, 1.251 mmol) was used instead of 2-bromo-5-(methylsulfonyl)pyridine. MS (ESI) m/z=335.1 (M+H)$^+$ Step 2. (6'-Chloro-4'-(((1s,4s)-4-hydroxy-4-methylcyclohexyl)amino)-[2,3'-bipyridin]-5-yl)(4-methylpiperazin-1-yl)methanone The title compound as a solid (126 mg) was prepared in the same fashion as Step 2 in Reference Example 1, except that (6'-chloro-4'-fluoro-[2,3'-bipyridin]-5-yl)(4-methylpiperazin-1-yl)methanone (117 mg, 0.349 mmol) prepared in Step 1 was used instead of 6'-chloro-4'-fluoro-5-((1-methylpiperidin-4-yl)oxy)-2,3'-bipyridine. MS (ESI) m/z=444.2 (M+H)$^+$ Step 3. (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(4-methylpiperazin-1-yl)methanone The title compound as a pale yellow solid (51.9 mg) was prepared in the same fashion as Step 3 in Example 1, except that (6'-chloro-4'-(((1s,4s)-4-hydroxy-4-methylcyclohexyl)amino)-[2,3'-bipyridin]-5-yl)(4-methylpiperazin-1-yl)methanone (117 mg, 0.264 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.45 (s, 1H), 8.65 (s, 2H), 8.47 (s, 2H), 8.42 (d, 1H), 8.21 (brs, 1H), 7.80 (t, 2H), 7.12 (d, 1H), 3.83-3.54 (m, 5H), 2.84-2.80 (m, 1H), 2.48 (brs, 4H), 2.36 (s, 3H), 2.00-1.97 (m, 2H), 1.74-1.54 (m, 8H), 1.29 (s, 3H), 1.25-1.21 (m, 2H); MS (ESI) m/z=673.2 (M+H)$^+$

Example 200. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(morpholino)methanone Step 1. (6'-Chloro-4'-fluoro-[2,3'-bipyridin]-5-yl)(morpholino)methanone The title compound as a solid (110 mg) was prepared in the same fashion as Reference Example 5, except that (6-bromopyridin-3-yl)(morpholino)methanone (100 mg, 0.369 mmol) was used instead of 2-bromo-5-(methylsulfonyl)pyridine. MS (ESI) m/z=399.0 (M+H)$^+$ Step 2. (6'-Chloro-4'-(((1s,4s)-4-(hydroxymethyl)cyclohexyl)amino)-[2,3'-bipyridin]-5-yl)(morpholino)methanone The title compound as a solid (121 mg) was prepared in the same fashion as Step 2 in Reference Example 1, except that (6'-chloro-4'-fluoro-[2,3'-bipyridin]-5-yl)(morpholino)methanone (100 mg, 0.311 mmol) prepared in Step 1 and ((1s,4s)-4-aminocyclohexyl)methanol hydrochloride (77 mg, 0.466 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=431.1 (M+H)$^+$ Step 3. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(morpholino)methanone The title compound as a pale yellow solid (5.4 mg) was prepared in the same fashion as Step 3 in Example 1, except that (6'-chloro-4'-(((1s,4s)-4-(hydroxy methyl)cyclohexyl)amino)-[2,3'-bipyridin]-5-yl)(morpholino)methanone (114 mg, 0.264 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.95 (d, 1H), 8.66 (s, 2H), 8.49 (s, 1H), 8.46 (s, 1H), 8.41 (d, 1H), 7.83 (s, 3H), 7.35 (s, 1H), 7.09 (d, 1H), 4.00 (brs, 1H), 3.75-3.54 (m, 8H), 3.53 (d, 2H), 2.85-2.82 (m, 1H), 2.05-2.02 (m, 2H), 1.83-1.72 (m, 5H), 1.53-1.22 (m, 6H); MS (ESI) m/z=660.3 (M+H)$^+$ Example 201. (6'-((2-(1-(Cyclopropylsulfonyl)-1H-pyrazol-4-yl)pyrimidin-4-yl)amino)-4'-(((1s,4s)-4-(2-hydroxy propan-2-yl)cyclohexyl)amino)-[2,3'-bipyridin]-5-yl)(morpholino)methanone Step 1. (6'-Chloro-4'-(((1s,4s)-4-(2-hydroxypropan-2-yl)cyclohexyl)amino)-[2,3'-bipyridin]-5-yl)(morpholino)methanone The title compound as a solid (131 mg) was prepared in the same fashion as Step 2 in Reference Example 1, except that (6'-chloro-4'-fluoro-[2,3'-bipyridin]-5-yl)(morpholino)methanone (100 mg, 0.311 mmol) prepared in Step 1 of Example 200 and 2-((1s,4s)-4-aminocyclohexyl)propan-2-ol (73 mg, 0.466 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=459.1 (M+H)$^+$ Step 2. (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(morpholino)methanone The title compound as a pale yellow solid (25.6 mg) was prepared in the same fashion as Step 3 in Example 1, except that (6'-chloro-4'-(((1s,4s)-4-(2-hydroxypropan-2-yl)cyclohexyl)amino)-[2,3'-bipyridin]-5-yl)(morpholino)methanone (121 mg, 0.264 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.96 (d, 1H), 8.65 (s, 2H), 8.50 (s, 1H), 8.46 (s, 1H), 8.40 (d, 1H), 7.83 (s, 3H), 7.38 (s, 1H), 7.06 (d, 1H), 4.01 (brs, 1H), 3.75-3.60 (m, 8H), 2.85-2.82 (m, 1H), 2.11-2.08 (m, 2H), 1.83-1.75 (m, 5H), 1.53-1.26 (m, 6H), 1.23 (s, 6H); MS (ESI) m/z=688.3 (M+H)$^+$ Example 202. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(4-methylpiperazin-1-yl)methanone Step 1. (6'-Chloro-4'-(((1s,4s)-4-(hydroxymethyl)cyclohexyl)amino)-[2,3'-bipyridin]-5-yl)(4-methylpiperazin-1-yl)methanone The title compound as a pale yellow sticky oil (85 mg) was prepared in the same fashion as Step 2 in Reference Example 1, except that (6'-chloro-4'-fluoro-[2,3'-bipyridin]-5-yl)(4-methylpiperazin-1-yl)methanone (100 mg, 0.299 mmol) prepared in Step 1 of Example 199 and ((1s,4s)-4-aminocyclohexyl)methanol hydrochloride (74 mg, 0.448 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=444.2 (M+H)$^+$ Step 2. (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(4-methylpiperazin-1-yl)methanone The title compound as a pale yellow solid (28.9 mg) was prepared in the same fashion as Step 3 in Example 1, except that (6'-chloro-4'-(((1s,4s)-4-(hydroxymethyl)cyclohexyl)amino)-[2,3'-bipyridin]-5-yl)(4-methylpiperazin-1-yl)methanone (75 mg. 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl$_3$, 400 MHz) δ 9.94 (d, 1H), 8.66 (s, 2H), 8.49 (s, 1H), 8.46 (s, 1H), 8.40 (d, 1H), 7.91 (brs, 1H), 7.81 (s, 2H), 7.34 (s, 1H), 7.09 (d, 1H), 3.99 (brs, 1H), 3.84 (brs, 2H), 3.54 (brs, 2H), 3.53 (d, 2H), 2.87-2.81 (m, 1H), 2.52-2.44 (m, 4H), 2.35 (s, 3H), 2.05-2.02 (m, 2H), 1.83-1.67 (m, 5H), 1.56-1.51 (m, 2H), 1.41-1.31 (m, 2H), 1.26-1.20 (m, 2H); MS (ESI) m/z=673.3 (M+H)$^+$ Example 203. (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(4-methylpiperazin-1-yl)methanone Step 1. (6'-Chloro-4'-(((1s,4s)-4-(2-hydroxypropan-2-yl)cyclohexyl)amino)-[2,3'-bipyridin]-5-yl)(4-methylpiperazin-1-yl)methanone The title compound as a pale yellow sticky oil (98 mg) was prepared in the same fashion as Step 2 in Reference Example 1, except that (6'-chloro-4'-fluoro-[2,3'-bipyridin]-5-yl)(4-methylpiperazin-1-yl)methanone (100 mg, 0.299 mmol) prepared in Step 1 of Example 199 and 2-((1s,4s)-4-aminocyclohexyl)propan-2-ol (70 mg. 0.448 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=472.2 (M+H)$^+$ Step 2. (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(4-methylpiperazin-1-yl)methanone The title compound as a pale yellow solid (38.8 mg) was prepared in the same fashion as Step 3 in Example 1, except that (6'-chloro-4'-(((1s,4s)-4-(2-hydroxypropan-2-yl)cyclohexyl)amino)-[2,3'-bipyridin]-5-yl)(4-methylpiperazin-1-yl)methanone (80 mg, 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.97 (d, 1H), 8.66 (s, 2H), 8.65 (d, 1H), 8.49 (s, 1H), 8.46 (s, 1H), 8.40 (d, 1H), 7.92 (brs, 1H), 7.82 (s, 2H), 7.38 (s, 1H), 7.06 (d, 1H), 4.00 (brs, 1H), 3.82 (brs, 2H), 3.54 (brs, 2H), 3.53 (d, 2H), 2.87-2.81 (m, 1H), 2.51-2.43 (m, 4H), 2.35 (s, 3H), 2.11-2.08 (m, 2H), 1.80-1.74 (m, 5H), 1.56-1.52 (m, 2H), 1.45-1.41 (m, 2H), 1.24-1.20 (m, 8H); MS (ESI) m/z=701.3 (M+H)$^+$ Example 204. (6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)(4-methylpiperazin-1-yl)methanone Step 1. (6'-Chloro-4'-(((1s,4s)-4-((dimethylamino)methyl)cyclohexyl)amino)-[2,3'-bipyridin]-5-yl)(4-methylpiperazin-1-yl)methanone The title compound as a pale yellow sticky oil (85 mg) was prepared in the same fashion as Step 2 in Reference Example 1, except that (6'-chloro-4'-fluoro-[2,3'-bipyridin]-5-yl)(4-methylpiperazin-1-yl)methanone (100 mg, 0.299 mmol) prepared in Step 1 of Example 199 and (1s,4s)-4-

((dimethylamino)methyl)cyclohexan-1-amine dihydrochloride (103 mg, 0.448 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=471.2 (M+H)$^+$ Step 2. (6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)(4-methylpiperazin-1-yl)methanone The title compound as a pale yellow solid (16.1 mg) was prepared in the same fashion as Step 3 in Example 1, except that (6'-chloro-4'-(((1s,4s)-4-((dimethylamino)methyl)cyclohexyl)amino)-[2,3'-bipyridin]-5-yl)(4-methylpiperazin-1-yl)methanone (80 mg, 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (CDCl$_3$, 400 MHz) δ 9.91 (d, 1H), 8.66 (d, 2H), 8.50 (s, 1H), 8.47 (d, 1H), 8.41 (d, 1H), 7.83 (q, 2H), 7.76 (brs, 1H), 7.28 (s, 1H), 7.12 (d, 1H), 3.96 (brs, 1H), 3.83 (brs, 2H), 3.57 (brs, 2H), 2.87-2.81 (m, 1H), 2.52-2.46 (m, 4H), 2.36 (s, 3H), 2.22 (s, 6H), 2.13 (d, 2H), 2.04-1.99 (m, 2H), 1.82-1.72 (m, 4H), 1.65-1.61 (m, 1H), 1.56-1.52 (m, 2H), 1.32-1.20 (m, 4H); MS (ESI) m/z=700.3 (M+H)$^+$ Example 205. (1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)-1-methylcyclohexan-1-ol Step 1. 2-((6'-Chloro-4'-fluoro-[2,3'-bipyridin]-5-yl)oxy)ethan-1-ol The title compound as a solid (396 mg) was prepared in the same fashion as Reference Example 5, except that 2-((6-bromopyridin-3-yl)oxy)ethan-1-ol (500 mg, 2.293 mmol) was used instead of 2-bromo-5-(methylsulfonyl)pyridine. $^1$H-NMR (CDCl$_3$, 400 MHz) δ 9.00 (d, 1H), 8.47 (d, 1H), 7.71 (dd, 1H), 7.33 (dd, 1H), 7.18 (d, 1H), 4.21 (t, 2H), 4.05 (s, 2H), 2.17 (s, 1H)

Step 2. (1s,4s)-4-((6'-Chloro-5-(2-hydroxyethoxy)-[2,3'-bipyridin]-4'-yl)amino)-1-methylcyclohexan-1-ol The title compound as a solid (86 mg) was prepared in the same fashion as Step 2 in Reference Example 1, except that 2-((6'-chloro-4'-fluoro-[2,3'-bipyridin]-5-yl)oxy)ethan-1-ol (100 mg, 0.372 mmol) prepared in Step 1 was used instead of 6'-chloro-4'-fluoro-5-((1-methylpiperidin-4-yl)oxy)-2,3'-bipyridine. MS (ESI) m/z=378.1 (M+H)$^+$ Step 3. (1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)-1-methylcyclohexan-1-ol The title compound as a pale yellow solid (22.2 mg) was prepared in the same fashion as Step 3 in Example 1, except that (1s,4s)-4-((6'-chloro-5-(2-hydroxyethoxy)-[2,3'-bipyridin]-4'-yl)amino)-1-methylcyclohexan-1-ol (71 mg, 0.187 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.96 (s, 1H), 9.12 (s, 1H), 8.65 (s, 1H), 8.46 (s, 1H), 8.41 (d, 1H), 8.40 (s, 1H), 8.34 (d, 1H), 7.89 (d, 1H), 7.56 (brs, 1H), 7.51 (dd, 1H), 7.25 (brs, 1H), 4.18 (brs, 1H), 4.12 (t, 2H), 3.74 (t, 2H), 3.26-3.20 (m, 1H), 1.84-1.82 (m, 2H), 1.67-1.56 (m, 4H), 1.45-1.39 (m, 2H), 1.36-1.32 (m, 2H), 1.27-1.22 (m, 2H), 1.13 (s, 3H); MS (ESI) m/z=607.2 (M+H)$^+$ Example 206. 2-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)oxy)ethan-1-ol Step 1. 2-((6'-Chloro-4'-(((1s,4s)-4-(hydroxymethyl)cyclohexyl)amino)-[2,3'-bipyridin]-5-yl)oxy)ethan-1-ol The title compound as a solid (84 mg) was prepared in the same fashion as Step 2 in Reference Example 1, except that 2-((6'-chloro-4'-fluoro-[2,3'-bipyridin]-5-yl)oxy)ethan-1-ol (100 mg. 0.372 mmol) prepared in Step 1 of Example 205 and ((1s,4s)-4-aminocyclohexyl)methanol hydrochloride (92 mg, 0.558 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=378.1 (M+H)$^+$ Step 2. 2-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)oxy)ethan-1-ol The title compound as a pale yellow solid (10.1 mg) was prepared in the same fashion as Step 3 in Example 1, except that 2-((6'-chloro-4'-(((1s,4s)-4-(hydroxy methyl)cyclohexyl)amino)-[2,3'-bipyridin]-5-yl)oxy)ethan-1-ol (71 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.00 (s, 1H), 9.67 (d, 1H), 8.62 (s, 1H), 8.46 (s, 1H), 8.45 (s, 1H), 8.41 (d, 1H), 8.30 (d, 1H), 7.94 (d, 1H), 7.53 (dd, 1H), 7.42 (brs, 2H), 4.95 (t, 1H), 4.46 (t, 1H), 4.13 (t, 2H), 3.89 (brs, 1H), 3.75 (q, 2H), 3.30-3.23 (m, 3H), 1.87-1.85 (m, 2H), 1.72-1.60 (m, 4H), 1.47 (brs, 1H), 1.36-1.32 (m, 2H), 1.30-1.22 (m, 4H); MS (ESI) m/z=607.2 (M+H)$^+$ Example 207. 2-(((1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)cyclohexyl)propan-2-ol Step 1. 2-(((1s,4s)-4-((6'-Chloro-5-(2-hydroxyethoxy)-[2,3'-bipyridin]-4'-yl)amino)cyclohexyl)propan-2-ol The title compound as a solid (92 mg) was prepared in the same fashion as Step 2 in Reference Example 1, except that 2-((6'-chloro-4'-fluoro-[2,3'-bipyridin]-5-yl)oxy)ethan-1-ol (100 mg, 0.372 mmol) prepared in Step 1 of Example 205 and 2-((1s,4s)-4-aminocyclohexyl)propan-2-ol (88 mg, 0.558 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=406.2 (M+H)$^+$ Step 2. 2-((1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)cyclohexyl)propan-2-ol The title compound as a pale yellow solid (13.6 mg) was prepared in the same fashion as Step 3 in Example 1, except that 2-((1s,4s)-4-((6'-chloro-5-(2-hydroxyethoxy)-[2,3'-bipyridin]-4'-yl)amino)cyclohexyl)propan-2-ol (69 mg, 0.17 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 10.01 (s, 1H), 9.72 (d, 1H), 8.61 (s, 1H), 8.46 (s, 1H), 8.44 (s, 1H), 8.40 (d, 1H), 8.26 (d, 1H), 7.95 (d, 1H), 7.53 (dd, 1H), 7.49 (brs, 1H), 7.37 (brs, 1H), 4.11 (t, 2H), 3.93 (brs, 1H), 3.74 (t, 2H), 3.30-3.25 (m, 1H), 1.96-1.93 (m, 2H), 1.69-1.62 (m, 4H), 1.34-1.21 (m, 7H), 1.05 (s, 6H); MS (ESI) m/z=635.2 (M+H)⁺

Example 208. (1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)-1-methylcyclohexan-1-ol Step 1. 2-((6'-Chloro-4'-fluoro-[2,3'-bipyridin]-5-yl)oxy)-N,N-dimethylethan-1-amine The title compound as a solid (390 mg) was prepared in the same fashion as Reference Example 5, except that 2-((6-bromopyridin-3-yl)oxy)-N,N-dimethylethan-1-amine (562 mg, 2.293 mmol) was used instead of 2-bromo-5-(methylsulfonyl)pyridine. MS (ESI) m/z=296.0 (M+H)⁺

Step 2. (1s,4s)-4-((6'-Chloro-5-(2-(dimethylamino) ethoxy)-[2,3'-bipyridin]-4'-yl)amino)-1-methylcyclohexan-1-ol The title compound as a solid (92 mg) was prepared in the same fashion as Step 2 in Reference Example 1, except that 2-((6'-chloro-4'-fluoro-[2,3'-bipyridin]-5-yl)oxy)-N,N-dimethylethan-1-amine (100 mg, 0.338 mmol) prepared in Step 1 was used instead of 6'-chloro-4'-fluoro-5-((1-methylpiperidin-4-yl)oxy)-2,3'-bipyridine. MS (ESI) m/z=405.2 (M+H)⁺

Step 3. (1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)-1-methylcyclohexan-1-ol The title compound as a pale yellow solid (19.5 mg) was prepared in the same fashion as Step 3 in Example 1, except that (1s,4s)-4-((6'-chloro-5-(2-(dimethylamino) ethoxy)-[2,3'-bipyridin]-4'-yl)amino)-1-methylcyclohexan-1-ol (92 mg, 0.226 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.12 (d, 1H), 8.66 (s, 1H), 8.48 (s, 1H), 8.41 (d, 1H), 8.33 (s, 1H), 8.29 (s, 1H), 7.73 (brs, 1H), 7.64 (d, 1H), 7.35 (d, 1H), 7.32 (d, 1H), 6.98 (s, 1H), 4.17 (t, 2H), 3.50 (brs, 1H), 2.86-2.77 (m, 3H), 2.37 (s, 6H), 2.01-1.98 (m, 2H), 1.80-1.73 (m, 4H), 1.63-1.52 (m, 4H), 1.31 (s, 3H), 1.26-1.20 (m, 2H); MS (ESI) m/z=634.2 (M+H)⁺

Example 209. ((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)methanol Step 1. ((1s,4s)-4-((6'-Chloro-5-(2-(dimethylamino) ethoxy)-[2,3'-bipyridin]-4'-yl)amino)cyclohexyl)methanol The title compound as a solid (102 mg) was prepared in the same fashion as Step 2 in Reference Example 1, except that 2-((6'-chloro-4'-fluoro-[2,3'-bipyridin]-5-yl)oxy)-N,N-dimethylethan-1-amine (100 mg, 0.338 mmol) prepared in Step 1 of Example 208 and ((1s,4s)-4-aminocyclohexyl)methanol hydrochloride (84 mg, 0.507 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=405.1 (M+H)⁺

Step 2. ((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino) cyclohexyl)methanol The title compound as a pale yellow solid (30 mg) was prepared in the same fashion as Step 3 in Example 1, except that ((1s,4s)-4-((6'-chloro-5-(2-(dimethylamino) ethoxy)-[2,3'-bipyridin]-4'-yl)amino)cyclohexyl)methanol (92 mg, 0.226 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.64 (d, 1H), 8.66 (s, 1H), 8.46 (s, 1H), 8.38 (d, 1H), 8.35 (d, 1H), 8.29 (d, 1H), 7.68 (d, 1H), 7.36 (dd, 1H), 7.26 (s, 1H), 7.11 (d, 1H), 4.17 (t, 2H), 3.96 (brs, 1H), 3.53 (d, 2H), 2.86-2.82 (m, 1H), 2.78 (t, 2H), 2.37 (s, 6H), 2.05-2.01 (m, 2H), 1.80-1.70 (m, 5H), 1.55-1.52 (m, 2H), 1.41-1.32 (m, 2H), 1.26-1.21 (m, 2H); MS (ESI) m/z=634.3 (M+H)⁺

Example 210. 2-((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)propan-2-ol Step 1. 2-((1s,4s)-4-((6'-Chloro-5-(2-(dimethylamino) ethoxy)-[2,3'-bipyridin]-4'-yl)amino)cyclohexyl)propan-2-ol The title compound as a solid (106 mg) was prepared in the same fashion as Step 2 in Reference Example 1, except that 2-((6'-chloro-4'-fluoro-[2,3'-bipyridin]-5-yl)oxy)-N,N-dimethylethan-1-amine (100 mg, 0.338 mmol) prepared in Step 1 of Example 208 and 2-((1s,4s)-4-aminocyclohexyl)propan-2-ol (80 mg, 0.507 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=433.2 (M+H)⁺

Step 2. 2-((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)propan-2-ol The title compound as a pale yellow solid (42.7 mg) was prepared in the same fashion as Step 3 in Example 1, except that 2-((1s,4s)-4-((6'-chloro-5-(2-(dimethylamino) ethoxy)-[2,3'-bipyridin]-4'-yl)amino)cyclohexyl)propan-2-ol (98 mg. 0.226 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.66 (d, 1H), 8.66 (s, 1H), 8.46 (s, 1H), 8.38 (d, 1H), 8.36 (s, 1H), 8.29 (d, 1H), 7.69 (d, 1H), 7.36 (dd, 1H), 7.29 (s, 1H), 7.09 (d, 1H), 4.15 (t, 2H), 3.98 (brs, 1H), 2.86-2.82 (m, 1H), 2.78 (t, 2H), 2.37 (s, 6H), 2.11-2.03 (m, 3H), 1.80-1.70 (m, 4H), 1.56-1.51 (m, 2H), 1.44-1.40 (m, 2H), 1.26-1.20 (m, 8H); MS (ESI) m/z=662.3 (M+H)⁺

Example 211. (1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)-1-methylcyclohexan-1-ol

Step 1. 4-(2-((6'-Chloro-4'-fluoro-[2,3'-bipyridin]-4-yl)oxy)ethyl) morpholine The title compound as a solid (661 mg) was prepared in the same fashion as Reference Example 5, except that 4-(2-((2-bromopyridin-4-yl)oxy)ethyl) morpholine (1000 mg, 3.483 mmol) was used instead of 2-bromo-5-(methylsulfonyl)pyridine. MS (ESI) m/z=338.0 (M+H)$^+$

Step 2. (1s,4s)-4-((6'-Chloro-4-(2-morpholinoethoxy)-[2,3'-bipyridin]-4'-yl)amino)-1-methylcyclohexan-1-ol The title compound as a solid (133 mg) was prepared in the same fashion as Step 2 in Reference Example 1, except that 4-(2-((6'-chloro-4'-fluoro-[2,3'-bipyridin]-4-yl)oxy)ethyl) morpholine (100 mg, 0.296 mmol) prepared in Step 1 was used instead of 6'-chloro-4'-fluoro-5-((1-methylpiperidin-4-yl)oxy)-2,3'-bipyridine. MS (ESI) m/z=447.1 (M+H)$^+$

Step 3. (1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)-1-methylcyclohexan-1-ol The title compound as a pale yellow solid (35 mg) was prepared in the same fashion as Step 3 in Example 1, except that (1s,4s)-4-((6'-chloro-4-(2-morpholinoethoxy)-[2,3'-bipyridin]-4'-yl)amino)-1-methylcyclohexan-1-ol (126 mg, 0.283 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.36 (d, 1H), 8.66 (s, 1H), 8.48 (s, 1H), 8.41 (t, 2H), 8.36 (s, 1H), 7.62 (br, 1H), 7.32 (d, 1H), 7.20 (s, 1H), 6.98 (s, 1H), 6.76 (d, 1H), 4.23 (t, 2H), 3.76 (t, 4H), 3.49 (br, 1H), 2.87-2.80 (m, 3H), 2.60 (t, 4H), 2.00-1.98 (m, 2H), 1.81-1.73 (m, 4H), 1.63-1.51 (m, 4H), 1.31 (s, 3H), 1.26-1.22 (m, 2H); MS (ESI) m/z=676.2 (M+H)$^+$

Example 212. ((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)methanol

Step 1. ((1s,4s)-4-((6'-Chloro-4-(2-morpholinoethoxy)-[2,3'-bipyridin]-4'-yl)amino)cyclohexyl)methanol The title compound as a solid (138 mg) was prepared in the same fashion as Step 2 in Reference Example 1, except that 4-(2-((6'-chloro-4'-fluoro-[2,3'-bipyridin]-4-yl)oxy)ethyl) morpholine (100 mg. 0.296 mmol) prepared in Step 1 of Example 211 and ((1s,4s)-4-aminocyclohexyl)methanol hydrochloride (74 mg, 0.444 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=447.2 (M+H)$^+$

Step 2. ((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)methanol The title compound as a pale yellow solid (46.9 mg) was prepared in the same fashion as Step 3 in Example 1, except that ((1s,4s)-4-((6'-chloro-4-(2-morpholinoethoxy)-[2,3'-bipyridin]-4'-yl)amino)cyclohexyl)methanol (126 mg, 0.283 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.88 (d, 1H), 8.65 (s, 1H), 8.46 (s, 1H), 8.39 (t, 2H), 7.29 (s, 1H), 7.23 (s, 1H), 7.09 (d, 1H), 6.76 (d, 1H), 4.23 (t, 2H), 3.96 (br, 1H), 3.75 (t, 4H), 3.53 (d, 2H), 2.85 (t, 3H), 2.60 (br, 4H), 2.04-2.01 (m, 2H), 1.84-1.69 (m, 5H), 1.55-1.52 (m, 2H), 1.41-1.35 (m, 2H), 1.24-1.19 (m, 2H); MS (ESI) m/z=676.2 (M+H)$^+$

Example 213. 2-((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)propan-2-ol

Step 1. 2-((1s,4s)-4-((6'-Chloro-4-(2-morpholinoethoxy)-[2,3'-bipyridin]-4'-yl)amino)cyclohexyl)propan-2-ol The title compound as a solid (146 mg) was prepared in the same fashion as Step 2 in Reference Example 1, except that 4-(2-((6'-chloro-4'-fluoro-[2,3'-bipyridin]-4-yl)oxy)ethyl) morpholine (100 mg, 0.296 mmol) prepared in Step 1 of Example 211 and 2-((1s,4s)-4-aminocyclohexyl)propan-2-ol (70 mg. 0.444 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=475.2 (M+H)$^+$

Step 2. 2-((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)propan-2-ol The title compound as a pale yellow solid (55.5 mg) was prepared in the same fashion as Step 3 in Example 1, except that 2-((1s,4s)-4-((6'-chloro-4-(2-morpholinoethoxy)-[2,3'-bipyridin]-4'-yl)amino)cyclohexyl)propan-2-ol (134 mg. 0.283 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.92 (d, 1H), 8.65 (s, 1H), 8.46 (s, 1H), 8.38 (s, 2H), 7.87 (d, 1H), 7.35 (s, 1H), 7.23 (s, 1H), 7.05 (d, 1H), 6.75 (d, 1H), 4.22 (t, 2H), 3.98 (br, 1H), 3.75 (t, 4H), 2.85 (t, 3H), 2.61-2.59 (m, 4H), 2.10-2.07 (m, 2H), 1.78-1.71 (m, 4H), 1.55-1.52 (m, 2H), 1.43-1.40 (m, 3H), 1.26-1.22 (m, 8H); MS (ESI) m/z=704.3 (M+H)$^+$

Example 214. ((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)methanol

Step 1. ((1s,4s)-4-((6'-Chloro-4-((3,3-difluorocyclobutyl)amino)-[2,3'-bipyridin]-4'-yl)amino)cyclohexyl)methanol The title compound as a solid (126 mg) was prepared in the same fashion as Step 2 in Reference Example 1, except that 6'-chloro-N-(3,3-difluorocyclobutyl)-4'-fluoro-[2,3'-bipyridin]-4-amine (100 mg, 0.319 mmol) prepared in Reference Example 15 and ((1s,4s)-4-aminocyclohexyl)methanol hydrochloride (79 mg, 0.478 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=423.1 (M+H)+

Step 2. ((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)methanol The title compound as a pale yellow solid (43.3 mg) was prepared in the same fashion as Step 3 in Example 1, except that ((1s,4s)-4-((6'-chloro-4-((3,3-difluorocyclobutyl)amino)-[2,3'-bipyridin]-4'-yl)amino)cyclohexyl)methanol (114 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.78 (d, 1H), 8.65 (s, 1H), 8.46 (s, 1H), 8.37 (d, 1H), 8.32 (s, 1H), 8.22 (d, 1H), 7.23 (s, 1H), 7.10 (d, 1H), 6.76 (s, 1H), 6.32 (d, 1H), 4.62 (d, 1H), 3.94 (br, 2H), 3.52 (d, 2H), 3.14-3.07 (m, 2H), 2.87-2.81 (m, 1H), 2.58-2.46 (m, 2H), 2.02-1.99 (m, 2H), 1.78-1.68 (m, 5H), 1.54-1.52 (m, 2H), 1.40-1.35 (m, 2H), 1.27-1.24 (m, 2H); MS (ESI) m/z=652.2 (M+H)+

Example 215. 2-((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)propan-2-ol Step 1. 2-((1s,4s)-4-((6'-Chloro-4-((3,3-difluorocyclobutyl)amino)-[2,3'-bipyridin]-4'-yl)amino)cyclohexyl)propan-2-ol The title compound as a solid (123 mg) was prepared in the same fashion as Step 2 in Reference Example 1, except that 6'-chloro-N-(3,3-difluorocyclobutyl)-4'-fluoro-[2,3'-bipyridin]-4-amine (100 mg, 0.319 mmol) prepared in Reference Example 15 and 2-((1s,4s)-4-aminocyclohexyl)propan-2-ol (75 mg, 0.478 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=451.2 (M+H)+

Step 2. 2-((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)propan-2-ol The title compound as a pale yellow solid (55 mg) was prepared in the same fashion as Step 3 in Example 1, except that 2-((1s,4s)-4-((6'-chloro-4-((3,3-difluorocyclobutyl)amino)-[2,3'-bipyridin]-4'-yl)amino)cyclohexyl)propan-2-ol (122 mg. 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.81 (d, 1H), 8.65 (s, 1H), 8.46 (s, 1H), 8.36 (d, 1H), 8.32 (s, 1H), 8.21 (d, 1H), 7.29 (s, 1H), 7.06 (d, 1H), 6.77 (s, 1H), 6.34 (d, 1H), 4.66 (d, 1H), 3.95 (br, 2H), 3.16-3.06 (m, 2H), 2.83 (br, 1H), 2.58-2.46 (m, 2H), 2.06-2.05 (m, 2H), 1.90 (br, 1H), 1.74-1.69 (m, 4H), 1.54-1.52 (m, 2H), 1.42-1.40 (m, 2H), 1.25-1.20 (m, 8H); MS (ESI) m/z=680.2 (M+H)+

Example 216. N$^{6'}$-(2-(1-(Cyclopropylsulfonyl)-1H-pyrazol-4-yl)pyrimidin-4-yl)-N$^4$-(3,3-difluorocyclobutyl)-N$^{4'}$-((1s,4s)-4-((dimethylamino)methyl)cyclohexyl)-[2,3'-bipyridine]-4,4',6'-triamine Step 1. 6'-Chloro-N$^4$-(3,3-difluorocyclobutyl)-N$^{4'}$-((1s,4s)-4-((dimethylamino)methyl)cyclohexyl)-[2,3'-bipyridine]-4,4'-diamine The title compound as a solid (144 mg) was prepared in the same fashion as Step 2 in Reference Example 1, except that 6'-chloro-N-(3,3-difluorocyclobutyl)-4'-fluoro-[2,3'-bipyridin]-4-amine (100 mg. 0.319 mmol) prepared in Reference Example 15 and (1s,4s)-4-((dimethylamino)methyl)cyclohexan-1-amine dihydrochloride (110 mg, 0.478 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=450.2 (M+H)+

Step 2. N$^{6'}$-(2-(1-(Cyclopropylsulfonyl)-1H-pyrazol-4-yl)pyrimidin-4-yl)-N$^{4'}$-(3,3-difluorocyclobutyl)-N$^{4'}$-((1s,4s)-4-((dimethylamino)methyl)cyclohexyl)-[2,3'-bipyridine]-4,4',6'-triamine The title compound as a pale yellow solid (24.6 mg) was prepared in the same fashion as Step 3 in Example 1, except that 6'-chloro-N$^4$-(3,3-difluorocyclobutyl)-N$^{4'}$-((1s,4s)-4-((dimethylamino)methyl)cyclohexyl)-[2,3'-bipyridine]-4,4'-diamine (110 mg, 0.245 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.83 (d, 1H), 8.66 (s, 1H), 8.46 (s, 1H), 8.38 (d, 1H), 8.32 (s, 1H), 8.23 (d, 1H), 7.17 (d, 2H), 6.77 (s, 1H), 6.36 (d, 1H), 4.57 (d, 1H), 3.94 (d, 2H), 3.18-3.11 (m, 2H), 2.84-2.81 (m, 1H), 2.58-2.47 (m, 2H), 2.22 (s, 6H), 2.13 (d, 2H), 1.99-1.95 (m, 2H), 1.78-1.72 (m, 4H), 1.61 (br, 1H), 1.54-1.52 (m, 2H), 1.30-1.24 (m, 4H); MS (ESI) m/z=679.3 (M+H)+

Example 217. 2-((1s,4s)-4-((5-(2-(Azetidin-1-yl)ethoxy)-6'-((2-(1-(cyclopropylsulfonyl)-1H-pyrazol-4-yl)pyrimidin-4-yl)amino)-[2,3'-bipyridin]-4'-yl)amino)cyclohexyl)propan-2-ol Step 1. 2-((1s,4s)-4-((5-(2-(Azetidin-1-yl) ethoxy)-6'-chloro-[2,3'-bipyridin]-4'-yl)amino)cyclohexyl)propan-2-ol The title compound as a solid (57 mg) was prepared in the same fashion as Step 2 in Reference Example 1, except that 5-(2-(azetidin-1-yl) ethoxy)-6'-chloro-4'-fluoro-2,3'-bipyridine (100 mg. 0.325 mmol) prepared in Reference Example 13 and 2-((1s,4s)-4-aminocyclohexyl)propan-2-ol (81 mg. 0.487 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=445.2 (M)+

Step 2. 2-((1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)cyclohexyl)propan-2-ol The title compound as a pale yellow solid (17.7 mg) was prepared in the same fashion as Step 3 in Example 1, except that 2-((1s,4s)-4-((5-(2-(azetidin-1-yl) ethoxy)-6'-chloro-[2,3'-bipyridin]-4'-yl)amino)cyclohexyl)propan-2-ol (50 mg. 0.113 mmol) prepared in Step 1 was used instead of (1-(6'- chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.74 (d, 1H), 8.65 (s, 1H), 8.46 (s, 1H), 8.38 (d, 1H), 8.34 (s, 1H), 8.26 (d, 1H), 7.68 (d, 1H), 7.34 (dd, 1H), 7.31 (s, 1H), 7.11 (d, 1H), 4.05 (t, 2H), 3.97 (br, 1H), 3.38 (t, 4H), 2.89 (t, 2H), 2.86-2.82 (m, 1H), 2.16 (quin, 2H), 2.11-2.08 (m, 2H), 1.79-1.71 (m, 4H), 1.56-1.52 (m, 2H), 1.44-1.40 (m, 3H), 1.25-1.21 (m, 8H); MS (ESI) m/z=674.3 (M+H)$^+$ Example 218. (1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)-1-methylcyclohexan-1-ol Step 1. (1s,4s)-4-((6'-Chloro-5-(2,2,2-trifluoroethyl)-[2,3'-bipyridin]-4'-yl)amino)-1-methylcyclohexan-1-ol The title compound as a solid (120 mg) was prepared in the same fashion as Step 2 in Reference Example 1, except that 6'-chloro-4'-fluoro-5-(2,2,2-trifluoroethyl)-2,3'-bipyridine (100 mg, 0.344 mmol) prepared in Reference Example 8 was used instead of 6'-chloro-4'-fluoro-5-((1-methylpiperidin-4-yl)oxy)-2,3'-bipyridine. MS (ESI) m/z=400.1 (M+H)$^+$ Step 2. (1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)-1-methylcyclohexan-1-ol The title compound as a pale yellow solid (44.1 mg) was prepared in the same fashion as Step 3 in Example 1, except that (1s,4s)-4-((6'-chloro-5-(2,2,2-trifluoroethyl)-[2,3'-bipyridin]-4'-yl)amino)-1-methylcyclohexan-1-ol (116 mg, 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.46 (d, 1H), 8.66 (s, 1H), 8.48 (t, 3H), 8.42 (d, 1H), 7.83 (br, 1H), 7.77-7.74 (m, 2H), 7.28 (d, 1H), 7.05 (s, 1H), 3.53-3.51 (m, 1H), 3.42 (q, 2H), 2.85-2.81 (m, 1H), 2.04-1.99 (m, 2H), 1.82-1.74 (m, 4H), 1.63-1.60 (m, 2H), 1.57-1.51 (m, 2H), 1.31 (s, 3H), 1.24-1.19 (m, 2H); MS (ESI) m/z=629.2 (M+H)$^+$ Example 219. ((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol Step 1. ((1s,4s)-4-((6'-Chloro-5-(2,2,2-trifluoroethyl)-[2,3'-bipyridin]-4'-yl)amino)cyclohexyl)methanol The title compound as a solid (131 mg) was prepared in the same fashion as Step 2 in Reference Example 1, except that 6'-chloro-4'-fluoro-5-(2,2,2-trifluoroethyl)-2,3'-bipyridine (100 mg, 0.344 mmol) prepared in Reference Example 8 and ((1s,4s)-4-aminocyclohexyl)methanol hydrochloride (86 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=400.1 (M+H)$^+$ Step 2. ((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol The title compound as a pale yellow solid (36.1 mg) was prepared in the same fashion as Step 3 in Example 1, except that ((1s,4s)-4-((6'-chloro-5-(2,2,2-trifluoroethyl)-[2,3'-bipyridin]-4'-yl)amino)cyclohexyl)methanol (116 mg, 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.68 (s, 1H), 8.56 (s, 1H), 8.46 (s, 1H), 8.42 (s, 1H), 8.33 (d, 1H), 7.91-7.83 (m, 2H), 7.42 (s, 1H), 7.23 (d, 1H), 3.98 (s, 1H), 3.60 (q, 2H), 3.43 (d, 2H), 3.08-3.01 (m, 1H), 2.01-1.99 (m, 2H), 1.83-1.71 (m, 4H), 1.64-1.59 (m, 1H), 1.47-1.43 (m, 2H), 1.39-1.25 (m, 4H); MS (ESI) m/z=629.2 (M+H)$^+$ Example 220. 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)propan-2-ol Step 1. 2-((1s,4s)-4-((6'-Chloro-5-(2,2,2-trifluoroethyl)-[2,3'-bipyridin]-4'-yl)amino)cyclohexyl)propan-2-ol The title compound as a solid (119 mg) was prepared in the same fashion as Step 2 in Reference Example 1, except that 6'-chloro-4'-fluoro-5-(2,2,2-trifluoroethyl)-2,3'-bipyridine (100 mg, 0.344 mmol) prepared in Reference Example 8 and 2-((1s,4s)-4-aminocyclohexyl)propan-2-ol (81 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=428.1 (M+H)$^+$ Step 2. 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)propan-2-ol The title compound as a pale yellow solid (43.6 mg) was prepared in the same fashion as Step 3 in Example 1, except that 2-((1s,4s)-4-((6'-chloro-5-(2,2,2-trifluoroethyl)-[2,3'-bipyridin]-4'-yl)amino)cyclohexyl)propan-2-ol (124 mg. 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.71 (s, 1H), 8.58 (s, 1H), 8.49 (s, 1H), 8.45 (s, 1H), 8.35 (d, 1H), 7.90 (dd, 2H), 7.48 (s, 1H), 7.23 (d, 1H), 4.03 (s, 1H), 3.62 (q, 2H), 3.08-3.01 (m, 1H), 2.11-2.02 (m, 4H), 1.81-1.75 (m, 4H), 1.47-1.40 (m, 3H), 1.34-1.24 (m, 2H), 1.17 (s, 6H); MS (ESI) m/z=657.2 (M+H)$^+$ Example 221. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2,2,2-trifluoroethyl)-[2,3'-bipyridine]-4',6'-diamine Step 1. 6'-Chloro-N-((1s,4s)-4-((dimethylamino)methyl)cyclohexyl)-5-(2,2,2-trifluoroethyl)-[2,3'-bipyridin]-4'-amine The title compound as a solid (120 mg) was prepared in the same fashion as Step 2 in Reference Example 1, except that 6'-chloro-4'-fluoro-5-(2,2,2-trifluoroethyl)-2,3'-bipyridine (100 mg. 0.344 mmol) prepared in Reference Example 8 and (1s,4s)-4-((dimethylamino)methyl)cyclohexan-1-amine dihydrochloride (118 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=427.1 (M+H)$^+$ Step 2. $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2,2,2-trifluoroethyl)-[2,3'-bipyridine]-4',6'-diamine The title compound as a pale yellow solid (35.4 mg) was prepared in the same fashion as Step 3 in Example 1, except that 6'-chloro-N-((1s,4s)-4-((dimethylamino)methyl)cyclohexyl)-5-(2,2,2-trifluoroethyl)-[2,3'-bipyridin]-4'-amine (113 mg, 0.264 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.67 (s, 1H), 8.54 (s, 1H), 8.45 (s, 1H), 8.41 (s, 1H), 8.31 (d, 1H), 7.89 (dd, 2H), 7.40 (s, 1H), 7.23 (d, 1H), 3.96 (s, 1H), 3.61 (q, 2H), 3.08-3.01 (m, 1H), 2.26 (s, 6H), 2.23 (d, 2H), 2.01-1.97 (m, 2H), 1.83-1.71 (m, 5H), 1.46-1.43 (m, 2H), 1.30-1.24 (m, 4H); MS (ESI) m/z=656.2 (M+H)$^+$ Example 222. ((1S,3S)-3-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol Step 1. ((1S,3S)-3-((6'-Chloro-5-(2,2,2-trifluoroethyl)-[2,3'-bipyridin]-4'-yl)amino)cyclohexyl)methanol The title compound as a solid (110 mg) was prepared in the same fashion as Step 2 in Reference Example 1, except that 6'-chloro-4'-fluoro-5-(2,2,2-trifluoroethyl)-2,3'-bipyridine (100 mg. 0.344 mmol) prepared in Reference Example 8 and ((1S,3S)-3-aminocyclohexyl)methanol hydrochloride (86 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=400.1 (M+H)$^+$ Step 2. ((1S,3S)-3-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol The title compound as a pale yellow solid (21 mg) was prepared in the same fashion as Step 3 in Example 1, except that ((1S,3S)-3-((6'-chloro-5-(2,2,2-trifluoroethyl)-[2,3'-bipyridin]-4'-yl)amino)cyclohexyl)methanol (75 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.06 (s, 1H), 9.98 (d, 1H), 8.63 (s, 1H), 8.59 (d, 2H), 8.45 (s, 1H), 8.41 (d, 1H), 8.07 (d, 1H), 7.88 (d, 1H), 7.47 (s, 1H), 7.42 (s, 1H), 4.46 (t, 1H), 4.04-4.00 (m, 1H), 3.77 (q, 2H), 3.25-3.21 (m, 2H), 1.97-1.85 (m, 2H), 1.76-1.73 (m, 1H), 1.65-1.50 (m, 4H), 1.38-1.28 (m, 5H), 1.04-1.00 (m, 1H); MS (ESI) m/z=629.2 (M+H)$^+$ Example 223. 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)ethan-1-ol Step 1. 2-((1s,4s)-4-((6'-Chloro-5-(2,2,2-trifluoroethyl)-[2,3'-bipyridin]-4'-yl)amino)cyclohexyl)ethan-1-ol The title compound as a solid (96 mg) was prepared in the same fashion as Step 2 in Reference Example 1, except that 6'-chloro-4'-fluoro-5-(2,2,2-trifluoroethyl)-2,3'-bipyridine (100 mg, 0.344 mmol) prepared in Reference Example 8 and 2-((1s,4s)-4-aminocyclohexyl)ethan-1-ol (74 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=414.1 (M+H)$^+$ Step 2. 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)ethan-1-ol The title compound as a pale yellow solid (31.4 mg) was prepared in the same fashion as Step 3 in Example 1, except that 2-((1s,4s)-4-((6'-chloro-5-(2,2,2-trifluoroethyl)-[2,3'-bipyridin]-4'-yl)amino)cyclohexyl)ethan-1-ol (77 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.67 (s, 1H), 8.53 (s, 1H), 8.44 (s, 1H), 8.41 (s, 1H), 8.31 (d, 1H), 7.86 (dd, 2H), 7.39 (s, 1H), 7.21 (d, 1H), 3.94 (s, 1H), 3.65-3.56 (m, 4H), 3.07-3.01 (m, 1H), 2.03-1.94 (m, 3H), 1.82-1.68 (m, 4H), 1.60-1.57 (m, 1H), 1.53-1.43 (m, 4H), 1.33-1.25 (m, 3H); MS (ESI) m/z=643.2 (M+H)$^+$ Example 224. (1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)-1-methylcyclohexan-1-ol Step 1. (1s,4s)-4-((6'-Chloro-5-(3,3-difluoroazetidin-1-yl)-[2,3'-bipyridin]-4'-yl)amino)-1-methylcyclohexan-1-ol The title compound as a solid (103 mg) was prepared in the same fashion as Step 2 in Reference Example 1, except that 6'-chloro-5-(3,3-difluoroazetidin-1-yl)-4'-fluoro-2,3'-bipyridine (90 mg, 0.3 mmol) prepared in Reference Example 9 was used instead of 6'-chloro-4'-fluoro-5-((1-methylpiperidin-4-yl)oxy)-2,3'-bipyridine. MS (ESI) m/z=409.1 (M+H)$^+$ Step 2. (1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)-1-methylcyclohexan-1-ol The title compound as a pale yellow solid (25.1 mg) was prepared in the same fashion as Step 3 in Example 1, except that (1s,4s)-4-((6'-chloro-5-(3,3-difluoroazetidin-1-yl)-[2,3'-bipyridin]-4'-yl)amino)-1-methylcyclohexan-1-ol (76 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.93 (s, 1H), 9.21 (d, 1H), 8.64 (s, 1H), 8.46 (s, 1H), 8.40 (d, 1H), 8.39 (s, 1H), 7.99 (d, 1H), 7.84 (d, 1H), 7.53 (br, 1H), 7.23 (br, 1H), 7.14 (dd, 1H), 4.39 (t, 4H), 4.19 (s, 1H), 3.28-3.23 (m, 1H), 1.83-1.81 (m, 2H), 1.62-1.56 (m, 4H), 1.44-1.39 (m, 2H), 1.33-1.31 (m, 2H), 1.25-1.22 (m, 2H), 1.13 (s, 3H); MS (ESI) m/z=638.2 (M+H)$^+$ Example 225. 2-((1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)cyclohexyl)propan-2-ol Step 1. 2-((1s,4s)-4-((6'-Chloro-5-(3,3-difluoroazetidin-1-yl)-[2,3'-bipyridin]-4'-yl)amino)cyclohexyl)propan-2-ol The title compound as a solid (85 mg) was prepared in the same fashion as Step 2 in Reference Example 1, except that 6'-chloro-5-(3,3-difluoroazetidin-1-yl)-4'-fluoro-2,3'-bipyridine (90 mg, 0.3 mmol) prepared in Reference Example 9 and 2-((1s,4s)-4-aminocyclohexyl)propan-2-ol (71 mg, 0.45 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=437.1 (M+H)$^+$ Step 2. 2-((1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)cyclohexyl)propan-2-ol The title compound as a pale yellow solid (20.3 mg) was prepared in the same fashion as Step 3 in Example 1, except that 2-((1s,4s)-4-((6'-chloro-5-(3,3-difluoroazetidin-1-yl)-[2,3'-bipyridin]-4'-yl)amino)cyclohexyl)propan-2-ol (82 mg. 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.63 (s, 1H), 8.38 (s, 1H), 8.28 (d, 1H), 8.25 (s, 1H), 7.88 (d, 1H), 7.67 (d, 1H), 7.32 (s, 1H), 7.11 (d, 1H), 7.05 (dd, 1H), 4.31 (t, 4H), 3.92 (s, 1H), 3.06-3.00 (m, 1H), 2.05-2.02 (m, 2H), 1.75-1.69 (m, 4H), 1.44-1.34 (m, 3H), 1.30-1.23 (m, 2H), 1.16 (s, 6H); MS (ESI) m/z=603.2 (M+H)$^+$ Example 226. (1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)-1-methylcyclohexan-1-ol Step 1. (1s,4s)-4-((6'-Chloro-5-(2,2,2-trifluoro-1-hydroxyethyl)-[2,3'-bipyridin]-4'-yl)amino)-1-methylcyclohexan-1-ol The title compound as a solid (108 mg) was prepared in the same fashion as Step 2 in Reference Example 1, except that 1-(6'-chloro-4'-fluoro-[2,3'-bipyridin]-5-yl)-2,2,2-trifluoroethan-1-ol (80 mg, 0.261 mmol) prepared in Reference Example 10 was used instead of 6'-chloro-4'-fluoro-5-((1-methylpiperidin-4-yl)oxy)-2,3'-bipyridine. MS (ESI) m/z=416.2 (M+H)$^+$ Step 2. (1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)-1-methylcyclohexan-1-ol The title compound as a pale yellow solid (12.2 mg) was prepared in the same fashion as Step 3 in Example 1, except that (1s,4s)-4-((6'-chloro-5-(2,2,2-trifluoro-1-hydroxyethyl)-[2,3'-bipyridin]-4'-yl)amino)-1-methylcyclohexan-1-ol (103 mg, 0.249 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 8.63 (s, 1H), 8.38 (s, 1H), 8.28 (d, 1H), 8.25 (s, 1H), 7.88 (d, 1H), 7.67 (d, 1H), 7.32 (s, 1H), 7.11 (d, 1H), 7.05 (dd, 1H), 4.31 (t, 4H), 3.92 (s, 1H), 3.06-3.00 (m, 1H), 2.05-2.02 (m, 2H), 1.75-1.69 (m, 4H), 1.44-1.34 (m, 3H), 1.30-1.23 (m, 2H), 1.16 (s, 6H); MS (ESI) m/z=645.2 (M+H)$^+$ Example 227. 1-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2,2-trifluoroethan-1-ol Step 1. 1-(6'-Chloro-4'-(((1s,4s)-4-(hydroxymethyl)cyclohexyl)amino)-[2,3'-bipyridin]-5-yl)-2,2,2-trifluoroethan-1-ol The title compound as a solid (107 mg) was prepared in the same fashion as Step 2 in Reference Example 1, except that 1-(6'-chloro-4'-fluoro-[2,3'-bipyridin]-5-yl)-2,2,2-trifluoroethan-1-ol (80 mg, 0.261 mmol) prepared in Reference Example 10 and ((1s,4s)-4-aminocyclohexyl)methanol hydrochloride (65 mg, 0.391 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=416.1 (M+H)$^+$ Step 2. 1-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2,2-trifluoroethan-1-ol The title compound as a pale yellow solid (9.9 mg) was prepared in the same fashion as Step 3 in Example 1, except that 1-(6'-chloro-4'-(((1s,4s)-4-(hydroxymethyl)cyclohexyl)amino)-[2,3'-bipyridin]-5-yl)-2,2,2-trifluoroethan-1-ol (103 mg, 0.249 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.08 (s, 1H), 9.99 (d, 1H), 8.67 (s, 1H), 8.62 (d, 2H), 8.45 (s, 1H), 8.42 (d, 1H), 8.11 (d, 1H), 7.97 (d, 1H), 7.52 (br, 1H), 7.40 (br, 1H), 7.07 (d, 1H), 5.37 (quin, 1H), 4.44 (t, 1H), 3.94 (br, 1H), 3.28-3.24 (m, 3H), 1.97-1.88 (m, 2H), 1.74-1.64 (m, 4H), 1.49 (br, 1H), 1.34-1.30 (m, 2H), 1.29-1.22 (m, 4H); MS (ESI) m/z=645.2 (M+H)$^+$ Example 228. 1-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-2,2,2-trifluoroethan-1-ol Step 1. 1-(6'-Chloro-4'-(((1S,3S)-3-(hydroxymethyl)cyclohexyl)amino)-[2,3'-bipyridin]-5-yl)-2,2,2-trifluoroethan-1-ol The title compound as a solid (109 mg) was prepared in the same fashion as Step 2 in Reference Example 1, except that 1-(6'-chloro-4'-fluoro-[2,3'-bipyridin]-5-yl)-2,2,2-trifluoroethan-1-ol (80 mg, 0.261 mmol) prepared in Reference Example 10 and ((1S,3S)-3-aminocyclohexyl)methanol hydrochloride (65 mg, 0.391 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=416.1 (M+H)$^+$ Step 2. 1-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-2,2,2-trifluoroethan-1-ol The title compound as a pale yellow solid (15.5 mg) was prepared in the same fashion as Step 3 in Example 1, except that 1-(6'-chloro-4'-(((1S,3S)-3-(hydroxymethyl)cyclohexyl)amino)-[2,3'-bipyridin]-5-yl)-2,2,2-trifluoroethan-1-ol (103 mg, 0.249 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.08 (s, 1H), 9.99 (d, 1H), 8.67 (s, 1H), 8.62 (d, 2H), 8.45 (s, 1H), 8.42 (d, 1H), 8.11 (d, 1H), 7.97 (d, 1H), 7.52 (br, 1H), 7.40 (br, 1H), 7.07 (d, 1H), 5.37 (quin, 1H), 4.44 (t, 1H), 3.94 (br, 1H), 3.28-3.24 (m, 3H), 1.97-1.88 (m, 2H), 1.74-1.64 (m, 4H), 1.49 (br, 1H), 1.34-1.30 (m, 2H), 1.29-1.22 (m, 4H); MS (ESI) m/z=645.2 (M+H)$^+$ Example 229. 2-((1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)cyclohexyl)propan-2-ol Step 1. 2-((1s,4s)-4-((6'-Chloro-5-(2,2,2-trifluoro-1-hydroxyethyl)-[2,3'-bipyridin]-4'-yl)amino)cyclohexyl)propan-2-ol The title compound as a solid (109 mg) was prepared in the same fashion as Step 2 in Reference Example 1, except that 1-(6'-chloro-4'-fluoro-[2,3'-bipyridin]-5-yl)-2,2,2-trifluoroethan-1-ol (80 mg, 0.261 mmol) prepared in Reference Example 10 and 2-((1s,4s)-4-aminocyclohexyl)propan-2-ol (62 mg. 0.391 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=444.1 (M+H)$^+$ Step 2. 2-((1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)cyclohexyl)propan-2-ol The title compound as a pale yellow solid (17.3 mg) was prepared in the same fashion as Step 3 in Example 1, except that 2-((1s,4s)-4-((6'-chloro-5-(2,2,2-trifluoro-1-hydroxyethyl)-[2,3'-bipyridin]-4'-yl)amino)cyclohexyl)propan-2-ol (110 mg. 0.249 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol.
$^1$H-NMR (DMSO-d$_6$, 400 MHz) δ 10.08 (s, 1H), 10.05 (d, 1H), 8.66 (s, 1H), 8.62 (d, 2H), 8.45 (s, 1H), 8.42 (d, 1H), 8.11 (d, 1H), 7.97 (d, 1H), 7.56 (br, 1H), 7.36 (br, 1H), 7.07 (d, 1H), 5.37 (quin, 1H), 4.08 (s, 1H), 3.97 (br, 1H), 3.28-3.24 (m, 1H), 1.99-1.93 (m, 2H), 1.72-1.63 (m, 4H), 1.34-1.24 (m, 7H), 1.02 (s, 6H); MS (ESI) m/z=673.2 (M+H)$^+$ Example 230. (1s,4s)-4-((6'-((2-(1-(Cyclopropylsulfonyl)-1H-pyrazol-4-yl)pyrimidin-4-yl)amino)-5-(1,1,1-trifluoro-2-hydroxypropan-2-yl)-[2,3'-bipyridin]-4'-yl)amino)-1-methylcyclohexan-1-ol Step 1. (1s,4s)-4-((6'-Chloro-5-(1,1,1-trifluoro-2-hydroxypropan-2-yl)-[2,3'-bipyridin]-4'-yl)amino)-1-methylcyclohexan-1-ol The title compound as a solid (107 mg) was prepared in the same fashion as Step 2 in Reference Example 1, except that 2-(6'-chloro-4'-fluoro-[2,3'-bipyridin]-5-yl)-1,1,1-trifluoropropan-2-ol (85 mg. 0.265 mmol) prepared in Reference Example 11 was used instead of 6'-chloro-4'-fluoro-5-((1-methylpiperidin-4-yl)oxy)-2,3'-bipyridine. MS (ESI) m/z=430.1 (M+H)$^+$ Step 2. (1s,4s)-4-((6'-((2-(1-(Cyclopropylsulfonyl)-1H-pyrazol-4-yl)pyrimidin-4-yl)amino)-5-(1,1,1-trifluoro-2-hydroxypropan-2-yl)-[2,3'-bipyridin]-4'-yl)amino)-1-methylcyclohexan-1-ol The title compound as a pale yellow solid (37.7 mg) was prepared in the same fashion as Step 3 in Example 1, except that (1s,4s)-4-((6'-chloro-5-(1,1,1-trifluoro-2-hydroxypropan-2-yl)-[2,3'-bipyridin]-4'-yl)amino)-1-methylcyclohexan-1-ol (89 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.81 (s, 1H), 8.73 (s, 1H), 8.46 (d, 2H), 8.35 (d, 1H), 8.07 (d, 1H), 7.88 (d, 1H), 7.37 (d, 1H), 7.28 (s, 1H), 3.60-3.58 (m, 1H), 3.05-3.00 (m, 1H), 1.99-1.95 (m, 2H), 1.81 (s, 3H), 1.78-1.72 (m, 4H), 1.62-1.55 (m, 2H), 1.47-1.43 (m, 2H), 1.30-1.28 (m, 5H); MS (ESI) m/z=659.2 (M+H)$^+$ Example 231. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-1,1,1-trifluoropropan-2-ol Step 1. 2-(6'-Chloro-4'-(((1s,4s)-4-(hydroxymethyl)cyclohexyl)amino)-[2,3'-bipyridin]-5-yl)-1,1,1-trifluoropropan-2-ol The title compound as a solid (108 mg) was prepared in the same fashion as Step 2 in Reference Example 1, except that 2-(6'-chloro-4'-fluoro-[2,3'-bipyridin]-5-yl)-1,1,1-trifluoropropan-2-ol (85 mg. 0.265 mmol) prepared in Reference Example 11 and ((1s,4s)-4-aminocyclohexyl)methanol hydrochloride (66 mg, 0.398 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=430.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-1,1,1-trifluoropropan-2-ol The title compound as a pale yellow solid (40 mg) was prepared in the same fashion as Step 3 in Example 1, except that 2-(6'-chloro-4'-(((1s,4s)-4-(hydroxymethyl)cyclohexyl)amino)-[2,3'-bipyridin]-5-yl)-1,1,1-trifluoropropan-2-ol (89 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.80 (s, 1H), 8.68 (s, 1H), 8.47 (s, 1H), 8.42 (s, 1H), 8.32 (d, 1H), 8.05 (d, 1H), 7.90 (d, 1H), 7.42 (s, 1H), 7.23 (d, 1H), 3.98 (s, 1H), 3.43 (d, 2H), 3.07-3.01 (m, 1H), 2.02-1.99 (m, 2H), 1.83 (s, 3H), 1.81-1.72 (m, 4H), 1.64-1.61 (m, 1H), 1.47-1.43 (m, 2H), 1.39-1.33 (m, 2H), 1.30-1.28 (m, 2H); MS (ESI) m/z=659.2 (M+H)$^+$ Example 232. 2-(6'-((2-(1-(Cyclopropylsulfonyl)-1H-pyrazol-4-yl)pyrimidin-4-yl)amino)-4'-(((1S,3S)-3-(hydroxy methyl)cyclohexyl)amino)-[2,3'-bipyridin]-5-yl)-1,1,1-trifluoropropan-2-ol Step 1. 2-(6'-Chloro-4'-(((1S,3S)-3-(hydroxymethyl)cyclohexyl)amino)-[2,3'-bipyridin]-5-yl)-1,1,1-trifluoropropan-2-ol The title compound as a solid (107 mg) was prepared in the same fashion as Step 2 in Reference Example 1, except that 2-(6'-chloro-4'-fluoro-[2,3'-bipyridin]-5-yl)-1,1,1-trifluoropropan-2-ol (85 mg. 0.265 mmol) prepared in Reference Example 11 and ((1S,3S)-3-aminocyclohexyl)methanol hydrochloride (66 mg, 0.398 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=430.1 (M+H)$^+$ Step 2. 2-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-1,1,1-trifluoropropan-2-ol The title compound as a pale yellow solid (39.8 mg) was prepared in the same fashion as Step 3 in Example 1, except that 2-(6'-chloro-4'-(((1S,3S)-3-(hydroxy methyl)cyclohexyl)amino)-[2,3'-bipyridin]-5-yl)-1,1,1-trifluoropropan-2-ol (89 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.81 (s, 1H), 8.67 (s, 1H), 8.46 (s, 1H), 8.41 (s, 1H), 8.30 (d, 1H), 8.04 (d, 1H), 7.89 (d, 1H), 7.39 (s, 1H), 7.23 (d, 1H), 4.06 (s, 1H), 3.40 (d, 2H), 3.08-3.02 (m, 1H), 2.10-2.07 (m, 1H), 1.97-1.94 (m, 1H), 1.89-1.86 (m, 1H), 1.81 (s, 3H), 1.75-1.65 (m, 4H), 1.49-1.40 (m, 3H), 1.31-1.27 (m, 2H), 1.14-1.10 (m, 1H); MS (ESI) m/z=659.2.2 (M+H)$^+$ Example 233. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)-1, 1, 1-trifluoropropan-2-ol Step 1. 2-(6'-Chloro-4'-(((1s,4s)-4-(2-hydroxypropan-2-yl)cyclohexyl)amino)-[2,3'-bipyridin]-5-yl)-1,1,1-trifluoropropan-2-ol The title compound as a solid (109 mg) was prepared in the same fashion as Step 2 in Reference Example 1, except that 2-(6'-chloro-4'-fluoro-[2,3'-bipyridin]-5-yl)-1,1,1-trifluoropropan-2-ol (85 mg. 0.265 mmol) prepared in Reference Example 11 and 2-((1s,4s)-4-aminocyclohexyl)propan-2-ol (63 mg, 0.398 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=458.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)-1,1,1-trifluoropropan-2-ol The title compound as a pale yellow solid (43.1 mg) was prepared in the same fashion as Step 3 in Example 1, except that 2-(6'-chloro-4'-(((1s,4s)-4-(2-hydroxypropan-2-yl)cyclohexyl)amino)-[2,3'-bipyridin]-5-yl)-1,1,1-trifluoropropan-2-ol (95 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.82 (s, 1H), 8.71 (s, 1H), 8.51 (s, 1H), 8.44 (s, 1H), 8.35 (d, 1H), 8.07 (d, 1H), 7.93 (d, 1H), 7.48 (s, 1H), 7.23 (d, 1H), 4.03 (s, 1H), 3.08-3.02 (m, 1H), 2.11-2.08 (m, 2H), 1.80 (s, 3H), 1.78-1.75 (m, 4H), 1.47-1.40 (m, 4H), 1.30-1.25 (m, 2H), 1.17 (s, 6H); MS (ESI) m/z=687.2 (M+H)$^+$ Example 234. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-1, 1, 1-trifluoropropan-2-ol Step 1. 2-(6'-Chloro-4'-(((1s,4s)-4-((dimethylamino)methyl)cyclohexyl)amino)-[2,3'-bipyridin]-5-yl)-1,1, 1-trifluoropropan-2-ol The title compound as a solid (109 mg) was prepared in the same fashion as Step 2 in Reference Example 1, except that 2-(6'-chloro-4'-fluoro-[2,3'-bipyridin]-5-yl)-1,1,1-trifluoropropan-2-ol (85 mg, 0.265 mmol) prepared in Reference Example 11 and (1s,4s)-4-((dimethylamino)methyl)cyclohexan-1-amine dihydrochloride (91 mg, 0.398 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=457.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-1,1,1-trifluoropropan-2-ol The title compound as a pale yellow solid (27.5 mg) was prepared in the same fashion as Step 3 in Example 1, except that 2-(6'-chloro-4'-(((1s,4s)-4-((dimethylamino)methyl)cyclohexyl)amino)-[2,3'-bipyridin]-5-yl)-1,1,1-trifluoropropan-2-ol (86 mg. 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (MeOD, 400 MHz) δ 8.80 (s, 1H), 8.68 (s, 1H), 8.48 (s, 1H), 8.42 (s, 1H), 8.32 (d, 1H), 8.05 (d, 1H), 7.90 (d, 1H), 7.42 (s, 1H), 7.23 (d, 1H), 3.98 (s, 1H), 3.08-3.02 (m, 1H), 2.25 (s, 6H), 2.22 (d, 2H), 2.01-1.98 (m, 2H), 1.83-1.67 (m, 8H), 1.47-1.43 (m, 2H), 1.31-1.24 (m, 4H); MS (ESI) m/z=686.2 (M+H)$^+$ Example 235. ((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)methanol Step 1. ((1s,4s)-4-((6'-Chloro-5-(2-fluoropropan-2-yl)-[2,3'-bipyridin]-4'-yl)amino)cyclohexyl)methanol The title compound as a solid (119 mg) was prepared in the same fashion as Step 2 in Reference Example 1, except that 6'-chloro-4'-fluoro-5-(2-fluoropropan-2-yl)-2,3'-bipyridine (100 mg, 0.37 mmol) prepared in Reference Example 12 and ((1s,4s)-4-aminocyclohexyl)methanol hydrochloride (92 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=378.1 (M+H)$^+$ Step 2. ((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)methanol The title compound as a pale yellow solid (38.8 mg) was prepared in the same fashion as Step 3 in Example 1, except that ((1s,4s)-4-((6'-chloro-5-(2-fluoropropan-2-yl)-[2,3'-bipyridin]-4'-yl)amino)cyclohexyl)methanol (118 mg. 0.28 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.67 (s, 1H), 8.63 (s, 1H), 8.44 (s, 1H), 8.41 (s, 1H), 8.31 (d, 1H), 7.86 (s, 2H), 7.39 (s, 1H), 7.22 (d, 1H), 3.97 (s, 1H), 3.43 (d, 2H), 3.06-3.03 (m, 1H), 2.01-1.98 (m, 2H), 1.83-1.71 (m, 10H), 1.61-1.58 (m, 1H), 1.45-1.40 (m, 2H), 1.38-1.35 (m, 2H), 1.29-1.26 (m, 2H); MS (ESI) m/z=607.2 (M+H)$^+$ Example 236. 2-((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)propan-2-ol Step 1. 2-((1s,4s)-4-((6'-Chloro-5-(2-fluoropropan-2-yl)-[2,3'-bipyridin]-4'-yl)amino)cyclohexyl)propan-2-ol The title compound as a solid (122 mg) was prepared in the same fashion as Step 2 in Reference Example 1, except that 6'-chloro-4'-fluoro-5-(2-fluoropropan-2-yl)-2,3'-bipyridine (100 mg, 0.37 mmol) prepared in Reference Example 12 and 2-((1s,4s)-4-aminocyclohexyl)propan-2-ol (88 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=406.2 (M+H)$^+$ Step 2. 2-((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)propan-2-ol The title compound as a pale yellow solid (43 mg) was prepared in the same fashion as Step 3 in Example 1, except that 2-((1s,4s)-4-((6'-chloro-5-(2-fluoropropan-2-yl)-[2,3'-bipyridin]-4'-yl)amino)cyclohexyl)propan-2-ol (126 mg. 0.28 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.62 (s, 1H), 8.60 (s, 1H), 8.41-8.24 (m, 3H), 7.81 (d, 1H), 7.79 (s, 1H), 7.40 (d, 1H), 7.11 (d, 1H), 3.96-3.92 (m, 1H), 3.03 (br, 1H), 2.04-2.01 (m, 2H), 1.75-1.68 (m, 9H), 1.44-1.33 (m, 5H) 1.27-1.25 (m, 2H), 1.14 (s, 6H); MS (ESI) m/z=635.3 (M+H)$^+$ Example 237. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2-fluoropropan-2-yl)-[2,3'-bipyridine]-4',6'-diamine Step 1. 6'-Chloro-N-((1s,4s)-4-((dimethylamino)methyl)cyclohexyl)-5-(2-fluoropropan-2-yl)-[2,3'-bipyridin]-4'-amine The title compound as a solid (129 mg) was prepared in the same fashion as Step 2 in Reference Example 1, except that 6'-chloro-4'-fluoro-5-(2-fluoropropan-2-yl)-2,3'-bipyridine (100 mg. 0.37 mmol) prepared in Reference Example 12 and (1s,4s)-4-((dimethylamino)methyl)cyclohexan-1-amine dihydrochloride (128 mg, 0.56 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=405.2 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2-fluoropropan-2-yl)-[2,3'-bipyridine]-4',6'-diamine The title compound as a pale yellow solid (32.1 mg) was prepared in the same fashion as Step 3 in Example 1, except that 6'-chloro-N-((1s,4s)-4-((dimethylamino)methyl)cyclohexyl)-5-(2-fluoropropan-2-yl)-[2,3'-bipyridin]-4'-amine (114 mg. 0.28 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.70 (s, 1H), 8.65 (s, 1H), 8.47 (s, 1H), 8.44 (s, 1H), 8.34 (d, 1H), 7.89 (s, 2H), 7.42 (s, 1H), 7.26 (d, 1H), 3.98 (s, 1H), 3.27-3.23 (m, 1H), 2.27 (s, 6H), 2.25 (d, 2H), 2.02-1.99 (m, 2H), 1.85-1.63 (m, 11H), 1.44-1.25 (m, 6H); MS (ESI) m/z=635.3 (M+H)$^+$ Example 238. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-(2-fluoropropan-2-yl)-[2,3'-bipyridine]-4',6'-diamine Step 1. 6'-Chloro-N-((1s,4s)-4-fluorocyclohexyl)-5-(2-fluoropropan-2-yl)-[2,3'-bipyridin]-4'-amine The title compound as a solid (88 mg) was prepared in the same fashion as Step 2 in Reference Example 1, except that 6'-chloro-4'-fluoro-5-(2-fluoropropan-2-yl)-2,3'-bipyridine (75 mg, 0.28 mmol) prepared in Reference Example 12 and (1s,4s)-4-fluorocyclohexan-1-amine hydrochloride (64 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=366.2 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-fluorocyclohexyl)-5-(2-fluoropropan-2-yl)-[2,3'-bipyridine]-4',6'-diamine The title compound as a pale yellow solid (9 mg) was prepared in the same fashion as Step 3 in Example 1, except that 6'-chloro-N-((1s,4s)-4-fluorocyclohexyl)-5-(2-fluoropropan-2-yl)-[2,3'-bipyridin]-4'-amine (46 mg, 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.65 (s, 1H), 8.45 (d, 2H), 8.36 (d, 1H), 7.92-7.86 (m, 2H), 7.39 (d, 1H), 7.25 (s, 1H), 4.73 (d, 1H), 3.74-3.68 (m, 1H), 3.07-3.00 (m, 1H), 1.97-1.95 (m, 2H), 1.88-1.73 (m, 10H), 1.44-1.42 (m, 2H), 1.29-1.26 (m, 4H); MS (ESI) m/z=595.2 (M+H)$^+$ Example 239. N$^{6'}$-(2-(1-(Cyclopropylsulfonyl)-1H-pyrazol-4-yl)pyrimidin-4-yl)-N$^{4'}$-(4-fluorocyclohexyl)-5-(2-fluoropropan-2-yl)-[2,3'-bipyridine]-4',6'-diamine Step 1. 6'-Chloro-N-(4-fluorocyclohexyl)-5-(2-fluoropropan-2-yl)-[2,3'-bipyridin]-4'-amine The title compound as a solid (93 mg) was prepared in the same fashion as Step 2 in Reference Example 1, except that 6'-chloro-4'-fluoro-5-(2-fluoropropan-2-yl)-2,3'-bipyridine (75 mg. 0.28 mmol) prepared in Reference Example 12 and 4-fluorocyclohexan-1-amine hydrochloride (64 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=366.2 (M+H)$^+$ Step 2. N$^{6'}$-(2-(1-(Cyclopropylsulfonyl)-1H-pyrazol-4-yl)pyrimidin-4-yl)-N$^{4'}$-(4-fluorocyclohexyl)-5-(2-fluoropropan-2-yl)-[2,3'-bipyridine]-4',6'-diamine The title compound as a pale yellow solid (7.1 mg) was prepared in the same fashion as Step 3 in Example 1, except that 6'-chloro-N-(4-fluorocyclohexyl)-5-(2-fluoropropan-2-yl)-[2,3'-bipyridin]-4'-amine (46 mg. 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.65 (s, 1H), 8.46 (d, 2H), 8.36 (d, 1H), 7.93-7.87 (m, 2H), 7.41 (dd, 1H), 7.23 (d, 1H), 4.80-4.62 (m, 1H), 3.76 (br, 1H), 3.06-2.98 (m, 1H), 2.22-1.95 (m, 4H), 1.88-1.80 (m, 1H), 1.78 (s, 3H), 1.72 (s, 3H), 1.65-1.57 (m, 1H), 1.45-1.40 (m, 2H), 1.33-1.21 (m, 3H); MS (ESI) m/z=595.2 (M+H)$^+$ Example 240. N$^{6'}$-(2-(1-(Cyclopropylsulfonyl)-1H-pyrazol-4-yl)pyrimidin-4-yl)-N$^{4'}$-(4,4-difluorocyclohexyl)-5-(2-fluoropropan-2-yl)-[2,3'-bipyridine]-4',6'-diamine Step 1. 6'-Chloro-N-(4,4-difluorocyclohexyl)-5-(2-fluoropropan-2-yl)-[2,3'-bipyridin]-4'-amine The title compound as a solid (95 mg) was prepared in the same fashion as Step 2 in Reference Example 1, except that 6'-chloro-4'-fluoro-5-(2-fluoropropan-2-yl)-2,3'-bipyridine (75 mg, 0.28 mmol) prepared in Reference Example 12 and 4,4-difluorocyclohexan-1-amine hydrochloride (72 mg, 0.42 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=382.1 (M+H)$^+$ Step 2. N$^{6'}$-(2-(1-(Cyclopropylsulfonyl)-1H-pyrazol-4-yl)pyrimidin-4-yl)-N$^{4'}$-(4,4-difluorocyclohexyl)-5-(2-fluoropropan-2-yl)-[2,3'-bipyridine]-4',6'-diamine The title compound as a pale yellow solid (5.3 mg) was prepared in the same fashion as Step 3 in Example 1, except that 6'-chloro-N-(4,4-difluorocyclohexyl)-5-(2-fluoropropan-2-yl)-[2,3'-bipyridin]-4'-amine (48 mg. 0.12 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.73 (s, 1H), 8.65 (s, 1H), 8.49 (s, 1H), 8.46 (s, 1H), 8.37 (d, 1H), 7.93-7.88 (m, 2H), 7.43 (d, 1H), 7.24 (s, 1H), 3.81 (br, 1H), 3.06-2.97 (m, 1H), 2.24-1.97 (m, 6H), 1.86-1.81 (m, 2H), 1.78 (s, 3H), 1.73 (s, 3H), 1.47-1.43 (m, 2H), 1.33-1.24 (m, 2H); MS (ESI) m/z=613.2 (M+H)$^+$ Example 241. ((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)methanol Step 1. 6'-Chloro-5-(1,1-difluoroethyl)-4'-fluoro-2,3'-bipyridine The title compound as a solid (431 mg) was prepared in the same fashion as Reference Example 5, except that 2-bromo-5-(1,1-difluoroethyl)pyridine (444 mg, 2.0 mmol) was used instead of 2-bromo-5-(methylsulfonyl)pyridine. MS (ESI) m/z=273.0 (M+H)$^+$ Step 2. ((1s,4s)-4-((6'-Chloro-5-(1,1-difluoroethyl)-[2,3'-bipyridin]-4'-yl)amino)cyclohexyl)methanol The title compound as a solid (123 mg) was prepared in the same fashion as Step 2 in Reference Example 1, except that 6'-chloro-5-(1,1-difluoroethyl)-4'-fluoro-2,3'-bipyridine (100 mg, 0.37 mmol) prepared in Step 1 and ((1s,4s)-4-aminocyclohexyl)methanol hydrochloride (91 mg, 0.55 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=382.1 (M+H)$^+$ Step 3. ((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)methanol The title compound as a pale yellow solid (44 mg) was prepared in the same fashion as Step 3 in Example 1, except that ((1s,4s)-4-((6'-chloro-5-(1,1-difluoroethyl)-[2,3'-bipyridin]-4'-yl)amino)cyclohexyl)methanol (119 mg, 0.31 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.65 (s, 1H), 8.46 (s, 1H), 8.39 (s, 1H), 8.29 (d, 1H), 7.96-7.91 (m, 2H), 7.40 (s, 1H), 7.21 (d, 1H), 3.96 (s, 1H), 3.43 (d, 2H), 3.07-3.01 (m, 1H), 2.05-1.96 (m, 5H), 1.82-1.69 (m, 4H), 1.60 (br, 1H), 1.45-1.40 (m, 2H), 1.36-1.28 (m, 4H); MS (ESI) m/z=611.2 (M+H)$^+$ Example 242. 2-((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)propan-2-ol Step 1. 2-((1s,4s)-4-((6'-Chloro-5-(1,1-difluoroethyl)-[2,3'-bipyridin]-4'-yl)amino)cyclohexyl)propan-2-ol The title compound as a solid (134 mg) was prepared in the same fashion as Step 2 in Reference Example 1, except that 6'-chloro-5-(1,1-difluoroethyl)-4'-fluoro-2,3'-bipyridine (100 mg, 0.37 mmol) prepared in Step 1 of Example 241 and 2-((1s,4s)-4-aminocyclohexyl)propan-2-ol (87 mg, 0.55 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=410.1 (M+H)+

Step 2. 2-((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)propan-2-ol The title compound as a pale yellow solid (46.2 mg) was prepared in the same fashion as Step 3 in Example 1, except that 2-((1s,4s)-4-((6'-chloro-5-(1,1-difluoroethyl)-[2,3'-bipyridin]-4'-yl)amino)cyclohexyl)propan-2-ol (127 mg, 0.31 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.74 (s, 1H), 8.67 (s, 1H), 8.49 (s, 1H), 8.41 (s, 1H), 8.32 (d, 1H), 7.97 (s, 2H), 7.47 (s, 1H), 7.21 (d, 1H), 4.00 (s, 1H), 3.06-3.03 (m, 1H), 2.09-1.96 (m, 5H), 1.80-1.74 (m, 4H), 1.44-1.38 (m, 5H), 1.28-1.25 (m, 2H), 1.17 (s, 6H); MS (ESI) m/z=639.2 (M+H)+

Example 243. $N^{6'}$-(2-(1-(Cyclopropylsulfonyl)-1H-pyrazol-4-yl)pyrimidin-4-yl)-5-(1,1-difluoroethyl)-$N^{4'}$-((1s,4s)-4-((dimethylamino)methyl)cyclohexyl)-[2,3'-bipyridine]-4',6'-diamine Step 1. 6'-Chloro-5-(1,1-difluoroethyl)-N-((1s,4s)-4-((dimethylamino)methyl)cyclohexyl)-[2,3'-bipyridin]-4'-amine The title compound as a solid (133 mg) was prepared in the same fashion as Step 2 in Reference Example 1, except that 6'-chloro-5-(1,1-difluoroethyl)-4'-fluoro-2,3'-bipyridine (100 mg, 0.37 mmol) prepared in Step 1 of Example 241 and (1s,4s)-4-((dimethylamino)methyl)cyclohexan-1-amine dihydrochloride (126 mg, 0.55 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=409.2 (M+H)+

Step 2. $N^{6'}$-(2-(1-(Cyclopropylsulfonyl)-1H-pyrazol-4-yl)pyrimidin-4-yl)-5-(1,1-difluoroethyl)-$N^{4'}$-((1s,4s)-4-((dimethylamino)methyl)cyclohexyl)-[2,3'-bipyridine]-4',6'-diamine The title compound as a pale yellow solid (41.4 mg) was prepared in the same fashion as Step 3 in Example 1, except that 6'-chloro-5-(1,1-difluoroethyl)-N-((1s,4s)-4-((dimethylamino)methyl)cyclohexyl)-[2,3'-bipyridin]-4'-amine (116 mg, 0.31 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.71 (s, 1H), 8.64 (s, 1H), 8.46 (s, 1H), 8.39 (s, 1H), 8.29 (d, 1H), 7.97-7.92 (m, 2H), 7.38 (s, 1H), 7.22 (d, 1H), 3.94 (s, 1H), 3.05-3.01 (m, 1H), 2.24 (s, 6H), 2.21 (d, 2H), 2.06-1.97 (m, 5H), 1.82-1.67 (m, 5H), 1.44-1.26 (m, 6H); MS (ESI) m/z=634.3 (M+H)+

Example 244. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2-difluoroethan-1-ol Step 1. 2-(6'-Chloro-4'-fluoro-[2,3'-bipyridin]-5-yl)-2,2-difluoroethan-1-ol The title compound as a solid (365 mg) was prepared in the same fashion as Reference Example 5, except that 2-(6-bromopyridin-3-yl)-2,2-difluoroethan-1-ol (476 mg, 2.0 mmol) was used instead of 2-bromo-5-(methylsulfonyl)pyridine. MS (ESI) m/z=289.0 (M+H)+

Step 2. 2-(6'-Chloro-4'-(((1s,4s)-4-(hydroxymethyl)cyclohexyl)amino)-[2,3'-bipyridin]-5-yl)-2,2-difluoroethan-1-ol The title compound as a solid (113 mg) was prepared in the same fashion as Step 2 in Reference Example 1, except that 2-(6'-chloro-4'-fluoro-[2,3'-bipyridin]-5-yl)-2,2-difluoroethan-1-ol (100 mg, 0.35 mmol) prepared in Step 1 and ((1s,4s)-4-aminocyclohexyl)methanol hydrochloride (86 mg, 0.52 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=398.1 (M+H)+

Step 3. 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2-difluoroethan-1-ol The title compound as a pale yellow solid (17.8 mg) was prepared in the same fashion as Step 3 in Example 1, except that 2-(6'-chloro-4'-(((1s,4s)-4-(hydroxy methyl)cyclohexyl)amino)-[2,3'-bipyridin]-5-yl)-2,2-difluoroethan-1-ol (107 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.73 (s, 1H), 8.69 (s, 1H), 8.51 (s, 1H), 8.42 (s, 1H), 8.33 (d, 1H), 7.99 (s, 2H), 7.43 (s, 1H), 7.24 (d, 1H), 4.00 (t, 3H), 3.44 (d, 2H), 3.08-3.02 (m, 1H), 2.02-1.95 (m, 2H), 1.85-1.71 (m, 4H), 1.62 (br, 1H), 1.45-1.42 (m, 6H); MS (ESI) m/z=627.2 (M+H)+

Example 245. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-2,2-difluoroethan-1-ol Step 1. 2-(6'-Chloro-4'-(((1s,4s)-4-((dimethylamino)methyl)cyclohexyl)amino)-[2,3'-bipyridin]-5-yl)-2,2-difluoroethan-1-ol The title compound as a solid (105 mg) was prepared in the same fashion as Step 2 in Reference Example 1, except that 2-(6'-chloro-4'-fluoro-[2,3'-bipyridin]-5-yl)-2,2-difluoroethan-1-ol (100 mg, 0.35 mmol) prepared in Step 1 of Example 244 and (1s,4s)-4-((dimethylamino)methyl)cyclohexan-1-amine dihydrochloride (119 mg, 0.52 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=425.2 (M+H)+

Step 2. 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-2,2-difluoroethan-1-ol The title compound as a pale yellow solid (13.1 mg) was prepared in the same fashion as Step 3 in Example 1, except that 2-(6'-chloro-4'-(((1s,4s)-4-((dimethylamino)methyl)cyclohexyl)amino)-[2,3'-bipyridin]-5-yl)-2,2-difluoroethan-1-ol (104 mg, 0.25 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. 1H-NMR (MeOD, 400 MHz) δ 8.74 (s, 1H), 8.64 (s, 1H), 8.48 (s, 1H), 8.38 (s, 1H), 8.29 (d, 1H), 7.98 (s, 2H), 7.38 (d, 1H), 7.21 (d, 1H), 4.77 (t, 2H), 3.94 (br, 1H), 3.07-3.01 (m, 1H), 2.30 (s, 6H), 2.28 (d, 2H), 2.06-1.97 (m, 2H), 1.83-1.70 (m, 5H), 1.44-1.26 (m, 4H), 1.16-1.12 (m, 2H); MS (ESI) m/z=758.2 (M+H)$^+$ Example 246. ((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)methanol Step 1. 6'-Chloro-4'-fluoro-6-(2,2,2-trifluoroethyl)-2,3'-bipyridine The title compound as a solid (501 mg) was prepared in the same fashion as Reference Example 5, except that 2-bromo-6-(2,2,2-trifluoroethyl)pyridine (480 mg. 2 mmol) was used instead of 2-bromo-5-(methylsulfonyl)pyridine. MS (ESI) m/z=291.0 (M+H)$^+$ Step 2. ((1s,4s)-4-((6'-Chloro-6-(2,2,2-trifluoroethyl)-[2,3'-bipyridin]-4'-yl)amino)cyclohexyl)methanol The title compound as a solid (116 mg) was prepared in the same fashion as Step 2 in Reference Example 1, except that 6'-chloro-4'-fluoro-6-(2,2,2-trifluoroethyl)-2,3'-bipyridine (100 mg. 0.34 mmol) prepared in Step 1 and ((1s,4s)-4-aminocyclohexyl)methanol hydrochloride (86 mg, 0.52 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=400.1 (M+H)$^+$ Step 3. ((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)methanol The title compound as a pale yellow solid (36.1 mg) was prepared in the same fashion as Step 3 in Example 1, except that ((1s,4s)-4-((6'-chloro-6-(2,2,2-trifluoroethyl)-[2,3'-bipyridin]-4'-yl)amino)cyclohexyl)methanol (108 mg, 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.46 (s, 2H), 8.36 (d, 1H), 7.91-7.86 (m, 2H), 7.40 (s, 1H), 7.36 (d, 1H), 7.32 (d, 1H), 3.95 (s, 1H), 3.78 (q, 2H), 3.44 (d, 2H), 3.08-3.02 (m, 1H), 2.04-1.98 (m, 2H), 1.88-1.82 (m, 2H), 1.75-1.65 (m, 3H), 1.45-1.34 (m, 4H), 1.32-1.28 (m, 2H); MS (ESI) m/z=629.2 (M+H)$^+$ Example 247. 2-((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)propan-2-ol Step 1. 2-((1s,4s)-4-((6'-Chloro-6-(2,2,2-trifluoroethyl)-[2,3'-bipyridin]-4'-yl)amino)cyclohexyl)propan-2-ol The title compound as a solid (116 mg) was prepared in the same fashion as Step 2 in Reference Example 1, except that 6'-chloro-4'-fluoro-6-(2,2,2-trifluoroethyl)-2,3'-bipyridine (100 mg, 0.34 mmol) prepared in Step 1 of Example 247 and 2-((1s,4s)-4-aminocyclohexyl)propan-2-ol (81 mg, 0.52 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=428.1 (M+H)$^+$ Step 2. 2-((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)propan-2-ol The title compound as a pale yellow solid (38.3 mg) was prepared in the same fashion as Step 3 in Example 1, except that 2-((1s,4s)-4-((6'-chloro-6-(2,2,2-trifluoroethyl)-[2,3'-bipyridin]-4'-yl)amino)cyclohexyl)propan-2-ol (115 mg. 0.27 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.45 (s, 2H), 8.35 (d, 1H), 7.89-7.86 (m, 2H), 7.45 (s, 1H), 7.37 (d, 1H), 7.27 (d, 1H), 3.98 (s, 1H), 3.81 (q, 2H), 3.08-3.02 (m, 1H), 2.18-2.15 (m, 2H), 1.81-1.79 (m, 4H), 1.45-1.32 (m, 5H), 1.29-1.26 (m, 2H), 1.14 (s, 6H); MS (ESI) m/z=657.2 (M+H)$^+$ Example 248. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-6-(2,2,2-trifluoroethyl)-[2,3'-bipyridine]-4',6-diamine Step 1. 6'-Chloro-N-((1s,4s)-4-((dimethylamino)methyl)cyclohexyl)-6-(2,2,2-trifluoroethyl)-[2,3'-bipyridin]-4'-amine The title compound as a solid (106 mg) was prepared in the same fashion as Step 2 in Reference Example 1, except that 6'-chloro-4'-fluoro-6-(2,2,2-trifluoroethyl)-2,3'-bipyridine (100 mg. 0.34 mmol) prepared in Step 1 of Example 247 and (1s,4s)-4-((dimethylamino)methyl)cyclohexan-1-amine dihydrochloride (118 mg, 0.52 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=427.1 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-6-(2,2,2-trifluoroethyl)-[2,3'-bipyridine]-4',6-diamine The title compound as a pale yellow solid (27 mg) was prepared in the same fashion as Step 3 in Example 1, except that 6'-chloro-N-((1s,4s)-4-((dimethylamino)methyl)cyclohexyl)-6-(2,2,2-trifluoroethyl)-[2,3'-bipyridin]-4'-amine (105 mg, 0.25 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.71 (s, 1H), 8.44 (s, 2H), 8.34 (d, 1H), 7.89-7.86 (m, 2H), 7.38-7.30 (m, 3H), 3.93 (s, 1H), 3.77 (q, 2H), 3.06-3.04 (m, 1H), 2.24 (s, 8H), 1.98-1.94 (m, 2H), 1.88-1.82 (m, 2H), 1.77-1.73 (m, 3H), 1.45-1.40 (m, 2H), 1.39-1.33 (m, 2H), 1.28-1.24 (m, 2H); MS (ESI) m/z=656.2 (M+H)$^+$ Example 249. N$^{6'}$-(2-(1-(Cyclopropylsulfonyl)-1H-pyrazol-4-yl)pyrimidin-4-yl)-N$^{4'}$-isopropyl-5-((1-methylpiperidin-4-yl)oxy)-[2,3'-bipyridine]-4',6'-diamine Step 1. 6'-Chloro-N-isopropyl-5-((1-methylpiperidin-4-yl)oxy)-[2,3'-bipyridin]-4'-amine The title compound as a solid (95 mg) was prepared in the same fashion as Step 2 in Reference Example 1, except that 6'-chloro-4'-fluoro-5-((1-methylpiperidin-4-yl)oxy)-2,3'-bipyridine (100 mg, 0.311 mmol) prepared in Step 1 of Reference Example 1 and isopropylamine (28 mg, 0.466 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=361.1 (M+H)$^+$ Step 2. N$^{6'}$-(2-(1-(Cyclopropylsulfonyl)-1H-pyrazol-4-yl)pyrimidin-4-yl)-N$^{4'}$-isopropyl-5-((1-methylpiperidin-4-yl)oxy)-[2,3'-bipyridine]-4',6'-diamine The title compound as a pale yellow solid (45.1 mg) was prepared in the same fashion as Step 3 in Example 1, except that 6'-chloro-N-isopropyl-5-((1-methylpiperidin-4-yl)oxy)-[2,3'-bipyridin]-4'-amine (75 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.98 (d, 1H), 8.66 (s, 1H), 8.47 (s, 1H), 8.39 (d, 1H), 8.31 (s, 1H), 8.28 (d, 1H), 7.63 (d, 1H), 7.33 (dd, 1H), 7.25 (s, 1H), 7.14 (d, 1H), 4.41 (brs, 1H), 3.87-3.82 (m, 1H), 2.85-2.82 (m, 1H), 2.73 (brs, 2H), 2.33 (s, 5H), 2.09-2.04 (m, 2H), 1.93-1.88 (m, 2H), 1.54-1.51 (m, 2H), 1.38 (d, 6H), 1.24-1.20 (m, 2H); MS (ESI) m/z=590.2 (M+H)$^+$ Example 250. (1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol The title compound as a pale yellow solid (23.2 mg) was prepared in the same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (89 mg, 0.207 mmol) prepared in Reference Example 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.73 (s, 1H), 8.47 (s, 1H), 8.36-8.30 (m, 3H), 7.76 (d, 1H), 7.49 (dd, 1H), 7.35 (d, 1H), 7.24 (s, 1H), 4.58-4.56 (m, 1H), 3.56 (brs, 1H), 3.05-3.01 (m, 1H), 2.78 (brs, 2H), 2.46 (brs, 2H), 2.35 (s, 3H), 2.11-2.07 (m, 2H), 1.97-1.87 (m, 4H), 1.78-1.71 (m, 4H), 1.61-1.54 (m, 2H), 1.44-1.40 (m, 2H), 1.29-1.23 (m, 5H); MS (ESI) m/z=660.2 (M+H)$^+$ Example 251. ((1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol Step 1. ((1s,4s)-4-((6'-Chloro-5-((1-methylpiperidin-4-yl)oxy)-[2,3'-bipyridin]-4'-yl)amino)cyclohexyl)methanol The title compound as a solid (95 mg) was prepared in the same fashion as Step 2 in Reference Example 1, except that ((1s,4s)-4-aminocyclohexyl)methanol hydrochloride (77 mg, 0.466 mmol) was used instead of cis-4-amino-1-methylcyclohexanol. MS (ESI) m/z=431.2 (M+H)$^+$ Step 2. ((1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol The title compound as a pale yellow solid (15.7 mg) was prepared in the same fashion as Step 3 in Example 1, except that ((1s,4s)-4-((6'-chloro-5-((1-methylpiperidin-4-yl)oxy)-[2,3'-bipyridin]-4'-yl)amino)cyclohexyl)methanol (89 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.71 (s, 1H), 8.45 (s, 1H), 8.35-8.30 (m, 3H), 7.81 (d, 1H), 7.51 (dd, 1H), 7.38 (s, 1H), 7.26 (d, 1H), 4.59 (brs, 1H), 3.98 (brs, 1H), 3.44 (d, 2H), 3.08-3.02 (m, 1H), 2.80 (brs, 2H), 2.49 (brs, 2H), 2.37 (s, 3H), 2.11-2.06 (m, 2H), 2.02-1.98 (m, 2H), 1.91-1.69 (m, 6H), 1.61 (brs, 1H), 1.47-1.43 (m, 2H), 1.42-1.32 (m, 2H), 1.30-1.25 (m, 2H); MS (ESI) m/z=660.3 (M+H)$^+$ Example 252. 2-((1r,4r)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol Step 1. 2-((1r,4r)-4-((6'-Chloro-5-((1-methylpiperidin-4-yl)oxy)-[2,3'-bipyridin]-4'-yl)amino)cyclohexyl)ethan-1-ol The title compound as a solid (132 mg) was prepared in the same fashion as Step 2 in Reference Example 1, except that 2-((1r,4r)-4-aminocyclohexyl)ethan-1-ol hydrochloride (84 mg, 0.466 mmol) was used instead of cis-4-amino-1-methylcyclohexanol. MS (ESI) m/z=445.2 (M+H)$^+$ Step 2. 2-((1r,4r)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol The title compound as a pale yellow solid (14.3 mg) was prepared in the same fashion as Step 3 in Example 1, except that 2-((1r,4r)-4-((6'-chloro-5-((1-methylpiperidin-4-yl)oxy)-[2,3'-bipyridin]-4'-yl)amino)cyclohexyl)ethan-1-ol (50 mg, 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.95 (d, 1H), 8.66 (s, 1H), 8.48 (s, 1H), 8.41 (d, 1H), 8.32 (s, 1H), 8.26 (d, 1H), 7.63 (d, 1H), 7.38-7.31 (m, 2H), 6.90 (s, 1H), 4.40 (brs, 1H), 3.71 (t, 2H), 3.39 (brs, 1H), 2.87-2.80 (m, 1H), 2.72 (brs, 2H), 2.33 (brs, 5H), 2.23-2.20 (m, 2H), 2.05-1.84 (m, 8H), 1.58-1.51 (m, 4H), 1.37-1.12 (m, 5H); MS (ESI) m/z=675.3 (M+H)$^+$ Example 253. ((1S,3S)-3-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol Step 1. ((1S,3S)-3-((6'-Chloro-5-((1-methylpiperidin-4-yl)oxy)-[2,3'-bipyridin]-4'-yl)amino)cyclohexyl)methanol The title compound as a solid (132 mg) was prepared in the same fashion as Step 2 in Reference Example 1, except that ((1S,3S)-3-aminocyclohexyl)methanol hydrochloride (77 mg, 0.466 mmol) was used instead of cis-4-amino-1-methylcyclohexanol. MS (ESI) m/z=431.2 (M+H)$^+$ Step 2. ((1S,3S)-3-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol The title compound as a pale yellow solid (15.1 mg) was prepared in the same fashion as Step 3 in Example 1, except that ((1S,3S)-3-((6'-chloro-5-((1-methylpiperidin-4-yl)oxy)-[2,3'-bipyridin]-4'-yl)amino)cyclohexyl)methanol (49 mg, 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.63 (d, 1H), 8.65 (s, 1H), 8.46 (s, 1H), 8.38 (d, 1H), 8.35 (s, 1H), 8.27 (d, 1H), 7.67 (d, 1H), 7.34 (d, 1H), 7.13 (s, 1H), 7.12 (s, 1H), 4.42 (brs, 1H), 4.04 (brs, 1H), 3.52 (d, 2H), 2.87-2.79 (m, 1H), 2.72 (brs, 2H), 2.34 (s, 5H), 2.08-2.05 (m, 4H), 1.97-1.85 (m, 4H), 1.74-1.45 (m, 5H), 1.26-1.11 (m, 4H); MS (ESI) m/z=661.3 (M+H)$^+$ Example 254. N$^{6'}$-(2-(1-(Cyclopropylsulfonyl)-1H-pyrazol-4-yl)pyrimidin-4-yl)-N$^{4'}$-(4-fluorocyclohexyl)-5-((1-methylpiperidin-4-yl)oxy)-[2,3'-bipyridine]-4',6'-diamine The title compound as a pale yellow solid (11.3 mg) was prepared in the same fashion as Step 3 in Example 1, except that 6'-chloro-N-(4-fluorocyclohexyl)-5-((1-methylpiperidin-4-yl)oxy)-[2,3'-bipyridin]-4'-amine (30 mg. 0.072 mmol) prepared in Reference Example 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.91 (s, 1H), 8.62 (s, 1H), 8.56 (s, 1H), 8.54 (d, 1H), 8.43 (s, 1H), 7.97 (d, 1H), 7.67 (d, 1H), 7.02 (s, 1H), 6.71 (s, 1H), 4.78-4.63 (m, 1H), 3.73 (brs, 1H), 3.08 (brs, 1H), 2.95 (s, 3H), 2.27-2.02 (m, 8H), 1.82-1.55 (m, 6H), 1.47-1.27 (m, 6H); MS (ESI) m/z=648.3 (M+H)$^+$ Example 255. N$^{6'}$-(2-(1-(Cyclopropylsulfonyl)-1H-pyrazol-4-yl)pyrimidin-4-yl)-N$^{4'}$-(4,4-difluorocyclohexyl)-5-((1-methylpiperidin-4-yl)oxy)-[2,3'-bipyridine]-4',6'-diamine Step 1. 6'-Chloro-N-(4,4-difluorocyclohexyl)-5-((1-methylpiperidin-4-yl)oxy)-[2,3'-bipyridin]-4'-amine The title compound as a solid (106 mg) was prepared in the same fashion as Step 2 in Reference Example 1, except that 4,4-difluorocyclohexan-1-amine hydrochloride (80 mg, 0.466 mmol) was used instead of cis-4-amino-1-methylcyclohexanol. MS (ESI) m/z=437.2 (M+H)$^+$ Step 2. N$^{6'}$-(2-(1-(Cyclopropylsulfonyl)-1H-pyrazol-4-yl)pyrimidin-4-yl)-N$^{4'}$-(4,4-difluorocyclohexyl)-5-((1-methylpiperidin-4-yl)oxy)-[2,3'-bipyridine]-4',6'-diamine The title compound as a pale yellow solid (12.4 mg) was prepared in the same fashion as Step 3 in Example 1, except that 6'-chloro-N-(4,4-difluorocyclohexyl)-5-((1-methylpiperidin-4-yl)oxy)-[2,3'-bipyridin]-4'-amine (35 mg, 0.08 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.46 (s, 1H), 8.36-8.28 (m, 3H), 7.80 (d, 1H), 7.51 (dd, 1H), 7.41 (d, 1H), 7.21 (s, 1H), 4.58 (brs, 1H), 3.78-3.74 (m, 1H), 3.06-3.00 (m, 1H), 2.81 (brs, 2H), 2.50 (brs, 2H), 2.38 (s, 3H), 2.16-2.00 (m, 8H), 1.90-1.79 (m, 4H), 1.46-1.43 (m, 2H), 1.29-1.27 (m, 2H); MS (ESI) m/z=666.2 (M+H)$^+$ Example 256. N$^{6'}$-(2-(1-(Cyclopropylsulfonyl)-1H-pyrazol-4-yl)pyrimidin-4-yl)-N$^{4'}$-(1-(2-fluoroethyl) piperidin-4-yl)-5-((1-methylpiperidin-4-yl)oxy)-[2,3'-bipyridine]-4',6'-diamine Step 1. 6'-Chloro-N-(1-(2-fluoroethyl) piperidin-4-yl)-5-((1-methylpiperidin-4-yl)oxy)-[2,3'-bipyridin]-4'-amine The title compound as a solid (81 mg) was prepared in the same fashion as Step 2 in Reference Example 1, except that 1-(2-fluoroethyl) piperidin-4-amine hydrochloride (74 mg, 0.404 mmol) were used instead of cis-4-amino-1-methylcyclohexanol. MS (ESI) m/z=448.2 (M+H)$^+$ Step 2. N$^{6'}$-(2-(1-(Cyclopropylsulfonyl)-1H-pyrazol-4-yl)pyrimidin-4-yl)-N$^{4'}$-(1-(2-fluoroethyl) piperidin-4-yl)-5-((1-methylpiperidin-4-yl)oxy)-[2,3'-bipyridine]-4',6'-diamine The title compound as a pale yellow solid (6.6 mg) was prepared in the same fashion as Step 3 in Example 1, except that 6'-chloro-N-(1-(2-fluoroethyl) piperidin-4-yl)-5-((1-methylpiperidin-4-yl)oxy)-[2,3'-bipyridin]-4'-amine (51 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.96 (s, 1H), 9.28 (d, 1H), 8.64 (s, 1H), 8.45-8.41 (m, 3H), 8.32 (d, 1H), 7.90 (d, 1H), 7.60 (brs, 1H), 7.54 (dd, 1H), 7.21 (brs, 1H), 4.59 (t, 1H), 4.53 (brs, 1H), 4.47 (t, 1H), 2.72 (brs, 2H), 2.67 (t, 1H), 2.60 (t, 1H), 2.36-2.24 (m, 4H), 2.00-1.93 (m, 4H), 1.84-1.54 (m, 5H), 1.35-1.23 (m, 5H); MS (ESI) m/z=677.3 (M+H)$^+$ Example 257. N$^{6'}$-(2-(1-(Cyclopropylsulfonyl)-1H-pyrazol-4-yl)pyrimidin-4-yl)-N$^{4'}$-(1-(2-fluoroethyl) piperidin-3-yl)-5-((1-methylpiperidin-4-yl)oxy)-[2,3'-bipyridine]-4',6'-diamine Step 1. 6'-Chloro-N-(1-(2-fluoroethyl) piperidin-3-yl)-5-((1-methylpiperidin-4-yl)oxy)-[2,3'-bipyridin]-4'-amine The title compound as a solid (98 mg) was prepared in the same fashion as Step 2 in Reference Example 1, except that 1-(2-fluoroethyl) piperidin-3-amine dihydrochloride (89 mg. 0.404 mmol) was used instead of cis-4-amino-1-methylcyclohexanol. MS (ESI) m/z=448.2 (M+H)$^+$ Step 2. N$^{6'}$-(2-(1-(Cyclopropylsulfonyl)-1H-pyrazol-4-yl)pyrimidin-4-yl)-N$^{4'}$-(1-(2-fluoroethyl) piperidin-3-yl)-5-((1-methylpiperidin-4-yl)oxy)-[2,3'-bipyridine]-4',6'-diamine The title compound as a pale yellow solid (15.6 mg) was prepared in the same fashion as Step 3 in Example 1, except that 6'-chloro-N-(1-(2-fluoroethyl) piperidin-3-yl)-5-((1-methylpiperidin-4-yl)oxy)-[2,3'-bipyridin]-4'-amine (51 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.98 (s, 1H), 9.40 (d, 1H), 8.85 (s, 1H), 8.45 (s, 1H), 8.41 (d, 2H), 8.28 (d, 1H), 7.85 (dd, 1H), 7.53 (d, 2H), 4.59-4.46 (m, 3H), 3.73 (brs, 1H), 2.76 (brs, 2H), 2.69-2.57 (m, 2H), 2.34 (brs, 2H), 2.30 (s, 3H), 1.98-1.93 (m, 2H), 1.70-1.54 (m, 7H), 1.34-1.19 (m, 5H); MS (ESI) m/z=677.3 (M+H)$^+$ Example 258. N⁶'-(2-(1-(Cyclopropylsulfonyl)-1H-pyrazol-4-yl)pyrimidin-4-yl)-N⁴'-(1-(2,2-difluoroethyl) piperidin-4-yl)-5-((1-methylpiperidin-4-yl)oxy)-[2,3'-bipyridine]-4',6'-diamine Step 1. 6'-Chloro-N-(1-(2,2-difluoroethyl) piperidin-4-yl)-5-((1-methylpiperidin-4-yl)oxy)-[2,3'-bipyridin]-4'-amine The title compound as a solid (86 mg) was prepared in the same fashion as Step 2 in Reference Example 1, except that 1-(2,2-difluoroethyl) piperidin-4-amine (66 mg, 0.404 mmol) was used instead of cis-4-amino-1-methylcyclohexanol. MS (ESI) m/z=466.2 (M+H)⁺

Step 2. N⁶'-(2-(1-(Cyclopropylsulfonyl)-1H-pyrazol-4-yl)pyrimidin-4-yl)-N⁴'-(1-(2,2-difluoroethyl) piperidin-4-yl)-5-((1-methylpiperidin-4-yl)oxy)-[2,3'-bipyridine]-4',6'-diamine The title compound as a pale yellow solid (16 mg) was prepared in the same fashion as Step 3 in Example 1, except that 6'-chloro-N-(1-(2,2-difluoroethyl) piperidin-4-yl)-5-((1-methylpiperidin-4-yl)oxy)-[2,3'-bipyridin]-4'-amine (53 mg, 0.113 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 9.67 (s, 1H), 9.20 (dd, 1H), 8.75 (d, 1H), 8.46-8.34 (m, 3H), 7.79 (dd, 1H), 7.61 (brs, 1H), 7.56 (d, 1H), 7.21 (brs, 1H), 6.12 (tt, 1H), 4.58 (brs, 1H), 2.78-2.67 (m, 4H), 2.44-2.33 (m, 5H), 2.00-1.87 (m, 4H), 1.84-1.76 (m, 3H), 1.56-1.44 (m, 3H), 1.34-1.23 (m, 5H); MS (ESI) m/z=695.3 (M+H)⁺

Example 259. (4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-fluorocyclohexyl)methanol Step 1. (4-((6'-Chloro-5-((1-methylpiperidin-4-yl)oxy)-[2,3'-bipyridin]-4'-yl)amino)-1-fluorocyclohexyl)methanol The title compound as a solid (87 mg) was prepared in the same fashion as Step 2 in Reference Example 1, except that (4-amino-1-fluorocyclohexyl)methanol (59 mg, 0.404 mmol) were used instead of cis-4-amino-1-methylcyclohexanol. MS (ESI) m/z=449.2 (M+H)⁺

Step 2. (4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-fluorocyclohexyl)methanol The title compound as a pale yellow solid (9.5 mg) was prepared in the same fashion as Step 3 in Example 1, except that (4-((6'-chloro-5-((1-methylpiperidin-4-yl)oxy)-[2,3'-bipyridin]-4'-yl)amino)-1-fluorocyclohexyl)methanol (40 mg, 0.089 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. ¹H-NMR (DMSO-d₆, 400 MHz) δ 9.95 (s, 1H), 9.16 (d, 1H), 8.64 (s, 1H), 8.46 (s, 1H), 8.43 (s, 1H), 8.35 (s, 1H), 7.89 (d, 1H), 7.67 (brs, 1H), 7.53 (d, 1H), 7.16 (brs, 1H), 4.95 (t, 1H), 4.54 (brs, 1H), 4.33 (d, 2H), 2.71 (brs, 2H), 2.32-2.29 (m, 2H), 2.25 (s, 3H), 1.97-1.97 (m, 6H), 1.71-1.61 (3H), 1.53-1.50 (m, 3H), 1.34-1.26 (m, 2H), 1.24-1.16 (m, 2H); MS (ESI) m/z=678.3 (M+H)⁺

Example 260. (1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)-1-methylcyclohexan-1-ol Step 1. 6'-Chloro-4'-fluoro-5-(2,2,2-trifluoro-1-methoxyethyl)-2,3'-bipyridine The title compound as a solid (508 mg) was prepared in the same fashion as Reference Example 5, except that 2-bromo-5-(2,2,2-trifluoro-1-methoxyethyl)pyridine (1000 mg, 3.703 mmol) was used instead of 2-bromo-5-(methylsulfonyl)pyridine. ¹H-NMR (MeOD, 400 MHz) δ 8.96 (d, 1H), 8.80 (d, 1H), 8.05 (dd, 1H), 7.93 (dd, 1H), 7.53 (d, 1H), 5.02 (q, 1H), 3.52 (s, 3H)

Step 2. (1s,4s)-4-((6'-Chloro-5-(2,2,2-trifluoro-1-methoxyethyl)-[2,3'-bipyridin]-4'-yl)amino)-1-methylcyclohexan-1-ol The title compound as a solid (121 mg) was prepared in the same fashion as Step 2 in Reference Example 1, except that 6'-chloro-4'-fluoro-5-(2,2,2-trifluoro-1-methoxyethyl)-2,3'-bipyridine (100 mg, 0.312 mmol) prepared in Step 1 was used instead of 6'-chloro-4'-fluoro-5-((1-methylpiperidin-4-yl)oxy)-2,3'-bipyridine. MS (ESI) m/z=430.1 (M+H)⁺

Step 3. ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)-1-methylcyclohexan-1-ol The title compound as a pale yellow solid (47.3 mg) was prepared in the same fashion as Step 3 in Example 1, except that (1s,4s)-4-((6'-chloro-5-(2,2,2-trifluoro-1-methoxyethyl)-[2,3'-bipyridin]-4'-yl)amino)-1-methylcyclohexan-1-ol (98 mg, 0.228 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (MeOD, 400 MHz) δ 8.72 (s, 1H), 8.64 (s, 1H), 8.47 (d, 2H), 8.35 (d, 1H), 7.94 (s, 2H), 7.37 (s, 1H), 7.28 (s, 1H), 4.93 (q, 1H), 3.57 (brs, 1H), 3.50 (s, 3H), 3.03 (brs, 1H), 1.97-1.95 (m, 2H), 1.75-1.72 (m, 4H), 1.60-1.53 (m, 2H), 1.45-1.43 (m, 2H), 1.25 (s, 5H); MS (ESI) m/z=659.2 (M+H)⁺

Example 261. ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)cyclohexyl)methanol Step 1. ((1s,4s)-4-((6'-Chloro-5-(2,2,2-trifluoro-1-methoxyethyl)-[2,3'-bipyridin]-4'-yl)amino)cyclohexyl)methanol The title compound as a solid (135 mg) was prepared in the same fashion as Step 2 in Reference Example 1, except that 6'-chloro-4'-fluoro-5-(2,2,2-trifluoro-1-methoxyethyl)-2,3'-bipyridine (100 mg, 0.312 mmol) prepared in Step 1 of Example 260 and ((1s,4s)-4-aminocyclohexyl)methanol hydrochloride (77 mg, 0.468 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=430.1 (M+H)$^+$ Step 2. ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)cyclohexyl)methanol The title compound as a pale yellow solid (57 mg) was prepared in the same fashion as Step 3 in Example 1, except that ((1s,4s)-4-((6'-chloro-5-(2,2,2-trifluoro-1-methoxyethyl)-[2,3'-bipyridin]-4'-yl)amino)cyclohexyl)methanol (98 mg, 0.228 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.69 (s, 1H), 8.64 (d, 1H), 8.50 (s, 1H), 8.43 (s, 1H), 8.33 (d, 1H), 7.99-7.92 (m, 2H), 7.44 (s, 1H), 7.25 (d, 1H), 4.93 (q, 1H), 4.00 (brs, 1H), 3.50 (s, 3H), 3.43 (d, 2H), 3.08-3.02 (m, 1H), 2.03-1.99 (m, 2H), 1.84-1.71 (m, 4H), 1.66-1.59 (m, 1H), 1.47-1.43 (m, 2H), 1.40-1.32 (m, 2H), 1.30-1.24 (m, 2H); MS (ESI) m/z=659.1 (M+H)$^+$ Example 262. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2,2,2-trifluoro-1-methoxyethyl)-[2,3'-bipyridine]-4',6'-diamine Step 1. 6'-Chloro-N-((1s,4s)-4-((dimethylamino)methyl)cyclohexyl)-5-(2,2,2-trifluoro-1-methoxyethyl)-[2,3'-bipyridin]-4'-amine The title compound as a solid (100 mg) was prepared in the same fashion as Step 2 in Reference Example 1, except that 6'-chloro-4'-fluoro-5-(2,2,2-trifluoro-1-methoxyethyl)-2,3'-bipyridine (100 mg, 0.312 mmol) prepared in Step 1 of Example 260 and (1s,4s)-4-((dimethylamino)methyl)cyclohexan-1-amine dihydrochloride (107 mg, 0.516 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=457.1 (M+H)$^+$ Step 2. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-5-(2,2,2-trifluoro-1-methoxyethyl)-[2,3'-bipyridine]-4',6'-diamine The title compound as a pale yellow solid (27.5 mg) was prepared in the same fashion as Step 3 in Example 1, except that 6'-chloro-N-((1s,4s)-4-((dimethylamino)methyl)cyclohexyl)-5-(2,2,2-trifluoro-1-methoxyethyl)-[2,3'-bipyridin]-4'-amine (95 mg. 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.67 (s, 1H), 8.64 (d, 1H), 8.49 (s, 1H), 8.41 (s, 1H), 8.31 (d, 1H), 7.98-7.94 (m, 2H), 7.42 (s, 1H), 7.23 (d, 1H), 7.95 (q, 1H), 3.97 (brs, 1H), 3.51 (s, 3H), 3.08-3.01 (m, 1H), 2.28 (s, 6H), 2.25 (d, 2H), 2.01-1.98 (m, 2H), 1.84-1.67 (m, 5H), 1.47-1.43 (m, 2H), 1.33-1.24 (m, 4H); MS (ESI) m/z=686.3 (M+H)$^+$ Example 263. (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol Step 1. 6'-Chloro-4'-fluoro-5-(3,3,3-trifluoropropyl)-2,3'-bipyridine The title compound as a solid (525 mg) was prepared in the same fashion as Reference Example 5, except that 2-bromo-5-(3,3,3-trifluoropropyl)pyridine (500 mg, 1.968 mmol) was used instead of 2-bromo-5-(methylsulfonyl)pyridine. $^1$H-NMR (CDCl$_3$, 400 MHz) δ 9.04 (d, 1H), 8.63 (d, 1H), 7.73 (d, 1H), 7.65 (dd, 1H), 7.21 (d, 1H), 2.97 (dd, 2H), 2.53-2.41 (m, 2H)

Step 2. (1s,4s)-4-((6'-Chloro-5-(3,3,3-trifluoropropyl)-[2,3'-bipyridin]-4'-yl)amino)-1-methylcyclohexan-1-ol The title compound as a solid (109 mg) was prepared in the same fashion as Step 2 in Reference Example 1, except that 6'-chloro-4'-fluoro-5-(3,3,3-trifluoropropyl)-2,3'-bipyridine (100 mg, 0.328 mmol) prepared in Step 1 was used instead of 6'-chloro-4'-fluoro-5-((1-methylpiperidin-4-yl)oxy)-2,3'-bipyridine. $^1$H-NMR (DMSO-d$_6$, 400 MHz) δ 9.52 (d, 1H), 8.59 (d, 1H), 8.49 (s, 1H), 7.96 (d, 1H), 7.88 (dd, 1H), 6.73 (s, 1H), 4.15 (s, 1H), 3.46-3.44 (m, 1H), 2.92-2.88 (m, 2H), 2.74-2.62 (m, 1H), 1.74-1.72 (m, 2H), 1.67-1.42 (m, 6H), 1.13 (s, 3H)

Step 3. (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol The title compound as a pale yellow solid (33.6 mg) was prepared in the same fashion as Step 3 in Example 1, except that (1s,4s)-4-((6'-chloro-5-(3,3,3-trifluoropropyl)-[2,3'-bipyridin]-4'-yl)amino)-1-methylcyclohexan-1-ol (86 mg, 0.207 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.47 (s, 1H), 8.66 (s, 1H), 8.48-8.38 (m, 3H), 7.85 (brs, 1H), 7.66 (dd, 2H), 7.30 (s, 1H), 7.04 (s, 1H), 3.52 (brs, 1H), 2.96-2.92 (m, 2H), 2.86-2.82 (m, 1H), 2.49-2.42 (m, 2H), 2.03-1.99 (m, 2H), 1.77-1.73 (m, 4H), 1.63-1.53 (m, 4H), 1.32 (s, 3H), 1.26-1.21 (m, 2H); MS (ESI) m/z=643.2 (M+H)$^+$ Example 264. 5-(2-(Azetidin-1-yl) ethoxy)-N$^{6'}$-(2-(1-(cyclopropylsulfonyl)-1H-pyrazol-4-yl)pyrimidin-4-yl)-N$^{4'}$-((1s,4s)-4-fluorocyclohexyl)-[2,3'-bipyridine]-4',6'-diamine Step 1. 5-(2-(Azetidin-1-yl) ethoxy)-6'-chloro-N-((1s,4s)-4-fluorocyclohexyl)-[2,3'-bipyridin]-4'-amine The title compound as a solid (27 mg) was prepared in the same fashion as Step 2 in Reference Example 1, except that 5-(2-(azetidin-1-yl) ethoxy)-6'-chloro-4'-fluoro-2,3'-bipyridine (46 mg, 0.151 mmol) prepared in Reference Example 13 and (1s,4s)-4-fluorocyclohexan-1-amine hydrochloride (30 mg, 0.196 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=405.2 (M+H)$^+$ Step 2. 5-(2-(Azetidin-1-yl) ethoxy)-N$^{6'}$-(2-(1-(cyclopropylsulfonyl)-1H-pyrazol-4-yl)pyrimidin-4-yl)-N$^{4'}$-((1s,4s)-4-fluorocyclohexyl)-[2,3'-bipyridine]-4',6'-diamine The title compound as a pale yellow solid (6.1 mg) was prepared in the same fashion as Step 3 in Example 1, except that 5-(2-(azetidin-1-yl) ethoxy)-6'-chloro-N-((1s,4s)-4- fluorocyclohexyl)-[2,3'-bipyridin]-4'-amine (23 mg, 0.057 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.71 (s, 1H), 8.44 (s, 1H), 8.34 (d, 1H), 8.30 (s, 1H), 7.78 (d, 1H), 7.47 (d, 1H), 7.37 (d, 1H), 7.21 (s, 1H), 7.01 (s, 1H), 4.72 (d, 1H), 4.14 (t, 2H), 3.67 (brs, 1H), 3.50 (t, 4H), 3.04-3.02 (m, 1H), 2.98 (t, 2H), 2.21 (quin, 2H), 2.04-1.78 (m, 8H), 1.52-1.26 (m, 4H); MS (ESI) m/z=635.3 (M+H)$^+$ Example 265. 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)-1,1,1-trifluoropropan-2-ol Step 1. 2-(6'-Chloro-4'-(((1s,4s)-4-fluorocyclohexyl)amino)-[2,3'-bipyridin]-5-yl)-1,1,1-trifluoropropan-2-ol The title compound as a solid (141 mg) was prepared in the same fashion as Step 2 in Reference Example 1, except that 2-(6'-chloro-4'-fluoro-[2,3'-bipyridin]-5-yl)-1,1,1-trifluoropropan-2-ol (120 mg, 0.375 mmol) prepared in Reference Example 11 and (1s,4s)-4-fluorocyclohexan-1-amine hydrochloride (86 mg, 0.562 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=418.1 (M+H)$^+$ Step 2. 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)-1,1,1-trifluoropropan-2-ol The title compound as a pale yellow solid (8.5 mg) was prepared in the same fashion as Step 3 in Example 1, except that 2-(6'-chloro-4'-(((1s,4s)-4-fluorocyclohexyl)amino)-[2,3'-bipyridin]-5-yl)-1,1,1-trifluoropropan-2-ol (52 mg. 0.124 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 8.82 (s, 1H), 8.72 (s, 1H), 8.68 (s, 1H), 8.50 (d, 2H), 8.08 (s, 2H), 7.44 (brs, 1H), 7.16 (brs, 1H), 6.93 (s, 1H), 4.79 (d, 1H), 3.65 (brs, 1H), 3.26-3.24 (m, 1H), 1.96-1.82 (m, 5H), 1.77 (s, 3H), 1.74-1.72 (m, 2H), 1.35-1.22 (m, 5H); MS (ESI) m/z=647.2 (M+H)$^+$ Example 266. 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)-1,1,1-trifluoropropan-2-ol Step 1. 2-(6'-Chloro-4'-((4-fluorocyclohexyl)amino)-[2,3'-bipyridin]-5-yl)-1,1,1-trifluoropropan-2-ol The title compound as a solid (136 mg) was prepared in the same fashion as Step 2 in Reference Example 1, except that 2-(6'-chloro-4'-fluoro-[2,3'-bipyridin]-5-yl)-1,1,1-trifluoropropan-2-ol (120 mg. 0.375 mmol) prepared in Reference Example 11 and 4-fluorocyclohexan-1-amine hydrochloride (86 mg, 0.562 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=418.1 (M+H)$^+$ Step 2. 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)-1,1,1-trifluoropropan-2-ol The title compound as a pale yellow solid (11 mg) was prepared in the same fashion as Step 3 in Example 1, except that 2-(6'-chloro-4'-((4-fluorocyclohexyl)amino)-[2,3'-bipyridin]-5-yl)-1,1,1-trifluoropropan-2-ol (52 mg, 0.124 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 8.84 (d, 1H), 8.75 (s, 1H), 8.57 (s, 2H), 8.14-8.07 (m, 2H), 7.30 (brs, 1H), 7.02 (brs, 1H), 6.97 (s, 1H), 4.88-4.67 (m, 1H), 3.66 (brs, 1H), 3.26-3.24 (m, 1H), 2.09-1.82 (m, 4H), 1.78 (s, 3H), 1.75-1.55 (m, 3H), 1.35-1.26 (m, 5H); MS (ESI) m/z=647.2 (M+H)$^+$ Example 267. N$^2$-(2-(1-(Cyclopropylsulfonyl)-1H-pyrazol-4-yl)pyrimidin-4-yl)-5-(6-(4,4-difluoropiperidin-1-yl)pyridazin-3-yl)-N$^4$-(4-fluorocyclohexyl)pyridine-2,4-diamine Step 1. 3-(6-Chloro-4-fluoropyridin-3-yl)-6-(4,4-difluoropiperidin-1-yl)pyridazine The title compound as a solid (888 mg) was prepared in the same fashion as Reference Example 5, except that 3-bromo-6-(4,4-difluoropiperidin-1-yl)pyridazine (1287 mg, 4.628 mmol) was used instead of 2-bromo-5-(methylsulfonyl)pyridine. $^1$H-NMR (DMSO-d$_6$, 400 MHz) δ 8.88 (d, 1H), 7.78 (t, 2H), 7.51 (d, 1H), 3.86 (t, 4H), 2.11-2.01 (m, 4H)

Step 2. 2-Chloro-5-(6-(4,4-difluoropiperidin-1-yl)pyridazin-3-yl)-N-(4-fluorocyclohexyl)pyridin-4-amine The title compound as a solid (76 mg) was prepared in the same fashion as Step 2 in Reference Example 1, except that 3-(6-chloro-4-fluoropyridin-3-yl)-6-(4,4-difluoropiperidin-1-yl)pyridazine (100 mg, 0.304 mmol) prepared in Step 1 and 4-fluorocyclohexan-1-amine hydrochloride (70 mg, 0.456 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.41-9.35 (m, 1H), 8.29 (s, 1H) 7.71 (dd, 1H), 7.11 (d, 1H), 6.61 (s, 1H), 4.89-4.59 (m, 1H), 3.88 (brs, 4H), 3.54-3.47 (m, 1H), 2.18-2.08 (m, 7H), 1.97-1.94 (m, 1H), 1.87-1.66 (m, 4H), 1.58-1.52 (m, 1H)

Step 3. N$^2$-(2-(1-(Cyclopropylsulfonyl)-1H-pyrazol-4-yl)pyrimidin-4-yl)-5-(6-(4,4-difluoropiperidin-1-yl)pyridazin-3-yl)-N$^4$-(4-fluorocyclohexyl)pyridine-2,4-diamine The title compound as a pale yellow solid (24.4 mg) was prepared in the same fashion as Step 3 in Example 1, except that 2-chloro-5-(6-(4,4-difluoropiperidin-1-yl)pyridazin-3-yl)-N-(4-fluorocyclohexyl)pyridin-4-amine (71 mg. 0.166 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.70 (brs, 1H), 8.68 (d, 1H), 8.44 (dd, 2H), 8.32 (s, 1H), 7.74 (dd, 1H), 7.33 (brs, 1H), 7.13 (d, 1H), 7.01 (brs, 1H), 4.92-4.63 (m, 1H), 3.88 (brs, 4H), 3.68-3.64 (m, 1H), 2.86-2.81 (m, 1H), 2.23-1.61 (m, 12H), 1.54-1.51 (m, 2H), 1.26-1.21 (m, 2H); MS (ESI) m/z=655.3 (M+H)$^+$ Example 268. N$^2$-(2-(1-(Cyclopropylsulfonyl)-1H-pyrazol-4-yl)pyrimidin-4-yl)-N$^4$-(4,4-difluorocyclohexyl)-5-(6-(4,4-difluoropiperidin-1-yl)pyridazin-3-yl)pyridine-2,4-diamine Step 1. 2-Chloro-N-(4,4-difluorocyclohexyl)-5-(6-(4,4-difluoropiperidin-1-yl)pyridazin-3-yl)pyridin-4-amine The title compound as a solid (109 mg) was prepared in the same fashion as Step 2 in Reference Example 1, except that 3-(6-chloro-4-fluoropyridin-3-yl)-6-(4,4-difluoropiperidin-1-yl)pyridazine (100 mg, 0.304 mmol) prepared in Step 1 of Example 267 and 4,4-difluorocyclohexan-1-amine hydrochloride (78 mg, 0.456 mmol) were used instead of 6'-chloro-4'-fluoro-5-((1-methylpiperidin-4-yl)oxy)-2,3'-bipyridine and cis-4-amino-1-methylcyclohexanol. $^1$H-NMR (CDCl$_3$, 400 MHz) δ 9.52 (d, 1H), 8.31 (s, 1H), 7.72 (d, 1H), 7.12 (d, 1H), 6.61 (s, 1H), 3.89 (t, 4H), 3.61-3.59 (m, 1H), 2.16-2.07 (m, 8H), 2.03-1.78 (m, 4H)

Step 2. N$^2$-(2-(1-(Cyclopropylsulfonyl)-1H-pyrazol-4-yl)pyrimidin-4-yl)-N$^4$-(4,4-difluorocyclohexyl)-5-(6-(4,4-difluoropiperidin-1-yl)pyridazin-3-yl)pyridine-2,4-diamine The title compound as a pale yellow solid (26.5 mg) was prepared in the same fashion as Step 3 in Example 1, except that 2-chloro-N-(4,4-difluorocyclohexyl)-5-(6-(4,4-difluoropiperidin-1-yl)pyridazin-3-yl)pyridin-4-amine (74 mg. 0.166 mmol) prepared in Step 1 was used instead of (1-(6'-chloro-5-((4-methylpiperazin-1-yl)methyl)-[2,3'-bipyridin]-4'-yl-4-methylpiperidin-4-yl)methanol. $^1$H-NMR (CDCl$_3$, 400 MHz) δ 9.73 (brs, 1H), 8.67 (s, 1H), 8.46 (s, 1H), 8.42 (d, 1H), 8.34 (s, 1H), 7.76 (d, 1H), 7.13 (d, 2H), 3.88 (t, 4H), 3.74 (brs, 1H), 2.86-2.82 (m, 1H), 2.16-2.09 (m, 4H), 2.05-1.84 (m, 6H), 1.57-1.54 (m, 2H), 1.26-1.21 (m, 4H); MS (ESI) m/z=673.2 (M+H)$^+$ Example 269. (1s,4s)-4-((2-((2-(1-(Cyclopropylsulfonyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol Step 1. 3-(6-Chloro-4-fluoropyridin-3-yl)-6-((1-methylpiperidin-4-yl)oxy)pyridazine The title compound as a solid (246 mg) was prepared in the same fashion as Reference Example 5, except that 3-bromo-6-((1-methylpiperidin-4-yl)oxy)pyridazine (250 mg, 0.919 mmol) was used instead of 2-bromo-5-(methylsulfonyl)pyridine. MS (ESI) m/z=323.1 (M+H)$^+$ Step 2. (1s,4s)-4-((2-Chloro-5-(6-((1-methylpiperidin-4-yl)oxy)pyridazin-3-yl)pyridin-4-yl)amino)-1-methylcyclohexan-1-ol The title compound as a solid (105 mg) was prepared in the same fashion as Step 2 in Reference Example 1, except that 3-(6-chloro-4-fluoropyridin-3-yl)-6-((1-methylpiperidin-4-yl)oxy)pyridazine (100 mg, 0.31 mmol) prepared in Step 1 was used instead of 6'-chloro-4'-fluoro-5-((1-methylpiperidin-4-yl)oxy)-2,3'-bipyridine. MS (ESI) m/z=432.2 (M+H)$^+$ Step 3. (1s,4s)-4-((2-((2-(1-(Cyclopropylsulfonyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol The title compound as a pale yellow solid (13 mg) was prepared in the same fashion as Step 3 in Example 1, except that (1s,4s)-4-((2-chloro-5-(6-((1-methylpiperidin-4-yl)oxy)pyridazin-3-yl)pyridin-4-yl)amino)-1-methylcyclohexan-1-ol (50 mg, 0.116 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.79 (s, 1H), 8.52 (d, 2H), 8.44 (d, 1H), 8.19 (d, 1H), 7.32 (d, 1H), 7.27 (d, 1H), 7.09 (s, 1H), 5.58 (brs, 1H), 3.60-3.34 (m, 4H), 3.06-3.02 (m, 1H), 2.94 (s, 3H), 2.30 (brs, 2H), 2.05-1.96 (m, 4H), 1.83-1.73 (m, 4H), 1.62-1.56 (m, 2H), 1.56-1.29 (m, 4H), 1.29 (s, 3H); MS (ESI) m/z=661.3 (M+H)$^+$ Example 270. N$^2$-(2-(1-(Cyclopropylsulfonyl)-1H-pyrazol-4-yl)pyrimidin-4-yl)-N$^4$-((1s,4s)-4-fluorocyclohexyl)-5-(6-((1-methylpiperidin-4-yl)oxy)pyridazin-3-yl)pyridine-2,4-diamine Step 1. 2-Chloro-N-((1s,4s)-4-fluorocyclohexyl)-5-(6-((1-methylpiperidin-4-yl)oxy)pyridazin-3-yl)pyridin-4-amine The title compound as a solid (105 mg) was prepared in the same fashion as Step 2 in Reference Example 1, except that 3-(6-chloro-4-fluoropyridin-3-yl)-6-((1-methylpiperidin-4-yl)oxy)pyridazine (100 mg. 0.31 mmol) prepared in Step 1 of Example 269 and (1s,4s)-4-fluorocyclohexan-1-amine hydrochloride (71 mg, 0.465 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=420.2 (M+H)$^+$ Step 2. N$^2$-(2-(1-(Cyclopropylsulfonyl)-1H-pyrazol-4-yl)pyrimidin-4-yl)-N$^4$-((1s,4s)-4-fluorocyclohexyl)-5-(6-((1-methylpiperidin-4-yl)oxy)pyridazin-3-yl)pyridine-2,4-diamine The title compound as a pale yellow solid (19 mg) was prepared in the same fashion as Step 3 in Example 1, except that 2-chloro-N-((1s,4s)-4-fluorocyclohexyl)-5-(6-((1-methylpiperidin-4-yl)oxy)pyridazin-3-yl)pyridin-4-amine (50 mg, 0.119 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.45 (s, 2H), 8.37 (d, 1H), 8.17 (d, 1H), 7.42 (s, 1H), 7.28 (s, 1H), 7.26 (s, 1H), 5.51 (brs, 1H), 4.75 (d, 1H), 3.74-3.68 (m, 1H), 3.19-3.14 (m, 2H), 3.06-3.02 (m, 1H), 2.81 (s, 3H), 2.33-1.20 (m, 4H), 2.04-1.97 (m, 4H), 1.80-1.73 (m, 4H), 1.45-1.28 (m, 6H); MS (ESI) m/z=649.3 (M+H)$^+$ Example 271. (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol Step 1. (1s,4s)-4-((6'-Chloro-6-fluoro-[2,3'-bipyridin]-4'-yl)amino)-1-methylcyclohexan-1-ol The title compound as a solid (120 mg) was prepared in the same fashion as in Reference Example 6, except that (1s,4s)-4-((2-chloro-5-iodopyridin-4-yl)amino)-1-methylcyclohexan-1-ol (150 mg, 0.409 mmol) prepared in Reference Example 14 and 2-fluoro-6-(4,4,5,5-tetramethyl-1,3,2-dioxaborolan-2-yl)pyridine (119 mg, 0.532 mmol) were used instead of 2-chloro-4-fluoro-5-iodopyridine and 6-fluoropyridine-2-boronic acid. MS (ESI) m/z=336.1 (M+H)$^+$ Step 2. (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol The title compound as a pale yellow solid (55.1 mg) was prepared in the same fashion as Step 3 in Example 1, except that (1s,4s)-4-((6'-chloro-6-fluoro-[2,3'-bipyridin]-4'-yl)amino)-1-methylcyclohexan-1-ol (118 mg. 0.352 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.08 (s, 1H), 8.66 (s, 2H), 8.57 (s, 1H), 8.47 (s, 1H), 8.44 (d, 1H), 8.06 (q, 1H), 7.92 (dd, 1H), 7.54 (brs, 1H), 7.32 (brs, 1H), 7.08 (dd, 1H), 4.19 (s, 1H), 3.28-3.21 (m, 1H), 1.86-1.84 (m, 2H), 1.68-1.57 (m, 4H), 1.45-1.39 (m, 2H), 1.36-1.32 (m, 2H), 1.27-1.22 (m, 2H), 1.13 (s, 3H); MS (ESI) m/z=565.1 (M+H)$^+$ Example 272. ((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)methanol Step 1. ((1s,4s)-4-((6'-Chloro-6-fluoro-[2,3'-bipyridin]-4'-yl)amino)cyclohexyl)methanol The title compound as a solid (121 mg) was prepared in the same fashion as in Reference Example 6, except that ((1s,4s)-4-((2-chloro-5-iodopyridin-4-yl)amino)cyclohexyl)methanol (150 mg, 0.409 mmol) prepared in Reference Example 26 and 2-fluoro-6-(4,4,5,5-tetramethyl-1,3,2-dioxaborolan-2-yl)pyridine (119 mg, 0.532 mmol) was used instead of 2-chloro-4-fluoro-5-iodopyridine and 6-fluoropyridine-2-boronic acid. MS (ESI) m/z=336.1 (M+H)$^+$ Step 2. ((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)methanol The title compound as a pale yellow solid (30.2 mg) was prepared in the same fashion as Step 3 in Example 1, except that ((1s,4s)-4-((6'-chloro-6-fluoro-[2,3'-bipyridin]-4'-yl)amino)cyclohexyl)methanol (111 mg, 0.332 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.31 (d, 1H), 8.66 (s, 1H), 8.49 (s, 1H), 8.47 (s, 1H), 8.42 (d, 1H), 7.88 (q, 1H), 7.65 (d, 1H), 7.60 (brs, 1H), 7.29 (s, 1H), 7.12 (dd, 1H), 6.83 (dd, 1H), 4.01 (brs, 1H), 3.58 (d, 2H), 2.88-2.82 (m, 1H), 2.06-2.03 (m, 2H), 1.84-1.75 (m, 4H), 1.57-1.52 (m, 2H), 1.48-1.38 (m, 3H), 1.26-1.23 (m, 2H); MS (ESI) m/z=565.2 (M+H)$^+$ Example 273. N$^{6'}$-(2-(1-(Cyclopropylsulfonyl)-1H-pyrazol-4-yl)pyrimidin-4-yl)-6-fluoro-N$^{4'}$-((1s,4s)-4-((2-fluoroethyl)amino)cyclohexyl)-[2,3'-bipyridine]-4',6'-diamine Step 1. (1s,4s)—N$^1$-(6'-Chloro-6-fluoro-[2,3'-bipyridin]-4'-yl)-N$^4$-(2-fluoroethyl)cyclohexane-1,4-diamine The title compound as a solid (126 mg) was prepared in the same fashion as in Reference Example 6, except that (1s,4s)—N$^1$-(2-chloro-5-iodopyridin-4-yl)-N$^4$-(2-fluoroethyl)cyclohexane-1,4-diamine (150 mg, 0.377 mmol) prepared in Reference Example 27 and 2-fluoro-6-(4,4,5,5-tetramethyl-1,3,2-dioxaborolan-2-yl)pyridine (109 mg, 0.532 mmol) were used instead of 2-chloro-4-fluoro-5-iodopyridine and 6-fluoropyridine-2-boronic acid. MS (ESI) m/z=367.1 (M+H)$^+$ Step 2. N$^{6'}$-(2-(1-(Cyclopropylsulfonyl)-1H-pyrazol-4-yl)pyrimidin-4-yl)-6-fluoro-N$^{4'}$-((1s,4s)-4-((2-fluoroethyl)amino)cyclohexyl)-[2,3'-bipyridine]-4',6'-diamine The title compound as a pale yellow solid (72 mg) was prepared in the same fashion as Step 3 in Example 1, except that (1s,4s)—N$^1$-(6'-chloro-6-fluoro-[2,3'-bipyridin]-4'-yl)-N$^4$-(2-fluoroethyl)cyclohexane-1,4-diamine (111 mg. 0.302 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.22 (d, 1H), 8.66 (s, 1H), 8.47 (s, 2H), 8.41 (d, 1H), 7.87 (q, 2H), 7.62 (dd, 1H), 7.12 (d, 1H), 6.84 (dd, 1H), 4.57 (dt, 2H), 3.89 (brs, 1H), 2.97 (dt, 2H), 2.87-2.81 (m, 1H), 2.69-2.64 (m, 1H), 2.07-2.04 (m, 2H), 1.90-1.79 (m, 5H), 1.56-1.51 (m, 4H), 1.26-1.21 (m, 2H); MS (ESI) m/z=596.2 (M+H)$^+$ Example 274. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-6-fluoro-[2,3'-bipyridine]-4',6'-diamine Step 1. 6'-Chloro-N-((1s,4s)-4-((dimethylamino)methyl)cyclohexyl)-6-fluoro-[2,3'-bipyridin]-4'-amine The title compound as a solid (56 mg) was prepared in the same fashion as in Reference Example 6, except that 2-chloro-N-((1s,4s)-4-((dimethylamino)methyl)cyclohexyl)-5-iodopyridin-4-amine (100 mg, 0.254 mmol) prepared in Reference Example 28 and 2-fluoro-6-(4,4,5,5-tetramethyl-1,3,2-dioxaborolan-2-yl)pyridine (74 mg, 0.33 mmol) were used instead of 2-chloro-4-fluoro-5-iodopyridine and 6-fluoropyridine-2-boronic acid. $^1$H-NMR (CDCl$_3$, 400 MHz) δ 9.18 (d, 1H), 8.44 (s, 1H), 7.90 (q, 1H), 7.64 (d, 1H), 6.88 (d, 1H), 6.59 (s, 1H), 3.80 (brs, 1H), 2.22 (s, 6H), 2.17 (d, 2H), 1.89-1.86 (m, 2H), 1.75-1.63 (m, 5H), 1.37-1.28 (m, 2H)

Step 2. N$^{6'}$-(2-(1-(Cyclopropylsulfonyl)-1H-pyrazol-4-yl)pyrimidin-4-yl)-N$^{4'}$-((1s,4s)-4-((dimethylamino)methyl)cyclohexyl)-6-fluoro-[2,3'-bipyridine]-4',6'-diamine The title compound as a pale yellow solid (23.3 mg) was prepared in the same fashion as Step 3 in Example 1, except that 6'-chloro-N-((1s,4s)-4-((dimethylamino)methyl)cyclohexyl)-6-fluoro-[2,3'-bipyridin]-4'-amine (55 mg, 0.151 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.28 (d, 1H), 8.66 (s, 1H), 8.48 (s, 1H), 8.47 (s, 1H), 8.41 (d, 1H), 7.87 (q, 1H), 7.64 (d, 2H), 7.14 (d, 1H), 6.83 (d, 1H), 3.99 (brs, 1H), 2.85 (brs, 1H), 2.24 (s, 6H), 2.19 (d, 2H), 2.01-1.98 (m, 2H), 1.81-1.70 (m, 5H), 1.54-1.52 (m, 2H), 1.42-1.32 (m, 2H), 1.26-1.22 (m, 2H); MS (ESI) m/z=592.1 (M+H)$^+$

Example 275. N$^{6'}$-(2-(1-(Cyclopropylsulfonyl)-1H-pyrazol-4-yl)pyrimidin-4-yl)-N$^{4'}$-((1s,4s)-4-((2,2-difluoroethyl)amino)cyclohexyl)-6-fluoro-[2,3'-bipyridine]-4',6'-diamine

Step 1. (1s,4s)—N$^1$-(2-chloro-5-iodopyridin-4-yl)-N$^4$-(2,2-difluoroethyl)cyclohexane-1,4-diamine The title compound as a pale yellow liquid (753 mg) was prepared in the same fashion as Step 2 of Reference Example 1, except that 2-chloro-4-fluoro-5-iodopyridine (500 mg, 1.942 mmol) and (1s,4s)—N$^1$-(2,2-difluoroethyl)cyclohexane-1,4-diamine (519 mg, 2.913 mmol) were used instead of 6'-chloro-4'-fluoro-5-((1-methylpiperidin-4-yl)oxy)-2,3'-bipyridine and cis-4-amino-1-methylcyclohexanol. MS (ESI) m/z=416.0 (M+H)$^+$

Step 2. (1s,4s)—N$^1$-(6'-Chloro-6-fluoro-[2,3'-bipyridin]-4'-yl)-N$^4$-(2,2-difluoroethyl)cyclohexane-1,4-diamine The title compound as a solid (127 mg) was prepared in the same fashion as in Reference Example 6, except that (1s,4s)—N$^1$-(2-chloro-5-iodopyridin-4-yl)-N$^4$-(2,2-difluoroethyl)cyclohexane-1,4-diamine (150 mg, 0.361 mmol) prepared in Step 1 and 2-fluoro-6-(4,4,5,5-tetramethyl-1,3,2-dioxaborolan-2-yl)pyridine (105 mg, 0.469 mmol) was used instead of 2-chloro-4-fluoro-5-iodopyridine and 6-fluoropyridine-2-boronic acid. 1H-NMR (DMSO-d$_6$, 400 MHz) δ 8.91 (d, 1H), 8.54 (s, 1H), 8.12 (q, 1H), 7.96 (dd, 1H), 7.19 (dd, 1H), 6.76 (s, 1H), 5.94 (tt, 1H), 3.73 (s, 1H), 2.87 (td, 2H), 2.58 (brs, 1H), 1.83 (s, 1H), 1.70-1.59 (m, 6H), 1.41-1.35 (m, 2H)

Step 3. N$^{6'}$-(2-(1-(Cyclopropylsulfonyl)-1H-pyrazol-4-yl)pyrimidin-4-yl)-N$^{4'}$-((1s,4s)-4-((2,2-difluoroethyl)amino)cyclohexyl)-6-fluoro-[2,3'-bipyridine]-4',6'-diamine The title compound as a pale yellow solid (66 mg) was prepared in the same fashion as Step 3 in Example 1, except that (1s,4s)—N$^1$-(6'-chloro-6-fluoro-[2,3'-bipyridin]-4'-yl)-N$^4$-(2,2-difluoroethyl)cyclohexane-1,4-diamine (126 mg, 0.329 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.02 (s, 1H), 8.99 (d, 1H), 8.63 (s, 1H), 8.61 (s, 1H), 8.45 (s, 1H), 8.43 (d, 1H), 8.06 (q, 1H), 7.95 (dd, 1H), 7.44 (d, 2H), 7.09 (dd, 1H), 5.94 (tt, 1H), 3.78 (brs, 1H), 3.30-3.23 (m, 1H), 2.89 (td, 2H), 2.57 (brs, 1H), 1.88-1.85 (m, 3H), 1.75-1.71 (m, 4H), 1.44-1.32 (m, 4H), 1.28-1.23 (m, 2H); MS (ESI) m/z=614.2 (M+H)$^+$

Example 276. (1s,4s)-4-((6'-((2-(1-(Cyclopropylsulfonyl)-1H-pyrazol-4-yl)pyrimidin-4-yl)amino)-4-((2-(dimethylamino)ethyl)amino)-[2,3'-bipyridin]-4'-yl)amino)-1-methylcyclohexan-1-ol

Step 1. N$^1$-(2-Bromopyridin-4-yl)-N$^2$,N$^2$-dimethylethane-1,2-diamine

The reaction mixture of 2-bromo-4-fluoropyridine (200 mg, 1.14 mmol), N$^1$,N$^1$-dimethylethane-1,2-diamine (130 mg, 1.477 mmol) and DIPEA (594 uL, 3.41 mmol) in DMA (4 mL) was stirred at 90° C. for 3 hours. The reaction mixture was cooled to room temperature, diluted in DCM, washed by water, dried over MgSO$_4$, and then concentrated. The crude product was purified by column chromatography (EA/n-Hex=0-80%) to yield N$^1$-(2-bromopyridin-4-yl)-N$^2$,N$^2$-dimethylethane-1,2-diamine (235 mg) as a pale yellow solid. MS (ESI) m/z=246.0 (M+H)$^+$

Step 2. (1s,4s)-4-((6'-Chloro-4-((2-(dimethylamino)ethyl)amino)-[2,3'-bipyridin]-4'-yl)amino)-1-methylcyclohexan-1-ol The title compound as a solid (90 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (99 mg, 0.27 mmol) prepared in Reference Example 3 and N$^1$-(2-bromopyridin-4-yl)-N$^2$,N$^2$-dimethylethane-1,2-diamine (60 mg, 0.246 mmol) prepared in Step 1 were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=404.2 (M+H)$^+$

Step 3. (1s,4s)-4-((6'-((2-(1-(Cyclopropylsulfonyl)-1H-pyrazol-4-yl)pyrimidin-4-yl)amino)-4-((2-(dimethylamino)ethyl)amino)-[2,3'-bipyridin]-4'-yl)amino)-1-methylcyclohexan-1-ol The title compound as a pale yellow solid (6.2 mg) was prepared in the same fashion as Step 3 in Example 1, except that (1s,4s)-4-((6'-chloro-4-((2-(dimethylamino)ethyl)amino)-[2,3'-bipyridin]-4'-yl)amino)-1-methylcyclohexan-1-ol (61 mg, 0.151 mmol) prepared in Step 2 was used instead of (1-(6'-chloro-5-((4-methylpiperazin-1-yl)methyl)-[2,3'-bipyridin]-4'-yl-4-methylpiperidin-4-yl)methanol. $^1$H-NMR (CDCl$_3$, 400 MHz) δ 9.28 (d, 1H), 8.67 (s, 1H), 8.48 (s, 1H), 8.41 (s, 1H), 8.32 (s, 1H), 8.17 (s, 1H), 7.29 (s, 1H), 6.94 (d, 1H), 6.78 (s, 1H), 6.41 (s, 1H), 3.47 (brs, 1H), 3.23 (t, 2H), 2.84-2.80 (m, 1H), 2.59 (t, 2H), 2.28 (s, 6H), 2.04-2.01 (m, 2H), 1.84-1.74 (m, 4H), 1.52-1.50 (m, 2H), 1.33-1.30 (m, 2H), 1.28 (s, 3H), 1.27-1.24 (m, 2H); MS (ESI) m/z=633.3 (M+H)$^+$

Example 277. (1s,4s)-4-((6'-((2-(1-(Cyclopropylsulfonyl)-1H-pyrazol-4-yl)pyrimidin-4-yl)amino)-4-((3,3,3-trifluoropropyl)amino)-[2,3'-bipyridin]-4'-yl)amino)-1-methylcyclohexan-1-ol

Step 1. 2-Bromo-N-(3,3,3-trifluoropropyl)pyridin-4-amine

The title compound as a pale yellow solid (265 mg) was prepared in the same fashion as Step 1 of Example 276, except that 3,3,3-trifluoropropan-1-amine hydrochloride (221 mg, 1.477 mmol) was used instead of N$^1$,N$^1$-dimethylethane-1,2-diamine. MS (ESI) m/z=270.9 (M+H)$^+$

Step 2. (1s,4s)-4-((6'-Chloro-4-((3,3,3-trifluoropropyl)amino)-[2,3'-bipyridin]-4'-yl)amino)-1-methylcyclohexan-1-ol The title compound as a solid (87 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (99 mg, 0.27 mmol) prepared in Reference Example 3 and 2-bromo-N-(3,3,3-trifluoropropyl)pyridin-4-amine (66 mg, 0.246 mmol) prepared in Step 1 were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=429.1 (M+H)⁺

Step 3. (1s,4s)-4-((6'-((2-(1-(Cyclopropylsulfonyl)-1H-pyrazol-4-yl)pyrimidin-4-yl)amino)-4-((3,3,3-trifluoropropyl)amino)-[2,3'-bipyridin]-4'-yl)amino)-1-methylcyclohexan-1-ol The title compound as a pale yellow solid (22.6 mg) was prepared in the same fashion as Step 3 in Example 1, except that (1s,4s)-4-((6'-cloro-4-((3,3,3-trifluoropropyl)amino)-[2,3'-bipyridin]-4'-yl)amino)-1-methylcyclohexan-1-ol (71 mg. 0.166 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 9.27 (d, 1H), 8.67 (s, 1H), 8.48 (s, 1H), 8.41 (d, 1H), 8.30 (d, 1H), 8.23 (s, 1H), 7.94 (brs, 1H), 7.29 (s, 1H), 6.97 (d, 1H), 6.79 (d, 1H), 6.42 (s, 1H), 4.49 (brs, 1H), 3.56 (t, 2H), 2.47 (brs, 1H), 2.84-2.80 (m, 1H), 2.47 (t, 2H), 2.00-1.98 (m, 2H), 1.75-1.56 (m, 4H), 1.53-1.51 (m, 2H), 1.29-1.24 (m, 4H); MS (ESI) m/z=658.2 (M+H)⁺

Example 278. (1s,4s)-4-((6'-((2-(1-(Cylopropylsulfonyl)-1H-pyrazol-4-yl)pyrimidin-4-yl)amino)-4-((1-methylpiperidin-4-yl)amino)-[2,3'-bipyridin]-4'-yl)amino)-1-methylcyclohexan-1-ol Step 1. 2-Bromo-N-(1-methylpiperidin-4-yl)pyridin-4-amine The title compound as a pale yellow solid (239 mg) was prepared in the same fashion as Step 1 of Example 276, except that 1-methylpiperidin-4-amine (169 mg, 1.477 mmol) was used instead of N¹,N¹-dimethylethane-1,2-diamine. MS (ESI) m/z=272.0 (M+H)⁺

Step 2. (1s,4s)-4-((6'-Chloro-4-((1-methylpiperidin-4-yl)amino)-[2,3'-bipyridin]-4'-yl)amino)-1-methylcyclohexan-1-ol The title compound as a solid (91 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (99 mg, 0.27 mmol) prepared in Reference Example 3 and 2-bromo-N-(1-methylpiperidin-4-yl)pyridin-4-amine (66 mg, 0.246 mmol) prepared in Step 1 were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=430.2 (M+H)⁺

Step 3. (1s,4s)-4-((6'-((2-(1-(Cylopropylsulfonyl)-1H-pyrazol-4-yl)pyrimidin-4-yl)amino)-4-((1-methylpiperidin-4-yl)amino)-[2,3'-bipyridin]-4'-yl)amino)-1-methylcyclohexan-1-ol The title compound as a pale yellow solid (21 mg) was prepared in the same fashion as Step 3 in Example 1, except that (1s,4s)-4-((6'-chloro-4-((1-methylpiperidin-4-yl)amino)-[2,3'-bipyridin]-4'-yl)amino)-1-methylcyclohexan-1-ol (65 mg, 0.151 mmol) prepared in Step 2 was used instead of (1-(6'-chloro-5-((4-methylpiperazin-1-yl)methyl)-[2,3'-bipyridin]-4'-yl-4-methylpiperidin-4-yl)methanol. ¹H-NMR (CDCl₃, 400 MHz) δ 9.22 (d, 1H), 8.66 (s, 1H), 8.48 (s, 1H), 8.41 (d, 1H), 8.29 (d, 1H), 8.16 (s, 1H), 7.67 (dd, 1H), 7.35 (d, 1H), 6.91 (s, 1H), 6.74 (d, 1H), 6.38 (s, 1H), 4.91 (brs, 1H), 4.20 (brs, 1H), 3.44 (brs, 2H), 2.87-2.80 (m, 3H), 2.33 (s, 3H), 2.33-2.08 (m, 4H), 1.98-1.75 (m, 6H), 1.56-1.25 (m, 6H); MS (ESI) m/z=660.3 (M+H)⁺

Example 279. (1s,4s)-4-((6'-((2-(1-(Cyclopropylsulfonyl)-1H-pyrazol-4-yl)pyrimidin-4-yl)amino)-4((2-morpholinoethyl)amino)-[2,3'-bipyridin]-4'-yl)amino)-1-methylcyclohexan-1-ol Step 1. 2-Bromo-N-(2-morpholinoethyl)pyridin-4-amine The title compound as a pale yellow solid (265 mg) was prepared in the same fashion as Step 1 of Example 276, except that 2-morpholinoethan-1-amine (192 mg, 1.477 mmol) was used instead of N¹,N¹-dimethylethane-1,2-diamine. ¹H-NMR (CDCl₃, 400 MHz) δ 7.91 (d, 1H), 6.62 (d, 1H), 6.40 (dd, 1H), 5.02 (s, 1H), 3.72 (t, 4H), 3.17 (dd, 2H), 2.62 (t, 2H), 2.47 (t, 4H)

Step 2. (1s,4s)-4-((6'-Chloro-4-((2-morpholinoethyl)amino)-[2,3'-bipyridin]-4'-yl)amino)-1-methylcyclohexan-1-ol The title compound as a solid (95 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (99 mg, 0.27 mmol) prepared in Reference Example 3 and 2-bromo-N-(2-morpholinoethyl)pyridin-4-amine (70 mg, 0.246 mmol) prepared in Step 1 were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=446.2 (M+H)⁺

Step 3. (1s,4s)-4-((6'-((2-(1-(Cyclopropylsulfonyl)-1H-pyrazol-4-yl)pyrimidin-4-yl)amino)-4 ((2-morpholinoethyl)amino)-[2,3'-bipyridin]-4'-yl)amino)-1-methylcyclohexan-1-ol The title compound as a pale yellow solid (18.4 mg) was prepared in the same fashion as Step 3 in Example 1, except that (1s,4s)-4-((6'-chloro-4-((2-morpholinoethyl)amino)-[2,3'-bipyridin]-4'-yl)amino)-1-methylcyclohexan-1-ol prepared in Step 2 was used instead of (1-(6'-chloro-5-((4-methylpiperazin-1-yl)methyl)-[2,3'-bipyridin]-4'-yl)-4-methylpiperidin-4-yl)methanol. MS (ESI) m/z=675.3 (M+H)⁺

Example 280. (1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)-1-methylcyclohexan-1-ol Step 1. (1s,4s)-4-((6'-Chloro-4-((3,3-difluorocyclobutyl)amino)-[2,3'-bipyridin]-4'-yl)amino)-1-methylcyclohexan-1-ol The title compound as a solid (94 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (100 mg, 0.273 mmol) prepared in Reference Example 3 and 2-bromo-N-(3,3-difluorocyclobutyl)pyridin-4-amine (105 mg. 0.469 mmol) prepared in Step 1 of Reference Example 15 were used instead of 2-chloro-4-fluoro-5-(4,4,5,5-tetramethyl-1,3,2-dioxaborolan-2-yl)pyridine and 2-bromo-5-((1- methyl-4-piperidyl)oxy)pyridine. $^1$H-NMR (DMSO-d$_6$, 400 MHz) δ 9.52 (d, 1H), 8.32 (s, 1H), 8.12 (d, 1H), 7.21 (d, 1H), 6.86 (d, 1H), 6.65 (s, 1H), 6.50 (dd, 1H), 4.15 (s, 1H), 4.00 (brs, 1H), 3.16-3.06 (m, 2H), 2.54-2.44 (m, 2H), 1.70-1.68 (m, 2H), 1.55-1.49 (m, 4H), 1.46-1.41 (m, 2H), 1.11 (s, 3H)

Step 2. (1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)-1-methylcyclohexan-1-ol The title compound as a pale yellow solid (30.1 mg) was prepared in the same fashion as Step 3 in Example 1, except that (1s,4s)-4-((6'-chloro-4-((3,3-difluorocyclobutyl)amino)-[2,3'-bipyridin]-4'-yl)amino)-1-methylcyclohexan-1-ol (70 mg. 0.166 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.27 (d, 1H), 8.66 (s, 1H), 8.47 (s, 1H), 8.39 (d, 1H), 8.28 (s, 1H), 8.21 (d, 1H), 7.28 (d, 1H), 6.97 (s, 1H), 6.72 (s, 1H), 6.35 (d, 1H), 4.60 (d, 1H), 3.96 (brs, 1H), 3.46 (brs, 1H), 3.17-3.07 (m, 2H), 2.83-2.81 (m, 1H), 2.58-2.46 (m, 2H), 2.05-1.96 (m, 2H), 1.79-1.71 (m, 4H), 1.61-1.52 (m, 4H), 1.30 (s, 3H), 1.23-1.18 (m, 2H); MS (ESI) m/z=652.2 (M+H)$^+$ Example 281. (1s,4s)-4-((6'-((2-(1-(Cyclopropylsulfonyl)-1H-pyrazol-4-yl)pyrimidin-4-yl)amino)-4-((2-(3-fluoroazetidin-1-yl)ethyl)amino)-[2,3'-bipyridin]-4'-yl)amino)-1-methylcyclohexan-1-ol Step 1. 2-Bromo-N-(2-(3-fluoroazetidin-1-yl)ethyl)pyridin-4-amine The title compound as a solid (262 mg) was prepared in the same fashion as Step 1 of Example 276, except that 2-(3-fluoroazetidin-1-yl)ethan-1-amine (215 mg, 1.847 mmol) was used instead of N$^1$,N$^1$-dimethylethane-1,2-diamine. MS (ESI) m/z=274.0 (M+H)$^+$ Step 2. (1s,4s)-4-((6'-Chloro-4-((2-(3-fluoroazetidin-1-yl)ethyl)amino)-[2,3'-bipyridin]-4'-yl)amino)-1-methylcyclohexan-1-ol The title compound as a solid (64 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (100 mg, 0.273 mmol) prepared in Reference Example 3 and 2-bromo-N-(2-(3-fluoroazetidin-1-yl)ethyl)pyridin-4-amine (105 mg, 0.469 mmol) prepared in Step 1 was used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. $^1$H-NMR (DMSO-d$_6$, 400 MHz) δ 9.58 (d, 1H), 8.28 (s, 1H), 8.06 (d, 1H), 6.90 (d, 1H), 6.64 (s, 1H), 6.61 (t, 1H), 6.51 (dd, 1H), 5.14 (dt, 1H), 4.15 (s, 1H), 3.61-3.53 (m, 2H), 3.17-3.08 (m, 4H), 2.61 (t, 2H), 1.70-1.68 (m, 2H), 1.55-1.49 (m, 4H), 1.48-1.40 (m, 2H), 1.11 (s, 3H)

Step 3. (1s,4s)-4-((6'-((2-(1-(Cyclopropylsulfonyl)-1H-pyrazol-4-yl)pyrimidin-4-yl)amino)-4-((2-(3-fluoroazetidin-1-yl)ethyl)amino)-[2,3'-bipyridin]-4'-yl)amino)-1-methylcyclohexan-1-ol The title compound as a pale yellow solid (12.2 mg) was prepared in the same fashion as Step 3 in Example 1, except that (1s,4s)-4-((6'-chloro-4-((2-(3-fluoroazetidin-1-yl)ethyl)amino)-[2,3'-bipyridin]-4'-yl)amino)-1-methylcyclohexan-1-ol (49 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.93 (s, 1H), 9.47 (brs, 1H), 8.63 (s, 1H), 8.46 (s, 1H), 8.41 (d, 1H), 8.32 (s, 1H), 8.05 (d, 1H), 7.55 (brs, 1H), 7.20 (brs, 1H), 6.90 (d, 1H), 6.54 (s, 1H), 6.47 (dd, 1H), 5.23-5.07 (m, 1H), 4.17 (s, 1H), 3.63-3.56 (m, 2H), 3.26-3.20 (m, 1H), 3.20-3.10 (m, 4H), 2.65 (t, 2H), 1.81-1.78 (m, 2H), 1.63-1.51 (m, 4H), 1.44-1.36 (m, 4H), 1.30-1.27 (m, 2H), 1.13 (s, 3H); MS (ESI) m/z=663.3 (M+H)$^+$ Example 282. (1s,4s)-4-((6'-((2-(1-(Cyclopropylsulfonyl)-1H-pyrazol-4-yl)pyrimidin-4-yl)amino)-4-((3-hydroxypropyl)amino)-[2,3'-bipyridin]-4'-yl)amino)-1-methylcyclohexan-1-ol Step 1. 3-((2-Bromopyridin-4-yl)amino)propan-1-ol The title compound as a solid (220 mg) was prepared in the same fashion as Step 1 of Example 276, except that 3-aminopropan-1-ol (139 mg, 1.847 mmol) was used instead of N$^1$,N$^1$-dimethylethane-1,2-diamine. MS (ESI) m/z=231.0 (M)$^+$ Step 2. (1s,4s)-4-((6'-Chloro-4-((3-hydroxypropyl)amino)-[2,3'-bipyridin]-4'-yl)amino)-1-methylcyclohexan-1-ol The title compound as a solid (64 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (100 mg, 0.273 mmol) prepared in Reference Example 3 and 3-((2-bromopyridin-4-yl)amino)propan-1-ol (81 mg, 0.351 mmol) prepared in Step 1 was used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. 1H-NMR (DMSO-d$_6$, 400 MHz) δ 9.56 (s, 1H), 8.26 (s, 1H), 8.06 (d, 1H), 6.88 (s, 1H), 6.70 (s, 1H), 6.64 (s, 1H), 6.58 (dd, 1H), 4.55 (t, 1H), 4.15 (s, 1H), 3.50 (q, 2H), 3.19 (q, 2H), 1.71-1.67 (m, 4H), 1.55-1.39 (m, 6H), 1.11 (s, 3H) Step 3. (1s,4s)-4-((6'-((2-(1-(Cyclopropylsulfonyl)-1H-pyrazol-4-yl)pyrimidin-4-yl)amino)-4-((3-hydroxypropyl)amino)-[2,3'-bipyridin]-4'-yl)amino)-1-methylcyclohexan-1-ol The title compound as a pale yellow solid (10.3 mg) was prepared in the same fashion as Step 3 in Example 1, except that (1s,4s)-4-((6'-chloro-4-((3-hydroxypropyl)amino)-[2,3'-bipyridin]-4'-yl)amino)-1-methylcyclohexan-1-ol (44 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.73 (s, 1H), 8.47 (s, 1H), 8.35 (d, 1H), 8.15 (s, 1H), 8.08 (d, 1H), 7.35 (d, 1H), 7.19 (s, 1H), 6.80 (d, 1H), 6.52 (dd, 1H), 3.70 (t, 1H), 3.49 (brs, 1H), 3.06-3.00 (m, 1H), 1.94-1.84 (m, 4H), 1.71-1.65 (m, 4H), 1.58-1.51 (m, 2H), 1.46-1.42 (m, 2H), 1.27-1.25 (m, 4H), 1.23 (s, 3H); MS (ESI) m/z=620.2 (M+H)$^+$ Example 283. (1s,4s)-4-((6'-((2-(1-(Cyclopropylsulfonyl)-1H-pyrazol-4-yl)pyrimidin-4-yl)amino)-4-((3-hydroxy cyclobutyl)amino)-[2,3'-bipyridin]-4'-yl)amino)-1-methylcyclohexan-1-ol Step 1. 3-((2-Bromopyridin-4-yl)amino)cyclobutan-1-ol The title compound as a solid (183 mg) was prepared in the same fashion as Step 1 of Example 276, except that 3-aminocyclobutan-1-ol (161 mg, 1.847 mmol) was used instead of $N^1,N^1$-dimethylethane-1,2-diamine. MS (ESI) m/z=244.0 (M+H)$^+$ Step 2. (1s,4s)-4-((6'-Chloro-4-((3-hydroxycyclobutyl)amino)-[2,3'-bipyridin]-4'-yl)amino)-1-methylcyclohexan-1-ol The title compound as a solid (48 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (100 mg, 0.273 mmol) prepared in Reference Example 3 and 3-((2-bromopyridin-4-yl)amino)cyclobutan-1-ol (85 mg. 0.351 mmol) prepared in Step 1 were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. $^1$H-NMR (DMSO-d$_6$, 400 MHz) δ 9.53 (d, 1H), 8.24 (s, 1H), 8.07 (d, 1H), 6.95 (d, 1H), 6.79 (s, 1H), 6.63 (s, 1H), 6.43 (d, 1H), 5.14 (t, 1H), 4.15 (s, 1H), 3.90-3.84 (m, 1H), 3.45-3.40 (m, 2H), 2.72-2.67 (m, 2H), 2.22-2.14 (m, 1H), 1.73-1.68 (m, 4H), 1.56-1.46 (m, 6H), 1.11 (s, 3H)

Step 3. (1s,4s)-4-((6'-((2-(1-(Cyclopropylsulfonyl)-1H-pyrazol-4-yl)pyrimidin-4-yl)amino)-4-((3-hydroxy cyclobutyl)amino)-[2,3'-bipyridin]-4'-yl)amino)-1-methylcyclohexan-1-ol The title compound as a pale yellow solid (7.9 mg) was prepared in the same fashion as Step 3 in Example 1, except that (1s,4s)-4-((6'-chloro-4-((3-hydroxycyclobutyl)amino)-[2,3'-bipyridin]-4'-yl)amino)-1-methylcyclohexan-1-ol (46 mg, 0.113 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.73 (s, 1H), 8.47 (s, 1H), 8.35 (d, 1H), 8.13 (s, 1H), 8.08 (d, 1H), 7.36 (d, 1H), 7.19 (s, 1H), 6.73 (d, 1H), 6.45 (dd, 1H), 4.11-4.06 (m, 1H), 3.59-3.49 (m, 2H), 3.06-3.00 (m, 1H), 2.89-2.83 (m, 1H), 2.38-2.32 (m, 1H), 1.94-1.84 (m, 4H), 1.71-1.65 (m, 4H), 1.58-1.51 (m, 2H), 1.46-1.42 (m, 2H), 1.27-1.25 (m, 2H), 1.23 (s, 3H); MS (ESI) m/z=632.2 (M+H)$^+$ Example 284. (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(morpholino)methanone Step 1. (6'-Chloro-4'-(((1s,4s)-4-hydroxy-4-methylcyclohexyl)amino)-[2,3'-bipyridin]-5-yl)(morpholino)methanone The title compound as a pale yellow solid (127 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (163 mg, 0.44 mmol) prepared in Reference Example 3 and (6-bromopyridin-3-yl)(morpholino)methanone (100 mg, 0.37 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. $^1$H-NMR (CDCl$_3$, 400 MHz) δ 9.29 (d, 1H), 8.66 (d, 1H), 8.42 (s, 1H), 7.86 (dd, 1H), 7.79 (d, 1H), 6.60 (s, 1H), 3.76-3.59 (m, 8H), 3.40-3.33 (m, 1H), 1.95-1.93 (m, 2H), 1.79-1.68 (m, 4H), 1.61-1.31 (m, 2H), 1.31 (s, 3H)

Step 2. (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(morpholino)methanone The title compound as a pale yellow solid (50.7 mg) was prepared in the same fashion as Step 3 in Example 1, except that (6'-chloro-4'-(((1s,4s)-4-hydroxy-4-methylcyclohexyl)amino)-[2,3'-bipyridin]-5-yl)(morpholino)methanone (122 mg, 0.283 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.46 (d, 1H), 8.66 (s, 1H), 8.64 (d, 1H), 8.47 (d, 1H), 8.42 (d, 1H), 7.99 (brs, 1H), 7.85-7.77 (m, 2H), 7.26 (s, 1H), 7.09 (s, 1H), 3.76-3.51 (m, 9H), 2.85-2.79 (m, 1H), 2.01-1.97 (m, 2H), 1.81-1.73 (m, 4H), 1.62-1.50 (m, 4H), 1.31 (s, 3H), 1.24-1.18 (m, 2H); MS (ESI) m/z=660.2 (M+H)$^+$ Example 285. (1s,4s)-4-((6'-((2-(1-(Cyclopropylsulfonyl)-1H-pyrazol-4-yl)pyrimidin-4-yl)amino)-6-((2-hydroxyethyl)amino)-[2,3'-bipyridin]-4'-yl)amino)-1-methylcyclohexan-1-ol Step 1. (1s,4s)-4-((6'-Chloro-6-((2-hydroxyethyl)amino)-[2,3'-bipyridin]-4'-yl)amino)-1-methylcyclohexan-1-ol The title compound as a pale yellow solid (121 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (318 mg, 1.01 mmol) prepared in Reference Example 3 and 2-((6-bromopyridin-2-yl)amino)ethan-1-ol (200 mg, 0.92 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=377.2 (M+H)$^+$ Step 2. (1s,4s)-4-((6'-((2-(1-(Cyclopropylsulfonyl)-1H-pyrazol-4-yl)pyrimidin-4-yl)amino)-6-((2-hydroxyethyl)amino)-[2,3'-bipyridin]-4'-yl)amino)-1-methylcyclohexan-1-ol The title compound as a pale yellow solid (23.7 mg) was prepared in the same fashion as Step 3 in Example 1, except that (1s,4s)-4-((6'-chloro-6-((2-hydroxyethyl)amino)-[2,3'-bipyridin]-4'-yl)amino)-1-methylcyclohexan-1-ol (86 mg, 0.228 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.88 (brs, 1H), 8.65 (s, 1H), 8.47 (s, 1H), 8.39 (d, 1H), 8.30 (s, 1H), 7.53 (dd, 1H), 7.20 (brs, 1H), 7.13 (brs, 1H), 6.94 (d, 1H), 6.35 (d, 1H), 5.03 (brs, 1H), 3.87 (t, 2H), 3.63 (brs, 1H), 3.52 (q, 2H), 2.86-2.80 (m, 1H), 1.97-1.94 (m, 2H), 1.95-1.59 (m, 6H), 1.55-1.51 (m, 2H), 1.33 (s, 3H), 1.24-1.19 (m, 2H); MS (ESI) m/z=606.2 (M+H)$^+$ Example 286. (1s,4s)-4-((6'-((2-(1-(Cyclopropylsulfonyl)-1H-pyrazol-4-yl)pyrimidin-4-yl)amino)-6-((1-methylpiperidin-4-yl)oxy)-[2,3'-bipyridin]-4'-yl)amino)-1-methylcyclohexan-1-ol Step 1. (1s,4s)-4-((6'-Chloro-6-((1-methylpiperidin-4-yl)oxy)-[2,3'-bipyridin]-4'-yl)amino)-1-methylcyclohexan-1-ol The title compound as a pale yellow solid (96 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (318 mg, 1.01 mmol) prepared in Reference Example 3 and 2-bromo-6-((1-methylpiperidin-4-yl)oxy)pyridine (250 mg, 0.92 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=431.2 (M+H)$^+$ Step 2. (1s,4s)-4-((6'-((2-(1-(Cyclopropylsulfonyl)-1H-pyrazol-4-yl)pyrimidin-4-yl)amino)-6-((1-methylpiperidin-4-yl)oxy)-[2,3'-bipyridin]-4'-yl)amino)-1-methylcyclohexan-1-ol The title compound as a pale yellow solid (33.3 mg) was prepared in the same fashion as Step 3 in Example 1, except that (1s,4s)-4-((6'-chloro-6-((1-methylpiperidin-4-yl)oxy)-[2,3'-bipyridin]-4'-yl)amino)-1-methylcyclohexan-1-ol (89 mg, 0.207 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.48 (s, 1H), 8.41 (d, 1H), 8.30 (s, 1H), 8.22 (d, 1H), 7.68 (t, 1H), 7.34 (d, 1H), 7.20 (d, 1H), 6.97 (s, 1H), 6.67 (d, 1H), 5.04-5.02 (m, 1H), 3.51-3.45 (m, 1H), 2.86-2.79 (m, 1H), 2.73 (brs, 2H), 2.41 (brs, 2H), 2.34 (s, 3H), 2.15-2.10 (m, 2H), 2.03-2.00 (m, 2H), 1.92-1.68 (m, 6H), 1.61-1.51 (m, 4H), 1.30 (s, 3H), 1.24-1.19 (m, 2H); MS (ESI) m/z=660.3 (M+H)$^+$ Example 287. (1s,4s)-4-((6'-((2-(1-(Cyclopropylsulfonyl)-1H-pyrazol-4-yl)pyrimidin-4-yl)amino)-4-(2-(dimethylamino) ethoxy)-[2,3'-bipyridin]-4'-yl)amino)-1-methylcyclohexan-1-ol Step 1. (1s,4s)-4-((6'-Chloro-4-(2-(dimethylamino) ethoxy)-[2,3'-bipyridin]-4'-yl)amino)-1-methylcyclohexan-1-ol The title compound as a pale yellow solid (77 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (180 mg, 0.49 mmol) prepared in Reference Example 3 and 2-((2-bromopyridin-4-yl)oxy)-N,N-dimethylethan-1-amine (100 mg, 0.408 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=405.2 (M+H)$^+$ Step 2. (1s,4s)-4-((6'-((2-(1-(Cyclopropylsulfonyl)-1H-pyrazol-4-yl)pyrimidin-4-yl)amino)-4-(2-(dimethylamino) ethoxy)-[2,3'-bipyridin]-4'-yl)amino)-1-methylcyclohexan-1-ol The title compound as a pale yellow solid (31.8 mg) was prepared in the same fashion as Step 3 in Example 1, except that (1s,4s)-4-((6'-chloro-4-(2-(dimethylamino) ethoxy)-[2,3'-bipyridin]-4'-yl)amino)-1-methylcyclohexan-1-ol (76 mg, 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.99 (s, 1H), 9.47 (d, 1H), 8.65 (s, 1H), 8.53 (s, 1H), 8.46 (d, 1H), 8.41 (dd, 2H), 7.55 (brs, 1H), 7.44 (d, 1H), 7.27 (brs, 1H), 6.89 (dd, 1H), 4.24 (t, 1H), 4.19 (s, 1H), 3.28-3.24 (m, 1H), 2.65 (t, 2H), 2.22 (s, 6H), 1.84-1.81 (m, 2H), 1.63-1.56 (m, 4H), 1.44-1.39 (m, 2H), 1.36-1.32 (m, 2H), 1.27-1.22 (m, 2H), 1.13 (s, 3H); MS (ESI) m/z=634.2 (M+H)$^+$ Example 288. 1-((6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-4-yl)methyl) azetidin-3-ol Step 1. 1-((6'-Chloro-4'-(((1s,4s)-4-hydroxy-4-methylcyclohexyl)amino)-[2,3'-bipyridin]-4-yl)methyl) azetidin-3-ol The title compound as a pale yellow solid (79 mg) was prepared in the same fashion Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (180 mg, 0.49 mmol) prepared in Reference Example 3 and 1-((2-bromopyridin-4-yl)methyl) azetidin-3-ol (99 mg, 0.408 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=403.1 (M+H)$^+$ Step 2. 1-((6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-4-yl)methyl) azetidin-3-ol The title compound as a pale yellow solid (20.3 mg) was prepared in the same fashion as Step 3 in Example 1, except that 1-((6'-chloro-4'-(((1s,4s)-4-hydroxy-4-methylcyclohexyl)amino)-[2,3'-bipyridin]-4-yl)methyl) azetidin-3-ol (76 mg, 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 10.02 (s, 1H), 9.44 (d, 1H), 8.65 (s, 1H), 8.51 (d, 1H), 8.49 (s, 1H), 8.47 (s, 1H), 8.42 (d, 1H), 7.79 (s, 1H), 7.53 (brs, 1H), 7.31 (brs, 1H), 7.19 (d, 1H), 6.37 (d, 1H), 4.25-4.21 (m, 1H), 4.19 (s, 1H), 3.65 (s, 2H), 3.56 (t, 2H), 3.26-3.20 (m, 1H), 2.83 (t, 2H), 1.84-1.82 (m, 2H), 1.67-1.56 (m, 4H), 1.45-1.39 (m, 2H), 1.36-1.32 (m, 2H), 1.27-1.24 (m, 2H), 1.13 (s, 3H); MS (ESI) m/z=632.3 (M+H)$^+$ Example 289. (1s,4s)-4-((6'-((2-(1-(Cyclopropylsulfonyl)-1H-pyrazol-4-yl)pyrimidin-4-yl)amino)-5-((1-methylazetidin-3-yl)oxy)-[2,3'-bipyridin]-4'-yl)amino)-1-methylcyclohexan-1-ol Step 1. (1s,4s)-4-((6'-Chloro-5-((1-methylazetidin-3-yl)oxy)-[2,3'-bipyridin]-4'-yl)amino)-1-methylcyclohexan-1-ol The title compound as a pale yellow solid (82 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (180 mg, 0.49 mmol) prepared in Reference Example 3 and 2-bromo-5-((1-methylazetidin-3-yl)oxy)pyridine (99 mg. 0.408 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=403.1 (M+H)$^+$

Step 2. (1s,4s)-4-((6'-((2-(1-(Cyclopropylsulfonyl)-1H-pyrazol-4-yl)pyrimidin-4-yl)amino)-5-((1-methylazetidin-3-yl)oxy)-[2,3'-bipyridin]-4'-yl)amino)-1-methylcyclohexan-1-ol The title compound as a pale yellow solid (15.8 mg) was prepared in the same fashion as Step 3 in Example 1, except that (1s,4s)-4-((6'-chloro-5-((1-methylazetidin-3-yl)oxy)-[2,3'-bipyridin]-4'-yl)amino)-1-methylcyclohexan-1-ol (76 mg. 0.188 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 9.95 (s, 1H), 9.05 (d, 1H), 8.64 (s, 1H), 8.46 (s, 1H), 8.41 (d, 1H), 8.40 (s, 1H), 8.22 (d, 1H), 7.88 (d, 1H), 7.57 (brs, 1H), 7.39 (dd, 1H), 7.24 (s, 1H), 4.92-4.86 (m, 1H), 4.18 (s, 1H), 3.76 (q, 2H), 3.26-3.20 (m, 1H), 3.02 (t, 2H), 2.29 (s, 3H), 1.84-1.81 (m, 2H), 1.63-1.56 (m, 4H), 1.44-1.39 (m, 2H), 1.34-1.32 (m, 2H), 1.27-1.24 (m, 2H), 1.13 (s, 3H); MS (ESI) m/z=632.2 (M+H)$^+$

Example 290. (1s,4s)-4-((5-(2-(Azetidin-1-yl)ethoxy)-6'-((2-(1-(cyclopropylsulfonyl)-1H-pyrazol-4-yl)pyrimidin-4-yl)amino)-[2,3'-bipyridin]-4'-yl)amino)-1-methylcyclohexan-1-ol

Step 1. (1s,4s)-4-((5-(2-(Azetidin-1-yl) ethoxy)-6'-chloro-[2,3'-bipyridin]-4'-yl)amino)-1-methylcyclohexan-1-ol The title compound as a pale brown solid (113 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (171 mg, 0.467 mmol) prepared in Reference Example 3 and 5-(2-(azetidin-1-yl) ethoxy)-2-bromopyridine (100 mg, 0.89 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=417.2 (M+H)$^+$

Step 2. (1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)-1-methylcyclohexan-1-ol The title compound as a pale yellow solid (40.4 mg) was prepared in the same fashion as Step 3 in Example 1, except that (1s,4s)-4-((5-(2-(azetidin-1-yl) ethoxy)-6'-chloro-[2,3'-bipyridin]-4'-yl)amino)-1-methylcyclohexan-1-ol (110 mg, 0.264 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.10 (d, 1H), 8.65 (s, 1H), 8.47 (s, 1H), 8.39 (d, 1H), 8.33 (s, 1H), 8.25 (d, 1H), 7.95 (brs, 1H), 7.62 (d, 1H), 7.32 (dd, 2H), 6.99 (s, 1H), 4.04 (t, 2H), 3.47 (brs, 1H), 3.34 (t, 4H), 2.87-2.78 (m, 3H), 2.14 (quin, 2H), 2.00-1.96 (m, 2H), 1.79-1.72 (m, 4H), 1.61-1.51 (m, 4H), 1.30 (s, 3H), 1.27-1.24 (m, 2H); MS (ESI) m/z=646.2 (M+H)$^+$

Example 291. (1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)-1-methylcyclohexan-1-ol

Step 1. (1s,4s)-4-((6'-Chloro-5-(2-fluoropropan-2-yl)-[2,3'-bipyridin]-4'-yl)amino)-1-methylcyclohexan-1-ol The title compound as a pale yellow solid (110 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (219 mg, 0.596 mmol) prepared in Reference Example 3 and 2-bromo-5-(2-fluoropropan-2-yl) pyridine (100 mg, 0.459 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=378.1 (M+H)$^+$

Step 2. (1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)-1-methylcyclohexan-1-ol The title compound as a pale yellow solid (39.1 mg) was prepared in the same fashion as Step 3 in Example 1, except that (1s,4s)-4-((6'-chloro-5-(2-fluoropropan-2-yl)-[2,3'-bipyridin]-4'-yl)amino)-1-methylcyclohexan-1-ol (110 mg. 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.49 (d, 1H), 8.67 (s, 1H), 8.61 (s, 1H), 8.48 (s, 1H), 8.45 (s, 1H), 8.42 (d, 1H), 7.77 (dd, 2H), 7.59 (brs, 1H), 7.34 (d, 1H), 6.99 (s, 1H), 3.51 (brs, 1H), 2.84-2.80 (m, 1H), 2.03-2.00 (m, 2H), 1.79-1.74 (m, 9H), 1.65-1.53 (m, 5H), 1.32 (s, 3H), 1.26-1.19 (m, 2H); MS (ESI) m/z=607.2 (M+H)$^+$

Example 292. (1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)-1-methylcyclohexan-1-ol

Step 1. (1s,4s)-4-((6'-Chloro-5-(1,1-difluoroethyl)-[2,3'-bipyridin]-4'-yl)amino)-1-methylcyclohexan-1-ol The title compound as a pale yellow solid (141 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (219 mg, 0.596 mmol) prepared in Reference Example 3 and 2-bromo-5-(1,1-difluoroethyl) pyridine (102 mg, 0.459 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=382.1 (M+H)$^+$

Step 2. (1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)-1-methylcyclohexan-1-ol The title compound as a pale yellow solid (40.2 mg) was prepared in the same fashion as Step 3 in Example 1, except that (1s,4s)-4-((6'-chloro-5-(1,1-difluoroethyl)-[2,3'-bipyridin]-4'-yl)amino)-1-methylcyclohexan-1-ol (111 mg. 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 9.47 (d, 1H), 8.72 (s, 1H), 8.67 (s, 1H), 8.48 (s, 2H), 8.41 (d, 1H), 7.97 (brs, 1H), 7.89 (d, 1H), 7.79 (d, 1H), 7.29 (s, 1H), 7.07 (s, 1H), 3.52 (brs, 1H), 2.85-2.79 (m, 1H), 2.05-1.96 (m, 5H), 1.82-1.74 (m, 4H), 1.63-1.51 (m, 4H), 1.31 (s, 3H), 1.24-1.18 (m, 2H); MS (ESI) m/z=611.2 (M+H)$^+$

Example 293. (1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)-1-methylcyclohexan-1-ol

Step 1. (1s,4s)-4-((6'-Chloro-6-(2,2,2-trifluoroethyl)-[2,3'-bipyridin]-4'-yl)amino)-1-methylcyclohexan-1-ol The title compound as a pale yellow solid (145 mg) was prepared in the same fashion as Step 1 of Reference Example 1, except that (1s,4s)-4-((2-chloro-5-(4,4,5,5-tetramethyl-1,3,2-dioxaborolan-2-yl)pyridin-4-yl)amino)-1-methylcyclohexan-1-ol (219 mg, 0.596 mmol) prepared in Reference Example 3 and 2-bromo-6-(2,2,2-trifluoroethyl)pyridine (110 mg, 0.459 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=400.1 $(M+H)^+$

Step 2. (1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)-1-methylcyclohexan-1-ol The title compound as a pale yellow solid (28.8 mg) was prepared in the same fashion as Step 3 in Example 1, except that (1s,4s)-4-((6'-chloro-6-(2,2,2-trifluoroethyl)-[2,3'-bipyridin]-4'-yl)amino)-1-methylcyclohexan-1-ol (116 mg, 0.29 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.72 (s, 1H), 8.46 (s, 1H), 8.42 (s, 1H), 8.34 (d, 1H), 7.88-7.80 (m, 2H), 7.40 (d, 1H), 7.32 (d, 1H), 7.21 (s, 1H), 3.74 (q, 2H), 3.51-3.49 (m, 1H), 3.06-3.00 (m, 1H), 1.96-1.94 (m, 2H), 1.80-1.71 (m, 4H), 1.60-1.53 (m, 2H), 1.47-1.44 (m, 2H), 1.26-1.24 (m, 5H); MS (ESI) m/z=629.2 $(M+H)^+$

Example 294. 1-(6'-((2-(1-(Cyclopropylsulfonyl)-1H-pyrazol-4-yl)pyrimidin-4-yl)amino)-4'-(isopropylamino)-[2,3'-bipyridin]-5-yl)-2,2,2-trifluoroethan-1-ol

Step 1. 1-(6'-Chloro-4'-(isopropylamino)-[2,3'-bipyridin]-5-yl)-2,2,2-trifluoroethan-1-ol The title compound as a pale yellow solid (67 mg) was prepared in the same fashion as Step 1 of Reference Example 1, except that 2-chloro-N-isopropyl-5-(4,4,5,5-tetramethyl-1,3,2-dioxaborolan-2-yl)pyridin-4-amine (136 mg, 0.457 mmol) and 1-(6-bromopyridin-3-yl)-2,2,2-trifluoroethan-1-ol (90 mg, 0.352 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=346.0 $(M+H)^+$

Step 2. 1-(6'-((2-(1-(Cyclopropylsulfonyl)-1H-pyrazol-4-yl)pyrimidin-4-yl)amino)-4'-(isopropylamino)-[2,3'-bipyridin]-5-yl)-2,2,2-trifluoroethan-1-ol The title compound as a pale yellow solid (7.3 mg) was prepared in the same fashion as Step 3 in Example 1, except that 1-(6'-chloro-4'-(isopropylamino)-[2,3'-bipyridin]-5-yl)-2,2,2-trifluoroethan-1-ol (62 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.74 (s, 1H), 8.67 (d, 1H), 8.54 (s, 1H), 8.45 (s, 1H), 8.37 (d, 1H), 8.00 (dd, 1H), 7.91 (d, 1H), 7.44 (s, 1H), 7.32 (s, 1H), 5.19 (q, 1H), 3.95-3.87 (m, 1H), 3.06-3.02 (m, 1H), 1.47-1.43 (m, 2H), 1.39 (d, 6H), 1.30-1.25 (m, 2H); MS (ESI) m/z=575.2 $(M+H)^+$

Example 295. 2-(6'-((2-(1-(Cyclopropylsulfonyl)-1H-pyrazol-4-yl)pyrimidin-4-yl)amino)-4'-(isopropylamino)-[2,3'-bipyridin]-5-yl)-1,1,1-trifluoropropan-2-ol

Step 1. 2-(6'-Chloro-4'-(isopropylamino)-[2,3'-bipyridin]-5-yl)-1,1,1-trifluoropropan-2-ol The title compound as a pale yellow solid (82 mg) was prepared in the same fashion as Step 1 of Reference Example 1, except that 2-chloro-N-isopropyl-5-(4,4,5,5-tetramethyl-1,3,2-dioxaborolan-2-yl)pyridin-4-amine (136 mg, 0.457 mmol) and 2-(6-bromopyridin-3-yl)-1,1,1-trifluoropropan-2-ol (95 mg, 0.352 mmol) were used instead of 2-chloro-4-fluoro-5-(4,4,5,5-tetramethyl-1,3,2-dioxaborolan-2-yl)pyridine and 2-bromo-5-((1-methyl-4-piperidyl)oxy)pyridine. MS (ESI) m/z=360.0 $(M+H)^+$

Step 2. 2-(6'-((2-(1-(Cyclopropylsulfonyl)-1H-pyrazol-4-yl)pyrimidin-4-yl)amino)-4'-(isopropylamino)-[2,3'-bipyridin]-5-yl)-1,1,1-trifluoropropan-2-ol The title compound as a pale yellow solid (35.8 mg) was prepared in the same fashion as Step 3 in Example 1, except that 2-(6'-chloro-4'-(isopropylamino)-[2,3'-bipyridin]-5-yl)-1,1,1-trifluoropropan-2-ol (67 mg, 0.187 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 9.41 (d, 1H), 8.79 (d, 1H), 8.68 (s, 1H), 8.48 (s, 1H), 8.41 (d, 2H), 7.98 (dd, 1H), 7.76 (d, 2H), 7.31 (s, 1H), 7.11 (d, 1H), 3.92-3.84 (m, 1H), 2.87-2.81 (m, 1H), 1.87 (s, 3H), 1.56-1.52 (m, 2H), 1.40 (d, 6H), 1.26-1.20 (m, 2H); MS (ESI) m/z=589.2 $(M+H)^+$

Example 296. 4-(4-((4'-(((1s,4s)-4-Hydroxy-4-methylcyclohexyl)amino)-5-(2,2,2-trifluoroethyl)-[2,3'-bipyridin]-6'-yl)amino)pyrimidin-2-yl)-N,N-dimethyl-1H-pyrazole-1-sulfonamide The title compound as a pale yellow solid (13.2 mg) was prepared in same fashion as Step 3 in Example 1, except that (1s,4s)-4-((6'-chloro-5-(2,2,2-trifluoroethyl)-[2,3'-bipyridin]-4'-yl)amino)-1-methylcyclohexan-1-ol (45 mg, 0.11 mmol) prepared in Step 1 of Example 218 and 4-(4-aminopyrimidin-2-yl)-N,N-dimethyl-1H-pyrazole-1-sulfonamide (30 mg, 0.11 mmol) prepared in Reference Example 20 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-$d_6$, 400 MHz) δ 10.01 (s, 1H), 9.46 (d, 1H), 8.59 (s, 2H), 8.56 (s, 1H), 8.42 (d, 1H), 8.41 (s, 1H), 8.02 (d, 1H), 7.87 (dd, 1H), 7.51 (d, 2H), 7.32 (s, 1H), 4.20 (s, 1H), 3.76 (q, 2H), 3.43 (brs, 1H), 2.91 (s, 6H), 1.86-1.83 (m, 2H), 1.70-1.58 (m, 4H), 1.46-1.41 (m, 2H), 1.14 (s, 3H); MS (ESI) m/z=632.2 $(M+H)^+$

Example 297. 4-(4-((4'-(((1s,4s)-4-Hydroxy-4-methylcyclohexyl)amino)-5-(2,2,2-trifluoro-1-hydroxyethyl)-[2,3'-bipyridin]-6'-yl)amino)pyrimidin-2-yl)-N,N-dimethyl-1H-pyrazole-1-sulfonamide The title compound as a pale yellow solid (13 mg) was prepared in the same fashion as Step 3 in Example 1, except that (1s,4s)-4-((6'-chloro-5-(2,2,2-trifluoro-1-hydroxyethyl)-[2,3'-bipyridin]-4'-yl)amino)-1-methylcyclohexan-1-ol (47 mg. 0.11 mmol) prepared in Step 1 of Example 226 and 4-(4-aminopyrimidin-2-yl)-N,N-dimethyl-1H-pyrazole-1-sulfonamide (30 mg, 0.11 mmol) prepared in Reference Example 20 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-$d_6$, 400 MHz) δ 10.02 (s, 1H), 9.50 (d, 1H), 8.69 (d, 1H), 8.59 (s, 1H), 8.57 (s, 1H), 8.42 (d, 1H), 8.41 (s, 1H), 8.06 (d, 1H), 7.96 (dd, 1H), 7.51 (s, 1H), 7.34 (s, 1H), 7.07 (d, 1H), 5.37-5.30 (m, 1H), 4.20 (s, 1H), 3.45-3.42 (m, 1H), 2.91 (s, 6H), 1.87-1.83 (m, 2H), 1.78-1.58 (m, 4H), 1.46-1.44 (m, 2H), 1.14 (s, 3H); MS (ESI) m/z=648.2 (M+H)$^+$ Example 298. 4-(4-((4'-(((1s,4s)-4-Hydroxy-4-methylcyclohexyl)amino)-5-(1,1,1-trifluoro-2-hydroxypropan-2-yl)-[2,3'-bipyridin]-6'-yl)amino)pyrimidin-2-yl)-N,N-dimethyl-1H-pyrazole-1-sulfonamide The title compound as a pale yellow solid (10.8 mg) was prepared in the same fashion as Step 3 in Example 1, except that (1s,4s)-4-((6'-chloro-5-(1,1,1-trifluoro-2-hydroxypropan-2-yl)-[2,3'-bipyridin]-4'-yl)amino)-1-methylcyclohexan-1-ol (48 mg. 0.11 mmol) prepared in Step 1 of Example 230 and 4-(4-aminopyrimidin-2-yl)-N,N-dimethyl-1H-pyrazole-1-sulfonamide (30 mg, 0.11 mmol) prepared in Reference Example 20 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-$d_6$, 400 MHz) δ 10.02 (s, 1H), 9.55 (d, 1H), 8.79 (d, 1H), 8.58 (d, 1H), 8.42 (d, 1H), 8.41 (s, 1H), 8.04 (d, 1H), 7.52 (s, 1H), 7.33 (s, 1H), 6.87 (s, 1H), 4.20 (s, 1H), 3.44 (brs, 1H), 2.91 (s, 6H), 1.86-1.84 (m, 2H), 1.77 (s, 3H), 1.70-1.58 (m, 4H), 1.46-1.41 (m, 2H), 1.14 (s, 3H); MS (ESI) m/z=662.2 (M+H)$^+$ Example 299. (1s,4s)-4-((6'-((2-(1-(Cyclopropylsulfonyl)-1H-pyrazol-4-yl)-5-fluoropyrimidin-4-yl)amino)-5-(2,2,2-trifluoroethyl)-[2,3'-bipyridin]-4'-yl)amino)-1-methylcyclohexan-1-ol The title compound as a pale yellow solid (15.5 mg) was prepared in the same fashion as Step 3 in Example 1, except that (1s,4s)-4-((6'-chloro-5-(2,2,2-trifluoroethyl)-[2,3'-bipyridin]-4'-yl)amino)-1-methylcyclohexan-1-ol (47 mg, 0.12 mmol) prepared in Step 1 of Example 218 and 2-(1-(cyclopropylsulfonyl)-1H-pyrazol-4-yl)-5-fluoropyrimidin-4-amine (30 mg, 0.11 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-$d_6$, 400 MHz) δ 9.65 (s, 1H), 9.59 (d, 1H), 8.62 (s, 1H), 8.60 (d, 1H), 8.59 (s, 1H), 8.51 (d, 1H), 8.45 (s, 1H), 8.07 (d, 1H), 7.89 (d, 1H), 7.66 (s, 1H), 4.17 (s, 1H), 3.78 (q, 2H), 3.53 (brs, 1H), 3.25-3.19 (m, 1H), 1.84-1.82 (m, 2H), 1.70-1.62 (m, 2H), 1.55-1.52 (m, 2H), 1.40-1.33 (m, 4H), 1.29-1.23 (m, 2H), 1.13 (s, 3H); MS (ESI) m/z=647.2 (M+H)$^+$ Example 300. (1s,4s)-4-((6'-((2-(1-(Cyclopropylsulfonyl)-1H-pyrazol-4-yl)-5-fluoropyrimidin-4-yl)amino)-5-((1-methylpiperidin-4-yl)oxy)-[2,3'-bipyridin]-4'-yl)amino)-1-methylcyclohexan-1-ol The title compound as a pale yellow solid (21 mg) was prepared in the same fashion as same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (50 mg, 0.12 mmol) prepared in Reference Example 1 and 2-(1-(cyclopropylsulfonyl)-1H-pyrazol-4-yl)-5-fluoropyrimidin-4-amine (36 mg, 0.13 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.31 (d, 1H), 8.61 (s, 1H), 8.46 (s, 1H), 8.32 (s, 1H), 8.27 (dd, 2H), 7.84 (s, 1H), 7.68 (s, 1H), 7.65 (s, 1H), 7.34 (dd, 1H), 4.42 (s, 1H), 3.65 (s, 1H), 2.84-2.74 (m, 1H), 2.74 (brs, 2H), 2.35 (brs, 5H), 2.10-2.03 (m, 4H), 1.94-1.70 (m, 2H), 1.84-1.72 (m, 4H), 1.67-1.60 (m, 2H), 1.56-1.52 (m, 2H), 1.32 (s, 3H), 1.30-1.22 (m, 2H); MS (ESI) m/z=678.3 (M+H)$^+$ Example 301. 4-(4-((4'-(((1s,4s)-4-Hydroxy-4-methylcyclohexyl)amino)-5-((1-methylpiperidin-4-yl)oxy)-[2,3'-bipyridin]-6'-yl)amino)pyrimidin-2-yl)-N,N-dimethyl-1H-pyrazole-1-sulfonamide The title compound as a pale yellow solid (19.1 mg) was prepared in the same fashion as same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (50 mg, 0.12 mmol) prepared in Reference Example 1 and 4-(4-aminopyrimidin-2-yl)-N,N-dimethyl-1H-pyrazole-1-sulfonamide (34 mg, 0.13 mmol) prepared in Reference Example 20 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.18 (d, 1H), 8.64 (s, 1H), 8.41 (s, 1H), 8.40 (d, 1H), 8.32 (s, 1H), 8.27 (d, 1H), 7.64 (d, 2H), 7.33 (dd, 2H), 7.02 (s, 1H), 4.41 (brs, 1H), 3.50 (brs, 1H), 3.00 (s, 6H), 2.76-2.73 (m, 2H), 2.34 (brs, 5H), 2.09-2.00 (m, 4H), 1.94-1.89 (m, 2H), 1.81-1.74 (m, 4H), 1.65-1.58 (m, 2H), 1.31 (s, 3H); MS (ESI) m/z=663.3 (M+H)$^+$ Example 302. (1s,4s)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol The title compound as a pale yellow solid (2.7 mg) was prepared in the same fashion as same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (50 mg, 0.12 mmol) prepared in Reference Example 1 and 2-(1-(2,2-difluoroethyl)-1H-pyrazol-4-yl)pyrimidin-4-amine (29 mg, 0.13 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.09 (d, 1H), 8.39 (d, 1H), 8.33 (s, 1H), 8.27 (d, 1H), 8.26 (s, 1H), 8.17 (s, 1H), 7.64 (d, 1H), 7.50 (brs, 1H), 7.34 (d, 1H), 7.31 (dd, 1H), 6.95 (s, 1H), 6.15 (tt, 1H), 4.52 (td, 2H), 4.39 (brs, 1H), 3.50 (brs, 1H), 2.73 (brs, 2H), 2.34 (brs, 3H), 2.30 (brs, 2H), 2.09-1.93 (m, 4H), 1.92-1.86 (m, 2H), 1.77-1.56 (m, 6H), 1.31 (s, 3H); MS (ESI) m/z=620.3 (M+H)$^+$ Example 303. (1s,4s)-1-Methyl-4-((6'-((2-(3-methyl-1-(2,2,2-trifluoroethyl)-1H-pyrazol-4-yl)pyrimidin-4-yl)amino)-5-((1-methylpiperidin-4-yl)oxy)-[2,3'-bipyridin]-4'-yl)amino)cyclohexan-1-ol The title compound as a pale yellow solid (17 mg) was prepared in the same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (59 mg, 0.14 mmol) prepared in Reference Example 1 and 2-(3-methyl-1-(2,2,2-trifluoroethyl)-1H-pyrazol-4-yl)pyrimidin-4-amine (35 mg, 0.14 mmol) prepared in Reference Example 19 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.04 (s, 1H), 8.43 (d, 1H), 8.34 (s, 1H), 8.26 (d, 1H), 8.16 (s, 1H), 7.64 (d, 1H), 7.59 (d, 1H), 7.38 (brs, 1H), 7.33 (dd, 1H), 6.47 (s, 1H), 4.67 (q, 2H), 4.40 (brs, 1H), 3.40-3.38 (m, 1H), 2.73 (brs, 2H), 2.67 (s, 3H), 2.34 (s, 5H), 2.05 (brs, 2H), 1.97-1.89 (m, 4H), 1.77-1.70 (m, 4H), 1.57-1.50 (m, 2H), 1.30 (s, 3H); MS (ESI) m/z=652.2 (M+H)$^+$ Example 304. (1s,4s)-1-Methyl-4-((5-((1-methylpiperidin-4-yl)oxy)-6'-((2-(1-(2,2,2-trifluoroethyl)-1H-pyrazol-4-yl)pyrimidin-4-yl)amino)-[2,3'-bipyridin]-4'-yl)amino)cyclohexan-1-ol The title compound as a pale yellow solid (22.4 mg) was prepared in the same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (53 mg, 0.12 mmol) prepared in Reference Example 1 and 2-(1-(2,2,2-trifluoroethyl)-1H-pyrazol-4-yl)pyrimidin-4-amine (30 mg, 0.12 mmol) prepared in Reference Example 18 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.37 (s, 1H), 8.30 (d, 1H), 8.29 (s, 2H), 8.25 (s, 1H), 7.74 (d, 1H), 7.47 (dd, 1H), 7.32 (d, 1H), 7.19 (s, 1H), 5.04 (q, 2H), 4.53 (brs, 1H), 3.53 (brs, 1H), 2.75 (brs, 2H), 2.42 (brs, 2H), 2.33 (s, 3H), 2.05 (brs, 2H), 1.94-1.1.85 (m, 4H), 1.76-1.71 (m, 4H), 1.59-1.52 (m, 2H), 1.23 (s, 3H); MS (ESI) m/z=638.3 (M+H)$^+$ Example 305. 2-((1r,4r)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol The title compound as a pale yellow solid (12.2 mg) was prepared in the same fashion as same fashion as Step 3 in Example 1, except that 2-((1r,4r)-4-((6'-chloro-5-((1-methylpiperidin-4-yl)oxy)-[2,3'-bipyridin]-4'-yl)amino)cyclohexyl)ethan-1-ol (49 mg, 0.113 mmol) prepared Step 1 in Example 252 and 2-(1-(2,2-difluoroethyl)-1H-pyrazol-4-yl)pyrimidin-4-amine (25 mg. 0.12 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.32 (s, 1H), 8.31 (s, 1H), 8.29 (s, 1H), 8.28 (s, 1H), 8.23 (s, 1H), 7.74 (d, 1H), 7.49 (dd, 1H), 7.33 (d, 1H), 7.14 (s, 1H), 6.25 (tt, 1H), 4.66 (td, 2H), 4.55 (brs, 1H), 3.61 (t, 2H), 3.47 (brs, 1H), 2.72 (brs, 2H), 2.42 (brs, 2H), 2.33 (s, 3H), 2.22-2.19 (m, 2H), 2.07-2.02 (m, 3H), 1.90-1.84 (m, 4H), 1.51-1.48 (m, 2H), 1.36-1.28 (m, 3H), 1.21-1.14 (m, 1H); MS (ESI) m/z=634.3 (M+H)$^+$ Example 306. ((1S,3S)-3-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol The title compound as a pale yellow solid (12.6 mg) was prepared in the same fashion as Step 3 in Example 1, except that ((1S,3S)-3-((6'-chloro-5-((1-methylpiperidin-4-yl)oxy)-[2,3'-bipyridin]-4'-yl)amino)cyclohexyl)methanol (48 mg. 0.113 mmol) prepared Step 1 in Example 253 and 2-(1-(2,2-difluoroethyl)-1H-pyrazol-4-yl)pyrimidin-4-amine (25 mg. 0.12 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.45-8.29 (m, 4H), 8.20 (s, 1H), 7.81 (d, 1H), 7.51 (dd, 1H), 7.29 (s, 1H), 7.26 (d, 1H), 6.27 (tt, 1H), 4.66 (td, 2H), 4.57 (brs, 1H), 4.06 (s, 1H), 3.41 (d, 2H), 2.75 (brs, 2H), 2.43 (brs, 2H), 2.33 (s, 3H), 2.07-1.95 (m, 4H), 1.88-1.85 (m, 4H), 1.74-1.1.64 (m, 3H), 1.45-1.40 (m, 1H), 1.13-1.00 (m, 1H); MS (ESI) m/z=621.3 (M+H)$^+$ Example 307. N$^{4'}$-((1s,4s)-4-fluorocyclohexyl)-5-((1-methylpiperidin-4-yl)oxy)-N$^{6'}$-(2-(1-(2,2,2-trifluoroethyl)-1H-pyrazol-4-yl)pyrimidin-4-yl)-[2,3'-bipyridine]-4',6-diamine The title compound as a pale yellow solid (17.7 mg) was prepared in the same fashion as Step 3 in Example 1, except that 6'-chloro-N-((1s,4s)-4-fluorocyclohexyl)-5-((1-methylpiperidin-4-yl)oxy)-[2,3'-bipyridin]-4'-amine (30 mg. 0.07 mmol) prepared in Step 1 of Example 132 and 2-(1-(2,2,2-trifluoroethyl)-1H-pyrazol-4-yl)pyrimidin-4-amine (21 mg. 0.09 mmol) prepared in Reference Example 18 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.37 (s, 1H), 8.32 (d, 3H), 8.24 (s, 1H), 7.79 (d, 1H), 7.51 (dd, 1H), 7.35 (d, 1H), 7.20 (s, 1H), 5.05 (q. 2H), 4.74 (d, 1H), 4.57 (brs, 1H), 3.67 (brs, 1H), 2.77 (brs, 2H), 2.45 (brs, 2H), 2.35 (s, 3H), 2.08-1.90 (m, 6H), 1.86-1.73 (m, 6H); MS (ESI) m/z=626.3 (M+H)$^+$ Example 308. N$^{6'}$-(2-(1-(2,2-Difluoroethyl)-1H-pyrazol-4-yl)pyrimidin-4-yl)-N$^{4'}$-(4-fluorocyclohexyl)-5-((1-methylpiperidin-4-yl)oxy)-[2,3'-bipyridine]-4',6-diamine The title compound as a pale yellow solid (11.5 mg) was prepared in the same fashion as same fashion as Step 3 in Example 1, except that 6'-chloro-N-(4-fluorocyclohexyl)-5-((1-methylpiperidin-4-yl)oxy)-[2,3'-bipyridin]-4'-amine (30 mg, 0.07 mmol) prepared in Reference Example 2 and 2-(1-(2,2-difluoroethyl)-1H-pyrazol-4-yl)pyrimidin-4-amine (19 mg. 0.09 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.32-8.21 (m, 4H), 8.17 (s, 1H), 7.78 (d, 1H), 7.51 (dd, 1H), 7.34 (dd, 1H), 7.19 (d, 1H), 6.25 (tt, 1H), 4.70-4.56 (m, 3H), 3.71-3.68 (m, 1H), 2.76 (brs, 2H), 2.43 (brs, 2H), 2.34 (s, 3H), 2.18-2.17 (m, 1H), 2.05-1.93 (m, 5H), 1.88-1.69 (m, 4H), 1.58-1.52 (m, 2H); MS (ESI) m/z=608.3 (M+H)$^+$ Example 309. N$^{6'}$-(2-(1-(Cyclopropylsulfonyl)-1H-pyrazol-4-yl)-5-fluoropyrimidin-4-yl)-N$^{4'}$-(4-fluorocyclohexyl)-5-((1-methylpiperidin-4-yl)oxy)-[2,3'-bipyridine]-4',6-diamine The title compound as a pale yellow solid (24.6 mg) was prepared in the same fashion as Step 3 in Example 1, except that 6'-chloro-N-(4-fluorocyclohexyl)-5-((1-methylpiperidin-4-yl)oxy)-[2,3'-bipyridin]-4'-amine (35 mg, 0.08 mmol) prepared in Reference Example 2 and 2-(1-(cyclopropylsulfonyl)-1H-pyrazol-4-yl)-5-fluoropyrimidin-4-amine (28 mg. 0.10 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.61 (d, 1H), 8.39 (d, 1H), 8.35-8.24 (m, 3H), 7.77 (dd, 1H), 7.70 (d, 1H), 7.48 (d, 1H), 4.68 (d, 1H), 4.56 (brs, 1H), 3.71-3.68 (m, 1H), 3.05-2.98 (m, 1H), 2.78 (brs, 2H), 2.46 (brs, 2H), 2.36 (s, 3H), 2.19-2.16 (m, 1H), 2.07-2.02 (m, 3H), 1.95-1.71 (m, 7H), 1.60 (brs, 1H), 1.44-1.40 (m, 2H), 1.27-1.23 (m, 2H); MS (ESI) m/z=666.3 (M+H);

Example 310. (1s,4s)-4-((6-Fluoro-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol The title compound as a pale yellow solid (28.8 mg) was prepared in the same fashion as Step 3 in Example 1, except that (1s,4s)-4-((6'-chloro-6-fluoro-[2,3'-bipyridin]-4'-yl)amino)-1-methylcyclohexan-1-ol (39 mg. 0.12 mmol) prepared in Step 1 of Example 271 and 2-(3-methyl-1-(2,2,2-trifluoroethyl)-1H-pyrazol-4-yl)pyrimidin-4-amine (27 mg. 0.10 mmol) prepared in Reference Example 19 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 9.77 (s, 1H), 8.55 (s, 1H), 8.52 (d, 1H), 8.42 (d, 1H), 8.31 (s, 1H), 8.05 (q. 1H), 7.90 (d, 1H), 7.81 (d, 1H), 7.08 (d, 1H), 6.86 (s, 1H), 5.13 (q. 2H), 4.18 (s, 1H), 2.55 (s, 3H), 1.83-1.81 (m, 2H), 1.65-1.57 (m, 4H), 1.39-1.33 (m, 2H), 1.12 (s, 3H); MS (ESI) m/z=557.2 (M+H);

Example 311. (1s,4s)-4-((6'-((2-(1-(Cyclopropylsulfonyl)-1H-pyrazol-4-yl)-5-fluoropyrimidin-4-yl)amino)-6-fluoro-[2,3'-bipyridin]-4'-yl)amino)-1-methylcyclohexan-1-ol The title compound as a pale yellow solid (14.4 mg) was prepared in the same fashion as Step 3 in Example 1, except that (1s,4s)-4-((6'-chloro-6-fluoro-[2,3'-bipyridin]-4'-yl)amino)-1-methylcyclohexan-1-ol (39 mg. 0.12 mmol) prepared in Step 1 of Example 271 and 2-(1-(cyclopropylsulfonyl)-1H-pyrazol-4-yl)-5-fluoropyrimidin-4-amine (30 mg. 0.11 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 9.70 (s, 1H), 8.76 (d, 1H), 8.63 (s, 1H), 8.59 (s, 1H), 8.52 (d, 1H), 8.45 (s, 1H), 8.07 (q. 1H), 7.95 (d, 1H), 7.66 (s, 1H), 7.11 (dd, 1H), 4.16 (s, 1H), 3.51 (brs, 1H), 3.25-3.19 (m, 1H), 1.85-1.82 (m, 2H), 1.69-1.61 (m, 2H), 1.55-1.52 (m, 2H), 1.39-1.33 (m, 4H), 1.24-1.21 (m. 2H), 1.09 (s, 3H); MS (ESI) m/z=583.1 (M+H);

Example 312. (1s,4s)-4-((5-(3,3-Difluoroazetidin-1-yl)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol The title compound as a pale yellow solid (16 mg) was prepared in the same fashion as Step 3 in Example 1, except that (1s,4s)-4-((6'-chloro-5-(3,3-difluoroazetidin-1-yl)-[2,3'-bipyridin]-4'-yl)amino)-1-methylcyclohexan-1-ol (47 mg. 0.12 mmol) prepared in Step 1 of Example 224 and 2-(3-methyl-1-(2,2,2-trifluoroethyl)-1H-pyrazol-4-yl)pyrimidin-4-amine (27 mg. 0.10 mmol) prepared in Reference Example 19 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400) MHz) δ 9.64 (s, 1H), 9.09 (d, 1H), 8.38 (s, 1H), 8.37 (d, 1H), 8.30 (s, 1H), 7.99 (d, 1H), 7.84 (s, 1H), 7.82 (s, 1H), 7.14 (dd. 1H), 6.79 (s, 1H), 5.13 (q. 2H), 4.39 (t, 4H), 4.15 (s, 1H), 2.55 (s, 3H), 1.81-1.79 (m, 2H), 1.63-1.57 (m, 4H), 1.39-1.33 (m, 2H), 1.13 (s, 3H); MS (ESI) m/z=630.2 (M+H)$^+$ Example 313. (1s,4s)-4-((6'-((2-(1-(Cyclopropylsulfonyl)-1H-pyrazol-4-yl)-5-fluoropyrimidin-4-yl)amino)-5-(3,3-difluoroazetidin-1-yl)-[2,3'-bipyridin]-4'-yl)amino)-1-methylcyclohexan-1-ol The title compound as a pale yellow solid (11.9 mg) was prepared in the same fashion as same fashion as Step 3 in Example 1, except that (1s,4s)-4-((6'-chloro-5-(3,3-difluoroazetidin-1-yl)-[2,3'-bipyridin]-4'-yl)amino)-1-methylcyclohexan-1-ol (48 mg, 0.12 mmol) prepared in Step 1 of Example 224 and 2-(1-(cyclopropylsulfonyl)-1H-pyrazol-4-yl)-5-fluoropyrimidin-4-amine (30 mg, 0.11 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 9.54 (s, 1H), 9.37 (d, 1H), 8.61 (s, 1H), 8.49 (s, 1H), 8.43 (d, 2H), 8.01 (d, 1H), 7.88 (d, 1H), 7.60 (s, 1H), 7.15 (dd, 1H), 4.41 (t, 4H), 4.13 (s, 1H), 3.49 (brs, 1H), 3.25-3.21 (m, 1H), 1.83-1.81 (m, 2H), 1.67-1.51 (m, 4H), 1.40-1.33 (m, 4H), 1.24-1.22 (m, 2H), 1.09 (s, 3H); MS (ESI) m/z=656.2 (M+H)$^+$ Example 314. 2-(6'-((2-(1-(Cyclopropylsulfonyl)-1H-pyrazol-4-yl)-5-fluoropyrimidin-4-yl)amino)-4'-(((1s,4s)-4-fluorocyclohexyl)amino)-[2,3'-bipyridin]-5-yl)propan-2-ol The title compound as a pale yellow solid (15.5 mg) was prepared in the same fashion as Step 3 in Example 1, except that 2-(6'-chloro-4'-(((1s,4s)-4-fluorocyclohexyl)amino)-[2,3'-bipyridin]-5-yl)propan-2-ol (50 mg, 0.14 mmol) prepared in Step 1 of Example 173 and 2-(1-(cyclopropylsulfonyl)-1H-pyrazol-4-yl)-5-fluoropyrimidin-4-amine (35 mg, 0.12 mmol) prepared in Reference Example 16 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 8.74 (s, 1H), 8.69 (s, 1H), 8.68 (s, 1H), 8.60 (s, 1H), 8.49 (s, 1H), 8.01 (s, 2H), 7.46 (s, 1H), 5.33 (s, 1H), 4.76 (d, 1H), 3.71 (brs, 1H), 3.23-3.21 (m, 1H), 1.96-1.71 (m, 8H), 1.50 (s, 6H), 1.34-1.24 (m, 4H); MS (ESI) m/z=611.2 (M+H)$^+$ Example 315. (1s,4s)-4-((2-((2-(1-(2,2-Difluoroethyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol The title compound as a pale yellow solid (11 mg) was prepared in the same fashion as Step 3 in Example 1, except that (1s,4s)-4-((2-chloro-5-(6-((1-methylpiperidin-4-yl)oxy)pyridazin-3-yl)pyridin-4-yl)amino)-1-methylcyclohexan-1-ol (50 mg. 0.116 mmol) prepared in Step 2 of Example 269 and 2-(1-(2,2-difluoroethyl)-1H-pyrazol-4-yl)pyrimidin-4-amine (31 mg, 0.12 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.62 (s, 1H), 8.44 (s, 1H), 8.42 (d, 1H), 8.29 (s, 1H), 8.23 (d, 1H), 7.33 (d, 1H), 7.14 (brs, 1H), 7.01 (brs, 1H), 6.28 (tt, 1H), 5.62-5.58 (m, 1H), 4.69 (td, 2H), 3.60-3.43 (m, 4H), 2.94 (s, 3H), 2.30 (brs, 4H), 2.02-1.96 (m, 2H), 1.81-1.75 (m, 4H), 1.62-1.57 (m, 2H), 1.26 (s, 3H); MS (ESI) m/z=621.3 (M+H)$^+$ Example 316. (1s,4s)-4-((5-(2-(Azetidin-1-yl)ethoxy)-6'-((2-(1-(2,2-difluoroethyl)-1H-pyrazol-4-yl)pyrimidin-4-yl)amino)-[2,3'-bipyridin]-4'-yl)amino)-1-methylcyclohexan-1-ol The title compound as a pale yellow solid (15.6 mg) was prepared in the same fashion as Step 3 in Example 1, except that (1s,4s)-4-((5-(2-(azetidin-1-yl) ethoxy)-6'-chloro-[2,3'-bipyridin]-4'-yl)amino)-1-methylcyclohexan-1-ol (50 mg. 0.12 mmol) prepared in Step 1 of Example 290 and 2-(1-(2,2-difluoroethyl)-1H-pyrazol-4-yl)pyrimidin-4-amine (32 mg, 0.144 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.06 (d, 1H), 8.38 (d, 1H), 8.33 (s, 1H), 8.26 (s, 1H), 8.17 (s, 1H), 7.63 (d, 1H), 7.46 (brs, 1H), 7.33-7.29 (m, 2H), 6.92 (s, 1H), 6.14 (tt, 1H), 4.52 (td, 2H), 4.05 (t, 2H), 3.49 (brs, 1H), 3.35 (t, 4H), 2.87 (t, 2H), 2.15 (quin, 2H), 2.00-1.97 (m, 2H), 1.77-1.70 (m, 4H), 1.62-1.55 (m, 2H), 1.31 (s, 3H); MS (ESI) m/z=606.3 (M+H);

Example 317. (1s,4s)-4-((5-(2-(Azetidin-1-yl)ethoxy)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol The title compound as a pale yellow solid (16.6 mg) was prepared in the same fashion as Step 3 in Example 1, except that (1s,4s)-4-((5-(2-(azetidin-1-yl) ethoxy)-6'-chloro-[2,3'-bipyridin]-4'-yl)amino)-1-methylcyclohexan-1-ol (50 mg. 0.12 mmol) prepared in Step 1 of Example 290 and 2-(3-methyl-1-(2,2,2-trifluoroethyl)-1H-pyrazol-4-yl)pyrimidin-4-amine (35 mg, 0.136 mmol) prepared in Reference Example 19 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.00 (d, 1H), 8.43 (d, 1H), 8.34 (s, 1H), 8.26 (d, 1H), 8.15 (s, 1H), 7.63 (d, 1H), 7.60 (d, 1H), 7.34 (s, 1H), 7.33 (dd, 1H), 6.46 (s, 1H), 4.67 (q, 2H), 4.05 (t, 2H), 3.34 (t, 5H), 2.86 (t, 2H), 2.66 (s, 3H), 2.15 (quin, 2H), 1.98-1.93 (m, 2H), 1.77-1.69 (m, 4H), 1.56-1.49 (m, 2H), 1.29 (s, 3H); MS (ESI) m/z=639.3 (M+H)$^+$ Example 318. (1s,4s)-4-((5-(2-(Azetidin-1-yl)ethoxy)-6'-((2-(1-(2,2-difluoroethyl)-3,5-dimethyl-1H-pyrazol-4-yl)pyrimidin-4-yl)amino)-[2,3'-bipyridin]-4'-yl)amino)-1-methylcyclohexan-1-ol The title compound as a pale yellow solid (15.9 mg) was prepared in the same fashion as Step 3 in Example 1, except that (1s,4s)-4-((5-(2-(azetidin-1-yl) ethoxy)-6'-chloro-[2,3'-bipyridin]-4'-yl)amino)-1-methylcyclohexan-1-ol (30 mg, 0.072 mmol) prepared in Step 1 of Example 290 and 2-(1-(2,2-difluoroethyl)-3,5-dimethyl-1H-pyrazol-4-yl)pyrimidin-4-amine (22 mg, 0.086 mmol) prepared in Reference Example 21 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.00 (d, 1H), 8.47 (d, 1H), 8.33 (s, 1H), 8.25 (d, 1H), 7.63 (d, 1H), 7.45 (d, 2H), 7.33 (dd, 1H), 6.64 (s, 1H), 6.14 (tt, 1H), 4.40 (td, 2H), 4.05 (t, 2H), 3.35 (t, 5H), 2.87 (t, 2H), 2.63 (s, 3H), 2.55 (s, 3H), 2.15 (quin, 2H), 1.95-1.93 (m, 2H), 1.72-1.66 (m, 4H), 1.52-1.46 (m, 2H), 1.28 (s, 3H); MS (ESI) m/z=634.3 (M+H)$^+$ Example 319. (1s,4s)-4-((5-(2-(Azetidin-1-yl)ethoxy)-6'-((2-(1-(2,2,3,3-tetrafluoropropyl)-1H-pyrazol-4-yl)pyrimidin-4-yl)amino)-[2,3'-bipyridin]-4'-yl)amino)-1-methylcyclohexan-1-ol The title compound as a pale yellow solid (12.5 mg) was prepared in the same fashion as Step 3 in Example 1, except that (1s,4s)-4-((5-(2-(azetidin-1-yl) ethoxy)-6'-chloro-[2,3'-bipyridin]-4'-yl)amino)-1-methylcyclohexan-1-ol (30 mg, 0.072 mmol) prepared in Step 1 of Example 290 and 2-(1-(2,2,3,3-tetrafluoropropyl)-1H-pyrazol-4-yl)pyrimidin-4-amine (24 mg. 0.086 mmol) prepared in Reference Example 22 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (CDCl$_3$, 400 MHz) δ 9.05 (d, 1H), 8.41 (d, 1H), 8.39 (d, 1H), 8.34 (d, 1H), 8.26 (t, 1H), 8.20 (s, 1H), 7.64 (d, 1H), 7.43 (brs 1H), 7.32 (d, 2H), 6.91 (s, 1H), 6.90 (tt, 1H), 4.72 (td, 1H), 4.05 (t, 2H), 3.48 (brs, 1H), 3.35 (t, 4H), 2.87 (t, 2H), 2.15 (quin, 2H), 2.05-1.98 (m, 2H), 1.77-1.71 (m, 4H), 1.63-1.57 (m, 2H), 1.31 (s, 3H); MS (ESI) m/z=656.3 (M+H)$^+$ Example 320. 3,3-Difluoro-1-(5-fluoro-4-((4'-(((1s,4s)-4-hydroxy-4-methylcyclohexyl)amino)-5-((1-methylpiperidin-4-yl)oxy)-[2,3'-bipyridin]-6'-yl)amino)pyrimidin-2-yl) piperidin-4-ol The title compound as a pale yellow solid (23 mg) was prepared in the same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (50 mg, 0.116 mmol) prepared in Reference Example 1 and 1-(4-amino-5-fluoropyrimidin-2-yl)-3,3-difluoropiperidin-4-ol (35 mg, 0.139 mmol) prepared in Reference Example 23 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 9.27 (d, 1H), 9.01 (s, 1H), 8.42 (s, 2H), 8.10 (d, 1H), 7.93 (d, 1H), 7.59 (d, 1H), 7.29 (s, 1H), 5.78 (d, 1H), 4.77 (s, 1H), 4.22 (s, 1H), 4.16 (dd, 1H), 3.95-3.87 (m, 3H), 3.68-3.66 (m, 2H), 3.25-3.09 (m, 3H), 2.70 (s, 3H), 2.16 (brs, 2H), 1.98-1.93 (m, 2H), 1.83-1.76 (m, 3H), 1.66-1.57 (m, 5H), 1.43-1.38 (m, 2H), 1.14 (s, 3H); MS (ESI) m/z=643.3 (M+H)$^+$ Example 321. (1s,4s)-4-((6'-((5-Fluoro-2-((3R,4S)-3-fluoro-4-methoxy piperidin-1-yl)pyrimidin-4-yl)amino)-5-((1-methylpiperidin-4-yl)oxy)-[2,3'-bipyridin]-4'-yl)amino)-1-methylcyclohexan-1-ol The title compound as a pale yellow solid (32 mg) was prepared in the same fashion as same fashion as Step 3 in Example 1, except that (1s,4s)-4-((6'-chloro-5-((1-methylpiperidin-4-yl)oxy)-[2,3'-bipyridin]-4'-yl)amino)-1-methylcyclohexan-1-ol (50 mg, 0.116 mmol) prepared in Reference Example 1 and 5-fluoro-2-((3R,4S)-3-fluoro-4-methoxypiperidin-1-yl)pyrimidin-4-amine (34 mg. 0.139 mmol) prepared in Reference Example 24 were used instead of (1-(6'-chloro-5-((4-methylpiperazin-1-yl)methyl)-[2,3'-bipyridin]-4'-yl)-4-methylpiperidin-4-yl) methano and 2-(1-(cyclopropylsulfonyl)-1H-pyrazol-4-yl)pyrimidin-4-amine. $^1$H-NMR (DMSO-d$_6$, 400 MHz) δ 9.23 (d, 1H), 8.92 (brs, 1H), 8.40 (s, 1H), 8.39 (d, 1H), 8.07 (d, 1H), 7.91 (d, 1H), 7.56 (dd, 1H), 7.31 (s, 1H), 4.89 (d, 1H), 4.67 (brs, 1H), 4.55-4.50 (m, 1H), 4.26 (d, 1H), 4.22 (s, 1H), 3.61-3.57 (m, 2H), 3.32-3.22 (m, 2H), 3.02 (brs, 2H), 2.76 (brs, 1H), 2.08 (brs, 2H), 1.86-1.76 (m, 6H), 1.67-1.58 (m, 4H), 1.43-1.36 (m, 2H), 1.27-1.22 (m, 1H), 1.15 (s, 3H); MS (ESI) m/z=639.3 (M+H)$^+$ Example 322. (1s,4s)-4-((6'-((2-(1-(Cyclopropylsulfonyl)-1H-pyrazol-4-yl)pyrimidin-4-yl)amino)-5-((1-(2-fluoroethyl) piperidin-4-yl)oxy)-[2,3'-bipyridin]-4'-yl)amino)-1-methylcyclohexan-1-ol Step 1. tert-Butyl 4-(tosyloxy)piperidine-1-carboxylate To a solution of 1-(tert-butoxy carbonyl)-4-hydroxypiperidine (500 mg, 2.484 mmol) in DCM (10 mL) were added triethylamine (0.87 mL, 6.211 mmol) and p-toluenesulfonyl chloride (710 mg, 3.727 mmol). The reaction mixture was stirred at room temperature for 3 hours. It was poured over ice-water, stirred and extracted with DCM. The organic layers were washed with sat. NaHCO$_3$ soln. followed by brine, dried over MgSO$_4$, filtered, and concentrated. The crude residue was purified by silica gel column chromatography (EA/n-Hex=0-30%) to give tert-butyl 4-(p-tolylsulfonyloxy)piperidine-1-carboxylate (777 mg) as a white solid. $^1$H-NMR (CDCl$_3$, 400 MHz) δ 7.79 (d, 1H), 7.34 (d, 1H), 4.69-4.66 (m, 1H), 3.62-3.3.56 (m, 2H), 3.28-3.22 (m, 2H), 2.45 (s, 3H), 1.79-1.64 (m, 4H), 1.43 (s, 9H)

Step 2. tert-Butyl 4-((6-bromopyridin-3-yl)oxy)piperidine-1-carboxylate

To a solution of tert-butyl 4-(tosyloxy)piperidine-1-carboxylate (770 mg. 2.166 mmol) prepared in Step 1 in DMF (15.4 mL) were added 2-bromo-5-hydroxypyridine (377 mg, 2.166 mmol) and K$_2$CO$_3$ (599 mg, 4.333 mmol). The reaction mixture was stirred at 90° C. for 3 hours. The reaction mixture was cooled to room temperature, quenched with water, and then extracted with DCM. The organic layer was dried over MgSO$_4$, filtered, and concentrated. The crude residue was purified by silica gel column chromatography (EA/n-Hex=0-30%) to give tert-butyl 4-[(6-bromo-3-pyridyl)oxy]piperidine-1-carboxylate (523 mg) as a white solid. MS (ESI) m/z=358.1 (M+H)$^+$ Step 3. 6'-Chloro-4'-fluoro-5-(piperidin-4-yloxy)-2,3'-bipyridine To a solution of 2-chloro-4-fluoropyridine-5-boronic acid pinacol ester (412 mg, 1.6 mmol) in 1,4-dioxane (4.52 mL) were added tert-butyl 4-((6-bromopyridin-3-yl)oxy)piperidine-1-carboxylate (520 mg, 1.46 mmol) prepared in Step 2, [1,1'-bis(diphenylphosphino)ferrocene]dichloropalladium (II), complex with dichloromethane (119 mg, 0.150 mmol) and 3M K$_2$CO$_3$ soln. (1.46 mL, 4.37 mmol). The reaction mixture was stirred at 80° C. for 1 hour. The reaction mixture was cooled to room temperature, quenched with water, and then extracted with DCM. The organic layer was dried over MgSO$_4$, filtered, and concentrated. The crude residue diluted in DCM, filtered through Celite, and then concentrated. The crude product and TFA (0.5 mL) in DCM (5 mL) was stirred at room temperature for 3 hours, and then concentrated. The residue was diluted in DCM, added 1 N NaOH soln. (>pH 8), washed by water, dried over MgSO$_4$, and then concentrated. The crude residue was slurried with EA for 1 hour and then filtered to give 6'-chloro-4'-fluoro-5-(piperidin-4-yloxy)-2,3'-bipyridine (202 mg) as a white solid. MS (ESI) m/z=308.2 (M+H)$^+$ Step 4. 6'-Chloro-4'-fluoro-5-((1-(2-fluoroethyl) piperidin-4-yl)oxy)-2,3'-bipyridine To a solution of 6'-chloro-4'-fluoro-5-(piperidin-4-yloxy)-2,3'-bipyridine (200 mg, 0.6500 mmol) prepared in Step 3 in DMF (4 mL) were added 1-fluoro-2-iodoethane (170 mg, 0.970 mmol) and K$_2$CO$_3$ (225 mg, 1.625 mmol). The reaction mixture was stirred at 90° C. for 3 hours. The reaction mixture was cooled to room temperature, and quenched with water, then extracted with DCM. The organic layer was dried over MgSO$_4$, filtered, and concentrated. The crude residue was purified by silica gel column chromatography (EA/n-Hex=0-30%) to give 6'-chloro-4'-fluoro-5-((1-(2-fluoroethyl) piperidin-4-yl)oxy)-2,3'-bipyridine (155 mg) as a white solid. MS (ESI) m/z=354.2 (M+H)$^+$ Step 5. (1s,4s)-4-((6'-Chloro-5-((1-(2-fluoroethyl) piperidin-4-yl)oxy)-[2,3'-bipyridin]-4'-yl)amino)-1-methylcyclohexan-1-ol The title compound as a pale yellow solid (57 mg) was prepared in the same fashion as Step 2 in Reference Example 1, except that 6'-chloro-4'-fluoro-5-((1-(2-fluoroethyl) piperidin-4-yl)oxy)-2,3'-bipyridine (50 mg, 0.141 mmol) prepared in Step 4 was used instead of 6'-chloro-4'-fluoro-5-((1-methylpiperidin-4-yl)oxy)-2,3'-bipyridine. MS (ESI) m/z=463.2 (M+H)$^+$ Step 6. (1s,4s)-4-((6'-((2-(1-(Cyclopropylsulfonyl)-1H-pyrazol-4-yl)pyrimidin-4-yl)amino)-5-((1-(2-fluoroethyl) piperidin-4-yl)oxy)-[2,3'-bipyridin]-4'-yl)amino)-1-methylcyclohexan-1-ol The title compound as a pale yellow solid (17.7 mg) was prepared in the same fashion as Step 3 in Example 1, except that (1s,4s)-4-((6'-chloro-5-((1-(2-fluoroethyl) piperidin-4-yl)oxy)-[2,3'-bipyridin]-4'-yl)amino)-1-methylcyclohexan-1-ol (55 mg, 0.119 mmol) prepared in Step 5 was used instead of (1-(6'-chloro-5-((4-methylpiperazin-1-yl)methyl)-[2,3'-bipyridin]-4'-yl)-4-methylpiperidin-4-yl) methanol. $^1$H-NMR (DMSO-d$_6$, 400 MHz) δ 9.97 (s, 1H), 9.14 (s, 1H), 8.65 (s, 1H), 8.46-8.36 (m, 4H), 7.90 (d, 1H), 7.55 (d, 2H), 7.24 (brs, 1H), 4.77-4.57 (m, 3H), 4.15 (s, 1H), 3.41 (brs, 1H), 3.28-3.21 (m, 1H), 2.72 (brs, 2H), 2.02-1.93 (m, 4H), 1.84-1.82 (m, 2H), 1.73-1.56 (m, 6H), 1.45-1.33 (m, 4H), 1.24-1.21 (m, 4H), 1.14 (s, 3H); MS (ESI) m/z=692.3 (M+H)$^+$ Example 323. $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine Step 1. 6'-Chloro-N-((1s,4s)-4-fluorocyclohexyl)-5-((1-(2-fluoroethyl) piperidin-4-yl)oxy)-[2,3'-bipyridin]-4'-amine The title compound as a pale yellow solid (42 mg) was prepared in the same fashion as Step 2 in Reference Example 1, except that 6'-chloro-4'-fluoro-5-((1-(2-fluoroethyl) piperidin-4-yl)oxy)-2,3'-bipyridine (50 mg. 0.141 mmol) prepared in Step 4 of Example 322 and (1s,4s)-4-fluorocyclohexan-1-amine hydrochloride (33 mg, 0.212 mmol) were used instead of (1-(6'-chloro-5-((4-methylpiperazin-1-yl)methyl)-[2,3'-bipyridin]-4'-yl)-4-methylpiperidin-4-yl)methanol and cis-4-amino-1-methylcyclohexanol. MS (ESI) m/z=451.2 (M+H)$^+$ Step 2. $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine The title compound as a pale yellow solid (4.3 mg) was prepared in the same fashion as Step 3 in Example 1, except that 6'-chloro-N-((1s,4s)-4-fluorocyclohexyl)-5-((1-(2-fluoroethyl) piperidin-4-yl)oxy)-[2,3'-bipyridin]-4'-amine (20 mg. 0.044 mmol) prepared in Step 1 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.99 (s, 1H), 9.32 (d, 1H), 8.64 (s, 1H), 8.45 (s, 2H), 8.43 (d, 1H), 8.35 (s, 1H), 7.92 (d, 1H), 7.60 (s, 1H), 7.56 (d, 1H), 7.23 (brs, 1H), 4.78 (d, 1H), 4.66-4.57 (m, 4H), 3.59 (brs, 1H), 3.28-3.23 (m, 1H), 2.85 (brs, 4H), 2.03-1.65 (m, 13H), 1.34-1.25 (m, 5H); MS (ESI) m/z=680.2 (M+H);

Example 324. $N^{6'}$-(2-(1-(2,2-Difluoroethyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine The title compound as a pale yellow solid (5.2 mg) was prepared in the same fashion as Step 3 in Example 1, except that 6'-chloro-N-((1s,4s)-4-fluorocyclohexyl)-5-((1-(2-fluoroethyl) piperidin-4-yl)oxy)-[2,3'-bipyridin]-4'-amine (20 mg. 0.044 mmol) prepared in Step 1 of Example 323 and 2-(1-(2,2-difluoroethyl)-1H-pyrazol-4-yl)pyrimidin-4-amine (10.99 mg, 0.049 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (DMSO-d$_6$, 400 MHz) δ 11.21 (s, 1H), 9.69 (d, 1H), 9.44 (s, 1H), 8.67-8.36 (m, 3H), 7.78 (s, 1H), 7.71 (d, 2H), 6.78 (d, 1H), 6.63 (s, 1H), 6.33 (tt, 1H), 5.02 (td, 2H), 4.91-4.61 (m, 4H), 3.58-3.49 (m, 3H), 2.73 (brs, 4H), 2.12-1.64 (m, 12H); MS (ESI) m/z=640.3 (M+H)$^+$ Example 325. (1s,4s)-4-((2-((2-(1-(Cyclopropylsulfonyl)-1H-pyrazol-4-yl)pyrimidin-4-yl)amino)-5-(6-((1-(2-fluoroethyl) piperidin-4-yl)oxy)pyridazin-3-yl)pyridin-4-yl)amino)-1-methylcyclohexan-1-ol Step 1. tert-Butyl 4-((6-bromopyridazin-3-yl)oxy)piperidine-1-carboxylate To a solution of 1-(tert-butoxy carbonyl)-4-hydroxypiperidine (423 mg. 2. 1 mmol) in DMF (5 mL) was added sodium hydride (101 mg, 2.52 mmol) and the reaction mixture was stirred at room temperature for 30 minutes. To the reaction mixture was added 3,6-dibromo-pyridazine (500 mg, 2.1 mmol), and then stirred at room temperature for 3 hours. The reaction mixture was quenched with water added slowly to the mixture until no precipitation observed. The resulting solids were collected by filtration, washed with water followed by n-hexane, then dried under vacuum to give tert-butyl 4-(6-bromopyridazin-3-yl)oxypiperidine-1-carboxylate (344 mg) as a white solid. $^1$H-NMR (CDCl$_3$, 400 MHz) δ 7.50 (d, 1H), 6.84 (d, 1H), 5.45-5.41 (m, 1H), 3.82-3.79 (m, 2H), 3.29-3.23 (m, 2H), 2.09-2.05 (m, 3H), 1.77-1.75 (m, 4H), 1.48 (s, 9H)

Step 2. tert-Butyl 4-((6-(6-chloro-4-fluoropyridin-3-yl)pyridazin-3-yl)oxy)piperidine-1-carboxylate To a solution of tert-butyl 4-((6-bromopyridazin-3-yl)oxy)piperidine-1-carboxylate (340 mg, 0.949 mmol) prepared in Step 1 in 1,4-dioxane (5 mL) were added 2-chloro-4-fluoropyridine-5-boronic acid pinacol ester (244 mg. 0.949 mmol), [1,1'-bis(diphenylphosphino)ferrocene]dichloropalladium (II), complex with dichloromethane (78 mg. 0.090 mmol) and 3M K$_2$CO$_3$ soln. (0.95 mL, 2.85 mmol). The reaction mixture was stirred at 80° C. for 1 hour. The reaction mixture was cooled to room temperature, quenched with water, and then extracted with DCM. The organic layer was dried over MgSO$_4$, filtered, and concentrated. The crude residue was purified by silica gel column chromatography (MeOH/DCM=0-20%) to give tert-butyl 4-[6-(6-chloro-4-fluoro-3-pyridyl)pyridazin-3-yl]oxypiperidine-1-carboxylate (194 mg) as a white solid. $^1$H-NMR (CDCl$_3$, 400 MHz) δ 9.14 (d, 1H), 7.83 (d, 1H), 7.25 (d, 1H), 7.08 (d, 1H), 5.60-5.56 (m, 1H), 3.85 (brs, 2H), 3.32-3.26 (m, 2H), 2.15-2.13 (m, 2H), 1.84-1.81 (m, 2H), 1.49 (s, 9H)

Step 3. tert-Butyl 4-((6-(6-chloro-4-(((1s,4s)-4-hydroxy-4-methylcyclohexyl)amino)pyridin-3-yl)pyridazin-3-yl)oxy)piperidine-1-carboxylate The title compound as a pale yellow solid (99 mg) was prepared in the same fashion as Step 2 in Reference Example 1, except that tert-butyl 4-((6-(6-chloro-4-fluoropyridin-3-yl)pyridazin-3-yl)oxy)piperidine-1-carboxylate (97 mg, 0.237 mmol) prepared in Step 2 was used instead of 6'-chloro-4'-fluoro-5-((1-methylpiperidin-4-yl)oxy)-2,3'-bipyridine. MS (ESI) m/z=518.2 (M+H)$^+$ Step 4. (1s,4s)-4-((2-Chloro-5-(6-(piperidin-4-yloxy)pyridazin-3-yl)pyridin-4-yl)amino)-1-methylcyclohexan-1-ol To a solution of tert-butyl 4-((6-(6-chloro-4-(((1s,4s)-4-hydroxy-4-methylcyclohexyl)amino)pyridin-3-yl) pyridazin-3-yl)oxy)piperidine-1-carboxylate (80 mg, 0.1500 mmol) prepared in Step 3 in DCM (2 mL), added trifluoroacetic acid (118.17 uL, 1.54 mmol), and the reaction mixture was stirred at room temperature for 3 hours. The rxn mixture was concentrated under reduced pressure and to the residue was added DCM. To the residue was added 1N NaOH soln. (>pH8), washed by water, dried over MgSO$_4$, and concentrated under reduced pressure. The crude residue was slurried with EA for 1 hour and then filtered to give (1s,4s)-4-((2-chloro-5-(6-(piperidin-4-yloxy)pyridazin-3-yl)pyridin-4-yl)amino)-1-methylcyclohexan-1-ol (59 mg) as a white solid. MS (ESI) m/z=418.2 (M+H)$^+$ Step 5. (1s,4s)-4-((2-Chloro-5-(6-((1-(2-fluoroethyl) piperidin-4-yl)oxy)pyridazin-3-yl)pyridin-4-yl) amino)-1-methylcyclohexan-1-ol To a solution of (1s,4s)-4-((2-chloro-5-(6-(piperidin-4-yloxy)pyridazin-3-yl)pyridin-4-yl)amino)-1-methylcyclohexan-1-ol (57 mg, 0.136 mmol) prepared in Step 4 in DMF (1 mL) were added 1-fluoro-2-iodoethane (35.59 mg, 0.205 mmol) and $K_2CO_3$ (47.12 mg, 0.341 mmol). The reaction mixture was stirred at 90° C. for 3 hours. The reaction mixture was cooled to room temperature, and quenched with water, then extracted with DCM. The organic layer was dried over $MgSO_4$, filtered, and concentrated. The crude residue was purified by silica gel column chromatography (MeOH/DCM=0-10%) to give (1s,4s)-4-((2-chloro-5-(6-((1-(2-fluoroethyl) piperidin-4-yl)oxy)pyridazin-3-yl)pyridin-4-yl)amino)-1-methylcyclohexan-1-ol (36 mg) as a white solid. MS (ESI) m/z=464.2 (M+H);

Step 6. (1s,4s)-4-((2-((2-(1-(Cyclopropylsulfonyl)-1H-pyrazol-4-yl)pyrimidin-4-yl)amino)-5-(6-((1-(2-fluoroethyl) piperidin-4-yl)oxy)pyridazin-3-yl)pyridin-4-yl)amino)-1-methylcyclohexan-1-ol The title compound as a pale yellow solid (5.1 mg) was prepared in the same fashion as Step 3 in Example 1, except that (1s,4s)-4-((2-chloro-5-(6-((1-(2-fluoroethyl) piperidin-4-yl)oxy)pyridazin-3-yl)pyridin-4-yl)amino)-1-methylcyclohexan-1-ol (30 mg, 0.065 mmol) prepared in Step 5 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.06 (s, 1H), 9.24 (d, 1H), 8.66 (s, 1H), 8.53 (s, 1H), 8.47 (s, 1H), 8.44 (d, 1H), 8.29 (d, 1H), 7.55 (brs, 1H), 7.36 (brs, 1H), 7.30 (d, 1H), 5.37 (brs, 1H), 4.72-4.61 (m, 2H), 4.18 (t, 2H), 3.46 (brs, 1H), 3.26-3.22 (m, 1H), 2.16 (brs, 2H), 1.93-1.84 (m, 4H), 1.67-1.55 (m, 6H), 1.46-1.40 (m, 2H), 1.34-1.24 (m, 6H), 1.14 (s, 3H); MS (ESI) m/z=693.3 (M+H);

Example 326. (1s,4s)-4-((2-((2-(1-(Cyclopropylsulfonyl)-1H-pyrazol-4-yl)pyrimidin-4-yl)amino)-5-(3-methoxypyrazin-2-yl)pyridin-4-yl)amino)-1-methylcyclohexan-1-ol Step 1. 2-(6-Chloro-4-fluoropyridin-3-yl)-3-methoxypyrazine The title compound as a white solid (242.8 mg) was prepared in the same fashion as Step 1 in Example 1, except that 2-bromo-3-methoxypyrazine (257 mg, 1.359 mmol) was used instead of 1-((6-bromopyridin-3-yl)methyl)-4-methylpiperazine. $^1$H-NMR (CDCl$_3$, 400 MHz) δ 8.51 (d, 1H), 8.24 (s, 1H), 8.16 (s, 1H), 7.16 (d, 1H), 3.96 (s, 3H); MS (ESI) m/z=239.8 (M+H)$^+$ Step 2. (1s,4s)-4-((2-Chloro-5-(3-methoxypyrazin-2-yl)pyridin-4-yl)amino)-1-methylcyclohexan-1-ol The title compound as a white solid (285.4 mg) was prepared in the same fashion as Step 2 in Example 1, except that 2-(6-chloro-4-fluoropyridin-3-yl)-3-methoxypyrazine (243 mg, 1.013 mmol) prepared in Step 1 and cis-4-amino-1-methylcyclohexanol (196 mg, 1.52 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.71 (s, 1H), 8.15 (s, 1H), 8.07 (s, 1H), 8.05-8.03 (m, 1H), 4.02 (s, 3H), 3.34-3.33 (m, 1H), 1.93-1.90 (m, 1H), 1.76-1.58 (m, 7H), 1.30 (s, 3H); MS (ESI) m/z=349.9 (M+H)$^+$ Step 3. (1s,4s)-4-((2-((2-(1-(Cyclopropylsulfonyl)-1H-pyrazol-4-yl)pyrimidin-4-yl)amino)-5-(3-methoxypyrazin-2-yl)pyridin-4-yl)amino)-1-methylcyclohexan-1-ol The title compound as a white solid (127.3 mg) was prepared in the same fashion as Step 3 in Example 1, except that (1s,4s)-4-((2-chloro-5-(3-methoxypyrazin-2-yl)pyridin-4-yl)amino)-1-methylcyclohexan-1-ol (285 mg, 0.818 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-$d_6$, 400 MHz) δ 10.00 (s, 1H), 8.65 (s, 1H), 8.46 (s, 1H), 8.43 (d, 1H), 8.38 (s, 1H), 8.28 (s, 1H), 8.16 (s, 1H), 7.61 (brs, 1H), 7.39 (d, 1H), 7.24 (brs, 1H), 4.11 (s, 1H), 3.95 (s, 3H), 3.30 (m, 1H), 3.24 (m, 1H), 1.75 (d, 2H), 1.57-1.54 (m, 4H), 1.39-1.34 (m, 4H), 1.25-1.24 (m, 2H), 1.12 (s, 3H); MS (ESI) m/z=578.2 (M+H)$^+$ Example 327. (1s,4s)-4-((2-((2-(1-(Cyclopropylsulfonyl)-1H-pyrazol-4-yl)pyrimidin-4-yl)amino)-5-(3-fluoropyrazin-2-yl)pyridin-4-yl)amino)-1-methylcyclohexan-1-ol Step 1. 2-(6-Chloro-4-fluoropyridin-3-yl)-3-fluoropyrazine The title compound as a white solid (146.4 mg) was prepared in the same fashion as Step 1 in Example 1, except that 2-bromo-3-fluoropyrazine (172 mg, 0.971 mmol) was used instead of 1-((6-bromopyridin-3-yl)methyl)-4-methylpiperazine. $^1$H-NMR (CDCl$_3$, 400 MHz) δ 8.67-8.63 (m, 2H), 8.30 (s, 1H), 7.24 (d, 1H)

Step 2. (1s,4s)-4-((2-Chloro-5-(3-fluoropyrazin-2-yl)pyridin-4-yl)amino)-1-methylcyclohexan-1-ol The title compound as an off-white solid (87.6 mg) was prepared in the same fashion as Step 2 in Example 1, except that 2-(6-chloro-4-fluoropyridin-3-yl)-3-fluoropyrazine (93 mg, 0.409 mmol) prepared in Step 1 and cis-4-amino-1-methylcyclohexanol (79 mg, 0.613 mmol) were used instead of 6'-chloro-4'-fluoro-5-((4-methylpiperazin-1-yl)methyl)-2,3'-bipyridine and (4-methylpiperidin-4-yl)methanol. $^1$H-NMR (CDCl$_3$, 400 MHz) δ 8.53 (s, 1H), 8.46 (s, 1H), 8.31 (d, 1H), 8.11 (s, 1H), 6.60 (s, 1H), 3.32 (m, 1H), 1.89-1.86 (m, 2H), 1.75-1.70 (m, 4H), 1.67-1.52 (m, 2H), 1.27 (s, 3H); MS (ESI) m/z=337.0 (M+H)$^+$ Step 3. (1s,4s)-4-((2-((2-(1-(Cyclopropylsulfonyl)-1H-pyrazol-4-yl)pyrimidin-4-yl)amino)-5-(3-fluoropyrazin-2-yl)pyridin-4-yl)amino)-1-methylcyclohexan-1-ol The title compound as a white solid (4.5 mg) was prepared in the same fashion as Step 3 in Example 1, except that (1s,4s)-4-((2-chloro-5-(3-fluoropyrazin-2-yl)pyridin-4-yl)amino)-1-methylcyclohexan-1-ol (87 mg, 0.259 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.75 (s, 1H), 8.59 (s, 2H), 8.50 (s, 2H), 8.40 (d, 1H), 7.45-7.43 (m, 1H), 7.38 (s, 1H), 3.60 (m, 1H), 3.03 (m, 1H), 1.94 (m, 2H), 1.72-1.69 (m, 2H), 1.57 (t, 2H), 1.45 (m, 2H), 1.25 (m, 5H), 1.13 (d, 2H); MS (ESI) m/z=566.2 (M+H)⁺

Example 328. (1s, 4s)-4-((6'-((2-(1-(Cyclopropylsulfonyl)-1H-pyrazol-4-yl)pyrimidin-4-yl)amino)-5-fluoro-3-methoxy-[2,3'-bipyridin]-4'-yl)amino)-1-methylcyclohexan-1-ol Step 1. 2-Chloro-4-fluoro-5-(5-fluoro-3-methoxy-2-pyridyl)pyridine The title compound as a white solid (148.2 mg) was prepared in the same fashion as Step 1 in Example 1, except that 2-bromo-5-fluoro-3-methoxypyridine (200 mg, 0.971 mmol) was used instead of 1-((6-bromopyridin-3-yl)methyl)-4-methylpiperazine. ¹H-NMR (CDCl₃, 400 MHz) δ 8.47 (d, 1H), 8.18 (s, 1H), 7.13 (d, 1H), 7.08 (d, 1H), 3.83 (s, 3H); MS (ESI) m/z=256.9 (M+H)⁺

Step 2. (1s,4s)-4-((6'-Chloro-5-fluoro-3-methoxy-[2,3'-bipyridin]-4'-yl)amino)-1-methylcyclohexan-1-ol The title compound as an off-white solid (200 mg) was prepared in the same fashion as Step 2 in Example 1, except that 2-chloro-4-fluoro-5-(5-fluoro-3-methoxy-2-pyridyl)pyridine (148 mg, 0.577 mmol) prepared in Step 1 and cis-4-amino-1-methylcyclohexanol (112 mg, 0.866 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 8.18 (s, 1H), 8.03 (s, 1H), 7.04 (d, 1H), 6.79-6.77 (m, 1H), 6.49 (s, 1H), 3.74 (s, 3H), 3.20-3.19 (m, 1H), 2.54 (m, 1H), 1.79-1.76 (m, 2H), 1.66-1.54 (m, 4H), 1.45-1.42 (m, 2H), 1.18 (s, 3H); MS (ESI) m/z=366.0 (M+H)⁺

Step 3. (1s,4s)-4-((6'-((2-(1-(Cyclopropylsulfonyl)-1H-pyrazol-4-yl)pyrimidin-4-yl)amino)-5-fluoro-3-methoxy-[2,3'-bipyridin]-4'-yl)amino)-1-methylcyclohexan-1-ol The title compound as a white solid (6.7 mg) was prepared in the same fashion as Step 3 in Example 1, except that (1s,4s)-4-((6'-chloro-5-fluoro-3-methoxy-[2,3'-bipyridin]-4'-yl)amino)-1-methylcyclohexan-1-ol (90 mg, 0.245 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 8.66 (s, 1H), 8.48 (s, 1H), 8.42 (d, 1H), 8.34 (s, 1H), 8.16 (s, 1H), 7.39 (s, 1H), 7.13 (d, 1H), 7.01-6.96 (m, 2H), 3.87 (s, 3H), 3.44 (m, 1H), 2.84-2.82 (m, 1H), 1.98-1.95 (m, 2H), 1.70-1.54 (m, 8H), 1.30 (s, 3H), 1.23-1.21 (m, 2H); MS (ESI) m/z=595.2 (M+H)⁺

Example 329. (1s,4s)-4-((6'-((2-(1-(Cyclopropylsulfonyl)-1H-pyrazol-4-yl)pyrimidin-4-yl)amino)-6-fluoro-3-methoxy-[2,3'-bipyridin]-4'-yl)amino)-1-methylcyclohexan-1-ol Step 1. 2-Chloro-4-fluoro-5-(6-fluoro-3-methoxy-2-pyridyl)pyridine The title compound as a white solid (118.5 mg) was prepared in the same fashion as Step 1 in Example 1, except that 2-bromo-6-fluoro-3-methoxypyridine (200 mg, 0.971 mmol) was used instead of 1-((6-bromopyridin-3-yl)methyl)-4-methylpiperazine. ¹H-NMR (CDCl₃, 400 MHz) δ 8.50 (d, 1H), 7.45 (t, 1H), 7.14 (d, 1H), 6.96 (d, 1H), 3.82 (s, 3H); MS (ESI) m/z=256.9 (M+H)⁺

Step 2. (1s,4s)-4-((6'-Chloro-6-fluoro-3-methoxy-[2,3'-bipyridin]-4'-yl)amino)-1-methylcyclohexan-1-ol The title compound as an off-white solid (197.9 mg) was prepared in the same fashion as Step 2 in Example 1, except that 2-chloro-4-fluoro-5-(6-fluoro-3-methoxy-2-pyridyl)pyridine (119 mg, 0.462 mmol) prepared in Step 1 and cis-4-amino-1-methylcyclohexanol (89 mg, 0.693 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 8.33 (s, 1H), 7.42-7.40 (m, 1H), 6.90-6.81 (m, 2H), 6.51 (s, 1H), 3.77 (s, 3H), 3.25-3.24 (m, 1H), 1.99 (m, 2H), 1.83-1.62 (m, 4H), 1.59-1.47 (m, 2H), 1.22 (s, 3H); MS (ESI) m/z=366.0 (M+H)⁺

Step 3. (1s,4s)-4-((6'-((2-(1-(Cyclopropylsulfonyl)-1H-pyrazol-4-yl)pyrimidin-4-yl)amino)-6-fluoro-3-methoxy-[2,3'-bipyridin]-4'-yl)amino)-1-methylcyclohexan-1-ol The title compound as a white solid (3.3 mg) was prepared in the same fashion as Step 3 in Example 1, except that (1s,4s)-4-((6'-chloro-6-fluoro-3-methoxy-[2,3'-bipyridin]-4'-yl)amino)-1-methylcyclohexan-1-ol (90 mg, 0.245 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. ¹H-NMR (CDCl₃, 400 MHz) δ 8.66 (s, 1H), 8.48 (s, 1H), 8.42 (d, 1H), 7.49-5.46 (m, 1H), 7.36 (m, 1H), 7.20 (m, 1H), 7.01-6.98 (m, 1H), 6.88-6.86 (m, 1H), 3.88 (s, 3H), 3.49 (m, 1H), 2.83 (m, 1H), 2.03-1.96 (m, 2H), 1.72-1.53 (m, 8H), 1.30 (s, 3H), 1.23-1.21 (m, 2H); MS (ESI) m/z=595.2 (M+H)⁺

Example 330. (1s,4s)-4-((6'-((2-(1-(Cyclopropylsulfonyl)-1H-pyrazol-4-yl)pyrimidin-4-yl)amino)-3-(difluoromethoxy)-[2,3'-bipyridin]-4'-yl)amino)-1-methylcyclohexan-1-ol Step 1. 6'-Chloro-3-(difluoromethoxy)-4'-fluoro-2,3'-bipyridine The title compound as a white solid (153.9 mg) was prepared in the same fashion as Step 1 in Example 1, except that 2-bromo-3-(difluoromethoxy)pyridine (217 mg, 0.971 mmol) was used instead of 1-((6-bromopyridin-3-yl)methyl)-4-methylpiperazine. ¹H-NMR (CDCl₃, 400 MHz) δ 8.57-8.52 (m, 2H), 7.64 (d, 1H), 7.40 (t, 1H), 7.18 (d, 1H), 6.49 (t, 1H); MS (ESI) m/z=275.9 (M+H)⁺

Step 2. (1s,4s)-4-((6'-Chloro-3-(difluoromethoxy)-[2,3'-bipyridin]-4'-yl)amino)-1-methylcyclohexan-1-ol The title compound as an off-white solid (213.7 mg) was prepared in the same fashion as Step 2 in Example 1, except that 6'-chloro-3-(difluoromethoxy)-4'-fluoro-2,3'-bipyridine (154 mg, 0.560 mmol) prepared in Step 1 and cis-4-amino-1-methylcyclohexanol (109 mg, 0.841 mmol) were used instead of 6'-chloro-4'-fluoro-5-((4-methylpiperazin-1-yl)methyl)-2,3'-bipyridine and (4-methylpiperidin-4-yl)methanol. ¹H-NMR (CDCl₃, 400 MHz) δ 8.44 (d, 1H), 8.15 (s, 1H), 7.63-7.61 (m, 1H), 7.27-7.26 (m, 1H), 6.79-6.78 (m, 1H), 6.53 (s, 1H), 6.41 (t, 1H), 3.24-3.22 (m, 1H), 2.32-2.28 (m, 1H), 1.97 (m, 2H), 1.78-1.44 (m, 6H), 1.97 (s, 3H); MS (ESI) m/z=384.0 (M+H)$^+$

Step 3. (1s,4s)-4-((6'-((2-(1-(Cyclopropylsulfonyl)-1H-pyrazol-4-yl)pyrimidin-4-yl)amino)-3-(difluoromethoxy)-[2,3'-bipyridin]-4'-yl)amino)-1-methylcyclohexan-1-ol The title compound as a white solid (9.9 mg) was prepared in the same fashion as Step 3 in Example 1, except that (1s,4s)-4-((6'-chloro-3-(difluoromethoxy)-[2,3'-bipyridin]-4'-yl)amino)-1-methylcyclohexan-1-ol (94 mg, 0.245 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (CDCl$_3$, 400 MHz) δ 8.67 (s, 1H), 8.55-8.54 (m, 1H), 8.48 (s, 1H), 8.44 (d, 1H), 8.31 (s, 1H), 7.69 (d, 1H), 7.48 (s, 1H), 7.34-7.29 (m, 2H), 7.08-7.03 (m, 2H), 6.44 (t, 1H), 3.46 (m, 1H), 2.83-2.82 (m, 1H), 2.05-1.96 (m, 2H), 1.74-1.54 (m, 8H), 1.30 (s, 3H), 1.23-1.21 (m, 2H); MS (ESI) m/z=613.2 (M+H)$^+$

Example 331. (1s,4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol

Step 1. 6'-Chloro-4-(difluoromethoxy)-4'-fluoro-2,3'-bipyridine

The title compound as a white solid (183 mg) was prepared in the same fashion as Reference Example 5, except that 2-bromo-4-(difluoromethoxy)pyridine (200 mg, 0.893 mmol) was used instead of 2-bromo-5-(methylsulfonyl)pyridine. $^1$H-NMR (CDCl$_3$, 400 MHz) δ 9.08 (d, 1H), 8.72 (d, 1H), 7.51 (s, 1H), 7.23 (d, 1H), 7.10 (d, 1H), 6.70 (t, 1H). Step 2. (1s,4s)-4-((6'-Chloro-4-(difluoromethoxy)-[2,3'-bipyridin]-4'-yl)amino)-1-methylcyclohexan-1-ol The title compound as a white solid (105 mg) was prepared in the same fashion as Step 2 in Reference Example 1, except that 6'-chloro-4-(difluoromethoxy)-4'-fluoro-2,3'-bipyridine (90 mg, 0.328 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 9.22 (d, 1H), 8.54 (d, 1H), 8.35 (s, 1H), 7.40 (s, 1H), 7.01 (d, 1H), 6.70 (t, 1H), 6.58 (s, 1H), 3.34 (brs, 1H), 1.94 (d, 2H), 1.78-1.68 (m, 4H), 1.61-1.55 (m, 2H), 1.31 (s, 3H); MS (ESI) m/z=384.1 (M+H)$^+$

Step 3. (1s. 4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol The title compound as pale yellow solid (36 mg) was prepared in the same fashion as Step 3 in Example 1, except that (1s,4s)-4-((6'-chloro-4-(difluoromethoxy)-[2,3'-bipyridin]-4'-yl)amino)-1-methylcyclohexan-1-ol (95.5 mg, 0.249 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.39 (d, 1H), 8.66 (s, 1H), 8.60 (d, 1H), 8.56 (s, 1H), 8.47 (s, 1H), 8.43 (d, 1H), 7.72 (s, 1H), 7.60 (t, 1H), 7.52 (brs, 1H), 7.32 (brs, 1H), 7.13 (d, 1H), 4.22 (s, 1H), 3.23 (brs, 1H), 1.88-1.81 (m, 2H), 1.64-1.56 (m, 4H), 1.46-1.42 (m, 2H), 1.33-1.23 (m, 4H), 1.13 (s, 3H); MS (ESI) m/z=613.2 (M+H)$^+$

Example 332. (1s. 4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol

Step 1. 6'-Chloro-5-(difluoromethoxy)-4'-fluoro-2,3'-bipyridine

The title compound as a white solid (467 mg) was prepared in the same fashion as Reference Example 5, except that 2-bromo-5-(difluoromethoxy)pyridine (500 mg, 2.232 mmol) was used instead of 2-bromo-5-(methylsulfonyl)pyridine. $^1$H-NMR (CDCl$_3$, 400 MHz) δ 9.04 (d, 1H), 8.63 (s, 1H), 7.80 (d, 1H), 7.61 (d, 1H), 7.22 (d, 1H), 6.63 (t, 1H) Step 2. (1s,4s)-4-((6'-Chloro-5-(difluoromethoxy)-[2,3'-bipyridin]-4'-yl)amino)-1-methylcyclohexan-1-ol The title compound as a white solid (111 mg) was prepared in the same fashion as Step 2 in Reference Example 1, except that 6'-chloro-5-(difluoromethoxy)-4'-fluoro-2,3'-bipyridine (90 mg, 0.328 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 9.04 (d, 1H), 8.46 (s, 1H), 8.36 (s, 1H), 7.74 (d, 1H), 7.61 (d, 1H), 6.60 (t, 1H), 6.59 (s, 1H), 3.36-3.34 (m, 1H), 1.95 (d, 2H), 1.79-1.67 (m, 4H), 1.61-1.55 (m, 2H), 1.31 (s, 3H); MS (ESI) m/z=384.1 (M+H)$^+$

Step 3. (1s,4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol The title compound as pale yellow solid (41 mg) was prepared in the same fashion as Step 3 in Example 1, except that (1s,4s)-4-((6'-chloro-5-(difluoromethoxy)-[2,3'-bipyridin]-4'-yl)amino)-1-methylcyclohexan-1-ol (95.5 mg. 0.249 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (DMSO-d$_6$, 400 MHz) δ 9.23 (brs, 1H), 8.69 (s, 1H), 8.54 (d, 2H), 8.49 (s, 1H), 8.46 (d, 1H), 8.05 (d, 1H), 7.78 (d, 1H), 7.45 (brs, 1H), 7.34 (t, 1H), 7.21 (brs, 1H), 4.23 (s, 1H), 3.23 (brs, 1H), 1.88-1.81 (m, 2H), 1.66-1.57 (m, 4H), 1.45-1.39 (m, 2H), 1.34-1.24 (m, 4H), 1.13 (s, 3H); MS (ESI) m/z=613.2 (M+H)$^+$

Example 333. (1s,4s)-4-((6'-((2-(1-(Cyclopropylsulfonyl)-1H-pyrazol-4-yl)pyrimidin-4-yl)amino)-3-(2,2,2-trifluoroethoxy)-[2,3'-bipyridin]-4'-yl)amino)-1-methylcyclohexan-1-ol

Step 1. 6'-Chloro-4'-fluoro-3-(2,2,2-trifluoroethoxy)-2,3'-bipyridine

The title compound as a white solid (196.5 mg) was prepared in the same fashion as Step 1 in Example 1, except that 2-bromo-3-(2,2,2-trifluoroethoxy)pyridine (249 mg, 0.971 mmol) was used instead of 1-((6-bromopyridin-3-yl)methyl)-4-methylpiperazine. $^1$H-NMR (CDCl$_3$, 400 MHz) δ 8.49 (d, 1H), 8.37 (d, 1H), 7.33-7.32 (m, 2H), 7.13 (d, 1H), 4.38 (q, 2H); MS (ESI) m/z=306.9 (M+H)$^+$

Step 2. (1s,4s)-4-((6'-Chloro-3-(2,2,2-trifluoroethoxy)-[2,3'-bipyridin]-4'-yl)amino)-1-methylcyclohexan-1-ol The title compound as a white solid (245.2 mg) was prepared in the same fashion as Step 2 in Reference Example 1, except that 6'-chloro-4'-fluoro-3-(2,2,2-trifluoroethoxy)-2,3'-bipyridine (196.5 mg, 0.641 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 8.30-8.28 (m, 2H), 7.34 (d, 1H), 7.24-1.21 (m, 1H), 7.16 (d, 1H), 6.53 (s, 1H), 4.29 (q, 2H), 3.25-3.22 (m, 1H), 2.09 (s, 1H), 1.80 (m, 2H), 1.69-1.46 (m, 6H), 1.21 (s, 3H); MS (ESI) m/z=416.0 (M+H)$^+$

Step 3. (1s,4s)-4-((6'-((2-(1-(Cyclopropylsulfonyl)-1H-pyrazol-4-yl)pyrimidin-4-yl)amino)-3-(2,2,2-trifluoroethoxy)-[2,3'-bipyridin]-4'-yl)amino)-1-methylcyclohexan-1-ol The title compound as an off-white solid (16.3 mg) was prepared in the same fashion as Step 3 in Example 1, except that (1s,4s)-4-((6'-chloro-3-(2,2,2-trifluoroethoxy)-[2,3'-bipyridin]-4'-yl)amino)-1-methylcyclohexan-1-ol (108 mg, 0.259 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.75 (s, 1H), 8.49 (s, 1H), 8.38-8.35 (m, 2H), 8.18 (s, 1H), 7.68 (d, 1H), 7.44-7.42 (m, 1H), 7.35 (d, 1H), 7.29 (s, 1H), 4.64 (q, 2H), 3.52-3.48 (m, 1H), 3.05-3.01 (m, 1H), 1.91-1.87 (m, 2H), 1.69-1.44 (m, 8H), 1.27-2.25 (m, 2H), 1.22 (s, 3H); MS (ESI) m/z=645.2 (M+H)$^+$

Example 334. (1s,4s)-4-((6'-((2-(1-(Cyclopropylsulfonyl)-1H-pyrazol-4-yl)pyrimidin-4-yl)amino)-3-(2,2-difluoroethoxy)-[2,3'-bipyridin]-4'-yl)amino)-1-methylcyclohexan-1-ol

Step 1. 6'-Chloro-3-(2,2-difluoroethoxy)-4'-fluoro-2,3'-bipyridine

The title compound as a white solid (170.7 mg) was prepared in the same fashion as Step 1 in Example 1, except that 2-bromo-3-(2,2-difluoroethoxy)pyridine (231 mg, 0.971 mmol) was used instead of 1-((6-bromopyridin-3-yl)methyl)-4-methylpiperazine. $^1$H-NMR (CDCl$_3$, 400 MHz) δ 8.50 (d, 1H), 8.34 (d, 1H), 7.32-7.30 (m, 2H), 7.12 (d, 1H), 5.95 (t, 1H), 4.19 (td, 2H); MS (ESI) m/z=288.9 (M+H)$^+$

Step 2. (1s,4s)-4-((6'-Chloro-3-(2,2-difluoroethoxy)-[2,3'-bipyridin]-4'-yl)amino)-1-methylcyclohexan-1-ol The title compound as a white solid (217.3 mg) was prepared in the same fashion as Step 2 in Reference Example 1, except that 6'-chloro-3-(2,2-difluoroethoxy)-4'-fluoro-2,3'-bipyridine (170.7 mg, 0.591 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 8.29 (s, 1H), 8.25 (d, 1H), 7.30 (d, 1H), 7.23-7.20 (m, 2H), 6.53 (s, 1H), 6.01 (t, 1H), 4.13 (t, 2H), 3.25-3.22 (m, 1H), 1.84-1.80 (m, 2H), 1.66-1.46 (m, 6H), 1.22 (s, 3H); MS (ESI) m/z=398.0 (M+H)$^+$

Step 3. (1s,4s)-4-((6'-((2-(1-(Cyclopropylsulfonyl)-1H-pyrazol-4-yl)pyrimidin-4-yl)amino)-3-(2,2-difluoroethoxy)-[2,3'-bipyridin]-4'-yl)amino)-1-methylcyclohexan-1-ol The title compound as an off-white solid (9.1 mg) was prepared in the same fashion as Step 3 in Example 1, except that (1s,4s)-4-((6'-chloro-3-(2,2-difluoroethoxy)-[2,3'-bipyridin]-4'-yl)amino)-1-methylcyclohexan-1-ol (103 mg, 0.259 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.75 (s, 1H), 8.49 (s, 1H), 8.34 (d, 1H), 8.31 (d, 1H), 8.20 (s, 1H), 7.60 (d, 1H), 7.43-7.41 (m, 1H), 7.36-7.35 (m, 1H), 7.25 (s, 1H), 6.17 (t, 1H), 4.34 (t, 2H), 3.51-3.48 (m, 1H), 3.05-3.01 (m, 1H), 1.91-1.88 (m, 2H), 1.70-1.44 (m, 8H), 1.45-1.44 (m, 2H), 1.25 (s, 3H); MS (ESI) m/z=627.2 (M+H)$^+$

Example 335. (1s,4s)-4-((6'-((2-(1-(Cyclopropylsulfonyl)-1H-pyrazol-4-yl)pyrimidin-4-yl)amino)-4-fluoro-3-methoxy-[2,3'-bipyridin]-4'-yl)amino)-1-methylcyclohexan-1-ol

Step 1. 6'-Chloro-4,4'-difluoro-3-methoxy-2,3'-bipyridine

The title compound as a white solid (180 mg) was prepared in the same fashion as Step 1 in Example 1, except that 2-bromo-4-fluoro-3-methoxypyridine (200 mg, 0.971 mmol) was used instead of 1-((6-bromopyridin-3-yl)methyl)-4-methylpiperazine. $^1$H-NMR (CDCl$_3$, 400 MHz) δ 8.48 (d, 1H), 8.30 (t, 1H), 7.16-7.09 (m, 2H), 3.91 (s, 3H); MS (ESI) m/z=256.8 (M+H)$^+$

Step 2. (1s,4s)-4-((6'-Chloro-4-fluoro-3-methoxy-[2,3'-bipyridin]-4'-yl)amino)-1-methylcyclohexan-1-ol The title compound as a white solid (226.2 mg) was prepared in the same fashion as Step 2 in Reference Example 1, except that 6'-chloro-4,4'-difluoro-3-methoxy-2,3'-bipyridine (180 mg, 0.700 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 8.29 (s, 1H), 8.22 (t, 1H), 7.21 (d, 1H), 7.03-6.99 (m, 1H), 6.52 (s, 1H), 3.75 (s, 3H), 3.24-3.22 (m, 1H), 1.82-1.79 (m, 2H), 1.69-1.54 (m, 4H), 1.48-1.42 (m, 2H), 1.20 (s, 3H); MS (ESI) m/z=366.0 (M+H)$^+$

Step 3. (1s,4s)-4-((6'-((2-(1-(Cyclopropylsulfonyl)-1H-pyrazol-4-yl)pyrimidin-4-yl)amino)-4-fluoro-3-methoxy-[2,3'-bipyridin]-4'-yl)amino)-1-methylcyclohexan-1-ol The title compound as an off-white solid (15.7 mg) was prepared in the same fashion as Step 3 in Example 1, except that (1s,4s)-4-((6'-chloro-4-fluoro-3-methoxy-[2,3'-bipyridin]-4'-yl)amino)-1-methylcyclohexan-1-ol (95 mg, 0.259 mmol) prepared in Step 2 was used instead of (1-(6'-chloro-5-((4-methylpiperazin-1-yl)methyl)-[2,3'-bipyridin]-4'-yl)-4-methylpiperidin-4-yl)methanol. $^1$H-NMR (MeOD, 400 MHz) δ 8.75 (s, 1H), 8.49 (s, 1H), 8.39-8.35 (m, 2H), 8.22 (s, 1H), 7.40 (d, 1H), 7.29-7.25 (m, 2H), 3.84 (s, 3H), 3.52 (m, 1H), 3.05-3.01 (m, 1H), 1.93-1.90 (m, 2H), 1.70-1.1.44 (m, 8H), 1.30-1.29 (m, 2H), 1.27 (s, 3H); MS (ESI) m/z=595.2 (M+H)$^+$

Example 336. (1s,4s)-4-((6'-((2-(1-(2,2-Difluoroethyl)-1H-pyrazol-4-yl)pyrimidin-4-yl)amino)-4-fluoro-3-methoxy-[2,3'-bipyridin]-4'-yl)amino)-1-methylcyclohexan-1-ol The title compound (1.1 mg) as a white solid was prepared in the same fashion as Step 3 in Example 1, except that (1s,4s)-4-((6'-chloro-4-fluoro-3-methoxy-[2,3'-bipyridin]-4'-yl)amino)-1-methylcyclohexan-1-ol (81 mg, 0.222 mmol) prepared in Step 2 of Example 335 and 2-(1-(2,2-difluoroethyl)-1H-pyrazol-4-yl)pyrimidin-4-amine (40 mg, 0.178 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. $^1$H-NMR (MeOD, 400 MHz) δ 8.37-8.36 (m, 3H), 8.25 (s, 2H), 7.31-7.26 (m, 2H), 7.15 (m, 1H), 6.26 (t, 1H), 4.66 (t, 2H), 3.87 (s, 3H), 3.52-3.51 (m, 1H), 1.91-1.88 (m, 2H), 1.72-1.67 (m, 4H), 1.57-1.54 (m, 2H), 1.23 (s, 3H); MS (ESI) m/z=555.2 (M+H)$^+$ Example 337. (1s,4s)-4-((6'-((2-(1-(2,2-Difluoro-ethyl)-1H-pyrazol-4-yl)pyrimidin-4-yl)amino)-3-methoxy-5-((1-(2,2,2-trifluoroethyl) piperidin-4-yl)oxy)-[2,3'-bipyridin]-4'-yl)amino)-1-methylcyclohexan-1-ol Step 1. 2-Bromo-3-methoxy-5-((1-(2,2,2-trifluoroethyl) piperidin-4-yl)oxy)pyridine The title compound as a white solid (382 mg) was prepared in the same fashion as Step 2 in Example 322, except that 6-bromo-5-methoxypyridin-3-ol (499 mg, 2.445 mmol) and 1-(2,2,2-trifluoroethyl) piperidin-4-yl 4-methylbenzenesulfonate (750 mg, 2.223 mmol) were used instead of 2-bromo-5-hydroxypyridine and tert-butyl 4-(p-tolyloxy) piperidine-1-carboxylate. $^1$H-NMR (CDCl$_3$, 400 MHz) δ 7.68 (s, 1H), 6.74 (s, 1H), 4.39 (s, 1H), 3.90 (s, 3H), 3.05-2.98 (q, 2H), 2.91-2.90 (m, 2H), 2.67-2.62 (m, 2H), 2.05-1.86 (m, 4H); MS (ESI) m/z=369.6 (M+H)$^+$ Step 2. 6'-Chloro-4'-fluoro-3-methoxy-5-((1-(2,2,2-trifluoroethyl) piperidin-4-yl)oxy)-2,3'-bipyridine The title compound as a white solid (301 mg) was prepared in the same fashion as Step 1 in Example 1, except that 2-bromo-3-methoxy-5-((1-(2,2,2-trifluoroethyl) piperidin-4-yl)oxy)pyridine (380 mg, 1.029 mmol) was used instead of 1-((6-bromopyridin-3-yl)methyl)-4-methylpiperazine. $^1$H-NMR (CDCl$_3$, 400 MHz) δ 8.50 (d, 1H), 8.02 (s, 1H), 7.15 (d, 1H), 6.87 (s, 1H), 4.49 (m, 1H), 3.83 (s, 3H), 3.07-2.93 (m, 4H), 2.69-2.65 (m, 2H), 2.09-2.05 (m, 2H), 1.94-1.91 (m, 2H); MS (ESI) m/z=420.1 (M+H)$^+$ Step 3. (1s,4s)-4-((6'-chloro-3-methoxy-5-((1-(2,2,2-trifluoroethyl) piperidin-4-yl)oxy)-[2,3'-bipyridin]-4'-yl)amino)-1-methylcyclohexan-1-ol The title compound as a white solid (94 mg) was prepared in the same fashion as Step 2 in Reference Example 1, except that 6'-chloro-4'-fluoro-3-methoxy-5-((1-(2,2,2-trifluoroethyl) piperidin-4-yl)oxy)-2,3'-bipyridine (87 mg. 0.217 mmol) prepared in step 1 was used instead of 6'-chloro-4'-fluoro-5-((1-methylpiperidin-4-yl)oxy)-2,3'-bipyridine. $^1$H-NMR (CDCl$_3$, 400 MHz) δ 8.25 (s, 1H), 7.90 (s, 1H), 7.01-6.99 (m, 1H), 6.86 (s, 1H), 6.52 (s, 1H), 4.43 (m, 1H), 3.77 (s, 3H), 3.25-3.24 (m, 1H), 3.01 (q, 2H), 2.96-2.91 (m, 2H), 2.65-2.61 (m, 2H), 2.02-1.83 (m, 8H), 1.57-1.48 (m, 4H), 1.24 (s, 3H); MS (ESI) m/z=529.2 (M+H)$^+$ Step 4. (1s,4s)-4-((6'-((2-(1-(2,2-Difluoroethyl)-1H-pyrazol-4-yl)pyrimidin-4-yl)amino)-3-methoxy-5-((1-(2,2,2-trifluoroethyl) piperidin-4-yl)oxy)-[2,3'-bipyridin]-4'-yl)amino)-1-methylcyclohexan-1-ol The title compound as an off-white solid (1.4 mg) was prepared in the same fashion as Step 3 in Example 1, except that (1s,4s)-4-((6'-chloro-3-methoxy-5-((1-(2,2,2-trifluoroethyl) piperidin-4-yl)oxy)-[2,3'-bipyridin]-4'-yl)amino)-1-methylcyclohexan-1-ol (94 mg. 0.178 mmol) prepared in Step 3 and 2-(1-(2,2-difluoroethyl)-1H-pyrazol-4-yl)pyrimidin-4-amine (40 mg, 0.178 mmol) prepared in Reference Example 17 were used instead of (1-(6'-chloro-5-((4-methylpiperazin-1-yl)methyl)-[2,3'-bipyridin]-4'-yl)-4-methylpiperidin-4-yl)methanol and 2-(1-(cyclopropylsulfonyl)-1H-pyrazol-4-yl)pyrimidin-4-amine. MS (ESI) m/z=718.3 (M+H);

Biological Assays

1. Biochemical EGFR Inhibition Assays

Biochemical EGFR kinase assays were conducted using Lance Ultra time-resolved fluorescence resonance energy transfer (TR-FRET) technology from Perkin-Elmer. Compounds of the invention were initially diluted to 20 mM in 100% DMSO for storage and made into kinase buffer solution to create a compound concentration ranging from 0.003 μM and 10 μM.

Briefly, each EGFR enzyme wildtype, double mutant [del19/C797S and L858R/C797S], triple mutant [del19/T790M/C797S and L858R/T790M/C797S], serial diluted EGFR inhibitors, substrate of ULight-poly-GT peptide (PerkinElmer: TRF0100-M) and different concentrations of ATP (Km and 100 μM final assay concentration) were mixed in kinase assay buffer (50 mM HEPES pH 7.4, 10 mM MgCl$_2$, 1 mM EGTA, 2 mM DTT and 0.01% Tween-20) and were added to a 384-well plate (Optiplate™ 384, white, PerkinElmer: 6007290).

Each kinase reactions were incubated at room temperature for 1 hour and then stopped by the addition of 4 μL of stop solution (10 mM EDTA). The specific Europium-labeled-anti-phosphopeptide antibody (PerkinElmer, AD0069) diluted in LANCE detection buffer was then added to a final concentration of 2 nM. After 60 minutes incubation at room temperature the LANCE signal was measured on an EnVision Multilabel Reader (Perkin-Elmer). Excitation wavelength was set at 320 nm and emission monitored at 615 nm (donor) and 665 nm (acceptor). The IC$_{50}$ values were determined using GraphPad prism software (GraphPad Software, Inc., San Diego, CA, USA).

The IC$_{50}$ values of compounds of formula (I) on the activity of each EGFR kinase evaluated as above are shown in Tables 3 to 14 below.

TABLE 3

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 1 | 1.2 | 0.8 | 0.4 | 1.3 | 37.5 | 52.3 | 10.5 | 222.7 | 211.8 | >10000 |
| 2 | 0.2 | 0.1 | | 0.2 | 0.3 | 0.2 | 0.1 | 1.8 | 1.4 | 541.0 |
| 3 | 0.4 | | 0.3 | | 23.7 | | 15.3 | | 99.6 | |
| 4 | 0.1 | | 0.1 | | 2.1 | | 2.2 | | 19.9 | |

TABLE 3-continued

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 5 | 0.2 | 0.1 | 0.1 | 0.1 | 0.2 | 0.4 | 0.3 | 2.0 | 0.5 | >10000 |
| 6 | 0.2 | 0.1 | 0.1 | 0.1 | 0.2 | 0.4 | 0.3 | 6.5 | 1.1 | >10000 |
| 7 | 0.4 | 0.2 | 0.1 | 0.2 | 0.5 | 1.3 | 0.6 | 12.4 | 3.0 | >10000 |
| 8 | 0.4 | 0.2 | 0.1 | 0.2 | 0.4 | 0.7 | 0.4 | 6.3 | 1.0 | 8893.0 |
| 9 |  | 0.1 | 0.1 | 0.3 | 0.2 | 0.7 | 0.2 | 1.9 | 1.0 | 166.7 |
| 10 |  | 0.1 | 0.1 | 0.2 | 0.1 | 0.3 | 0.2 | 1.2 | 0.6 | 46.6 |
| 11 |  | 0.1 | 0.1 | 0.2 | 0.2 | 0.4 | 0.4 | 2.1 | 1.4 | 586.5 |
| 12 |  | 0.4 | 0.2 | 0.6 | 0.4 | 1.0 | 1.1 | 11.5 | 3.6 | 2691.0 |
| 13 |  | 0.1 | 0.1 | 0.6 | 0.5 | 1.4 | 3.4 | 66.8 | 13.3 | >10000 |
| 14 |  | 0.2 | 0.4 | 10.9 | 1.1 | 6.4 | 13.7 | 686.9 | 154.2 | >10000 |
| 15 |  | 0.1 | 0.1 | 1.5 | 0.3 | 0.6 | 1.8 | 22.1 | 5.7 | 889.5 |
| 16 |  | 0.04 | 0.1 | 0.4 | 0.2 | 0.3 | 0.5 | 8.7 | 2.1 | 1899.0 |
| 17 |  | 2.9 |  | 2.6 |  | 5.6 |  | 305.3 |  | >10000 |
| 18 |  | 0.7 |  | 3.1 |  | 8.7 |  | 113.0 |  | >10000 |
| 19 |  | 1.4 |  | 1.6 |  | 1.7 |  | 11.1 |  | >10000 |
| 20 |  | 2.1 |  | 3.6 |  | 5.5 |  | 69.3 |  | >10000 |
| 21 | 0.3 | 0.3 | 0.3 | 0.6 | 0.5 | 1.2 | 1.0 | 11.6 | 6.3 | 5572.0 |
| 22 | 0.3 | 0.3 | 0.2 | 0.2 | 0.1 | 0.2 | 0.2 | 1.1 | 0.3 | 164.8 |
| 23 | 1.6 | 1.1 |  | 1.0 | 1.8 | 5.0 | 0.6 | 6.2 | 13.7 | >10000 |
| 24 | 1.0 | 8.4 |  | 0.9 | 1.0 | 2.2 | 0.7 | 3.5 | 2.8 | >10000 |
| 25 | 1.0 | 1.1 | 0.8 | 1.2 | 0.5 | 0.5 | 0.3 | 2.0 | 1.9 | 1829.0 |
| 26 | 0.4 | 0.4 | 0.2 | 0.4 | 0.2 | 0.2 | 0.1 | 0.7 | 0.9 | 107.4 |
| 27 | 0.3 | 0.3 | 0.2 | 0.4 | 0.1 | 0.3 | 0.1 | 1.6 | 1.7 | 370.3 |
| 28 |  | 0.1 |  | 0.1 |  | 0.6 |  | 1.6 |  | 1526.0 |
| 29 |  | 0.2 |  | 0.4 |  | 1.8 |  | 26.2 |  | >10000 |
| 30 |  | 0.1 |  | 0.1 |  | 0.4 |  | 2.0 |  | 2915.0 |

TABLE 4

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 31 | 0.2 | 0.2 | 0.1 | 0.1 | 0.1 | 0.1 | 0.1 | 0.8 | 0.3 | 52.6 |
| 32 | 0.2 | 0.4 | 0.2 | 0.3 | 0.2 | 0.1 | 0.1 | 1.9 | 0.3 | 119.9 |
| 33 | 2.6 | 3.9 | 1.7 | 3.1 | 2.1 | 1.3 | 1.7 | 29.3 | 7.9 | 812.7 |
| 34 | 0.6 | 0.6 | 0.1 | 0.3 | 0.2 | 0.4 | 0.1 | 0.2 | 0.5 | 61.1 |
| 35 | 0.6 | 0.3 | 0.2 | 0.3 | 0.3 | 0.2 | 0.3 | 1.2 | 1.3 | 810.9 |
| 36 | 0.1 | 0.2 | 0.1 | 0.1 | 0.5 | 0.9 | 1.0 | 15.7 | 5.8 | 3084.0 |
| 37 | 0.2 | 0.2 | 0.1 | 0.3 | 0.7 | 1.1 | 0.7 | 21.3 | 6.6 | >10000 |
| 38 |  | 0.4 | 0.2 | 0.7 | 0.3 | 0.6 | 0.9 | 4.3 | 1.5 | 1434.0 |
| 39 | 1.0 | 2.1 | 0.4 | 0.7 | 2.5 | 3.3 | 8.7 | 74.8 | 26.0 | >10000 |
| 40 | 0.7 | 2.1 | 0.5 | 1.7 | 2.3 | 3.2 | 1.7 | 7.7 | 5.0 | 1445.0 |
| 41 | 0.3 | 0.8 | 0.2 | 0.9 | 4.5 | 5.1 | 4.0 | 523.3 | 43.6 | >10000 |
| 42 | 0.1 | 0.1 | 0.03 | 0.1 | 0.3 | 0.2 | 0.4 | 2.3 | 2.6 | 1360.0 |
| 43 | 0.1 | 2.5 | 0.1 | 2.7 | 0.4 | 0.5 | 0.6 | 1.6 | 2.0 | 1557.0 |
| 44 |  | 0.6 |  | 0.6 |  | 0.8 |  | 7.1 |  | >10000 |
| 45 |  | 1.7 |  | 2.6 |  | 1.7 |  | 4.2 |  | 602.0 |
| 46 | 0.2 | 0.3 | 0.1 | 0.2 | 0.2 | 0.4 | 0.2 | 0.9 | 0.9 | >10000 |
| 47 | 2.0 | 1.2 | 1.0 | 3.0 | 3.2 | 4.2 | 7.9 | 17.7 | 7.1 | >10000 |
| 48 | 0.5 | 0.6 | 0.3 | 2.1 | 2.6 | 5.8 | 14.1 | 83.3 | 24.7 | >10000 |
| 49 | 0.3 | 0.3 | 0.1 | 0.3 | 0.5 | 0.8 | 0.3 | 2.4 | 0.5 | 294.1 |
| 50 | 0.3 | 0.2 | 0.1 | 0.1 | 0.5 | 1.1 | 0.4 | 2.2 |  | >10000 |
| 51 | 0.8 | 0.6 | 0.3 | 0.6 | 3.1 | 10.6 | 1.0 | 16.7 |  | >10000 |
| 52 | 0.3 | 0.5 | 0.1 | 0.3 | 0.5 | 0.6 | 0.6 | 1.1 | 3.0 | >10000 |
| 53 | 0.4 | 0.4 | 0.1 | 0.5 | 1.3 | 1.2 | 1.0 | 1.0 | 6.9 | >10000 |
| 54 | 12.5 | 11.4 |  | 5.1 | 5.6 | 9.7 | 1.4 | 7.3 | 9.2 | 5836.0 |
| 55 | 0.7 | 1.7 |  | 0.4 | 0.5 | 1.1 | 0.3 | 1.0 | 1.9 | 753.5 |
| 56 |  | 1.4 |  | 2.4 | 5.9 | 8.8 | 2.6 | 122.3 | 168.8 | >10000 |
| 57 |  | 1.7 |  | 1.0 | 2.0 | 1.7 | 0.7 | 4.5 | 4.8 | 635.8 |
| 58 |  | 1.1 |  | 1.1 | 8.0 | 7.2 | 1.7 | 56.4 | 97.7 | >10000 |
| 59 | 0.3 | 0.4 | 0.5 | 0.7 | 0.6 | 0.9 | 1.0 | 7.4 | 14.8 | >10000 |
| 60 | 0.2 | 0.2 | 0.2 | 0.4 | 0.4 | 0.5 | 0.4 | 4.2 | 6.8 | >10000 |

TABLE 5

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 61 | | 0.2 | | 0.2 | | 0.4 | | 1.8 | | 3941.0 |
| 62 | | 0.1 | | 0.1 | | 0.2 | | 0.9 | | 744.7 |
| 63 | | 0.2 | | 0.2 | | 0.8 | | 5.4 | | >10000 |
| 64 | 0.1 | 0.1 | 0.1 | 0.3 | | 0.2 | 0.2 | 0.9 | 2.4 | 1168.0 |
| 65 | 0.1 | 0.1 | 0.1 | 0.3 | 0.3 | 0.2 | 0.1 | 0.9 | 2.4 | 1136.0 |
| 66 | 0.3 | 0.5 | 0.1 | 0.5 | 0.4 | 0.9 | 0.5 | 12.2 | 11.5 | >10000 |
| 67 | 0.3 | 0.3 | 0.1 | 0.3 | 0.5 | 0.5 | 0.8 | 4.5 | 3.7 | >10000 |
| 68 | 0.9 | 1.5 | 0.8 | 0.8 | 2.8 | 4.9 | 1.1 | 123.6 | 23.2 | >10000 |
| 69 | 1.9 | 1.6 | 0.8 | 1.4 | 2.4 | 5.3 | 1.4 | 52.7 | 14.5 | 4782.0 |
| 70 | | 3.9 | | 4.9 | | 13.1 | | 81.1 | | >10000 |
| 71 | | 4.5 | | 4.1 | | 44.2 | | 354.7 | | >10000 |
| 72 | 10.7 | 12.7 | 1.7 | 12.2 | 22.4 | 21.7 | 61.4 | 2432.0 | 84.2 | >10000 |
| 73 | 0.4 | 0.7 | 0.2 | 0.5 | 0.4 | 0.5 | 1.5 | 16.3 | 2.2 | 561.5 |
| 74 | 1.6 | 2.2 | 0.6 | 2.8 | 0.7 | 2.4 | 3.2 | 43.9 | 9.1 | 1608.0 |
| 75 | 8.7 | 15.2 | 6.6 | 15.2 | 34.0 | 33.2 | 68.9 | 313.2 | 143.0 | >10000 |
| 76 | 2.0 | 1.0 | 0.9 | 0.8 | 1.6 | 2.0 | 2.1 | 14.5 | 8.1 | >10000 |
| 77 | 2.1 | 1.7 | 1.1 | 1.4 | 2.2 | 2.3 | 4.1 | 13.0 | 4.0 | 1556.0 |
| 78 | 6.8 | 5.5 | 2.7 | 5.4 | 8.8 | 15.8 | 16.6 | 85.5 | 23.6 | >10000 |
| 79 | 0.8 | 0.5 | 0.3 | 0.5 | 0.4 | 0.6 | 0.7 | 4.7 | 1.4 | 450.1 |
| 80 | 3.8 | 6.2 | 2.8 | 6.3 | 2.5 | 8.4 | 2.3 | 11.1 | 11.4 | 4407.0 |
| 81 | 2.4 | 3.1 | 2.0 | 6.0 | 4.0 | 19.0 | 3.3 | 13.0 | 11.7 | 3652.0 |
| 82 | 6.5 | 10.5 | 2.8 | 15.4 | 7.9 | 13.3 | 7.8 | 73.3 | 29.6 | >10000 |
| 83 | 0.7 | 0.6 | 0.2 | 0.3 | 0.2 | 0.2 | 0.1 | 0.4 | 0.2 | 24.9 |
| 84 | 0.9 | 0.7 | 0.3 | 0.5 | 0.4 | 0.6 | 0.2 | 0.5 | 0.6 | 181.0 |
| 85 | 0.4 | 0.4 | 0.1 | 0.3 | 0.1 | 0.3 | 0.1 | 0.2 | 0.2 | 31.7 |
| 86 | 0.2 | 1.6 | 0.1 | 0.2 | 0.3 | 0.4 | 0.4 | 11.4 | 3.6 | 1478.0 |
| 87 | 0.1 | 5.9 | 0.1 | 0.1 | 0.4 | 0.5 | 0.6 | 4.7 | 2.2 | 991.7 |
| 88 | 0.4 | 4.9 | 0.1 | 0.4 | 1.5 | 2.2 | 2.1 | 31.1 | 15.3 | >10000 |
| 89 | 0.1 | 0.1 | 0.1 | 0.1 | 0.3 | 0.1 | 0.2 | 3.9 | 2.7 | 1641.0 |
| 90 | 0.6 | 0.4 | 0.3 | 0.4 | 0.4 | 0.9 | 0.4 | 15.1 | 0.4 | 406.0 |

TABLE 6

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 91 | 0.5 | 1.3 | 0.9 | 1.1 | 0.9 | 2.8 | 0.8 | 9.7 | 2.5 | >10000 |
| 92 | 1.0 | 1.6 | 1.4 | 2.3 | 4.4 | 7.2 | 4.7 | 78.8 | 0.1 | 171.8 |
| 93 | 0.3 | 0.4 | 0.1 | 0.3 | 0.2 | 0.5 | 0.3 | 2.2 | 0.1 | 171.8 |
| 94 | 2.7 | 4.4 | 0.9 | 1.5 | 3.9 | 13.3 | 6.0 | 170.1 | 7.2 | >10000 |
| 95 | 2.5 | 5.6 | 0.9 | 2.0 | 66.9 | 1542.0 | 8479.0 | 9156.0 | 222.3 | >10000 |
| 96 | 1.5 | 2.0 | 0.7 | 0.8 | 68.0 | 224.2 | 27.4 | 2216.0 | 84.7 | >10000 |
| 97 | 2.1 | 2.2 | 0.5 | 1.0 | 2.3 | 6.0 | 2.0 | 52.6 | 7.4 | >10000 |
| 98 | 0.4 | 0.5 | 0.1 | 0.2 | | 0.3 | | 1.9 | | 152.5 |
| 99 | 0.1 | 0.1 | 0.04 | 0.1 | 0.3 | 0.3 | 0.1 | 0.7 | 0.3 | 61.5 |
| 100 | 6.4 | 8.1 | 1.3 | 5.3 | 6.5 | 10.8 | 12.9 | 24.9 | 12.7 | 7220.0 |
| 101 | 1.7 | 0.9 | 0.4 | 0.7 | 2.1 | 2.4 | 2.1 | 14.4 | 2.2 | 574.5 |
| 102 | 2.8 | 1.5 | 0.7 | 1.0 | 4.6 | 9.1 | 8.2 | 29.9 | 21.3 | >10000 |
| 103 | | 6.6 | | 3.9 | | 66.5 | | 653.7 | | >10000 |
| 104 | 1.1 | 1.8 | 0.6 | 0.8 | 2.2 | 3.1 | 0.9 | 21.6 | 21.9 | >10000 |
| 105 | 2.1 | 3.2 | 1.5 | 1.2 | 3.0 | 3.9 | 0.6 | 5.4 | 5.3 | 787.1 |
| 106 | 6.2 | 8.6 | 2.6 | 4.1 | 11.7 | 11.2 | 4.1 | 9.6 | 37.8 | 3712.0 |
| 107 | 0.3 | 0.4 | 0.2 | 0.2 | 0.1 | 0.5 | 0.1 | 1.8 | 0.4 | 327.3 |
| 108 | 0.4 | 0.4 | 0.2 | 0.2 | 0.4 | 0.9 | 0.4 | 3.6 | 6.9 | 1859.0 |
| 109 | 2.0 | 1.5 | 0.6 | 0.5 | 0.8 | 6.4 | 0.1 | 11.1 | 5.2 | 1365.0 |
| 110 | 0.1 | 0.2 | 0.1 | 0.1 | 0.3 | 0.3 | 0.04 | 0.5 | 0.9 | 178.0 |
| 111 | 0.3 | 0.5 | 0.2 | 0.2 | 0.2 | 0.7 | 0.03 | 0.4 | 0.7 | 198.1 |
| 112 | 4.5 | 5.7 | 2.0 | 3.6 | 5.1 | 23.2 | 6.8 | 6.9 | 11.7 | >10000 |
| 113 | 7.5 | 5.3 | 2.3 | 3.2 | 11.0 | 19.9 | 8.8 | 20.8 | 15.0 | >10000 |
| 114 | 8.5 | 11.2 | 2.8 | 4.5 | 27.1 | 29.9 | 15.7 | 33.7 | 46.8 | 652.9 |
| 115 | 0.1 | 0.4 | 0.1 | 0.1 | 0.4 | 0.8 | 0.1 | 0.5 | 1.8 | >10000 |
| 116 | 0.1 | 0.1 | 0.04 | 0.04 | 0.1 | 0.1 | 0.1 | 0.3 | 0.4 | 384.0 |
| 117 | 0.2 | 0.4 | 0.1 | 0.1 | 0.3 | 0.5 | 0.2 | 0.5 | 1.9 | 6504.0 |

TABLE 6-continued

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 118 | 0.1 | 0.04 | 0.1 | 0.2 | 0.1 | 0.3 | 0.05 | 0.7 | 1.3 | 399.5 |
| 119 | 0.1 | 0.1 | 0.1 | 0.2 | 0.1 | 0.2 | 0.03 | 0.3 | 1.0 | 108.5 |
| 120 | 0.2 | 0.2 | 0.1 | 0.4 | 0.5 | 0.7 | 0.1 | 2.1 | 4.3 | 967.8 |

TABLE 7

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 121 | 0.5 |  | 0.2 |  | 4.6 |  | 2.9 |  | 22.6 |  |
| 122 | 0.3 |  | 0.1 |  | 9.7 |  | 4.3 |  | 7.4 |  |
| 123 | 2.6 |  | 0.7 |  | 28.6 |  | 2.3 |  | 22.0 |  |
| 124 | 0.3 |  | 0.4 |  | 3.3 |  | 0.4 |  | 12.7 |  |
| 125 | 0.7 |  | 0.3 |  | 8.9 |  | 12.1 |  | 44.8 |  |
| 126 | 2.7 |  | 1.2 |  | 12.1 |  | 12.6 |  | 45.7 |  |
| 127 | 17.5 |  | 6.6 |  | >10000 |  | >10000 |  | >10000 |  |
| 128 | 1.2 |  | 0.5 |  | 41.2 |  | 95.8 |  | >10000 |  |
| 129 | 1.4 |  | 0.5 |  | 12.6 |  | 12.9 |  | 116.1 |  |
| 130 | 3.9 |  | 1.7 |  | 281.5 |  | 239.0 |  | >10000 |  |
| 131 | 0.2 |  | 0.1 |  | 2.1 |  | 2.2 |  | 8.1 |  |
| 132 | 0.4 |  | 0.4 |  | 0.4 |  | 0.3 |  | 0.8 |  |
| 133 | 0.5 |  | 0.3 |  | 1.7 |  | 1.4 |  | 9.3 |  |
| 134 | 0.9 |  | 0.6 |  | 32.1 |  | 15.6 |  | 34.2 |  |
| 135 | 0.3 |  | 0.2 |  | 2.9 |  | 0.6 |  | 10.8 |  |
| 136 | 0.5 |  | 0.2 |  | 19.1 |  | 6.4 |  | 69.8 |  |
| 137 | 1.1 |  | 0.2 |  | 74.4 |  | 6.4 |  | 271.9 |  |
| 138 | 0.1 |  | 0.2 |  | 4.9 |  | 1.6 |  | 32.0 |  |
| 139 | 0.3 |  | 0.3 |  | 19.4 |  | 5.0 |  | 208.2 |  |
| 140 | 0.2 |  | 0.2 |  | 8.3 |  | 15.1 |  | 67.6 |  |
| 141 | 0.03 |  | 0.1 |  | 1.2 |  | 0.8 |  | 12.4 |  |
| 142 | 0.01 |  | 0.03 |  | 2.0 |  | 0.8 |  | 17.1 |  |
| 143 | 0.1 |  | 0.2 |  | 1.0 |  | 1.1 |  | 7.9 |  |
| 144 | 0.3 |  | 0.1 |  | 2.2 |  | 1.2 |  | 26.3 |  |
| 145 | 0.1 |  | 0.03 |  | 0.3 |  | 0.1 |  | 1.2 |  |
| 146 | 0.1 |  | 0.02 |  | 0.3 |  | 0.1 |  | 0.8 |  |
| 147 | 0.3 |  | 0.1 |  | 0.4 |  | 0.1 |  | 2.3 |  |
| 148 | 0.3 |  | 0.3 |  | 2.0 |  | 1.0 |  | 15.1 |  |
| 149 | 0.4 |  | 0.3 |  | 1.0 |  | 0.4 |  | 11.2 |  |
| 150 | 0.2 |  | 0.1 |  | 0.5 |  | 0.4 |  | 6.2 |  |

TABLE 8

| EX. NO. | del19/T790M/C797S (nM) Km ATP | del19/T790M/C797S (nM) 100 μM ATP | L858R/T790M/C797S (nM) Km ATP | L858R/T790M/C797S (nM) 100 μM ATP | del19/C797S (nM) Km ATP | del19/C797S (nM) 100 μM ATP | L858R/C797S (nM) Km ATP | L858R/C797S (nM) 100 μM ATP | WT (nM) Km ATP | WT (nM) 100 μM ATP |
|---|---|---|---|---|---|---|---|---|---|---|
| 151 | 0.8 |  | 0.1 |  | 34.0 |  | 17.2 |  | 1908.0 |  |
| 152 | 0.5 |  | 0.1 |  | 214.4 |  | 13.1 |  | >10000 |  |
| 153 | 0.4 |  | 0.1 |  | 0.2 |  | 0.2 |  | 3.2 |  |
| 154 | 0.2 |  | 0.1 |  | 0.3 |  | 0.2 |  | 2.7 |  |
| 155 | 0.3 | 0.7 | 0.1 | 0.5 | 0.7 | 0.7 | 1.1 | 3.7 | 2.5 | 3278.0 |
| 156 | 0.1 | 0.2 | 0.1 | 0.2 | 0.3 | 0.3 | 0.4 | 2.6 | 1.3 | >10000 |
| 157 | 0.1 | 0.1 | 0.1 | 0.1 | 0.8 | 0.6 | 0.8 | 11.2 | 6.9 | 2927.0 |
| 158 |  | 0.3 |  | 0.4 |  | 0.4 |  | 2.4 |  | 541.3 |
| 159 |  | 0.1 |  | 0.1 |  | 0.2 |  | 1.2 |  | 322.8 |
| 160 | 0.5 | 0.8 | 0.2 | 0.7 | 0.5 | 1.3 | 3.0 | 15.0 | 5.1 | >10000 |
| 161 | 0.1 | 0.1 | 0.1 | 0.5 | 0.9 | 1.2 | 1.9 | 12.4 | 11.6 | >10000 |

TABLE 8-continued

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 162 | 0.5 | 1.3 | 0.4 | 3.0 | 13.1 | 21.0 | 19.9 | 1532.0 | 2966.0 | >10000 |
| 163 | 1.4 | 2.6 | 0.7 | 2.3 | 2.6 | 3.1 | 13.0 | 49.4 | 18.7 | >10000 |
| 164 | 0.8 | 0.4 | 0.3 | 0.4 | 0.5 | 1.1 | 0.6 | 1.8 | | >10000 |
| 165 | 3.5 | 1.2 | 1.0 | 1.7 | 1.8 | 7.6 | 1.6 | 18.5 | | >10000 |
| 166 | 1.9 | 5.1 | | 0.6 | 1.2 | 2.4 | 1.1 | 2.4 | 2.0 | >10000 |
| 167 | | 2.7 | | 3.5 | | 45.8 | | 52.2 | | >10000 |
| 168 | 0.4 | 0.3 | 0.2 | 0.2 | 0.2 | 0.4 | 0.2 | 0.5 | | 92.2 |
| 169 | 1.3 | 0.9 | | 0.7 | 0.5 | 1.3 | 0.4 | 2.1 | | 416.3 |
| 170 | 0.8 | 1.3 | 0.2 | 0.9 | 0.7 | 2.0 | 0.6 | 2.1 | 1.5 | 140.7 |
| 171 | 0.3 | 0.5 | 0.1 | 0.2 | 0.1 | 0.3 | 0.2 | 0.3 | 0.2 | 67.9 |
| 172 | 0.7 | 0.6 | 0.2 | 0.2 | 0.3 | 0.8 | 1.3 | 4.8 | 0.4 | 93.2 |
| 173 | 1.8 | | | 0.9 | | 7.9 | | 1.6 | | 23.2 |
| 174 | 2.5 | | | 1.1 | | 7.7 | | 1.8 | | 23.4 |
| 175 | 2.4 | | | 1.1 | | 20.4 | | 3.9 | | 90.3 |
| 176 | 0.2 | | | 0.4 | | 5.5 | | 1.5 | | 43.4 |
| 177 | 0.9 | | | 1.9 | | 3.7 | | 9.0 | | 40.5 |
| 178 | 0.7 | | | 1.0 | | 2.6 | | 4.7 | | 96.5 |
| 179 | 0.9 | 1.3 | 0.4 | 1.3 | 0.6 | 2.8 | 1.5 | 3.6 | 4.1 | >10000 |
| 180 | 5.8 | 8.5 | 2.5 | 9.1 | 6.0 | 30.7 | 12.0 | 67.7 | 47.5 | >10000 |

TABLE 9

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 µM ATP | Km ATP | 100 µM ATP | Km ATP | 100 µM ATP | Km ATP | 100 µM ATP | Km ATP | 100 µM ATP |
| 181 | 5.5 | 10.0 | 2.2 | 20.3 | 16.2 | 41.5 | 19.7 | 157.0 | 129.3 | >10000 |
| 182 | 2.9 | 6.4 | | 1.1 | 1.5 | 3.7 | 0.9 | 3.5 | 4.5 | >10000 |
| 183 | 2.7 | 10.0 | | 1.0 | 1.6 | 3.4 | 0.6 | 3.0 | 3.1 | 678.0 |
| 184 | 9.1 | 2.8 | | 0.8 | 2.7 | 12.2 | 2.2 | 12.9 | 15.2 | >10000 |
| 185 | 2.0 | 8.3 | | 1.9 | 6.7 | 20.3 | 3.0 | 32.1 | 111.2 | >10000 |
| 186 | 3.8 | 29.0 | | 4.8 | 11.5 | 56.8 | 5.8 | 165.2 | 744.2 | >10000 |
| 187 | | 239.2 | | 96.9 | | 178.0 | | 1952.0 | | >10000 |
| 188 | | 1.1 | | 1.0 | 2.3 | 1.8 | 0.8 | 11.3 | 9.5 | >10000 |
| 189 | | 1.4 | | 0.8 | 2.2 | 1.7 | 0.9 | 7.9 | 6.9 | 1774.0 |
| 190 | 3.3 | 4.0 | 0.7 | 3.0 | 6.8 | 20.3 | 3.1 | 31.1 | 32.0 | >10000 |
| 191 | 1.0 | 1.7 | 0.3 | 1.2 | 2.3 | 6.5 | 1.6 | 26.4 | 27.4 | >10000 |
| 192 | | 0.6 | | 0.5 | | 2.0 | | 7.8 | | 6508.0 |
| 193 | | 3.0 | | 3.8 | | 23.5 | | 186.8 | | >10000 |
| 194 | 2.5 | 3.4 | 0.6 | 2.2 | 5.5 | 16.9 | 3.9 | 43.7 | 36.7 | >10000 |
| 195 | 3.3 | 3.6 | 1.0 | 2.5 | 6.6 | 16.3 | 3.6 | 36.9 | 25.0 | >10000 |
| 196 | | 14.7 | | 9.5 | | 134.8 | | >10000 | | |
| 197 | 0.6 | 0.5 | 0.3 | 0.5 | 1.0 | 1.1 | 0.3 | 5.3 | 3.0 | 1237.0 |
| 198 | 0.5 | 0.8 | 0.2 | 0.4 | 0.7 | 2.9 | 0.8 | 2.9 | 3.7 | >10000 |
| 199 | 0.4 | 0.7 | 0.1 | 0.3 | 0.1 | 0.3 | 0.04 | 0.4 | 0.3 | 137.2 |
| 200 | 0.1 | 0.2 | 0.1 | 0.2 | 0.3 | 0.3 | 0.2 | 0.6 | 0.6 | 133.9 |
| 201 | 0.3 | 0.4 | 0.1 | 0.4 | 0.5 | 0.6 | 0.5 | 1.8 | 2.2 | 1039.0 |
| 202 | 0.2 | 0.3 | 0.1 | 0.1 | 0.1 | 0.2 | 0.03 | 0.3 | 0.2 | 94.2 |
| 203 | 0.4 | 0.7 | 0.2 | 0.3 | 0.1 | 0.3 | 0.1 | 0.8 | 0.3 | 394.6 |
| 204 | 0.1 | 0.1 | 0.1 | 0.1 | 0.2 | 0.2 | 0.1 | 1.0 | 0.4 | 124.1 |
| 205 | 0.3 | 0.7 | 0.2 | 0.2 | 0.7 | 0.6 | 0.4 | 3.5 | 2.0 | 1443.0 |
| 206 | 0.6 | 0.9 | 0.3 | 0.4 | 0.7 | 0.6 | 0.4 | 2.4 | 1.2 | 348.2 |
| 207 | 1.3 | 1.6 | 0.3 | 0.8 | 1.4 | 1.5 | 1.0 | 14.0 | 3.8 | 1793.0 |
| 208 | 0.1 | 0.2 | 0.1 | 0.2 | 0.2 | 0.3 | 0.1 | 0.6 | 0.3 | 242.5 |
| 209 | 0.1 | 0.2 | 0.1 | 0.2 | 0.1 | 0.3 | 0.1 | 0.6 | 0.2 | 99.2 |
| 210 | 0.3 | 0.4 | 0.2 | 0.3 | 0.3 | 0.5 | 0.1 | 1.8 | 0.6 | 425.9 |

TABLE 10

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 211 | 0.3 | 0.5 | 0.1 | 0.4 | 1.2 | 2.4 | 0.5 | 30.1 | 6.9 | 9480.0 |
| 212 | 0.5 | 1.0 | 0.4 | 0.6 | 1.2 | 2.7 | 0.5 | 18.7 | 3.4 | 7861.0 |
| 213 | 1.2 | 1.5 | 0.8 | 1.3 | 3.8 | 7.7 | 1.4 | 85.4 | 0.6 | >10000 |
| 214 | 3.0 | 5.6 | 3.5 | 4.5 | 1.8 | 8.0 | 2.2 | 6.9 | 4.5 | 711.4 |
| 215 | 9.1 | 25.4 | 7.6 | 17.5 | 7.8 | 36.4 | 13.6 | 46.4 | 21.4 | 6108.0 |
| 216 | 1.2 | 1.2 | 0.8 | 0.7 | 0.8 | 1.3 | 0.3 | 1.4 | 0.8 | 136.0 |
| 217 | 0.8 | 0.7 | 0.3 | 0.3 | 0.2 | 0.3 | 0.2 | 0.4 | 0.8 | 118.2 |
| 218 | 2.1 | 0.6 | 0.7 | 1.8 | 3.3 | 7.1 | 3.6 | 59.4 | 10.3 | >10000 |
| 219 | 3.2 | 1.8 | 1.5 | 2.9 | 4.9 | 8.7 | 2.9 | 27.4 | 12.1 | 2672.0 |
| 220 | 8.5 | 2.3 | 5.4 | 9.3 | 27.8 | 30.5 | 25.9 | 289.0 | 115.0 | >10000 |
| 221 | 1.1 | 1.4 | 0.3 | 0.5 | 1.1 | 1.5 | 1.0 | 5.7 | 2.1 | 767.0 |
| 222 | 3.9 | 3.4 | 1.7 | 2.0 | 8.9 | 16.8 | 11.7 | 296.2 | 37.4 | >10000 |
| 223 | 6.4 | 3.5 | 2.4 | 5.0 | 10.2 | 14.6 | 4.4 | 115.8 | 11.5 | >10000 |
| 224 | 2.0 | 1.6 | 0.4 | 1.4 | 2.1 | 3.5 | 1.5 | 171.4 | 5.2 | >10000 |
| 225 | 6.9 | 6.0 | 2.5 | 4.4 | 16.1 | 19.8 | 10.2 | 799.0 | 33.8 | >10000 |
| 226 | 0.8 | 0.8 | 0.3 | 0.5 | 1.5 | 4.7 | 2.0 | 8.4 | 4.9 | 5122.0 |
| 227 | 0.9 | 1.5 | 0.4 | 0.8 | 1.9 | 7.0 | 2.5 | 10.0 | 5.2 | 834.8 |
| 228 | 1.9 | 2.9 | 0.5 | 1.0 | 5.6 | 14.3 | 12.2 | 64.9 | 19.3 | >10000 |
| 229 | 3.3 | 4.4 | 0.9 | 1.9 | 4.8 | 20.8 | 11.5 | 96.1 | 17.4 | 9479.0 |
| 230 | 1.1 | 1.3 | 0.4 | 0.6 | 1.7 | 6.0 | 2.4 | 7.8 | 5.0 | 1660.0 |
| 231 | 1.4 | 2.0 | 0.4 | 0.9 | 1.7 | 6.4 | 1.2 | 4.6 | 4.1 | 502.3 |
| 232 | 3.9 | 2.1 | 0.8 | 0.8 | 3.3 | 9.5 | 6.7 | 60.2 | 19.0 | 8760.0 |
| 233 | 4.7 | 6.3 | 0.9 | 2.7 | 7.1 | 19.2 | 4.7 | 36.0 | 18.3 | 6746.0 |
| 234 | 0.5 | 0.3 | 0.2 | 0.2 | 0.2 | 0.5 | 0.3 | 0.7 | 0.7 | 121.7 |
| 235 | 1.0 | 1.5 | 0.8 | 2.7 | 3.1 | 1.5 | 1.0 | 8.1 | 4.9 | 691.7 |
| 236 | 2.5 | 9.1 | 1.9 | 6.4 | 9.1 | 24.4 | 3.0 | 176.5 | 41.8 | >10000 |
| 237 | 0.2 | 0.3 | 0.2 | 0.6 | 0.2 | 0.7 | 0.3 | 1.1 | 0.9 | 216.2 |
| 238 | 28.4 | | 9.2 | | 95.1 | | 18.7 | | 317.4 | |
| 239 | 15.1 | | 3.9 | | 72.7 | | 31.6 | | 216.2 | |
| 240 | 19.8 | | 5.9 | | 134.3 | | 15.4 | | 733.2 | |

TABLE 11

| EX. NO. | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| | Km ATP | 100 μM ATP | Km ATP | 100 μM ATP | Km ATP | 100 μM ATP | Km ATP | 100 μM ATP | Km ATP | 100 μM ATP |
| 241 | 2.3 | 4.4 | 1.8 | 6.9 | 6.3 | 12.9 | 2.9 | 22.0 | 20.3 | 2642.0 |
| 242 | 4.8 | 9.7 | 2.5 | 11.3 | 15.2 | 18.7 | 10.7 | 178.8 | 53.5 | >10000 |
| 243 | 0.4 | 0.8 | 0.4 | 1.3 | 1.9 | 2.4 | 0.2 | 5.3 | 4.2 | 2557.0 |
| 244 | 0.9 | 1.7 | 0.2 | 0.3 | 0.6 | 0.9 | 0.4 | 0.9 | 1.8 | 1422.0 |
| 245 | 1.2 | 2.6 | 0.3 | 0.4 | 1.1 | 2.3 | 0.9 | 3.0 | 3.1 | 2202.0 |
| 246 | 3.0 | 7.2 | 0.4 | 1.1 | 6.9 | 21.1 | 12.4 | 45.2 | 42.0 | >10000 |
| 247 | | 14.7 | | 2.6 | | 80.6 | | 51.1 | 110.9 | >10000 |
| 248 | 0.4 | 0.4 | 0.1 | 0.3 | 2.0 | 5.0 | 1.8 | 9.7 | 4.6 | 7625.0 |
| 249 | 0.5 | | 0.2 | | 0.4 | | 0.2 | | 2.8 | |
| 250 | 0.4 | | 0.2 | | 0.4 | | 0.4 | | 0.3 | |
| 251 | 0.5 | | 0.1 | | 0.2 | | 0.3 | | 0.2 | |
| 252 | 0.3 | | 0.2 | | 0.6 | | 0.4 | | 1.3 | |
| 253 | 0.7 | | 0.4 | | 0.4 | | 0.2 | | 1.0 | |
| 254 | 0.04 | | 0.02 | | 0.1 | | 0.4 | | 0.7 | |
| 255 | 0.1 | | 0.03 | | 0.5 | | 0.02 | | 1.9 | |
| 256 | 0.1 | | 0.1 | | 3.8 | | 0.6 | | 61.6 | |
| 257 | 0.4 | | 0.2 | | 1.0 | | 0.4 | | 7.4 | |
| 258 | 0.2 | | 0.1 | | 0.7 | | 0.1 | | 14.1 | |
| 259 | 1.0 | | 0.4 | | 1.9 | | 0.2 | | 9.0 | |
| 260 | 6.9 | | 4.1 | | 10.7 | | 8.8 | | 7.8 | |
| 261 | 9.6 | | 4.1 | | 10.3 | | 7.5 | | 9.2 | |
| 262 | 1.9 | | 0.5 | | 1.9 | | 0.9 | | 2.0 | |
| 263 | 8.0 | | 3.4 | | 23.1 | | 0.9 | | 14.1 | |
| 264 | 1.1 | | 0.3 | | 1.2 | | 1.6 | | 17.7 | |
| 265 | 31.0 | | 22.0 | | 16.9 | | 85.3 | | 364.5 | |
| 266 | 33.0 | | 18.6 | | 12.5 | | 39.6 | | 168.2 | |
| 267 | 15.4 | | 21.7 | | 82.1 | | 356.8 | | 2915.0 | |

TABLE 11-continued

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 268 | 28.9 | | 22.4 | | 761.8 | | 1217.0 | | 4769.0 | |
| 269 | 0.1 | | 0.1 | | 0.4 | | 0.1 | | 2.6 | |
| 270 | 0.3 | | 0.1 | | 3.2 | | 1.1 | | 36.0 | |

TABLE 12

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 271 | 0.5 | 0.6 | 0.2 | 0.4 | 0.9 | 0.7 | 0.6 | 7.9 | 3.8 | >10000 |
| 272 | 0.3 | 0.5 | 0.1 | 0.3 | 0.6 | 0.7 | 1.0 | 2.5 | 1.4 | 494.9 |
| 273 | | 0.2 | | 0.3 | | 1.0 | | 8.6 | | 2230.0 |
| 274 | 0.02 | 0.1 | 0.03 | 0.1 | 0.1 | 0.1 | 0.1 | 0.4 | 0.5 | 108.5 |
| 275 | 0.9 | 1.1 | 0.7 | 1.2 | 2.5 | 2.6 | 4.1 | 11.4 | 18.5 | >10000 |
| 276 | 0.8 | 1.1 | 0.2 | 0.5 | 0.3 | 0.7 | 0.7 | 2.3 | 2.9 | 2527.0 |
| 277 | 4.4 | 4.7 | 1.6 | 3.3 | 0.9 | 3.9 | 2.2 | 11.2 | 9.8 | >10000 |
| 278 | 0.6 | 0.9 | 0.2 | 0.3 | 0.2 | 0.7 | 0.5 | 0.4 | 1.0 | 769.6 |
| 279 | 2.0 | 2.9 | 0.6 | 1.2 | 1.7 | 5.0 | 0.9 | 6.6 | 11.9 | >10000 |
| 280 | | 1.0 | | 0.5 | | 2.7 | | 20.3 | | >10000 |
| 281 | | 0.2 | | 0.2 | | 0.6 | | 2.1 | | 6337.0 |
| 282 | | 0.2 | | 0.4 | | 1.4 | | 7.0 | | 3973.0 |
| 283 | | 0.1 | | 0.4 | | 0.6 | | 2.3 | | 1971.0 |
| 284 | | 0.1 | | 0.2 | | 0.2 | | 0.4 | | 176.0 |
| 285 | 0.1 | 0.2 | | 0.2 | 0.4 | 0.9 | 0.5 | 14.1 | 7.8 | 6307.0 |
| 286 | 0.2 | 0.3 | 0.1 | 0.3 | 0.3 | 0.3 | 0.1 | 2.5 | 1.5 | 734.9 |
| 287 | 0.2 | 0.3 | 0.1 | 0.1 | 0.4 | 1.0 | 0.8 | 44.0 | 3.0 | 5138.0 |
| 288 | 0.2 | 0.3 | 0.1 | 0.2 | 0.2 | 0.5 | 0.3 | 6.8 | 0.7 | 1995.0 |
| 289 | 0.2 | 0.2 | 0.1 | 0.1 | 0.1 | 0.2 | 0.1 | 0.8 | 0.3 | 205.8 |
| 290 | 0.4 | 0.4 | 0.1 | 0.2 | 0.2 | 0.3 | 0.1 | 0.6 | 0.5 | 117.7 |
| 291 | 0.5 | 1.5 | 0.5 | 1.0 | 1.1 | 4.9 | 2.3 | 2.8 | 3.7 | >10000 |
| 292 | 0.6 | 2.6 | 0.3 | 1.1 | 1.4 | 9.8 | 4.4 | 19.1 | 8.9 | 5169.0 |
| 293 | 0.7 | 3.4 | 0.7 | 1.3 | 9.6 | 16.2 | 15.4 | 63.0 | 137.5 | 1544.0 |
| 294 | 9.8 | | 2.3 | | 60.8 | | 38.5 | | 28.0 | |
| 295 | 10.4 | | 1.5 | | 49.2 | | 26.5 | | 44.7 | |
| 296 | 4.5 | | 3.7 | | 17.6 | | 10.1 | | 89.8 | |
| 297 | 1.6 | | 1.4 | | 4.0 | | 3.0 | | 39.9 | |
| 298 | 1.8 | | 1.1 | | 2.9 | | 1.7 | | 15.4 | |
| 299 | 5.7 | | 3.2 | | 28.6 | | 8.5 | | 245.1 | |
| 300 | 0.3 | | 0.1 | | 0.4 | | 0.2 | | 1.5 | |

TABLE 13

| | del19/T790M/C797S (nM) | | L858R/T790M/C797S (nM) | | del19/C797S (nM) | | L858R/C797S (nM) | | WT (nM) | |
|---|---|---|---|---|---|---|---|---|---|---|
| EX. NO. | Km ATP | 100 μM ATP | Km ATP | 100 μM ATP | Km ATP | 100 μM ATP | Km ATP | 100 μM ATP | Km ATP | 100 μM ATP |
| 301 | 0.3 | | 0.1 | | 0.8 | | 0.3 | | 1.1 | |
| 302 | 0.04 | | 0.04 | | 0.9 | | 0.2 | | 4.7 | |
| 303 | 0.5 | | 0.2 | | 0.4 | | 0.2 | | 5.5 | |
| 304 | 0.4 | | 0.2 | | 1.4 | | 0.3 | | 10.9 | |
| 305 | 0.1 | | 0.1 | | 1.2 | | 0.8 | | 11.2 | |
| 306 | 0.2 | | 0.1 | | 0.5 | | 0.4 | | 14.5 | |
| 307 | 0.02 | | 0.04 | | 0.7 | | 0.6 | | 8.1 | |
| 308 | 0.01 | | 0.02 | | 0.8 | | 0.1 | | 3.0 | |
| 309 | 0.4 | | 0.4 | | 1.9 | | 1.4 | | 45.3 | |
| 310 | 0.7 | | 0.4 | | 7.5 | | 5.5 | | 22.1 | |
| 311 | 2.5 | | 1.6 | | 37.6 | | 3.6 | | 541.1 | |

TABLE 13-continued

| EX. NO. | del19/T790M/C797S (nM) Km ATP | del19/T790M/C797S (nM) 100 µM ATP | L858R/T790M/C797S (nM) Km ATP | L858R/T790M/C797S (nM) 100 µM ATP | del19/C797S (nM) Km ATP | del19/C797S (nM) 100 µM ATP | L858R/C797S (nM) Km ATP | L858R/C797S (nM) 100 µM ATP | WT (nM) Km ATP | WT (nM) 100 µM ATP |
|---|---|---|---|---|---|---|---|---|---|---|
| 312 | 2.1 | | 1.4 | | 13.7 | | 14.3 | | 53.3 | |
| 313 | 2.7 | | 2.1 | | 21.3 | | 4.8 | | 187.2 | |
| 314 | 19.2 | | 33.4 | | 600.0 | | 970.4 | | 6551.0 | |
| 315 | 0.3 | | 0.1 | | 7.0 | | 2.7 | | 165.6 | |
| 316 | 0.1 | | 0.1 | | 1.7 | | 0.7 | | 15.8 | |
| 317 | 0.5 | | 0.2 | | 0.9 | | 0.4 | | 12.4 | |
| 318 | 1.9 | | 1.2 | | 12.6 | | 7.8 | | 14.3 | |
| 319 | 0.3 | | 0.1 | | 23.1 | | 7.3 | | 41.3 | |
| 320 | 3.6 | | 1.0 | | 306.5 | | 28.3 | | 526.2 | |
| 321 | 7.4 | | 0.7 | | 1025.0 | | 53.1 | | 470.4 | |
| 322 | 0.8 | | 0.4 | | 0.7 | | 0.3 | | 0.9 | |
| 323 | 2.4 | | 0.9 | | 3.4 | | 2.1 | | 19.1 | |
| 324 | 5.6 | | 1.2 | | 8.5 | | 6.6 | | 166.7 | |
| 325 | 2.4 | | 1.0 | | 1.7 | | 0.7 | | 9.6 | |
| 326 | 0.1 | | 0.1 | | 7.5 | | 9.6 | | 58.5 | |
| 327 | 0.1 | | 0.0 | | 10.9 | | 10.9 | | 88.3 | |
| 328 | 3.0 | | 1.8 | | 98.0 | | 98.8 | | 178.0 | |
| 329 | 2.0 | | 1.9 | | 17.7 | | 15.0 | | 93.7 | |
| 330 | 1.4 | | 1.3 | | 71.1 | | 94.5 | | 128.5 | |

TABLE 14

| EX. NO. | del19/T790M/C797S (nM) Km ATP | del19/T790M/C797S (nM) 100 µM ATP | L858R/T790M/C797S (nM) Km ATP | L858R/T790M/C797S (nM) 100 µM ATP | del19/C797S (nM) Km ATP | del19/C797S (nM) 100 µM ATP | L858R/C797S (nM) Km ATP | L858R/C797S (nM) 100 µM ATP | WT (nM) Km ATP | WT (nM) 100 µM ATP |
|---|---|---|---|---|---|---|---|---|---|---|
| 331 | 1.9 | | 0.7 | | 3.5 | | 2.4 | | 17.4 | |
| 332 | 1.6 | | 0.7 | | 2.4 | | 1.8 | | 21.0 | |
| 333 | 4.1 | | 2.6 | | 460.1 | | 795.2 | | 116.7 | |
| 334 | 2.1 | | 1.4 | | 169.7 | | 191.4 | | 188.8 | |
| 335 | 5.8 | | 2.6 | | 1838.0 | | 1784.0 | | 248.1 | |
| 336 | 344.7 | | 43.9 | | 3818.0 | | 1675.0 | | 235.5 | |

What is claimed is:

1. A compound of formula (I) or a pharmaceutically acceptable salt thereof,

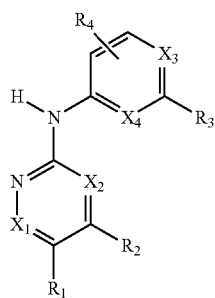

(I)

wherein
$X_1$ and $X_2$ are —CH=,
$X_3$, and $X_4$ are —N=,
$R_1$ is -A or -A-$(R_{1A})_m$,
A is 6-10 membered heteroaryl,
$R_{1A}$ is independently selected from the group consisting of OH;
halogen;
cyano;
$C_{1-6}$alkyl optionally substituted by one or more substituents selected from the group consisting of OH, halogen, $C_{1-3}$alkoxy, $C_{3-6}$cycloalkyl, —NH$C_{1-6}$alkyl, —N($C_{1-6}$alkyl)$_2$, and 4-7 membered heterocyclyl optionally or independently substituted by one or more substituents selected from the group consisting of OH, halogen, and $C_{1-6}$alkyl;
$C_{3-6}$cycloalkyl;
$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;
—NH$C_{1-6}$alkyl optionally substituted by one or more substituents selected from the group consisting of OH, halogen, —N($C_{1-6}$alkyl)$_2$ and 3-7 membered heterocyclyl optionally substituted by one or more substituents selected from the group consisting of OH, halogen, and $C_{1-6}$alkyl;
—NH$C_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more substituents selected from the group consisting of OH, halogen, and $C_{1-6}$alkyl;

—N($C_{1-6}$alkyl)$_2$ optionally substituted by one or more substituents selected from the group consisting of OH and halogen;

—NHC(O)$C_{1-6}$alkyl optionally substituted by one or more substituents selected from the group consisting of OH and halogen;

—NHC(O)$C_{3-6}$cycloalkyl optionally substituted by one or more substituents selected from the group consisting of OH and halogen;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, $C_{1-3}$alkoxy, $C_{1-6}$hydroxyalkyl, and $C_{1-6}$haloalkyl;

—S(O)$_2$$C_{1-6}$alkyl optionally substituted by one or more halogens;

—S(O)$_2$$C_{3-6}$cycloalkyl optionally substituted by one or more halogens;

—S(O)$_2$N($C_{1-6}$alkyl)$_2$ optionally substituted by one or more halogens;

—S(O)$_2$-3-7 membered heterocyclyl optionally substituted by one or more substituents selected from the group consisting of OH, halogen, and $C_{1-6}$alkyl;

—C(O)O$C_{1-6}$alkyl;

—C(O)$C_{1-6}$alkyl; and

—C(O)-3-7 membered heterocyclyl optionally substituted by one or more substituents selected from the group consisting of OH, halogen, and $C_{1-6}$alkyl, m is an integer of 0 to 2, $R_2$ is —X$C_{1-6}$alkyl optionally substituted by one or more substituents selected from the group consisting of OH, halogen, and —N($C_{1-6}$alkyl)$_2$; —X(CH$_2$)$_n$—B or —X(CH$_2$)$_n$—B—($R_{2A}$)$_o$, X is —NH—, —O—, bond or —C≡C—, n is an integer of 0 to 2, is an integer of 0 to 3, B is selected from the group consisting of $C_{3-8}$cycloalkyl, $C_{6-10}$ aryl; 4-11 membered heterocyclyl; and 5-6 membered heteroaryl, $R_{2A}$ is independently selected from the group consisting of

OH;

halogen;

NH$_2$;

$C_{1-6}$alkyl optionally substituted by one or more substituents selected from the group consisting of OH, NH$_2$, halogen, $C_{3-6}$cycloalkyl, $C_{1-3}$alkoxy, —NH$C_{1-6}$ alkyl, —NH$C_{1-6}$hydroxyalkyl, —NH$C_{1-6}$haloalkyl, —NH$C_{3-6}$cycloalkyl, —N($C_{1-6}$alkyl)$_2$, —N($C_{1-6}$haloalkyl)$_2$, —NHC(O)$C_{1-6}$alkyl, —C(O)NH$C_{1-6}$alkyl, —C(O)N($C_{1-6}$alkyl)$_2$, 3-7 membered heterocyclyl and 5-6 membered heteroaryl;

$C_{3-6}$cycloalkyl;

$C_{1-3}$alkoxy optionally substituted by one or more halogens;

—C(O) NH$C_{1-6}$alkyl optionally substituted by one or more substituents selected from the group consisting of OH and halogen;

—C(O)N($C_{1-6}$alkyl)$_2$ optionally substituted by one or more substituents selected from the group consisting of OH and halogen;

—NH$C_{1-6}$alkyl optionally substituted by one or more substituents selected from the group consisting of OH, halogen, —NH$C_{1-6}$alkyl, —N($C_{1-6}$alkyl)$_2$, 3-7 membered heterocyclyl optionally substituted by halogen or —N($C_{1-6}$alkyl)$_2$;

—N($C_{1-6}$alkyl)$_2$ where $C_{1-6}$alkyl is optionally substituted by one or more halogens;

—NH-4-7 membered heterocyclyl optionally substituted by $C_{1-6}$alkyl; and 4-7 membered heterocyclyl, $R_3$ is Y-Q or Y-Q-($R_{3A}$)$_p$, Y is —NH— or bond, Q is selected from the group consisting of acetylene; dihydropyranopyridinyl; 4-7 membered heterocyclyl; $C_{6-10}$ aryl; and 5-10 membered heteroaryl, p is an integer of 0 to 2, $R_{3A}$ is independently selected from the group consisting of

OH;

halogen;

$C_{1-3}$alkoxy;

$C_{1-6}$alkyl optionally substituted by one or more substituents selected from the group consisting of OH, halogen, $C_{3-6}$cycloalkyl, S(O)$_2$$C_{1-6}$alkyl, and $C_{1-3}$alkoxy;

$C_{2-6}$alkenyl;

$C_{3-6}$cycloalkyl;

4-7 membered heterocyclyl;

—C(O)$C_{1-6}$alkyl;

—C(O)N($C_{1-6}$alkyl)$_2$;

—S(O)$_2$$C_{1-6}$alkyl optionally substituted by one or more halogens;

—S(O)$_2$$C_{2-6}$alkenyl;

—S(O)$_2$$C_{3-6}$cycloalkyl optionally substituted by one or more halogens;

—S(O)$_2$N($C_{1-6}$alkyl)$_2$; and

—S(O)$_2$-4-7 membered heterocyclyl optionally substituted by one or more substituents selected from the group consisting of OH and halogen, and $R_4$ is selected from the group consisting of H, halogen and $C_{1-6}$alkyl.

2. The compound of claim 1, or a pharmaceutically acceptable salt thereof, wherein A is pyridinyl, pyrimidinyl, pyridazinyl, or pyrazinyl.

3. The compound of claim 1, or a pharmaceutically acceptable salt thereof, wherein $R_{1A}$ is $C_{1-6}$alkyl optionally substituted by one or more substituents selected from the group consisting of OH, halogen, $C_{1-3}$alkoxy, $C_{3-6}$cycloalkyl, —NH$C_{1-6}$alkyl, —N($C_{1-6}$alkyl)$_2$, and 4-7 membered heterocyclyl optionally substituted by one or more substituents selected from the group consisting of OH, halogen and $C_{1-6}$alkyl.

4. The compound of claim 1, or a pharmaceutically acceptable salt thereof, wherein $R_{1A}$ is independently selected from the group consisting of

OH;

halogen;

cyano;

$C_{1-6}$alkyl optionally substituted by one or more substituents selected from the group consisting of OH, halogen, $C_{1-3}$alkoxy, —N($C_{1-6}$alkyl)$_2$, and 4-7 membered heterocyclyl optionally or independently substituted by one or more substituents selected from the group consisting of OH, halogen, and $C_{1-6}$alkyl;

$C_{1-3}$alkoxy optionally substituted by one or more substituents selected from the group consisting of OH, halogen, —N($C_{1-6}$alkyl)$_2$, and 3-7 membered heterocyclyl optionally or independently substituted by one or more substituents selected from the group consisting of halogen and $C_{1-6}$alkyl;

—NH$C_{1-6}$alkyl optionally substituted by one or more substituents selected from the group consisting of OH, halogen, —N($C_{1-6}$alkyl)$_2$ and 3-7 membered heterocyclyl optionally substituted by one or more halogens;

—NH$C_{3-6}$cycloalkyl optionally substituted by one or more substituents selected from the group consisting of OH, halogen and $C_{1-6}$alkyl optionally substituted by OH;

—NH 3-7 membered heterocyclyl optionally substituted by one or more $C_{1-6}$alkyls;

—N($C_{1-6}$alkyl)$_2$;

—O-4-7 membered heterocyclyl optionally or independently substituted by one or more substituents selected from the group consisting of $C_{1-6}$alkyl and $C_{1-6}$haloalkyl;

4-7 membered heterocyclyl optionally or independently substituted by one or more substituents selected from the group consisting of OH, halogen, $C_{1-6}$alkyl, and $C_{1-3}$alkoxy;

—S(O)$_2$$C_{1-6}$alkyl;

—S(O)$_2$N($C_{1-6}$alkyl)$_2$;

—S(O)$_2$-3-7 membered heterocyclyl optionally substituted by one or more $C_{1-6}$alkyls;

—C(O)$C_{1-6}$alkyl; and

—C(O)-3-7 membered heterocyclyl optionally substituted by one or more $C_{1-6}$alkyls.

5. The compound of claim 4, or a pharmaceutically acceptable salt thereof, wherein the 3-7 membered heterocyclyl or 4-7 membered heterocyclyl is independently selected from the group consisting of azetidinyl, piperidinyl, piperazinyl, morpholinyl, tetrahydropyranyl, tetrahydrofuranyl, oxetanyl, 2-oxa-6-azaspiro[3.3]heptanyl, and pyrrolidinyl.

6. The compound of claim 1, or a pharmaceutically acceptable salt thereof, wherein $R_2$ is —X$C_{1-6}$alkyl.

7. The compound of claim 1, or a pharmaceutically acceptable salt thereof, wherein $R_2$ is —X(CH$_2$)$_n$—B—(R$_{2A}$)$_o$.

8. The compound of claim 1, or a pharmaceutically acceptable salt thereof, wherein X is —NH— or bond.

9. The compound of claim 1, or a pharmaceutically acceptable salt thereof, wherein B is $C_{3-6}$cycloalkyl; phenyl; 4-10 membered heterocycloalkyl having one to three heteroatoms selected from a group consisting of N, O and S; or 5-6 membered heteroaryl having one to three heteroatoms selected from a group consisting of N, O and S.

10. The compound of claim 1, or a pharmaceutically acceptable salt thereof, wherein B is $C_{3-6}$cycloalkyl.

11. The compound of claim 1, or a pharmaceutically acceptable salt thereof, wherein B is 4-10 membered heterocycloalkyl or 5-6 membered heteroaryl having one to three heteroatoms selected from a group consisting of N and O.

12. The compound of claim 1, or a pharmaceutically acceptable salt thereof, wherein B is $C_{3-8}$cycloalkyl, piperidinyl, or oxetanyl.

13. The compound of claim 1, or a pharmaceutically acceptable salt thereof, wherein $R_{2A}$ is OH; halogens; $C_{1-6}$alkyl optionally substituted by one or more substituents selected from the group consisting of OH, NH$_2$, halogen, $C_{3-6}$cycloalkyl, $C_{1-3}$alkoxy, —NH$C_{1-6}$alkyl, —NH$C_{1-6}$hydroxyalkyl, —NH$C_{1-6}$haloalkyl, —NH$C_{3-6}$cycloalkyl, —N($C_{1-6}$alkyl)$_2$, —N($C_{1-6}$haloalkyl)$_2$, —NHC(O)$C_{1-6}$alkyl, —C(O) NH$C_{1-6}$alkyl, —C(O)N($C_{1-6}$alkyl)$_2$, 3-7 membered heterocyclyl and 5-6 membered heteroaryl having one to three heteroatoms selected from a group consisting of N, O and S; —C(O) NH$C_{1-3}$alkyl optionally substituted by one to three substituents selected from the group consisting of OH, F and Cl; —C(O)N($C_{1-3}$alkyl)$_2$ optionally substituted by one to three substituents selected from the group consisting of OH, F and Cl; or —NH$C_{1-3}$alkyl optionally substituted by one to three substituents selected from the group consisting of OH, halogen, —NH$C_{1-3}$alkyl, —N($C_{1-3}$alkyl)$_2$, 3-7 membered heterocyclyl one to three heteroatoms selected from a group consisting of N, O and S optionally substituted by halogen or —N($C_{1-3}$alkyl)$_2$.

14. The compound of claim 1, or a pharmaceutically acceptable salt thereof, wherein $R_{2A}$ is independently selected from the group consisting of

OH;

halogen;

$C_{1-6}$alkyl optionally substituted by one or more substituents selected from the group consisting of OH, halogen, and —N($C_{1-6}$alkyl)$_2$;

—C(O)N($C_{1-6}$alkyl)$_2$; and

—NH$C_{1-6}$alkyl optionally substituted by one or more halogens.

15. The compound of claim 1, or a pharmaceutically acceptable salt thereof, wherein Y is bond.

16. The compound of claim 1, or a pharmaceutically acceptable salt thereof, wherein Q is pyrazolyl, 3,4-dihydropyrano[2,3-b]pyridinyl, or piperidinyl.

17. The compound of claim 1, or a pharmaceutically acceptable salt thereof, wherein $R_{3A}$ is independently selected from the group consisting of

OH;

halogen;

$C_{1-3}$alkoxy;

$C_{1-6}$alkyl optionally substituted by one or more halogens;

—S(O)$_2$$C_{3-6}$cycloalkyl; and

—S(O)$_2$N($C_{1-6}$alkyl)$_2$.

18. The compound of claim 1, or a pharmaceutically acceptable salt thereof, wherein $R^4$ is H or halogen.

19. The compound of claim 1, which is selected from any one of the compounds as described below, or a pharmaceutically acceptable salt thereof;

(1) (1-(6'-((2-(1-(Cyclopropylsulfonyl)-1H-pyrazol-4-yl) pyrimidin-4-yl)amino)-5-((4-methylpiperazin-1-yl) methyl)-[2,3'-bipyridin]-4'-yl)-4-methylpiperidin-4-yl) methanol;

(2) N$^{6'}$-(2-(1-(Cyclopropylsulfonyl)-1H-pyrazol-4-yl)pyrimidin-4-yl)-N$^{4'}$-((1 s,4s)-4-((2-fluoroethyl)amino)cyclohexyl)-5-((4-methylpiperazin-1-yl)methyl)-[2,3'-bipyridine]-4',6'-diamine;

(3) (1s,4s)-4-((6'-((2-(1-(Cyclopropylsulfonyl)-1H-pyrazol-4-yl)pyrimidin-4-yl)amino)-3-methoxy-[2,3'-bipyridin]-4'-yl)amino)-1-methylcyclohexan-1-ol;

(4) (1s,4s)-4-((6'-((2-(1-(Cyclopropylsulfonyl)-1H-pyrazol-4-yl)pyrimidin-4-yl)amino)-3-fluoro-[2,3'-bipyridin]-4'-yl)amino)-1-methylcyclohexan-1-ol;

(5) (1s,4s)-4-((6'-((2-(1-(Cyclopropylsulfonyl)-1H-pyrazol-4-yl)pyrimidin-4-yl)amino)-5-(hydroxymethyl)-[2, 3'-bipyridin]-4'-yl)amino)-1-methylcyclohexan-1-ol;

(6) (1s,4s)-4-((6'-((2-(1-(Cyclopropylsulfonyl)-1H-pyrazol-4-yl)pyrimidin-4-yl)amino)-5-fluoro-[2,3'-bipyridin]-4'-yl)amino)-1-methylcyclohexan-1-ol;

(7) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridine]-5-carbonitrile;

(8) (1s,4s)-4-((6'-((2-(1-(Cyclopropylsulfonyl)-1H-pyrazol-4-yl)pyrimidin-4-yl)amino)-5-methyl-[2,3'-bipyridin]-4'-yl)amino)-1-methylcyclohexan-1-ol;

(9) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-methylcyclohexan-1-ol;

(10) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)cyclohexyl)methanol;

(11) (1s,4s)-4-((6'-((2-(1-(Cyclopropylsulfonyl)-1H-pyrazol-4-yl)pyrimidin-4-yl)amino)-5-((4-methylpiperazin-1-yl)methyl)-[2,3'-bipyridin]-4'-yl)amino)-1-(hydroxymethyl)cyclohexan-1-ol;

(12) (1s,4s)-4-((6'-((2-(1-(Cyclopropylsulfonyl)-1H-pyrazol-4-yl)pyrimidin-4-yl)amino)-4-methyl-[2,3'-bipyridin]-4'-yl)amino)-1-methylcyclohexan-1-ol;

(13) (1s,4s)-4-((6'-((2-(1-(Cyclopropylsulfonyl)-1H-pyrazol-4-yl)pyrimidin-4-yl)amino)-3-fluoro-4-(hydroxymethyl)-[2,3'-bipyridin]-4'-yl)amino)-1-methylcyclohexan-1-ol;

(14) (1s,4s)-4-((6'-((2-(1-(cyclopropylsulfonyl)-1H-pyrazol-4-yl)pyrimidin-4-yl)amino)-6-(trifluoromethyl)-[2,3'-bipyridin]-4'-yl)amino)-1-methylcyclohexan-1-ol;

(15) (1s,4s)-4-((6'-((2-(1-(Cyclopropylsulfonyl)-1H-pyrazol-4-yl)pyrimidin-4-yl)amino)-6-methyl-[2,3'-bipyridin]-4'-yl)amino)-1-methylcyclohexan-1-ol;

(16) (1s,4s)-4-((6'-((2-(1-(Cyclopropylsulfonyl)-1H-pyrazol-4-yl)pyrimidin-4-yl)amino)-4-(hydroxymethyl)-[2,3'-bipyridin]-4'-yl)amino)-1-methylcyclohexan-1-ol;

(17) (1s,4s)-4-((6'-((2-(1-(Cyclopropylsulfonyl)-1H-pyrazol-4-yl)pyrimidin-4-yl)amino)-5-(trifluoromethyl)-[2,3'-bipyridin]-4'-yl)amino)-1-methylcyclohexan-1-ol;

(18) 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-6-yl)ethan-1-one;

(19) (1s,4s)-4-((6'-((2-(1-(Cyclopropylsulfonyl)-1H-pyrazol-4-yl)pyrimidin-4-yl)amino)-6-fluoro-4-methyl-[2,3'-bipyridin]-4'-yl)amino)-1-methylcyclohexan-1-ol;

(20) (1s,4s)-4-((6'-((2-(1-(Cyclopropylsulfonyl)-1H-pyrazol-4-yl)pyrimidin-4-yl)amino)-4-(trifluoromethyl)-[2,3'-bipyridin]-4'-yl)amino)-1-methylcyclohexan-1-ol;

(21) (6'-((2-(1-(Cyclopropylsulfonyl)-1H-pyrazol-4-yl)pyrimidin-4-yl)amino)-4'-(((1s,4s)-4-((2-fluoroethyl)amino)cyclohexyl)amino)-[2,3'-bipyridin]-5-yl)methanol;

(22) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methanol;

(23) (1s,4s)-4-((6'-((2-(1-(Cyclopropylsulfonyl)-1H-pyrazol-4-yl)pyrimidin-4-yl)amino)-6-(1-hydroxyethyl)-[2,3'-bipyridin]-4'-yl)amino)-1-methylcyclohexan-1-ol;

(24) 2-((1s,4s)-4-((6'-((2-(1-(Cyclopropylsulfonyl)-1H-pyrazol-4-yl)pyrimidin-4-yl)amino)-5-(hydroxymethyl)-[2,3'-bipyridin]-4'-yl)amino)cyclohexyl)propan-2-ol;

(25) 2-((1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)cyclohexyl)propan-2-ol;

(26) 2-((1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)cyclohexyl)propan-2-ol;

(27) (1s,4s)-4-((6'-((2-(1-(Cyclopropylsulfonyl)-1H-pyrazol-4-yl)pyrimidin-4-yl)amino)-6-(hydroxymethyl)-[2,3'-bipyridin]-4'-yl)amino)-1-methylcyclohexan-1-ol;

(28) (1s,4s)-4-((6'-((2-(1-(Cyclopropylsulfonyl)-1H-pyrazol-4-yl)pyrimidin-4-yl)amino)-6-((4-methylpiperazin-1-yl)methyl)-[2,3'-bipyridin]-4'-yl)amino)-1-methylcyclohexan-1-ol;

(29) (1s,4s)-4-((6'-((2-(1-(Cyclopropylsulfonyl)-1H-pyrazol-4-yl)pyrimidin-4-yl)amino)-6-(morpholinomethyl)-[2,3'-bipyridin]-4'-yl)amino)-1-methylcyclohexan-1-ol;

(30) (1s,4s)-4-((6'-((2-(1-(Cyclopropylsulfonyl)-1H-pyrazol-4-yl)pyrimidin-4-yl)amino)-6-((dimethylamino)methyl)-[2,3'-bipyridin]-4'-yl)amino)-1-methylcyclohexan-1-ol;

(31) (1s,4s)-4-((6'-((2-(1-(Cyclopropylsulfonyl)-1H-pyrazol-4-yl)pyrimidin-4-yl)amino)-5-((dimethylamino)methyl)-[2,3'-bipyridin]-4'-yl)amino)-1-methylcyclohexan-1-ol;

(32) (1s,4s)-4-((6'-((2-(1-(Cyclopropylsulfonyl)-1H-pyrazol-4-yl)pyrimidin-4-yl)amino)-5-(morpholinomethyl)-[2,3'-bipyridin]-4'-yl)amino)-1-methylcyclohexan-1-ol;

(33) (1s,4s)-4-((6'-((2-(1-(Cyclopropylsulfonyl)-1H-pyrazol-4-yl)pyrimidin-4-yl)amino)-5-((4,4-difluoropiperidin-1-yl)methyl)-[2,3'-bipyridin]-4'-yl)amino)-1-methylcyclohexan-1-ol;

(34) (1s,4s)-4-((6'-((2-(1-(Cyclopropylsulfonyl)-1H-pyrazol-4-yl)pyrimidin-4-yl)amino)-5-((4-isopropylpiperazin-1-yl)methyl)-[2,3'-bipyridin]-4'-yl)amino)-1-methylcyclohexan-1-ol;

(35) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-methylcyclohexan-1-ol;

(36) $N^{6'}$-(2-(1-(Cyclopropylsulfonyl)-1H-pyrazol-4-yl)pyrimidin-4-yl)-$N^{4'}$-((1s,4s)-4-((2-fluoroethyl)amino)cyclohexyl)-[2,3'-bipyridine]-4',6'-diamine;

(37) (1s,4s)-4-((6'-((2-(1-(Cyclopropylsulfonyl)-1H-pyrazol-4-yl)pyrimidin-4-yl)amino)-[2,3'-bipyridin]-4'-yl)amino)-1-(hydroxymethyl)cyclohexan-1-ol;

(38) (1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)-1-methylcyclohexan-1-ol;

(39) (1s,4s)-4-((2-((2-(1-(Cyclopropylsulfonyl)-1H-pyrazol-4-yl)pyrimidin-4-yl)amino)-5-(5-(dimethylamino)pyrimidin-2-yl)pyridin-4-yl)amino)-1-methylcyclohexan-1-ol;

(40) (1s,4s)-4-((6'-((2-(1-(Cyclopropylsulfonyl)-1H-pyrazol-4-yl)pyrimidin-4-yl)amino)-5-(dimethylamino)-[2,3'-bipyridin]-4'-yl)amino)-1-methylcyclohexan-1-ol;

(41) (1s,4s)-4-((2-((2-(1-(Cyclopropylsulfonyl)-1H-pyrazol-4-yl)pyrimidin-4-yl)amino)-5-(4-(dimethylamino)pyrimidin-2-yl)pyridin-4-yl)amino)-1-methylcyclohexan-1-ol;

(42) (1s,4s)-4-((2-((2-(1-(Cyclopropylsulfonyl)-1H-pyrazol-4-yl)pyrimidin-4-yl)amino)-5-(pyridazin-3-yl)pyridin-4-yl)amino)-1-methylcyclohexan-1-ol;

(43) (1s,4s)-4-((2-((2-(1-(Cyclopropylsulfonyl)-1H-pyrazol-4-yl)pyrimidin-4-yl)amino)-5-(6-morpholinopyridazin-3-yl)pyridin-4-yl)amino)-1-methylcyclohexan-1-ol;

(44) (1s,4s)-4-((2-((2-(1-(Cyclopropylsulfonyl)-1H-pyrazol-4-yl)pyrimidin-4-yl)amino)-5-(5-morpholinopyrazin-2-yl)pyridin-4-yl)amino)-1-methylcyclohexan-1-ol;

(45) 2-((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)propan-2-ol;

(46) (1s,4s)-4-((2-((2-(1-(Cyclopropylsulfonyl)-1H-pyrazol-4-yl)pyrimidin-4-yl)amino)-5-(6-(4-methylpiperazin-1-yl)pyridazin-3-yl)pyridin-4-yl)amino)-1-methylcyclohexan-1-ol;

(47) (1s,4s)-4-((6'-((2-(1-(Cyclopropylsulfonyl)-1H-pyrazol-4-yl)pyrimidin-4-yl)amino)-5-(4,4-difluoropiperidin-1-yl)-[2,3'-bipyridin]-4'-yl)amino)-1-methylcyclohexan-1-ol;

(48) (1s,4s)-4-((6'-((2-(1-(Cyclopropylsulfonyl)-1H-pyrazol-4-yl)pyrimidin-4-yl)amino)-4-morpholino-[2,3'-bipyridin]-4'-yl)amino)-1-methylcyclohexan-1-ol;

(49) 1-(6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl) piperidin-4-ol;

(50) (1s,4s)-4-((2-((2-(1-(Cyclopropylsulfonyl)-1H-pyrazol-4-yl)pyrimidin-4-yl)amino)-5-(5,6-dimethylpyridazin-3-yl)pyridin-4-yl)amino)-1-methylcyclohexan-1-ol;

(51) (1s,4s)-4-((2-((2-(1-(Cyclopropylsulfonyl)-1H-pyrazol-4-yl)pyrimidin-4-yl)amino)-5-(6-(trifluoromethyl)pyridazin-3-yl)pyridin-4-yl)amino)-1-methylcyclohexan-1-ol;

(52) (1s,4s)-4-((2-((2-(1-(Cyclopropylsulfonyl)-1H-pyrazol-4-yl)pyrimidin-4-yl)amino)-5-(6-methylpyridazin-3-yl)pyridin-4-yl)amino)-1-methylcyclohexan-1-ol;

(53) (1s,4s)-4-((2-((2-(1-(Cyclopropylsulfonyl)-1H-pyrazol-4-yl)pyrimidin-4-yl)amino)-5-(6-methoxypyridazin-3-yl)pyridin-4-yl)amino)-1-methylcyclohexan-1-ol;

(54) (1s,4s)-4-((6'-((2-(1-(Cyclopropylsulfonyl)-1H-pyrazol-4-yl)pyrimidin-4-yl)amino)-5-(piperidin-1-yl)-[2,3'-bipyridin]-4'-yl)amino)-1-methylcyclohexan-1-ol;

(55) (1s,4s)-4-((6'-((2-(1-(Cyclopropylsulfonyl)-1H-pyrazol-4-yl)pyrimidin-4-yl)amino)-4-((4-methylpiperazin-1-yl)methyl)-[2,3'-bipyridin]-4'-yl)amino)-1-methylcyclohexan-1-ol;

(56) (1s,4s)-4-((2-((2-(1-(Cyclopropylsulfonyl)-1H-pyrazol-4-yl)pyrimidin-4-yl)amino)-5-(5-methoxypyrazin-2-yl)pyridin-4-yl)amino)-1-methylcyclohexan-1-ol;

(57) ((1s,4s)-4-((6'-((2-(1-(Cyclopropylsulfonyl)-1H-pyrazol-4-yl)pyrimidin-4-yl)amino)-5-morpholino-[2,3'-bipyridin]-4'-yl)amino)cyclohexyl)methanol;

(58) (1s,4s)-4-((6'-((2-(1-(Cyclopropylsulfonyl)-1H-pyrazol-4-yl)pyrimidin-4-yl)amino)-4-(4-methylpiperazin-1-yl)-[2,3'-bipyridin]-4'-yl)amino)-1-methylcyclohexan-1-ol;

(59) (1s,4s)-4-((2-((2-(1-(Cyclopropylsulfonyl)-1H-pyrazol-4-yl)pyrimidin-4-yl)amino)-5-(5-methylpyrazin-2-yl)pyridin-4-yl)amino)-1-methylcyclohexan-1-ol;

(60) (1s,4s)-4-((2-((2-(1-(Cyclopropylsulfonyl)-1H-pyrazol-4-yl)pyrimidin-4-yl)amino)-5-(5-(hydroxymethyl)pyrazin-2-yl)pyridin-4-yl)amino)-1-methylcyclohexan-1-ol;

(61) (1s,4s)-4-((6'-((2-(1-(Cyclopropylsulfonyl)-1H-pyrazol-4-yl)pyrimidin-4-yl)amino)-4-(morpholinomethyl)-[2,3'-bipyridin]-4'-yl)amino)-1-methylcyclohexan-1-ol;

(62) (1s,4s)-4-((2-((2-(1-(Cyclopropylsulfonyl)-1H-pyrazol-4-yl)pyrimidin-4-yl)amino)-5-(5-((4-methylpiperazin-1-yl)methyl) pyrazin-2-yl)pyridin-4-yl)amino)-1-methylcyclohexan-1-ol;

(63) (1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)-1-methylcyclohexan-1-ol;

(64) (1s,4s)-4-((6'-((2-(1-(Cyclopropylsulfonyl)-1H-pyrazol-4-yl)pyrimidin-4-yl)amino)-4-((dimethylamino)methyl)-[2,3'-bipyridin]-4'-yl)amino)-1-methylcyclohexan-1-ol;

(65) (1s,4s)-4-((2-((2-(1-(Cyclopropylsulfonyl)-1H-pyrazol-4-yl)pyrimidin-4-yl)amino)-5-(5-((dimethylamino)methyl) pyrazin-2-yl)pyridin-4-yl)amino)-1-methylcyclohexan-1-ol;

(66) (1s,4s)-4-((2-((2-(1-(Cyclopropylsulfonyl)-1H-pyrazol-4-yl)pyrimidin-4-yl)amino)-5-(6-(3,3-difluoroazetidin-1-yl)pyridazin-3-yl)pyridin-4-yl)amino)-1-methylcyclohexan-1-ol;

(67) (1s,4s)-4-((5-(6-(2-Oxa-6-azaspiro[3.3]heptan-6-yl)pyridazin-3-yl)-2-((2-(1-(cyclopropylsulfonyl)-1H-pyrazol-4-yl)pyrimidin-4-yl)amino)pyridin-4-yl)amino)-1-methylcyclohexan-1-ol;

(68) (1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)-1-methylcyclohexan-1-ol;

(69) ((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)methanol;

(70) ((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)methanol;

(71) 2-((1s,4s)-4-((2-((2-(1-(Cyclopropylsulfonyl)-1H-pyrazol-4-yl)pyrimidin-4-yl)amino)-5-(6-(4,4-difluoropiperidin-1-yl)pyridazin-3-yl)pyridin-4-yl)amino)cyclohexyl)propan-2-ol;

(72) 2-((1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)cyclohexyl)propan-2-ol;

(73) $N^2$-(2-(1-(Cyclopropylsulfonyl)-1H-pyrazol-4-yl)pyrimidin-4-yl)-5-(6-(4,4-difluoropiperidin-1-yl)pyridazin-3-yl)-$N^4$-((1s,4s)-4-((dimethylamino)methyl)cyclohexyl)pyridine-2,4-diamine;

(74) $N^2$-(2-(1-(Cyclopropylsulfonyl)-1H-pyrazol-4-yl)pyrimidin-4-yl)-5-(5-(4,4-difluoropiperidin-1-yl) pyrazin-2-yl)-$N^4$-((1s,4s)-4-((dimethylamino)methyl)cyclohexyl)pyridine-2,4-diamine;

(75) (1s,4s)-4-((2-((2-(1-(Cyclopropylsulfonyl)-1H-pyrazol-4-yl)pyrimidin-4-yl)amino)-5-(5-(4,4-difluoropiperidin-1-yl) pyrazin-2-yl)pyridin-4-yl)amino)-1-methylcyclohexan-1-ol;

(76) (1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)-1-methylcyclohexan-1-ol;

(77) ((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)methanol;
(78) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)propan-2-ol;
(79) $N^{6'}$-(2-(1-(Cyclopropylsulfonyl)-1H-pyrazol-4-yl)pyrimidin-4-yl)-4-(difluoromethyl)-$N^{4'}$-((1s,4s)-4-((dimethylamino)methyl)cyclohexyl)-[2,3'-bipyridine]-4',6'-diamine;
(80) (1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)-1-methylcyclohexan-1-ol;
(81) ((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)methanol;
(82) 2-((1s,4s)-4-((6'-((2-(1-(Cyclopropylsulfonyl)-1H-pyrazol-4-yl)pyrimidin-4-yl)amino)-5-(pyrrolidin-1-yl)-[2,3'-bipyridin]-4'-yl)amino)cyclohexyl)propan-2-ol;
(83) (1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)-1-methylcyclohexan-1-ol;
(84) 2-((1s,4s)-4-((6'-((2-(1-(Cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)propan-2-ol;
(85) ((1s,4s)-4-((6'-((2-(1-(cyclopropylsulfonyl)-1H-pyrazol-4-yl)pyrimidin-4-yl)amino)-5-(4-methylpiperazin-1-yl)-[2,3'-bipyridin]-4'-yl)amino)cyclohexyl)methanol;
(86) (1s,4s)-4-((2-((2-(1-(Cyclopropylsulfonyl)-1H-pyrazol-4-yl)pyrimidin-4-yl)amino)-5-(6-(2-hydroxypropan-2-yl)pyridazin-3-yl)pyridin-4-yl)amino)-1-methylcyclohexan-1-ol;
(87) 2-(6-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyridazin-3-yl)propan-2-ol;
(88) 2-(6-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyridazin-3-yl)propan-2-ol;
(89) 2-(6-(6-((2-(1-(Cyclopropylsulfonyl)-1H-pyrazol-4-yl)pyrimidin-4-yl)amino)-4-(((1s,4s)-4-((dimethylamino)methyl)cyclohexyl)amino)pyridin-3-yl)pyridazin-3-yl)propan-2-ol;
(90) (1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)-1-methylcyclohexan-1-ol;
(91) ((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)methanol;
(92) 2-((1s,4s)-4-((6'-((2-(1-(Cyclopropylsulfonyl)-1H-pyrazol-4-yl)pyrimidin-4-yl)amino)-5-(3-methoxyazetidin-1-yl)-[2,3'-bipyridin]-4'-yl)amino)cyclohexyl)propan-2-ol;
(93) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(3-methoxyazetidin-1-yl)-[2,3'-bipyridine]-4',6'-diamine;
(94) 2-((1s,4s)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol;
(95) 2-((1r,4r)-4-((6'-((2-(1-(Cyclopropylsulfonyl)-1H-pyrazol-4-yl)pyrimidin-4-yl)amino)-5-(difluoromethyl)-[2,3'-bipyridin]-4'-yl)amino)cyclohexyl)ethan-1-ol;
(96) 2-((1r,4r)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol;
(97) 2-((1s,4s)-4-((6'-((2-(1-(Cyclopropylsulfonyl)-1H-pyrazol-4-yl)pyrimidin-4-yl)amino)-4-(difluoromethyl)-[2,3'-bipyridin]-4'-yl)amino)cyclohexyl)ethan-1-ol;
(98) 1-((6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)methyl) piperidin-4-ol;
(99) 1-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)methyl)piperidin-4-ol;
(100) ((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)methanol;
(101) $N^{6'}$-(2-(1-(Cyclopropylsulfonyl)-1H-pyrazol-4-yl)pyrimidin-4-yl)-4-(4,4-difluoropiperidin-1-yl)-$N^{4'}$-((1s,4s)-4-((dimethylamino)methyl)cyclohexyl)-[2,3'-bipyridine]-4',6'-diamine;
(102) (1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)-1-methylcyclohexan-1-ol;
(103) 2-((1s,4s)-4-((6'-((2-(1-(Cyclopropylsulfonyl)-1H-pyrazol-4-yl)pyrimidin-4-yl)amino)-4-(4,4-difluoropiperidin-1-yl)-[2,3'-bipyridin]-4'-yl)amino)cyclohexyl)propan-2-ol;
(104) (1s,4s)-4-((6'-((2-(1-(Cyclopropylsulfonyl)-1H-pyrazol-4-yl)pyrimidin-4-yl)amino)-5-fluoro-4-(2-hydroxypropan-2-yl)-[2,3'-bipyridin]-4'-yl)amino)-1-methylcyclohexan-1-ol;
(105) 2-(6'-((2-(1-(Cyclopropylsulfonyl)-1H-pyrazol-4-yl)pyrimidin-4-yl)amino)-5-fluoro-4'-(((1s,4s)-4-(hydroxymethyl)cyclohexyl)amino)-[2,3'-bipyridin]-4-yl)propan-2-ol;
(106) 2-(6'-((2-(1-(Cyclopropylsulfonyl)-1H-pyrazol-4-yl)pyrimidin-4-yl)amino)-5-fluoro-4'-(((1s,4s)-4-(2-hydroxypropan-2-yl)cyclohexyl)amino)-[2,3'-bipyridin]-4-yl)propan-2-ol;
(107) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-5-fluoro-[2,3'-bipyridin]-4-yl)propan-2-ol;
(108) (1s,4s)-4-((6'-((2-(1-(Cyclopropylsulfonyl)-1H-pyrazol-4-yl)pyrimidin-4-yl)amino)-4-(2-hydroxypropan-2-yl)-[2,3'-bipyridin]-4'-yl)amino)-1-methylcyclohexan-1-ol;
(109) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-4-yl)propan-2-ol;

(110) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-4-yl)propan-2-ol;

(111) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-4-yl)propan-2-ol;

(112) (1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)-1-methylcyclohexan-1-ol;

(113) ((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)methanol;

(114) 2-((1s,4s)-4-((6'-((2-(1-(Cyclopropylsulfonyl)-1H-pyrazol-4-yl)pyrimidin-4-yl)amino)-4-((4,4-difluoropiperidin-1-yl)methyl)-[2,3'-bipyridin]-4'-yl)amino)cyclohexyl)propan-2-ol;

(115) (1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)-1-methylcyclohexan-1-ol;

(116) ((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)methanol;

(117) 2-((1s,4s)-4-((2-((2-(1-(Cyclopropylsulfonyl)-1H-pyrazol-4-yl)pyrimidin-4-yl)amino)-5-(5-(2-(dimethylamino) ethoxy) pyrazin-2-yl)pyridin-4-yl)amino)cyclohexyl)propan-2-ol;

(118) (1s,4s)-4-((2-((2-(1-(Cyclopropylsulfonyl)-1H-pyrazol-4-yl)pyrimidin-4-yl)amino)-5-(5-(2-hydroxypropan-2-yl) pyrazin-2-yl)pyridin-4-yl)amino)-1-methylcyclohexan-1-ol;

(119) 2-(5-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl) pyrazin-2-yl)propan-2-ol;

(120) 2-(5-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl) pyrazin-2-yl)propan-2-ol;

(121) 2-(5-(6-((2-(1-(Cyclopropylsulfonyl)-1H-pyrazol-4-yl)pyrimidin-4-yl)amino)-4-(isopropylamino)pyridin-3-yl) pyrazin-2-yl)propan-2-ol;

(122) $N^2$-(2-(1-(Cyclopropylsulfonyl)-1H-pyrazol-4-yl)pyrimidin-4-yl)-5-(5-(2-(dimethylamino) ethoxy) pyrazin-2-yl)-$N^4$-isopropylpyridine-2,4-diamine;

(123) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-morpholino-[2,3'-bipyridine]-4',6'-diamine;

(124) $N^{6'}$-(2-(1-(Cyclopropylsulfonyl)-1H-pyrazol-4-yl)pyrimidin-4-yl)-$N^{4'}$-isopropyl-5-morpholino-[2,3'-bipyridine]-4',6'-diamine;

(125) $N^{6'}$-(2-(1-(Cyclopropylsulfonyl)-1H-pyrazol-4-yl)pyrimidin-4-yl)-$N^{4'}$-isopropyl-5-(morpholinomethyl)-[2,3'-bipyridine]-4',6'-diamine;

(126) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-(morpholinomethyl)-[2,3'-bipyridine]-4',6'-diamine;

(127) $N^2$-(2-(1-(Cyclopropylsulfonyl)-1H-pyrazol-4-yl)pyrimidin-4-yl)-5-(5-(difluoromethoxy) pyrazin-2-yl)-$N^4$-isopropylpyridine-2,4-diamine;

(128) (1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)-1-methylcyclohexan-1-ol;

(129) ((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)methanol;

(130) 2-((1s,4s)-4-((2-((2-(1-(Cyclopropylsulfonyl)-1H-pyrazol-4-yl)pyrimidin-4-yl)amino)-5-(5-(difluoromethoxy) pyrazin-2-yl)pyridin-4-yl)amino)cyclohexyl)propan-2-ol;

(131) $N^2$-(2-(1-(Cyclopropylsulfonyl)-1H-pyrazol-4-yl)pyrimidin-4-yl)-5-(5-(difluoromethoxy) pyrazin-2-yl)-$N^4$-((1s,4s)-4-((dimethylamino)methyl)cyclohexyl)pyridine-2,4-diamine;

(132) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-((1-methylpiperidin-4-yl)oxy)-[2,3'-bipyridine]-4',6'-diamine;

(133) $N^{6'}$-(2-(1-(2,2-Difluoroethyl)-1H-pyrazol-4-yl)pyrimidin-4-yl)-$N^{4'}$-((1s,4s)-4-fluorocyclohexyl)-5-((1-methylpiperidin-4-yl)oxy)-[2,3'-bipyridine]-4',6'-diamine;

(134) (1s,4s)-4-((2-((2-(1-(Cyclopropylsulfonyl)-1H-pyrazol-4-yl)pyrimidin-4-yl)amino)-5-(5-(trifluoromethyl) pyrazin-2-yl)pyridin-4-yl)amino)-1-methylcyclohexan-1-ol;

(135) $N^{6'}$-(2-(1-(2,2-Difluoroethyl)-1H-pyrazol-4-yl)pyrimidin-4-yl)-$N^{4'}$-((1s,4s)-4-fluorocyclohexyl)-5-((4-methylpiperazin-1-yl)methyl)-[2,3'-bipyridine]-4',6'-diamine;

(136) $N^{6'}$-(2-(1-(2,2-difluoroethyl)-1H-pyrazol-4-yl)pyrimidin-4-yl)-$NA'$-(1 s,4s)-4-fluorocyclohexyl)-5-(morpholinomethyl)-[2,3'-bipyridine]-4',6'-diamine;

(137) $N^{6'}$-(2-(1-(2,2-Difluoroethyl)-1H-pyrazol-4-yl)pyrimidin-4-yl)-$N^{4'}$-((1s,4s)-4-fluorocyclohexyl)-5-morpholino-[2,3'-bipyridine]-4',6'-diamine;

(138) $N^{4'}$-(3,3-Difluorocyclopentyl)-$N^{6'}$-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine;

(139) $N^{4'}$-(3,3-Difluorocyclobutyl)-$N^{6'}$-(2-(1-(2,2-difluoroethyl)-1H-pyrazol-4-yl)pyrimidin-4-yl)-5-((1-methylpiperidin-4-yl)oxy)-[2,3'-bipyridine]-4',6'-diamine;

(140) $N^{6'}$-(2-(1-(Cyclopropylsulfonyl)-1H-pyrazol-4-yl)pyrimidin-4-yl)-$N^{4'}$-(3,3-difluorocyclobutyl)-5-((1-methylpiperidin-4-yl)oxy)-[2,3'-bipyridine]-4',6'-diamine;

(141) $N^{6'}$-(2-(1-(2,2-Difluoroethyl)-1H-pyrazol-4-yl)pyrimidin-4-yl)-$N^{4'}$-(3-fluorocyclohexyl)-5-((1-methylpiperidin-4-yl)oxy)-[2,3'-bipyridine]-4',6'-diamine;

(142) (1s,4s)-4-((6'-((2-(3,4-Dihydro-2H-pyrano[2,3-b]pyridin-6-yl)pyrimidin-4-yl)amino)-5-((1-methylpiperidin-4-yl)oxy)-[2,3'-bipyridin]-4'-yl)amino)-1-methylcyclohexan-1-ol;

(143) $N^{6'}$-(2-(1-(Cyclopropylsulfonyl)-1H-pyrazol-4-yl)pyrimidin-4-yl)-$N^{4'}$-(3,3-difluorocyclopentyl)-5-((1-methylpiperidin-4-yl)oxy)-[2,3'-bipyridine]-4',6'-diamine;

(144) $N^2$-(2-(1-(Cyclopropylsulfonyl)-1H-pyrazol-4-yl)pyrimidin-4-yl)-$N^4$-((1s,4s)-4-fluorocyclohexyl)-5-(5-((1-methylpiperidin-4-yl)oxy) pyrazin-2-yl)pyridine-2,4-diamine;

(145) (1s,4s)-4-((2-((2-(1-(Cyclopropylsulfonyl)-1H-pyrazol-4-yl)pyrimidin-4-yl)amino)-5-(5-((1-meth- (145) ...ylpiperidin-4-yl)oxy) pyrazin-2-yl)pyridin-4-yl)amino)-1-methylcyclohexan-1-ol;
(146) ((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino) cyclohexyl)methanol;
(147) 2-((1s,4s)-4-((2-((2-(1-(Cyclopropylsulfonyl)-1H-pyrazol-4-yl)pyrimidin-4-yl)amino)-5-(5-((1-methylpiperidin-4-yl)oxy) pyrazin-2-yl)pyridin-4-yl)amino) cyclohexyl)propan-2-ol;
(148) (1s,4s)-4-((2-((2-(1-(Cyclopropylsulfonyl)-1H-pyrazol-4-yl)pyrimidin-4-yl)amino)-5-(5-((tetrahydro-2H-pyran-4-yl)oxy) pyrazin-2-yl)pyridin-4-yl)amino)-1-methylcyclohexan-1-ol;
(149) (1s,4s)-4-((2-((2-(1-(Cyclopropylsulfonyl)-1H-pyrazol-4-yl)pyrimidin-4-yl)amino)-5-(5-((tetrahydrofuran-3-yl)oxy) pyrazin-2-yl)pyridin-4-yl)amino)-1-methylcyclohexan-1-ol;
(150) (1s,4s)-4-((2-((2-(1-(Cyclopropylsulfonyl)-1H-pyrazol-4-yl)pyrimidin-4-yl)amino)-5-(5-(oxetan-3-yloxy) pyrazin-2-yl)pyridin-4-yl)amino)-1-methylcyclohexan-1-ol;
(151) $N^2$-(2-(1-(Cyclopropylsulfonyl)-1H-pyrazol-4-yl)pyrimidin-4-yl)-$N^4$-((1s,4s)-4-fluorocyclohexyl)-5-(5-((tetrahydro-2H-pyran-4-yl)oxy) pyrazin-2-yl)pyridine-2,4-diamine;
(152) $N^2$-(2-(1-(Cyclopropylsulfonyl)-1H-pyrazol-4-yl)pyrimidin-4-yl)-$N^4$-((1s,4s)-4-fluorocyclohexyl)-5-(5-((tetrahydrofuran-3-yl)oxy) pyrazin-2-yl)pyridine-2,4-diamine;
(153) (1s,4s)-4-((2-((2-(1-(Cyclopropylsulfonyl)-1H-pyrazol-4-yl)pyrimidin-4-yl)amino)-5-(5-((1-(2-fluoroethyl) piperidin-4-yl)oxy) pyrazin-2-yl)pyridin-4-yl)amino)-1-methylcyclohexan-1-ol;
(154) (1s,4s)-4-((2-((2-(1-(Cyclopropylsulfonyl)-1H-pyrazol-4-yl)pyrimidin-4-yl)amino)-5-(5-((4-fluoro-1-methylpiperidin-4-yl) methoxy) pyrazin-2-yl)pyridin-4-yl)amino)-1-methylcyclohexan-1-ol;
(155) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-ol;
(156) (1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)-1-methylcyclohexan-1-ol;
(157) $N^{6'}$-(2-(1-(Cyclopropylsulfonyl)-1H-pyrazol-4-yl)pyrimidin-4-yl)-$N^{4'}$-((1s,4s)-4-((2-fluoroethyl)amino) cyclohexyl)-5-(methylsulfonyl)-[2,3'-bipyridine]-4',6'-diamine;
(158) ((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)methanol;
(159) $N^{6'}$-(2-(1-(Cyclopropylsulfonyl)-1H-pyrazol-4-yl)pyrimidin-4-yl)-$N^{4'}$-(1s,4s)-4-((dimethylamino) methyl)cyclohexyl)-5-(methylsulfonyl)-[2,3'-bipyridine]-4',6'-diamine;
(160) 2-((1s,4s)-4-((6'-((2-(1-(Cyclopropylsulfonyl)-1H-pyrazol-4-yl)pyrimidin-4-yl)amino)-5-(methylsulfonyl)-[2,3'-bipyridin]-4'-yl)amino)cyclohexyl)propan-2-ol;
(161) (3-(((6'-((2-(1-(Cyclopropylsulfonyl)-1H-pyrazol-4-yl)pyrimidin-4-yl)amino)-6-fluoro-[2,3'-bipyridin]-4'-yl)amino)methyl) oxetan-3-yl)methanol;
(162) (4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-fluorocyclohexyl)methanol;
(163) 2-((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)propan-2-ol;
(164) 6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-N,N-dimethyl-[2,3'-bipyridine]-5-sulfonamide;
(165) 6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-N,N-dimethyl-[2,3'-bipyridine]-5-sulfonamide;
(166) 6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-N,N-dimethyl-[2,3'-bipyridine]-5-sulfonamide;
(167) (1s,4s)-4-((6'-((2-(1-(Cyclopropylsulfonyl)-1H-pyrazol-4-yl)pyrimidin-4-yl)amino)-4-(dimethylamino)-[2,3'-bipyridin]-4'-yl)amino)-1-methylcyclohexan-1-ol;
(168) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-1-methylcyclohexan-1-ol;
(169) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl) propan-2-ol;
(170) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)propan-2-ol;
(171) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)propan-2-ol;
(172) (1s,4s)-4-((6'-((2-(1-(Cyclopropylsulfonyl)-1H-pyrazol-4-yl)pyrimidin-4-yl)amino)-5-(2-hydroxypropan-2-yl)-[2,3'-bipyridin]-4'-yl)amino)-N,N-dimethylcyclohexane-1-carboxamide;
(173) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)propan-2-ol;
(174) 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)propan-2-ol;
(175) 2-(6'-((2-(1-(Cyclopropylsulfonyl)-1H-pyrazol-4-yl)pyrimidin-4-yl)amino)-4'-((4,4-difluorocyclohexyl)amino)-[2,3'-bipyridin]-5-yl)propan-2-ol;
(176) 2-(6'-((2-(1-(Cyclopropylsulfonyl)-1H-pyrazol-4-yl)pyrimidin-4-yl)amino)-4'-((1-(2-fluoroethyl) piperidin-4-yl)amino)-[2,3'-bipyridin]-5-yl)propan-2-ol;
(177) 2-(6'-((2-(1-(Cyclopropylsulfonyl)-1H-pyrazol-4-yl)pyrimidin-4-yl)amino)-4'-((1-(2-fluoroethyl) piperidin-3-yl)amino)-[2,3'-bipyridin]-5-yl)propan-2-ol;
(178) 2-(6'-((2-(1-(Cyclopropylsulfonyl)-1H-pyrazol-4-yl)pyrimidin-4-yl)amino)-4'-((1-(2,2-difluoroethyl) piperidin-4-yl)amino)-[2,3'-bipyridin]-5-yl)propan-2-ol;
(179) (1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)-1-methylcyclohexan-1-ol;
(180) 2-((1s,4s)-4-((6'-((2-(1-(Cyclopropylsulfonyl)-1H-pyrazol-4-yl)pyrimidin-4-yl)amino)-6-fluoro-5-methyl-[2,3'-bipyridin]-4'-yl)amino)cyclohexyl)propan-2-ol;

(181) (1s,4s)-4-((6'-((2-(1-(Cyclopropylsulfonyl)-1H-pyrazol-4-yl)pyrimidin-4-yl)amino)-6-fluoro-5-(trifluoromethyl)-[2,3'-bipyridin]-4'-yl)amino)-1-methylcyclohexan-1-ol;

(182) (1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)-1-methylcyclohexan-1-ol;

(183) ((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)methanol;

(184) 2-((1s,4s)-4-((6'-((2-(1-(Cyclopropylsulfonyl)-1H-pyrazol-4-yl)pyrimidin-4-yl)amino)-5-(morpholinosulfonyl)-[2,3'-bipyridin]-4'-yl)amino)cyclohexyl)propan-2-ol;

(185) (1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)-1-methylcyclohexan-1-ol;

(186) 2-((1s,4s)-4-((2-((2-(1-(Cyclopropylsulfonyl)-1H-pyrazol-4-yl)pyrimidin-4-yl)amino)-5-(5-fluoropyrazin-2-yl)pyridin-4-yl)amino)cyclohexyl)propan-2-ol;

(187) 2-((1s,4s)-4-((6'-((2-(1-(Cyclopropylsulfonyl)-1H-pyrazol-4-yl)pyrimidin-4-yl)amino)-5-((4-methylpiperidin-1-yl) sulfonyl)-[2,3'-bipyridin]-4'-yl)amino)cyclohexyl)propan-2-ol;

(188) (1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)-1-methylcyclohexan-1-ol;

(189) ((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)methanol;

(190) 2-((1s,4s)-4-((6'-((2-(1-(Cyclopropylsulfonyl)-1H-pyrazol-4-yl)pyrimidin-4-yl)amino)-5-((4-methylpiperazin-1-yl) sulfonyl)-[2,3'-bipyridin]-4'-yl)amino)cyclohexyl)propan-2-ol;

(191) (1s,4s)-4-((4-(6-((2-(1-(Cyclopropylsulfonyl)-1H-pyrazol-4-yl)pyrimidin-4-yl)amino)-4-(((1s,4s)-4-hydroxy-4-methylcyclohexyl)amino)pyridin-3-yl)pyrimidin-2-yl)amino)-1-methylcyclohexan-1-ol;

(192) ((1s,4s)-4-((4-(6-((2-(1-(Cyclopropylsulfonyl)-1H-pyrazol-4-yl)pyrimidin-4-yl)amino)-4-(((1s,4s)-4-(hydroxymethyl)cyclohexyl)amino)pyridin-3-yl)pyrimidin-2-yl)amino)cyclohexyl)methanol;

(193) 2-((1s,4s)-4-((4-(6-((2-(1-(Cyclopropylsulfonyl)-1H-pyrazol-4-yl)pyrimidin-4-yl)amino)-4-(((1s,4s)-4-(2-hydroxypropan-2-yl)cyclohexyl)amino)pyridin-3-yl)pyrimidin-2-yl)amino)cyclohexyl)propan-2-ol;

(194) (1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)-1-methylcyclohexan-1-ol;

(195) ((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)methanol;

(196) 2-((1s,4s)-4-((6'-((2-(1-(Cyclopropylsulfonyl)-1H-pyrazol-4-yl)pyrimidin-4-yl)amino)-5-(trifluoromethoxy)-[2,3'-bipyridin]-4'-yl)amino)cyclohexyl)propan-2-ol;

(197) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(trifluoromethoxy)-[2,3'-bipyridine]-4',6'-diamine;

(198) (1s,4s)-4-((6'-((2-(1-(Cyclopropylsulfonyl)-1H-pyrazol-4-yl)pyrimidin-4-yl)amino)-4-(methylsulfonyl)-[2,3'-bipyridin]-4'-yl)amino)-1-methylcyclohexan-1-ol;

(199) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(4-methylpiperazin-1-yl)methanone;

(200) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(morpholino)methanone;

(201) (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(morpholino)methanone;

(202) (6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)(4-methylpiperazin-1-yl)methanone;

(203) (6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)(4-methylpiperazin-1-yl)methanone;

(204) (6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)(4-methylpiperazin-1-yl)methanone;

(205) (1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)-1-methylcyclohexan-1-ol;

(206) 2-((6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)oxy)ethan-1-ol;

(207) 2-((1s,4s)-4-((6'-((2-(1-(Cyclopropylsulfonyl)-1H-pyrazol-4-yl)pyrimidin-4-yl)amino)-5-(2-hydroxyethoxy)-[2,3'-bipyridin]-4'-yl)amino)cyclohexyl)propan-2-ol;

(208) (1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)-1-methylcyclohexan-1-ol;

(209) ((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)methanol;

(210) 2-((1s,4s)-4-((6'-((2-(1-(Cyclopropylsulfonyl)-1H-pyrazol-4-yl)pyrimidin-4-yl)amino)-5-(2-(dimethylamino) ethoxy)-[2,3'-bipyridin]-4'-yl)amino)cyclohexyl)propan-2-ol;

(211) (1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)-1-methylcyclohexan-1-ol;

(212) ((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)methanol;

(213) 2-((1s,4s)-4-((6'-((2-(1-(Cyclopropylsulfonyl)-1H-pyrazol-4-yl)pyrimidin-4-yl)amino)-4-(2-morpholinoethoxy)-[2,3'-bipyridin]-4'-yl)amino)cyclohexyl)propan-2-ol;

(214) ((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)methanol;

(215) 2-((1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)cyclohexyl)propan-2-ol;

(216) $N^{6'}$-(2-(1-(Cyclopropylsulfonyl)-1H-pyrazol-4-yl)pyrimidin-4-yl)-$N^{4'}$-(3,3-difluorocyclobutyl)-$N^{4'}$-((1s,4s)-4-((dimethylamino)methyl)cyclohexyl)-[2,3'-bipyridine]-4,4',6'-triamine;

(217) 2-((1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)cyclohexyl)propan-2-ol;

(218) (1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)-1-methylcyclohexan-1-ol;

(219) ((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol;

(220) 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)propan-2-ol;

(221) $N^{6'}$-(2-(1-(Cyclopropylsulfonyl)-1H-pyrazol-4-yl)pyrimidin-4-yl)-$N^{4'}$-(1s,4s)-4-((dimethylamino)methyl)cyclohexyl)-5-(2,2,2-trifluoroethyl)-[2,3'-bipyridine]-4',6'-diamine;

(222) ((1S,3S)-3-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)methanol;

(223) 2-((1s,4s)-4-((6'-((2-(1-(Cyclopropylsulfonyl)-1H-pyrazol-4-yl)pyrimidin-4-yl)amino)-5-(2,2,2-trifluoroethyl)-[2,3'-bipyridin]-4'-yl)amino)cyclohexyl)ethan-1-ol;

(224) (1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)-1-methylcyclohexan-1-ol;

(225) 2-((1s,4s)-4-((6'-((2-(1-(Cyclopropylsulfonyl)-1H-pyrazol-4-yl)pyrimidin-4-yl)amino)-5-(3,3-difluoroazetidin-1-yl)-[2,3'-bipyridin]-4'-yl)amino)cyclohexyl)propan-2-ol;

(226) (1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)-1-methylcyclohexan-1-ol;

(227) 1-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2,2-trifluoroethan-1-ol;

(228) 1-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-2,2,2-trifluoroethan-1-ol;

(229) 2-((1s,4s)-4-((6'-((2-(1-(Cyclopropylsulfonyl)-1H-pyrazol-4-yl)pyrimidin-4-yl)amino)-5-(2,2,2-trifluoro-1-hydroxyethyl)-[2,3'-bipyridin]-4'-yl)amino)cyclohexyl)propan-2-ol;

(230) (1s,4s)-4-((6'-((2-(1-(Cyclopropylsulfonyl)-1H-pyrazol-4-yl)pyrimidin-4-yl)amino)-5-(1,1,1-trifluoro-2-hydroxypropan-2-yl)-[2,3'-bipyridin]-4'-yl)amino)-1-methylcyclohexan-1-ol;

(231) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-1,1,1-trifluoropropan-2-ol;

(232) 2-(6'-((2-(1-(Cyclopropylsulfonyl)-1H-pyrazol-4-yl)pyrimidin-4-yl)amino)-4'-(((1S,3S)-3-(hydroxymethyl)cyclohexyl)amino)-[2,3'-bipyridin]-5-yl)-1,1,1-trifluoropropan-2-ol;

(233) 2-(6'-((2-(1-(Cyclopropylsulfonyl)-1H-pyrazol-4-yl)pyrimidin-4-yl)amino)-4'-(((1s,4s)-4-(2-hydroxypropan-2-yl)cyclohexyl)amino)-[2,3'-bipyridin]-5-yl)-1,1,1-trifluoropropan-2-ol;

(234) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-1,1,1-trifluoropropan-2-ol;

(235) ((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)methanol;

(236) 2-((1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)cyclohexyl)propan-2-ol;

(237) $N^{6'}$-(2-(1-(Cyclopropylsulfonyl)-1H-pyrazol-4-yl)pyrimidin-4-yl)-$N^{4'}$-(1s,4s)-4-((dimethylamino)methyl)cyclohexyl)-5-(2-fluoropropan-2-yl)-[2,3'-bipyridine]-4',6'-diamine;

(238) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-(2-fluoropropan-2-yl)-[2,3'-bipyridine]-4',6'-diamine;

(239) $N^{6'}$-(2-(1-(Cyclopropylsulfonyl)-1H-pyrazol-4-yl)pyrimidin-4-yl)-$N^{4'}$-(4-fluorocyclohexyl)-5-(2-fluoropropan-2-yl)-[2,3'-bipyridine]-4',6'-diamine;

(240) $N^{6'}$-(2-(1-(Cyclopropylsulfonyl)-1H-pyrazol-4-yl)pyrimidin-4-yl)-$N^{4'}$-(4,4-difluorocyclohexyl)-5-(2-fluoropropan-2-yl)-[2,3'-bipyridine]-4',6'-diamine;

(241) ((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)methanol;

(242) 2-((1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)cyclohexyl)propan-2-ol;

(243) $N^{6'}$-(2-(1-(Cyclopropylsulfonyl)-1H-pyrazol-4-yl)pyrimidin-4-yl)-5-(1,1-difluoroethyl)-$N^{4'}$-((1s,4s)-4-((dimethylamino)methyl)cyclohexyl)-[2,3'-bipyridine]-4',6'-diamine;

(244) 2-(6'-((2-(1-(Cyclopropylsulfonyl)-1H-pyrazol-4-yl)pyrimidin-4-yl)amino)-4'-(((1s,4s)-4-(hydroxymethyl)cyclohexyl)amino)-[2,3'-bipyridin]-5-yl)-2,2-difluoroethan-1-ol;

(245) 2-(6'-((2-(1-(Cyclopropylsulfonyl)-1H-pyrazol-4-yl)pyrimidin-4-yl)amino)-4'-(((1s,4s)-4-((dimethylamino)methyl)cyclohexyl)amino)-[2,3'-bipyridin]-5-yl)-2,2-difluoroethan-1-ol;

(246) ((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)methanol;

(247) 2-((1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)cyclohexyl)propan-2-ol;

(248) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-6-(2,2,2-trifluoroethyl)-[2,3'-bipyridine]-4',6'-diamine;

(249) $N^{6'}$-(2-(1-(Cyclopropylsulfonyl)-1H-pyrazol-4-yl)pyrimidin-4-yl)-$N^{4'}$-isopropyl-5-((1-methylpiperidin-4-yl)oxy)-[2,3'-bipyridine]-4',6'-diamine;

(250) (1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(251) ((1s,4s)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(252) 2-((1r,4r)-4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol;

(253) ((1S,3S)-3-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)cyclohexyl)methanol;

(254) $N^{6'}$-(2-(1-(Cyclopropylsulfonyl)-1H-pyrazol-4-yl)pyrimidin-4-yl)-$N^{4'}$-(4-fluorocyclohexyl)-5-((1-methylpiperidin-4-yl)oxy)-[2,3'-bipyridine]-4',6'-diamine;

(255) $N^{6'}$-(2-(1-(Cyclopropylsulfonyl)-1H-pyrazol-4-yl)pyrimidin-4-yl)-$N^{4'}$-(4,4-difluorocyclohexyl)-5-((1-methylpiperidin-4-yl)oxy)-[2,3'-bipyridine]-4',6'-diamine;

(256) $N^{6'}$-(2-(1-(Cyclopropylsulfonyl)-1H-pyrazol-4-yl)pyrimidin-4-yl)-$N^{4'}$-(1-(2-fluoroethyl) piperidin-4-yl)-5-((1-methylpiperidin-4-yl)oxy)-[2,3'-bipyridine]-4',6'-diamine;

(257) $N^{6'}$-(2-(1-(Cyclopropylsulfonyl)-1H-pyrazol-4-yl)pyrimidin-4-yl)-$N^{4'}$-(1-(2-fluoroethyl) piperidin-3-yl)-5-((1-methylpiperidin-4-yl)oxy)-[2,3'-bipyridine]-4',6'-diamine;

(258) $N^{6'}$-(2-(1-(Cyclopropylsulfonyl)-1H-pyrazol-4-yl)pyrimidin-4-yl)-$N^{4'}$-(1-(2,2-difluoroethyl) piperidin-4-yl)-5-((1-methylpiperidin-4-yl)oxy)-[2,3'-bipyridine]-4',6'-diamine;

(259) (4-((6'-((2-(1-(Cyclopropylsulfonyl)-1H-pyrazol-4-yl)pyrimidin-4-yl)amino)-5-((1-methylpiperidin-4-yl)oxy)-[2,3'-bipyridin]-4'-yl)amino)-1-fluorocyclohexyl)methanol;

(260) (1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)-1-methylcyclohexan-1-ol;

(261) ((1s,4s)-4-((6'-((2-(1-(Cyclopropylsulfonyl)-1H-pyrazol-4-yl)pyrimidin-4-yl)amino)-5-(2,2,2-trifluoro-1-methoxyethyl)-[2,3'-bipyridin]-4'-yl)amino)cyclohexyl)methanol;

(262) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-5-(2,2,2-trifluoro-1-methoxyethyl)-[2,3'-bipyridine]-4',6'-diamine;

(263) (1s,4s)-4-((6'-((2-(1-(Cyclopropylsulfonyl)-1H-pyrazol-4-yl)pyrimidin-4-yl)amino)-5-(3,3,3-trifluoropropyl)-[2,3'-bipyridin]-4'-yl)amino)-1-methylcyclohexan-1-ol;

(264) 5-(2-(Azetidin-1-yl) ethoxy)-$N^{6'}$-(2-(1-(cyclopropylsulfonyl)-1H-pyrazol-4-yl)pyrimidin-4-yl)-$N^{4'}$-((1s,4s)-4-fluorocyclohexyl)-[2,3'-bipyridine]-4',6'-diamine;

(265) 2-(6'-((2-(1-(Cyclopropylsulfonyl)-1H-pyrazol-4-yl)pyrimidin-4-yl)amino)-4'-(((1s,4s)-4-fluorocyclohexyl)amino)-[2,3'-bipyridin]-5-yl)-1,1,1-trifluoropropan-2-ol;

(266) 2-(6'-((2-(1-(Cyclopropylsulfonyl)-1H-pyrazol-4-yl)pyrimidin-4-yl)amino)-4'-((4-fluorocyclohexyl)amino)-[2,3'-bipyridin]-5-yl)-1,1,1-trifluoropropan-2-ol;

(267) $N^2$-(2-(1-(Cyclopropylsulfonyl)-1H-pyrazol-4-yl)pyrimidin-4-yl)-5-(6-(4,4-difluoropiperidin-1-yl)pyridazin-3-yl)-$N^4$-(4-fluorocyclohexyl)pyridine-2,4-diamine;

(268) $N^2$-(2-(1-(Cyclopropylsulfonyl)-1H-pyrazol-4-yl)pyrimidin-4-yl)-$N^4$-(4,4-difluorocyclohexyl)-5-(6-(4,4-difluoropiperidin-1-yl)pyridazin-3-yl)pyridine-2,4-diamine;

(269) (1s,4s)-4-((2-((2-(1-(Cyclopropylsulfonyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol;

(270) $N^2$-(2-(1-(Cyclopropylsulfonyl)-1H-pyrazol-4-yl)pyrimidin-4-yl)-$N^4$-((1s,4s)-4-fluorocyclohexyl)-5-(6-((1-methylpiperidin-4-yl)oxy)pyridazin-3-yl)pyridine-2,4-diamine;

(271) (1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)-1-methylcyclohexan-1-ol;

(272) ((1s,4s)-4-((6'-((2-(1-(Cyclopropylsulfonyl)-1H-pyrazol-4-yl)pyrimidin-4-yl)amino)-6-fluoro-[2,3'-bipyridin]-4'-yl)amino)cyclohexyl)methanol;

(273) $N^{6'}$-(2-(1-(Cyclopropylsulfonyl)-1H-pyrazol-4-yl)pyrimidin-4-yl)-6-fluoro-$N^{4'}$-((1s,4s)-4-((2-fluoroethyl)amino)cyclohexyl)-[2,3'-bipyridine]-4',6'-diamine;

(274) $N^{6'}$-(2-(1-(Cyclopropylsulfonyl)-1H-pyrazol-4-yl)pyrimidin-4-yl)-$N^{4'}$-((1s,4s)-4-((dimethylamino)methyl)cyclohexyl)-6-fluoro-[2,3'-bipyridine]-4',6'-diamine;

(275) $N^{6'}$-(2-(1-(Cyclopropylsulfonyl)-1H-pyrazol-4-yl)pyrimidin-4-yl)-$N^{4'}$-((1s,4s)-4-((2,2-difluoroethyl)amino)cyclohexyl)-6-fluoro-[2,3'-bipyridine]-4',6'-diamine;

(276) (1s,4s)-4-((6'-((2-(1-(Cyclopropylsulfonyl)-1H-pyrazol-4-yl)pyrimidin-4-yl)amino)-4-((2-(dimethylamino)ethyl)amino)-[2,3'-bipyridin]-4'-yl)amino)-1-methylcyclohexan-1-ol;

(277) (1s,4s)-4-((6'-((2-(1-(Cyclopropylsulfonyl)-1H-pyrazol-4-yl)pyrimidin-4-yl)amino)-4-((3,3,3-trifluoropropyl)amino)-[2,3'-bipyridin]-4'-yl)amino)-1-methylcyclohexan-1-ol;

(278) (1s,4s)-4-((6'-((2-(1-(Cylopropylsulfonyl)-1H-pyrazol-4-yl)pyrimidin-4-yl)amino)-4-((1-methylpiperidin-4-yl)amino)-[2,3'-bipyridin]-4'-yl)amino)-1-methylcyclohexan-1-ol;

(279) (1s,4s)-4-((6'-((2-(1-(Cyclopropylsulfonyl)-1H-pyrazol-4-yl)pyrimidin-4-yl)amino)-4 ((2-morpholinoethyl)amino)-[2,3'-bipyridin]-4'-yl)amino)-1-methylcyclohexan-1-ol;

(280) (1s,4s)-4-((6'-((2-(1-(Cyclopropylsulfonyl)-1H-pyrazol-4-yl)pyrimidin-4-yl)amino)-4-((3,3-difluorocyclobutyl)amino)-[2,3'-bipyridin]-4'-yl)amino)-1-methylcyclohexan-1-ol;

(281) (1s,4s)-4-((6'-((2-(1-(Cyclopropylsulfonyl)-1H-pyrazol-4-yl)pyrimidin-4-yl)amino)-4-((2-(3-fluoroazetidin-1-yl)ethyl)amino)-[2,3'-bipyridin]-4'-yl)amino)-1-methylcyclohexan-1-ol;

(282) (1s,4s)-4-((6'-((2-(1-(Cyclopropylsulfonyl)-1H-pyrazol-4-yl)pyrimidin-4-yl)amino)-4-((3-hydroxypropyl)amino)-[2,3'-bipyridin]-4'-yl)amino)-1-methylcyclohexan-1-ol;

(283) (1s,4s)-4-((6'-((2-(1-(Cyclopropylsulfonyl)-1H-pyrazol-4-yl)pyrimidin-4-yl)amino)-4-((3-hydroxycyclobutyl)amino)-[2,3'-bipyridin]-4'-yl)amino)-1-methylcyclohexan-1-ol;

(284) (6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-5-yl)(morpholino)methanone;

(285) (1s,4s)-4-((6'-((2-(1-(Cyclopropylsulfonyl)-1H-pyrazol-4-yl)pyrimidin-4-yl)amino)-6-((2-hydroxyethyl)amino)-[2,3'-bipyridin]-4'-yl)amino)-1-methylcyclohexan-1-ol;

(286) (1s,4s)-4-((6'-((2-(1-(Cyclopropylsulfonyl)-1H-pyrazol-4-yl)pyrimidin-4-yl)amino)-6-((1-methylpiperidin-4-yl)oxy)-[2,3'-bipyridin]-4'-yl)amino)-1-methylcyclohexan-1-ol;

(287) (1s,4s)-4-((6'-((2-(1-(Cyclopropylsulfonyl)-1H-pyrazol-4-yl)pyrimidin-4-yl)amino)-4-(2-(dimethylamino) ethoxy)-[2,3'-bipyridin]-4'-yl)amino)-1-methylcyclohexan-1-ol;

(288) 1-((6'-((2-(1-(Cyclopropylsulfonyl)-1H-pyrazol-4-yl)pyrimidin-4-yl)amino)-4'-(((1s,4s)-4-hydroxy-4-methylcyclohexyl)amino)-[2,3'-bipyridin]-4-yl) methyl) azetidin-3-ol;

(289) (1s,4s)-4-((6'-((2-(1-(Cyclopropylsulfonyl)-1H-pyrazol-4-yl)pyrimidin-4-yl)amino)-5-((1-methylazetidin-3-yl)oxy)-[2,3'-bipyridin]-4'-yl)amino)-1-methylcyclohexan-1-ol;

(290) (1s,4s)-4-((5-(2-(Azetidin-1-yl) ethoxy)-6'-((2-(1-(cyclopropylsulfonyl)-1H-pyrazol-4-yl)pyrimidin-4-yl)amino)-[2,3'-bipyridin]-4'-yl)amino)-1-methylcyclohexan-1-ol;

(291) (1s,4s)-4-((6'-((2-(1-(Cyclopropylsulfonyl)-1H-pyrazol-4-yl)pyrimidin-4-yl)amino)-5-(2-fluoropropan-2-yl)-[2,3'-bipyridin]-4'-yl)amino)-1-methylcyclohexan-1-ol;

(292) (1s,4s)-4-((6'-((2-(1-(Cyclopropylsulfonyl)-1H-pyrazol-4-yl)pyrimidin-4-yl)amino)-5-(1,1-difluoroethyl)-[2,3'-bipyridin]-4'-yl)amino)-1-methylcyclohexan-1-ol;

(293) (1s,4s)-4-((6'-((2-(1-(Cyclopropylsulfonyl)-1H-pyrazol-4-yl)pyrimidin-4-yl)amino)-6-(2,2,2-trifluoroethyl)-[2,3'-bipyridin]-4'-yl)amino)-1-methylcyclohexan-1-ol;

(294) 1-(6'-((2-(1-(Cyclopropylsulfonyl)-1H-pyrazol-4-yl)pyrimidin-4-yl)amino)-4'-(isopropylamino)-[2,3'-bipyridin]-5-yl)-2,2,2-trifluoroethan-1-ol;

(295) 2-(6'-((2-(1-(Cyclopropylsulfonyl)-1H-pyrazol-4-yl)pyrimidin-4-yl)amino)-4'-(isopropylamino)-[2,3'-bipyridin]-5-yl)-1,1,1-trifluoropropan-2-ol;

(296) 4-(4-((4'-(((1s,4s)-4-Hydroxy-4-methylcyclohexyl)amino)-5-(2,2,2-trifluoroethyl)-[2,3'-bipyridin]-6'-yl)amino)pyrimidin-2-yl)-N,N-dimethyl-1H-pyrazole-1-sulfonamide;

(297) 4-(4-((4'-(((1s,4s)-4-Hydroxy-4-methylcyclohexyl)amino)-5-(2,2,2-trifluoro-1-hydroxyethyl)-[2,3'-bipyridin]-6'-yl)amino)pyrimidin-2-yl)-N,N-dimethyl-1H-pyrazole-1-sulfonamide;

(298) 4-(4-((4'-(((1s,4s)-4-Hydroxy-4-methylcyclohexyl)amino)-5-(1,1,1-trifluoro-2-hydroxypropan-2-yl)-[2,3'-bipyridin]-6'-yl)amino)pyrimidin-2-yl)-N,N-dimethyl-1H-pyrazole-1-sulfonamide;

(299) (1s,4s)-4-((6'-((2-(1-(Cyclopropylsulfonyl)-1H-pyrazol-4-yl)-5-fluoropyrimidin-4-yl)amino)-5-(2,2,2-trifluoroethyl)-[2,3'-bipyridin]-4'-yl)amino)-1-methylcyclohexan-1-ol;

(300) (1s,4s)-4-((6'-((2-(1-(Cyclopropylsulfonyl)-1H-pyrazol-4-yl)-5-fluoropyrimidin-4-yl)amino)-5-((1-methylpiperidin-4-yl)oxy)-[2,3'-bipyridin]-4'-yl)amino)-1-methylcyclohexan-1-ol;

(301) 4-(4-((4'-(((1s,4s)-4-Hydroxy-4-methylcyclohexyl)amino)-5-((1-methylpiperidin-4-yl)oxy)-[2,3'-bipyridin]-6'-yl)amino)pyrimidin-2-yl)-N,N-dimethyl-1H-pyrazole-1-sulfonamide;

(302) (1s,4s)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)-1-methylcyclohexan-1-ol;

(303) (1s,4s)-1-Methyl-4-((6'-((2-(3-methyl-1-(2,2,2-trifluoroethyl)-1H-pyrazol-4-yl)pyrimidin-4-yl)amino)-5-((1-methylpiperidin-4-yl)oxy)-[2,3'-bipyridin]-4'-yl)amino)cyclohexan-1-ol;

(304) (1s,4s)-1-Methyl-4-((5-((1-methylpiperidin-4-yl)oxy)-6'-((2-(1-(2,2,2-trifluoroethyl)-1H-pyrazol-4-yl)pyrimidin-4-yl)amino)-[2,3'-bipyridin]-4'-yl)amino)cyclohexan-1-ol;

(305) 2-((1r,4r)-4-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl)ethan-1-ol;

(306) ((1S,3S)-3-((6'-((2-(1-(2,2-Difluoroethyl)-1H-pyrazol-4-yl)pyrimidin-4-yl)amino)-5-((1-methylpiperidin-4-yl)oxy)-[2,3'-bipyridin]-4'-yl)amino)cyclohexyl) methanol;

(307) $N^{4'}$-((1s,4s)-4-fluorocyclohexyl)-5-((1-methylpiperidin-4-yl)oxy)-$N^{6'}$-(2-(1-(2,2,2-trifluoroethyl)-1H-pyrazol-4-yl)pyrimidin-4-yl)-[2,3'-bipyridine]-4',6'-diamine;

(308) $N^{6'}$-(2-(1-(2,2-Difluoroethyl)-1H-pyrazol-4-yl)pyrimidin-4-yl)-$N^{4'}$-(4-fluorocyclohexyl)-5-((1-methylpiperidin-4-yl)oxy)-[2,3'-bipyridine]-4',6'-diamine;

(309) $N^{6'}$-(2-(1-(Cyclopropylsulfonyl)-1H-pyrazol-4-yl)-5-fluoropyrimidin-4-yl)-$N^{4'}$-(4-fluorocyclohexyl)-5-((1-methylpiperidin-4-yl)oxy)-[2,3'-bipyridine]-4',6'-diamine;

(310) (1s,4s)-4-((6-Fluoro-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(311) (1s,4s)-4-((6'-((2-(1-(Cyclopropylsulfonyl)-1H-pyrazol-4-yl)-5-fluoropyrimidin-4-yl)amino)-6-fluoro-[2,3'-bipyridin]-4'-yl)amino)-1-methylcyclohexan-1-ol;

(312) (1s,4s)-4-((5-(3,3-Difluoroazetidin-1-yl)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(313) (1s,4s)-4-((6'-((2-(1-(Cyclopropylsulfonyl)-1H-pyrazol-4-yl)-5-fluoropyrimidin-4-yl)amino)-5-(3,3-difluoroazetidin-1-yl)-[2,3'-bipyridin]-4'-yl)amino)-1-methylcyclohexan-1-ol;

(314) 2-(6'-((2-(1-(Cyclopropylsulfonyl)-1H-pyrazol-4-yl)-5-fluoropyrimidin-4-yl)amino)-4'-(((1s,4s)-4-fluorocyclohexyl)amino)-[2,3'-bipyridin]-5-yl)propan-2-ol;

(315) (1s,4s)-4-((2-((2-(1-(2,2-Difluoroethyl)-1H-pyrazol-4-yl)pyrimidin-4-yl)amino)-5-(6-((1-methylpiperidin-4-yl)oxy)pyridazin-3-yl)pyridin-4-yl)amino)-1-methylcyclohexan-1-ol;

(316) (1s,4s)-4-((5-(2-(Azetidin-1-yl) ethoxy)-6'-((2-(1-(2,2-difluoroethyl)-1H-pyrazol-4-yl)pyrimidin-4-yl)amino)-[2,3'-bipyridin]-4'-yl)amino)-1-methylcyclohexan-1-ol;

(317) (1s,4s)-4-((5-(2-(Azetidin-1-yl) ethoxy)-6'-((2-(3-methyl-1-(2,2,2-trifluoroethyl)-1H-pyrazol-4-yl)pyrimidin-4-yl)amino)-[2,3'-bipyridin]-4'-yl)amino)-1-methylcyclohexan-1-ol;

(318) (1s,4s)-4-((5-(2-(Azetidin-1-yl) ethoxy)-6'-((2-(1-(2,2-difluoroethyl)-3,5-dimethyl-1H-pyrazol-4-yl)pyrimidin-4-yl)amino)-[2,3'-bipyridin]-4'-yl)amino)-1-methylcyclohexan-1-ol;

(319) (1s,4s)-4-((5-(2-(Azetidin-1-yl) ethoxy)-6'-((2-(1-(2,2,3,3-tetrafluoropropyl)-1H-pyrazol-4-yl)pyrimidin-4-yl)amino)-[2,3'-bipyridin]-4'-yl)amino)-1-methylcyclohexan-1-ol;

(320) 3,3-Difluoro-1-(5-fluoro-4-((4'-(((1s,4s)-4-hydroxy-4-methylcyclohexyl)amino)-5-((1-methylpiperidin-4-yl)oxy)-[2,3'-bipyridin]-6'-yl)amino)pyrimidin-2-yl) piperidin-4-ol;

(321) (1s,4s)-4-((6'-((5-Fluoro-2-((3R,4S)-3-fluoro-4-methoxypiperidin-1-yl)pyrimidin-4-yl)amino)-5-((1-methylpiperidin-4-yl)oxy)-[2,3'-bipyridin]-4'-yl)amino)-1-methylcyclohexan-1-ol;

(322) (1s,4s)-4-((6'-((2-(1-(Cyclopropylsulfonyl)-1H-pyrazol-4-yl)pyrimidin-4-yl)amino)-5-((1-(2-fluoroethyl) piperidin-4-yl)oxy)-[2,3'-bipyridin]-4'-yl)amino)-1-methylcyclohexan-1-ol;

(323) $N^{6'}$-(2-(1-(Cyclopropylsulfonyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine;

(324) $N^{6'}$-(2-(1-(2,2-Difluoroethyl)-1H-pyrazol-4-yl)pyrimidin-4-yl)-$N^{4'}$-((1s,4s)-4-fluorocyclohexyl)-5-((1-(2-fluoroethyl) piperidin-4-yl)oxy)-[2,3'-bipyridine]-4',6'-diamine;

(325) (1s,4s)-4-((2-((2-(1-(Cyclopropylsulfonyl)-1H-pyrazol-4-yl)pyrimidin-4-yl)amino)-5-(6-((1-(2-fluoroethyl) piperidin-4-yl)oxy)pyridazin-3-yl)pyridin-4-yl)amino)-1-methylcyclohexan-1-ol;

(326) (1s,4s)-4-((2-((2-(1-(Cyclopropylsulfonyl)-1H-pyrazol-4-yl)pyrimidin-4-yl)amino)-5-(3-methoxypyrazin-2-yl)pyridin-4-yl)amino)-1-methylcyclohexan-1-ol;

(327) (1s,4s)-4-((2-((2-(1-(Cyclopropylsulfonyl)-1H-pyrazol-4-yl)pyrimidin-4-yl)amino)-5-(3-fluoropyrazin-2-yl)pyridin-4-yl)amino)-1-methylcyclohexan-1-ol;

(328) (1s,4s)-4-((6'-((2-(1-(Cyclopropylsulfonyl)-1H-pyrazol-4-yl)pyrimidin-4-yl)amino)-5-fluoro-3-methoxy-[2,3'-bipyridin]-4'-yl)amino)-1-methylcyclohexan-1-ol;

(329) (1s,4s)-4-((6'-((2-(1-(Cyclopropylsulfonyl)-1H-pyrazol-4-yl)pyrimidin-4-yl)amino)-6-fluoro-3-methoxy-[2,3'-bipyridin]-4'-yl)amino)-1-methylcyclohexan-1-ol;

(330) (1s,4s)-4-((6'-((2-(1-(Cyclopropylsulfonyl)-1H-pyrazol-4-yl)pyrimidin-4-yl)amino)-3-(difluoromethoxy)-[2,3'-bipyridin]-4'-yl)amino)-1-methylcyclohexan-1-ol;

(331) (1s,4s)-4-((6'-((2-(1-(Cyclopropylsulfonyl)-1H-pyrazol-4-yl)pyrimidin-4-yl)amino)-4-(difluoromethoxy)-[2,3'-bipyridin]-4'-yl)amino)-1-methylcyclohexan-1-ol;

(332) (1s,4s)-4-((6'-((2-(1-(Cyclopropylsulfonyl)-1H-pyrazol-4-yl)pyrimidin-4-yl)amino)-5-(difluoromethoxy)-[2,3'-bipyridin]-4'-yl)amino)-1-methylcyclohexan-1-ol;

(333) (1s,4s)-4-((6'-((2-(1-(Cyclopropylsulfonyl)-1H-pyrazol-4-yl)pyrimidin-4-yl)amino)-3-(2,2,2-trifluoroethoxy)-[2,3'-bipyridin]-4'-yl)amino)-1-methylcyclohexan-1-ol;

(334) (1s,4s)-4-((6'-((2-(1-(Cyclopropylsulfonyl)-1H-pyrazol-4-yl)pyrimidin-4-yl)amino)-3-(2,2-difluoroethoxy)-[2,3'-bipyridin]-4'-yl)amino)-1-methylcyclohexan-1-ol;

(335) (1s,4s)-4-((6'-((2-(1-(Cyclopropylsulfonyl)-1H-pyrazol-4-yl)pyrimidin-4-yl)amino)-4-fluoro-3-methoxy-[2,3'-bipyridin]-4'-yl)amino)-1-methylcyclohexan-1-ol;

(336) (1s,4s)-4-((6'-((2-(1-(2,2-Difluoroethyl)-1H-pyrazol-4-yl)pyrimidin-4-yl)amino)-4-fluoro-3-methoxy-[2,3'-bipyridin]-4'-yl)amino)-1-methylcyclohexan-1-ol; and (337) (1s,4s)-4-((6'-((2-(1-(2,2-Difluoroethyl)-1H-pyrazol-4-yl)pyrimidin-4-yl)amino)-3-methoxy-5-((1-(2,2,2-trifluoroethyl) piperidin-4-yl)oxy)-[2,3'-bipyridin]-4'-yl)amino)-1-methylcyclohexan-1-ol.

20. A pharmaceutical composition comprising a compound of claim 1, or a pharmaceutically acceptable salt thereof as active ingredients, and a pharmaceutically acceptable carrier.

* * * * *

UNITED STATES PATENT AND TRADEMARK OFFICE
CERTIFICATE OF CORRECTION

PATENT NO. : 12,258,328 B2
APPLICATION NO. : 17/822445
DATED : March 25, 2025
INVENTOR(S) : Lee et al.

It is certified that error appears in the above-identified patent and that said Letters Patent is hereby corrected as shown below:

In the Specification

Column 5, Line 46:
Please delete "is an integer of 0 to 3,"
And replace with -- o is an integer of 0 to 3, --

Column 5, Line 65:
Please delete "-C(O) $NHC_{1-6}$alkyl"
And replace with -- -C(O)$NHC_{1-6}$alkyl --

Column 10, Line 44:
Please delete "is an integer of 0 to 3,"
And replace with -- o is an integer of 0 to 3, --

Column 10, Line 65:
Please delete "-C(O) $NHC_{1-6}$alkyl"
And replace with -- -C(O)$NHC_{1-6}$alkyl --

Column 13, Line 32:
Please delete "-C(O) $NHC_{1-3}$alkyl"
And replace with -- -C(O)$NHC_{1-3}$alkyl --

Column 13, Line 36:
Please delete "-C(O) $NHC_{1-3}$alkyl"
And replace with -- -C(O)$NHC_{1-3}$alkyl --

Signed and Sealed this
Thirteenth Day of January, 2026

John A. Squires
*Director of the United States Patent and Trademark Office*

CERTIFICATE OF CORRECTION (continued)
U.S. Pat. No. 12,258,328 B2

In the Claims

Column 287, Claim 1, Line 45:
Please delete "is an integer of 0 to 3,"
And replace with -- o is an integer of 0 to 3, --

Column 287, Claim 1, Line 65:
Please delete "-C(O) NHC$_{1-6}$alkyl"
And replace with -- -C(O)NHC$_{1-6}$alkyl --

Column 290, Claim 13, Line 4:
Please delete "-C(O) NHC$_{1-6}$alkyl,"
And replace with -- -C(O)NHC$_{1-6}$alkyl, --

Column 290, Claim 13, Line 7:
Please delete "-C(O) NHC$_{1-3}$alkyl"
And replace with -- -C(O)NHC$_{1-3}$alkyl --

Column 290, Claim 18, Line 44:
Please delete "R$^4$"
And replace with -- R$_4$ --

Column 298, Claim 19, Line 35:
Please delete "-NA'-(1 s,4s)"
And replace with -- -N$^{4'}$-((1s,4s) --

Column 299, Claim 19, Line 55:
Please delete "-N$^{4'}$-(1 s,4s)"
And replace with -- -N$^{4'}$-((1s,4s) --

Column 303, Claim 19, Line 31:
Please delete "-N$^{4'}$-(1 s,4s)"
And replace with -- -N$^{4'}$-((1s,4s) --

Column 304, Claim 19, Line 31:
Please delete "-N$^{4'}$-(1 s,4s)"
And replace with -- -N$^{4'}$-((1s,4s) --